US012636275B2

(12) United States Patent
Liu et al.

(10) Patent No.: US 12,636,275 B2
(45) **Date of Patent: *May 26, 2026**

(54) PHARMACEUTICAL USE OF KETOAMIDE-BASED COMPOUND

(71) Applicant: Shanghai Institute of Materia Medica, Chinese Academy of Sciences, Shanghai (CN)

(72) Inventors: Hong Liu, Shanghai (CN); Jian Li, Shanghai (CN); Jingjing Peng, Shanghai (CN); Xiong Xie, Shanghai (CN); Wenhao Dai, Shanghai (CN); Shulei Hu, Shanghai (CN); Chunpu Li, Shanghai (CN); Leike Zhang, Hubei (CN); Zhenming Jin, Shanghai (CN); Yechun Xu, Shanghai (CN); Gengfu Xiao, Hubei (CN); Haitao Yang, Shanghai (CN); Fang Bai, Shanghai (CN); Xi Cheng, Shanghai (CN); Hualiang Jiang, Shanghai (CN); Kaixian Chen, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 855 days.

This patent is subject to a terminal disclaimer.

(21) Appl. No.: 17/796,076

(22) PCT Filed: Jan. 28, 2021

(86) PCT No.: PCT/CN2021/074228

§ 371 (c)(1),
(2) Date: Aug. 1, 2022

(87) PCT Pub. No.: WO2021/151387

PCT Pub. Date: Aug. 5, 2021

(65) Prior Publication Data

US 2023/0133600 A1 May 4, 2023

(30) Foreign Application Priority Data

Jan. 31, 2020 (CN) ......................... 202010077723.7

(51) Int. Cl.
*A61K 31/404* (2006.01)
*A61K 31/4025* (2006.01)
(Continued)

(52) U.S. Cl.
CPC ........ *A61K 31/404* (2013.01); *A61K 31/4025* (2013.01); *A61K 31/4155* (2013.01);
(Continued)

(58) Field of Classification Search
CPC .............. A61K 31/4025; A61K 31/404; A61K 31/4155; A61K 31/437; A61K 31/4412;
(Continued)

(56) References Cited

U.S. PATENT DOCUMENTS

2022/0112177 A1 4/2022 Liu et al.

FOREIGN PATENT DOCUMENTS

CN 103145608 A 6/2013
CN 104592349 A 5/2015
(Continued)

OTHER PUBLICATIONS

Wiersinga et al. (JAMA 2020,:324(8); 782-793), (Year: 2020).*
(Continued)

*Primary Examiner* — Savitha M Rao
(74) *Attorney, Agent, or Firm* — Panitch Schwarze Belisario & Nadel LLP

(57) ABSTRACT

A class of ketoamide-based compounds, in particular, a ketoarnide-based compound as represented by general for-
(Continued)

mula A is provided. The ketoamide compound may be used as a 2019 novel coronavirus (2019-nCov) 3 CL protease inhibitor and/or human cathepsin L inhibitor, and/or may be used in the preparation of a medicament for treating and/or preventing and relieving respiratory tract infection, pneumonia and other related diseases caused by 2019 novel coronavirus infection. Pharmaceutical compositions of the class of compounds, pharmaceutical salts, enantiomeric forms, diastereoisomers and racemic compounds thereof in the preparation of a medicament for treating and/or preventing and relieving respiratory tract infections and other related diseases caused by the 2019 novel coronavirus infection are also provided.

(A)

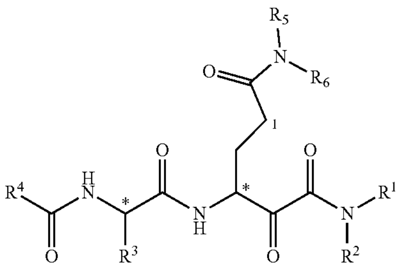

15 Claims, 1 Drawing Sheet

(51) Int. Cl.

| | |
|---|---|
| ***A61K 31/4155*** | (2006.01) |
| ***A61K 31/437*** | (2006.01) |
| ***A61K 31/4412*** | (2006.01) |
| ***A61K 31/443*** | (2006.01) |
| ***A61K 31/4439*** | (2006.01) |
| ***A61K 31/4525*** | (2006.01) |
| ***A61K 31/453*** | (2006.01) |
| ***A61K 31/4535*** | (2006.01) |
| ***A61K 31/454*** | (2006.01) |
| ***A61K 31/4545*** | (2006.01) |
| ***A61K 31/4709*** | (2006.01) |
| ***A61K 31/498*** | (2006.01) |

(52) U.S. Cl.

CPC ........ *A61K 31/437* (2013.01); *A61K 31/4412* (2013.01); *A61K 31/443* (2013.01); *A61K 31/4439* (2013.01); *A61K 31/4525* (2013.01); *A61K 31/453* (2013.01); *A61K 31/4535* (2013.01); *A61K 31/454* (2013.01); *A61K 31/4545* (2013.01); *A61K 31/4709* (2013.01); *A61K 31/498* (2013.01)

(58) Field of Classification Search

CPC .............. A61K 31/443; A61K 31/4439; A61K 31/4525; A61K 31/453; A61K 31/4535; A61K 31/454; A61K 31/4545; A61K 31/4709; A61K 31/498; A61K 38/00; A61P 11/00; A61P 29/00; A61P 31/14; C07K 5/06139; C07K 5/06191; Y02A 50/30

See application file for complete search history.

(56) References Cited

FOREIGN PATENT DOCUMENTS

| | | | |
|---|---|---|---|
| CN | 105837487 | A | 8/2016 |
| CN | 110818691 | A | 2/2020 |
| CN | 106928206 | B | 2/2022 |
| JP | 2021-507010 | A | 2/2021 |
| RU | 2733361 | C1 | 10/2020 |
| WO | 2006061714 | A2 | 6/2006 |
| WO | 2013049382 | A2 | 4/2013 |
| WO | 2018042343 | A2 | 3/2018 |
| WO | 2018067847 | A1 | 4/2018 |
| WO | 2020030143 | A1 | 2/2020 |

OTHER PUBLICATIONS

Office Action issued Apr. 25, 2023 in CN 201980052674.7.

Thanigaimalai et al., "Development of potent dipeptide-type SARS-CoV 3CL protease inhibitors with novel P3 scaffolds: Design, synthesis, biological evaluation, and docking studies," European Journal of Medicinal Chemistry, vol. 68, pp. 372-384 (2013).

Liu et al., "Potential inhibitors for 2019-nCOV coronavirus M protease from clinically approved medicines," Journal of Genetics and Genomics, vol. 47, No. 2, pp. 119-121 (2020).

Office Action issued Oct. 23, 2023 in JP 2022-546507.

Frecer et al., "Antiviral agents against COVID-19: structure-based design of specific peptidomimetic inhibitors of SARS-CoV-2 main protease," RSC advances, vol. 10(66), pp. 40244-40263 (2020).

Genovese et al., "Microscopic factors modulating the interactions between the SARS-Cov-2 main protease and a-ketoamide inhibitors," ChemRxiv, pp. 1-19 (2020).

Wang et al., "Inhibition of enterovirus 71 replication by an a-hydroxy-nitrile derivative NK-1.9k," Antiviral Research, vol. 141, pp. 91-100 (2017).

Search Report issued Dec. 13, 2022 in RU Application 2022123261/04.

Bai et al., "Peptidomimetic a-Acyloxymethylketone Warheads with Six-Membered Lactam P1 Glutamine Mimic: SARS-CoV-2 3CL Protease Inhibition, Coronavirus Antiviral Activity, and in Vitro Biological Stability," Journal of Medicinal Chemistry, vol. 65, pp. 2905-2925 (2022).

Extended European Search Report issued Jan. 30, 2024 in EP Application No. 21748369.2.

Lopez-Leon et al., "More than 50 long-term effects of COVID-19: a systematic review and meta-analysis," Scientific Reports, vol. 11, No. 16144, pp. 1-11 (2021).

Nie et al., "3D-quantitative structure-activity relationship study for the design of novel enterovirus A71 3C protease inhibitors," Chemical Biology & Drug Design, vol. 92, pp. 1750-1762 (2018).

Ma et al., "Boceprevir, GC-376, and calpain inhibitors II, XII inhibit SARS-CoV-2 viral replication by targeting the viral main protease," bioRxiv, 49 pages (2020).

Chen et al., "Synthesis and Evaluation of Tripeptidyl a-Ketoamides as Human Rhinovirus 3C Protease Inhibitors," Bioorganic & Medicinal Chemistry Letters, vol. 13, pp. 3531-3536 (2003).

Gibadullin et al., "GalNAc-Tyrosine Is a Ligand of Plant Lectins, Antibodies, and Human and Murine Macrophage Galactose-Type Lectins," ACS Chemical Biology, 32 pages (2017).

Int'l Search Report issued Apr. 16, 2021 in Int'l Application No. PCT/CN2021/074228.

Kher et al, "Substrate derived peptidic alpha-ketoamides as inhibitors of the malarial protease PfSUB1," Bioorganic & Medicinal Chemistry Letters, vol. 24, pp. 4486-4489 (2014).

Sacco et al, "Structure and inhibition of the SARS-CoV-2 main protease reveal strategy for developing dual inhibitors against Mpro and cathepsin L," Science Advances, vol. 6, No. eabe0751, pp. 1-15 (2020).

Xu et al, "Nelfinavir was predicted to be a potential inhibitor of 2019-nCov main protease by an integrative approach combining homology modelling, molecular docking and binding free energy calculation," downloaded from web page: https://www.biorxiv.org/

(56) References Cited

OTHER PUBLICATIONS content/10.1101/2020.01.27.921627v1, Download date: Apr. 18, 2022, Original posting date: Jan. 28, 2020, 20 pages.
Zeng et al, "Synthesis and structure-activity relationship of alpha-keto amides as enterovirus 71 3C protease inhibitors," Bioorganic & Medicinal Chemistry Letters, vol. 26, pp. 1762-1766 (2016).
Zhai et al, "Cyanohydrin as an Anchoring Group for Potent and Selective Inhibitors of Enterovirus 71 3C Protease," Journal of Medicinal Chemistry, vol. 58, pp. 9414-9420 (2015).
Zhang et al, "a-Ketoamides as Broad-Spectrum Inhibitors of Coronavirus and Enterovirus Replication: Structure-Based Design, Synthesis, and Activity Assessment," Journal of Medical Chemistry, vol. 63, pp. 4562-4578 (2020).

* cited by examiner

PHARMACEUTICAL USE OF KETOAMIDE-BASED COMPOUND

CROSS-REFERENCE TO RELATED APPLICATIONS

This application is a Section 371 of International Application No. PCT/CN2021/074228, filed Jan. 28, 2021, which was published in the Chinese language on Aug. 5, 2021, under International Publication No. WO 2021/151387 A1, and which claims priority under 35 U.S.C. § 119 (b) to Chinese Application No. 202010077723.7, filed Jan. 31, 2020, the disclosure of each of which is incorporated herein by reference in its entirety.

TECHNICAL FIELD

The invention relates to the field of medicine, in particular to the medical use of a ketoamide compound.

BACKGROUND ART

In acute infectious diseases, most of them are viral infectious diseases. The incidence of viral infectious diseases is high and the mortality is also high. Due to the limited means of detection and diagnosis, new outbreaks caused by new viruses are often characterized by suddenness, randomness and unpredictability. Once an outbreak occurs, if there is no effective means of prevention and control, it is easy to cause a large-scale epidemic and seriously threaten people's health and life safety. Novel coronavirus (2019-nCoV or SARS-CoV-2) infection causes severe pneumonia. 2019-nCoV virus can be transmitted through droplets and contact, and there is a risk of person-to-person transmission and infection among medical staff. There is also a risk of community transmission, and the virus has the possibility of mutation. At present, there are no specific prevention and treatment methods for diseases caused by new coronavirus.

2019-nCoV coronavirus belongs to the genus Coronavirus of the Coronaviridae, and is a single-stranded positive sense RNA virus with an envelope. Similar to other known coronaviruses, the 2019-nCoV coronavirus also completes the proliferation of progeny viruses through several processes such as adsorption, penetration, decapsidation, biosynthesis, and assembly and release of progeny viruses. The 2019-nCoV coronavirus infection of the host cell starts from the spike glycoprotein on the surface of the virus envelope binds to the receptor on the surface of the host cell, and then membrane fusion occurs. The virus enters the host cell and releases the viral genetic material, single-stranded positive sense RNA, under the action of organelles such as cell lysosomes, which translates and produces polyproteins under the action of protein synthesis elements such as mitochondria and ribosomes of the host cell as well as essential raw materials, etc.

Afterwards, the two essential cysteine proteases of 2019-nCoV coronavirus: papain-like protease ($PL^{pro}$) and 3C-like protease ($3CL^{pro}$), cleave and process the polyprotein precursors at specific sites to produce multiple nonstructural proteins important for the viral life cycle. In the presence of these non-structural proteins, viral RNA replicates the progeny viral nucleic acid material and translates the required structural proteins in large quantities to complete the assembly and release of the progeny viruses. Any link or key enzyme in the life cycle of cells infected by the 2019-nCoV coronavirus can be used as a research target for antiviral drugs, such as cysteine proteases $PL^{pro}$ and $3CL^{pro}$ that hydrolyze and cleave polyprotein precursors, and RNA polymerase that completes the replication of genetic material of progeny viruses.

3CL protease (3 chymotrypsin-like protease, $3CL^{pro}$), also known as main protease ($M^{pro}$), is a key protease in the process of hydrolysis of polyproteins pp1a and pp1ab after the coronavirus RNA is translated to produce multiple non-structural proteins. It is very important for virus replication and infection. Inhibiting the catalytic function of 3CL protease can effectively inhibit the cleavage of viral polyprotein precursors, block virus replication, thus inhibiting the generation of the progeny virus. $3CL^{pro}$ belongs to cysteine protease and is a key protease that catalyzes the proteolysis of single positive-stranded RNA viral precursor. It plays an important role in 2019-nCoV and other coronavirus replication activity. Therefore, $3CL^{pro}$ is currently recognized as an ideal target for the development of anti-coronavirus drugs.

Human cathepsin L belongs to cysteine proteases of the lysosomal papain—like protease family, and it has a variety of biological functions, and its use as a target has been widely used in the development of drugs against parasitic infections, such as Chagas disease caused by Trypanosome infection. Cathepsin L first exists in the form of inactive zymogen in the cell, and needs to be cut by itself in the acidic environment of the endosome or lysosome, or activated by other proteases to form a mature enzyme with catalytic activity. A large number of studies have reported that human cathepsin L is closely related to the occurrence of various tumors and also plays an important role in heart diseases. In addition, studies have also found that human cathepsin is also involved in pathogenic microorganisms infecting host cells. More and more evidences show that human cathepsin L can be used as a drug target for the research and development of anti-tumor, heart disease and anti-infective drugs. The SARS-CoV-2 spike protein (S protein) needs to be hydrolyzed and activated by the host protease to mediate the membrane fusion of the virus and the host cell to promote the virus to invade the host cell. According to the difference in the action stage of the host protease, the virus invasion pathway can be divided into type II Transmembrane serine protease (TMPRSSII) mediated surface membrane fusion pathway, human cathepsin L mediated endocytosis membrane fusion pathway, therefore, these host proteases can be used as entry inhibitors for coronavirus invasion into host cells. Inhibition of human cathepsin L can effectively prevent virus from invading host cells, so human cathepsin L inhibitor is an ideal target for anti-SARS-CoV-2 research and development, and is expected to solve the potential risks and problems of mutation resistance of antiviral drugs targeting virus.

Currently, there are no specific vaccines and antiviral drugs for severe pneumonia caused by 2019-nCoV coronavirus. These infectious diseases have seriously affected people's lives and health, and it is urgent to develop small molecule antiviral drugs with good effects. It is of great social significance to develop antiviral drugs with novel structure, low toxicity and high efficiency and independent intellectual property rights for 2019-nCoV coronavirus $3CL^{pro}$ and/or human cathepsin L to meet the clinical needs of patients infected with 2019-nCoV coronavirus at home and abroad.

In summary, there is an urgent need in the art to develop inhibitors for 2019-nCoV coronavirus 3CL protease and/or human cathepsin L for the treatment of pneumonia caused by novel coronavirus infection.

SUMMARY OF THE INVENTION

The object of the present invention is to provide a new use of ketoamide compound.

Specifically, the present invention provides the use of the ketoamide compound represented by the formula A as a 2019 novel coronavirus (2019-nCov) 3CL protease inhibitor and/or human cathepsin L inhibitor in the manufacture of a medicament for treating and/or preventing and alleviating respiratory tract infection, pneumonia and other related diseases caused by 2019 novel coronavirus infection.

In the first aspect of the present invention, it provides a use of a ketoamide compound represented by formula (A), or a pharmaceutically acceptable salt, enantiomer, diastereomer or racemate thereof, for the manufacture of (a) a 3CL protease inhibitor and/or a human cathepsin L inhibitor against 2019 novel coronavirus (2019-nCov); and (b) a medicament for treating and/or preventing and alleviating related diseases caused by 2019 novel coronavirus (2019-nCov) infection:

formula (A)

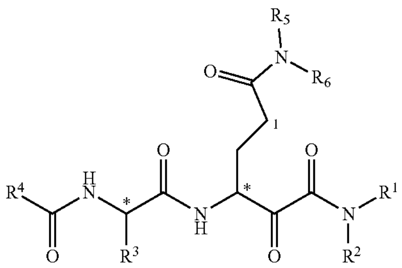

wherein,

* indicates that the stereochemical isomerism of carbon atoms is independently R and/or S respectively;

$R^1$ and $R^2$ are each independently selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 cycloalkyl C1-C10 alkylene, substituted or unsubstituted C3-C10 heterocycloalkyl, substituted or unsubstituted C3-C10 heterocycloalkyl C1-C10 alkylene, substituted or unsubstituted C6-C20 aryl, substituted or unsubstituted C3-C20 heteroaryl, substituted or unsubstituted C6-C20 aryl C1-C10 alkylene, substituted or unsubstituted C3-C20 heteroaryl C1-C10 alkylene, substituted or unsubstituted C6-C20 aryl C2-C10 alkenylene, substituted or unsubstituted C3-C20 heteroaryl C2-C10 alkenylene, acyl and sulfonyl $R^3$ is selected from the group consisting of substituted or unsubstituted C1-C10 alkyl, substituted or unsubstituted C2-C10 alkenyl, substituted or unsubstituted C2-C10 alkynyl, substituted or unsubstituted C3-C8 cycloalkyl, substituted or unsubstituted C3-C8 cycloalkyl C1-C10 alkylene, substituted or unsubstituted C3-C8 heterocycloalkyl, substituted or unsubstituted C3-C8 heterocycloalkyl C1-C10 alkylene, substituted or unsubstituted C6-C20 aryl, substituted or unsubstituted C3-C20 heteroaryl, substituted or unsubstituted C6-C20 aryl C1-C10 alkylene, substituted or unsubstituted C3-C20 heteroaryl C1-C10 alkylene, substituted or unsubstituted C6-C20 aryl C2-C6 alkenylene, substituted or unsubstituted C3-C20 heteroaryl C2-C6 alkenylene, substituted or unsubstituted C6-C20 aryl C2-C6 alkynylene, and substituted or unsubstituted C3-C20 heteroaryl C2-C6 alkynylene;

$R^4$ is selected from the group consisting of substituted or unsubstituted C1-C10 alkyl, substituted or unsubstituted C2-C10 alkenyl, substituted or unsubstituted C2-C10 alkynyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C6-C20 aryl C2-C6 alkynylene, substituted or unsubstituted C3-C20 heteroaryl C1-C9 alkylene, substituted or unsubstituted C3-C20 heteroaryl C2-C9 alkenylene, and substituted or unsubstituted C3-C20 heteroaryl C2-C9 alkynylene;

$R^6$ is selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C3-C20 heteroaryl C1-C9 alkylene, substituted or unsubstituted C3-C20 heteroaryl C2-C9 alkenylene, acyl and sulfonyl;

when $—NR^5$ and its adjacent $—(C{=}O)—CH_2—$ form a ring, $R^5$ is $—(CH_2)_n—$, n is 2 or 3;

when $—NR^5$ does not form a ring with its adjacent $—(C{=}O)—CH_2—$, $R^5$ is selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C3-C20 heteroaryl C1-C9 alkylene, substituted or unsubstituted C3-C20 heteroaryl C2-C9 alkenylene, acyl and sulfonyl;

wherein, in $R^1$, $R^2$, $R^3$, $R^4$, $R^5$ and $R^6$, the "substituted" each independently refers to being substituted by 1, 2, 3 or 4 substituents selected from the group consisting of halogen, hydroxyl, mercapto, nitro, cyano, amino, imino, tertiary amino, azido, C1-C8 alkyl, halogenated C1-C8 alkyl, C1-C8 alkoxy, halogenated C1-C8 alkoxy, C1-C6 alkylcarbonyl, C1-C6 alkylthio, C1-C8 alkoxycarbonyl, and trifluoromethyl; the heterocycloalkyl and the heteroaryl each independently comprise 1, 2, 3 or 4 heteroatoms selected from N, O, and S.

In another preferred embodiment, when $R^6$ is H, $—NR^5$ (or $—NR^5R^6$) and its adjacent $—(C{=}O)—CH_2—$ can form a ring (e.g., a 5-6-membered heterocycle) or they do not form a ring. The 5-6 membered heterocycle contains one N heteroatom on the ring, and the remaining ring atoms are C.

In another preferred embodiment, when $—NR^5$ and its adjacent $—(C{=}O)—CH_2—$ form a ring, $R^5$ is substituted or unsubstituted $—(CH_2)_n—$, n is 2 or 3, wherein the "substituted" each independently refers to being substituted by 1, 2, 3 or 4 substituents selected from the group consisting of halogen, hydroxyl, C1-C8 alkyl, C3-C8 cycloalkyl, halogenated C1-C8 alkyl, C1-C8 alkoxy, halogenated C1-C8 alkoxy, and trifluoromethyl.

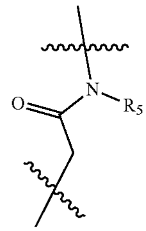

In another preferred embodiment, the moiety is a substituted or unsubstituted 5-6-membered heterocyclyl, wherein the "substituted" each independently refers to being substituted by 1, 2, 3 or 4 substituents selected from the group consisting of halogen, hydroxyl, mercapto, nitro, cyano, oxo, amino, imino, tertiary amino, azido, C1-C8 alkyl, C3-C8 cycloalkyl, halogenated C1-C8 alkyl, C1-C8 alkoxy, halogenated C1-C8 alkoxy, C1-C6 alkylcarbonyl, C1-C6 alkylthio, C1-C8 alkoxycarbonyl, and trifluoromethyl; preferably the

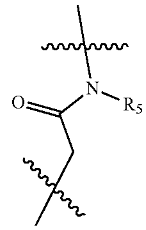

moiety is

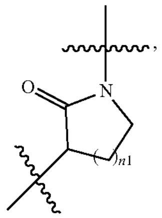

wherein n1 is 1 or 2.

In another preferred embodiment, the related diseases caused by 2019 novel coronavirus infection is selected from the group consisting of respiratory infections, pneumonia and complications thereof, or a combination thereof.

In another preferred embodiment, $R^1$ and $R^2$ are each independently selected from the group consisting of hydrogen, deuterium, tritium, amino, hydroxyl, substituted or unsubstituted C1-C6 alkyl, substituted or unsubstituted C3-C8 cycloalkyl, substituted or unsubstituted C3-C8 cycloalkyl C1-C5 alkylene, substituted or unsubstituted C3-C10 heterocycloalkyl, substituted or unsubstituted C3-C10 heterocycloalkyl C1-C5 alkylene, substituted or unsubstituted C6-C14 aryl, substituted or unsubstituted C3-C10 heteroaryl, substituted or unsubstituted C6-C14 aryl C1-C5 alkylene, substituted or unsubstituted C3-C10 heteroaryl C1-C5 alkylene, substituted or unsubstituted C6-C10 aryl C2-C5 alkenylene, substituted or unsubstituted C3-C10 heteroaryl C2-C5 alkenylene, acyl, and sulfonyl;

$R^3$ is selected from the group consisting of substituted or unsubstituted C1-C6 alkyl, substituted or unsubstituted C2-C6 alkenyl, substituted or unsubstituted C2-C6 alkynyl, substituted or unsubstituted C3-C8 cycloalkyl, substituted or unsubstituted C3-C8 cycloalkyl C1-C5 alkylene, substituted or unsubstituted C3-C8 heterocycloalkyl, substituted or unsubstituted C3-C8 heterocycloalkyl C1-C5 alkylene, substituted or unsubstituted C6-C10 aryl, substituted or unsubstituted C3-C10 heteroaryl, substituted or unsubstituted C6-C10 aryl C1-C5 alkylene, substituted or unsubstituted C3-C10 heteroaryl C1-C5 alkylene, substituted or unsubstituted C6-C10 aryl C2-C4 alkenylene, substituted or unsubstituted C3-C10 heteroaryl C2-C4 alkenylene, substituted or unsubstituted C6-C10 aryl C2-C4 alkynylene, and substituted or unsubstituted C3-C10 heteroaryl C2-C4 alkynylene;

wherein, in $R^1$, $R^2$ and $R^3$, the "substituted" each independently refers to being substituted by 1, 2 or 3 substituents selected from the group consisting of halogen, hydroxy, C1-C6 alkyl, halogenated C1-C6 alkyl, C1-C6 alkoxy, halogenated C1-C6 alkoxy, C1-C4 alkylcarbonyl, C1-C4 alkylthio, C1-C6 alkoxycarbonyl, and trifluoromethyl; the heterocycloalkyl and the heteroaryl each independently contain 1 or 2 heteroatoms selected from N, O and S.

In another preferred embodiment, the compound is a compound represented by formula AA, formula AA

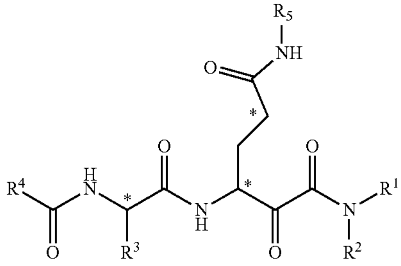

wherein, $R^1$, $R^2$, $R^3$, $R^4$, $R^5$ and n are as defined above;

* indicates that the stereochemical isomerism of carbon atoms is independently R and/or S respectively.

In another preferred embodiment, $R^4$ is selected from the group consisting of 9-10-membered heteroaromatic ring containing 1, 2 or 3 heteroatoms selected from N, O and S, and 5-6-membered heteroaromatic ring containing 1, 2 or 3 heteroatoms selected from N, O and S; the above groups are substituted or unsubstituted; wherein, the "substituted" refers to the hydrogen atom on the group is substituted by 1, 2, 3 or 4 substituents selected from the group consisting of halogen, hydroxyl, C1-C6 alkyl, halogenated C1-C6 alkyl, C3-C6 cycloalkyl, halogenated C3-C6 cycloalkyl, C1-C6 alkoxy, halogenated C1-C6 alkoxy, C1-C6 alkylthio and halogenated C1-C6 alkylthio.

In another preferred embodiment, $R^6$ is selected from the group consisting of hydrogen, deuterium, tritium, amino, hydroxyl, substituted or unsubstituted C1-C6 alkyl, substituted or unsubstituted C3-C8 cycloalkyl, and substituted or unsubstituted C3-C10 heterocycloalkyl.

In another preferred embodiment, the heteroaryl is a 5-, 6-, 7-, 8-, 9- or 10-membered saturated or partially saturated heteroaromatic ring.

In another preferred embodiment, the heterocycloalkyl is a 5-, 6-, 7-, 8-, 9- or 10-membered unsaturated heterocyclic ring.

In another preferred embodiment, $R^4$ is selected from the group consisting of substituted or unsubstituted quinoxalinyl, substituted or unsubstituted quinazolinyl, substituted or unsubstituted cinnolinyl, substituted or unsubstituted indolyl, substituted or unsubstituted isoindolyl, substituted or unsubstituted 1,3-benzodioxolyl, substituted or unsubstituted benzimidazolyl, substituted or unsubstituted indazolyl, substituted or unsubstituted imidazole[1,2-A]pyridyl, substituted or unsubstituted imidazole[1,5-A]pyridyl, substituted or unsubstituted pyrazolyl, substituted or unsubstituted imidazolyl, substituted or unsubstituted thiazolyl, substituted or unsubstituted oxazolyl, substituted or unsubstituted isoxazolyl, substituted or unsubstituted 1,2,3-triazolyl, substituted or unsubstituted 1,2-thiadiazolyl, substituted or unsubstituted 1,2,4-triazinyl, substituted or unsubstituted pyridyl, substituted or unsubstituted pyrrolyl, substituted or unsubstituted pyrazinyl, substituted or unsubstituted pyrimidinyl, substituted or unsubstituted 3,8a dihydro-2H-benzopyranyl, substituted or unsubstituted benzopyranyl, substituted or unsubstituted quinolinyl, substituted or unsubstituted isoquinolinyl, substituted or unsubstituted benzoxazolyl, substituted or unsubstituted benzothiazolyl, substituted or unsubstituted benzothienyl, and substituted or unsubstituted benzofuranyl;

wherein, the substituted means that the hydrogen atom on the group is substituted by 1, 2 or 3 substituents selected from the group consisting of F, Cl, Br, I, hydroxyl, C1-C6 alkyl, halogenated C1-C6 alkyl, C3-C6 cycloalkyl, halogenated C3-C6 cycloalkyl, C1-C6 alkoxy, halogenated C1-C6 alkoxy, C1-C6 alkylthio, halogenated C1-C6 alkylthio.

As used herein, $R^4$ is imidazole [1,2-A]pyridine corresponding to the compounds numbered as A156 to A161 of the present invention.

As used herein, "imidazole[1,2-A]pyridine", "imidazole [1,2-a]pyridine", "imidazo[1,2-A]pyridine" and "imidazo[1, 2-a]pyridine" can be used interchangeably.

As used herein, "imidazole[1,5-A]pyridine", "imidazole [1,5-a]pyridine", "imidazo[1,5-A]pyridine" and "imidazo[1, 5-a]pyridine" can be used interchangeably.

As used herein, $R^4$ is 3,8a dihydro-2H-benzopyran corresponding to the compounds numbered as A132 to A137 of the present invention.

In another preferred embodiment, when $R^6$ is H, $—NR^5$ and its adjacent $—(C{=}O)—CH_2—$ can form a ring (e.g., a 5-6-membered heterocycle) or they do not form a ring.

In another preferred embodiment, when $—NR^5$ (or $—NR^5R^6$) and its adjacent $—(C{=}O)—CH_2—$ form a ring, $R^5$ is $—(CH_2)_n—$, n is 3;

when $—NR^5$ (or $—NR^5R^6$) and its adjacent $—(C{=}O)—CH_2—$ do not form a ring, $R^5$ is selected from the group consisting of hydrogen, deuterium, tritium, hydroxyl, substituted or unsubstituted C1-C6 alkyl, substituted or unsubstituted C3-C8 cycloalkyl, substituted or unsubstituted C3-C8 heterocycloalkyl, substituted or unsubstituted C6-C10 aryl, substituted or unsubstituted C3-C10 heteroaryl, substituted or unsubstituted C6-C10 aryl C1-C4 alkylene, substituted or unsubstituted C6-C10 aryl C2-C4 alkenylene, substituted or unsubstituted C3-C10 heteroaryl C1-C4 alkylene, and substituted or unsubstituted C3-C10 heteroaryl C2-C4 alkenylene;

wherein, the "substituted" each independently refers to being substituted by 1, 2 or 3 substituents selected from the group consisting of F, Cl, Br, I, hydroxyl, C1-C6 alkyl, C1-C6 alkoxy, and C1-C6 alkylthio; the heterocycloalkyl and the heteroaryl each independently contain 1, 2 or 3 heteroatoms selected from N, O, and S.

In another preferred embodiment, R1, R2, R3, R4, R5 and R6 are each independently a corresponding group of the specific compounds (A1-A310) in the Examples.

In another preferred embodiment, the compound of formula (A) is selected from the group consisting of

| number | structure | name |
|---|---|---|
| A1 | 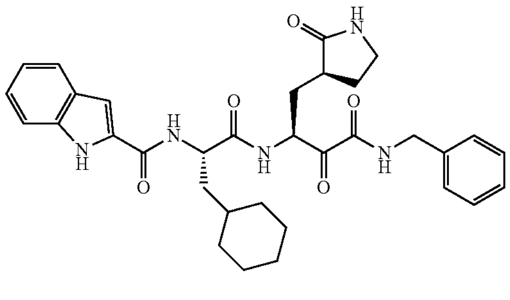 [SMILES: O=C(NCc1ccccc1)C(=O)[C@H](C[C@@H]1CCNC1=O)NC(=O)[C@H](CC1CCCCC1)NC(=O)c1cc2ccccc2[nH]1] | N-((S)-1-(((S)-4-(benzylamino)-3,4-dione-1-((S)-2-oxopyrrolidin-3-yl)but-2-yl)amino)-3-cyclohexyl-1-oxopropan-2-yl)-1H-indole-2-carboxamide |
| A2 | 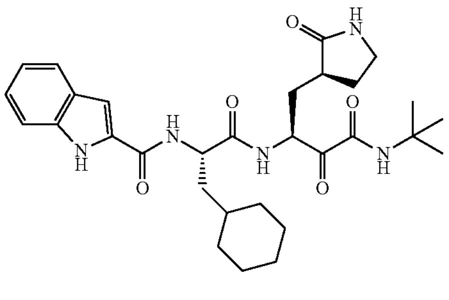 [SMILES: CC(C)(C)NC(=O)C(=O)[C@H](C[C@@H]1CCNC1=O)NC(=O)[C@H](CC1CCCCC1)NC(=O)c1cc2ccccc2[nH]1] | N-((S)-1-(((S)-4-(tert-butylamino)-3,4-dione-1-((S)-2-oxopyrrolidin-3-yl)but-2-yl)amino)-3-cyclohexyl-1-oxopropan-2-yl)-1H-indole-2-carboxamide |

-continued

| number | structure | name |
|---|---|---|
| A3 | 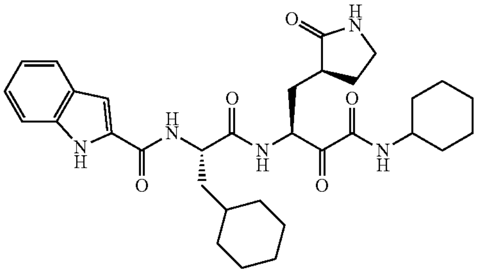 [SMILES: O=C(NC1CCCCC1)C(=O)[C@H](C[C@@H]1CCNC1=O)NC(=O)[C@H](CC1CCCCC1)NC(=O)c1cc2ccccc2[nH]1] | N-((S)-3-cyclohexyl-1-(((S)-4-(cyclohexylamino)-3,4-dione-1-((S)-2-oxopyrrolidin-3-yl)but-2-yl) amino)-3-cyclohexyl-1-oxopropan-2-yl)-1H-indole-2-carboxamide |
| A4 | 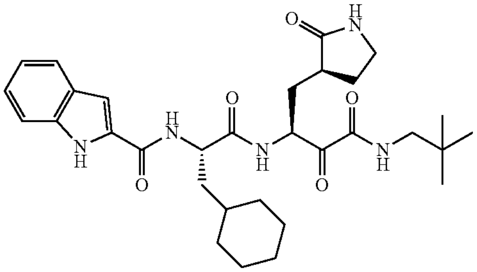 [SMILES: CC(C)(C)CNC(=O)C(=O)[C@H](C[C@@H]1CCNC1=O)NC(=O)[C@H](CC1CCCCC1)NC(=O)c1cc2ccccc2[nH]1] | N-((S)-3-cyclohexyl-1-(((S)-4-(neopentylamino)-3,4-dione-1-((S)-2-oxopyrrolidin-3-yl)but-2-yl)amino)-3-cyclohexyl-1-oxopropan-2-yl)-1H-indole-2-carboxamide |
| A5 | 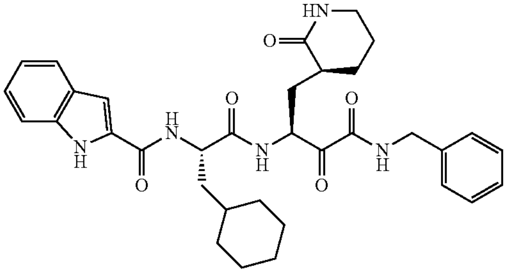 | N-((S)-1-(((S)-4-(benzylamino)-3,4-dione-1-((S)-2-oxopiperidin-3-yl)but-2-yl)amino)-3-cyclohexyl-1-oxopropan-2-yl)-1H-indole-2-carboxamide |
| A6 | 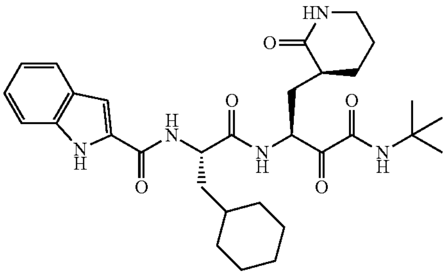 [SMILES: CC(C)(C)NC(=O)C(=O)[C@H](C[C@@H]1CCCNC1=O)NC(=O)[C@H](CC1CCCCC1)NC(=O)c1cc2ccccc2[nH]1] | N-((S)-1-(((S)-4-(tert-butylamino)-3,4-dione-1-((S)-2-oxopiperidin-3-yl)but-2-yl)amino)-3-cyclohexyl-1-oxopropan-2-yl)-1H-indole-2-carboxamide |
| A7 | 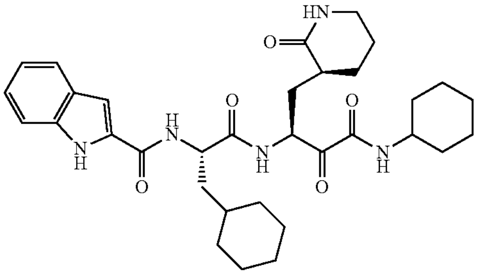 [SMILES: O=C(NC1CCCCC1)C(=O)[C@H](C[C@@H]1CCCNC1=O)NC(=O)[C@H](CC1CCCCC1)NC(=O)c1cc2ccccc2[nH]1] | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopropan-2-yl)-1H-indole-2-carboxamide |

-continued

| number | structure | name |
|---|---|---|
| A8 | 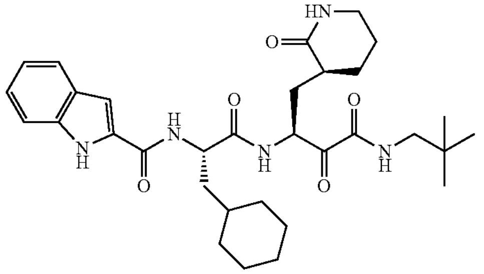 [SMILES: CC(C)(C)CNC(=O)C(=O)[C@H](C[C@@H]1CCCNC1=O)NC(=O)[C@H](CC1CCCCC1)NC(=O)c1cc2ccccc2[nH]1] | N-((S)-3-cyclohexyl-1-(((S)-4-(neopentylamino)-3,4-dione-1-((S)-2-oxopiperidin-3-yl)but-2-yl)amino)-3-cyclohexyl-1-oxopropan-2-yl)-1H-indole-2-carboxamide |
| A9 | 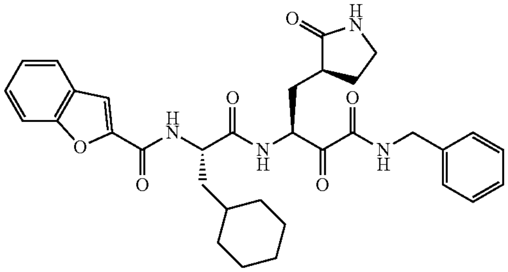 [SMILES: O=C(NCc1ccccc1)C(=O)[C@H](C[C@@H]1CCNC1=O)NC(=O)[C@H](CC1CCCCC1)NC(=O)c1cc2ccccc2o1] | N-((S)-l-(((S)-4-(benzylamino)-3,4-dione-1-((S)-2-oxopyrrolidin-3-yl)but-2-yl)amino)-3-cyclohexyl-1-oxopropan-2-yl)-benzofuran-2-carboxamide |
| A10 | 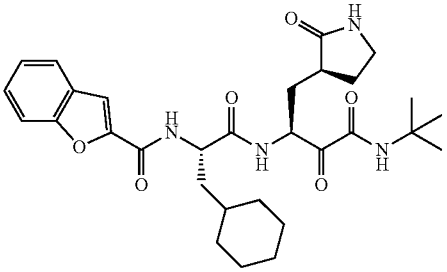 [SMILES: CC(C)(C)NC(=O)C(=O)[C@H](C[C@@H]1CCNC1=O)NC(=O)[C@H](CC1CCCCC1)NC(=O)c1cc2ccccc2o1] | N-((S)-1-(((S)-4-(tert-butylamino)-3,4-dione-1-((S)-2-oxopyrrolidin-3-yl)but-2-yl)amino)-3-cyclohexyl-1-oxopropan-2-yl)-benzofuran-2-carboxamide |
| A11 | 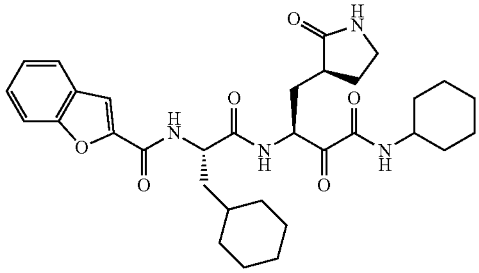 [SMILES: O=C(NC1CCCCC1)C(=O)[C@H](C[C@@H]1CCNC1=O)NC(=O)[C@H](CC1CCCCC1)NC(=O)c1cc2ccccc2o1] | N-((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopropan-2-yl)-benzofuran-2-carboxamide |
| A12 | 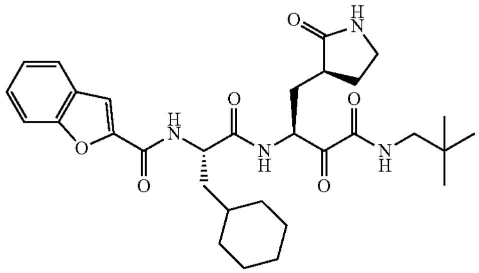 [SMILES: CC(C)(C)CNC(=O)C(=O)[C@H](C[C@@H]1CCNC1=O)NC(=O)[C@H](CC1CCCCC1)NC(=O)c1cc2ccccc2o1] | N-((S)-3-cyclohexyl-1-(((S)-4-(neopentylamino)-3,4-dione-1-((S)-2-oxopyrrolidin-3-yl)but-2-yl)amino)-3-cyclohexyl-1-oxopropan-2-yl)-benzofuran-2-carboxamide |

-continued

| number | structure | name |
|---|---|---|
| A13 | 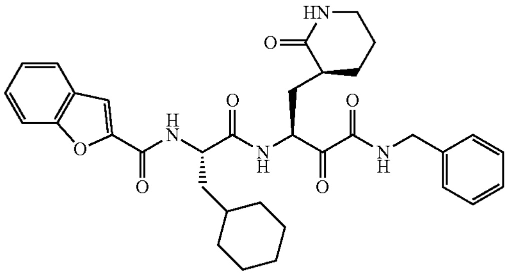 [SMILES: O=C(NCc1ccccc1)C(=O)[C@H](C[C@@H]1CCCNC1=O)NC(=O)[C@H](CC1CCCCC1)NC(=O)c1cc2ccccc2o1] | N-((S)-l-(((S)-4-(benzylamino)-3,4-dione-1-((S)-2-oxopiperidin-3-yl)but-2-yl)amino)-3-cyclohexyl-1-oxopropan-2-yl)-benzofuran-2-carboxamide |
| A14 | 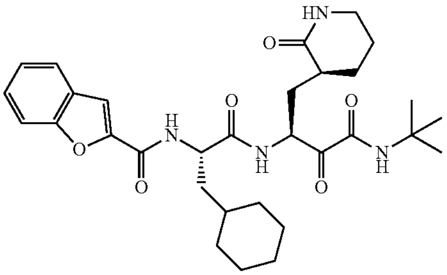 [SMILES: CC(C)(C)NC(=O)C(=O)[C@H](C[C@@H]1CCCNC1=O)NC(=O)[C@H](CC1CCCCC1)NC(=O)c1cc2ccccc2o1] | N-((S)-1-(((S)-4-(tert-butylamino)-3,4-dione-1-((S)-2-oxopiperidin-3-yl)but-2-yl)amino)-3-cyclohexyl-1-oxopropan-2-yl)-benzofuran-2-carboxamide |
| A15 | 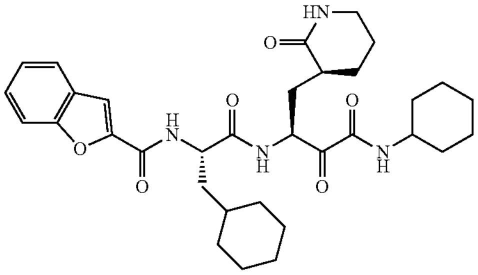 | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopropan-2-yl)-benzofuran-2-carboxamide |
| A16 | 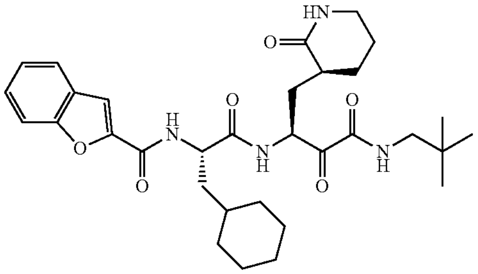 [SMILES: CC(C)(C)CNC(=O)C(=O)[C@H](C[C@@H]1CCCNC1=O)NC(=O)[C@H](CC1CCCCC1)NC(=O)c1cc2ccccc2o1] | N-((S)-3-cyclohexyl-1-(((S)-4-(neopentylamino)-3,4-dione-1-((S)-2-oxopiperidin-3-yl)but-2-yl)amino)-3-cyclohexyl-1-oxopropan-2-yl)-benzofuran-2-carboxamide |
| A17 | 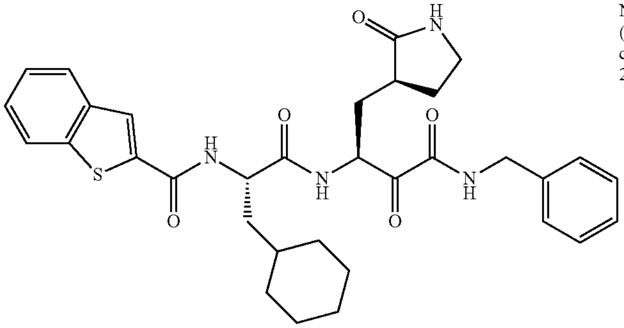 | N-((S)-1-(((S)-4-(benzylamino)-3,4-dione-1-((S)-2-oxopyrrolidin-3-yl)but-2-yl)amino)-3-cyclohexyl-1-oxopropan-2-yl)-benzothiophene-2-carboxamide |

-continued

| number | structure | name |
|---|---|---|
| A18 | 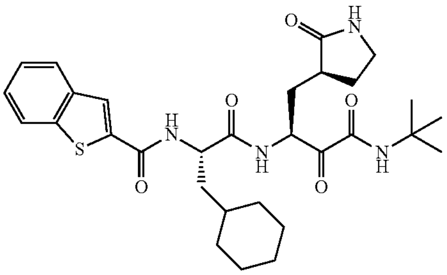 | N-((S)-1-(((S)-4-(tert-butylamino)-3,4-dione-1-((S)-2-oxopyrrolidin-3-yl)but-2-yl)amino)-3-cyclohexyl-1-oxopropan-2-yl)-benzothiophene-2-carboxamide |
| A19 | 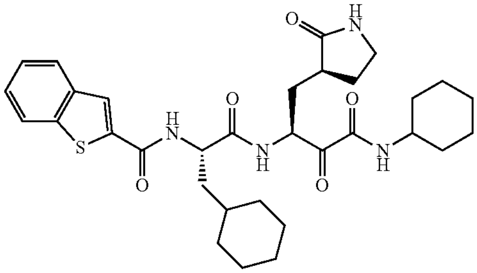 [SMILES: O=C(NC1CCCCC1)C(=O)[C@H](C[C@@H]1CCNC1=O)NC(=O)[C@H](CC1CCCCC1)NC(=O)c1cc2ccccc2s1] | N-((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopropan-2-yl)-benzothiophene-2-carboxamide |
| A20 | 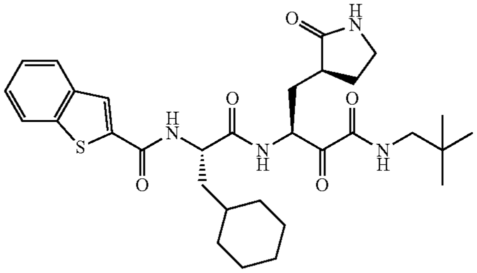 [SMILES: CC(C)(C)CNC(=O)C(=O)[C@H](C[C@@H]1CCNC1=O)NC(=O)[C@H](CC1CCCCC1)NC(=O)c1cc2ccccc2s1] | N-((S)-3-cyclohexyl-1-(((S)-4-(neopentylamino)-3,4-dione-1-((S)-2-oxopyrrolidin-3-yl)but-2-yl)amino)-3-cyclohexyl-1-oxopropan-2-yl)-benzothiophene-2-carboxamide |
| A21 | 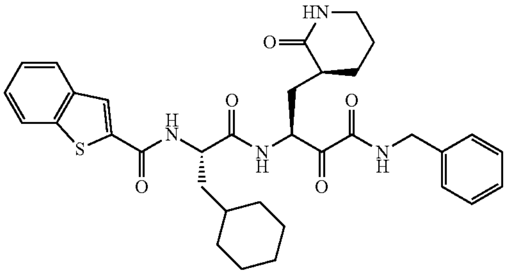 | N-((S)-l-(((S)-4-(benzylamino)-3,4-dione-1-((S)-2-oxopiperidin-3-yl)but-2-yl)amino)-3-cyclohexyl-1-oxopropan-2-yl)-benzothiophene-2-carboxamide |
| A22 | 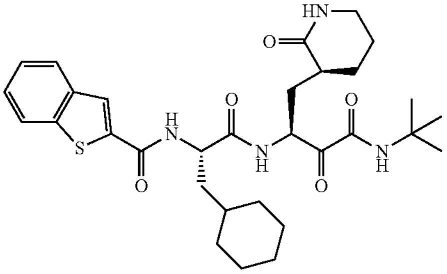 | N-((S)-1-(((S)-4-(tert-butylamino)-3,4-dione-1-((S)-2-oxopiperidin-3-yl)but-2-yl)amino)-3-cyclohexyl-1-oxopropan-2-yl)-benzothiophene-2-carboxamide |

-continued

| number | structure | name |
|---|---|---|
| A23 | 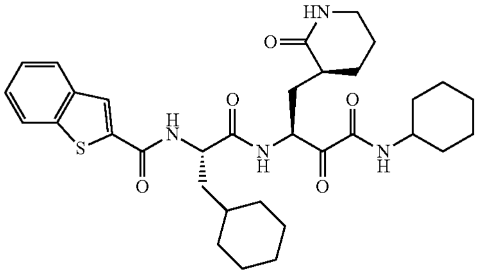 [SMILES: O=C(NC1CCCCC1)C(=O)[C@H](C[C@@H]1CCCNC1=O)NC(=O)[C@H](CC1CCCCC1)NC(=O)c1cc2ccccc2s1] | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopropan-2-yl)-benzothiophene-2-carboxamide |
| A24 | 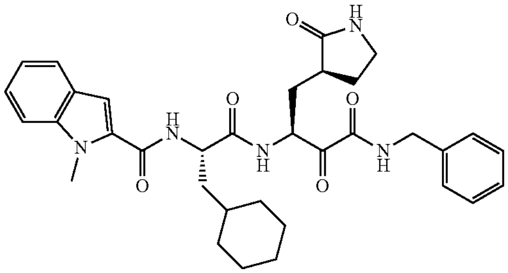 [SMILES: Cn1c(C(=O)N[C@@H](CC2CCCCC2)C(=O)N[C@@H](C[C@@H]2CCNC2=O)C(=O)C(=O)NCc2ccccc2)cc2ccccc21] | N-((S)-1-(((S)-4-(benzylamino)-3,4-dione-1-((S)-2-oxopyrrolidin-3-yl)but-2-yl)amino)-3-cyclohexyl-1-oxopropan-2-yl)-1-methyl-1H-indole-2-carboxamide |
| A25 | 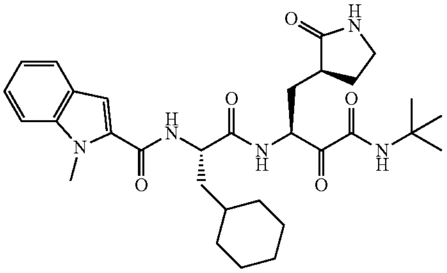 [SMILES: Cn1c(C(=O)N[C@@H](CC2CCCCC2)C(=O)N[C@@H](C[C@@H]2CCNC2=O)C(=O)C(=O)NC(C)(C)C)cc2ccccc21] | N-((S)-l-(((S)-4-(tert-butylamino)-3,4-dione-1-((S)-2-oxopyrrolidin-3-yl)but-2-yl)amino)-3-cyclohexyl-1-oxopropan-2-yl)-1-methyl-1H-indole-2-carboxamide |
| A26 | 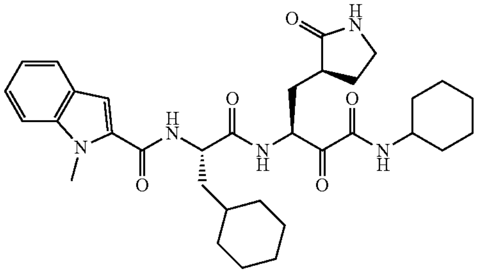 [SMILES: Cn1c(C(=O)N[C@@H](CC2CCCCC2)C(=O)N[C@@H](C[C@@H]2CCNC2=O)C(=O)C(=O)NC2CCCCC2)cc2ccccc21] | N-((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopropan-2-yl)-1-methyl-1H-indole-2-carboxamide |
| A27 | 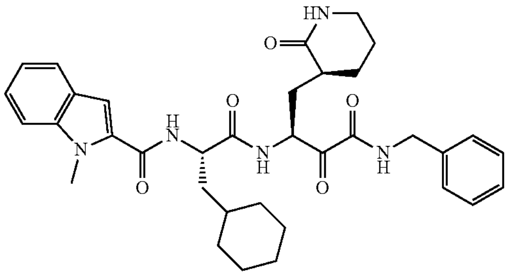 [SMILES: Cn1c(C(=O)N[C@@H](CC2CCCCC2)C(=O)N[C@@H](C[C@@H]2CCCNC2=O)C(=O)C(=O)NCc2ccccc2)cc2ccccc21] | N-((S)-l-(((S)-4-(benzylamino)-3,4-dione-1-((S)-2-oxopiperidin-3-yl)but-2-yl)amino)-3-cyclohexyl-1-oxopropan-2-yl)-1-methyl-1H-indole-2-carboxamide |

-continued

| number | structure | name |
|---|---|---|
| A28 | 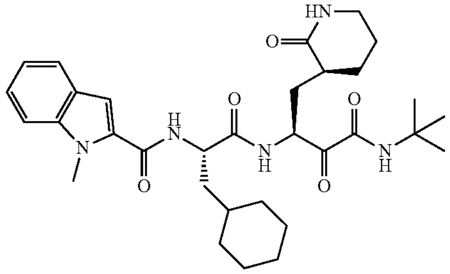 [SMILES: Cn1c(C(=O)N[C@@H](CC2CCCCC2)C(=O)N[C@@H](C[C@@H]2CCCNC2=O)C(=O)C(=O)NC(C)(C)C)cc2ccccc21] | N-((S)-1-(((S)-4-(tert-butylamino)-3,4-dione-1-((S)-2-oxopiperidin-3-yl)but-2-yl)amino)-3-cyclohexyl-1-oxopropan-2-yl)-1-methyl-1H-indole-2-carboxamide |
| A29 | 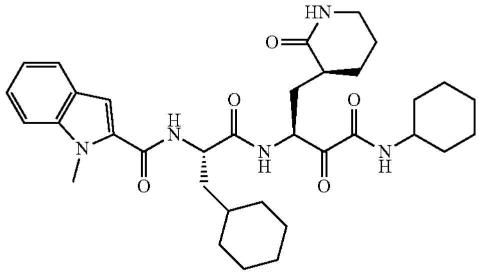 [SMILES: Cn1c(C(=O)N[C@@H](CC2CCCCC2)C(=O)N[C@@H](C[C@@H]2CCCNC2=O)C(=O)C(=O)NC2CCCCC2)cc2ccccc21] | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopropan-2-yl)-1-methyl-1H-indole-2-carboxamide |
| A30 | 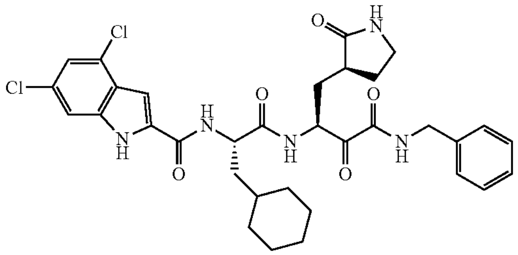 [SMILES: O=C(NCc1ccccc1)C(=O)[C@H](C[C@@H]1CCNC1=O)NC(=O)[C@H](CC1CCCCC1)NC(=O)c1cc2c(Cl)cc(Cl)cc2[nH]1] | N-((S)-1-(((S)-4-(benzylamino)-3,4-dione-1-((S)-2-oxopyrrolidin-3-yl)but-2-yl)amino)-3-cyclohexyl-1-oxopropan-2-yl)-4,6-dichloro-1H-indole-2-carboxamide |
| A31 | 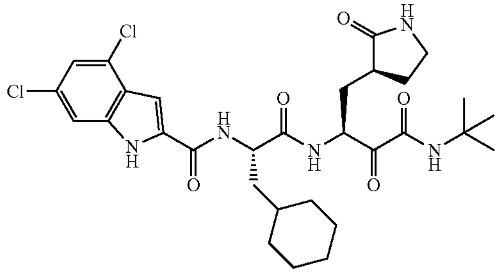 [SMILES: CC(C)(C)NC(=O)C(=O)[C@H](C[C@@H]1CCNC1=O)NC(=O)[C@H](CC1CCCCC1)NC(=O)c1cc2c(Cl)cc(Cl)cc2[nH]1] | N-((S)-1-(((S)-4-(tert-butylamino)-3,4-dione-1-((S)-2-oxopyrrolidin-3-yl)but-2-yl)amino)-3-cyclohexyl-1-oxopropan-2-yl)-4,6-dichloro-1H-indole-2-carboxamide |
| A32 | 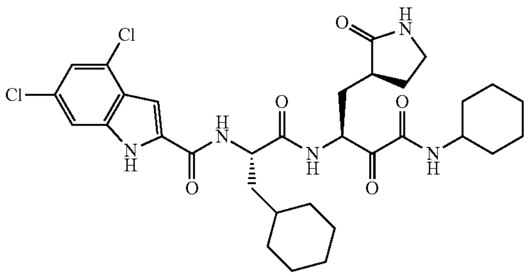 [SMILES: O=C(NC1CCCCC1)C(=O)[C@H](C[C@@H]1CCNC1=O)NC(=O)[C@H](CC1CCCCC1)NC(=O)c1cc2c(Cl)cc(Cl)cc2[nH]1] | N-((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopropan-2-yl)-4,6-dichloro-1H-indole-2-carboxamide |

-continued

| number | structure | name |
|---|---|---|
| A33 | 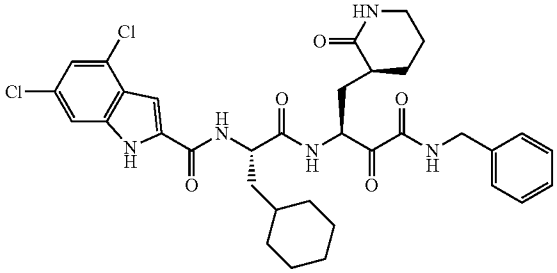 [SMILES: O=C(NCc1ccccc1)C(=O)[C@H](C[C@@H]1CCCNC1=O)NC(=O)[C@H](CC1CCCCC1)NC(=O)c1cc2c(Cl)cc(Cl)cc2[nH]1] | N-((S)-1-(((S)-4-(benzylamino)-3,4-dione-1-((S)-2-oxopiperidin-3-yl)but-2-yl)amino)-3-cyclohexyl-1-oxopropan-2-yl)-4,6-dichloro-1H-indole-2-carboxamide |
| A34 | 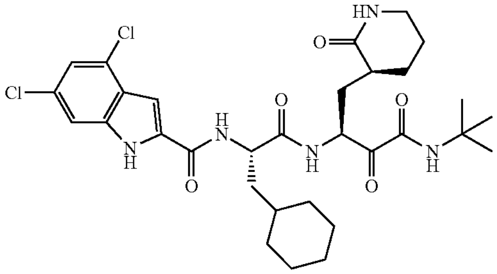 [SMILES: CC(C)(C)NC(=O)C(=O)[C@H](C[C@@H]1CCCNC1=O)NC(=O)[C@H](CC1CCCCC1)NC(=O)c1cc2c(Cl)cc(Cl)cc2[nH]1] | N-((S)-1-(((S)-4-(tert-butylamino)-3,4-dione-1-((S)-2-oxopiperidin-3-yl)but-2-yl)amino)-3-cyclohexyl-1-oxopropan-2-yl)-4,6-dichloro-1H-indole-2-carboxamide |
| A35 | 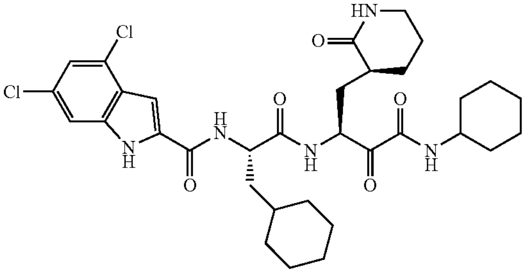 [SMILES: O=C(NC1CCCCC1)C(=O)[C@H](C[C@@H]1CCCNC1=O)NC(=O)[C@H](CC1CCCCC1)NC(=O)c1cc2c(Cl)cc(Cl)cc2[nH]1] | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopropan-2-yl)-4,6-dichloro-1H-indole-2-carboxamide |
| A36 | 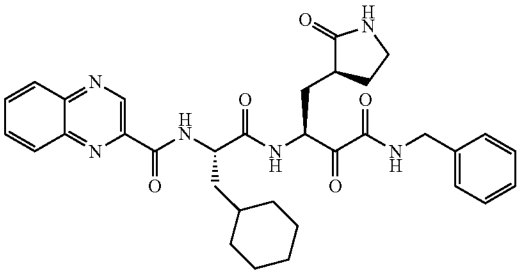 | N-((S)-1-(((S)-4-(benzylamino)-3,4-dione-1-((S)-2-oxopyrrolidin-3-yl)but-2-yl)amino)-3-cyclohexyl-1-oxopropan-2-yl)-quinoxaline-2-carboxamide |
| A37 | 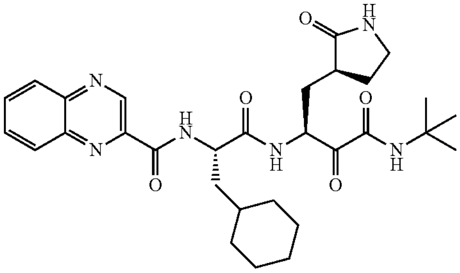 | N-((S)-1-(((S)-4-(tert-butylamino)-3,4-dione-1-((S)-2-oxopyrrolidin-3-yl)but-2-yl)amino)-3-cyclohexyl-1-oxopropan-2-yl)-quinoxaline-2-carboxamide |

-continued

| number | structure | name |
| --- | --- | --- |
| A38 | 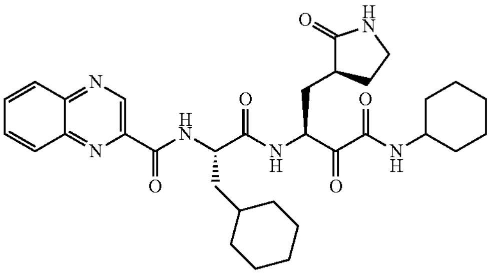 [SMILES: O=C(NC1CCCCC1)C(=O)[C@H](C[C@@H]1CCNC1=O)NC(=O)[C@H](CC1CCCCC1)NC(=O)c1cnc2ccccc2n1] | N-((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopropan-2-yl)-quinoxaline-2-carboxamide |
| A39 | 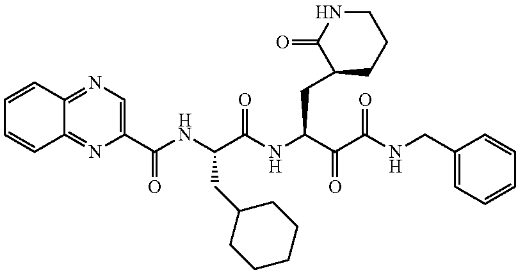 [SMILES: O=C(NCc1ccccc1)C(=O)[C@H](C[C@@H]1CCCNC1=O)NC(=O)[C@H](CC1CCCCC1)NC(=O)c1cnc2ccccc2n1] | N-((S)-l-(((S)-4-(benzylamino)-3,4-dione-1-((S)-2-oxopiperidin-3-yl)but-2-yl)amino)-3-cyclohexyl-1-oxopropan-2-yl)-quinoxaline-2-carboxamide |
| A40 | 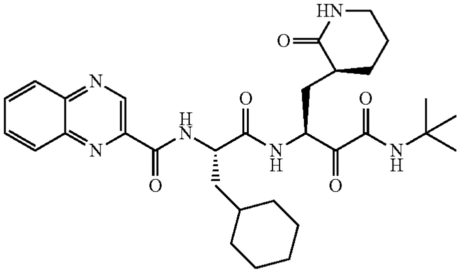 [SMILES: CC(C)(C)NC(=O)C(=O)[C@H](C[C@@H]1CCCNC1=O)NC(=O)[C@H](CC1CCCCC1)NC(=O)c1cnc2ccccc2n1] | N-((S)-1-(((S)-4-(tert-butylamino)-3,4-dione-1-((S)-2-oxopiperidin-3-yl)but-2-yl)amino)-3-cyclohexyl-1-oxopropan-2-yl)-quinoxaline-2-carboxamide |
| A41 | 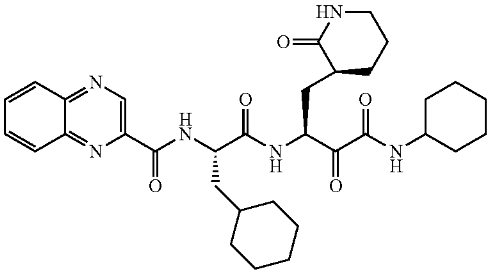 [SMILES: O=C(NC1CCCCC1)C(=O)[C@H](C[C@@H]1CCCNC1=O)NC(=O)[C@H](CC1CCCCC1)NC(=O)c1cnc2ccccc2n1] | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopropan-2-yl)-quinoxaline-2-carboxamide |
| A42 | 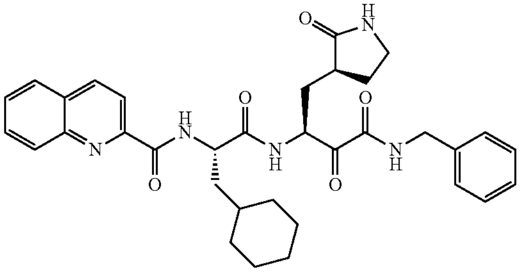 [SMILES: O=C(NCc1ccccc1)C(=O)[C@H](C[C@@H]1CCNC1=O)NC(=O)[C@H](CC1CCCCC1)NC(=O)c1ccc2ccccc2n1] | N-((S)-1-(((S)-4-(benzylamino)-3,4-dione-1-((S)-2-oxopyrrolidin-3-yl)but-2-yl)amino)-3-cyclohexyl-1-oxopropan-2-yl)-quinoline-2-carboxamide |

-continued

| number | structure | name |
|---|---|---|
| A43 | 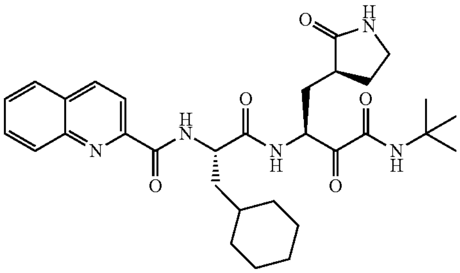 [SMILES: CC(C)(C)NC(=O)C(=O)[C@H](C[C@@H]1CCNC1=O)NC(=O)[C@H](CC1CCCCC1)NC(=O)c1ccc2ccccc2n1] | N-((S)-1-(((S)-4-(tert-butylamino)-3,4-dione-1-((S)-2-oxopyrrolidin-3-yl)but-2-yl)amino)-3-cyclohexyl-1-oxopropan-2-yl)-quinoline-2-carboxamide |
| A44 | 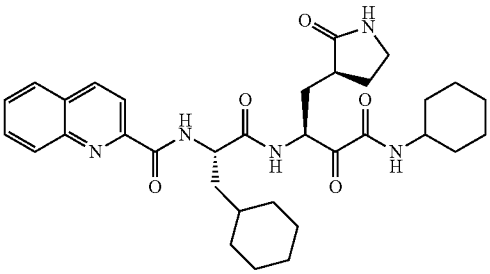 [SMILES: O=C(NC1CCCCC1)C(=O)[C@H](C[C@@H]1CCNC1=O)NC(=O)[C@H](CC1CCCCC1)NC(=O)c1ccc2ccccc2n1] | N-((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopropan-2-yl)-quinoline-2-carboxamide |
| A45 | 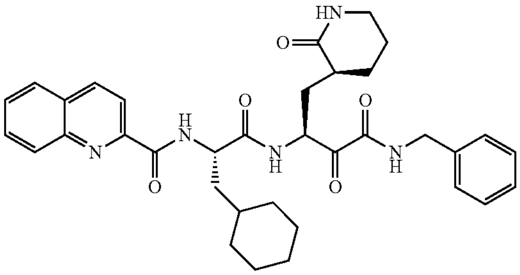 [SMILES: O=C(NCc1ccccc1)C(=O)[C@H](C[C@@H]1CCCNC1=O)NC(=O)[C@H](CC1CCCCC1)NC(=O)c1ccc2ccccc2n1] | N-((S)-1-(((S)-4-(benzylamino)-3,4-dione-1-((S)-2-oxopiperidin-3-yl)but-2-yl)amino)-3-cyclohexyl-1-oxopropan-2-yl)-quinoline-2-carboxamide |
| A46 | 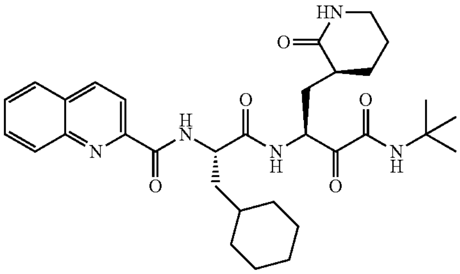 | N-((S)-1-(((S)-4-(tert-butylamino)-3,4-dione-1-((S)-2-oxopiperidin-3-yl)but-2-yl)amino)-3-cyclohexyl-1-oxopropan-2-yl)-quinoline-2-carboxamide |
| A47 | 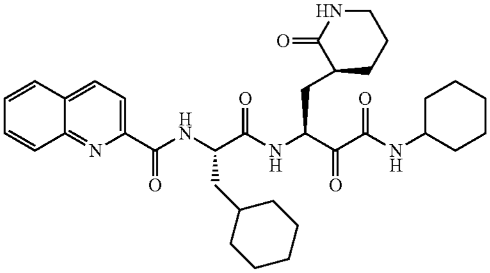 [SMILES: O=C(NC1CCCCC1)C(=O)[C@H](C[C@@H]1CCCNC1=O)NC(=O)[C@H](CC1CCCCC1)NC(=O)c1ccc2ccccc2n1] | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopropan-2-yl)-quinoline-2-carboxamide |

-continued

| number | structure | name |
|---|---|---|
| A48 | 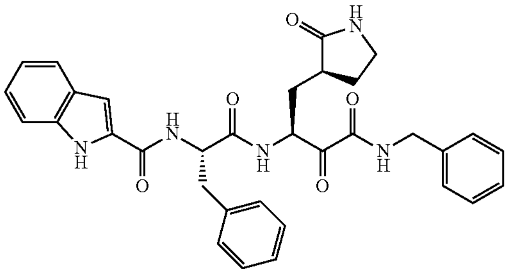 [SMILES: O=C(NCc1ccccc1)C(=O)[C@H](C[C@@H]1CCNC1=O)NC(=O)[C@H](Cc1ccccc1)NC(=O)c1cc2ccccc2[nH]1] | N-((S)-1-(((S)-4-(benzylamino)-3,4-dione-1-((S)-2-oxopyrrolidin-3-yl)but-2-yl)amino)-1-oxo-3-phenylpropan-2-yl)-1H-indole-2-carboxamide |
| A49 | 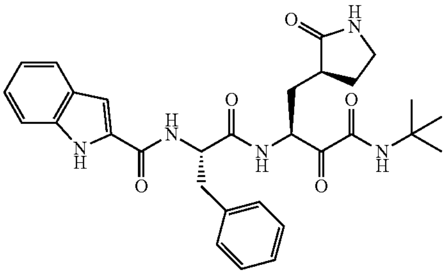 [SMILES: CC(C)(C)NC(=O)C(=O)[C@H](C[C@@H]1CCNC1=O)NC(=O)[C@H](Cc1ccccc1)NC(=O)c1cc2ccccc2[nH]1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-1H-indole-2-carboxamide |
| A50 | 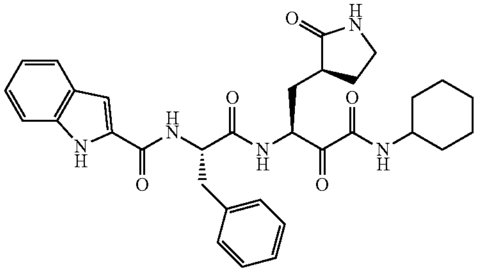 [SMILES: O=C(NC1CCCCC1)C(=O)[C@H](C[C@@H]1CCNC1=O)NC(=O)[C@H](Cc1ccccc1)NC(=O)c1cc2ccccc2[nH]1] | N-((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-1H-indole-2-carboxamide |
| A51 | 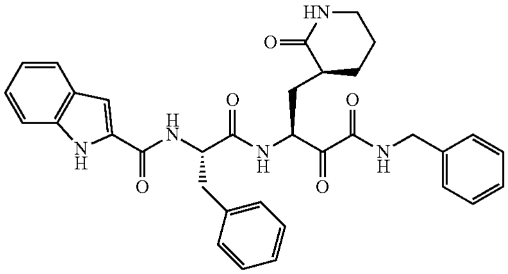 | N-((S)-1-(((S)-4-(benzylamino)-3,4-dione-1-((S)-2-oxopiperidin-3-yl)but-2-yl)amino)-1-oxo-3-phenylpropan-2-yl)-1H-indole-2-carboxamide |
| A52 | 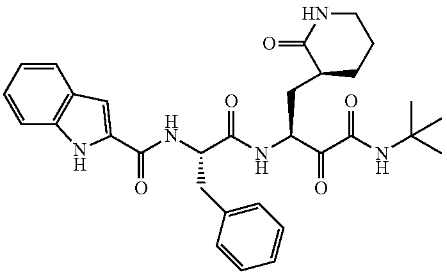 | N-((S)-1-(((S)-4-(tert-butylamino)-3,4-dione-1-((S)-2-oxopiperidin-3-yl)but-2-yl)amino)-1-oxo-3-phenylpropan-2-yl)-1H-indole-2-carboxamide |

-continued

| number | structure | name |
|---|---|---|
| A53 | 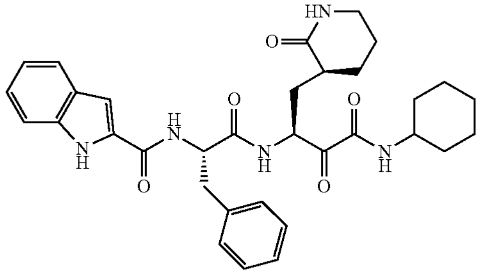 [SMILES: O=C(NC1CCCCC1)C(=O)[C@H](C[C@@H]1CCCNC1=O)NC(=O)[C@H](Cc1ccccc1)NC(=O)c1cc2ccccc2[nH]1] | N-((S)-3-cyclohexyl-1-(((S)-4-(cyclohexylamino)-3,4-dione-1-((S)-2-oxopiperidin-3-yl)but-2-yl)amino)-1-oxo-3-phenylpropan-2-yl)-1H-indole-2-carboxamide |
| A54 | 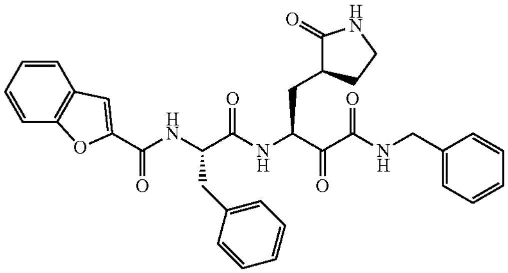 [SMILES: O=C(NCc1ccccc1)C(=O)[C@H](C[C@@H]1CCNC1=O)NC(=O)[C@H](Cc1ccccc1)NC(=O)c1cc2ccccc2o1] | N-((S)-1-(((S)-4-(benzylamino)-3,4-dione-1-((S)-2-oxopyrrolidin-3-yl)but-2-yl)amino)-1-oxo-3-phenylpropan-2-yl)-benzofuran-2-carboxamide |
| A55 | 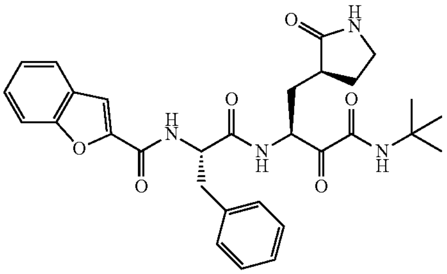 | N-((S)-1-(((S)-4-(tert-butylamino)-3,4-dione-1-((S)-2-oxopyrrolidin-3-yl)but-2-yl)amino)-1-oxo-3-phenylpropan-2-yl)-benzofuran-2-carboxamide |
| A56 | 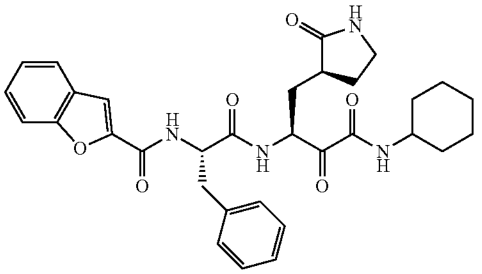 [SMILES: O=C(NC1CCCCC1)C(=O)[C@H](C[C@@H]1CCNC1=O)NC(=O)[C@H](Cc1ccccc1)NC(=O)c1cc2ccccc2o1] | N-((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-benzofuran-2-carboxamide |
| A57 | 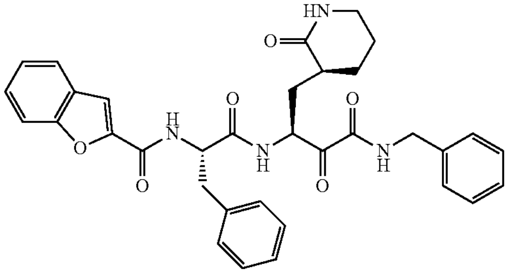 [SMILES: O=C(NCc1ccccc1)C(=O)[C@H](C[C@@H]1CCCNC1=O)NC(=O)[C@H](Cc1ccccc1)NC(=O)c1cc2ccccc2o1] | N-((S)-1-(((S)-4-(benzylamino)-3,4-dione-1-((S)-2-oxopiperidin-3-yl)but-2-yl)amino)-1-oxo-3-phenylpropan-2-yl)-benzofuran-2-carboxamide |

-continued

| number | structure | name |
|---|---|---|
| A58 | 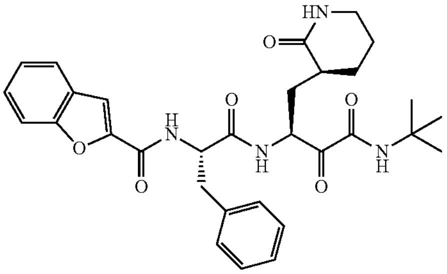 [SMILES: CC(C)(C)NC(=O)C(=O)[C@H](C[C@@H]1CCCNC1=O)NC(=O)[C@H](Cc1ccccc1)NC(=O)c1cc2ccccc2o1] | N-((S)-1-(((S)-4-(tert-butylamino)-3,4-dione-1-((S)-2-oxopiperidin-3-yl)but-2-yl)amino)-1-oxo-3-phenylpropan-2-yl)-benzofuran-2-carboxamide |
| A59 | 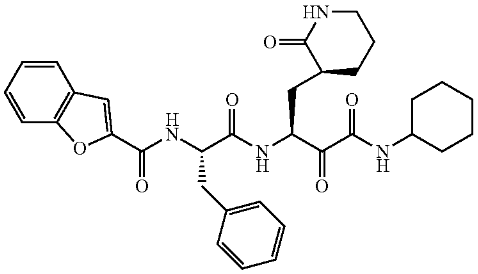 | N-((S)-3-cyclohexyl-1-(((S)-4-(cyclohexylamino)-3,4-dione-1-((S)-2-oxopiperidin-3-yl)but-2-yl)amino)-1-oxo-3-phenylpropan-2-yl)-benzofuran-2-carboxamide |
| A60 | 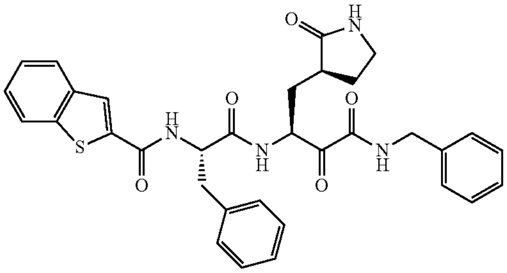 [SMILES: O=C(NCc1ccccc1)C(=O)[C@H](C[C@@H]1CCNC1=O)NC(=O)[C@H](Cc1ccccc1)NC(=O)c1cc2ccccc2s1] | N-((S)-1-(((S)-4-(benzylamino)-3,4-dione-1-((S)-2-oxopyrrolidin-3-yl)but-2-yl)amino)-1-oxo-3-phenylpropan-2-yl)-benzothiophene-2-carboxamide |
| A61 | 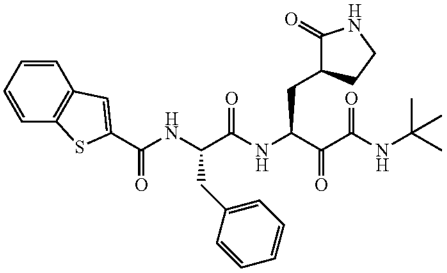 [SMILES: CC(C)(C)NC(=O)C(=O)[C@H](C[C@@H]1CCNC1=O)NC(=O)[C@H](Cc1ccccc1)NC(=O)c1cc2ccccc2s1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-benzothiophene-2-carboxamide |
| A62 | 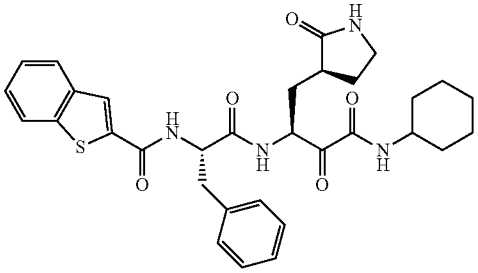 [SMILES: O=C(NC1CCCCC1)C(=O)[C@H](C[C@@H]1CCNC1=O)NC(=O)[C@H](Cc1ccccc1)NC(=O)c1cc2ccccc2s1] | N-((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-benzothiophene-2-carboxamide |

-continued

| number | structure | name |
|---|---|---|
| A63 | 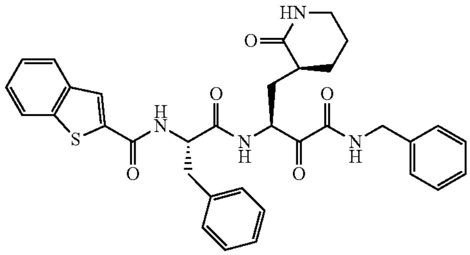 [SMILES: O=C(NCc1ccccc1)C(=O)[C@H](C[C@@H]1CCCNC1=O)NC(=O)[C@H](Cc1ccccc1)NC(=O)c1cc2ccccc2s1] | N-((S)-1-(((S)-4-(benzylamino)-3,4-dione-1-((S)-2-oxopiperidin-3-yl)but-2-yl)amino)-1-oxo-3-phenylpropan-2-yl)-benzothiophene-2-carboxamide |
| A64 | 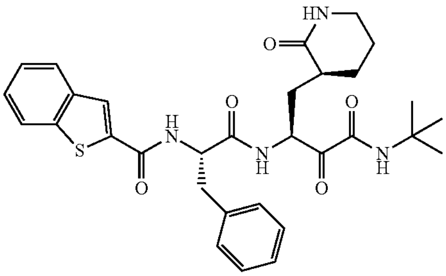 | N-((S)-1-(((S)-4-(tert-butylamino)-3,4-dione-1-((S)-2-oxopiperidin-3-yl)but-2-yl)amino)-1-oxo-3-phenylpropan-2-yl)-benzothiophene-2-carboxamide |
| A65 | 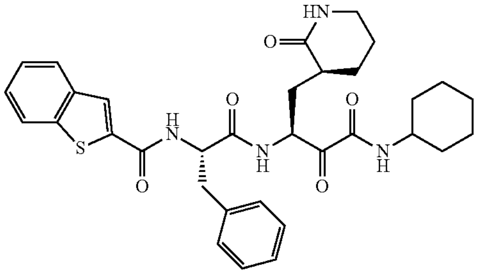 [SMILES: O=C(NC1CCCCC1)C(=O)[C@H](C[C@@H]1CCCNC1=O)NC(=O)[C@H](Cc1ccccc1)NC(=O)c1cc2ccccc2s1] | N-((S)-3-cyclohexyl-1-(((S)-4-(cyclohexylamino)-3,4-dione-1-((S)-2-oxopiperidin-3-yl)but-2-yl)amino)-1-oxo-3-phenylpropan-2-yl)-benzothiophene-2-carboxamide |
| A66 | 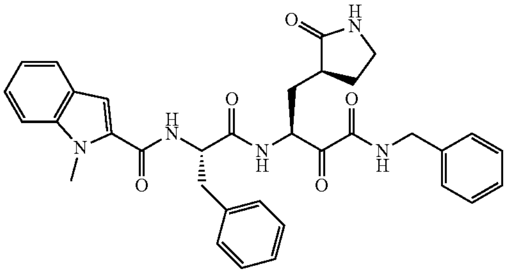 [SMILES: Cn1c(C(=O)N[C@@H](Cc2ccccc2)C(=O)N[C@@H](C[C@@H]2CCNC2=O)C(=O)C(=O)NCc2ccccc2)cc2ccccc21] | N-((S)-1-(((S)-4-(benzylamino)-3,4-dione-1-((S)-2-oxopyrrolidin-3-yl)but-2-yl)amino)-1-oxo-3-phenylpropan-2-yl)-1-methyl-1H-indole-2-carboxamide |
| A67 | 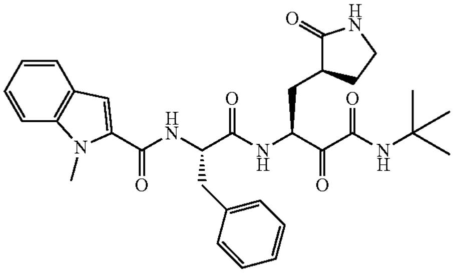 [SMILES: Cn1c(C(=O)N[C@@H](Cc2ccccc2)C(=O)N[C@@H](C[C@@H]2CCNC2=O)C(=O)C(=O)NC(C)(C)C)cc2ccccc21] | N-((S)-1-(((S)-4-(tert-butylamino)-3,4-dione-1-((S)-2-oxopyrrolidin-3-yl)but-2-yl)amino)-1-oxo-3-phenylpropan-2-yl)-1-methyl-1H-indole-2-carboxamide |

-continued

| number | structure | name |
|---|---|---|
| A68 | 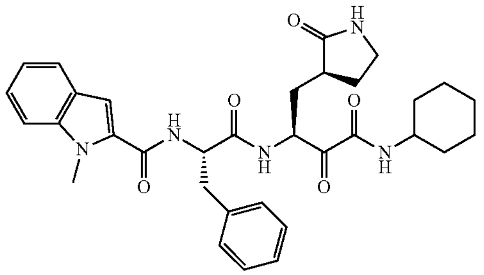 [SMILES: Cn1c(C(=O)N[C@@H](Cc2ccccc2)C(=O)N[C@@H](C[C@@H]2CCNC2=O)C(=O)C(=O)NC2CCCCC2)cc2ccccc21] | N-((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-1-methyl-1H-indole-2-carboxamide |
| A69 | 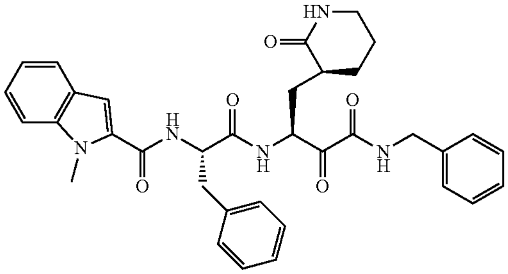 | N-((S)-l-(((S)-4-(benzylamino)-3,4-dione-1-((S)-2-oxopiperidin-3-yl)but-2-yl)amino)-1-oxo-3-phenylpropan-2-yl)-l-methyl-1H-indole-2-carboxamide |
| A70 | 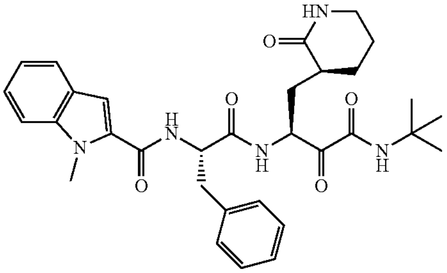 [SMILES: Cn1c(C(=O)N[C@@H](Cc2ccccc2)C(=O)N[C@@H](C[C@@H]2CCCNC2=O)C(=O)C(=O)NC(C)(C)C)cc2ccccc21] | N-((S)-1-(((S)-4-(tert-butylamino)-3,4-dione-1-((S)-2-oxopiperidin-3-yl)but-2-yl)amino)-1-oxo-3-phenylpropan-2-yl)-1-methyl-1H-indole-2-carboxamide |
| A71 | 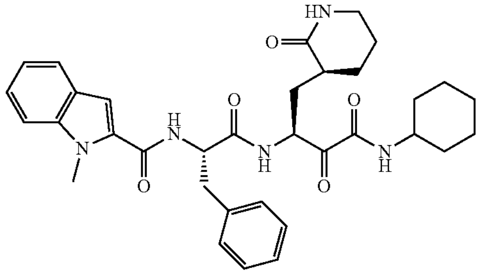 [SMILES: Cn1c(C(=O)N[C@@H](Cc2ccccc2)C(=O)N[C@@H](C[C@@H]2CCCNC2=O)C(=O)C(=O)NC2CCCCC2)cc2ccccc21] | N-((S)-3-cyclohexyl-1-(((S)-4-(cyclohexylamino)-3,4-dione-1-((S)-2-oxopiperidin-3-yl)but-2-yl)amino)-1-oxo-3-phenylpropan-2-yl)-1-methyl-1H-indole-2-carboxamide |
| A72 | 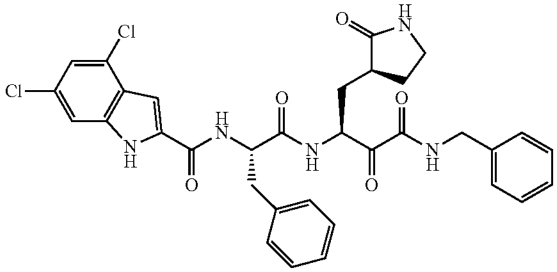 [SMILES: O=C(NCc1ccccc1)C(=O)[C@H](C[C@@H]1CCNC1=O)NC(=O)[C@H](Cc1ccccc1)NC(=O)c1cc2c(Cl)cc(Cl)cc2[nH]1] | N-((S)-1-(((S)-4-(benzylamino)-3,4-dione-1-((S)-2-oxopyrrolidin-3-yl)but-2-yl)amino)-1-oxo-3-phenylpropan-2-yl)-4,6-dichloro-1H-indole-2-carboxamide |

-continued

| number | structure | name |
|---|---|---|
| A73 | 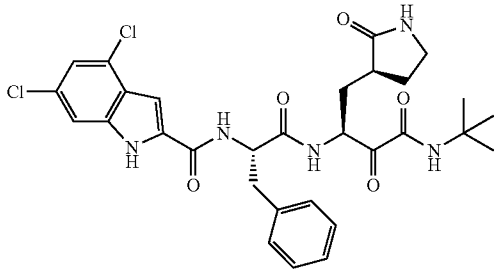 [SMILES: CC(C)(C)NC(=O)C(=O)[C@H](C[C@@H]1CCNC1=O)NC(=O)[C@H](Cc1ccccc1)NC(=O)c1cc2c(Cl)cc(Cl)cc2[nH]1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-4,6-dichloro-1H-indole-2-carboxamide |
| A74 | 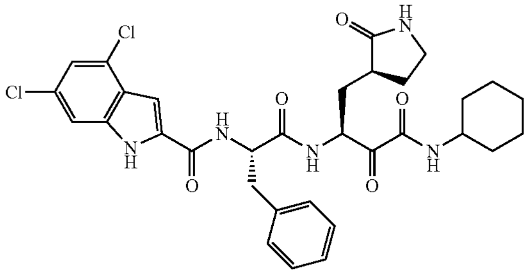 [SMILES: O=C(NC1CCCCC1)C(=O)[C@H](C[C@@H]1CCNC1=O)NC(=O)[C@H](Cc1ccccc1)NC(=O)c1cc2c(Cl)cc(Cl)cc2[nH]1] | N-((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-4,6-dichloro-1H-indole-2-carboxamide |
| A75 | 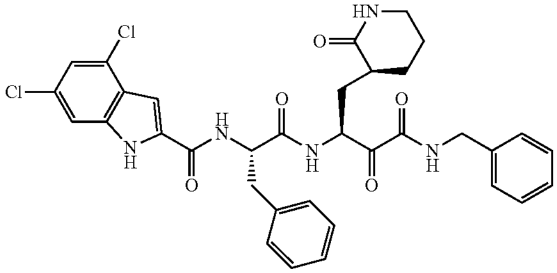 [SMILES: O=C(NCc1ccccc1)C(=O)[C@H](C[C@@H]1CCCNC1=O)NC(=O)[C@H](Cc1ccccc1)NC(=O)c1cc2c(Cl)cc(Cl)cc2[nH]1] | N-((S)-1-(((S)-4-(benzylamino)-3,4-dione-1-((S)-2-oxopiperidin-3-yl)but-2-yl)amino)-1-oxo-3-phenylpropan-2-yl)-4,6-dichloro-1H-indole-2-carboxamide |
| A76 | 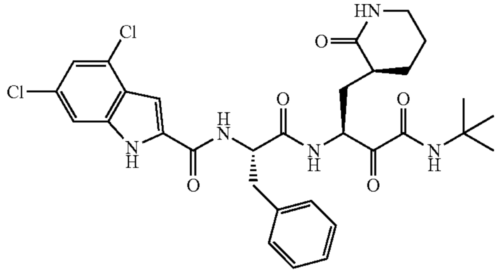 [SMILES: CC(C)(C)NC(=O)C(=O)[C@H](C[C@@H]1CCCNC1=O)NC(=O)[C@H](Cc1ccccc1)NC(=O)c1cc2c(Cl)cc(Cl)cc2[nH]1] | N-((S)-1-(((S)-4-(tert-butylamino)-3,4-dione-1-((S)-2-oxopiperidin-3-yl)but-2-yl)amino)-1-oxo-3-phenylpropan-2-yl)-4,6-dichloro-1H-indole-2-carboxamide |
| A77 | 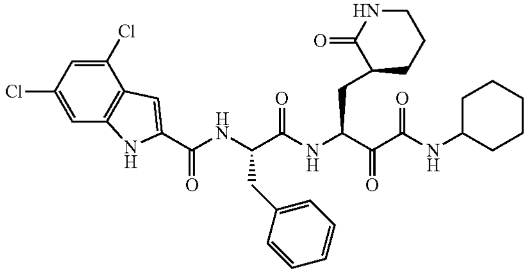 [SMILES: O=C(NC1CCCCC1)C(=O)[C@H](C[C@@H]1CCCNC1=O)NC(=O)[C@H](Cc1ccccc1)NC(=O)c1cc2c(Cl)cc(Cl)cc2[nH]1] | N-((S)-3-cyclohexyl-1-(((S)-4-(cyclohexylamino)-3,4-dione-1-((S)-2-oxopiperidin-3-yl)but-2-yl)amino)-1-oxo-3-phenylpropan-2-yl)-4,6-dichloro-1H-indole-2-carboxamide |

-continued

| number | structure | name |
|---|---|---|
| A78 | 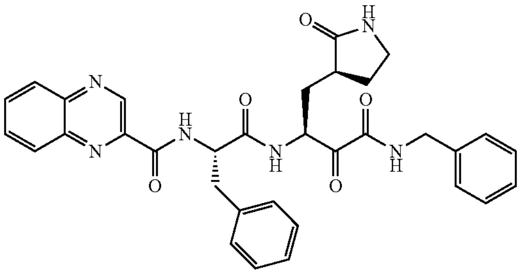 [SMILES: O=C(NCc1ccccc1)C(=O)[C@H](C[C@@H]1CCNC1=O)NC(=O)[C@H](Cc1ccccc1)NC(=O)c1cnc2ccccc2n1] | N-((S)-1-(((S)-4-(benzylamino)-3,4-dione-1-((S)-2-oxopyrrolidin-3-yl)but-2-yl)amino)-1-oxo-3-phenylpropan-2-yl)-quinoxaline-2-carboxamide |
| A79 | 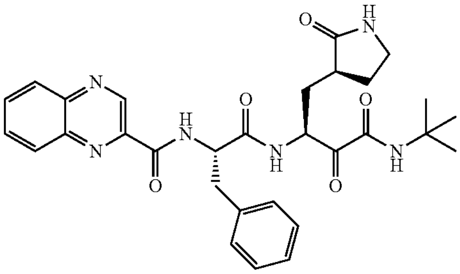 | N-((S)-1-(((S)-4-(tert-butylamino)-3,4-dione-1-((S)-2-oxopyrrolidin-3-yl)but-2-yl)amino)-1-oxo-3-phenylpropan-2-yl)-quinoxaline-2-carboxamide |
| A80 | 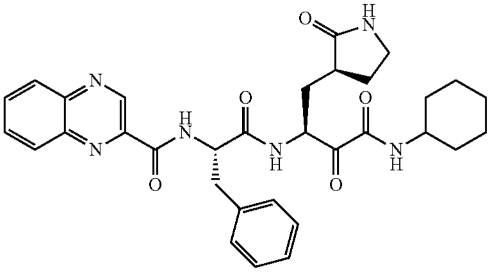 [SMILES: O=C(NC1CCCCC1)C(=O)[C@H](C[C@@H]1CCNC1=O)NC(=O)[C@H](Cc1ccccc1)NC(=O)c1cnc2ccccc2n1] | N-((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-quinoxaline-2-carboxamide |
| A81 | 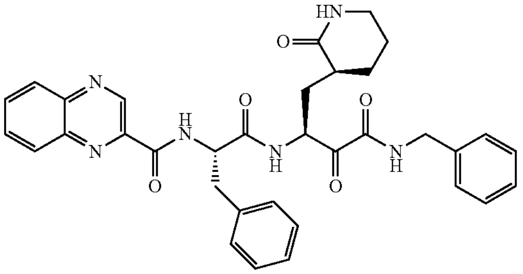 [SMILES: O=C(NCc1ccccc1)C(=O)[C@H](C[C@@H]1CCCNC1=O)NC(=O)[C@H](Cc1ccccc1)NC(=O)c1cnc2ccccc2n1] | N-((S)-1-(((S)-4-(benzylamino)-3,4-dione-1-((S)-2-oxopiperidin-3-yl)but-2-yl)amino)-1-oxo-3-phenylpropan-2-yl)-quinoxaline-2-carboxamide |
| A82 | 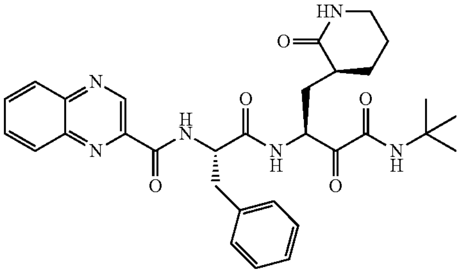 [SMILES: CC(C)(C)NC(=O)C(=O)[C@H](C[C@@H]1CCCNC1=O)NC(=O)[C@H](Cc1ccccc1)NC(=O)c1cnc2ccccc2n1] | N-((S)-1-(((S)-4-(tert-butylamino)-3,4-dione-1-((S)-2-oxopiperidin-3-yl)but-2-yl)amino)-1-oxo-3-phenylpropan-2-yl)-quinoxaline-2-carboxamide |

-continued

| number | structure | name |
|---|---|---|
| A83 | 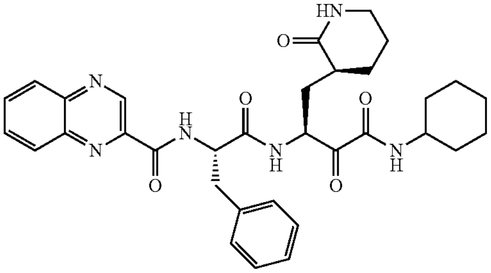 [SMILES: O=C(NC1CCCCC1)C(=O)[C@H](C[C@@H]1CCCNC1=O)NC(=O)[C@H](Cc1ccccc1)NC(=O)c1cnc2ccccc2n1] | N-((S)-3-cyclohexyl-1-(((S)-4-(cyclohexylamino)-3,4-dione-1-((S)-2-oxopiperidin-3-yl)but-2-yl)amino)-1-oxo-3-phenylpropan-2-yl)-quinoxaline-2-carboxamide |
| A84 | 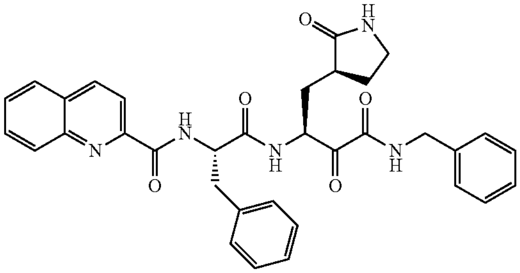 [SMILES: O=C(NCc1ccccc1)C(=O)[C@H](C[C@@H]1CCNC1=O)NC(=O)[C@H](Cc1ccccc1)NC(=O)c1ccc2ccccc2n1] | N-((S)-1-(((S)-4-(benzylamino)-3,4-dione-1-((S)-2-oxopyrrolidin-3-yl)but-2-yl)amino)-1-oxo-3-phenylpropan-2-yl)-quinolin-2-carboxamide |
| A85 | 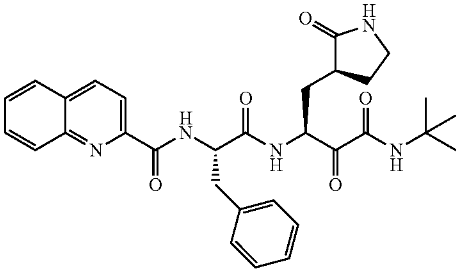 [SMILES: CC(C)(C)NC(=O)C(=O)[C@H](C[C@@H]1CCNC1=O)NC(=O)[C@H](Cc1ccccc1)NC(=O)c1ccc2ccccc2n1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-quinoline-2-carboxamide |
| A86 | 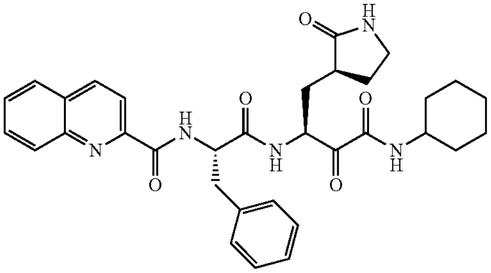 [SMILES: O=C(NC1CCCCC1)C(=O)[C@H](C[C@@H]1CCNC1=O)NC(=O)[C@H](Cc1ccccc1)NC(=O)c1ccc2ccccc2n1] | N-((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-quinoline-2-carboxamide |
| A87 | 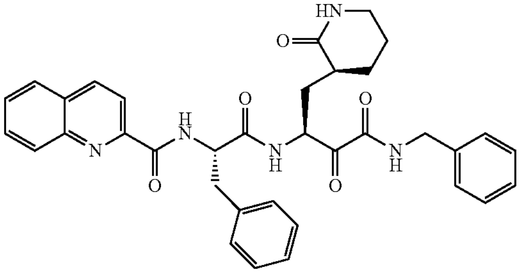 [SMILES: O=C(NCc1ccccc1)C(=O)[C@H](C[C@@H]1CCCNC1=O)NC(=O)[C@H](Cc1ccccc1)NC(=O)c1ccc2ccccc2n1] | N-((S)-l-(((S)-4-(benzylamino)-3,4-dione-1-((S)-2-oxopiperidin-3-yl)but-2-yl)amino)-1-oxo-3-phenylpropan-2-yl)-quinoline-2-carboxamide |

-continued

| number | structure | name |
| --- | --- | --- |
| A88 | 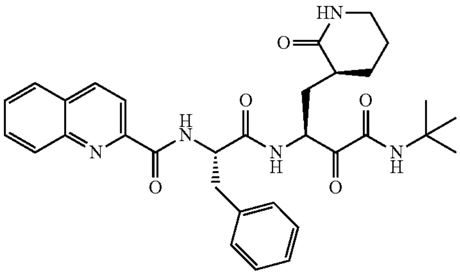 [SMILES: CC(C)(C)NC(=O)C(=O)[C@H](C[C@@H]1CCCNC1=O)NC(=O)[C@H](Cc1ccccc1)NC(=O)c1ccc2ccccc2n1] | N-((S)-1-(((S)-4-(tert-butylamino)-3,4-dione-1-((S)-2-oxopiperidin-3-yl)but-2-yl)amino)-1-oxo-3-phenylpropan-2-yl)-quinoline-2-carboxamide |
| A89 | 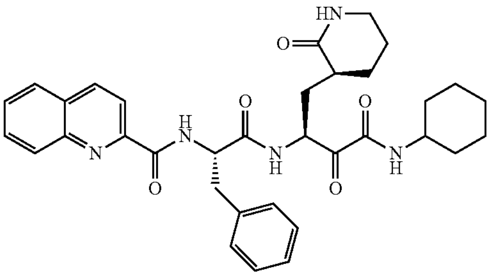 [SMILES: O=C(NC1CCCCC1)C(=O)[C@H](C[C@@H]1CCCNC1=O)NC(=O)[C@H](Cc1ccccc1)NC(=O)c1ccc2ccccc2n1] | N-((S)-3-cyclohexyl-1-(((S)-4-(cyclohexylamino)-3,4-dione-1-((S)-2-oxopiperidin-3-yl)but-2-yl)amino)-1-oxo-3-phenylpropane-2-yl)-quinolin-2-carboxamide |
| A90 | 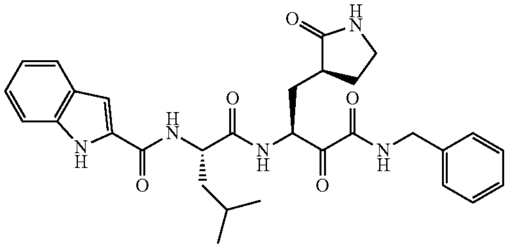 [SMILES: CC(C)C[C@H](NC(=O)c1cc2ccccc2[nH]1)C(=O)N[C@@H](C[C@@H]1CCNC1=O)C(=O)C(=O)NCc1ccccc1] | N-((S)-1-(((S)-4-(benzylamino)-3,4-dione-1-((S)-2-oxopyrrolidin-3-yl)but-2-yl)amino)-4-methyl-1-oxopentan-2-yl)-1H-indole-2-carboxamide |
| A91 | 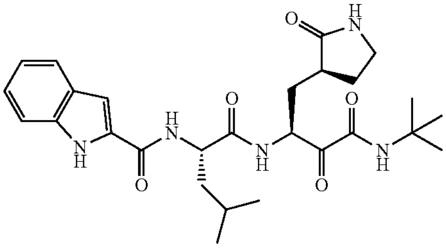 [SMILES: CC(C)C[C@H](NC(=O)c1cc2ccccc2[nH]1)C(=O)N[C@@H](C[C@@H]1CCNC1=O)C(=O)C(=O)NC(C)(C)C] | N-((S)-1-(((S)-4-(tert-butylamino)-3,4-dione-1-((S)-2-oxopyrrolidin-3-yl)but-2-yl)amino)-3-cyclohexyl-1-oxopentan-2-yl)-1H-indole-2-carboxamide |
| A92 | 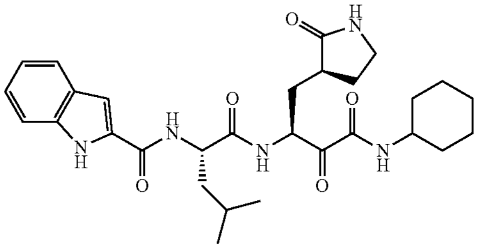 [SMILES: CC(C)C[C@H](NC(=O)c1cc2ccccc2[nH]1)C(=O)N[C@@H](C[C@@H]1CCNC1=O)C(=O)C(=O)NC1CCCCC1] | N-((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-1H-indole-2-carboxamide |
| A93 | 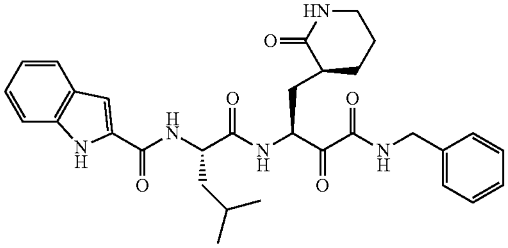 [SMILES: CC(C)C[C@H](NC(=O)c1cc2ccccc2[nH]1)C(=O)N[C@@H](C[C@@H]1CCCNC1=O)C(=O)C(=O)NCc1ccccc1] | N-((S)-1-(((S)-4-(benzylamino)-3,4-dione-1-((S)-2-oxopiperidin-3-yl)but-2-yl)amino)-4-methyl-1-oxopentan-2-yl)-1H-indole-2-carboxamide |

-continued

| number | structure | name |
| --- | --- | --- |
| A94 | 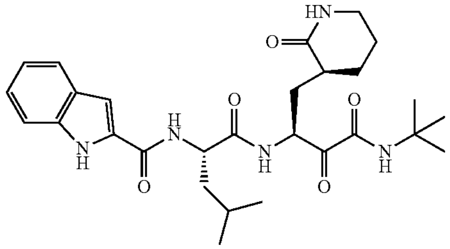 | N-((S)-1-(((S)-4-(tert-butylamino)-3,4-dione-1-((S)-2-oxopiperidin-3-yl)but-2-yl)amino)-3-cyclohexyl-1-oxopentan-2-yl)-1H-indole-2-carboxamide |
| A95 | 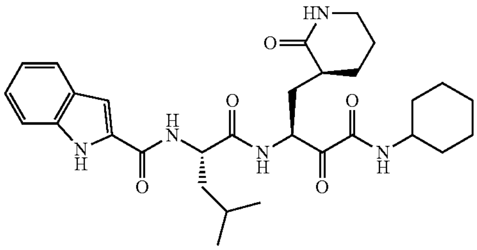 [SMILES: CC(C)C[C@H](NC(=O)c1cc2ccccc2[nH]1)C(=O)N[C@@H](C[C@@H]1CCCNC1=O)C(=O)C(=O)NC1CCCCC1] | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopentan-2-yl)-1H-indole-2-carboxamide |
| A96 | 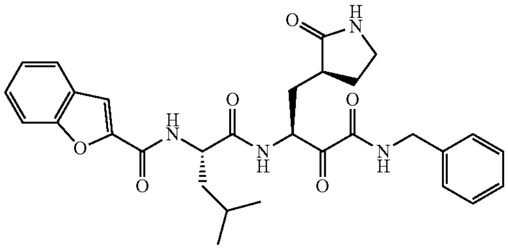 [SMILES: CC(C)C[C@H](NC(=O)c1cc2ccccc2o1)C(=O)N[C@@H](C[C@@H]1CCNC1=O)C(=O)C(=O)NCc1ccccc1] | N-((S)-1-(((S)-4-(benzylamino)-3,4-dione-1-((S)-2-oxopyrrolidin-3-yl)but-2-yl)amino)-4-methyl-1-oxopentan-2-yl)-benzofuran-2-carboxamide |
| A97 | 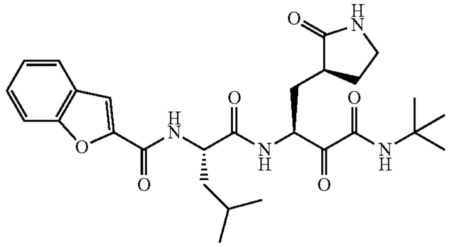 [SMILES: CC(C)C[C@H](NC(=O)c1cc2ccccc2o1)C(=O)N[C@@H](C[C@@H]1CCNC1=O)C(=O)C(=O)NC(C)(C)C] | N-((S)-1-(((S)-4-(tert-butylamino)-3,4-dione-1-((S)-2-oxopyrrolidin-3-yl)but-2-yl)amino)-3-cyclohexyl-1-oxopentan-2-yl)-benzofuran-2-carboxamide |
| A98 | 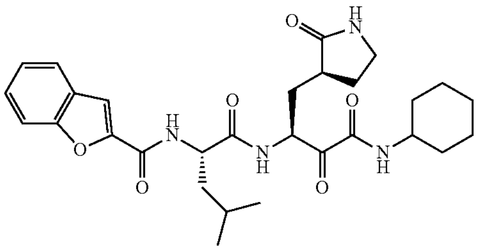 [SMILES: CC(C)C[C@H](NC(=O)c1cc2ccccc2o1)C(=O)N[C@@H](C[C@@H]1CCNC1=O)C(=O)C(=O)NC1CCCCC1] | N-((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-benzofuran-2-carboxamide |
| A99 | 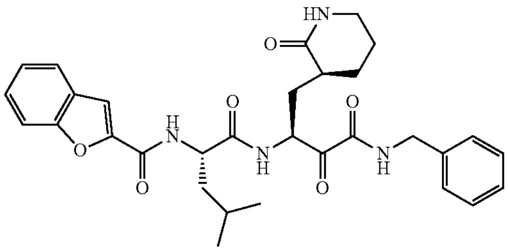 [SMILES: CC(C)C[C@H](NC(=O)c1cc2ccccc2s1)C(=O)N[C@@H](C[C@@H]1CCCNC1=O)C(=O)C(=O)NCc1ccccc1] | N-((S)-1-(((S)-4-(benzylamino)-3,4-dione-1-((S)-2-oxopiperidin-3-yl)but-2-yl)amino)-4-methyl-1-oxopentan-2-yl)-benzofuran-2-carboxamide |

-continued

| number | structure | name |
|---|---|---|
| A100 | 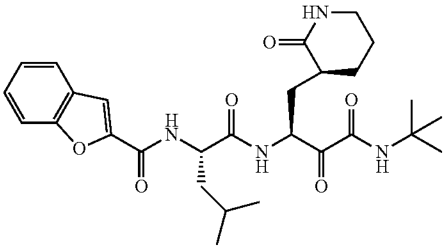 [SMILES: CC(C)C[C@H](NC(=O)c1cc2ccccc2s1)C(=O)N[C@@H](C[C@@H]1CCCNC1=O)C(=O)C(=O)NC(C)(C)C] | N-((S)-1-(((S)-4-(tert-butylamino)-3,4-dione-1-((S)-2-oxopiperidin-3-yl)but-2-yl)amino)-3-cyclohexyl-1-oxopentan-2-yl)-benzofuran-2-carboxamide |
| A101 | 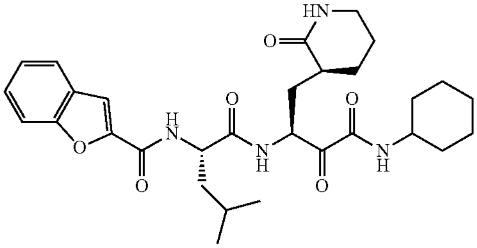 [SMILES: CC(C)C[C@H](NC(=O)c1cc2ccccc2s1)C(=O)N[C@@H](C[C@@H]1CCCNC1=O)C(=O)C(=O)NC1CCCCC1] | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopentan-2-yl)-benzofuran-2-carboxamide |
| A102 | 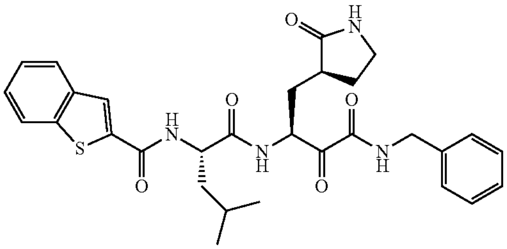 | N-((S)-1-(((S)-4-(benzylamino)-3,4-dione-1-((S)-2-oxopyrrolidin-3-yl)but-2-yl)amino)-4-methyl-1-oxopentan-2-yl)-benzothiophene-2-carboxamide |
| A103 | 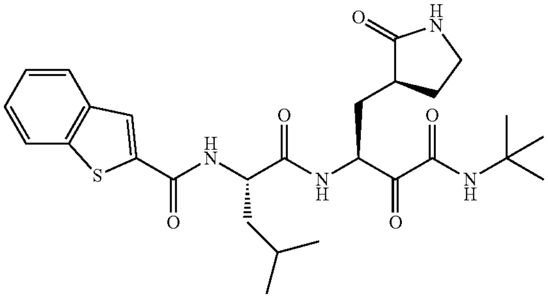 | N-((S)-1-(((S)-4-(tert-butylamino)-3,4-dione-1-((S)-2-oxopyrrolidin-3-yl)but-2-yl)amino)-3-cyclohexyl-1-oxopentan-2-yl)-benzothiophene-2-carboxamide |
| A104 | 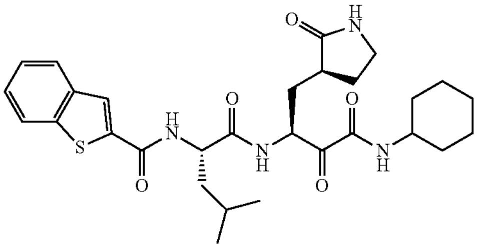 | N-((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-benzothiophene-2-carboxamide |
| A105 | 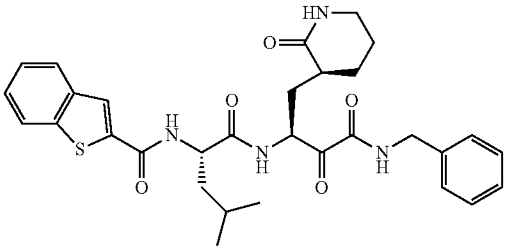 | N-((S)-1-(((S)-4-(benzylamino)-3,4-dione-1-((S)-2-oxopiperidin-3-yl)but-2-yl)amino)-4-methyl-1-oxopentan-2-yl)-benzothiophene-2-carboxamide |

-continued

| number | structure | name |
|---|---|---|
| A106 | 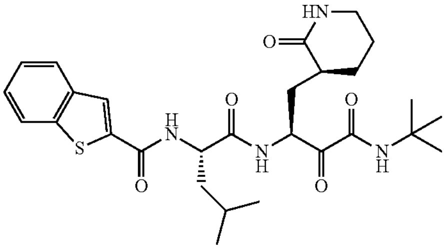 | N-((S)-1-(((S)-4-(tert-butylamino)-3,4-dione-1-((S)-2-oxopiperidin-3-yl)but-2-yl)amino)-3-cyclohexyl-1-oxopentan-2-yl)-benzothiophene-2-carboxamide |
| A107 | 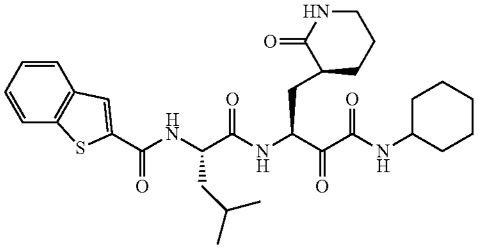 | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopentan-2-yl)-benzothiophene-2-carboxamide |
| A108 | 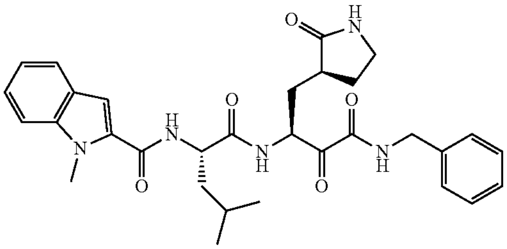 [SMILES: CC(C)C[C@H](NC(=O)c1cc2ccccc2n1C)C(=O)N[C@@H](C[C@@H]1CCNC1=O)C(=O)C(=O)NCc1ccccc1] | N-((S)-1-(((S)-4-(benzylamino)-3,4-dione-1-((S)-2-oxopyrrolidin-3-yl)but-2-yl)amino)-4-methyl-1-oxopentan-2-yl)-1-methyl-1H-indole-2-carboxamide |
| A109 | 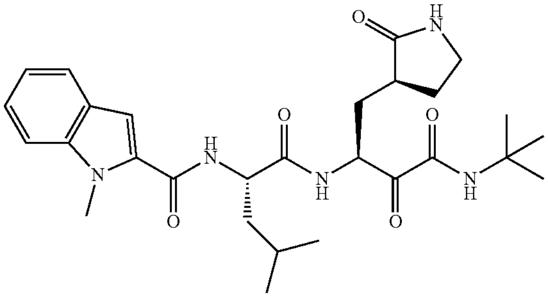 [SMILES: CC(C)C[C@H](NC(=O)c1cc2ccccc2n1C)C(=O)N[C@@H](C[C@@H]1CCNC1=O)C(=O)C(=O)NC(C)(C)C] | N-((S)-1-(((S)-4-(tert-butylamino)-3,4-dione-1-((S)-2-oxopyrrolidin-3-yl)but-2-yl)amino)-3-cyclohexyl-1-oxopentan-2-yl)-1-methyl-1H-indole-2-carboxamide |
| A110 | 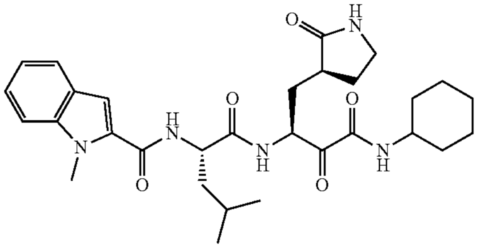 [SMILES: CC(C)C[C@H](NC(=O)c1cc2ccccc2n1C)C(=O)N[C@@H](C[C@@H]1CCNC1=O)C(=O)C(=O)NC1CCCCC1] | N-((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-1-methyl-1H-indole-2-carboxamide |
| A111 | 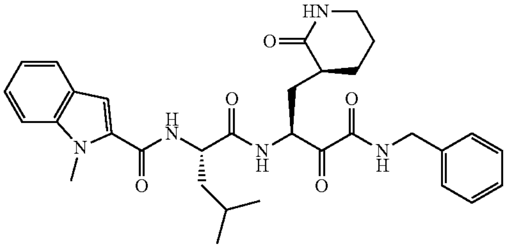 [SMILES: CC(C)C[C@H](NC(=O)c1cc2ccccc2n1C)C(=O)N[C@@H](C[C@@H]1CCCNC1=O)C(=O)C(=O)NCc1ccccc1] | N-((S)-1-(((S)-4-(benzylamino)-3,4-dione-1-((S)-2-oxopiperidin-3-yl)but-2-yl)amino)-4-methyl-1-oxopentan-2-yl)-1-methyl-1H-indole-2-carboxamide |

-continued

| number | structure | name |
|---|---|---|
| A112 | 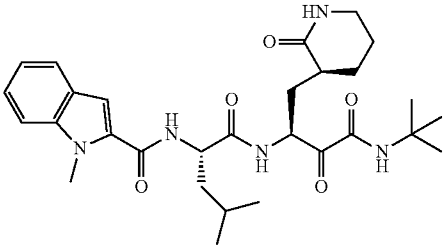 [SMILES: CC(C)C[C@H](NC(=O)c1cc2ccccc2n1C)C(=O)N[C@@H](C[C@@H]1CCCNC1=O)C(=O)C(=O)NC(C)(C)C] | N-((S)-1-(((S)-4-(tert-butylamino)-3,4-dione-1-((S)-2-oxopiperidin-3-yl)but-2-yl)amino)-3-cyclohexyl-1-oxopentan-2-yl)-1-methyl-1H-indole-2-carboxamide |
| A113 | 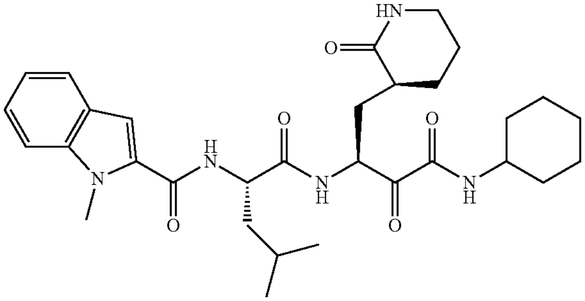 [SMILES: CC(C)C[C@H](NC(=O)c1cc2ccccc2n1C)C(=O)N[C@@H](C[C@@H]1CCCNC1=O)C(=O)C(=O)NC1CCCCC1] | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopentan-2-yl)-1-methyl-1H-indole-2-carboxamide |
| A114 | 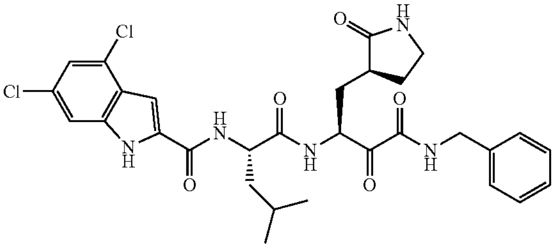 [SMILES: CC(C)C[C@H](NC(=O)c1cc2c(Cl)cc(Cl)cc2[nH]1)C(=O)N[C@@H](C[C@@H]1CCNC1=O)C(=O)C(=O)NCc1ccccc1] | N-((S)-1-(((S)-4-(benzylamino)-3,4-dione-1-((S)-2-oxopyrrolidin-3-yl)but-2-yl)amino)-4-methyl-1-oxopentan-2-yl)-4,6-dichloro-1H-indole-2-carboxamide |
| A115 | 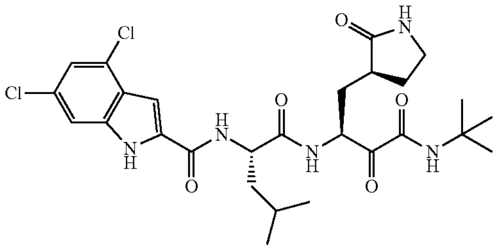 [SMILES: CC(C)C[C@H](NC(=O)c1cc2c(Cl)cc(Cl)cc2[nH]1)C(=O)N[C@@H](C[C@@H]1CCNC1=O)C(=O)C(=O)NC(C)(C)C] | N-((S)-1-(((S)-4-(tert-butylamino)-3,4-dione-1-((S)-2-oxopyrrolidin-3-yl)but-2-yl)amino)-3-cyclohexyl-1-oxopentan-2-yl)-4,6-dichloro-1H-indole-2-carboxamide |
| A116 | 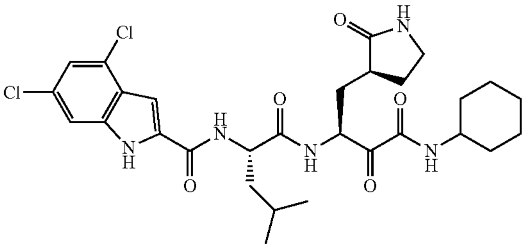 [SMILES: CC(C)C[C@H](NC(=O)c1cc2c(Cl)cc(Cl)cc2[nH]1)C(=O)N[C@@H](C[C@@H]1CCNC1=O)C(=O)C(=O)NC1CCCCC1] | N-((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-4,6-dichloro-1H-indole-2-carboxamide |
| A117 | 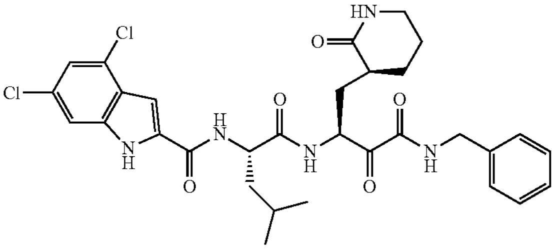 [SMILES: CC(C)C[C@H](NC(=O)c1cc2c(Cl)cc(Cl)cc2[nH]1)C(=O)N[C@@H](C[C@@H]1CCCNC1=O)C(=O)C(=O)NCc1ccccc1] | N-((S)-1-(((S)-4-(benzylamino)-3,4-dione-1-((S)-2-oxopiperidin-3-yl)but-2-yl)amino)-4-methyl-1-oxopentan-2-yl)-4,6-dichloro-1H-indole-2-carboxamide |

-continued

| number | structure | name |
|---|---|---|
| A118 | 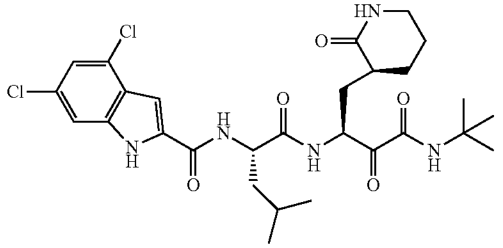 [SMILES: CC(C)C[C@H](NC(=O)c1cc2c(Cl)cc(Cl)cc2[nH]1)C(=O)N[C@@H](C[C@@H]1CCCNC1=O)C(=O)C(=O)NC(C)(C)C] | N-((S)-1-(((S)-4-(tert-butylamino)-3,4-dione-1-((S)-2-oxopiperidin-3-yl)but-2-yl)amino)-3-cyclohexyl-1-oxopentan-2-yl)-4,6-dichloro-1H-indole-2-carboxamide |
| A119 | 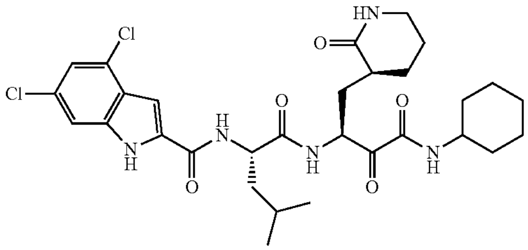 [SMILES: CC(C)C[C@H](NC(=O)c1cc2c(Cl)cc(Cl)cc2[nH]1)C(=O)N[C@@H](C[C@@H]1CCCNC1=O)C(=O)C(=O)NC1CCCCC1] | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopentan-2-yl)-4,6-dichloro-1H-indole-2-carboxamide |
| A120 | 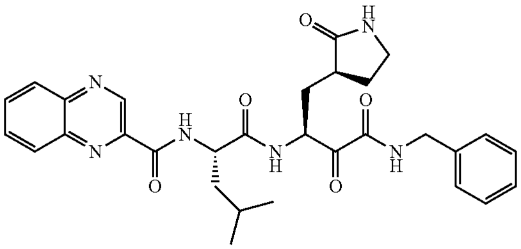 [SMILES: CC(C)C[C@H](NC(=O)c1cnc2ccccc2n1)C(=O)N[C@@H](C[C@@H]1CCNC1=O)C(=O)C(=O)NCc1ccccc1] | N-((S)-1-(((S)-4-(benzylamino)-3,4-dione-1-((S)-2-oxopyrrolidin-3-yl)but-2-yl)amino)-4-methyl-1-oxopentan-2-yl)-quinoxaline-2-carboxamide |
| A121 | 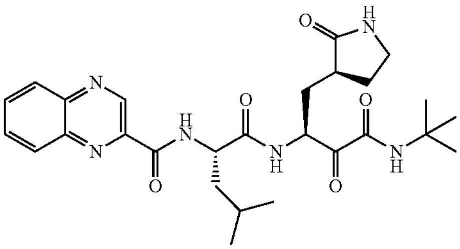 [SMILES: CC(C)C[C@H](NC(=O)c1cnc2ccccc2n1)C(=O)N[C@@H](C[C@@H]1CCNC1=O)C(=O)C(=O)NC(C)(C)C] | N-((S)-1-(((S)-4-(tert-butylamino)-3,4-dione-1-((S)-2-oxopyrrolidin-3-yl)but-2-yl)amino)-3-cyclohexyl-1-oxopentan-2-yl)-quinoxaline-2-carboxamide |
| A122 | 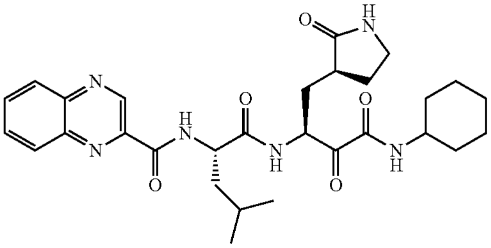 [SMILES: CC(C)C[C@H](NC(=O)c1cnc2ccccc2n1)C(=O)N[C@@H](C[C@@H]1CCNC1=O)C(=O)C(=O)NC1CCCCC1] | N-((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-quinoxaline-2-carboxamide |
| A123 | 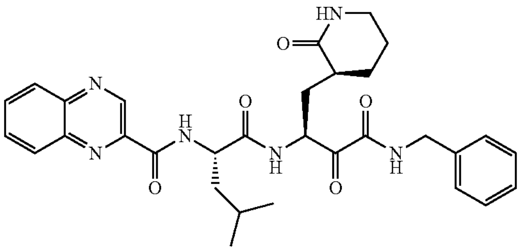 [SMILES: CC(C)C[C@H](NC(=O)c1cnc2ccccc2n1)C(=O)N[C@@H](C[C@@H]1CCCNC1=O)C(=O)C(=O)NCc1ccccc1] | N-((S)-1-(((S)-4-(benzylamino)-3,4-dione-1-((S)-2-oxopiperidin-3-yl)but-2-yl)amino)-4-methyl-1-oxopentan-2-yl)-quinoxaline-2-carboxamide |

-continued

| number | structure | name |
|---|---|---|
| A124 | 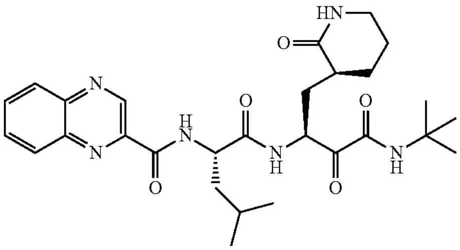 [SMILES: CC(C)C[C@H](NC(=O)c1cnc2ccccc2n1)C(=O)N[C@@H](C[C@@H]1CCCNC1=O)C(=O)C(=O)NC(C)(C)C] | N-((S)-1-(((S)-4-(tert-butylamino)-3,4-dione-1-((S)-2-oxopiperidin-3-yl)but-2-yl)amino)-3-cyclohexyl-1-oxopentan-2-yl)-quinoxaline-2-carboxamide |
| A125 | 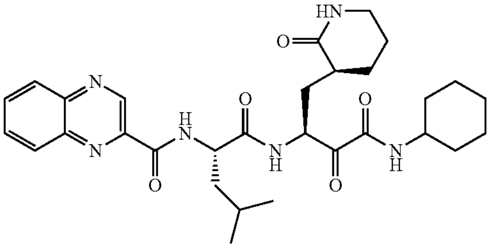 [SMILES: CC(C)C[C@H](NC(=O)c1cnc2ccccc2n1)C(=O)N[C@@H](C[C@@H]1CCCNC1=O)C(=O)C(=O)NC1CCCCC1] | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopentan-2-yl)-quinoxaline-2-carboxamide |
| A126 | 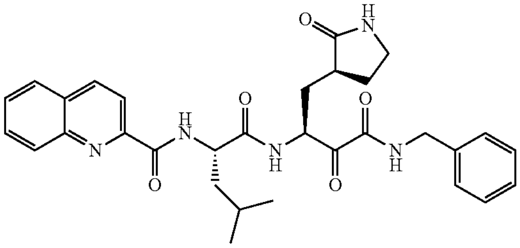 [SMILES: CC(C)C[C@H](NC(=O)c1ccc2ccccc2n1)C(=O)N[C@@H](C[C@@H]1CCNC1=O)C(=O)C(=O)NCc1ccccc1] | N-((S)-l-(((S)-4-(benzylamino)-3,4-dione-1-((S)-2-oxopyrrolidin-3-yl)but-2-yl)amino)-4-methyl-1-oxopentan-2-yl)-quinoline-2-carboxamide |
| A127 | 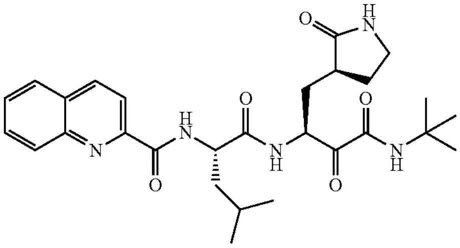 [SMILES: CC(C)C[C@H](NC(=O)c1ccc2ccccc2n1)C(=O)N[C@@H](C[C@@H]1CCNC1=O)C(=O)C(=O)NC(C)(C)C] | N-((S)-1-(((S)-4-(tert-butylamino)-3,4-dione-1-((S)-2-oxopyrrolidin-3-yl)but-2-yl)amino)-3-cyclohexyl-1-oxopentan-2-yl)-quinoline-2-carboxamide |
| A128 | 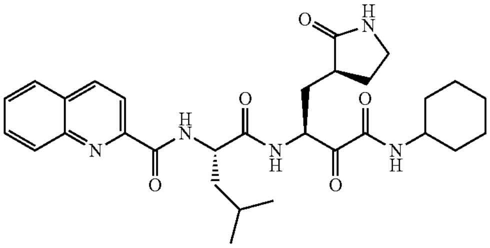 [SMILES: CC(C)C[C@H](NC(=O)c1ccc2ccccc2n1)C(=O)N[C@@H](C[C@@H]1CCNC1=O)C(=O)C(=O)NC1CCCCC1] | N-((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-quinoline-2-carboxamide |
| A129 | 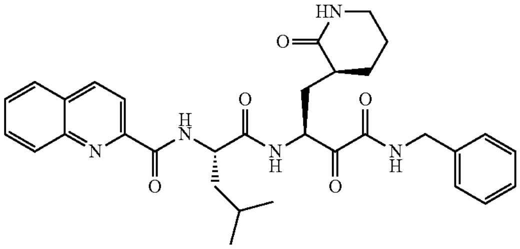 | N-((S)-1-(((S)-4-(benzylamino)-3,4-dione-1-((S)-2-oxopiperidin-3-yl)but-2-yl)amino)-4-methyl-1-oxopentan-2-yl)-quinoline-2-carboxamide |

-continued

| number | structure | name |
|---|---|---|
| A130 | 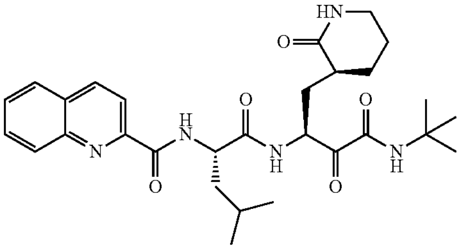 [SMILES: CC(C)C[C@H](NC(=O)c1ccc2ccccc2n1)C(=O)N[C@@H](C[C@@H]1CCCNC1=O)C(=O)C(=O)NC(C)(C)C] | N-((S)-1-(((S)-4-(tert-butylamino)-3,4-dione-1-((S)-2-oxopiperidin-3-yl)but-2-yl)amino)-3-cyclohexyl-1-oxopentan-2-yl)-quinoline-2-carboxamide |
| A131 | 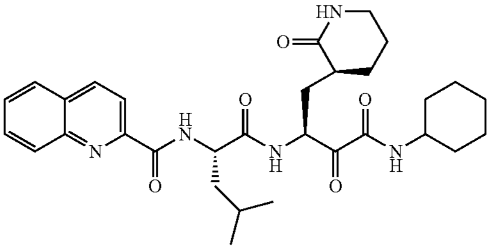 [SMILES: CC(C)C[C@H](NC(=O)c1ccc2ccccc2n1)C(=O)N[C@@H](C[C@@H]1CCCNC1=O)C(=O)C(=O)NC1CCCCC1] | N-((S)-3-cyclohexyl-1-(((S)-4-(cyclohexylamino)-3,4-dione-1-((S)-2-oxopiperidin-3-yl)but-2-yl)amino)-3-cyclohexyl-1-oxopentan-2-yl)-quinoline-2-carboxamide |
| A132 | 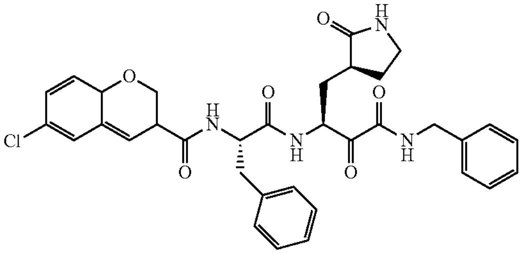 [SMILES: O=C(NCc1ccccc1)C(=O)[C@H](C[C@@H]1CCNC1=O)NC(=O)[C@H](Cc1ccccc1)NC(=O)C1C=C2C=C(Cl)C=CC2OC1] | N-((S)-1-(((S)-4-(benzylamino)-3,4-dione-1-((S)-2-oxopyrrolidin-3-yl)but-2-yl)amino)-1-oxo-3-phenylpropan-2-yl)-6-chloro-3,8a-dihydro-2H-benzopyran-3-carboxamide |
| A133 | 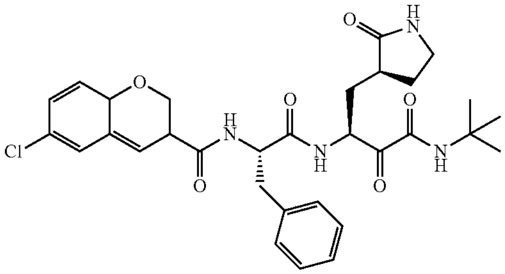 [SMILES: CC(C)(C)NC(=O)C(=O)[C@H](C[C@@H]1CCNC1=O)NC(=O)[C@H](Cc1ccccc1)NC(=O)C1C=C2C=C(Cl)C=CC2OC1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-6-chloro-3,8a-dihydro-2H-benzopyran-3-carboxamide |
| A134 | 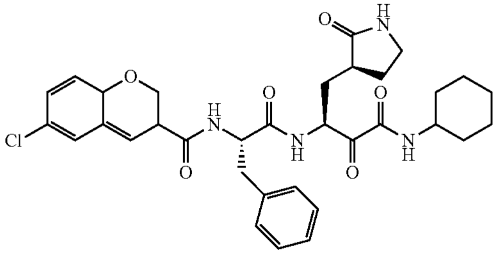 [SMILES: O=C(NC1CCCCC1)C(=O)[C@H](C[C@@H]1CCNC1=O)NC(=O)[C@H](Cc1ccccc1)NC(=O)C1C=C2C=C(Cl)C=CC2OC1] | N-((S)-1-(((S)-4-(cyclohexylamino)-3,4-dione-1-((S)-2-oxopyrrolidin-3-yl)but-2-yl)amino)-1-oxo-3-phenylpropan-2-yl)-6-chloro-3,8a-dihydro-2H-benzopyran-3-carboxamide |
| A135 | 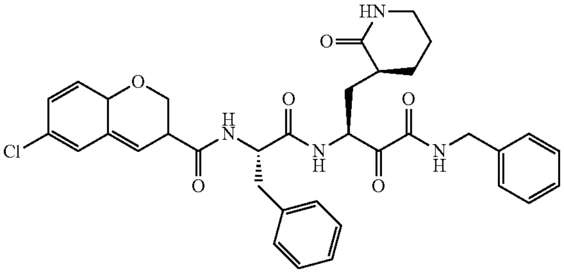 [SMILES: O=C(NCc1ccccc1)C(=O)[C@H](C[C@@H]1CCCNC1=O)NC(=O)[C@H](Cc1ccccc1)NC(=O)C1C=C2C=C(Cl)C=CC2OC1] | N-((S)-1-(((S)-4-(benzylamino)-3,4-dione-1-((S)-2-oxopiperidin-3-yl)but-2-yl)amino)-1-oxo-3-phenylpropan-2-yl)-6-chloro-3,8a-dihydro-2H-benzopyran-3-carboxamide |

-continued

| number | structure | name |
| --- | --- | --- |
| A136 | 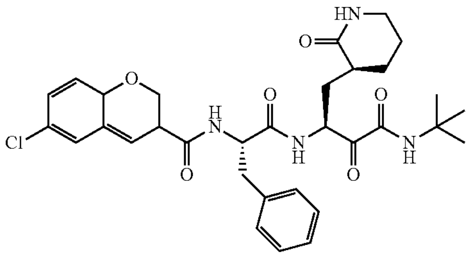 [SMILES: CC(C)(C)NC(=O)C(=O)[C@H](C[C@@H]1CCCNC1=O)NC(=O)[C@H](Cc1ccccc1)NC(=O)C1C=C2C=C(Cl)C=CC2OC1] | N-((S)-1-(((S)-4-(tert-butylamino)-3,4-dione-1-((S)-2-oxopiperidin-3-yl)but-2-yl)amino)-1-oxo-3-phenylpropan-2-yl)-6-chloro-3,8a-dihydro-2H-benzopyran-3-carboxamide |
| A137 | 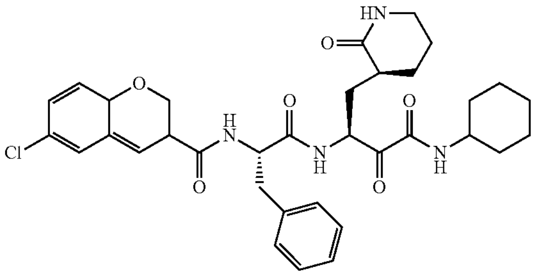 [SMILES: O=C(NC1CCCCC1)C(=O)[C@H](C[C@@H]1CCCNC1=O)NC(=O)[C@H](Cc1ccccc1)NC(=O)C1C=C2C=C(Cl)C=CC2OC1] | N-((S)-1-(((S)-4-(cyclohexylamino)-3,4-dione-1-((S)-2-oxopiperidin-3-yl)but-2-yl)amino)-1-oxo-3-phenylpropan-2-yl)-6-chloro-3,8a-dihydro-2H-benzopyran-3-carboxamide |
| A138 | 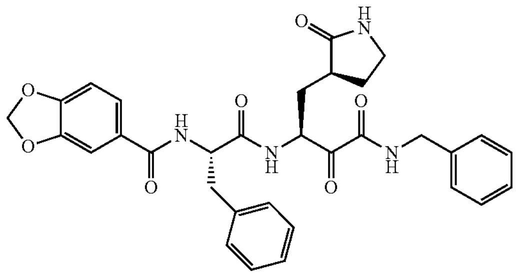 [SMILES: O=C(NCc1ccccc1)C(=O)[C@H](C[C@@H]1CCNC1=O)NC(=O)[C@H](Cc1ccccc1)NC(=O)c1ccc2c(c1)OCO2] | N-((S)-1-((S)-4-(benzylamino)-3,4-dione-1-((S)-2-oxopyrrolidin-3-yl)but-2-yl) amino)-1-oxo-3-phenylpropan-2-yl) benzo[d][1,3]dioxol-5-carboxamide |
| A139 | 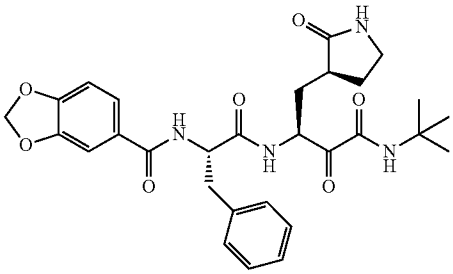 [SMILES: CC(C)(C)NC(=O)C(=O)[C@H](C[C@@H]1CCNC1=O)NC(=O)[C@H](Cc1ccccc1)NC(=O)c1ccc2c(c1)OCO2] | N-((S)-1-(((S)-4-(tert-butyl amino)-3, 4-dione-1-((S)-2-oxopyrrolidin-3-yl)but-2-yl) amino)-1-oxo-3-phenylpropan-2-yl) benzo[d][1,3]dioxol-5-carboxamide |
| A140 | 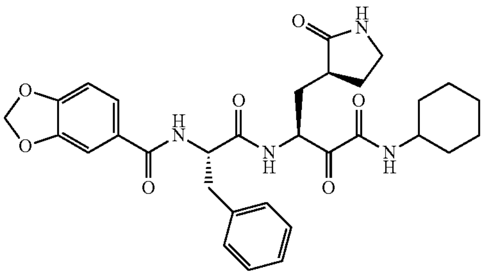 [SMILES: O=C(NC1CCCCC1)C(=O)[C@H](C[C@@H]1CCNC1=O)NC(=O)[C@H](Cc1ccccc1)NC(=O)c1ccc2c(c1)OCO2] | N-((S)-1-(((S)-4-(cyclohexylamino)-3,4-dione-1-((S)-2-oxopyrrolidin-3-yl)but-2-yl)amino)-l-oxo-3-phenylpropan-2-yl) benzo[d][1,3]dioxol-5-carboxamide |

-continued

| number | structure | name |
| --- | --- | --- |
| A141 | 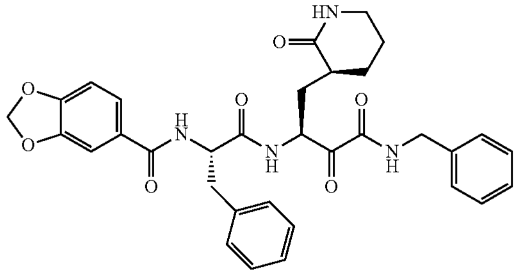 [SMILES: O=C(NCc1ccccc1)C(=O)[C@H](C[C@@H]1CCCNC1=O)NC(=O)[C@H](Cc1ccccc1)NC(=O)c1ccc2c(c1)OCO2] | N-((S)-1-(((S)-4-(benzylamino)-3,4-dione-1-((S)-2-oxopiperidin-3-yl)but-2-yl)amino)-1-oxo-3-phenylpropan-2-yl)benzo[d][1,3]dioxol-5-carboxamide |
| A142 | 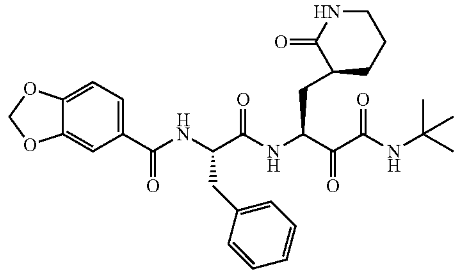 [SMILES: CC(C)(C)NC(=O)C(=O)[C@H](C[C@@H]1CCCNC1=O)NC(=O)[C@H](Cc1ccccc1)NC(=O)c1ccc2c(c1)OCO2] | N-((S)-1-(((S)-4-(tert-butylamino)-3,4-dione-1-((S)-2-oxopiperidin-3-yl)but-2-yl)amino)-1-oxo-3-phenylpropan-2-yl)benzo[d][1,3]dioxol-5-carboxamide |
| A143 | 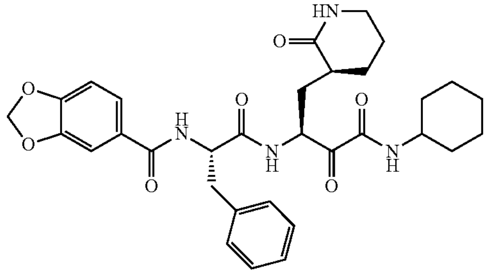 [SMILES: O=C(NC1CCCCC1)C(=O)[C@H](C[C@@H]1CCCNC1=O)NC(=O)[C@H](Cc1ccccc1)NC(=O)c1ccc2c(c1)OCO2] | N-((S)-1-(((S)-4-(cyclohexylamino)-3,4-dione-1-((S)-2-oxopiperidin-3-yl)but-2-yl)amino)-1-oxo-3-phenylpropan-2-yl)benzo[d][l,3]dioxol-5-carboxamide |
| A144 | 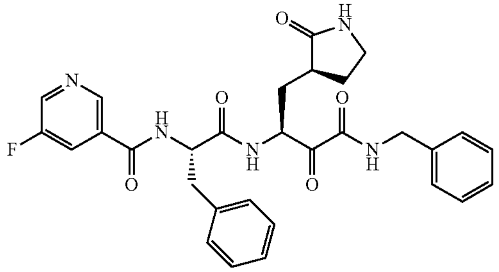 [SMILES: O=C(NCc1ccccc1)C(=O)[C@H](C[C@@H]1CCNC1=O)NC(=O)[C@H](Cc1ccccc1)NC(=O)c1cncc(F)c1] | N-((S)-1-(((S)-4-(benzylamino)-3,4-dione-1-((S)-2-oxopyrrolidin-3-yl)but-2-yl)amino)-1-oxo-3-phenylpropan-2-yl)-5-fluoronicotinamide |
| A145 | 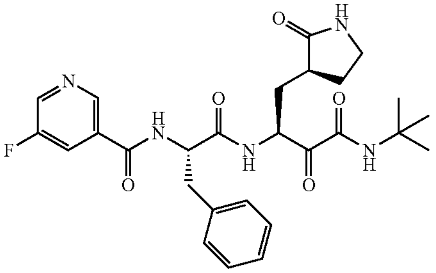 [SMILES: CC(C)(C)NC(=O)C(=O)[C@H](C[C@@H]1CCNC1=O)NC(=O)[C@H](Cc1ccccc1)NC(=O)c1cncc(F)c1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-5-fluoro nicotinamide |

-continued

| number | structure | name |
|---|---|---|
| A146 | 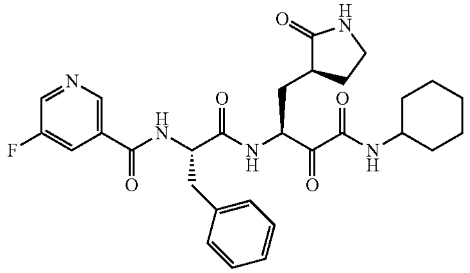 [SMILES: O=C(NC1CCCCC1)C(=O)[C@H](C[C@@H]1CCNC1=O)NC(=O)[C@H](Cc1ccccc1)NC(=O)c1cncc(F)c1] | N-((S)-1-(((S)-4-(cyclohexylamino)-3,4-dione-1-((S)-2-oxopyrrolidin-3-yl)but-2-yl)amino)-1-oxo-3-phenylpropan-2-yl)-5-fluoro nicotinamide |
| A147 | 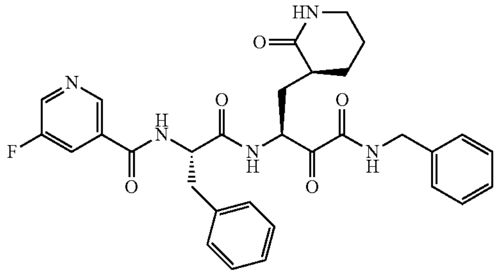 [SMILES: O=C(NCc1ccccc1)C(=O)[C@H](C[C@@H]1CCCNC1=O)NC(=O)[C@H](Cc1ccccc1)NC(=O)c1cncc(F)c1] | N-((S)-1-(((S)-4-(benzylamino)-3,4-dione-1-((S)-2-oxopiperidin-3-yl)but-2-yl)amino)-1-oxo-3-phenylpropan-2-yl)-5-fluoro nicotinamide |
| A148 | 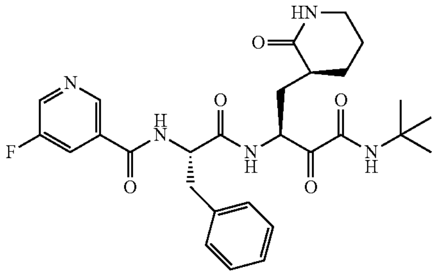 [SMILES: CC(C)(C)NC(=O)C(=O)[C@H](C[C@@H]1CCCNC1=O)NC(=O)[C@H](Cc1ccccc1)NC(=O)c1cncc(F)c1] | N-((S)-1-(((S)-4-(tert-butylamino)-3,4-dione-1-((S)-2-oxopiperidin-3-yl)but-2-yl)amino)-1-oxo-3-phenylpropan-2-yl)-5-fluoro nicotinamide |
| A149 | 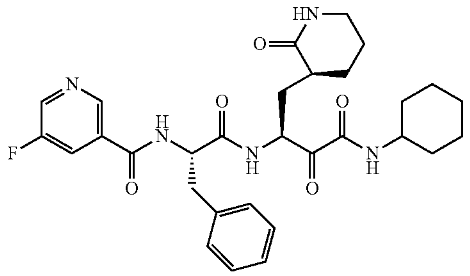 [SMILES: O=C(NC1CCCCC1)C(=O)[C@H](C[C@@H]1CCCNC1=O)NC(=O)[C@H](Cc1ccccc1)NC(=O)c1cncc(F)c1] | N-((S)-1-(((S)-4-(cyclohexylamino)-3,4-dione-1-((S)-2-oxopiperidin-3-yl)but-2-yl)amino)-1-oxo-3-phenylpropan-2-yl)-5-fluoronicotinamide |
| A150 | 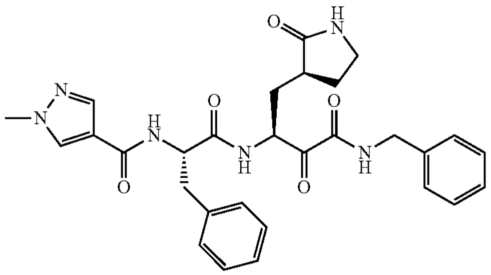 [SMILES: Cn1cc(C(=O)N[C@@H](Cc2ccccc2)C(=O)N[C@@H](C[C@@H]2CCNC2=O)C(=O)C(=O)NCc2ccccc2)cn1] | N-((S)-1-(((S)-4-(benzylamino)-3,4-dione-1-((S)-2-oxopyrrolidin-3-yl)but-2-yl)amino)-1-oxo-3-phenylpropan-2-yl)-1-methyl-1H-pyrazol-4-carboxamide |

-continued

| number | structure | name |
|---|---|---|
| A151 | 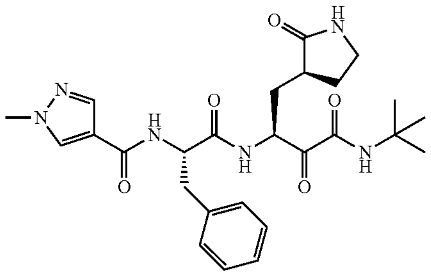 [SMILES: Cn1cc(C(=O)N[C@@H](Cc2ccccc2)C(=O)N[C@@H](C[C@@H]2CCNC2=O)C(=O)C(=O)NC(C)(C)C)cn1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-1-methyl-1H-pyrazol-4-carboxamide |
| A152 | 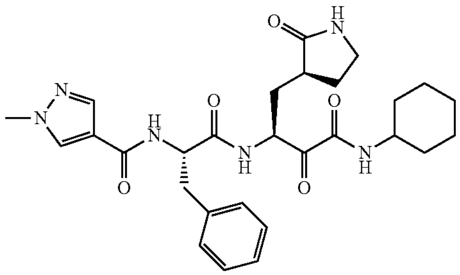 [SMILES: Cn1cc(C(=O)N[C@@H](Cc2ccccc2)C(=O)N[C@@H](C[C@@H]2CCNC2=O)C(=O)C(=O)NC2CCCCC2)cn1] | N-((S)-1-(((S)-4-(cyclohexylamino)-3,4-dione-1-((S)-2-oxopyrrolidin-3-yl)but-2-yl)amino)-1-oxo-3-phenylpropan-2-yl)-1-methyl-1H-pyrazole-4-carboxamide |
| A153 | 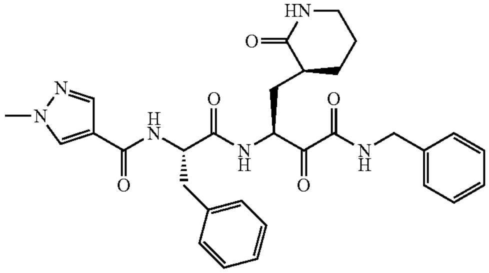 [SMILES: Cn1cc(C(=O)N[C@@H](Cc2ccccc2)C(=O)N[C@@H](C[C@@H]2CCCNC2=O)C(=O)C(=O)NCc2ccccc2)cn1] | N-((S)-1-(((S)-4-(benzylamino)-3,4-dione-1-((S)-2-oxopiperidin-3-yl)but-2-yl)amino)-1-oxo-3-phenylpropan-2-yl)-1-methyl-1H-pyrazole-4-carboxamide |
| A154 | 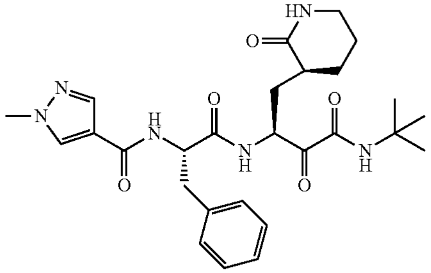 [SMILES: Cn1cc(C(=O)N[C@@H](Cc2ccccc2)C(=O)N[C@@H](C[C@@H]2CCCNC2=O)C(=O)C(=O)NC(C)(C)C)cn1] | N-((S)-1-(((S)-4-(tert-butylamino)-3,4-dione-1-((S)-2-oxopiperidin-3-yl)but-2-yl)amino)-1-oxo-3-phenylpropan-2-yl)-1-methyl-1H-pyrazole-4-carboxamide |
| A155 | 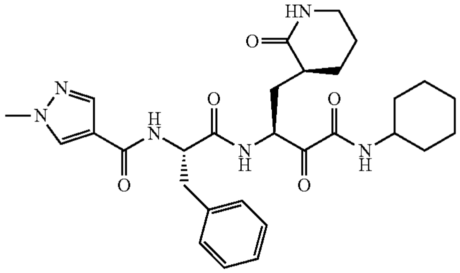 [SMILES: Cn1cc(C(=O)N[C@@H](Cc2ccccc2)C(=O)N[C@@H](C[C@@H]2CCCNC2=O)C(=O)C(=O)NC2CCCCC2)cn1] | N-((S)-1-(((S)-4-(cyclohexylamino)-3,4-dione-1-((S)-2-oxopiperidin-3-yl)but-2-yl)amino)-1-oxo-3-phenylpropan-2-yl)-1-methyl-1H-pyrazole-4-carboxamide |

-continued

| number | structure | name |
|---|---|---|
| A156 | 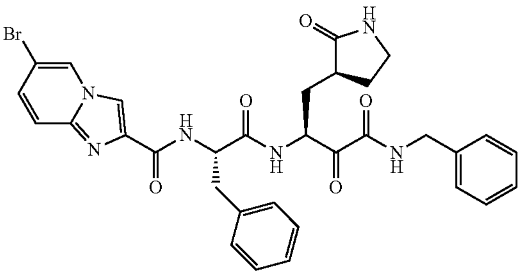 [SMILES: O=C(NCc1ccccc1)C(=O)[C@H](C[C@@H]1CCNC1=O)NC(=O)[C@H](Cc1ccccc1)NC(=O)c1cn2cc(Br)ccc2n1] | N-((S)-1-(((S)-4-(benzylamino)-3,4-dione-1-((S)-2-oxopyrrolidin-3-yl)but-2-yl)amino)-1-oxo-3-phenylpropan-2-yl)-6-bromoimidazo [1,2-a]pyridine-2-carboxamide |
| A157 | 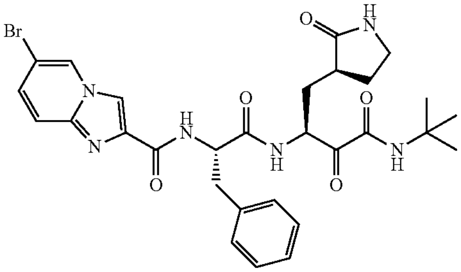 [SMILES: CC(C)(C)NC(=O)C(=O)[C@H](C[C@@H]1CCNC1=O)NC(=O)[C@H](Cc1ccccc1)NC(=O)c1cn2cc(Br)ccc2n1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-6-bromoimidazo [1,2-a]pyridine-2-carboxamide |
| A158 | 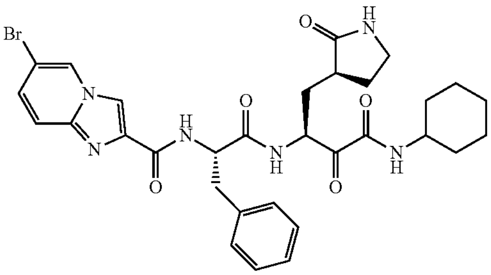 [SMILES: O=C(NC1CCCCC1)C(=O)[C@H](C[C@@H]1CCNC1=O)NC(=O)[C@H](Cc1ccccc1)NC(=O)c1cn2cc(Br)ccc2n1] | N-((S)-1-(((S)-4-(cyclohexylamino)-3,4-dione-1-((S)-2-oxopyrrolidin-3-yl)but-2-yl)amino)-1-oxo-3-phenylpropan-2-yl)-6-bromoimidazo [1,2-a]pyridine-2-carboxamide |
| A159 | 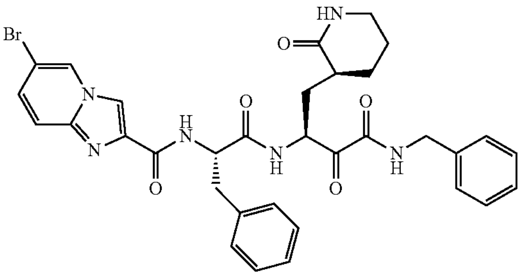 [SMILES: O=C(NCc1ccccc1)C(=O)[C@H](C[C@@H]1CCCNC1=O)NC(=O)[C@H](Cc1ccccc1)NC(=O)c1cn2cc(Br)ccc2n1] | N-((S)-1-(((S)-4-(benzylamino)-3,4-dione-1-((S)-2-oxopiperidin-3-yl)but-2-yl)amino)-1-oxo-3-phenylpropan-2-yl)-6-bromoimidazo [1,2-a]pyridine-2-carboxamide |
| A160 | 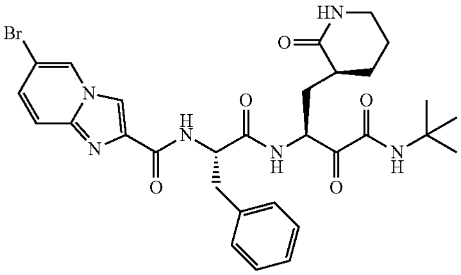 [SMILES: CC(C)(C)NC(=O)C(=O)[C@H](C[C@@H]1CCCNC1=O)NC(=O)[C@H](Cc1ccccc1)NC(=O)c1cn2cc(Br)ccc2n1] | N-((S)-1-(((S)-4-(tert-butylamino)-3,4-dione-1-((S)-2-oxopiperidin-3-yl)but-2-yl)amino)-1-oxo-3-phenylpropan-2-yl)-6-bromoimidazo [1,2-a]pyridine-2-carboxamide |

-continued

| number | structure | name |
|---|---|---|
| A161 | 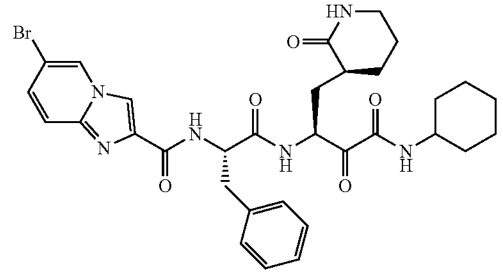 [SMILES: O=C(NC1CCCCC1)C(=O)[C@H](C[C@@H]1CCCNC1=O)NC(=O)[C@H](Cc1ccccc1)NC(=O)c1cn2cc(Br)ccc2n1] | N-((S)-1-(((S)-4-(cyclohexylamino)-3,4-dione-1-((S)-2-oxopiperidin-3-yl)but-2-yl)amino)-1-oxo-3-phenylpropan-2-yl)-6-bromoimidazo [1,2-a]pyridine-2-carboxamide |
| A162 | 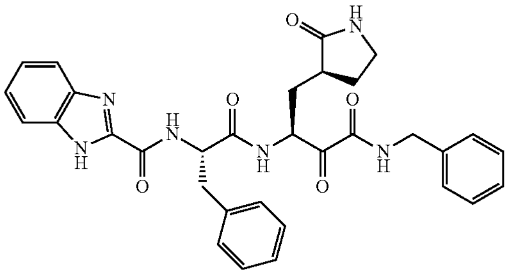 [SMILES: O=C(NCc1ccccc1)C(=O)[C@H](C[C@@H]1CCNC1=O)NC(=O)[C@H](Cc1ccccc1)NC(=O)c1nc2ccccc2[nH]1] | N-((S)-1-(((S)-4-(phenylamino)-3,4-dione-1-((S)-2-oxopyrrolidin-3-yl)but-2-yl)amino)-1-oxo-3-phenylpropan-2-yl)-1H-benzo[d] imidazole-2-carboxamide |
| A163 | 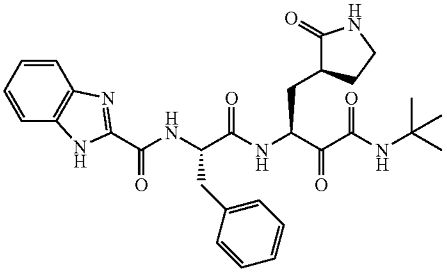 [SMILES: CC(C)(C)NC(=O)C(=O)[C@H](C[C@@H]1CCNC1=O)NC(=O)[C@H](Cc1ccccc1)NC(=O)c1nc2ccccc2[nH]1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-1H-benzo[d] imidazole-2-carboxamide |
| A164 | 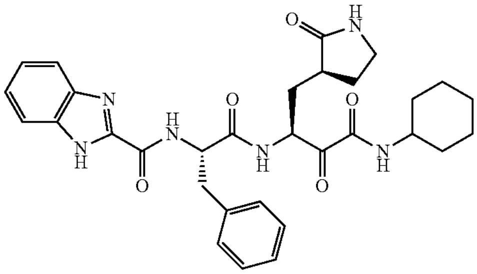 [SMILES: O=C(NC1CCCCC1)C(=O)[C@H](C[C@@H]1CCNC1=O)NC(=O)[C@H](Cc1ccccc1)NC(=O)c1nc2ccccc2[nH]1] | N-((S)-1-(((S)-4-(cyclohexylamino)-3,4-dione-1-((S)-2-oxopyrrolidin-3-yl)but-2-yl)amino)-1-oxo-3-phenylpropan-2-yl)-1H-benzo[d] imidazole-2-carboxamide |
| A165 | 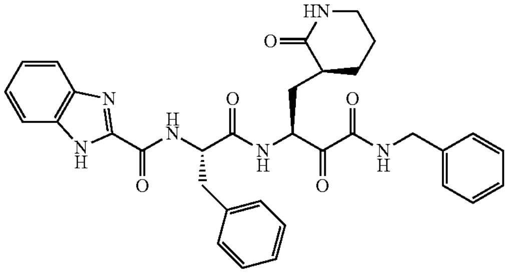 [SMILES: O=C(NCc1ccccc1)C(=O)[C@H](C[C@@H]1CCCNC1=O)NC(=O)[C@H](Cc1ccccc1)NC(=O)c1nc2ccccc2[nH]1] | N-((S)-1-(((S)-4-(phenylamino)-3,4-dione-1-((S)-2-oxopiperidin-3-yl)but-2-yl)amino)-1-oxo-3-phenylpropan-2-yl)-1H-benzo[d]imidazole-2-carboxamide |

-continued

| number | structure | name |
|---|---|---|
| A166 | 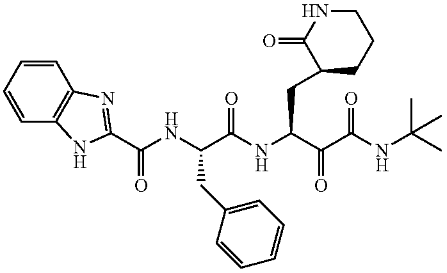 [SMILES: CC(C)(C)NC(=O)C(=O)[C@H](C[C@@H]1CCCNC1=O)NC(=O)[C@H](Cc1ccccc1)NC(=O)c1nc2ccccc2[nH]1] | N-((S)-1-(((S)-4-(tert-butylamino)-3,4-dione-1-((S)-2-oxopiperidin-3-yl)but-2-yl)amino)-1-oxo-3-phenylpropan-2-yl)-1H-benzo[d]imidazole-2-carboxamide |
| A167 | 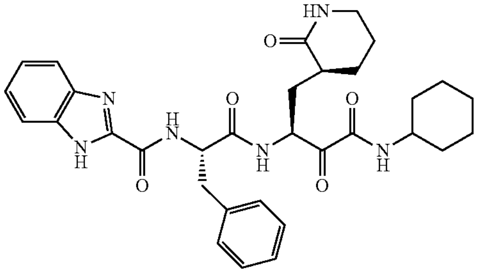 [SMILES: O=C(NC1CCCCC1)C(=O)[C@H](C[C@@H]1CCCNC1=O)NC(=O)[C@H](Cc1ccccc1)NC(=O)c1nc2ccccc2[nH]1] | N-((S)-1-(((S)-4-(cyclohexylamino)-3,4-dione-1-((S)-2-oxopiperidin-3-yl)but-2-yl)amino)-1-oxo-3-phenylpropan-2-yl)-1H-benzo[d]imidazole-2-carboxamide |
| A168 | 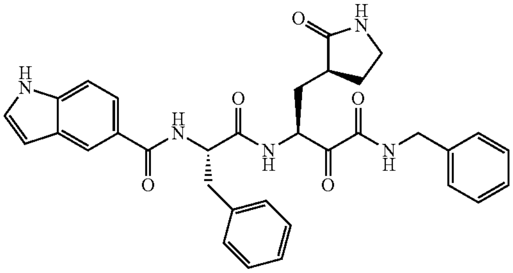 [SMILES: O=C(NCc1ccccc1)C(=O)[C@H](C[C@@H]1CCNC1=O)NC(=O)[C@H](Cc1ccccc1)NC(=O)c1ccc2[nH]ccc2c1] | N-((S)-1-(((S)-4-(benzylamino)-3,4-dione-1-((S)-2-oxopyrrolidin-3-yl)but-2-yl)amino)-1-oxo-3-phenylpropan-2-yl)-1H-indole-5-carboxamide |
| A169 | 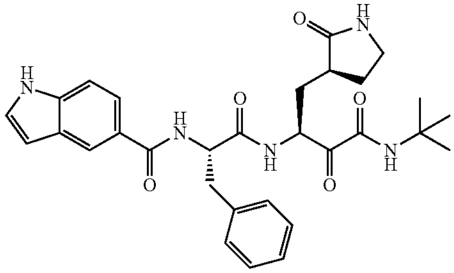 [SMILES: CC(C)(C)NC(=O)C(=O)[C@H](C[C@@H]1CCNC1=O)NC(=O)[C@H](Cc1ccccc1)NC(=O)c1ccc2[nH]ccc2c1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-1H-indole-5-carboxamide |
| A170 | 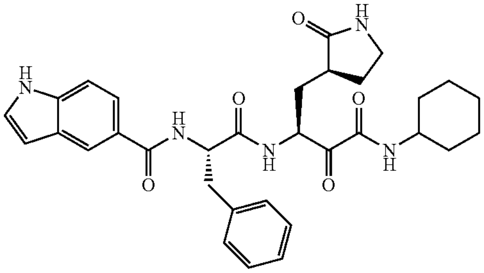 [SMILES: O=C(NC1CCCCC1)C(=O)[C@H](C[C@@H]1CCNC1=O)NC(=O)[C@H](Cc1ccccc1)NC(=O)c1ccc2[nH]ccc2c1] | N-((S)-1-(((S)-4-(cyclohexylamino)-3,4-dione-1-((S)-2-oxopyrrolidin-3-yl)but-2-yl)amino)-1-oxo-3-phenylpropan-2-yl)-1H-indole-5-carboxamide |

-continued

| number | structure | name |
|---|---|---|
| A171 | 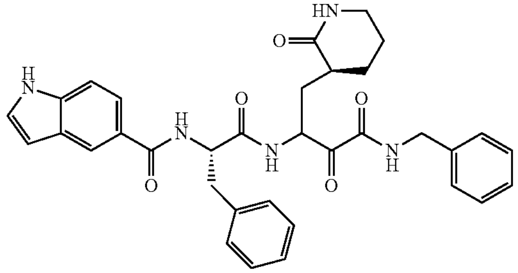 [SMILES: O=C(NCc1ccccc1)C(=O)C(C[C@@H]1CCCNC1=O)NC(=O)[C@H](Cc1ccccc1)NC(=O)c1ccc2[nH]ccc2c1] | N-((S)-1-(((S)-4-(benzylamino)-3,4-dione-1-((S)-2-oxopiperidin-3-yl)but-2-yl)amino)-1-oxo-3-phenylpropan-2-yl)-1H-indole-5-carboxamide |
| A172 | 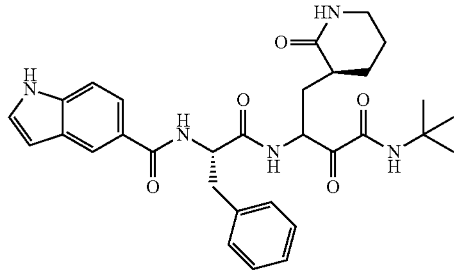 [SMILES: CC(C)(C)NC(=O)C(=O)C(C[C@@H]1CCCNC1=O)NC(=O)[C@H](Cc1ccccc1)NC(=O)c1ccc2[nH]ccc2c1] | N-((S)-1-(((S)-4-(tert-butylamino)-3,4-dione-1-((S)-2-oxopiperidin-3-yl)but-2-yl)amino)-1-oxo-3-phenylpropan-2-yl)-1H-indole-5-carboxamide |
| A173 | 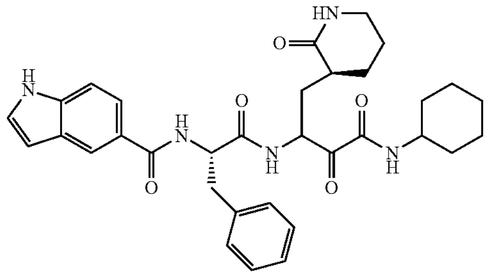 [SMILES: O=C(NC1CCCCC1)C(=O)C(C[C@@H]1CCCNC1=O)NC(=O)[C@H](Cc1ccccc1)NC(=O)c1ccc2[nH]ccc2c1] | N-((S)-1-(((S)-4-(cyclohexylamino)-3,4-dione-1-((S)-2-oxopiperidin-3-yl)but-2-yl)amino)-1-oxo-3-phenylpropan-2-yl)-1H-indole-5-carboxamide |
| A174 | 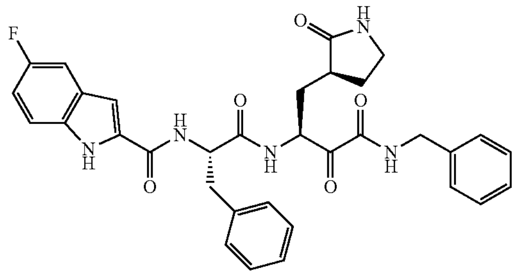 [SMILES: O=C(NCc1ccccc1)C(=O)[C@H](C[C@@H]1CCNC1=O)NC(=O)[C@H](Cc1ccccc1)NC(=O)c1cc2cc(F)ccc2[nH]1] | N-((S)-1-(((S)-4-(benzylamino)-3,4-dione-1-((S)-2-oxopyrrolidin-3-yl)but-2-yl)amino)-1-oxo-3-phenylpropan-2-yl)-5-fluoro-1H-indole-2-carboxamide |
| A175 | 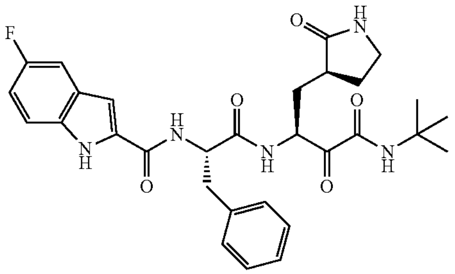 [SMILES: CC(C)(C)NC(=O)C(=O)[C@H](C[C@@H]1CCNC1=O)NC(=O)[C@H](Cc1ccccc1)NC(=O)c1cc2cc(F)ccc2[nH]1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-5-fluoro-1H-indole-2-carboxamide |

-continued

| number | structure | name |
| --- | --- | --- |
| A176 | 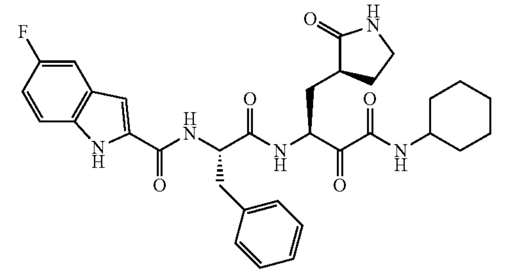 [SMILES: O=C(NC1CCCCC1)C(=O)[C@H](C[C@@H]1CCNC1=O)NC(=O)[C@H](Cc1ccccc1)NC(=O)c1cc2cc(F)ccc2[nH]1] | N-((S)-1-(((S)-4-(cyclohexylamino)-3,4-dione-1-((S)-2-oxopyrrolidin-3-yl)but-2-yl)amino)-1-oxo-3-phenylpropan-2-yl)-5-fluoro-1H-indole-2-carboxamide |
| A177 | 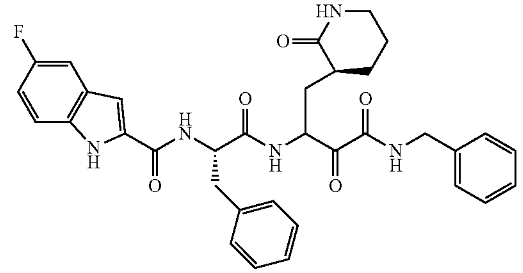 [SMILES: O=C(NCc1ccccc1)C(=O)C(C[C@@H]1CCCNC1=O)NC(=O)[C@H](Cc1ccccc1)NC(=O)c1cc2cc(F)ccc2[nH]1] | N-((S)-1-(((S)-4-(benzylamino)-3,4-dione-1-((S)-2-oxopiperidin-3-yl)but-2-yl)amino)-1-oxo-3-phenylpropan-2-yl)-5-fluoro-1H-indole-2-carboxamide |
| A178 | 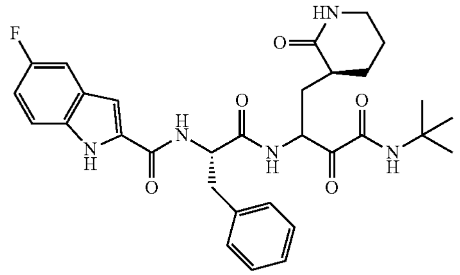 [SMILES: CC(C)(C)NC(=O)C(=O)C(C[C@@H]1CCCNC1=O)NC(=O)[C@H](Cc1ccccc1)NC(=O)c1cc2cc(F)ccc2[nH]1] | N-((S)-1-(((S)-4-(tert-butylamino)-3,4-dione-1-((S)-2-oxopiperidin-3-yl)but-2-yl)amino)-1-oxo-3-phenylpropan-2-yl)-5-fluoro-1H-indole-2-carboxamide |
| A179 | 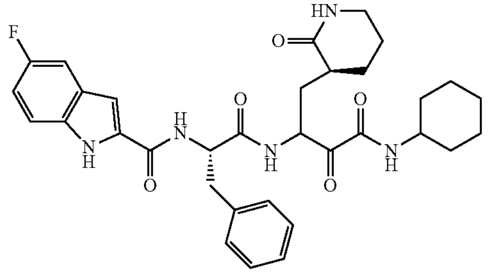 [SMILES: O=C(NC1CCCCC1)C(=O)C(C[C@@H]1CCCNC1=O)NC(=O)[C@H](Cc1ccccc1)NC(=O)c1cc2cc(F)ccc2[nH]1] | N-((S)-1-(((S)-4-(cyclohexylamino)-3,4-dione-1-((S)-2-oxopiperidin-3-yl)but-2-yl)amino)-1-oxo-3-phenylpropan-2-yl)-5-fluoro-1H-indole-2-carboxamide |
| A180 | 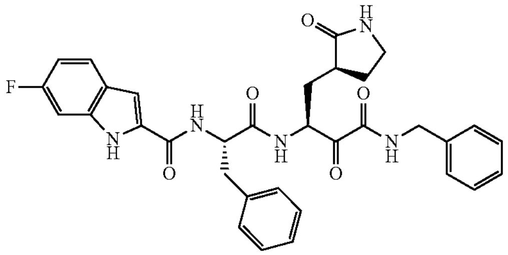 [SMILES: O=C(NCc1ccccc1)C(=O)[C@H](C[C@@H]1CCNC1=O)NC(=O)[C@H](Cc1ccccc1)NC(=O)c1cc2ccc(F)cc2[nH]1] | N-((S)-1-(((S)-4-(benzylamino)-3,4-dione-1-((S)-2-oxopyrrolidin-3-yl)but-2-yl)amino)-1-oxo-3-phenylpropan-2-yl)-6-fluoro-1H-indole-2-carboxamide |

-continued

| number | structure | name |
| --- | --- | --- |
| A181 | 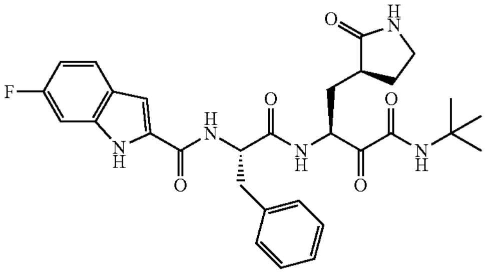 [SMILES: CC(C)(C)NC(=O)C(=O)[C@H](C[C@@H]1CCNC1=O)NC(=O)[C@H](Cc1ccccc1)NC(=O)c1cc2ccc(F)cc2[nH]1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-6-fluoro-1H-indole-2-carboxamide |
| A182 | 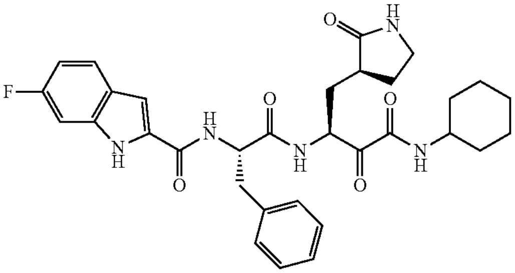 [SMILES: O=C(NC1CCCCC1)C(=O)[C@H](C[C@@H]1CCNC1=O)NC(=O)[C@H](Cc1ccccc1)NC(=O)c1cc2ccc(F)cc2[nH]1] | N-((S)-1-(((S)-4-(cyclohexylamino)-3,4-dione-1-((S)-2-oxopyrrolidin-3-yl)but-2-yl)amino)-1-oxo-3-phenylpropan-2-yl)-6-fluoro-1H-indole-2-carboxamide |
| A183 | 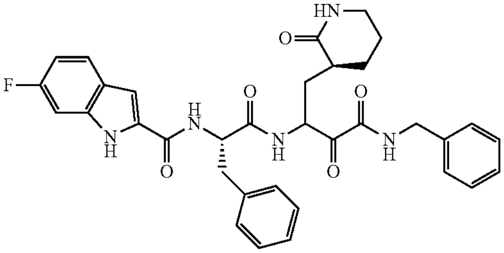 [SMILES: O=C(NCc1ccccc1)C(=O)C(C[C@@H]1CCCNC1=O)NC(=O)[C@H](Cc1ccccc1)NC(=O)c1cc2ccc(F)cc2[nH]1] | N-((S)-1-(((S)-4-(benzylamino)-3,4-dione-1-((S)-2-oxopiperidin-3-yl)but-2-yl)amino)-1-oxo-3-phenylpropan-2-yl)-6-fluoro-1H-indole-2-carboxamide |
| A184 | 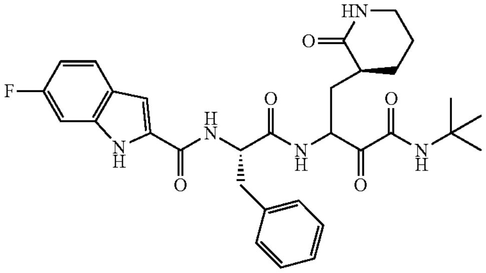 [SMILES: CC(C)(C)NC(=O)C(=O)C(C[C@@H]1CCCNC1=O)NC(=O)[C@H](Cc1ccccc1)NC(=O)c1cc2ccc(F)cc2[nH]1] | N-((S)-1-(((S)-4-(tert-butylamino)-3,4-dione-1-((S)-2-oxopiperidin-3-yl)but-2-yl)amino)-1-oxo-3-phenylpropan-2-yl)-6-fluoro-1H-indole-2-carboxamide |
| A185 | 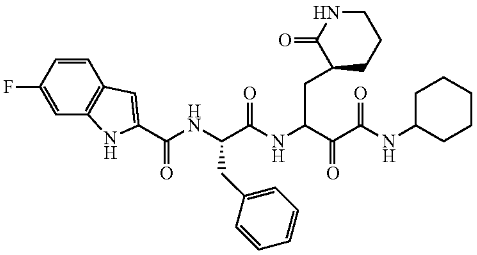 [SMILES: O=C(NC1CCCCC1)C(=O)C(C[C@@H]1CCCNC1=O)NC(=O)[C@H](Cc1ccccc1)NC(=O)c1cc2ccc(F)cc2[nH]1] | N-((S)-1-(((S)-4-(cyclohexylamino)-3,4-dione-1-((S)-2-oxopiperidin-3-yl)but-2-yl)amino)-1-oxo-3-phenylpropan-2-yl)-6-fluoro-1H-indole-2-carboxamide |

-continued

| number | structure | name |
|---|---|---|
| A186 | 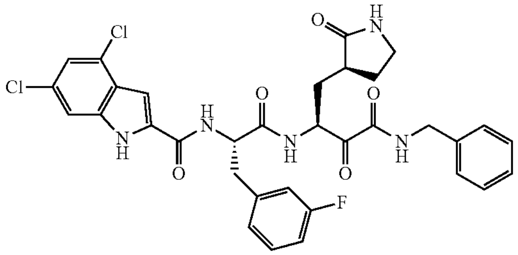 [SMILES: O=C(NCc1ccccc1)C(=O)[C@H](C[C@@H]1CCNC1=O)NC(=O)[C@H](Cc1cccc(F)c1)NC(=O)c1cc2c(Cl)cc(Cl)cc2[nH]1] | N-((S)-1-(((S)-4-(benzylamino)-3,4-dione-1-((S)-2-oxopyrrolidin-3-yl)but-2-yl)amino)-3-(3-fluorophenyl)-1-oxopropan-2-yl)-4,6-dichloro-1H-indole-2-carboxamide |
| A187 | 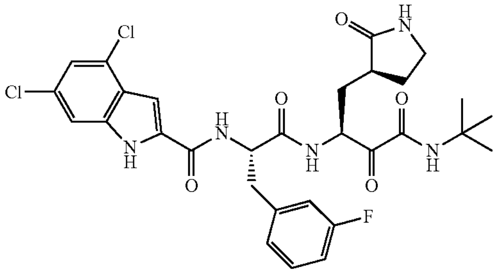 [SMILES: CC(C)(C)NC(=O)C(=O)[C@H](C[C@@H]1CCNC1=O)NC(=O)[C@H](Cc1cccc(F)c1)NC(=O)c1cc2c(Cl)cc(Cl)cc2[nH]1] | N-((S)-1-(((S)-4-(tert-butylamino)-3,4-dione-1-((S)-2-oxopyrrolidin-3-yl)but-2-yl)amino)-3-(3-fluorophenyl)-1-oxopropan-2-yl)-4,6-dichloro-1H-indole-2-carboxamide |
| A188 | 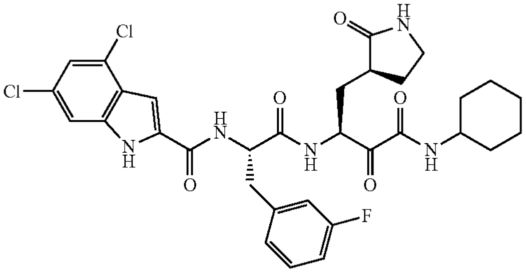 [SMILES: O=C(NC1CCCCC1)C(=O)[C@H](C[C@@H]1CCNC1=O)NC(=O)[C@H](Cc1cccc(F)c1)NC(=O)c1cc2c(Cl)cc(Cl)cc2[nH]1] | N-((S)-1-(((S)-4-(cyclohexylamino)-3,4-dione-1-((S)-2-oxopyrrolidin-3-yl)but-2-yl)amino)-3-(3-fluorophenyl)-1-oxopropan-2-yl)-4,6-dichloro-1H-indole-2-carboxamide |
| A189 | 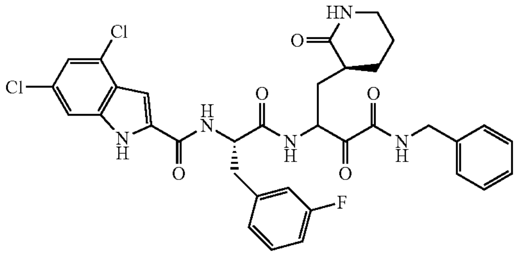 [SMILES: O=C(NCc1ccccc1)C(=O)C(C[C@@H]1CCCNC1=O)NC(=O)[C@H](Cc1cccc(F)c1)NC(=O)c1cc2c(Cl)cc(Cl)cc2[nH]1] | N-((S)-1-(((S)-4-(benzylamino)-3,4-dione-1-((S)-2-oxopiperidin-3-yl)but-2-yl)amino)-3-(3-fluorophenyl)-1-oxopropan-2-yl)-4,6-dichloro-1H-indole-2-carboxamide |
| A190 | 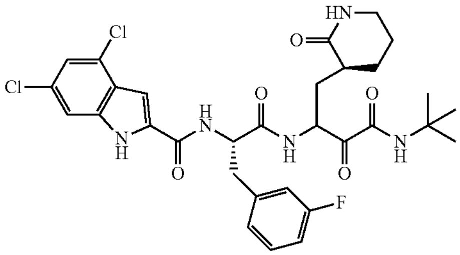 [SMILES: CC(C)(C)NC(=O)C(=O)C(C[C@@H]1CCCNC1=O)NC(=O)[C@H](Cc1cccc(F)c1)NC(=O)c1cc2c(Cl)cc(Cl)cc2[nH]1] | N-((S)-1-(((S)-4-(tert-butylamino)-3,4-dione-1-((S)-2-oxopiperidin-3-yl)but-2-yl)amino)-3-(3-fluorophenyl)-1-oxopropan-2-yl)-4,6-dichloro-1H-indole-2-carboxamide |

-continued

| number | structure | name |
|---|---|---|
| A191 | 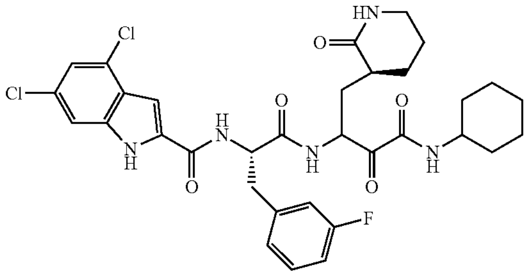 [SMILES: O=C(NC1CCCCC1)C(=O)C(C[C@@H]1CCCNC1=O)NC(=O)[C@H](Cc1cccc(F)c1)NC(=O)c1cc2c(Cl)cc(Cl)cc2[nH]1] | N-((S)-1-(((S)-4-(cyclohexylamino)-3,4-dione-1-((S)-2-oxopiperidin-3-yl)but-2-yl)amino)-3-(3-fluorophenyl)-1-oxopropan-2-yl)-4,6-dichloro-1H-indole-2-carboxamide |
| A192 | 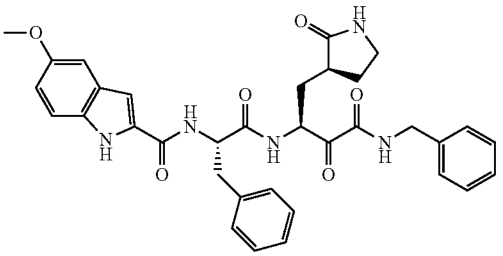 [SMILES: COc1ccc2[nH]c(C(=O)N[C@@H](Cc3ccccc3)C(=O)N[C@@H](C[C@@H]3CCNC3=O)C(=O)C(=O)NCc3ccccc3)cc2c1] | N-((S)-1-(((S)-4-(benzylamino)-3,4-dione-1-((S)-2-oxopyrrolidin-3-yl)but-2-yl)amino)-1-oxo-3-phenylpropan-2-yl)-5-methoxy-1H-indole-2-carboxamide |
| A193 | 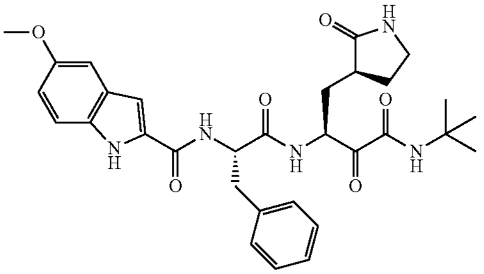 [SMILES: COc1ccc2[nH]c(C(=O)N[C@@H](Cc3ccccc3)C(=O)N[C@@H](C[C@@H]3CCNC3=O)C(=O)C(=O)NC(C)(C)C)cc2c1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-5-methoxy-1H-indole-2-carboxamide |
| A194 | 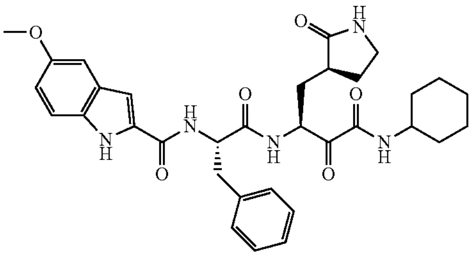 [SMILES: COc1ccc2[nH]c(C(=O)N[C@@H](Cc3ccccc3)C(=O)N[C@@H](C[C@@H]3CCNC3=O)C(=O)C(=O)NC3CCCCC3)cc2c1] | N-((S)-1-(((S)-4-(cyclohexylamino)-3,4-dione-1-((S)-2-oxopyrrolidin-3-yl)but-2-yl)amino)-1-oxo-3-phenylpropan-2-yl)-5-methoxy-1H-indole-2-carboxamide |
| A195 | 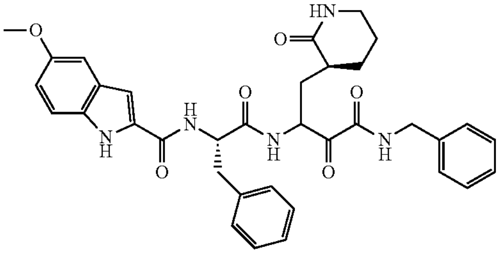 [SMILES: COc1ccc2[nH]c(C(=O)N[C@@H](Cc3ccccc3)C(=O)NC(C[C@@H]3CCCNC3=O)C(=O)C(=O)NCc3ccccc3)cc2c1] | N-((S)-1-(((S)-4-(benzylamino)-3,4-dione-1-((S)-2-oxopiperidin-3-yl)but-2-yl)amino)-1-oxo-3-phenylpropan-2-yl)-5-methoxy-1H-indole-2-carboxamide |

-continued

| number | structure | name |
|---|---|---|
| A196 | 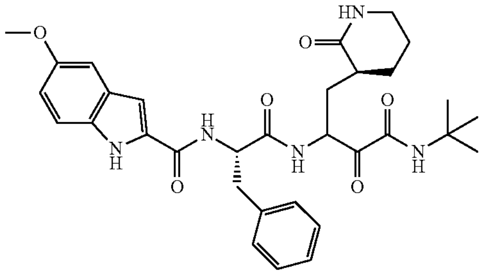 [SMILES: COc1ccc2[nH]c(C(=O)N[C@@H](Cc3ccccc3)C(=O)NC(C[C@@H]3CCCNC3=O)C(=O)C(=O)NC(C)(C)C)cc2c1] | N-((S)-1-(((S)-4-(tert-butylamino)-3,4-dione-1-((S)-2-oxopiperidin-3-yl)but-2-yl)amino)-1-oxo-3-phenylpropan-2-yl)-5-methoxy-1H-indole-2-carboxamide |
| A197 | 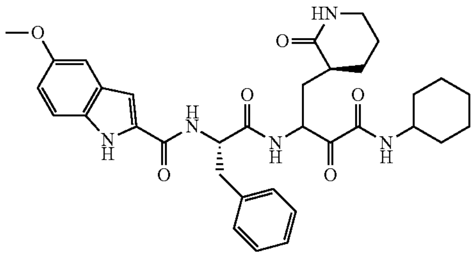 [SMILES: COc1ccc2[nH]c(C(=O)N[C@@H](Cc3ccccc3)C(=O)NC(C[C@@H]3CCCNC3=O)C(=O)C(=O)NC3CCCCC3)cc2c1] | N-((S)-1-(((S)-4-(cyclohexylamino)-3,4-dione-1-((S)-2-oxopiperidin-3-yl)but-2-yl)amino)-1-oxo-3-phenylpropan-2-yl)-5-methoxy-1H-indole-2-carboxamide |
| A198 | 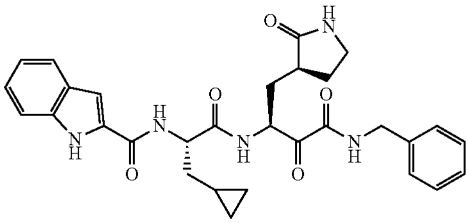 [SMILES: O=C(NCc1ccccc1)C(=O)[C@H](C[C@@H]1CCNC1=O)NC(=O)[C@H](CC1CC1)NC(=O)c1cc2ccccc2[nH]1] | N-((S)-1-(((S)-4-(benzylamino)-3,4-dione-1-((S)-2-oxopyrrolidin-3-yl)but-2-yl)amino)-3-cyclopropyl-1-oxopropan-2-yl)-1H-indole-2-carboxamide |
| A199 | 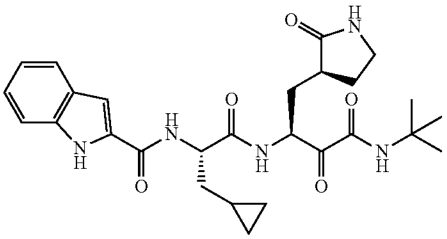 [SMILES: CC(C)(C)NC(=O)C(=O)[C@H](C[C@@H]1CCNC1=O)NC(=O)[C@H](CC1CC1)NC(=O)c1cc2ccccc2[nH]1] | N-((S)-1-(((S)-4-(tert-butylamino)-3,4-dione-1-((S)-2-oxopyrrolidin-3-yl)but-2-yl)amino)-3-cyclopropyl-1-oxopropan-2-yl)-1H-indole-2-carboxamide |
| A200 | 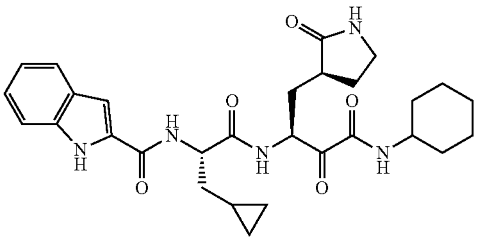 [SMILES: O=C(NC1CCCCC1)C(=O)[C@H](C[C@@H]1CCNC1=O)NC(=O)[C@H](CC1CC1)NC(=O)c1cc2ccccc2[nH]1] | N-((S)-1-(((S)-4-(cyclohexylamino)-3,4-dione-1-((S)-2-oxopyrrolidin-3-yl)but-2-yl)amino)-3-cyclopropyl-1-oxopropan-2-yl)-1H-indole-2-carboxamide |
| A201 | 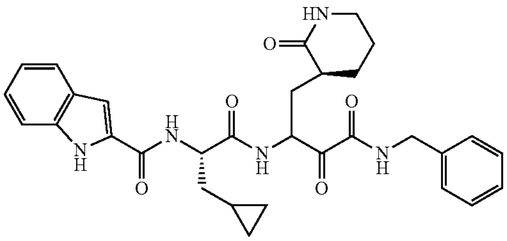 [SMILES: O=C(NCc1ccccc1)C(=O)C(C[C@@H]1CCCNC1=O)NC(=O)[C@H](CC1CC1)NC(=O)c1cc2ccccc2[nH]1] | N-((S)-1-(((S)-4-(cyclohexylamino)-3,4-dione-1-((S)-2-oxopiperidin-3-yl)but-2-yl)amino)-3-cyclopropyl-1-oxopropan-2-yl)-1H-indole-2-carboxamide |

-continued

| number | structure | name |
|---|---|---|
| A202 | 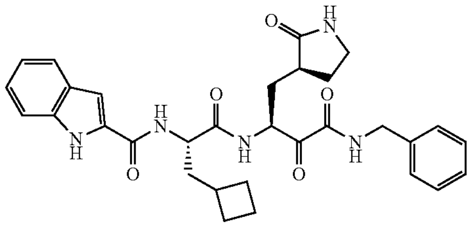 [SMILES: O=C(NCc1ccccc1)C(=O)[C@H](C[C@@H]1CCNC1=O)NC(=O)[C@H](CC1CCC1)NC(=O)c1cc2ccccc2[nH]1] | N-((S)-1-(((S)-4-(benzylamino)-3,4-dione-1-((S)-2-oxopyrrolidin-3-yl)but-2-yl)amino)-3-cyclobutyl-1-oxopropan-2-yl)-1H-indole-2-carboxamide |
| A203 | 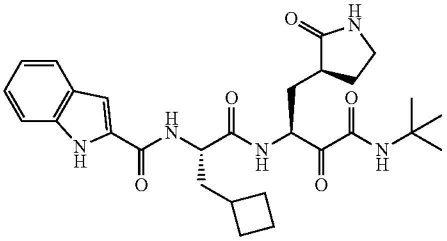 [SMILES: CC(C)(C)NC(=O)C(=O)[C@H](C[C@@H]1CCNC1=O)NC(=O)[C@H](CC1CCC1)NC(=O)c1cc2ccccc2[nH]1] | N-((S)-1-(((S)-4-(tert-butylamino)-3,4-dione-1-((S)-2-oxopyrrolidin-3-yl)but-2-yl)amino)-3-cyclobutyl-1-oxopropan-2-yl)-1H-indole-2-carboxamide |
| A204 | 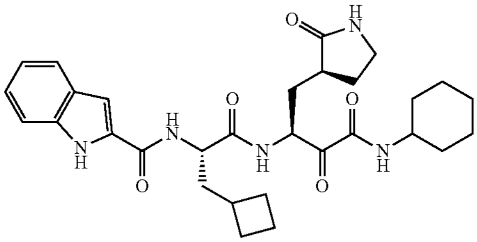 [SMILES: O=C(NC1CCCCC1)C(=O)[C@H](C[C@@H]1CCNC1=O)NC(=O)[C@H](CC1CCC1)NC(=O)c1cc2ccccc2[nH]1] | N-((S)-1-(((S)-4-(cyclohexylamino)-3,4-dione-1-((S)-2-oxopyrrolidin-3-yl)but-2-yl)amino)-3-cyclobutyl-1-oxopropan-2-yl)-1H-indole-2-carboxamide |
| A205 | 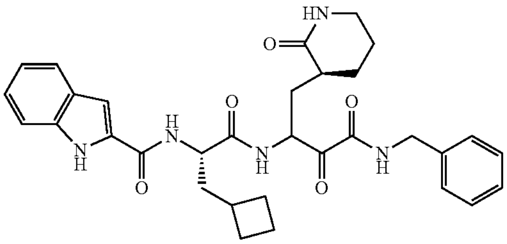 [SMILES: O=C(NCc1ccccc1)C(=O)C(C[C@@H]1CCCNC1=O)NC(=O)[C@H](CC1CCC1)NC(=O)c1cc2ccccc2[nH]1] | N-((S)-1-(((S)-4-(benzylamino)-3,4-dione-1-((S)-2-oxopiperidin-3-yl)but-2-yl)amino)-3-cyclobutyl-1-oxopropan-2-yl)-1H-indole-2-carboxamide |
| A206 | 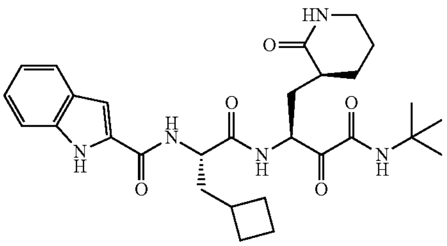 [SMILES: CC(C)(C)NC(=O)C(=O)[C@H](C[C@@H]1CCCNC1=O)NC(=O)[C@H](CC1CCC1)NC(=O)c1cc2ccccc2[nH]1] | N-((S)-1-(((S)-4-(tert-butylamino)-3,4-dione-1-((S)-2-oxopiperidin-3-yl)but-2-yl)amino)-3-cyclobutyl-1-oxopropan-2-yl)-1H-indole-2-carboxamide |
| A207 | 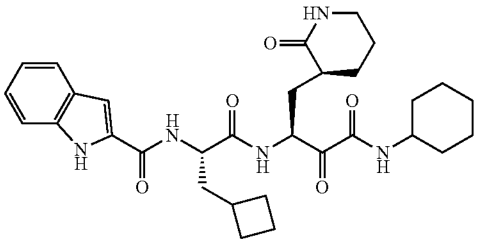 [SMILES: O=C(NC1CCCCC1)C(=O)[C@H](C[C@@H]1CCCNC1=O)NC(=O)[C@H](CC1CCC1)NC(=O)c1cc2ccccc2[nH]1] | N-((S)-1-(((S)-4-(cyclohexylamino)-3,4-dione-1-((S)-2-oxopiperidin-3-yl)but-2-yl)amino)-3-cyclobutyl-1-oxopropan-2-yl)-1H-indole-2-carboxamide |

-continued

| number | structure | name |
|---|---|---|
| A208 | 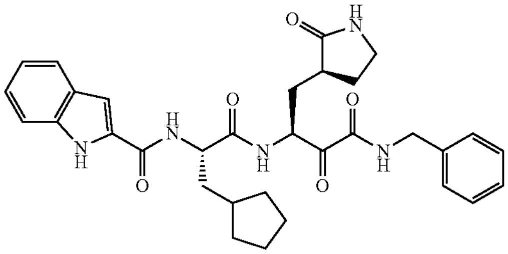 [SMILES: O=C(NCc1ccccc1)C(=O)[C@H](C[C@@H]1CCNC1=O)NC(=O)[C@H](CC1CCCC1)NC(=O)c1cc2ccccc2[nH]1] | N-((S)-1-(((S)-4-(benzylamino)-3,4-dione-1-((S)-2-oxopyrrolidin-3-yl)but-2-yl)amino)-3-cyclopentyl-1-oxopropan-2-yl)-1H-indole-2-carboxamide |
| A209 | 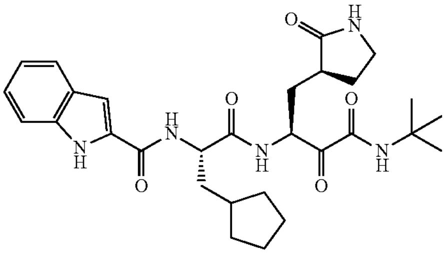 [SMILES: CC(C)(C)NC(=O)C(=O)[C@H](C[C@@H]1CCNC1=O)NC(=O)[C@H](CC1CCCC1)NC(=O)c1cc2ccccc2[nH]1] | N-((S)-1-(((S)-4-(tert-butylamino)-3,4-dione-1-((S)-2-oxopyrrolidin-3-yl)but-2-yl)amino)-3-cyclopentyl-1-oxopropan-2-yl)-1H-indole-2-carboxamide |
| A210 | 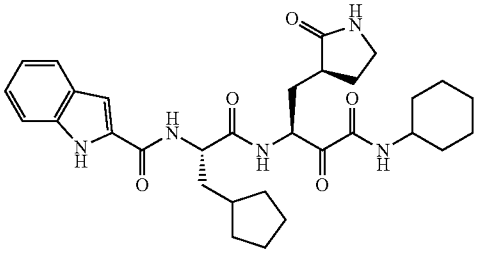 [SMILES: O=C(NC1CCCCC1)C(=O)[C@H](C[C@@H]1CCNC1=O)NC(=O)[C@H](CC1CCCC1)NC(=O)c1cc2ccccc2[nH]1] | N-((S)-1-(((S)-4-(cyclohexylamino)-3,4-dione-1-((S)-2-oxopyrrolidin-3-yl)but-2-yl)amino)-3-cyclopentyl-1-oxopropan-2-yl)-1H-indole-2-carboxamide |
| A211 | 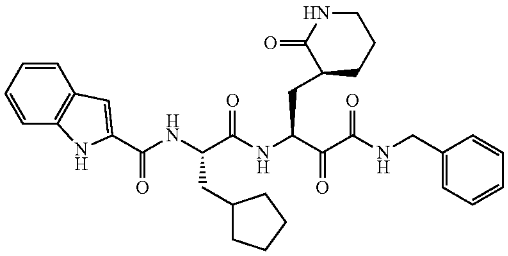 [SMILES: O=C(NCc1ccccc1)C(=O)[C@H](C[C@@H]1CCCNC1=O)NC(=O)[C@H](CC1CCCC1)NC(=O)c1cc2ccccc2[nH]1] | N-((S)-1-(((S)-4-(benzylamino)-3,4-dione-1-((S)-2-oxopiperidin-3-yl)but-2-yl)amino)-3-cyclopentyl-1-oxopropan-2-yl)-1H-indole-2-carboxamide |
| A212 | 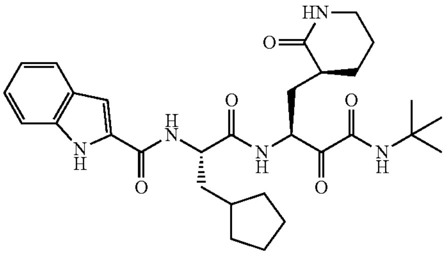 [SMILES: CC(C)(C)NC(=O)C(=O)[C@H](C[C@@H]1CCCNC1=O)NC(=O)[C@H](CC1CCCC1)NC(=O)c1cc2ccccc2[nH]1] | N-((S)-1-(((S)-4-(tert-butylamino)-3,4-dione-1-((S)-2-oxopiperidin-3-yl)but-2-yl)amino)-3-cyclopentyl-1-oxopropan-2-yl)-1H-indole-2-carboxamide |
| A213 | 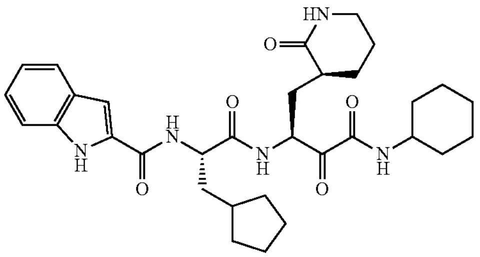 [SMILES: O=C(NC1CCCCC1)C(=O)[C@H](C[C@@H]1CCCNC1=O)NC(=O)[C@H](CC1CCCC1)NC(=O)c1cc2ccccc2[nH]1] | N-((S)-1-(((S)-4-(cyclohexylamino)-3,4-dione-1-((S)-2-oxopiperidin-3-yl)but-2-yl)amino)-3-cyclopentyl-1-oxopropan-2-yl)-1H-indole-2-carboxamide |

-continued

| number | structure | name |
|---|---|---|
| A214 | 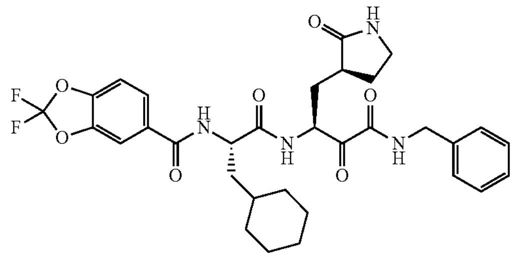 [SMILES: O=C(NCc1ccccc1)C(=O)[C@H](C[C@@H]1CCNC1=O)NC(=O)[C@H](CC1CCCCC1)NC(=O)c1ccc2c(c1)OC(F)(F)O2] | N-((S)-1-(((S)-4-(benzylamino)-3,4-dione-1-((S)-2-oxopyrrolidin-3-yl)but-2-yl)amino)-3-cyclohexyl-1-oxopropan-2-yl)-2,2-difluorobenzo[d][1,3]dioxol-5-carboxamide |
| A215 | 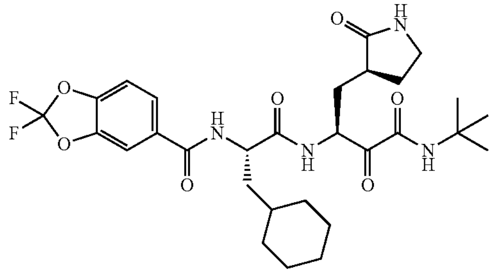 [SMILES: CC(C)(C)NC(=O)C(=O)[C@H](C[C@@H]1CCNC1=O)NC(=O)[C@H](CC1CCCCC1)NC(=O)c1ccc2c(c1)OC(F)(F)O2] | N-((S)-1-(((S)-4-(tert-butylamino)-3,4-dione-1-((S)-2-oxopyrrolidin-3-yl)but-2-yl)amino)-3-cyclohexyl-1-oxopropan-2-yl)-2,2-difluorobenzo[d][l,3]dioxol-5-carboxamide |
| A216 | 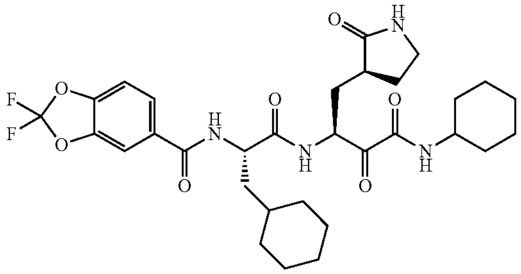 [SMILES: O=C(NC1CCCCC1)C(=O)[C@H](C[C@@H]1CCNC1=O)NC(=O)[C@H](CC1CCCCC1)NC(=O)c1ccc2c(c1)OC(F)(F)O2] | N-((S)-1-(((S)-4-(cyclohexylamino)-3,4-dione-1-((S)-2-oxopyrrolidin-3-yl)but-2-yl)amino)-3-cyclohexyl-1-oxopropan-2-yl)-2,2-difluorobenzo[d][l,3]dioxol-5-carboxamide |
| A217 | 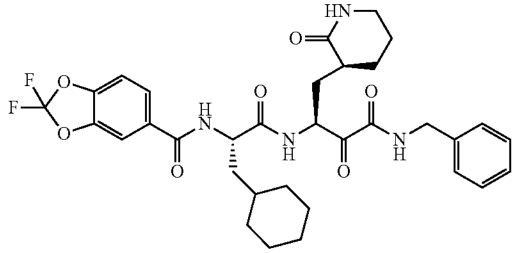 [SMILES: O=C(NCc1ccccc1)C(=O)[C@H](C[C@@H]1CCCNC1=O)NC(=O)[C@H](CC1CCCCC1)NC(=O)c1ccc2c(c1)OC(F)(F)O2] | N-((S)-1-(((S)-4-(benzylamino)-3,4-dione-1-((S)-2-oxopiperidin-3-yl)but-2-yl)amino)-3-cyclohexyl-1-oxopropan-2-yl)-2,2-difluorobenzo[d][l,3]dioxol-5-carboxamide |
| A218 | 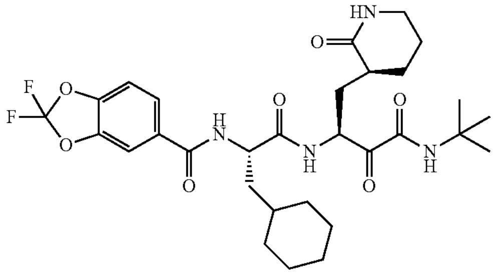 [SMILES: CC(C)(C)NC(=O)C(=O)[C@H](C[C@@H]1CCCNC1=O)NC(=O)[C@H](CC1CCCCC1)NC(=O)c1ccc2c(c1)OC(F)(F)O2] | N-((S)-1-(((S)-4-(tert-butylamino)-3,4-dione-1-((S)-2-oxopiperidin-3-yl)but-2-yl)amino)-3-cyclohexyl-1-oxopropan-2-yl)-2,2-difluorobenzo[d][l,3]dioxol-5-carboxamide |

-continued

| number | structure | name |
|---|---|---|
| A219 | 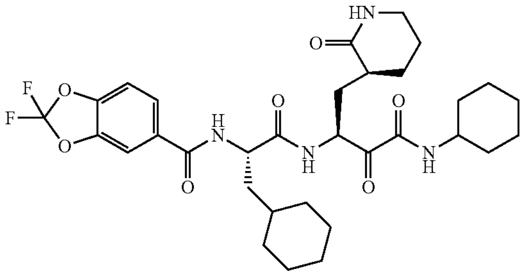 [SMILES: O=C(NC1CCCCC1)C(=O)[C@H](C[C@@H]1CCCNC1=O)NC(=O)[C@H](CC1CCCCC1)NC(=O)c1ccc2c(c1)OC(F)(F)O2] | N-((S)-1-(((S)-4-(cyclohexylamino)-3,4-dione-1-((S)-2-oxopiperidin-3-yl)but-2-yl)amino)-3-cyclohexyl-1-oxopropan-2-yl)-2,2-difluorobenzo[d][1,3]dioxol-5-carboxamide |
| A220 | 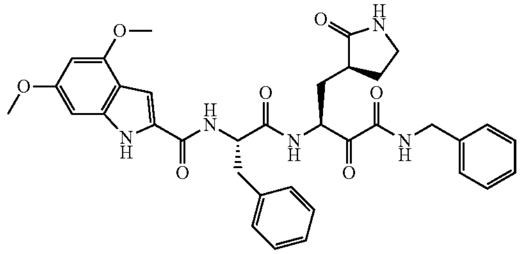 [SMILES: COc1cc(OC)c2cc(C(=O)N[C@@H](Cc3ccccc3)C(=O)N[C@@H](C[C@@H]3CCNC3=O)C(=O)C(=O)NCc3ccccc3)[nH]c2c1] | N-((S)-1-(((S)-4-(benzylamino)-3,4-dione-1-((S)-2-oxopyrrolidin-3-yl)but-2-yl)amino)-1-oxo-3-phenylpropan-2-yl)-4,6-dimethoxy-1H-indole-2-carboxamide |
| A221 | 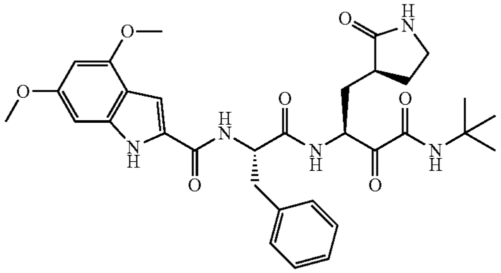 [SMILES: COc1cc(OC)c2cc(C(=O)N[C@@H](Cc3ccccc3)C(=O)N[C@@H](C[C@@H]3CCNC3=O)C(=O)C(=O)NC(C)(C)C)[nH]c2c1] | N-((S)-1-(((S)-4-(tert-butylamino)-3,4-dione-1-((S)-2-oxopyrrolidin-3-yl)but-2-yl)amino)-1-oxo-3-phenylpropan-2-yl)-4,6-dimethoxy-1H-indole-2-carboxamide |
| A222 | 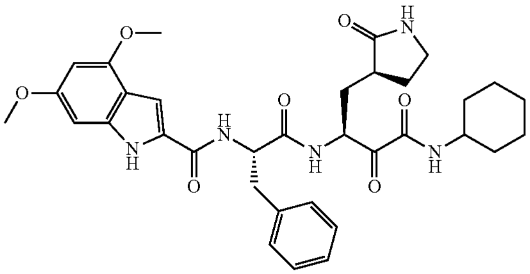 [SMILES: COc1cc(OC)c2cc(C(=O)N[C@@H](Cc3ccccc3)C(=O)N[C@@H](C[C@@H]3CCNC3=O)C(=O)C(=O)NC3CCCCC3)[nH]c2c1] | N-((S)-1-(((S)-4-(cyclohexylamino)-3,4-dione-1-((S)-2-oxopyrrolidin-3-yl)but-2-yl)amino)-1-oxo-3-phenylpropan-2-yl)-4,6-dimethoxy-1H-indole-2-carboxamide |
| A223 | 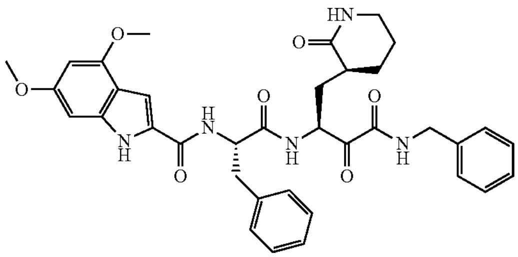 [SMILES: COc1cc(OC)c2cc(C(=O)N[C@@H](Cc3ccccc3)C(=O)N[C@@H](C[C@@H]3CCCNC3=O)C(=O)C(=O)NCc3ccccc3)[nH]c2c1] | N-((S)-1-(((S)-4-(benzylamino)-3,4-dione-1-((S)-2-oxopiperidin-3-yl)but-2-yl)amino)-1-oxo-3-phenylpropan-2-yl)-4,6-dimethoxy-1H-indole-2-carboxamide |

-continued

| number | structure | name |
|---|---|---|
| A224 | 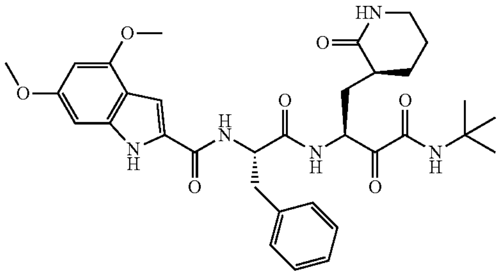 [SMILES: COc1cc(OC)c2cc(C(=O)N[C@@H](Cc3ccccc3)C(=O)N[C@@H](C[C@@H]3CCCNC3=O)C(=O)C(=O)NC(C)(C)C)[nH]c2c1] | N-((S)-1-(((S)-4-(tert-butylamino)-3,4-dione-1-((S)-2-oxopiperidin-3-yl)but-2-yl)amino)-1-oxo-3-phenylpropan-2-yl)-4,6-dimethoxy-1H-indole-2-carboxamide |
| A225 | 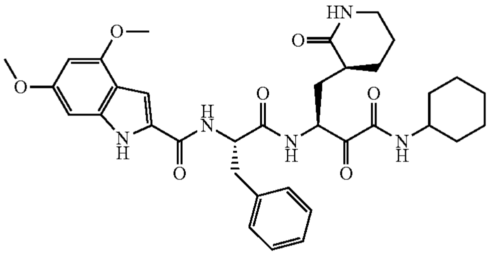 [SMILES: COc1cc(OC)c2cc(C(=O)N[C@@H](Cc3ccccc3)C(=O)N[C@@H](C[C@@H]3CCCNC3=O)C(=O)C(=O)NC3CCCCC3)[nH]c2c1] | N-((S)-1-(((S)-4-(cyclohexylamino)-3,4-dione-1-((S)-2-oxopiperidin-3-yl)but-2-yl)amino)-1-oxo-3-phenylpropan-2-yl)-4,6-dimethoxy-1H-indole-2-carboxamide |
| A226 | 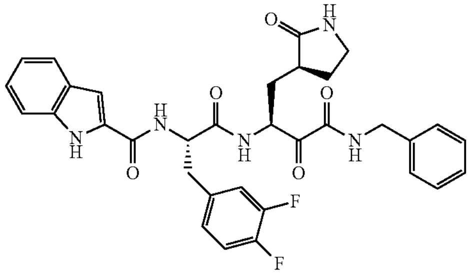 [SMILES: O=C(NCc1ccccc1)C(=O)[C@H](C[C@@H]1CCNC1=O)NC(=O)[C@H](Cc1ccc(F)c(F)c1)NC(=O)c1cc2ccccc2[nH]1] | N-((S)-1-(((S)-4-(benzylamino)-3,4-dione-1-((S)-2-oxopyrrolidin-3-yl)but-2-yl)amino)-3-(3,4-difluorophenyl)-1-oxopropan-2-yl)-1H-indole-2-carboxamide |
| A227 | 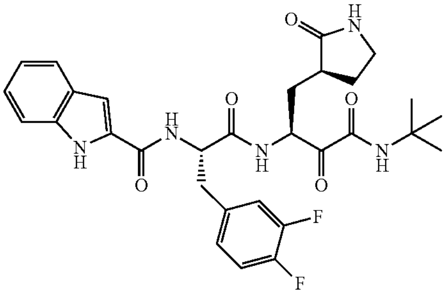 [SMILES: CC(C)(C)NC(=O)C(=O)[C@H](C[C@@H]1CCNC1=O)NC(=O)[C@H](Cc1ccc(F)c(F)c1)NC(=O)c1cc2ccccc2[nH]1] | N-((S)-1-(((S)-4-(tert-butylamino)-3,4-dione-1-((S)-2-oxopyrrolidin-3-yl)but-2-yl)amino)-3-(3,4-difluorophenyl)-1-oxopropan-2-yl)-1H-indole-2-carboxamide |
| A228 | 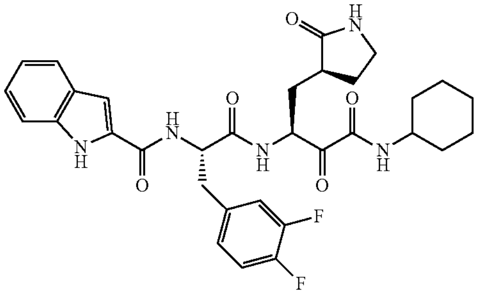 [SMILES: O=C(NC1CCCCC1)C(=O)[C@H](C[C@@H]1CCNC1=O)NC(=O)[C@H](Cc1ccc(F)c(F)c1)NC(=O)c1cc2ccccc2[nH]1] | N-((S)-1-(((S)-4-(cyclohexylamino)-3,4-dione-1-((S)-2-oxopyrrolidin-3-yl)but-2-yl)amino)-3-(3,4-difluorophenyl)-1-oxopropan-2-yl)-1H-indole-2-carboxamide |

-continued

| number | structure | name |
| --- | --- | --- |
| A229 | 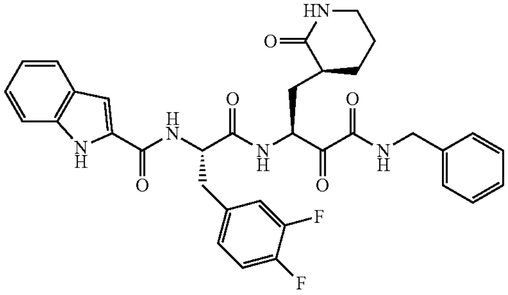 [SMILES: O=C(NCc1ccccc1)C(=O)[C@H](C[C@@H]1CCCNC1=O)NC(=O)[C@H](Cc1ccc(F)c(F)c1)NC(=O)c1cc2ccccc2[nH]1] | N-((S)-1-(((S)-4-(benzylamino)-3,4-dione-1-((S)-2-oxopiperidin-3-yl)but-2-yl)amino)-3-(3,4-difluorophenyl)-1-oxopropan-2-yl)-1H-indole-2-carboxamide |
| A230 | 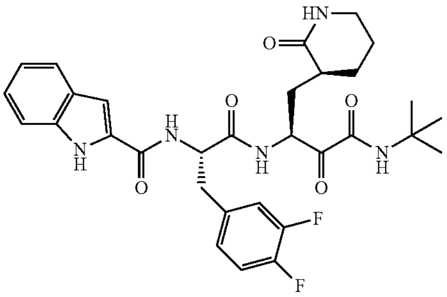 [SMILES: CC(C)(C)NC(=O)C(=O)[C@H](C[C@@H]1CCCNC1=O)NC(=O)[C@H](Cc1ccc(F)c(F)c1)NC(=O)c1cc2ccccc2[nH]1] | N-((S)-1-(((S)-4-(tert-butylamino)-3,4-dione-1-((S)-2-oxopiperidin-3-yl)but-2-yl)amino)-3-(3,4-difluorophenyl)-1-oxopropan-2-yl)-1H-indole-2-carboxamide |
| A231 | 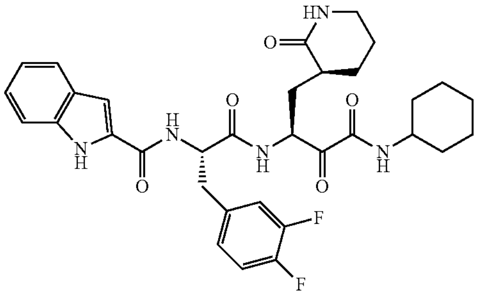 [SMILES: O=C(NC1CCCCC1)C(=O)[C@H](C[C@@H]1CCCNC1=O)NC(=O)[C@H](Cc1ccc(F)c(F)c1)NC(=O)c1cc2ccccc2[nH]1] | N-((S)-1-(((S)-4-(cyclohexylamino)-3,4-dione-1-((S)-2-oxopiperidin-3-yl)but-2-yl)amino)-3-(3,4-difluorophenyl)-1-oxopropan-2-yl)-1H-indole-2-carboxamide |
| A232 | 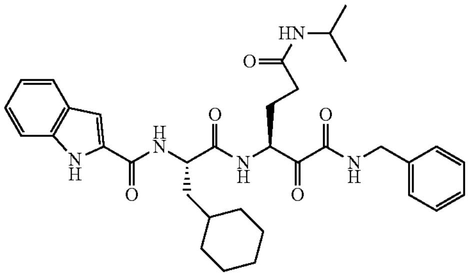 [SMILES: CC(C)NC(=O)CC[C@H](NC(=O)[C@H](CC1CCCCC1)NC(=O)c1cc2ccccc2[nH]1)C(=O)C(=O)NCc1ccccc1] | N-((S)-1-(((S)-4-(benzyl)-3,4-dione-1-(isopropylamino)-2-yl)amino)-3-(cyclohexyl)-1-oxopropan-2-yl)-1H-indole-2-carboxamide |
| A233 | 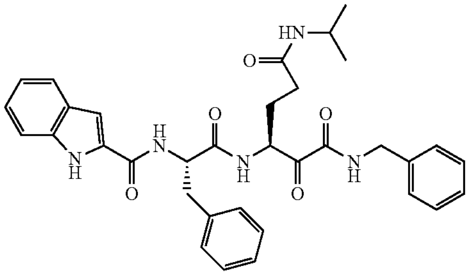 [SMILES: CC(C)NC(=O)CC[C@H](NC(=O)[C@H](Cc1ccccc1)NC(=O)c1cc2ccccc2[nH]1)C(=O)C(=O)NCc1ccccc1] | N-((S)-1-(((S)-4-(benzyl)-3,4-dione-1-(isopropylamino)-2-yl)amino)-3-(phenyl)-1-oxopropan-2-yl)-1H-indole-2-carboxamide |

-continued

| number | structure | name |
|---|---|---|
| A234 | 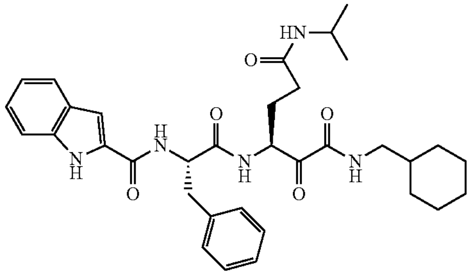 [SMILES: CC(C)NC(=O)CC[C@H](NC(=O)[C@H](Cc1ccccc1)NC(=O)c1cc2ccccc2[nH]1)C(=O)C(=O)NCC1CCCCC1] | N-((S)-1-(((S)-4-(cyclohexyl)-3,4-dione-1-(isopropylamino)-2-yl)amino)-3-(phenyl)-1-oxopropan-2-yl)-1H-indole-2-carboxamide |
| A235 | 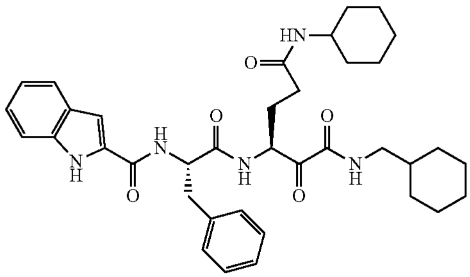 [SMILES: O=C(CC[C@H](NC(=O)[C@H](Cc1ccccc1)NC(=O)c1cc2ccccc2[nH]1)C(=O)C(=O)NCC1CCCCC1)NC1CCCCC1] | N-((S)-1-(((S)-4-(cyclohexyl)-3,4-dione-1-(cyclohexylamino)-2-yl)amino)-3-(phenyl)-1-oxopropan-2-yl)-1H-indole-2-carboxamide |
| A236 | 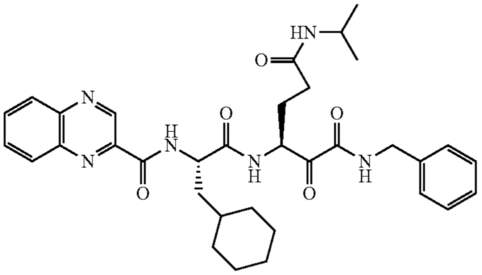 | N-((S)-1-(((S)-4-(benzyl)-3,4-dione-1-(isopropylamino)-2-yl)amino)-3-(cyclohexyl)-1-oxopropan-2-yl)-quinoxaline-2-carboxamide |
| A237 | 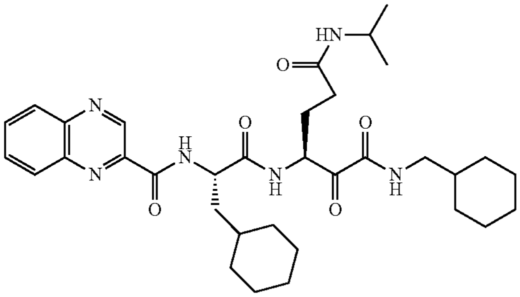 [SMILES: CC(C)NC(=O)CC[C@H](NC(=O)[C@H](CC1CCCCC1)NC(=O)c1cnc2ccccc2n1)C(=O)C(=O)NCC1CCCCC1] | N-((S)-1-(((S)-4-(cyclohexyl)-3,4-dione-1-(isopropylamino)-2-yl)amino)-3-(cyclohexyl)-1-oxopropan-2-yl)-quinoxaline-2-carboxamide |
| A238 | 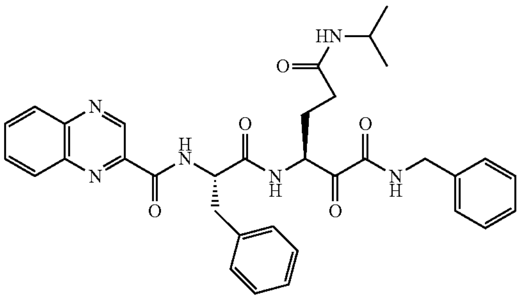 [SMILES: CC(C)NC(=O)CC[C@H](NC(=O)[C@H](Cc1ccccc1)NC(=O)c1cnc2ccccc2n1)C(=O)C(=O)NCc1ccccc1] | N-((S)-1-(((S)-4-(benzyl)-3,4-dione-1-(isopropylamino)-2-yl)amino)-3-(phenyl)-1-oxopropan-2-yl)-quinoxaline-2-carboxamide |

-continued

| number | structure | name |
|---|---|---|
| A239 | 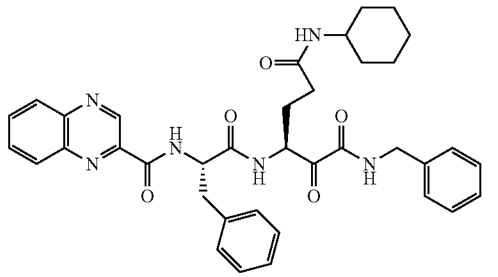 [SMILES: O=C(CC[C@H](NC(=O)[C@H](Cc1ccccc1)NC(=O)c1cnc2ccccc2n1)C(=O)C(=O)NCc1ccccc1)NC1CCCCC1] | N-((S)-1-(((S)-4-(benzyl)-3,4-dione-1-(cyclohexylamino)-2-yl)amino)-3-(phenyl)-1-oxopropan-2-yl)-quinoxaline-2-carboxamide |
| A240 | 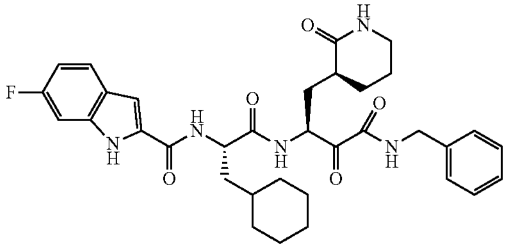 [SMILES: O=C(NCc1ccccc1)C(=O)[C@H](C[C@@H]1CCCNC1=O)NC(=O)[C@H](CC1CCCCC1)NC(=O)c1cc2ccc(F)cc2[nH]1] | N-((S)-1-(((S)-4-(benzylamino)-3,4-dione-1-((S)-2-oxopiperidin-3-yl)but-2-yl)amino)-3-cyclohexyl-1-oxopropan-2-yl)-1H-indole-6-fluoro-2-carboxamide |
| A241 | 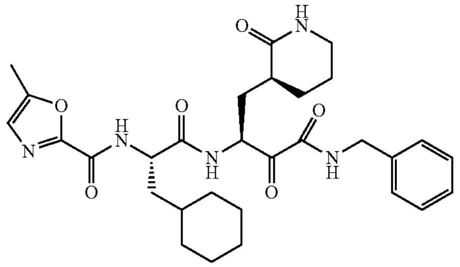 [SMILES: Cc1cnc(C(=O)N[C@@H](CC2CCCCC2)C(=O)N[C@@H](C[C@@H]2CCCNC2=O)C(=O)C(=O)NCc2ccccc2)o1] | N-((S)-1-(((S)-4-(benzylamino)-3,4-dione-1-((S)-2-oxopiperidin-3-yl)but-2-yl)amino)-3-cyclohexyl-1-oxopropan-2-yl)-5-methyloxazole-2-carboxamide |
| A242 | 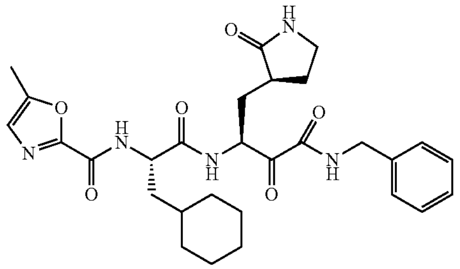 [SMILES: Cc1cnc(C(=O)N[C@@H](CC2CCCCC2)C(=O)N[C@@H](C[C@@H]2CCNC2=O)C(=O)C(=O)NCc2ccccc2)o1] | N-((S)-1-(((S)-4-(benzylamino)-3,4-dione-1-((S)-2-oxopyrrolidin-3-yl)but-2-yl)amino)-3-cyclohexyl-1-oxopropan-2-yl)-5-methyloxazole-2-carboxamide |
| A243 | 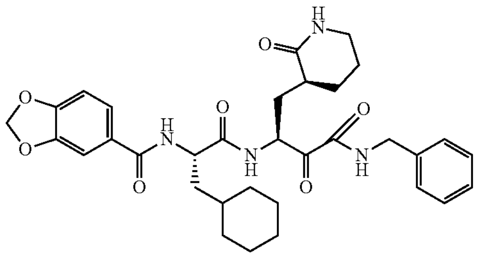 [SMILES: O=C(NCc1ccccc1)C(=O)[C@H](C[C@@H]1CCCNC1=O)NC(=O)[C@H](CC1CCCCC1)NC(=O)c1ccc2c(c1)OCO2] | N-((S)-1-(((S)-4-(benzylamino)-3,4-dione-1-((S)-2-oxopiperidin-3-yl)but-2-yl)amino)-3-cyclohexyl-1-oxopropan-2-yl)-benzo[d]1,3-dioxole-5-carboxamide |

-continued

| number | structure | name |
|---|---|---|
| A244 | 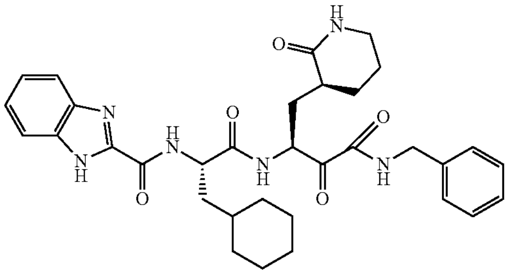 [SMILES: O=C(NCc1ccccc1)C(=O)[C@H](C[C@@H]1CCCNC1=O)NC(=O)[C@H](CC1CCCCC1)NC(=O)c1nc2ccccc2[nH]1] | N-((S)-1-(((S)-4-(benzylamino)-3,4-dione-1-((S)-2-oxopiperidin-3-yl)but-2-yl)amino)-3-cyclohexyl-1-oxopropan-2-yl)-1H-benzo[d]imidazole-2-carboxamide |
| A245 | 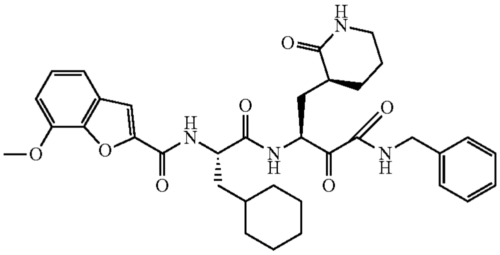 [SMILES: COc1cccc2cc(C(=O)N[C@@H](CC3CCCCC3)C(=O)N[C@@H](C[C@@H]3CCCNC3=O)C(=O)C(=O)NCc3ccccc3)oc12] | N-((S)-1-(((S)-4-(benzylamino)-3,4-dione-1-((S)-2-oxopiperidin-3-yl)but-2-yl)amino)-3-cyclohexyl-1-oxopropan-2-yl)-7-methoxy-benzofuran-2-carboxamide |
| A246 | 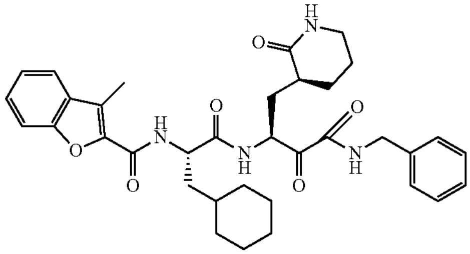 [SMILES: Cc1c(C(=O)N[C@@H](CC2CCCCC2)C(=O)N[C@@H](C[C@@H]2CCCNC2=O)C(=O)C(=O)NCc2ccccc2)oc2ccccc12] | N-((S)-1-(((S)-4-(benzylamino)-3,4-dione-1-((S)-2-oxopiperidin-3-yl)but-2-yl)amino)-3-cyclohexyl-1-oxopropan-2-yl)-3-methyl-benzofuran-2-carboxamide |
| A247 | 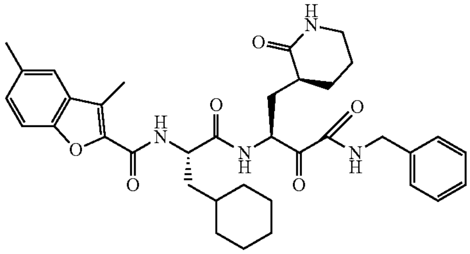 [SMILES: Cc1ccc2oc(C(=O)N[C@@H](CC3CCCCC3)C(=O)N[C@@H](C[C@@H]3CCCNC3=O)C(=O)C(=O)NCc3ccccc3)c(C)c2c1] | N-((S)-1-(((S)-4-(benzylamino)-3,4-dione-1-((S)-2-oxopiperidin-3-yl)but-2-yl)amino)-3-cyclohexyl-1-oxopropan-2-yl)-3,5-dimethyl-benzofuran-2-carboxamide |
| A248 | 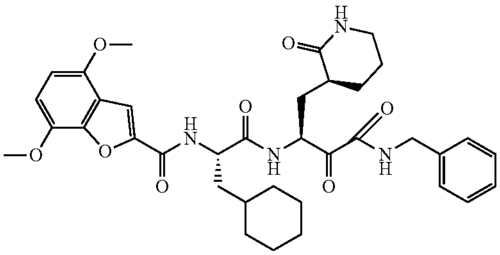 [SMILES: COc1ccc(OC)c2oc(C(=O)N[C@@H](CC3CCCCC3)C(=O)N[C@@H](C[C@@H]3CCCNC3=O)C(=O)C(=O)NCc3ccccc3)cc12] | N-((S)-1-(((S)-4-(benzylamino)-3,4-dione-1-((S)-2-oxopiperidin-3-yl)but-2-yl)amino)-3-cyclohexyl-1-oxopropan-2-yl)-4,7-dimethoxy-benzofuran-2-carboxamide |

-continued

| number | structure | name |
|---|---|---|
| A249 | 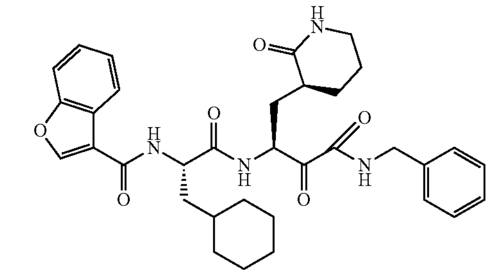 [SMILES: O=C(NCc1ccccc1)C(=O)[C@H](C[C@@H]1CCCNC1=O)NC(=O)[C@H](CC1CCCCC1)NC(=O)c1coc2ccccc12] | N-((S)-1-(((S)-4-(benzylamino)-3,4-dione-1-((S)-2-oxopiperidin-3-yl)but-2-yl)amino)-3-cyclohexyl-1-oxopropan-2-yl)-benzofuran-3-carboxamide |
| A250 | 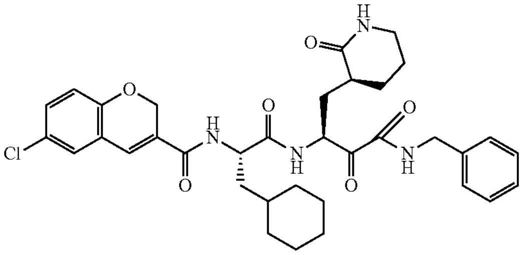 [SMILES: O=C(NCc1ccccc1)C(=O)[C@H](C[C@@H]1CCCNC1=O)NC(=O)[C@H](CC1CCCCC1)NC(=O)C1=Cc2cc(Cl)ccc2OC1] | N-((S)--(((S)-4-(benzylamino)-3,4-dione-1-((S)-2-oxopiperidin-3-yl)but-2-yl)amino)-3-cyclohexyl-1-oxopropan-2-yl)-6-chloro-2H-chromene-3-carboxamide |
| A251 | 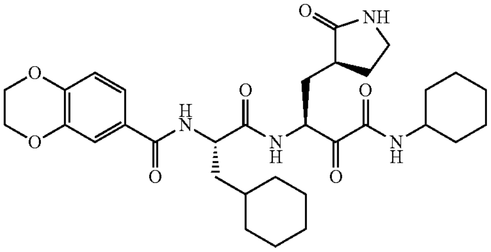 | N-((S)-1-(((S)-4-(cyclohexylamino)-3,4-dione-1-((S)-2-oxopyrrolidin-3-yl)but-2-yl)amino)-3-cyclohexyl-1-oxopropan-2-yl)-2,3-dihydrobenzo[b]1,4-dioxin-6-carboxamide |
| A252 | 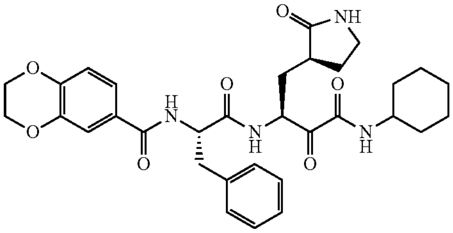 [SMILES: O=C(NC1CCCCC1)C(=O)[C@H](C[C@@H]1CCNC1=O)NC(=O)[C@H](Cc1ccccc1)NC(=O)c1ccc2c(c1)OCCO2] | N-((S)-1-(((S)-4-(cyclohexylamino)-3,4-dione-1-((S)-2-oxopyrrolidin-3-yl)but-2-yl)amino)-3-phenyl-1-oxopropan-2-yl)-2,3-dihydrobenzo[b]1,4-dioxin-6-carboxamide |
| A253 | 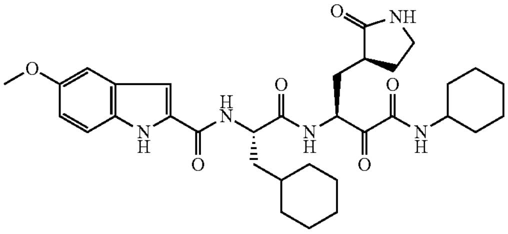 [SMILES: COc1ccc2[nH]c(C(=O)N[C@@H](CC3CCCCC3)C(=O)N[C@@H](C[C@@H]3CCNC3=O)C(=O)C(=O)NC3CCCCC3)cc2c1] | N-((S)-1-(((S)-4-(cyclohexylamino)-3,4-dione-1-((S)-2-oxopyrrolidin-3-yl)but-2-yl)amino)-3-cyclohexyl-1-oxopropan-2-yl)-5-methoxyindol-6-carboxamide |
| A254 | 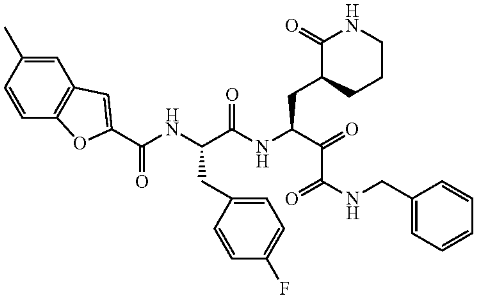 [SMILES: Cc1ccc2oc(C(=O)N[C@@H](Cc3ccc(F)cc3)C(=O)N[C@@H](C[C@@H]3CCCNC3=O)C(=O)C(=O)NCc3ccccc3)cc2c1] | N-((S)-1-(((S)-4-(benzylamino)-3,4-dione-1-((S)-2-oxopiperidin-3-yl)but-2-yl)amino)-3-4-fluorophenyl-1-oxopropan-2-yl)-5-methyl-benzofuran-2-carboxamide |

-continued

| number | structure | name |
| --- | --- | --- |
| A255 | 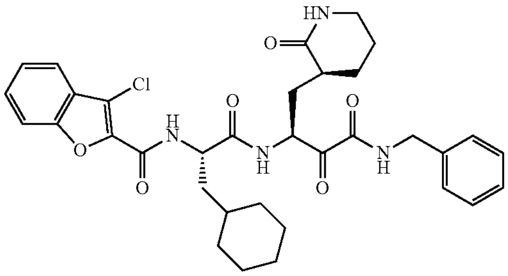 [SMILES: O=C(NCc1ccccc1)C(=O)[C@H](C[C@@H]1CCCNC1=O)NC(=O)[C@H](CC1CCCCC1)NC(=O)c1oc2ccccc2c1Cl] | N-((S)-1-(((S)-4-(benzylamino)-3, 4-dione-1-((S)-2-oxopiperidin-3-yl) but-2-yl) amino)-3-cyclohexyl-1-oxopropan-2-yl)-3-chioro-benzofuran-2-carboxamide |
| A256 | 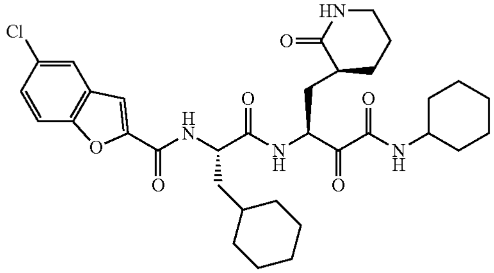 [SMILES: O=C(NC1CCCCC1)C(=O)[C@H](C[C@@H]1CCCNC1=O)NC(=O)[C@H](CC1CCCCC1)NC(=O)c1cc2cc(Cl)ccc2o1] | N-((S)-1-(((S)-4-(cyclohexylamino)-3, 4-dione-1-((S)-2-oxopiperidin-3-yl) but-2-yl) amino)-3-cyclohexyl-1-oxopropan-2-yl)-5-chloro-benzofuran-2-carboxamide |
| A257 | 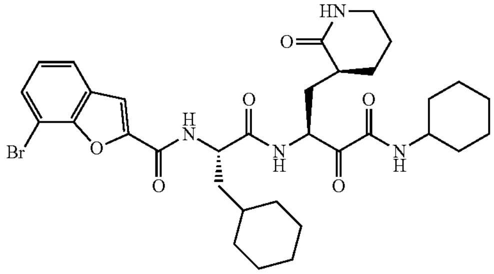 [SMILES: O=C(NC1CCCCC1)C(=O)[C@H](C[C@@H]1CCCNC1=O)NC(=O)[C@H](CC1CCCCC1)NC(=O)c1cc2cccc(Br)c2o1] | N-((S)-1-(((S)-4-(cyclohexylamino)-3, 4-dione-1-((S)-2-oxopiperidin-3-yl) but-2-yl) amino)-3-cyclohexyl-1-oxopropan-2-yl)-6-bromo-benzofuran-2-carboxamide |
| A258 | 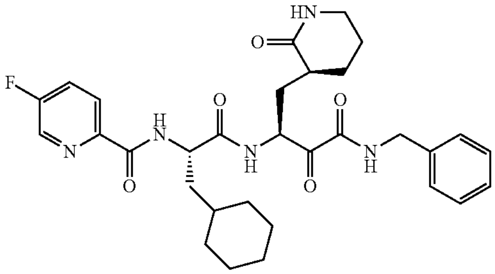 [SMILES: O=C(NCc1ccccc1)C(=O)[C@H](C[C@@H]1CCCNC1=O)NC(=O)[C@H](CC1CCCCC1)NC(=O)c1ccc(F)cn1] | N-((S)-1-(((S)-4-(benzylamino)-3, 4-dione-1-((S)-2-oxopiperidin-3-yl) but-2-yl) amino)-1-oxo-3-cyclohexylpropyl-2-yl)-5-fluoronicotinamide |
| A259 | 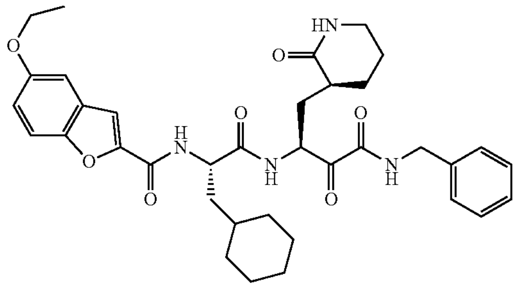 [SMILES: CCOc1ccc2oc(C(=O)N[C@@H](CC3CCCCC3)C(=O)N[C@@H](C[C@@H]3CCCNC3=O)C(=O)C(=O)NCc3ccccc3)cc2c1] | N-((S)-1-(((S)-4-(benzylamino)-3, 4-dione-1-((S)-2-oxopiperidin-3-yl) but-2-yl) amino)-3-cyclohexyl-1-oxopropan-2-yl)-5-ethoxy-benzofuran-2-carboxamide |

-continued

| number | structure | name |
| --- | --- | --- |
| A260 | 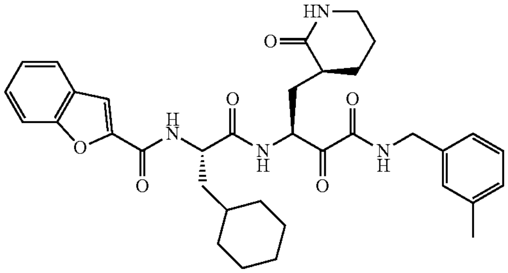 | N-((S)-1-(((S)-4-(3-methylbenzylamino)-3, 4-dione-1-((S)-2-oxopiperidin-3-yl) but-2-yl) amino)-3-cyclohexyl-1-oxopropan-2-yl)-benzofuran-2-carboxamide |
| A261 | 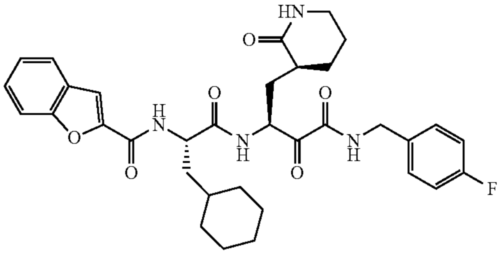 [SMILES: O=C(NCc1ccc(F)cc1)C(=O)[C@H](C[C@@H]1CCCNC1=O)NC(=O)[C@H](CC1CCCCC1)NC(=O)c1cc2ccccc2o1] | N-((S)-1-(((S)-4-(4-fluorobenzylamino)-3, 4-dione-1-((S)-2-oxopiperidin-3-yl) but-2-yl) amino)-3-cyclohexyl-1-oxopropan-2-yl)-benzofuran-2-carboxamide |
| A262 | 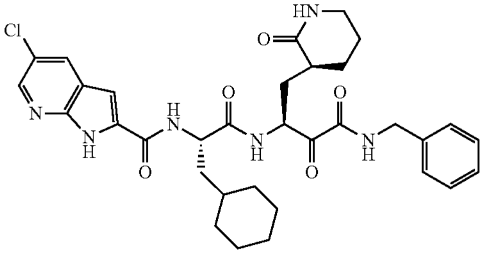 [SMILES: O=C(NCc1ccccc1)C(=O)[C@H](C[C@@H]1CCCNC1=O)NC(=O)[C@H](CC1CCCCC1)NC(=O)c1cc2cc(Cl)cnc2[nH]1] | N-((S)-1-(((S)-4-(benzylamino)-3, 4-dione-1-((S)-2-oxopiperidin-3-yl) but-2-yl) amino)-3-cyclohexyl-1-oxopropan-2-yl)-5-chloro-7-azaindole-2-carboxamide |
| A263 | 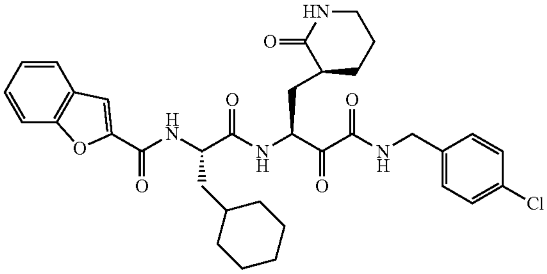 [SMILES: O=C(NCc1ccc(Cl)cc1)C(=O)[C@H](C[C@@H]1CCCNC1=O)NC(=O)[C@H](CC1CCCCC1)NC(=O)c1cc2ccccc2o1] | N-((S)-1-(((S)-4-(4-chlorobenzylamino)-3, 4-dione-1-((S)-2-oxo-piperidin-3-yl) but-2-yl)amino)-3-cyclohexyl-1-oxopropan-2-yl)-benzofuran-2-carboxamide |
| A264 | 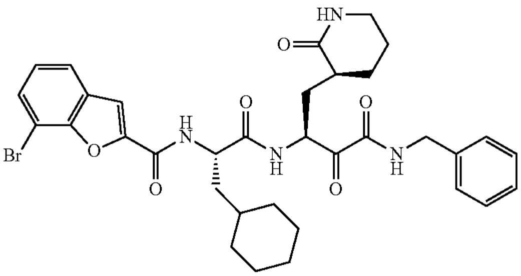 [SMILES: O=C(NCc1ccccc1)C(=O)[C@H](C[C@@H]1CCCNC1=O)NC(=O)[C@H](CC1CCCCC1)NC(=O)c1cc2cccc(Br)c2o1] | N-((S)-1-(((S)-4-(benzylamino)-3, 4-dione-1-((S)-2-oxopiperidin-3-yl) but-2-yl) amino)-3-cyclohexyl-1-oxopropan-2-yl)-6-bromo-benzofuran-2-carboxamide |

-continued

| number | structure | name |
|---|---|---|
| A265 | 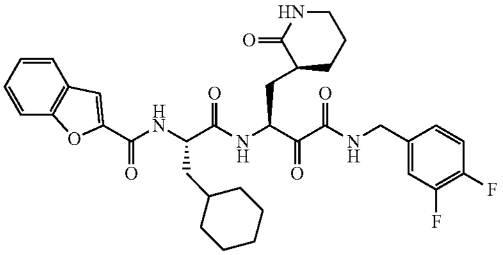 [SMILES: O=C(NCc1ccc(F)c(F)c1)C(=O)[C@H](C[C@@H]1CCCNC1=O)NC(=O)[C@H](CC1CCCCC1)NC(=O)c1cc2ccccc2o1] | N-((S)-1-(((S)-4-(3, 4-difluorobenzylamino)-3, 4-dione-1-(2-oxopiperidin-3-yl) but-2-yl) amino)-3-cyclohexyl-1-oxopropan-2-yl)-benzofuran-2-carboxamide |
| A266 | 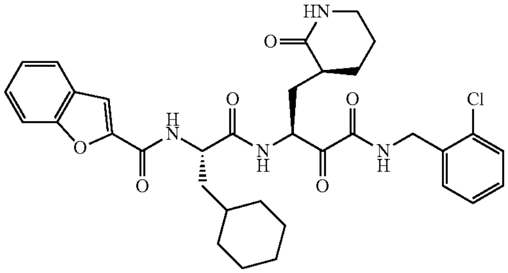 | N-((S)-1-(((S)-4-(2-chlorobenzylamino)-3,4-dione-1-(2-oxopiperidin-3-yl)but-2-yl)amino)-3-cyclohexyl-1-oxopropan-2-yl)-benzofuran-2-carboxamide |
| A267 | 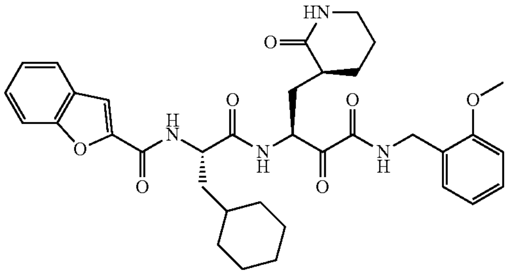 [SMILES: COc1ccccc1CNC(=O)C(=O)[C@H](C[C@@H]1CCCNC1=O)NC(=O)[C@H](CC1CCCCC1)NC(=O)c1cc2ccccc2o1] | N-((S)-1-(((S)-4-(2-methoxybenzylamino)-3, 4-dione-1-((S)-2-oxopiperidin-3-yl) but-2-yl) amino)-3-cyclohexyl-1-oxopropan-2-yl)-benzofuran-2-carboxamide |
| A268 | 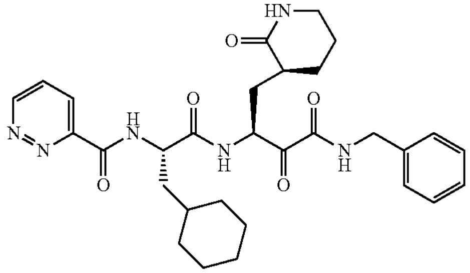 [SMILES: O=C(NCc1ccccc1)C(=O)[C@H](C[C@@H]1CCCNC1=O)NC(=O)[C@H](CC1CCCCC1)NC(=O)c1cccnn1] | N-((S)-1-(((S)-4-(benzylamino)-3, 4-dione-1-((S)-2-oxopiperidin-3-yl) but-2-yl) amino)-3-cyclohexyl-1-oxopropan-2-yl)-pyridazine-2-carboxamide |
| A269 | 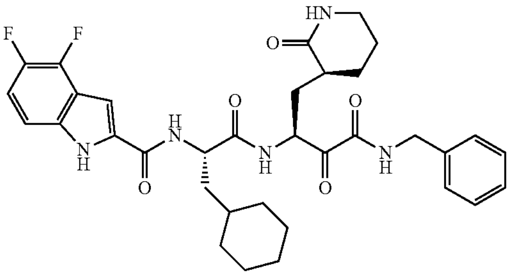 [SMILES: O=C(NCc1ccccc1)C(=O)[C@H](C[C@@H]1CCCNC1=O)NC(=O)[C@H](CC1CCCCC1)NC(=O)c1cc2c(F)c(F)ccc2[nH]1] | N-((S)-1-(((S)-4-(benzylamino)-3, 4-dione-1-((S)-2-oxopiperidin-3-yl) but-2-yl) amino)-3-cyclohexyl-1-oxopropan-2-yl)-4, 5-indole-2-carboxamide |

-continued

| number | structure | name |
|---|---|---|
| A270 | 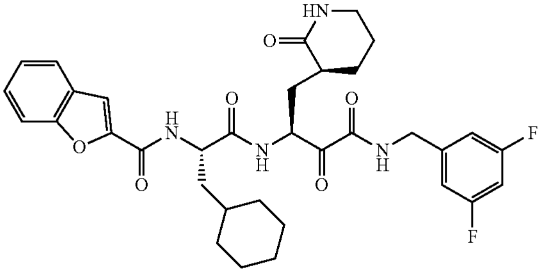 [SMILES: O=C(NCc1cc(F)cc(F)c1)C(=O)[C@H](C[C@@H]1CCCNC1=O)NC(=O)[C@H](CC1CCCCC1)NC(=O)c1cc2ccccc2o1] | N-((S)-1-(((S)-4-(3,5-difluorobenzylamino)-3, 4-dione-1-((S)-2-oxopiperidin-3-yl) but-2-yl) amino)-3-cyclohexyl-1-oxopropan-2-yl)-benzofuran-2-carboxamide |
| A271 | 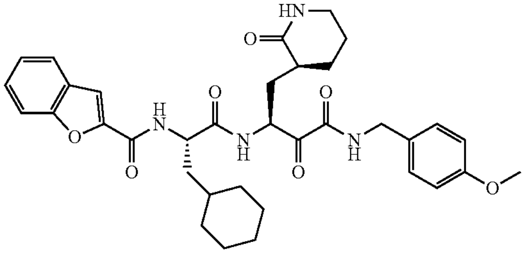 [SMILES: COc1ccc(CNC(=O)C(=O)[C@H](C[C@@H]2CCCNC2=O)NC(=O)[C@H](CC2CCCCC2)NC(=O)c2cc3ccccc3o2)cc1] | N-((S)-1-(((S)-4-(4-methoxybenzylamino)-3, 4-dione-1-((S)-2-oxopiperidin-3-yl)but-2-yl) amino)-3-cyclohexyl-1-oxopropan-2-yl)-benzofuran-2-carboxamide |
| A272 | 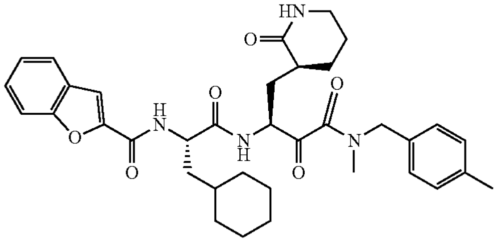 [SMILES: Cc1ccc(CN(C)C(=O)C(=O)[C@H](C[C@@H]2CCCNC2=O)NC(=O)[C@H](CC2CCCCC2)NC(=O)c2cc3ccccc3o2)cc1] | N-((S)-1-(((S)-4-(4-methylbenzylmethylamino)-3, 4-dione-1-((S)-2-oxopiperidin-3-yl)but-2-yl) amino)-3-cyclohexyl-1-oxopropan-2-yl)-benzofuran-2-carboxamide |
| A273 | 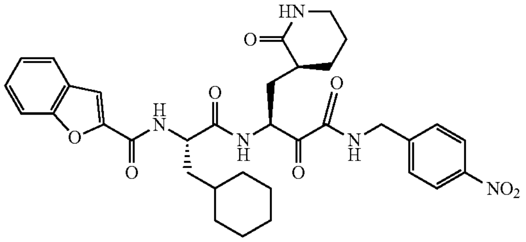 [SMILES: O=C(NCc1ccc([N+](=O)[O-])cc1)C(=O)[C@H](C[C@@H]1CCCNC1=O)NC(=O)[C@H](CC1CCCCC1)NC(=O)c1cc2ccccc2o1] | N-((S)-1-(((S)-4-(4-nitrobenzylamino)-3, 4-dione-1-((S)-2-oxopiperidin-3-yl)but-2-yl) amino)-3-cyclohexyl-1-oxopropan-2-yl)-benzofuran-2-carboxamide |
| A274 | 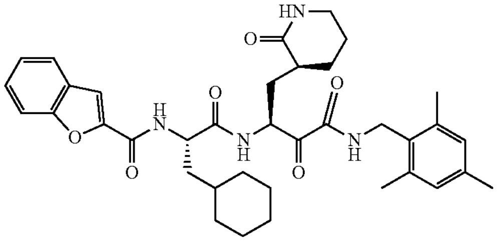 [SMILES: Cc1cc(C)c(CNC(=O)C(=O)[C@H](C[C@@H]2CCCNC2=O)NC(=O)[C@H](CC2CCCCC2)NC(=O)c2cc3ccccc3o2)c(C)c1] | N-((S)-1-(((S)-4-(2,4, 6-trimethylbenzylamino)-3, 4-dione-1-((S)-2-oxopiperidin-3-yl) but-2-yl) amino)-3-cyclohexyl-1-oxopropan-2-yl)-benzofuran-2-carboxamide |
| A275 | 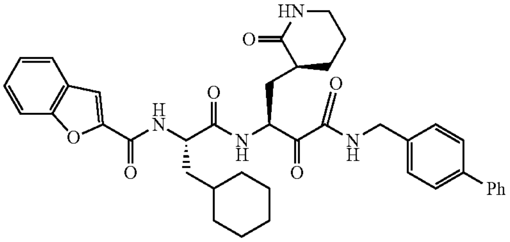 [SMILES: O=C(NCc1ccc(-c2ccccc2)cc1)C(=O)[C@H](C[C@@H]1CCCNC1=O)NC(=O)[C@H](CC1CCCCC1)NC(=O)c1cc2ccccc2o1] | N-((S)-1-((S)-4-(4-phenylbenzylamino)-3, 4-dione-1-((S)-2-oxopiperidin-3-yl)but-2-yl) amino)-3-cyclohexyl-1-oxopropan-2-yl)-benzofuran-2-carboxamide |

-continued

| number | structure | name |
|---|---|---|
| A276 | 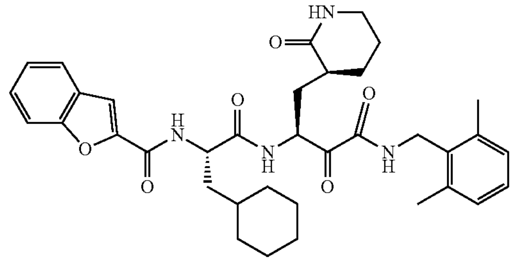 [SMILES: Cc1cccc(C)c1CNC(=O)C(=O)[C@H](C[C@@H]1CCCNC1=O)NC(=O)[C@H](CC1CCCCC1)NC(=O)c1cc2ccccc2o1] | N-((S)-1-(((S)-4-(2,4,6-trimethylbenzylamino)-3,4-dione-1-((S)-2-oxopiperidin-3-yl)but-2-yl)amino)-3-cyclohexyl-1-oxopropan-2-yl)-benzofuran-2-carboxamide |
| A277 | 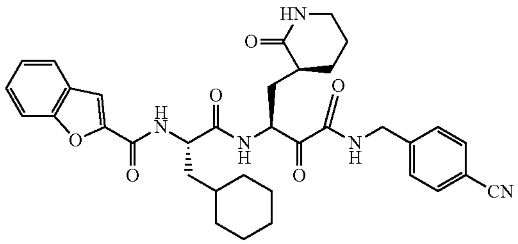 [SMILES: N#Cc1ccc(CNC(=O)C(=O)[C@H](C[C@@H]2CCCNC2=O)NC(=O)[C@H](CC2CCCCC2)NC(=O)c2cc3ccccc3o2)cc1] | N-((S)-1-(((S)-4-(4-cyanobenzylamino)-3,4-dione-1-((S)-2-oxopiperidin-3-yl)but-2-yl)amino)-3-cyclohexyl-1-oxopropan-2-yl)-benzofuran-2-carboxamide |
| A278 | 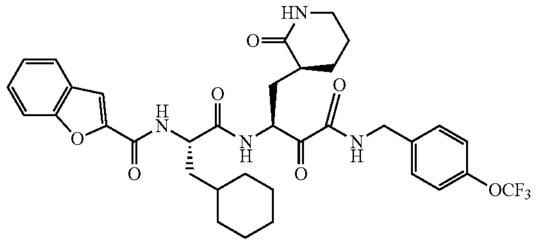 [SMILES: O=C(NCc1ccc(OC(F)(F)F)cc1)C(=O)[C@H](C[C@@H]1CCCNC1=O)NC(=O)[C@H](CC1CCCCC1)NC(=O)c1cc2ccccc2o1] | N-((S)-1-(((S)-4-(4-trifluoromethoxybenzylamino)-3,4-dione-1-((S)-2-oxopiperidin-3-yl)but-2-yl)amino)-3-cyclohexyl-1-oxopropan-2-yl)-benzofuran-2-carboxamide |
| A279 | 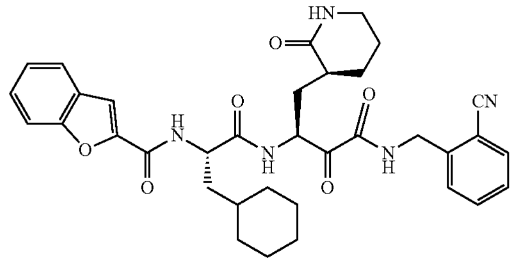 [SMILES: N#Cc1ccccc1CNC(=O)C(=O)[C@H](C[C@@H]1CCCNC1=O)NC(=O)[C@H](CC1CCCCC1)NC(=O)c1cc2ccccc2o1] | N-((S)-1-(((S)-4-(2-cyanobenzylamino)-3,4-dione-1-((S)-2-oxopiperidin-3-yl)but-2-yl)amino)-3-cyclohexyl-1-oxopropan-2-yl)-benzofuran-2-carboxamide |
| A280 | 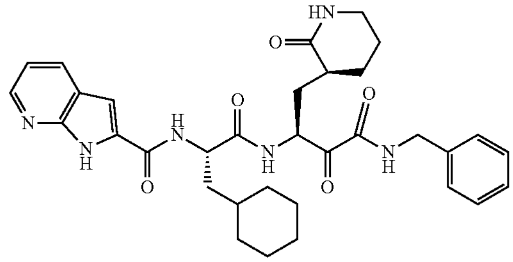 [SMILES: O=C(NCc1ccccc1)C(=O)[C@H](C[C@@H]1CCCNC1=O)NC(=O)[C@H](CC1CCCCC1)NC(=O)c1cc2cccnc2[nH]1] | N-((S)-1-(((S)-4-(benzylamino)-3,4-dione-1-((S)-2-oxopiperidin-3-yl)but-2-yl)amino)-3-cyclohexyl-1-oxopropan-2-yl)-7-azaindole-2-carboxamide |
| A281 | 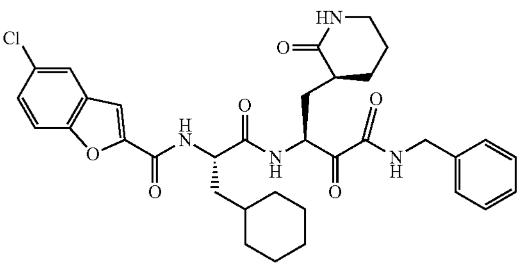 [SMILES: O=C(NCc1ccccc1)C(=O)[C@H](C[C@@H]1CCCNC1=O)NC(=O)[C@H](CC1CCCCC1)NC(=O)c1cc2cc(Cl)ccc2o1] | N-((S)-1-(((S)-4-(benzylamino)-3,4-dione-1-((S)-2-oxopiperidin-3-yl)but-2-yl)amino)-3-cyclohexyl-1-oxopropan-2-yl)-5-chloro-benzofuran-2-carboxamide |

-continued

| number | structure | name |
| --- | --- | --- |
| A282 | 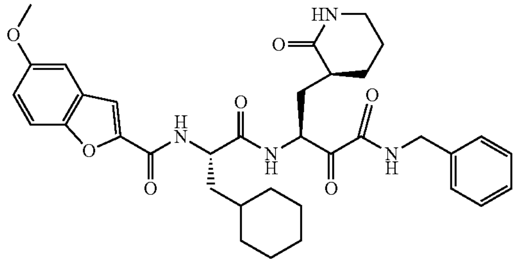 [SMILES: COc1ccc2oc(C(=O)N[C@@H](CC3CCCCC3)C(=O)N[C@@H](C[C@@H]3CCCNC3=O)C(=O)C(=O)NCc3ccccc3)cc2c1] | N-((S)-1-(((S)-4-(benzylamino)-3, 4-dione-1-((S)-2-oxopiperidin-3-yl)but-2-yl) amino)-3-cyclohexyl-1-oxopropan-2-yl)-5-methoxy-benzofuran-2-carboxamide |
| A283 | 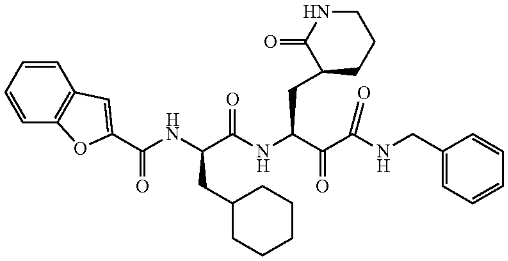 [SMILES: O=C(NCc1ccccc1)C(=O)[C@H](C[C@@H]1CCCNC1=O)NC(=O)[C@@H](CC1CCCCC1)NC(=O)c1cc2ccccc2o1] | N-((R)-1-(((S)-4-(benzylamino)-3, 4-dione-1-((S)-2-oxopiperidin-3-yl)but-2-yl) amino)-3-cyclohexyl-1-oxopropan-2-yl)-benzofuran-2-carboxamide |
| A284 | 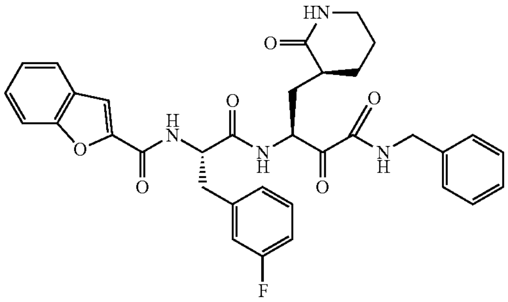 [SMILES: O=C(NCc1ccccc1)C(=O)[C@H](C[C@@H]1CCCNC1=O)NC(=O)[C@H](Cc1cccc(F)c1)NC(=O)c1cc2ccccc2o1] | N-((S)-1-(((S)-4-(benzylamino)-3, 4-dione-1-((S)-2-oxopiperidin-3-yl)but-2-yl) amino)-3-(3-fluorophenyl)-1-oxopropan-2-yl)-benzofuran-2-carboxamide |
| A285 | 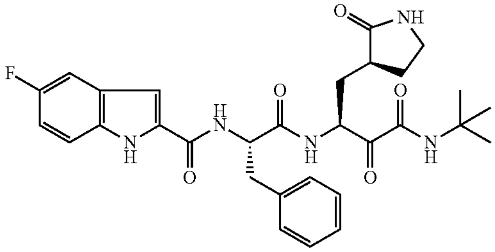 [SMILES: CC(C)(C)NC(=O)C(=O)[C@H](C[C@@H]1CCNC1=O)NC(=O)[C@H](Cc1ccccc1)NC(=O)c1cc2cc(F)ccc2[nH]1] | N-((S)-1-(((S)-4-(tert-butylamino)-3, 4-dione-1-((S)-2-oxopyrrolidin-3-yl)but-2-yl) amino)-3-phenyl-1-oxopropan-2-yl)-5-fluoro-indole-2-carboxamide |
| A286 | 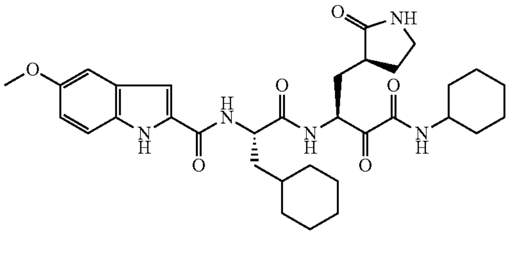 [SMILES: COc1ccc2[nH]c(C(=O)N[C@@H](CC3CCCCC3)C(=O)N[C@@H](C[C@@H]3CCNC3=O)C(=O)C(=O)NC3CCCCC3)cc2c1] | N-((S)-1-(((S)-4-(cyclohexylamino)-3, 4-dione-1-((S)-2-oxopyrrolidin-3-yl)but-2-yl) amino)-3-cyclohexyl-1-oxopropan-2-yl)-5-methoxy-indole-2-carboxamide |
| A287 | 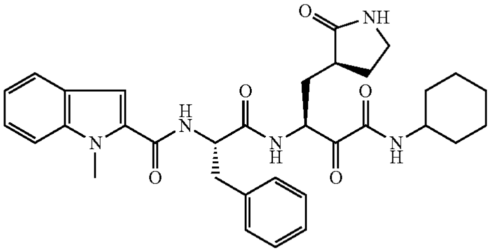 [SMILES: Cn1c(C(=O)N[C@@H](Cc2ccccc2)C(=O)N[C@@H](C[C@@H]2CCNC2=O)C(=O)C(=O)NC2CCCCC2)cc2ccccc21] | N-((S)-1-(((S)-4-(cyclohexylamino)-3, 4-dione-1-((S)-2-oxopyrrolidin-3-yl)but-2-yl) amino)-3-phenyl-1-oxopropan-2-yl)-1-methyl-indole-2-carboxamide |

-continued

| number | structure | name |
|---|---|---|
| A288 | 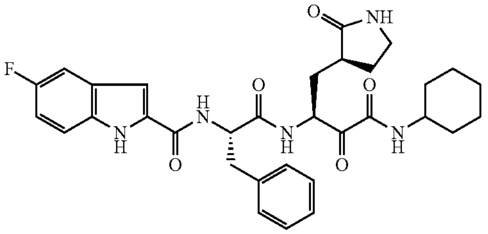 [SMILES: O=C(NC1CCCCC1)C(=O)[C@H](C[C@@H]1CCNC1=O)NC(=O)[C@H](Cc1ccccc1)NC(=O)c1cc2cc(F)ccc2[nH]1] | N-((S)-1-(((S)-4-(cyclohexylamino)-3,4-dione-1-((S)-2-oxopyrrolidin-3-yl)but-2-yl)amino)-3-phenyl-1-oxopropan-2-yl)-5-fluoro-indole-2-carboxamide |
| A289 | 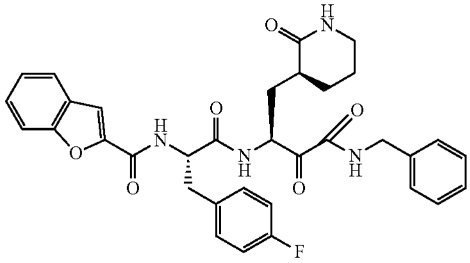 [SMILES: O=C(NCc1ccccc1)C(=O)[C@H](C[C@@H]1CCCNC1=O)NC(=O)[C@H](Cc1ccc(F)cc1)NC(=O)c1cc2ccccc2o1] | N-((S)-1-(((S)-4-(benzylamino)-3,4-dione-1-((S)-2-oxopiperidin-3-yl)but-2-yl)amino)-3-(4-fluorophenyl)-1-oxopropan-2-yl)-benzofuran-2-carboxamide |
| A290 | 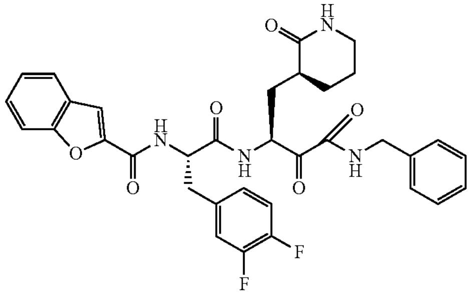 [SMILES: O=C(NCc1ccccc1)C(=O)[C@H](C[C@@H]1CCCNC1=O)NC(=O)[C@H](Cc1ccc(F)c(F)c1)NC(=O)c1cc2ccccc2o1] | N-((S)-1-(((S)-4-(benzylamino)-3,4-dione-1-((S)-2-oxopiperidin-3-yl)but-2-yl)amino)-3-(3,4-difluorophenyl)-1-oxopropan-2-yl)-benzofuran-2-carboxamide |
| A291 | 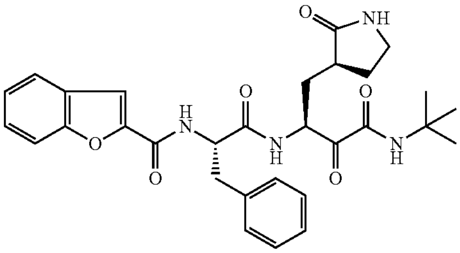 [SMILES: CC(C)(C)NC(=O)C(=O)[C@H](C[C@@H]1CCNC1=O)NC(=O)[C@H](Cc1ccccc1)NC(=O)c1cc2ccccc2o1] | N-((S)-1-(((S)-4-(tert-butylamino)-3,4-dione-1-((S)-2-oxopyrrolidin-3-yl)but-2-yl)amino)-3-phenyl-1-oxopropan-2-yl)-benzofuran-2-carboxamide |
| A292 | 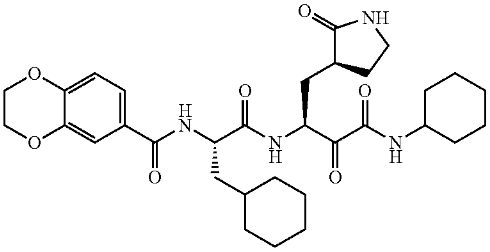 [SMILES: O=C(NC1CCCCC1)C(=O)[C@H](C[C@@H]1CCNC1=O)NC(=O)[C@H](CC1CCCCC1)NC(=O)c1ccc2c(c1)OCCO2] | N-((S)-1-(((S)-4-(cyclohexylamino)-3,4-dione-1-((S)-2-oxopyrrolidin-3-yl)but-2-yl)amino)-3-cyclohexyl-1-oxopropan-2-yl)-2,3-dihydrobenzo[b]1,4-dioxin-6-carboxamide |

-continued

| number | structure | name |
|---|---|---|
| A293 | 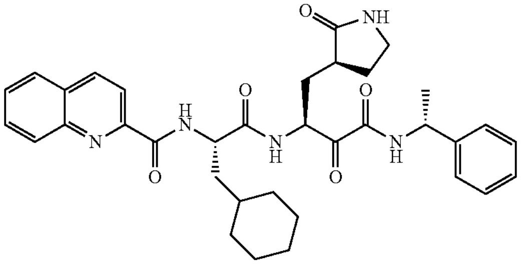 [SMILES: C[C@@H](NC(=O)C(=O)[C@H](C[C@@H]1CCNC1=O)NC(=O)[C@H](CC1CCCCC1)NC(=O)c1ccc2ccccc2n1)c1ccccc1] | N-((S)-1-(((S)-4-((R)-1-phenyl-ethyl)-amino)-3,4-dione-1-((S)-2-oxopyrrolidin-3-yl) but-2-yl)amino)-3-cyclohexyl-1-oxopropan-2-yl)-quinoline-2-carboxamide |
| A294 | 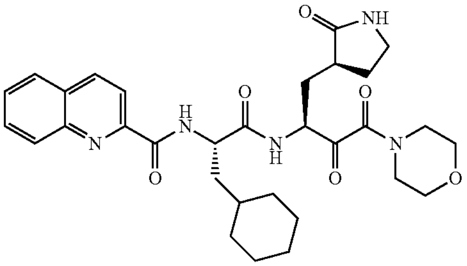 [SMILES: O=C(N[C@@H](CC1CCCCC1)C(=O)N[C@@H](C[C@@H]1CCNC1=O)C(=O)C(=O)N1CCOCC1)c1ccc2ccccc2n1] | N-((S)-1-(((S)-4-morpholinyl-3, 4-dione-1-((S)-2-oxopyrrolidin-3-yl)but-2-yl) amino)-3-cyclohexyl-1-oxopropan-2-yl)-quinoline-2-carboxamide |
| A295 | 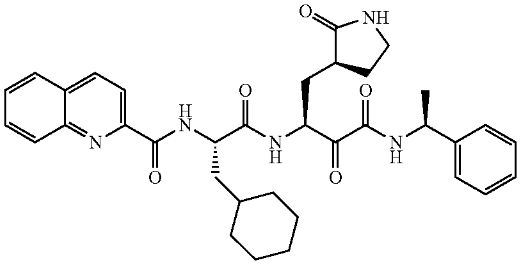 [SMILES: C[C@H](NC(=O)C(=O)[C@H](C[C@@H]1CCNC1=O)NC(=O)[C@H](CC1CCCCC1)NC(=O)c1ccc2ccccc2n1)c1ccccc1] | N-((S)-1-(((S)-4-((S)-1-phenyl-ethyl)-amino)-3, 4-dione-1-((S)-2-oxopyrrolidin-3-yl)but-2-yl) amino)-3-cyclohexyl-1-oxopropan-2-yl)-quinoline-2-carboxamide |
| A296 | 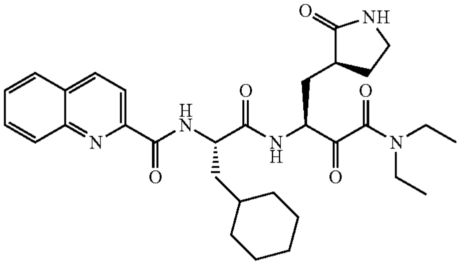 [SMILES: CCN(CC)C(=O)C(=O)[C@H](C[C@@H]1CCNC1=O)NC(=O)[C@H](CC1CCCCC1)NC(=O)c1ccc2ccccc2n1] | N-((S)-1-(((S)-4-diethylamino-3, 4-dione-1-((S)-2-oxopyrrolidin-3-yl)but-2-yl) amino)-3-cyclohexyl-1-oxopropan-2-yl)-quinoline-2-carboxamide |
| A297 | 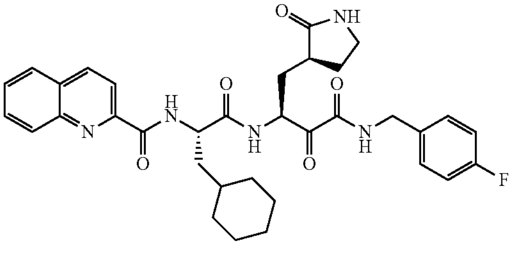 [SMILES: O=C(NCc1ccc(F)cc1)C(=O)[C@H](C[C@@H]1CCNC1=O)NC(=O)[C@H](CC1CCCCC1)NC(=O)c1ccc2ccccc2n1] | N-((S)-1-(((S)-4-(4-fluorobenzylamino)-3,4-dione-1-((S)-2-oxopyrrolidin-3-yl)but-2-yl) amino)-3-cyclohexyl-1-oxopropan-2-yl)-quinoline-2-carboxamide |
| A298 | 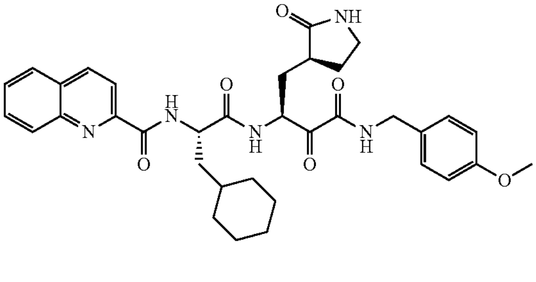 [SMILES: COc1ccc(CNC(=O)C(=O)[C@H](C[C@@H]2CCNC2=O)NC(=O)[C@H](CC2CCCCC2)NC(=O)c2ccc3ccccc3n2)cc1] | N-((S)-1-(((S)-4-(4-methoxybenzylamino)-3, 4-dione-1-((S)-2-oxopyrrolidin-3-yl)but-2-yl) amino)-3-cyclohexyl-1-oxopropan-2-yl)-quinoline-2-carboxamide |

-continued

| number | structure | name |
|---|---|---|
| A299 | 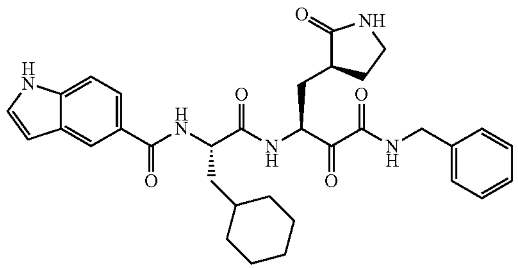 [SMILES: O=C(NCc1ccccc1)C(=O)[C@H](C[C@@H]1CCNC1=O)NC(=O)[C@H](CC1CCCCC1)NC(=O)c1ccc2[nH]ccc2c1] | N-((S)-1-(((S)-4-(benzylamino)-3, 4-dione-1-((S)-2-oxopyrrolidin-3-yl)but-2-yl) amino)-3-cyclohexyl-1-oxopropan-2-yl)-indole-5-carboxamide |
| A300 | 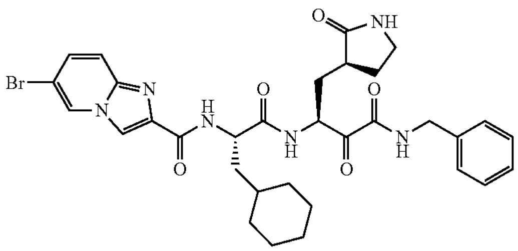 [SMILES: O=C(NCc1ccccc1)C(=O)[C@H](C[C@@H]1CCNC1=O)NC(=O)[C@H](CC1CCCCC1)NC(=O)c1cn2cc(Br)ccc2n1] | N-((S)-1-(((S)-4-(benzylamino)-3, 4-dione-1-((S)-2-oxopyrrolidin-3-yl)but-2-yl) amino)-3-cyclohexyl-1-oxopropan-2-yl)-5-bromoimidazolo[1,2-a]pyridine-2-carboxamide |
| A301 | 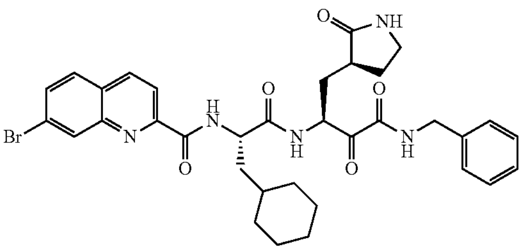 [SMILES: O=C(NCc1ccccc1)C(=O)[C@H](C[C@@H]1CCNC1=O)NC(=O)[C@H](CC1CCCCC1)NC(=O)c1ccc2ccc(Br)cc2n1] | N-((S)-1-(((S)-4-(benzylamino)-3, 4-dione-1-((S)-2-oxopyrrolidin-3-yl)but-2-yl) amino)-3-cyclohexyl-1-oxopropan-2-yl)-7-bromo-quinoline-2-carboxamide |
| A302 | 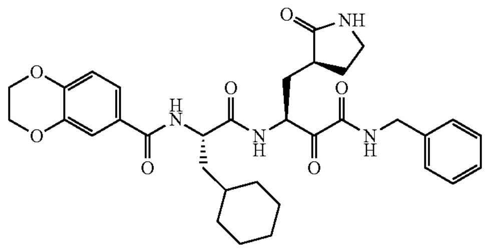 [SMILES: O=C(NCc1ccccc1)C(=O)[C@H](C[C@@H]1CCNC1=O)NC(=O)[C@H](CC1CCCCC1)NC(=O)c1ccc2c(c1)OCCO2] | N-((S)-1-(((S)-4-(benzylamino)-3, 4-dione-1-((S)-2-oxopyrrolidin-3-yl)but-2-yl) amino)-3-cyclohexyl-1-oxopropan-2-yl)-2, 3-dihydrobenzo[b]1,4-dioxin-6-carboxamide |
| A303 | 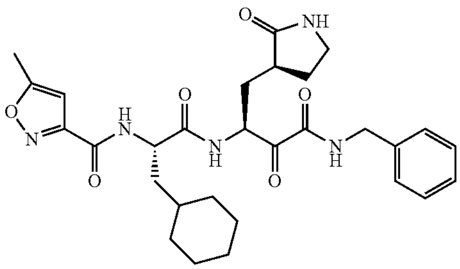 [SMILES: Cc1cc(C(=O)N[C@@H](CC2CCCCC2)C(=O)N[C@@H](C[C@@H]2CCNC2=O)C(=O)C(=O)NCc2ccccc2)no1] | N-((S)-1-(((S)-4-(benzylamino)-3, 4-dione-1-((S)-2-oxopyrrolidin-3-yl)but-2-yl) amino)-3-cyclohexyl-1-oxopropan-2-yl)-5-methyl-isoxazole-2-carboxamide |
| A304 | 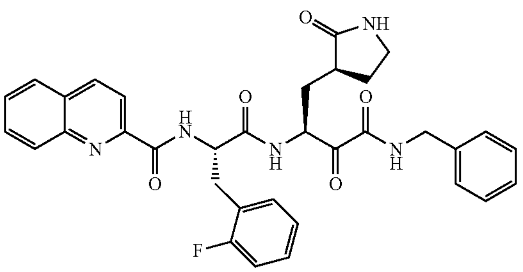 [SMILES: O=C(NCc1ccccc1)C(=O)[C@H](C[C@@H]1CCNC1=O)NC(=O)[C@H](Cc1ccccc1F)NC(=O)c1ccc2ccccc2n1] | N-((S)-1-(((S)-4-(benzylamino)-3, 4-dione-1-((S)-2-oxopyrrolidin-3-yl)but-2-yl) amino)-3-(2-fluorophenyl)-1-oxopropan-2-yl)-quinoline-2-carboxamide |

-continued

| number | structure | name |
|---|---|---|
| A305 | 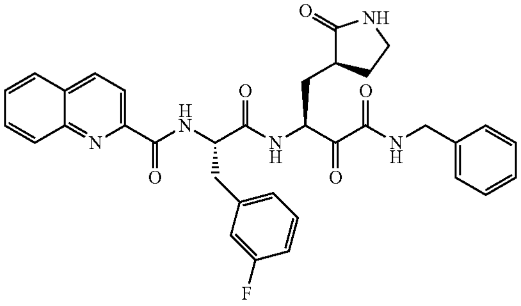 [SMILES: O=C(NCc1ccccc1)C(=O)[C@H](C[C@@H]1CCNC1=O)NC(=O)[C@H](Cc1cccc(F)c1)NC(=O)c1ccc2ccccc2n1] | N-((S)-1-(((S)-4-(benzylamino)-3, 4-dione-1-((S)-2-oxopyrrolidin-3-yl) but-2-yl) amino)-3-(3-fluorophenyl)-1-oxopropan-2-yl)-quinoline-2-carboxamide |
| A306 | 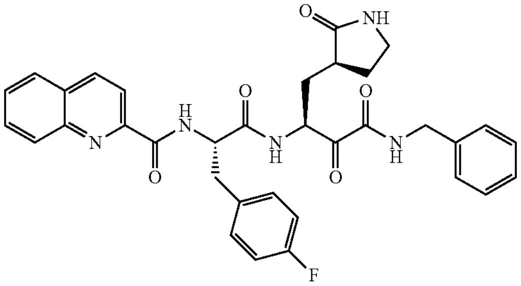 [SMILES: O=C(NCc1ccccc1)C(=O)[C@H](C[C@@H]1CCNC1=O)NC(=O)[C@H](Cc1ccc(F)cc1)NC(=O)c1ccc2ccccc2n1] | N-((S)-1-(((S)-4-(benzylamino)-3, 4-dione-1-((S)-2-oxopyrrolidin-3-yl)but-2-yl) amino)-3-(4-fluorophenyl)-1-oxopropan-2-yl)-quinoline-2-carboxamide |
| A307 | 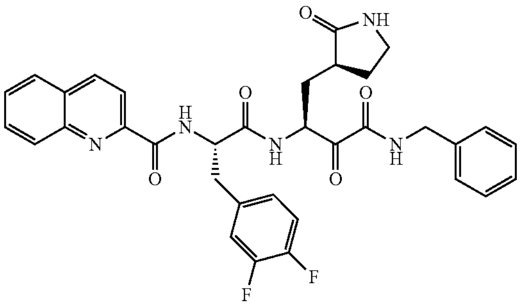 [SMILES: O=C(NCc1ccccc1)C(=O)[C@H](C[C@@H]1CCNC1=O)NC(=O)[C@H](Cc1ccc(F)c(F)c1)NC(=O)c1ccc2ccccc2n1] | N-((S)-1-(((S)-4-(benzylamino)-3, 4-dione-1-((S)-2-oxopyrrolidin-3-yl)but-2-yl) amino)-3-(3,4-difluorophenyl)-1-oxopropan-2-yl)-quinoline-2-carboxamide |
| A308 | 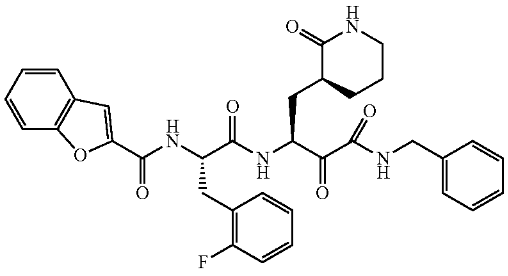 [SMILES: O=C(NCc1ccccc1)C(=O)[C@H](C[C@@H]1CCCNC1=O)NC(=O)[C@H](Cc1ccccc1F)NC(=O)c1cc2ccccc2o1] | N-((S)-1-(((S)-4-(benzylamino)-3, 4-dione-1-((S)-2-oxopiperidin-3-yl)but-2-yl) amino)-3-(2-fluorophenyl)-1-oxopropan-2-yl)-benzofuran-2-carboxamide |
| A309 | 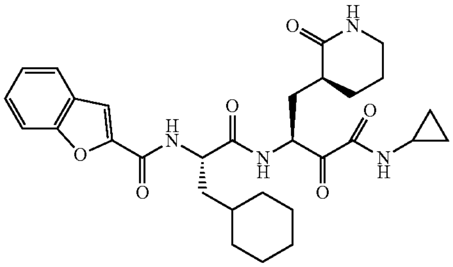 [SMILES: O=C(NC1CC1)C(=O)[C@H](C[C@@H]1CCCNC1=O)NC(=O)[C@H](CC1CCCCC1)NC(=O)c1cc2ccccc2o1] | N-((S)-1-(((S)-4-(cyclopropylamino)-3, 4-dione-1-((S)-2-oxopiperidin-3-yl)but-2-yl) amino)-3-cyclohexyl-1-oxopropan-2-yl)-benzofuran-2-carboxamide |

-continued

| number | structure | name |
|---|---|---|
| A310 | 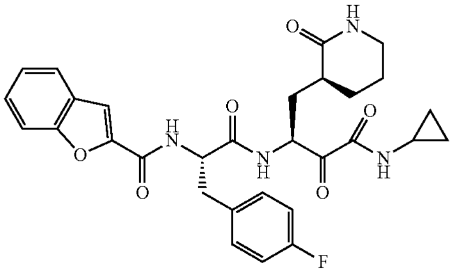 [SMILES: O=C(NC1CC1)C(=O)[C@H](C[C@@H]1CCCNC1=O)NC(=O)[C@H](Cc1ccc(F)cc1)NC(=O)c1cc2ccccc2o1] | N-((S)-1-(((S)-4-(cyclopropylamino)-3, 4-dione-1-((S)-2-oxopiperidin-3-yl)but-2-yl) amino)-3-(4-fluorophenyl)-1-oxopropan-2-yl)-benzofuran-2-carboxamide. |

In the second aspect of the present invention, it provides a pharmaceutical composition comprising (a) a therapeutically effective amount of the ketoamide compound represented by formula (A), or pharmaceutically acceptable salt, enantiomer, diastereomer or racemate or prodrug thereof, and (b) a pharmaceutically acceptable carrier, wherein, the ketoamide compound represented by formula (A) is as described in the first aspect of the present invention.

In the third aspect of the present invention, it provides a use of the pharmaceutical composition according to the second aspect of the present invention in the manufacture of a medicament for treating and/or preventing and alleviating related diseases caused by 2019 novel coronavirus (2019-nCov) infection.

In another preferred embodiment, the related diseases caused by 2019 novel coronavirus infection is selected from the group consisting of respiratory infections, pneumonia and complications thereof, and a combination thereof.

In the fourth aspect of the present invention, it provides a method for treating, preventing, and/or alleviating related diseases caused by 2019 novel coronavirus (2019-nCov) infection, comprising the step of administering to a subject in need a safe and effective amount of the ketoamide compound represented by formula (A), or pharmaceutically acceptable salt, enantiomer, diastereomer or racemate thereof, wherein the ketoamide compound represented by formula (A) is described above.

In another preferred embodiment, the subject is a primate mammal, such as a human.

In the fifth aspect of the present invention, it provides a method for inhibiting the activity of the 3CL protease of 2019 novel coronavirus (2019-nCov), comprising the step of contacting the ketoamide compound represented by formula (A), or pharmaceutically acceptable salt, enantiomer, diastereomer or racemate thereof with the 3CL protease and/or human cathepsin L of 2019-nCov, thereby inhibiting the activity of 3CL protease and/or human cathepsin L of 2019-nCov.

In another preferred embodiment, the method is non-therapeutic and non-diagnostic.

In another preferred embodiment, the method is in vitro.

In another preferred embodiment, the 3CL protease of 2019-nCov is a 3CL protease recombinant or expressed by 2019-nCov.

In the sixth aspect of the present invention, it provides the compound of formula (A), or pharmaceutically acceptable salt, enantiomer, diastereomer or racemate thereof described in the first aspect, formula (A)

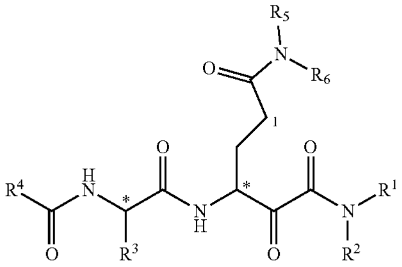

wherein,

* indicates that the stereochemical isomerism of carbon atoms is independently R and/or S respectively;

$R^1$ and $R^2$ are each independently selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 cycloalkyl C1-C10 alkylene, substituted or unsubstituted C3-C10 heterocycloalkyl, substituted or unsubstituted C3-C10 heterocycloalkyl C1-C10 alkylene, substituted or unsubstituted C6-C20 aryl, substituted or unsubstituted C3-C20 heteroaryl, substituted or unsubstituted C6-C20 aryl C1-C10 alkylene, substituted or unsubstituted C3-C20 heteroaryl C1-C10 alkylene, substituted or unsubstituted C6-C20 aryl C2-C10 alkenylene, substituted or unsubstituted C3-C20 heteroaryl C2-C10 alkenylene, acyl, and sulfonyl;

$R^3$ is selected from the group consisting of substituted or unsubstituted C1-C10 alkyl, substituted or unsubstituted C2-C10 alkenyl, substituted or unsubstituted C2-C10 alkynyl, substituted or unsubstituted C3-C8 cycloalkyl, substituted or unsubstituted C3-C8 cycloalkyl C1-C10 alkylene, substituted or unsubstituted C3-C8 heterocycloalkyl, substituted or unsubstituted C3-C8 heterocycloalkyl C1-C10 alkylene, substituted or unsubstituted C6-C20 aryl, substituted or unsubstituted C3-C20 heteroaryl, substituted or unsubstituted C6-C20 aryl C1-C10 alkylene, substituted or unsubstituted C3-C20 heteroaryl C1-C10 alkylene, substituted or unsubstituted C6-C20 aryl C2-C6 alkenylene, substituted or unsubstituted C3-C20 heteroaryl C2-C6 alkenylene, substituted or unsubstituted C6-C20 aryl C2-C6 alkynylene, and substituted or unsubstituted C3-C20 heteroaryl C2-C6 alkynylene;

$R^4$ is selected from the group consisting of substituted or unsubstituted C1-C10 alkyl, substituted or unsubstituted C2-C10 alkenyl, substituted or unsubstituted C2-C10 alkynyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C6-C20 aryl C2-C6 alkynylene, substituted or unsubstituted C3-C20 heteroaryl C1-C9 alkylene, substituted or unsubstituted C3-C20 heteroaryl C2-C9 alkenylene, and substituted or unsubstituted C3-C20 heteroaryl C2-C9 alkynylene;

$R^6$ is selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C3-C20 heteroaryl C1-C9 alkylene, substituted or unsubstituted C3-C20 heteroaryl C2-C9 alkenylene, acyl and sulfonyl;

when $-NR^5$ and its adjacent $-(C{=}O)-CH_2-$ form a ring, $R^5$ is $-(CH_2)_n-$, n is 2 or 3;

when $-NR^5$ does not form a ring with its adjacent $-(C{=}O)-CH_2-$, $R^5$ is selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C3-C20 heteroaryl C1-C9 alkylene, substituted or unsubstituted C3-C20 heteroaryl C2-C9 alkenylene, acyl and sulfonyl;

wherein, in $R^1$, $R^2$, $R^3$, $R^4$, $R^5$ and $R^6$, each of the "substituted" independently refers to being substituted by 1, 2, 3 or 4 substituents selected from the group consisting of halogen, hydroxyl, mercapto, nitro, cyano, amino, imino, tertiary amino, azido, C1-C8 alkyl, halogenated C1-C8 alkyl, C1-C8 alkoxy, halogenated C1-C8 alkoxy, C1-C6 alkylcarbonyl, C1-C6 alkylthio, C1-C8 alkoxycarbonyl, and trifluoromethyl; the heterocycloalkyl and the heteroaryl each independently comprise 1, 2, 3 or 4 heteroatoms selected from N, O, and S.

In another preferred embodiment, the compound is a compound represented by formula AA, formula AA

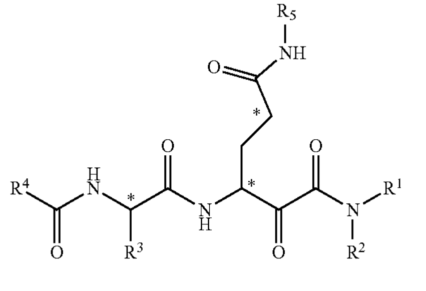

wherein, $R^1$, $R^2$, $R^3$, $R^4$, $R^5$ and n are as defined above;

* indicates that the stereochemical isomerism of carbon atoms is independently R and/or S respectively.

In another preferred embodiment, the compound is the compounds A254-A310 (i.e., Examples 254-310).

It should be understood that in the present invention, any of the technical features specifically described above and below (such as in the Examples) can be combined with each other, so as to constitute new or preferred technical solutions which will not redundantly be described one by one herein.

DETAILED DESCRIPTION OF THE INVENTION

Figure 1:
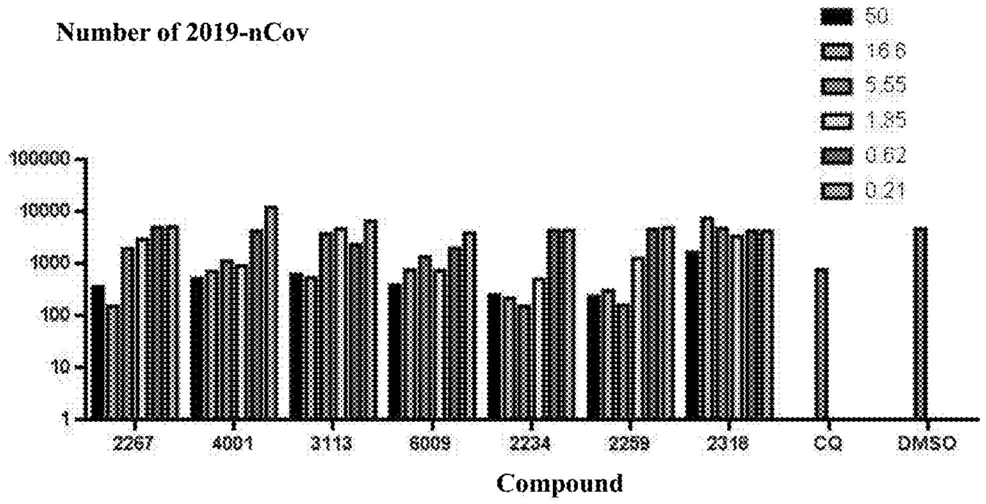
FIG. 1 shows that the compound of the present invention can inhibit the replication of the 2019nCoV virus.

After extensive and intensive research and extensive screening, the present inventors have unexpectedly developed, for the first time, a class of active ingredients that can effectively inhibit 2019 novel coronavirus (2019-nCov), namely the compound shown in formula A or the pharmaceutically acceptable salt, enantiomer, diastereoisomer or racemate thereof. The test shows that the active ingredient of the present invention can effectively inhibit the activity of 3CL protease and/or human cathepsin L of 2019 novel coronavirus (2019-nCov), thereby inhibiting the replication and vitality of 2019-nCov. On above basis, the present invention has been completed.

Terms

As used herein, the terms "novel coronavirus", "2019-nCov" or "SARS-CoV-2" are used interchangeably. The novel coronavirus is the seventh coronavirus known to infect humans and causes new coronary pneumonia (COVID-19), which is one of the serious infectious diseases threatening human health worldwide. In addition, the term includes wild-type and mutant virus strains.

As used herein, unless otherwise specified, the term "substituted" refers to that one or more hydrogen atoms on the group is substituted by the substituent selected from the group consisting of $C_1$-$C_{10}$ alkyl, $C_3$-$C_{10}$ cycloalkyl, $C_1$-$C_{10}$ alkoxy, halogen, hydroxyl, carboxyl($-COOH$), $C_1$-$C_{10}$ aldehyde group, $C_2$-$C_{10}$ acyl, $C_2$-$C_{10}$ ester group, amino, and phenyl; the phenyl includes unsubstituted phenyl or phenyl substituted with 1-3 substituents selected from halogen, $C_1$-$C_{10}$ alkyl, cyano, OH, nitro, $C_3$-$C_{10}$ cycloalkyl, $C_1$-$C_{10}$ alkoxy, amino.

Unless otherwise specified, each chiral carbon atom may optionally be in R configuration or S configuration, or a mixture of R configuration and S configuration among all the compounds of the present invention.

The term "C1-C6 alkyl" refers to a linear or branched chain alkyl having 1 to 6 carbon atoms, such as methyl, ethyl, propyl, isopropyl, butyl, isobutyl, sec-butyl, tert-butyl, or the like.

The term "3-8 membered heterocyclyl" refers to a group formed by the loss of one hydrogen atom from a 3-8 membered saturated ring having 1-3 heteroatoms selected from the group consisting of N, S and O; such as pyrrolidyl, piperidinyl, piperazinyl, morpholinyl, or the like.

The term "6-10 membered aryl" refers to a group formed by the loss of a hydrogen atom from 6-10 membered aryl, such as phenyl, naphthyl, or the like. The term "5-10-membered heteroaryl" refers to a group formed by the loss of one hydrogen atom from a 5-8 membered aryl having 1-3 heteroatoms selected from the group consisting of N, S and O, wherein the cyclic system of each heteroaryl may be monocyclic or polycyclic, such as pyrrolyl, pyridyl, thienyl, furyl, imidazolyl, pyrimidyl, benzothienyl, indolyl, imidazopyridyl, quinolyl, or the like. The term "C1-C6 alkoxy" refers to a linear or branched chain alkoxy having 1 to 6 carbon atoms, such as methoxy, ethoxy, propoxy, isopropoxy, butoxy, isobutoxy, sec-butoxy, tert-butoxy, or the like.

The term "C2-C6 ester group" refers to R—O—C(═O)— having 2-6 carbon atoms, such as $-COOCH_3$, $-COOC_2H_5$, $-COOC_3H_7$, $-COOC_4H_9$, or the like.

The term "C2-C6 alkenyl" refers to a group formed by the loss of one or two hydrogen atoms from an olefin having 2-6 carbon atoms. The olefin may be a monoolefin, a diene or a triolefin, such as $-CH{=}CH_2$, $-C_2H_4{=}CH_2$, $-CH{=}C_2H_4$, or the like.

The term "halogen" refers to F, Cl, Br and I.

Unless otherwise specified, the structural formula described herein are intended to include all isomeric forms (e.g., enantiomer, diastereomer, and geometric isomers (or conformational isomer): for example, R, S configurations containing asymmetric centers, (Z), (E) isomers of double bonds, and (Z), (E) conformational isomers. Thus, a single stereochemical isomer or a mixture of enantiomers, diastereoisomers or geometric isomers (or conformational isomers) thereof of the compound of the invention is within the scope of the invention.

The term "tautomer" means that structural isomers with different energies can exceed the low energy barrier, thus transforming into each other. For example, proton tautomers (i.e. proton shift) include intertransformation through proton migration, such as 1H-indazole and 2H-indazole, 1H-benzo [d] imidazole and 3H-benzo [d] imidazole, valence tautomers include intertransformation through some bonded electron recombination.

Herein, the form "C1-C6" indicates that the group may have 1 to 6 carbon atoms, for example, 1, 2, 3, 4, or 5 carbon atoms.

Active Ingredient

In the present invention, it provides an active ingredient that can effectively inhibit the replication of 2019 novel coronavirus (2019-nCov). The active ingredient is a compound represented by formula A, which is effective in preventing, treating and/or alleviating 2019-nCov-related diseases.

The tests have shown that the active ingredient of the present invention can effectively inhibit the 3CL protease and/or human cathepsin L of 2019 novel coronavirus (2019-nCov), thereby inhibiting the replication of 2019 novel coronavirus (2019-nCov), thereby preventing, treating and/or alleviating 2019-nCov related diseases.

It should be understood that the active ingredient of the present invention includes the ketoamide compound of formula (A), or the pharmaceutically acceptable salt, enantiomer, diastereomer or racemate thereof, or a prodrug thereof. It should be understood that the active ingredient of the present invention also includes crystalline forms of the compound of formula (A), amorphous compounds, and deuterated compounds, etc.

The "pharmaceutically acceptable salt" is a conventional non-toxic salt formed by the reaction of the compound of formula (A) with an inorganic acid or an organic acid. For example, conventional non-toxic salts can be prepared by reacting compounds of formula (A) with inorganic acids or organic acids, the inorganic acids include hydrochloric acid, hydrobromic acid, sulfuric acid, nitric acid, amino sulfonic acid and phosphoric acid, etc, and the organic acids include citric acid, tartaric acid, lactic acid, pyruvic acid, acetic acid, benzenesulfonic acid, p-toluenesulfonic acid, methanesulfonic acid, naphthalene sulfonic acid, ethylsulfonic acid, naphthalene disulfonic acid, maleic acid, malic acid, malonic acid, fumaric acid, succinic acid, propionic acid, oxalic acid, trifluoroacetic acid, stearic acid, embonic acid, hydroxymaleic acid, phenylacetic acid, benzoic acid, salicylic acid, glutamic acid, ascorbic acid, p-aminobenzenesulfonic acid, 2-acetoxybenzoic acid and hydroxyethanesulfonic acid; or the compound of formula (A) first forms an ester with propionic acid, oxalic acid, malonic acid, succinic acid, fumaric acid, maleic acid, lactic acid, malic acid, tartaric acid, citric acid, aspartic acid or glutamic acid, and then forms sodium salt, potassium salt, calcium salt, aluminum salt or ammonium salt with inorganic bases; or the compound of formula (A) forms methylamine salt, ethylamine salt or ethanolamine salt with organic bases; or the compound of formula (A) first forms an ester with lysine, arginine, ornithine and then forms a corresponding inorganic acid salts with hydrochloric acid, hydrobromic acid, hydrofluoric acid, sulfuric acid, nitric acid or phosphoric acid or forms a corresponding organic acid salts with formic acid, acetic acid, picric acid, methanesulfonic acid or ethanesulfonic acid.

Pharmaceutical Composition and Application

The present invention also provides a use of a ketoamide compound represented by formula (A), or a pharmaceutically acceptable salt, enantiomer, diastereomer, racemate or prodrug thereof or a mixture of one or more of the above as an active ingredient in the manufacture of a medicament for treating and/or preventing and alleviating respiratory tract infection, pneumonia and other related diseases caused by 2019 novel coronavirus infection.

The pharmaceutical composition provided by the present invention preferably contains an active ingredient in a weight ratio of 0.001 to 99 wt %, preferably a ratio of 0.1 wt % to 90 wt % of the total weight of the compound of formula (A) as the active ingredient, and the rest is pharmaceutically acceptable carrier, diluent or solution or salt solution.

When necessary, one or more pharmaceutically acceptable carriers can also be added to the medicament of the present invention. The carrier includes conventional diluents, excipients, fillers, binders, wetting agents, disintegrants, absorption promoters, surfactants, adsorption carriers, lubricants, and the like in the pharmaceutical field.

The compounds and pharmaceutical compositions provided by the present invention can be in various forms, such as tablets, capsules, powders, syrups, solutions, suspensions and aerosols, etc., and can be present in suitable solid or liquid carriers or diluents and sterilization equipment suitable for injection or drip.

Various dosage forms of the pharmaceutical composition of the present invention can be prepared according to conventional preparation methods in the pharmaceutical field. The unit measurement of the formulation generally contains 0.05-400 mg of the compound of formula A, preferably, the unit measurement of the formulation contains 1 mg-500 mg of the compound of formula A.

The compound and pharmaceutical composition of the present invention can be used clinically in mammals, including humans and animals, and can be administered through oral, nasal, skin, lung, gastrointestinal tract, etc. It is most preferably administered orally. The most preferred daily dose is 0.01-400 mg/kg (body weight) in a single dose, or 0.01-200 mg/kg (body weight) in divided doses. Regardless of the method of administration, the individual's optimal dosage should be determined based on the specific treatment. Normally, start with a small dose and gradually increase the dose until the most suitable dose is found.

The drugs or inhibitors of the present invention may be administered in a variety of different ways, for example, by injection, spray, nasal drops, eye drops, permeation, absorption, physical or chemically mediated introduction into the body such as intramuscular, intradermal, subcutaneous, intravenous, mucosal tissues; or introducing into the body by mixing or coating with other substances.

The main advantages of the invention include:

(a) The compounds of the present invention can efficiently inhibit the 2019-nCoV 3CL protease, and the $IC_{50}$ value of some compounds reaches about 2.4 μM.

(b) The compound of the present invention can efficiently inhibit human cathepsin L, and the $IC_{50}$ value of some compounds reaches about 0.45 nM.

(c) The compound of the present invention has a better inhibition rate against 2019-nCoV at the viral level than the positive control CQ, showing a better anti-2019-nCoV potential, and the $EC_{50}$ value of some compounds reaches about 0.3 μM.

(d) The compound of the present invention has low toxic and side effects and good druggability.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, percentage and parts are calculated by weight.

The analysis data of the sample were determined by the following instruments: nuclear magnetic resonance was determined by GEMINI-300, Bruker AMX-400 and INVOA-600 nuclear magnetic resonance instruments, TMS (tetramethylsilane) was as the internal standard, the chemical shift unit was ppm, and the coupling constant unit was Hz; Mass spectrometry was determined by Finnigan MAT-711, MAT-95 and LCQ-DECA mass spectrometers and IonSpec 4.7 Tesla mass spectrometer.

200-300 mesh silica gel for column chromatography (produced by Qingdao Ocean Chemical Plant); TLC silica gel plate is HSGF-254 thin layer chromatography prefabricated plate produced by Yantai Chemical Plant; petroleum ether boiling range is 60-90° C.; UV lamp is used, the iodine cylinder shows color. Unless otherwise stated, the conventional reagents and medicines used in the following examples were purchased from Sinopharm Group. The reagents and solvents used in the experiment were treated according to the specific conditions of the reaction.

Example 1 Compound A1

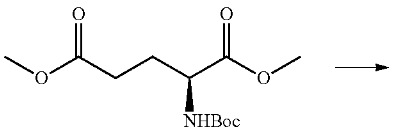

1-1

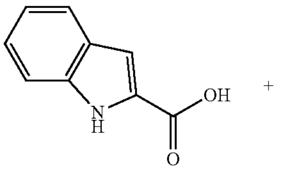

+

-continued

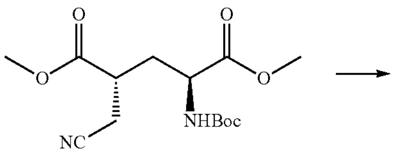

1-2

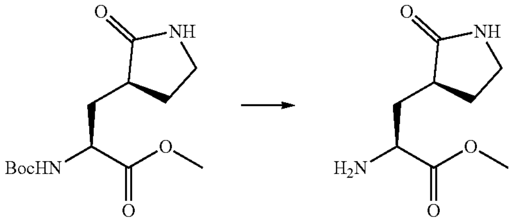

1-3 1-4

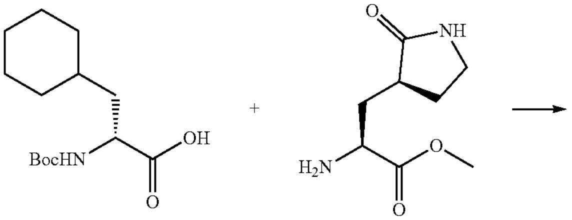

+

1-4

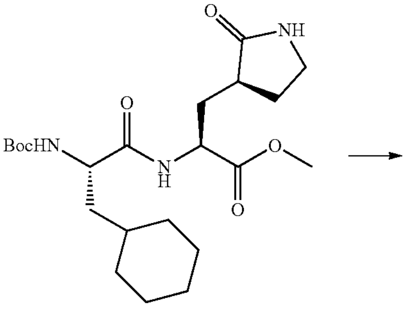

1-5

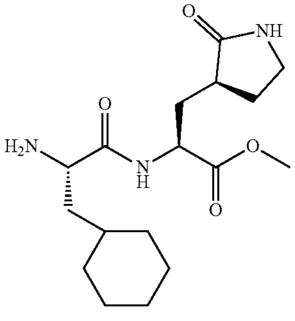

1-6

-continued

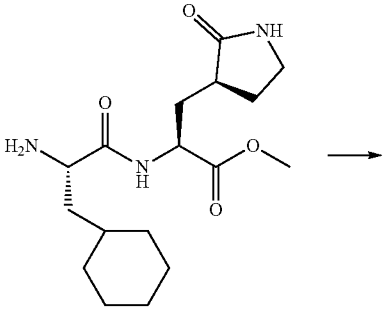

1-6

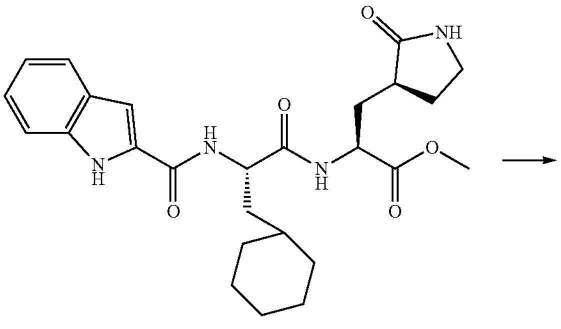

1-7

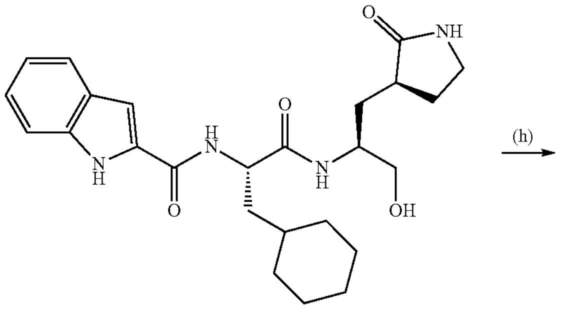

1-8

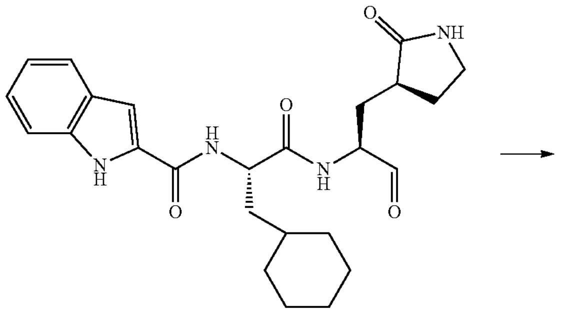

1-9

-continued

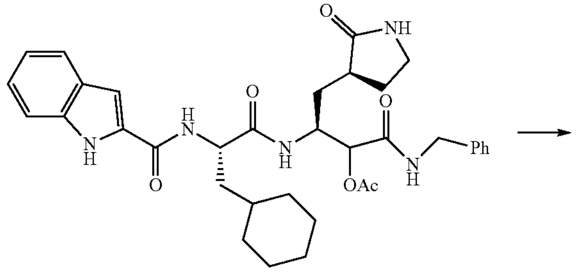

1-10

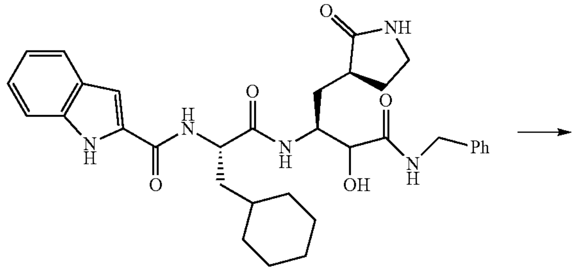

1-11

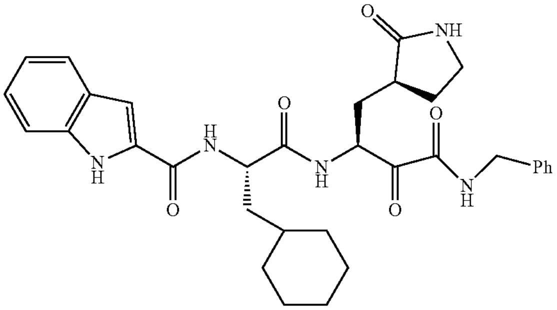

1-12

Synthesis of Compound 1-2

Under the protection of argon, N-tert-butoxycarbonyl-L-glutamic acid dimethyl ester (1-1) (6 g, 21.8 mmol) was dissolved in 60 mL of anhydrous tetrahydrofuran, and a solution of LiHMDS (1M in THF) in tetrahydrofuran (47 mL, 47 mmol) was slowly dropped at −78° C., and the temperature was kept stable at −78° C. during the dripping process for about 1 hour. After dripping, the reaction solution was stirred at −78° C. for 1 hour. Bromoacetonitrile (2.79 g, 23.3 mmol) was dissolved in 20 ml of tetrahydrofuran, and then the solution was slowly dropped into the reaction system. The dropping process was lasted for 1 to 2 hours. The temperature was controlled at −78° C. and the reaction was continued for 3 hours. When TLC monitoring (alkaline potassium permanganate color development) indicated the reaction was completed, NH4Cl solution was added to the reaction solution to quench the reaction, stirred for 10 min, and then warmed to room temperature. 40 mL of saturated sodium chloride solution was poured in and stirred well, and the reaction system appeared to separate into layers. The organic layer was separated, and the aqueous phase was extracted with ethyl acetate (EA). The organic layers were combined and dried over anhydrous sodium sulfate, concentrated, and purified by column chromatography (Flash, PE:EA=1:5) to obtain a pale yellow oil (1-2 3.9 g, the yield was 58%).

Synthesis of Compound 1-3

1-2 (1 g, 3.15 mmol) was dissolved in 25 mL of anhydrous methanol, stirred to 0° C. under an ice bath, then cobalt dichloride hexahydrate (450 mg, 1.89 mmol) was added. After 10 min, a small amount of sodium borohydride (715 mg, 18.9 mmol) was added in batches and the reaction solution continued to react under an ice bath for 1 h and then reacted at room temperature. After 15 h, the reaction was quenched with 5 mL of saturated NH4Cl solution, continued stirring for 10 min, and evaporated the filtrate after filtering the solid. The mixture was extracted with 20 mL of water and 30×3 mL of ethyl acetate. The combined organic phases was dried over anhydrous $Na_2SO_4$ for 1 h, concentrated under reduced pressure, and separated by column chromatography[PE:EA=1:2] to obtain 460 mg of white powdered solid with a yield of 51%.

Synthesis of Compound 1-4

Compound 1-3 (2.6 g) was dissolved in trifluoroacetic acid in dichloromethane solution (1/1, v/v), stirred at room temperature for 1 hour, 100 ml of dichloromethane was added after concentration, and washed with saturated sodium carbonate solution. The organic layer was dried over anhydrous sodium sulfate and concentrated to obtain oily substance 1-4 (2.7 g) with a yield of 99%.

Synthesis of Compound 1-5

Boc-cyclohexylalanine (1.26 g, 5 mmol), EDCI (1.36 g, 6 mmol) and HOBt (0.822 g, 6 mmol) were added to 80 ml dichloromethane solution, and stirred at room temperature for 30 min. Subsequently, compound 1-4 (0.896 g, 5 mmol) was added, 1.2 equivalent of triethylamine was added dropwise, and the mixture was stirred at room temperature. When TLC monitoring (UV) indicated the reaction was complete, extracted with dichloromethane, washed with dilute hydrochloric acid, saturated sodium bicarbonate solution and saturated sodium chloride, the organic layers were combined and dried over anhydrous sodium sulfate, and concentrated to obtain 1.2 g of white viscous solid, the yield is 60%.

Synthesis of Compound 1-6

Compound 1-5 (2.5 g) was dissolved in trifluoroacetic acid in dichloromethane solution (1/1, v/v), stirred at room temperature for 1 hour, 100 ml of dichloromethane was added after concentration, and washed with saturated sodium carbonate solution. The organic layer was dried over anhydrous sodium sulfate and concentrated to obtain oily substance 1-6 (2.61 g) with a yield of 99%.

Synthesis of Compound 1-7

Indole 2-formic acid (0.795 g, 5 mmol), EDCI (1.36 g, 6 mmol), and HOBt (0.822 g, 6 mmol) were added to 80 ml of dichloromethane solution, and stirred at room temperature for 30 min. Subsequently, compound 1-6 (2.2 g, 5 mmol) was added, 1.2 equivalent of triethylamine was added dropwise, and the mixture was stirred at room temperature. When TLC monitoring (UV) indicated the reaction was complete, extracted with dichloromethane, washed with dilute hydrochloric acid, saturated sodium bicarbonate solution and saturated sodium chloride, the organic layers were combined and dried over anhydrous sodium sulfate, and concentrated to obtain 1.3 g of white viscous solid, the yield is 60%.

Synthesis of Compound 1-8

1-7 (243 mg, 0.51 mmol) was dissolved in 20 ml of methanol, sodium borohydride (107 mg, 2.9 mmol) was slowly added in batches, and stirred at room temperature for about 2 hours to complete the reaction. After the reaction was completed, about 20 ml of saturated brine was added to quench the reaction, concentrated the reaction system to remove methanol, and dichloromethane was added for extraction. The organic phase was washed with saturated brine, dried over anhydrous sodium sulfate, and concentrated to obtain a white solid substance 1-8, which can be directly used in the next reaction.

Synthesis of Compound 1-9

Intermediate 1-8 (129 mg, 0.29 mmol) was dissolved in 20 ml of dichloromethane, and Dess-Martin oxidant (147 mg, 0.35 mmol) and sodium bicarbonate solid (29 mg, 0.35 mmol) were added, stirred at room temperature. When TLC monitoring (UV) indicated the reaction was completed, the reaction system was suction filtered, the filtrate obtained was extracted with saturated sodium bicarbonate, and the organic layer was subjected to wash with saturated salt water, dried over anhydrous sodium sulfate and concentrated. After separation and purification by flash column chromatography (CH2Cl2:MeOH=20:1), 77 mg of white solid powder compound 1 was obtained, with a yield of 60%.

Synthesis of Compound 1-10

Compound 1-9 (129 mg, 0.29 mmol) was dissolved in dichloromethane solvent, acetic acid (19.2 mg, 0.32 mmol) and benzyl isocyanate (37.6 mg, 0.32 mmol) were added to react to obtain compound 1-10, which was separated and purified by rapid column chromatography ($CH_2Cl_2$:MeOH=20:1) to obtain a total of 126 mg of white solid powder compound 1-10 with a yield of 70%.

Synthesis of Compound 1-11

Compound 1-10 (187 mg, 0.3 mmol) was dissolved in methanol solvent, and LiOH (0.6 mmol) was added to and stirred to obtain compound 1-11, which was separated and purified by rapid column chromatography ($CH_2Cl_2$:MeOH=20:1) to obtain a total of 148 mg of white solid powder compound 1-11 with a yield of 85%.

Synthesis of Compound 1-12

Compound 1-11 (174 mg, 0.3 mmol) was dissolved in dichloromethane solvent, Dess-Martin oxidant (152 mg, 0.36 mmol) was added, sodium bicarbonate (30 mg, 0.36 mmol) was added, and stirred to obtain the compound as a white solid powder compound 1-12 (140 mg in total, yield 80%).

$^1$H NMR (500 MHz, Chloroform) δ 9.76 (s, 1H), 7.73 (s, 1H), 7.39 (s, 1H), 7.32-7.26 (m, 2H), 7.22 (s, 1H), 7.20-7.10 (m, 3H), 7.01 (s, 1H), 6.82 (s, 1H), 6.68 (s, 1H), 6.14 (s, 1H), 5.57 (s, 1H), 5.43 (s, 1H), 4.38 (s, 1H), 4.32 (d, J=19.2 Hz, 2H), 3.45 (s, 1H), 3.35 (s, 1H), 3.06 (s, 1H), 2.20 (dd, J=15.4, 2.3 Hz, 4H), 2.12-2.03 (m, 2H), 1.92 (s, 1H), 1.77 (s, 1H), 1.73-1.67 (m, 3H), 1.66-1.53 (m, 6H), 1.37 (s, 1H).

Examples 2-310 was synthesized using the method similar to Example 1.

Example 2 N—((S)-1-(((S)-4-(tert-butylamino)-3,4-dione-1-((S)-2-oxopyrrolidin-3-yl)but-2-yl)amino)-3-cyclohexyl-1-oxopropan-2-yl)-1H-indole-2-carboxamide (A2)

$^1$H NMR (500 MHz, Chloroform) δ 8.38 (s, 1H), 7.51 (d, J=18.0 Hz, 2H), 7.38 (s, 1H), 7.12 (s, 1H), 7.06 (s, 1H), 6.26 (s, 1H), 6.04 (s, 1H), 5.80 (s, 1H), 5.25 (s, 1H), 4.81 (s, 1H), 4.67 (s, 1H), 3.45 (s, 1H), 3.35 (s, 1H), 2.55 (s, 1H), 2.18 (s, 1H), 2.09-2.05 (m, 2H), 1.96-1.91 (m, 3H), 1.73-1.52 (m, 5H), 1.40-1.36 (m, 2H), 1.35-1.29 (m, 10H), 1.20-1.09 (m, 3H).

Example 3 N—((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopropan-2-yl)-1H-indole-2-carboxamide (A3)

$^1$H NMR (500 MHz, Chloroform) δ 8.28 (s, 1H), 7.48 (d, J=1.2 Hz, 2H), 7.34 (s, 1H), 7.10 (d, J=1.0 Hz, 2H), 7.03 (s, 1H), 6.05 (s, 1H), 5.59 (s, 1H), 5.30 (s, 1H), 4.63 (s, 1H), 4.45 (s, 1H), 3.58 (s, 1H), 3.45 (s, 1H), 3.35 (s, 1H), 2.95 (s, 1H), 2.18 (s, 1H), 2.09-2.05 (m, 2H), 1.98-1.90 (m, 3H), 1.73-1.67 (m, 3H), 1.65-1.61 (m, 2H), 1.51 (dtd, J=12.9, 8.9, 1.3 Hz, 13H), 1.45-1.39 (m, 3H), 1.38-1.34 (m, 2H).

Example 4 N—((S)-3-cyclohexyl-1-(((S)-4-(neopentylamino)-3,4-dione-1-((S)-2-oxopyrrolidin-3-yl)but-2-yl)amino)-3-cyclohexyl-1-oxopropan-2-yl)-1H-indole-2-carboxamide (A4)

$^1$H NMR (500 MHz, Chloroform) δ 8.46 (s, 1H), 7.53 (d, J=3.4 Hz, 2H), 7.40 (d, J=17.1 Hz, 2H), 7.12 (s, 1H), 7.06 (s, 1H), 6.16 (d, J=14.3 Hz, 2H), 5.65 (s, 1H), 5.23 (s, 1H), 4.44 (s, 1H), 3.44 (d, J=11.4 Hz, 2H), 3.35 (s, 1H), 3.09 (s, 1H), 2.97 (s, 1H), 2.19 (s, 1H), 2.09-2.05 (m, 2H), 1.92 (s, 1H), 1.75-1.68 (m, 4H), 1.62 (s, 1H), 1.48 (dt, J=16.0, 8.0 Hz, 5H), 1.37-1.31 (m, 2H), 1.28 (s, 1H), 1.09-1.05 (m, 9H).

Example 5 N—((S)-1-(((S)-4-(benzylamino)-3,4-dione-1-((S)-2-oxopiperidin-3-yl)but-2-yl)amino)-3-cyclohexyl-1-oxopropan-2-yl)-1H-indole-2-carboxamide (A5)

$^1$H NMR (500 MHz, Chloroform) δ 8.22 (s, 1H), 7.96 (s, 1H), 7.53 (s, 1H), 7.42 (s, 1H), 7.38 (s, 1H), 7.29-7.24 (m, 4H), 7.17 (d, J=29.6 Hz, 2H), 7.07 (s, 1H), 6.54 (s, 1H), 5.74 (s, 1H), 5.27 (s, 1H), 5.06 (s, 1H), 4.49 (s, 1H), 4.41 (s, 1H), 4.31 (s, 1H), 3.24 (d, J=17.4 Hz, 2H), 2.56 (s, 1H), 2.08-2.04 (m, 2H), 1.95-1.88 (m, 2H), 1.78 (d, J=6.9 Hz, 2H), 1.69 (dt, J=6.3, 3.5 Hz, 7H), 1.51 (s, 1H), 1.40-1.36 (m, 2H), 1.32 (s, 1H), 1.15-1.11 (m, 2H), 1.08 (s, 1H).

Example 6 N—((S)-1-(((S)-4-(tert-butylamino)-3,4-dione-1-((S)-2-oxopiperidin-3-yl)but-2-yl)amino)-3-cyclohexyl-1-oxopropan-2-yl)-1H-indole-2-carboxamide (A6)

$^1$H NMR (500 MHz, Chloroform) δ 8.30 (s, 2H), 7.48 (s, 2H), 7.43 (s, 2H), 7.35 (s, 2H), 7.10 (s, 2H), 7.03 (s, 2H), 6.45 (s, 2H), 5.99 (s, 2H), 5.76 (s, 2H), 5.25 (s, 2H), 4.81 (s, 2H), 4.29 (s, 2H), 3.24 (d, J=17.1 Hz, 4H), 2.75 (s, 2H), 2.05 (t, J=8.9 Hz, 6H), 1.79 (s, 2H), 1.71 (t, J=2.5 Hz, 7H), 1.58-1.54 (m, 3H), 1.51-1.33 (m, 10H), 1.33-1.29 (m, 20H), 1.23 (s, 2H), 1.15-1.11 (m, 3H), 0.94-0.90 (m, 3H).

Example 7 N—((S)-3-cyclohexyl-1-(((S)-4-(cyclohexylamino)-3,4-dione-1-((S)-2-oxopiperidin-3-yl)but-2-yl)amino)-3-cyclohexyl-1-oxopropan-2-yl)-1H-indole-2-carboxamide (A7)

1H NMR (500 MHz, Chloroform) δ 9.29 (s, 1H), 8.69 (s, 1H), 7.52 (s, 1H), 7.43 (d, J=15.1 Hz, 2H), 7.13 (s, 1H), 7.06 (s, 1H), 5.93 (s, 1H), 5.59 (d, J=3.5 Hz, 2H), 5.11 (s, 1H), 4.51 (s, 1H), 3.41 (s, 1H), 3.24 (d, J=16.6 Hz, 2H), 2.66 (s, 1H), 2.54 (s, 1H), 2.08-2.04 (m, 2H), 2.01-1.89 (m, 2H), 1.89-1.77 (m, 4H), 1.73-1.61 (m, 7H), 1.55-1.50 (m, 3H), 1.48 (s, 1H), 1.44-1.39 (m, 2H), 1.39-1.35 (m, 2H), 1.31 (s, 1H), 1.09-0.99 (m, 3H).

Example 8 N—((S)-3-cyclohexyl-1-(((S)-4-(neopentylamino)-3,4-dione-1-((S)-2-oxopiperidin-3-yl)but-2-yl)amino)-3-cyclohexyl-1-oxopropan-2-yl)-1H-indole-2-carboxamide (A8)

1H NMR (500 MHz, Chloroform) δ 8.45 (s, 4H), 7.50 (d, J=31.7 Hz, 8H), 7.46-7.46 (m, 1H), 7.39 (s, 5H), 7.13 (s, 4H), 7.06 (s, 4H), 6.01 (s, 4H), 5.44 (s, 4H), 5.40 (s, 4H), 5.23 (s, 4H), 4.89 (s, 4H), 4.47 (s, 4H), 3.30-3.20 (m, 12H), 3.13 (s, 4H), 2.30 (s, 4H), 2.10-2.02 (m, 8H), 1.97 (s, 3H), 1.81-1.76 (m, 11H), 1.71 (t, J=1.6 Hz, 11H), 1.69-1.63 (m, 13H), 1.50 (s, 3H), 1.39-1.35 (m, 7H), 1.31 (s, 4H), 1.14-1.05 (m, 44H), 1.02 (s, 3H).

Example 9 N—((S)-1-(((S)-4-(benzylamino)-3,4-dione-1-((S)-2-oxopyrrolidin-3-yl)but-2-yl)amino)-3-cyclohexyl-1-oxopropan-2-yl)-benzofuran-2-carboxamide (A9)

1H NMR (500 MHz, Chloroform) δ 7.66 (s, 1H), 7.34-7.28 (m, 5H), 7.22 (d, J=7.1 Hz, 2H), 7.10 (s, 1H), 6.72 (s, 1H), 6.17 (s, 1H), 5.97 (s, 1H), 5.84 (s, 1H), 5.47 (s, 1H), 4.42 (s, 1H), 4.34 (d, J=9.3 Hz, 2H), 3.45 (s, 1H), 3.35 (s, 1H), 3.22 (s, 1H), 2.64 (s, 1H), 2.18 (s, 1H), 2.09-2.05 (m, 2H), 2.05-1.98 (m, 2H), 1.92 (s, 1H), 1.75-1.66 (m, 4H), 1.66-1.55 (m, 6H), 1.36 (s, 1H).

Example 10 N—((S)-1-(((S)-4-(tert-butylamino)-3,4-dione-1-((S)-2-oxopyrrolidin-3-yl)but-2-yl)amino)-3-cyclohexyl-1-oxopropan-2-yl)-benzofuran-2-carboxamide (A10)

1H NMR (500 MHz, Chloroform) δ 9.59 (s, 1H), 8.31 (s, 1H), 7.63 (s, 1H), 7.50 (s, 1H), 7.41 (s, 1H), 7.22 (s, 1H), 7.16 (s, 1H), 6.40 (s, 1H), 5.82 (s, 1H), 4.81 (s, 1H), 4.64 (s, 1H), 3.97 (s, 1H), 3.35 (s, 1H), 2.69 (s, 1H), 2.19 (s, 1H), 2.09-2.05 (m, 2H), 1.94-1.88 (m, 3H), 1.76-1.66 (m, 2H), 1.66-1.48 (m, 3H), 1.36-1.32 (m, 11H), 1.28 (s, 1H), 1.20 (s, 1H), 0.99-0.95 (m, 2H).

Example 11 N—((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopropan-2-yl)-benzofuran-2-carboxamide (A11)

1H NMR (500 MHz, Chloroform) δ 7.63 (s, 4H), 7.47 (s, 4H), 7.36 (s, 4H), 7.26 (s, 4H), 7.21 (s, 4H), 7.14 (s, 4H), 5.98 (s, 4H), 5.77 (s, 4H), 5.16 (s, 4H), 4.60 (s, 4H), 4.32 (s, 4H), 3.53 (s, 3H), 3.45 (s, 4H), 3.35 (s, 3H), 2.58 (s, 3H), 2.19 (s, 3H), 2.09-2.05 (m, 8H), 1.95-1.88 (m, 11H), 1.74-

1.68 (m, 27H), 1.65-1.61 (m, 6H), 1.61-1.47 (m, 31H), 1.44-1.39 (m, 8H), 1.35-1.31 (m, 6H), 1.24 (s, 3H).

Example 12 N—((S)-3-cyclohexyl-1-(((S)-4-(neo-pentylamino)-3,4-dione-1-((S)-2-oxopyrrolidin-3-yl) but-2-yl)amino)-3-cyclohexyl-1-oxopropan-2-yl)-benzofuran-2-carboxamide (A12)

1H NMR (500 MHz, Chloroform) δ 8.31 (s, 4H), 7.60 (s, 4H), 7.49 (s, 4H), 7.40 (s, 4H), 7.21 (s, 4H), 7.15 (s, 4H), 6.18 (s, 4H), 5.46 (s, 4H), 5.25 (s, 4H), 5.12 (s, 4H), 4.63 (s, 4H), 3.43 (d, J=18.9 Hz, 8H), 3.35 (s, 3H), 3.11 (s, 4H), 2.76 (s, 4H), 2.17 (s, 3H), 2.13-2.01 (m, 8H), 1.93 (s, 4H), 1.85-1.81 (m, 6H), 1.73-1.69 (m, 7H), 1.69-1.62 (m, 7H), 1.61-1.42 (m, 16H), 1.33-1.29 (m, 6H), 1.26 (s, 3H), 1.14-1.10 (m, 3H).

Example 13 N—((S)-1-(((S)-4-(benzylamino)-3,4-dione-1-((S)-2-oxopiperidin-3-yl)but-2-yl)amino)-3-cyclohexyl-1-oxopropan-2-yl)-benzofuran-2-carbox-amide (A13)

1H NMR (500 MHz, Chloroform) δ 7.59 (s, 4H), 7.51 (d, J=1.4 Hz, 1H), 7.46 (d, J=36.6 Hz, 7H), 7.32-7.14 (m, 29H), 6.56 (s, 4H), 5.75 (s, 4H), 5.66 (s, 4H), 5.09 (s, 4H), 4.56 (s, 4H), 4.41 (s, 4H), 4.32 (s, 4H), 3.24 (d, J=17.0 Hz, 8H), 2.32 (s, 4H), 2.10-2.02 (m, 9H), 1.99 (s, 4H), 1.97-1.89 (m, 8H), 1.79 (s, 4H), 1.75-1.52 (m, 28H), 1.40-1.36 (m, 7H), 1.32 (s, 4H), 1.23-1.19 (m, 8H), 1.16 (s, 3H).

Example 14 N—((S)-1-(((S)-4-(tert-butylamino)-3, 4-dione-1-((S)-2-oxopiperidin-3-yl)but-2-yl)amino)-3-cyclohexyl-1-oxopropan-2-yl)-benzofuran-2-car-boxamide (A14)

1H NMR (500 MHz, Chloroform) δ 7.63 (s, 1H), 7.50 (s, 1H), 7.37 (s, 1H), 7.22 (s, 1H), 7.16 (s, 1H), 6.25 (s, 1H), 6.08 (s, 1H), 5.76 (s, 1H), 4.70 (d, J=19.7 Hz, 2H), 3.24 (d, J=14.7 Hz, 2H), 2.83 (s, 1H), 2.08-2.04 (m, 2H), 2.01 (s, 1H), 1.90 (s, 1H), 1.85-1.78 (m, 3H), 1.75-1.64 (m, 5H), 1.56-1.41 (m, 6H), 1.32 (s, 1H), 1.25-1.21 (m, 9H).

Example 15 N—((S)-3-cyclohexyl-1-(((S)-4-(cyclo-hexylamino)-3,4-dione-1-((S)-2-oxopiperidin-3-yl) but-2-yl)amino)-3-cyclohexyl-1-oxopropan-2-yl)-benzofuran-2-carboxamide (A15)

1H NMR (500 MHz, Chloroform) δ 9.45 (s, 1H), 8.16 (s, 1H), 7.51 (s, 1H), 7.42 (s, 1H), 7.22 (s, 1H), 7.16 (s, 1H), 6.16 (s, 1H), 6.07 (s, 1H), 5.85 (s, 1H), 5.08 (s, 1H), 4.48 (s, 1H), 3.32 (s, 1H), 3.24 (d, J=16.1 Hz, 2H), 2.92 (s, 1H), 2.16-2.08 (m, 2H), 2.08-2.04 (m, 2H), 2.02 (s, 1H), 1.80 (s, 1H), 1.76-1.66 (m, 8H), 1.65 (s, 1H), 1.57 (s, 1H), 1.55-1.40 (m, 8H), 1.40-1.37 (m, 1H), 1.31 (s, 1H), 1.12 (s, 1H), 0.90-0.82 (m, 2H).

Example 16 N—((S)-3-cyclohexyl-1-(((S)-4-(neo-pentylamino)-3,4-dione-1-((S)-2-oxopiperidin-3-yl) but-2-yl)amino)-3-cyclohexyl-1-oxopropan-2-yl)-benzofuran-2-carboxamide (A16)

1H NMR (500 MHz, Chloroform) δ 7.60 (s, 1H), 7.49 (s, 1H), 7.40 (s, 1H), 7.21 (s, 1H), 7.15 (s, 1H), 6.20 (s, 1H), 5.99 (s, 1H), 5.91 (s, 1H), 5.65 (s, 1H), 4.86 (s, 1H), 4.76 (s, 1H), 3.30 (s, 1H), 3.24 (d, J=17.4 Hz, 2H), 2.92 (s, 1H), 2.65 (s, 1H), 2.08-2.04 (m, 2H), 2.01 (s, 1H), 1.90-1.84 (m, 2H), 1.82 (s, 1H), 1.77-1.65 (m, 5H), 1.60-1.53 (m, 4H), 1.52-1.48 (m, 2H), 1.40 (s, 1H), 1.34 (s, 1H), 1.07-1.03 (m, 9H).

Example 17 N—((S)-1-(((S)-4-(benzylamino)-3,4-dione-1-((S)-2-oxopyrrolidin-3-yl)but-2-yl)amino)-3-cyclohexyl-1-oxopropan-2-yl)-benzothiophene-2-carboxamide (A17)

1H NMR (500 MHz, Chloroform) δ 8.13 (s, 5H), 7.89 (s, 5H), 7.65 (s, 5H), 7.28 (dd, J=7.5, 4.2 Hz, 20H), 7.21 (dd, J=4.2, 2.6 Hz, 2H), 7.20-7.08 (m, 13H), 6.14 (s, 5H), 5.53 (s, 5H), 5.37 (s, 5H), 4.39-4.32 (m, 15H), 4.24 (s, 5H), 3.45 (s, 5H), 3.35 (s, 4H), 3.24 (s, 5H), 2.94 (s, 4H), 2.19 (s, 4H), 2.09-2.05 (m, 10H), 1.92 (s, 4H), 1.80-1.67 (m, 25H), 1.59-1.49 (m, 15H), 1.46-1.38 (m, 19H), 1.23 (s, 5H).

Example 18 N—((S)-14 (S)-4-(tert-butylamino)-3, 4-dione-14 (S)-2-oxopyrrolidin-3-yl)but-2-yl) amino)-3-cyclohexyl-1-oxopropan-2-yl)-benzothi-ophene-2-carboxamide (A18)

1H NMR (500 MHz, Chloroform) δ 8.37 (s, 1H), 7.89 (s, 1H), 7.73 (s, 1H), 7.31 (d, J=1.5 Hz, 2H), 6.28 (s, 1H), 6.05 (s, 1H), 5.80 (s, 1H), 5.25 (s, 1H), 4.82 (s, 1H), 4.68 (s, 1H), 3.45 (s, 1H), 3.35 (s, 1H), 2.56 (s, 1H), 2.18 (s, 1H), 2.09-2.05 (m, 2H), 1.95-1.88 (m, 3H), 1.73-1.52 (m, 5H), 1.41-1.37 (m, 2H), 1.35-1.29 (m, 10H), 1.18-1.09 (m, 3H).

Example 19 N—((S)-3-cyclohexyl-1-(((S)-4-(cyclo-hexylamino)-3,4-dione-1-((S)-2-oxopyrrolidin-3-yl) but-2-yl)amino)-3-cyclohexyl-1-oxopropan-2-yl)-benzothiophene-2-carboxamide (A19)

1H NMR (500 MHz, Chloroform) δ 8.95 (s, 1H), 8.43 (s, 1H), 8.26 (s, 1H), 7.90 (s, 1H), 7.74 (s, 1H), 7.61 (s, 1H), 7.31 (d, J=2.0 Hz, 2H), 5.94 (s, 1H), 4.69 (s, 1H), 4.53 (s, 1H), 3.44 (d, J=9.6 Hz, 2H), 3.35 (s, 1H), 2.95 (s, 1H), 2.19 (s, 1H), 2.09-2.05 (m, 2H), 1.91 (t, J=7.7 Hz, 3H), 1.75-1.68 (m, 5H), 1.68-1.63 (m, 2H), 1.62-1.58 (m, 2H), 1.58-1.46 (m, 8H), 1.45-1.40 (m, 2H), 1.22-1.14 (m, 2H), 1.07 (s, 1H).

Example 20 N—((S)-3-cyclohexyl-1-(((S)-4-(neo-pentylamino)-3,4-dione-1-((S)-2-oxopyrrolidin-3-yl) but-2-yl)amino)-3-cyclohexyl-1-oxopropan-2-yl)-benzothiophene-2-carboxamide (A20)

1H NMR (500 MHz, Chloroform) δ 8.36 (s, 1H), 7.88 (s, 1H), 7.73 (s, 1H), 7.30 (d, J=2.5 Hz, 2H), 6.53 (s, 1H), 6.04 (s, 1H), 5.82 (s, 1H), 5.52 (s, 1H), 4.68 (d, J=6.4 Hz, 2H), 3.45 (s, 1H), 3.35 (d, J=3.1 Hz, 2H), 2.90 (s, 1H), 2.43 (s, 1H), 2.19 (s, 1H), 2.09-2.05 (m, 2H), 1.91 (t, J=5.9 Hz, 3H), 1.74-1.65 (m, 4H), 1.60-1.51 (m, 6H), 1.34 (s, 1H), 1.08-1.04 (m, 9H).

Example 21 N—((S)-1-(((S)-4-(benzylamino)-3,4-dione-1-((S)-2-oxopiperidin-3-yl)but-2-yl)amino)-3-cyclohexyl-1-oxopropan-2-yl)-benzothiophene-2-carboxamide (A21)

1H NMR (500 MHz, Chloroform) δ 8.31 (s, 1H), 7.92 (s, 1H), 7.74 (s, 1H), 7.34-7.23 (m, 6H), 7.20 (s, 1H), 6.76 (s, 1H), 5.59 (s, 1H), 5.49 (s, 1H), 5.08 (s, 1H), 4.52 (s, 1H), 4.42 (s, 1H), 4.34 (s, 1H), 3.24 (d, J=17.6 Hz, 2H), 2.68 (s, 1H), 2.08-2.04 (m, 2H), 1.74-1.67 (m, 5H), 1.64 (dd, J=2.9, 1.7 Hz, 4H), 1.36-1.32 (m, 2H), 1.30 (s, 1H), 1.26 (s, 1H), 1.17 (s, 1H), 1.13-1.05 (m, 2H), 0.98 (s, 1H).

Example 22 N—((S)-1-(((S)-4-(tert-butylamino)-3,4-dione-1-((S)-2-oxopiperidin-3-yl)but-2-yl)amino)-3-cyclohexyl-1-oxopropan-2-yl)-benzothiophene-2-carboxamide (A22)

1H NMR (500 MHz, Chloroform) δ 8.34 (s, 1H), 8.22 (s, 1H), 7.88 (s, 1H), 7.72 (s, 1H), 7.30 (d, J=1.5 Hz, 2H), 6.15 (s, 1H), 6.10 (s, 1H), 5.41 (s, 1H), 4.64 (d, J=11.7 Hz, 2H), 3.24 (d, J=14.8 Hz, 2H), 2.90 (s, 1H), 2.11-2.01 (m, 2H), 1.89-1.81 (m, 4H), 1.77 (s, 1H), 1.73-1.68 (m, 4H), 1.66-1.59 (m, 5H), 1.55-1.49 (m, 2H), 1.35 (s, 1H), 1.32-1.28 (m, 9H).

Example 23 N—((S)-3-cyclohexyl-1-(((S)-4-(cyclohexylamino)-3,4-dione-1-((S)-2-oxopiperidin-3-yl)but-2-yl)amino)-3-cyclohexyl-1-oxopropan-2-yl)-benzothiophene-2-carboxamide (A23)

1H NMR (500 MHz, Chloroform) δ 8.93 (s, 1H), 8.55 (s, 1H), 7.91 (s, 1H), 7.72 (s, 1H), 7.30 (d, J=2.6 Hz, 2H), 6.05 (s, 1H), 5.83 (s, 1H), 5.68 (s, 1H), 5.13 (s, 1H), 4.34 (s, 1H), 3.33 (s, 1H), 3.24 (d, J=15.0 Hz, 2H), 2.73 (s, 1H), 2.43 (s, 1H), 2.08-2.04 (m, 5H), 1.85 (s, 1H), 1.78 (s, 1H), 1.73-1.67 (m, 5H), 1.66-1.52 (m, 7H), 1.51 (s, 2H), 1.44-1.39 (m, 3H), 1.34-1.30 (m, 2H), 1.27 (s, 1H), 0.83-0.72 (m, 2H).

Example 24 N—((S)-1-(((S)-4-(benzylamino)-3,4-dione-1-((S)-2-oxopyrrolidin-3-yl)but-2-yl)amino)-3-cyclohexyl-1-oxopropan-2-yl)-1-methyl-1H-indole-2-carboxamide (A24)

1H NMR (500 MHz, Chloroform) δ 7.61 (s, 2H), 7.40-7.26 (m, 10H), 7.18 (dd, J=24.7, 8.9 Hz, 9H), 6.51 (s, 2H), 6.14 (s, 2H), 5.17 (s, 2H), 4.61 (s, 2H), 4.40 (s, 2H), 4.27 (s, 2H), 4.19 (s, 2H), 3.60-3.56 (m, 6H), 3.52 (s, 2H), 3.45 (s, 2H), 3.35 (s, 2H), 2.87 (s, 2H), 2.18 (s, 2H), 2.09-2.05 (m, 4H), 1.92 (s, 2H), 1.73-1.69 (m, 4H), 1.60-1.50 (m, 11H), 1.36-1.32 (m, 3H), 1.18 (s, 2H), 1.07-1.03 (m, 3H).

Example 25 N—((S)-1-(((S)-4-(tert-butylamino)-3,4-dione-1-((S)-2-oxopyrrolidin-3-yl)but-2-yl)amino)-3-cyclohexyl-1-oxopropan-2-yl)-1-methyl-1H-indole-2-carboxamide (A25)

1H NMR (500 MHz, Chloroform) δ 7.40 (s, 1H), 7.27 (d, J=5.4 Hz, 2H), 7.18 (d, J=11.2 Hz, 2H), 6.05 (d, J=0.5 Hz, 2H), 5.79 (s, 1H), 5.25 (s, 1H), 4.80 (s, 1H), 4.65 (s, 1H), 3.88-3.84 (m, 3H), 3.45 (s, 1H), 3.35 (s, 1H), 2.58 (s, 1H), 2.18 (s, 1H), 2.09-2.05 (m, 2H), 1.95-1.91 (m, 3H), 1.73-1.52 (m, 5H), 1.41-1.37 (m, 2H), 1.35-1.29 (m, 10H), 1.19-1.09 (m, 3H).

Example 26 N—((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopropan-2-yl)-1-methyl-1H-indole-2-carboxamide (A26)

1H NMR (500 MHz, Chloroform) δ 7.24 (s, 1H), 7.17 (s, 1H), 7.12 (d, J=0.8 Hz, 2H), 7.05 (s, 1H), 6.01 (s, 1H), 5.68 (d, J=17.0 Hz, 2H), 4.92 (s, 1H), 4.81 (s, 1H), 3.98 (s, 1H), 3.81 (s, 1H), 3.74-3.70 (m, 3H), 3.35 (s, 1H), 2.62 (s, 1H), 2.19 (s, 1H), 2.09-2.05 (m, 2H), 1.95-1.91 (m, 3H), 1.90-1.77 (m, 4H), 1.73-1.69 (m, 2H), 1.66-1.54 (m, 13H), 1.39-1.35 (m, 2H), 1.33 (s, 1H).

Example 27 N—((S)-1-(((S)-4-(benzylamino)-3,4-dione-1-((S)-2-oxopiperidin-3-yl)but-2-yl)amino)-3-cyclohexyl-1-oxopropan-2-yl)-1-methyl-1H-indole-2-carboxamide (A27)

1H NMR (500 MHz, Chloroform) δ 7.43 (s, 1H), 7.38-7.24 (m, 7H), 7.20 (d, J=8.0 Hz, 2H), 5.93 (s, 1H), 5.87 (s, 1H), 5.57 (s, 1H), 5.47 (s, 1H), 4.73 (s, 1H), 4.55 (s, 1H), 4.39 (d, J=18.9 Hz, 2H), 3.61-3.57 (m, 3H), 3.23 (d, J=15.5 Hz, 2H), 2.08-2.04 (m, 2H), 1.96-1.92 (m, 3H), 1.85 (s, 1H), 1.73-1.64 (m, 6H), 1.61 (s, 1H), 1.41 (t, J=7.7 Hz, 3H), 1.32 (s, 1H), 1.24 (s, 1H), 1.14-1.07 (m, 2H).

Example 28 N—((S)-1-(((S)-4-(tert-butylamino)-3,4-dione-1-((S)-2-oxopiperidin-3-yl)but-2-yl)amino)-3-cyclohexyl-1-oxopropan-2-yl)-1-methyl-1H-indole-2-carboxamide (A28)

1H NMR (500 MHz, Chloroform) δ 7.46 (s, 47H), 7.26 (d, J=19.3 Hz, 98H), 7.17 (d, J=7.3 Hz, 95H), 6.39 (s, 47H), 5.92 (d, J=11.5 Hz, 95H), 5.44 (s, 47H), 4.71 (s, 46H), 4.53 (s, 46H), 3.74-3.70 (m, 141H), 3.24 (d, J=18.1 Hz, 90H), 2.77 (s, 44H), 2.11-2.01 (m, 97H), 1.91 (s, 34H), 1.81 (s, 43H), 1.77-1.69 (m, 222H), 1.66-1.62 (m, 70H), 1.61-1.42 (m, 241H), 1.49-1.42 (m, 10H), 1.40-1.36 (m, 70H), 1.32-1.22 (m, 478H).

Example 29 N—((S)-3-cyclohexyl-1-(((S)-4-(cyclohexylamino)-3,4-dione-1-((S)-2-oxopiperidin-3-yl)but-2-yl)amino)-3-cyclohexyl-1-oxopropan-2-yl)-1-methyl-1H-indole-2-carboxamide (A29)

1H NMR (500 MHz, Chloroform) δ 7.41 (s, 1H), 7.35-7.22 (m, 2H), 7.19 (d, J=7.5 Hz, 2H), 5.92 (s, 1H), 5.54 (s, 1H), 5.38 (s, 1H), 5.23 (s, 1H), 5.04 (s, 1H), 4.34 (s, 1H), 3.99-3.95 (m, 3H), 3.86 (s, 1H), 3.24 (d, J=15.7 Hz, 2H), 2.86 (s, 1H), 2.08-2.02 (m, 4H), 1.99 (s, 1H), 1.81 (s, 1H), 1.78-1.67 (m, 7H), 1.66-1.51 (m, 10H), 1.43 (s, 1H), 1.41-1.37 (m, 2H), 1.30 (s, 1H), 0.77-0.70 (m, 2H).

Example 30 N—((S)-3-cyclohexyl-1-(((S)-4-(cyclohexylamino)-3,4-dione-1-((S)-2-oxopiperidin-3-yl)but-2-yl)amino)-3-cyclohexyl-1-oxopropan-2-yl)-1-methyl-1H-indole-2-carboxamide (A30)

1H NMR (500 MHz, Chloroform) δ 7.87 (s, 1H), 7.29 (t, J=9.9 Hz, 3H), 7.22-7.11 (m, 2H), 6.98 (s, 1H), 6.61 (s, 1H), 6.43 (s, 1H), 6.20 (s, 1H), 5.62 (s, 1H), 4.55 (s, 1H), 4.43 (d, J=15.9 Hz, 2H), 4.32 (s, 1H), 3.45 (s, 1H), 3.35 (s, 1H), 3.12 (s, 1H), 2.33 (s, 1H), 2.18 (s, 1H), 2.09-2.05 (m, 2H), 1.94-1.88 (m, 3H), 1.74-1.66 (m, 4H), 1.63-1.55 (m, 6H), 1.35 (s, 1H).

Example 31 N—((S)-1-(((S)-4-(benzylamino)-3,4-dione-1-((S)-2-oxopyrrolidin-3-yl)but-2-yl)amino)-3-cyclohexyl-1-oxopropan-2-yl)-4,6-dichloro-1H-indole-2-carboxamide (A31)

1H NMR (500 MHz, Chloroform) δ 9.04 (s, 1H), 8.68 (s, 1H), 8.53 (s, 1H), 7.42 (s, 1H), 7.38 (s, 1H), 7.06 (s, 1H), 6.78 (s, 1H), 5.77 (s, 1H), 4.93 (s, 1H), 4.55 (s, 1H), 3.99 (s, 1H), 3.35 (s, 1H), 2.63 (s, 1H), 2.19 (s, 1H), 2.10-2.04 (m, 4H), 1.93 (s, 1H), 1.69 (dt, J=18.2, 9.1 Hz, 5H), 1.41-1.37 (m, 2H), 1.35-1.27 (m, 11H), 1.24 (s, 1H), 1.05-1.01 (m, 2H).

Example 32 N—((S)-1-(((S)-4-(tert-butylamino)-3,4-dione-1-((S)-2-oxopyrrolidin-3-yl)but-2-yl)amino)-3-cyclohexyl-1-oxopropan-2-yl)-4,6-dichloro-1H-indole-2-carboxamide (A32)

1H NMR (500 MHz, Chloroform) δ 8.86 (s, 1H), 8.48 (s, 1H), 7.54 (s, 1H), 7.41 (s, 1H), 7.06 (s, 1H), 6.01 (s, 1H), 5.47 (s, 1H), 5.20 (s, 1H), 5.05 (s, 1H), 4.55 (s, 1H), 4.00 (s, 1H), 3.58 (s, 1H), 3.51 (s, 1H), 3.35 (s, 1H), 2.19 (s, 1H), 2.12-2.02 (m, 2H), 2.00-1.96 (m, 2H), 1.94-1.87 (m, 3H), 1.73-1.46 (m, 14H), 1.40-1.36 (m, 2H), 1.32 (s, 1H), 1.12-1.06 (m, 3H).

Example 33 N—((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopropan-2-yl)-4,6-dichloro-1H-indole-2-carboxamide (A33)

1H NMR (500 MHz, Chloroform) δ 8.68 (s, 11H), 7.45 (s, 11H), 7.38 (s, 11H), 7.31-7.23 (m, 34H), 7.23-7.17 (m, 26H), 7.16 (s, 8H), 7.11 (s, 11H), 5.89 (s, 11H), 5.79 (s, 11H), 4.76 (s, 11H), 4.51 (s, 11H), 4.35 (s, 11H), 4.29 (s, 11H), 3.24 (d, J=17.5 Hz, 21H), 2.73 (s, 11H), 2.10-2.04 (m, 23H), 2.02 (s, 9H), 1.83 (s, 10H), 1.81-1.74 (m, 33H), 1.73-1.65 (m, 23H), 1.65-1.50 (m, 45H), 1.52 (d, J=5.6 Hz, 2H), 1.34-1.30 (m, 19H), 1.28 (s, 11H), 0.99-0.93 (m, 32H).

Example 34 N—((S)-1-(((S)-4-(benzylamino)-3,4-dione-1-((S)-2-oxopiperidin-3-yl)but-2-yl)amino)-3-cyclohexyl-1-oxopropan-2-yl)-4,6-dichloro-1H-indole-2-carboxamide (A34)

1H NMR (500 MHz, Chloroform) δ 8.35 (s, 1H), 7.62 (s, 1H), 7.39 (s, 1H), 7.05 (s, 1H), 6.43 (s, 1H), 5.97 (s, 1H), 5.59 (s, 1H), 5.50 (d, J=15.7 Hz, 2H), 4.67 (s, 1H), 3.24 (d, J=17.3 Hz, 2H), 2.48 (s, 1H), 2.08-2.04 (m, 2H), 1.87 (t, J=9.6 Hz, 3H), 1.78 (s, 1H), 1.72 (dd, J=8.3, 4.2 Hz, 4H), 1.67 (s, 1H), 1.65-1.50 (m, 6H), 1.45 (s, 1H), 1.36-1.28 (m, 10H).

Example 35 N—((S)-1-(((S)-4-(tert-butylamino)-3,4-dione-1-((S)-2-oxopiperidin-3-yl)but-2-yl)amino)-3-cyclohexyl-1-oxopropan-2-yl)-4,6-dichloro-1H-indole-2-carboxamide (A35)

1H NMR (500 MHz, Chloroform) δ 8.51 (s, 1H), 8.33 (s, 1H), 8.28 (s, 1H), 7.42 (s, 1H), 7.07 (s, 1H), 6.66 (s, 1H), 6.41 (s, 1H), 5.86 (s, 1H), 5.04 (s, 1H), 4.52 (s, 1H), 3.32 (s, 1H), 3.24 (d, J=16.6 Hz, 2H), 2.97 (s, 1H), 2.16-2.01 (m, 5H), 2.01-1.92 (m, 2H), 1.82 (s, 1H), 1.78-1.69 (m, 8H), 1.65 (d, J=15.4 Hz, 2H), 1.56-1.46 (m, 3H), 1.44-1.40 (m, 4H), 1.32 (s, 1H), 1.17 (s, 1H), 1.07-1.00 (m, 2H).

Example 36 N—((S)-3-cyclohexyl-1-(((S)-4-(cyclohexylamino)-3,4-dione-1-((S)-2-oxopiperidin-3-yl)but-2-yl)amino)-3-cyclohexyl-1-oxopropan-2-yl)-4,6-dichloro-1H-indole-2-carboxamide (A36)

1H NMR (500 MHz, Chloroform) δ 8.98 (s, 1H), 8.03 (d, J=1.1 Hz, 2H), 7.63 (d, J=5.1 Hz, 2H), 7.37-7.27 (m, 4H), 7.21 (s, 1H), 6.95 (s, 1H), 6.43 (s, 1H), 6.01 (s, 1H), 4.94 (s, 1H), 4.85 (s, 1H), 4.67 (s, 1H), 4.41 (s, 1H), 4.32 (s, 1H), 3.45 (s, 1H), 3.35 (s, 1H), 2.77 (s, 1H), 2.19 (s, 1H), 2.13-2.01 (m, 2H), 1.89 (s, 1H), 1.83-1.74 (m, 2H), 1.74-1.69 (m, 2H), 1.66 (d, J=5.7 Hz, 2H), 1.58-1.49 (m, 6H), 1.31 (s, 1H).

Example 37 N—((S)-1-(((S)-4-(benzylamino)-3,4-dione-1-((S)-2-oxopyrrolidin-3-yl)but-2-yl)amino)-3-cyclohexyl-1-oxopropan-2-yl)-quinoxaline-2-carboxamide (A37)

1H NMR (500 MHz, Chloroform) δ 9.39 (s, 1H), 8.47 (s, 1H), 8.11 (s, 1H), 7.62 (d, J=3.2 Hz, 2H), 6.17 (d, J=6.0 Hz, 2H), 5.59 (s, 1H), 5.27 (s, 1H), 4.98 (s, 1H), 4.91 (s, 1H), 3.45 (s, 1H), 3.35 (s, 1H), 2.51 (s, 1H), 2.19 (s, 1H), 2.09-2.05 (m, 2H), 1.98-1.95 (m, 2H), 1.92 (s, 1H), 1.73-1.61 (m, 5H), 1.41-1.37 (m, 2H), 1.34-1.28 (m, 10H), 1.21-1.11 (m, 3H).

Example 38 N—((S)-1-(((S)-4-(tert-butylamino)-3,4-dione-1-((S)-2-oxopyrrolidin-3-yl)but-2-yl)amino)-3-cyclohexyl-1-oxopropan-2-yl)-quinoxaline-2-carboxamide (A38)

1H NMR (500 MHz, Chloroform) δ 9.09 (s, 1H), 8.31 (s, 1H), 8.03 (d, J=4.8 Hz, 2H), 7.61 (d, J=2.2 Hz, 2H), 6.41 (s, 1H), 6.06 (s, 1H), 5.27 (s, 1H), 5.20 (s, 1H), 4.45 (s, 1H), 3.72 (s, 1H), 3.45 (s, 1H), 3.35 (s, 1H), 2.73 (s, 1H), 2.39-2.31 (m, 2H), 2.19 (s, 1H), 2.09-2.05 (m, 2H), 1.92 (s, 1H), 1.76-1.56 (m, 15H), 1.55-1.45 (m, 6H), 1.30 (s, 1H).

Example 39 N—((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopropan-2-yl)-quinoxaline-2-carboxamide (A39)

1H NMR (500 MHz, Chloroform) δ 9.55 (s, 1H), 9.32 (s, 1H), 8.12 (s, 1H), 7.96 (s, 1H), 7.64 (d, J=11.6 Hz, 2H), 7.29-7.22 (m, 4H), 7.19 (s, 1H), 6.56 (s, 1H), 6.06 (s, 1H), 5.63 (s, 1H), 5.02 (s, 1H), 4.71 (s, 1H), 4.41 (s, 1H), 4.31 (s, 1H), 3.24 (d, J=17.3 Hz, 2H), 2.37 (s, 1H), 2.10-2.02 (m, 2H), 2.02-1.96 (m, 3H), 1.82 (s, 1H), 1.72 (t, J=9.8 Hz, 3H), 1.69-1.57 (m, 3H), 1.53 (s, 1H), 1.38-1.34 (m, 2H), 1.31 (s, 1H), 1.13-1.04 (m, 3H).

Example 40 N—((S)-1-(((S)-4-(benzylamino)-3,4-dione-1-((S)-2-oxopiperidin-3-yl)but-2-yl)amino)-3-cyclohexyl-1-oxopropan-2-yl)-quinoxaline-2-carboxamide (A40)

1H NMR (500 MHz, Chloroform) δ 9.29 (s, 1H), 8.16 (s, 1H), 8.11 (s, 1H), 7.65 (d, J=4.6 Hz, 2H), 7.22 (s, 1H), 5.87 (d, J=8.3 Hz, 2H), 5.65 (s, 1H), 4.94 (s, 1H), 4.46 (s, 1H), 3.24 (d, J=14.8 Hz, 2H), 2.72 (s, 1H), 2.11-2.01 (m, 2H), 1.79 (d, J=1.0 Hz, 2H), 1.76-1.62 (m, 5H), 1.59 (s, 1H), 1.49-1.42 (m, 4H), 1.35-1.28 (m, 11H), 1.25 (s, 1H), 1.21-1.15 (m, 2H).

Example 41 N—((S)-1-(((S)-4-(tert-butylamino)-3,4-dione-1-((S)-2-oxopiperidin-3-yl)but-2-yl)amino)-3-cyclohexyl-1-oxopropan-2-yl)-quinoxaline-2-carboxamide (A41)

1H NMR (500 MHz, Chloroform) δ 9.64 (s, 4H), 8.11 (d, J=10.4 Hz, 8H), 7.65 (d, J=1.9 Hz, 8H), 6.00 (s, 4H), 5.76 (s, 4H), 5.70 (s, 4H), 5.64 (s, 4H), 5.04 (s, 4H), 4.45 (s, 4H), 3.86 (s, 4H), 3.24 (d, J=17.3 Hz, 8H), 2.85 (s, 4H), 2.11-2.01 (m, 9H), 1.99-1.91 (m, 12H), 1.91-1.80 (m, 9H), 1.75 (s, 2H), 1.75-1.53 (m, 62H), 1.55-1.53 (m, 1H), 1.51 (s, 3H), 1.38-1.34 (m, 7H), 1.30 (s, 4H), 1.06 (s, 3H), 1.03-0.99 (m, 8H).

Example 42 N—((S)-1-(((S)-4-(benzylamino)-3,4-dione-1-((S)-2-oxopyrrolidin-3-yl)but-2-yl)amino)-3-cyclohexyl-1-oxopropan-2-yl)-quinoline-2-carboxamide (A42)

1H NMR (500 MHz, Chloroform) δ 8.56 (s, 1H), 8.19 (s, 1H), 7.82 (s, 1H), 7.58 (s, 1H), 7.42 (s, 1H), 7.42-7.28 (m, 5H), 7.21 (s, 1H), 6.00 (d, J=2.7 Hz, 2H), 4.43 (s, 1H), 4.33 (s, 1H), 4.11 (s, 1H), 3.83 (d, J=3.7 Hz, 2H), 3.45 (s, 1H), 3.35 (s, 1H), 3.25 (s, 1H), 2.15 (s, 1H), 2.09-2.05 (m, 2H), 1.91 (s, 1H), 1.73-1.69 (m, 2H), 1.62-1.55 (m, 3H), 1.36-1.27 (m, 6H), 1.23 (s, 1H), 1.20-1.14 (m, 2H).

Example 43 N—((S)-1-(((S)-4-(tert-butylamino)-3,4-dione-1-((S)-2-oxopyrrolidin-3-yl)but-2-yl)amino)-3-cyclohexyl-1-oxopropan-2-yl)-quinoline-2-carboxamide (A43)

1H NMR (500 MHz, Chloroform) δ 9.34 (s, 1H), 8.46 (s, 1H), 8.17 (s, 1H), 7.82 (s, 1H), 7.72 (s, 1H), 7.55 (s, 1H), 7.50 (s, 1H), 5.96 (s, 1H), 5.84 (s, 1H), 5.40 (s, 1H), 5.22 (s, 1H), 4.77 (s, 1H), 3.45 (s, 1H), 3.35 (s, 1H), 2.83 (s, 1H), 2.18 (s, 1H), 2.09-2.05 (m, 2H), 1.94-1.81 (m, 3H), 1.73-1.63 (m, 5H), 1.40-1.36 (m, 2H), 1.36-1.27 (m, 10H), 1.18 (s, 1H), 1.14-1.10 (m, 2H).

Example 44 N—((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopropan-2-yl)-quinoline-2-carboxamide (A44)

1H NMR (500 MHz, Chloroform) δ 8.47 (s, 1H), 8.24 (s, 1H), 8.06 (s, 1H), 7.73 (s, 1H), 7.65 (s, 1H), 7.43 (d, J=13.7 Hz, 2H), 6.58 (s, 1H), 6.06 (s, 1H), 5.40 (s, 1H), 5.20 (s, 1H), 4.45 (s, 1H), 3.73 (s, 1H), 3.45 (s, 1H), 3.35 (s, 1H), 2.72 (s, 1H), 2.34-2.30 (m, 2H), 2.19 (s, 1H), 2.09-2.05 (m, 2H), 1.92 (s, 1H), 1.77-1.56 (m, 15H), 1.55-1.46 (m, 6H), 1.30 (s, 1H).

Example 45 N—((S)-1-(((S)-4-(benzylamino)-3,4-dione-1-((S)-2-oxopiperidin-3-yl)but-2-yl)amino)-3-cyclohexyl-1-oxopropan-2-yl)-quinoline-2-carboxamide (A45)

1H NMR (500 MHz, Chloroform) δ 8.42 (s, 1H), 8.15 (s, 1H), 7.79 (s, 1H), 7.69 (s, 1H), 7.47 (s, 1H), 7.42 (s, 1H), 7.34-7.25 (m, 4H), 7.20 (s, 1H), 6.77 (s, 1H), 5.89 (s, 1H), 5.82 (s, 1H), 5.57 (d, J=7.5 Hz, 2H), 4.42 (d, J=5.7 Hz, 2H), 4.34 (s, 1H), 3.24 (d, J=19.0 Hz, 2H), 2.81 (s, 1H), 2.43 (s, 1H), 2.11-2.01 (m, 2H), 1.95 (s, 1H), 1.86 (s, 1H), 1.81-1.74 (m, 3H), 1.69 (dt, J=17.1, 8.6 Hz, 5H), 1.47 (s, 1H), 1.41-1.37 (m, 2H), 1.31 (s, 1H), 0.84-0.77 (m, 2H).

Example 46 N—((S)-1-(((S)-4-(tert-butylamino)-3,4-dione-1-((S)-2-oxopiperidin-3-yl)but-2-yl)amino)-3-cyclohexyl-1-oxopropan-2-yl)-quinoline-2-carboxamide (A46)

1H NMR (500 MHz, Chloroform) δ 8.46 (s, 3H), 8.13 (s, 3H), 7.79 (s, 3H), 7.69 (d, J=0.8 Hz, 6H), 7.44 (d, J=32.8 Hz, 6H), 6.55 (s, 3H), 6.05 (s, 3H), 5.75 (s, 3H), 4.77 (d, J=2.1 Hz, 6H), 3.25 (s, 3H), 3.21 (s, 3H), 2.70 (s, 3H), 2.11-2.01 (m, 6H), 1.96-1.87 (m, 6H), 1.79 (d, J=13.1 Hz, 5H), 1.70 (dt, J=19.3, 3.5 Hz, 19H), 1.60-1.51 (m, 18H), 1.35-1.30 (m, 30H).

Example 47 N—((S)-3-cyclohexyl-1-(((S)-4-(cyclohexylamino)-3,4-dione-1-((S)-2-oxopiperidin-3-yl)but-2-yl)amino)-3-cyclohexyl-1-oxopropan-2-yl)-quinoline-2-carboxamide (A47)

1H NMR (500 MHz, Chloroform) δ 9.06 (s, 3H), 8.44 (s, 3H), 8.15 (s, 3H), 7.79 (s, 3H), 7.75 (s, 3H), 7.70 (s, 3H), 7.48 (d, J=8.2 Hz, 6H), 7.38 (s, 3H), 5.73 (s, 3H), 4.96 (s, 3H), 4.57 (s, 3H), 3.90 (s, 3H), 3.24 (d, J=14.7 Hz, 6H), 2.92 (s, 3H), 2.15-2.11 (m, 5H), 2.11-2.01 (m, 9H), 1.99 (t, J=7.9 Hz, 7H), 1.80 (s, 2H), 1.76-1.65 (m, 18H), 1.65-1.58 (m, 24H), 1.45 (t, J=13.5 Hz, 10H), 1.36 (dd, J=21.5, 15.7 Hz, 2H), 1.33 (s, 3H), 1.20 (s, 2H), 1.11-1.04 (m, 6H).

Example 48 N—((S)-1-(((S)-4-(benzylamino)-3,4-dione-14 (S)-2-oxopyrrolidin-3-yl)but-2-yl)amino)-1-oxophenylpropan-2-yl)-1H-indole-2-carboxamide (A48)

1H NMR (500 MHz, Chloroform) δ 8.36 (s, 1H), 7.55 (d, J=12.3 Hz, 2H), 7.34 (t, J=21.8 Hz, 3H), 7.30-7.17 (m, 9H), 7.15 (d, J=2.2 Hz, 2H), 7.09 (s, 1H), 6.35 (s, 1H), 6.01 (s, 1H), 5.67 (s, 1H), 5.03 (s, 1H), 4.88 (s, 1H), 4.37 (s, 1H), 4.30 (s, 1H), 3.45 (s, 1H), 3.35 (s, 1H), 3.15 (d, J=18.6 Hz, 2H), 2.94 (s, 1H), 2.19 (s, 1H), 2.10-2.04 (m, 2H), 1.92 (s, 1H).

Example 49 N—((S)-1-(((S)-4-(tert-butylamino)-3,4-dione-1-((S)-2-oxopyrrolidin-3-yl)but-2-yl)amino)-1-oxo-3-phenylpropan-2-yl)-1H-indole-2-carboxamide (A49)

1H NMR (500 MHz, Chloroform) δ 8.26 (s, 1H), 7.46 (s, 1H), 7.32 (t, J=17.0 Hz, 3H), 7.20 (dd, J=7.8, 5.2 Hz, 4H), 7.12 (s, 1H), 7.06 (s, 1H), 6.01 (s, 1H), 5.57 (s, 1H), 4.84 (s, 1H), 4.69 (s, 1H), 4.53 (s, 1H), 3.45 (s, 1H), 3.41 (s, 1H), 3.35 (s, 1H), 3.30 (s, 1H), 3.19 (s, 1H), 2.96 (s, 1H), 2.16 (s, 1H), 2.13-2.01 (m, 2H), 1.89 (s, 1H), 1.30-1.26 (m, 9H).

Example 50 N—((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-1H-indole-2-carboxamide (A50)

1H NMR (500 MHz, Chloroform) δ 8.35 (s, 1H), 7.90 (s, 1H), 7.52 (d, J=25.5 Hz, 2H), 7.39 (s, 1H), 7.29-7.21 (m, 4H), 7.14 (d, J=3.6 Hz, 2H), 7.08 (s, 1H), 6.52 (s, 1H), 6.16 (s, 1H), 5.70 (s, 1H), 4.92 (s, 1H), 4.78 (s, 1H), 3.46 (d, J=5.2 Hz, 2H), 3.35 (s, 1H), 3.21 (s, 1H), 2.85 (d, J=4.0 Hz, 2H), 2.17 (s, 1H), 2.13-2.02 (m, 2H), 2.00-1.90 (m, 3H), 1.68 (s, 1H), 1.56-1.50 (m, 2H), 1.49-1.45 (m, 3H), 1.44-1.40 (m, 2H).

Example 51 N—((S)-1-(((S)-4-(benzylamino)-3,4-dione-1-((S)-2-oxopiperidin-3-yl)but-2-yl)amino)-1-oxo-3-phenylpropan-2-yl)-1H-indole-2-carboxamide (A51)

1H NMR (500 MHz, Chloroform) δ 8.70 (s, 1H), 7.50 (s, 1H), 7.39-7.20 (m, 5H), 7.20-7.11 (m, 4H), 7.09 (d, J=4.4 Hz, 2H), 7.06-6.94 (m, 2H), 6.90 (s, 1H), 6.19 (s, 1H), 5.93 (s, 1H), 5.51 (s, 1H), 4.70 (s, 1H), 4.25 (d, J=17.1 Hz, 2H), 3.79 (d, J=9.5 Hz, 2H), 3.24 (t, J=8.3 Hz, 3H), 3.04 (s, 1H), 2.16 (s, 1H), 2.12-2.04 (m, 3H), 1.78 (s, 1H), 1.72 (s, 1H), 1.62 (s, 1H).

Example 52 N—((S)-1-(((S)-4-(tert-butylamino)-3,4-dione-1-((S)-2-oxopiperidin-3-yl)but-2-yl)amino)-1-oxo-3-phenylpropan-2-yl)-1H-indole-2-carboxamide (A52)

1H NMR (500 MHz, Chloroform) δ 8.64 (d, J=17.0 Hz, 2H), 8.19 (s, 1H), 7.56 (s, 1H), 7.43 (s, 1H), 7.36-7.27 (m, 2H), 7.27-7.22 (m, 2H), 7.14 (d, J=12.9 Hz, 2H), 7.08 (s, 1H), 5.63 (s, 1H), 5.01 (d, J=14.2 Hz, 2H), 4.78 (d, J=1.3 Hz, 2H), 3.24 (d, J=18.2 Hz, 2H), 3.18 (s, 1H), 3.03 (s, 1H), 2.97 (s, 1H), 2.06 (t, J=3.5 Hz, 3H), 1.94 (s, 1H), 1.88 (s, 1H), 1.81 (s, 1H), 1.21-1.17 (m, 9H).

Example 53 N—((S)-3-cyclohexyl-1-(((S)-4-(cyclohexylamino)-3,4-dione-1-((S)-2-oxopiperidin-3-yl)but-2-yl)amino)-1-oxo-3-phenylpropan-2-yl)-1H-indole-2-carboxamide (A53)

1H NMR (500 MHz, Chloroform) δ 8.76 (s, 1H), 7.53 (s, 1H), 7.41 (d, J=25.5 Hz, 2H), 7.27-7.21 (m, 2H), 7.21-7.18 (m, 2H), 7.15 (d, J=7.6 Hz, 2H), 7.08 (s, 1H), 5.95 (s, 1H), 5.61 (s, 1H), 5.25 (s, 1H), 5.14 (s, 1H), 4.78 (s, 1H), 3.42 (s, 1H), 3.25 (t, J=12.6 Hz, 3H), 2.87 (s, 1H), 2.70 (s, 1H), 2.56 (s, 1H), 2.08-2.04 (m, 2H), 2.02-1.90 (m, 2H), 1.87 (s, 1H), 1.80 (s, 1H), 1.68 (d, J=3.3 Hz, 2H), 1.55-1.51 (m, 4H), 1.48 (s, 1H), 1.45-1.39 (m, 2H).

Example 54 N—((S)-1-(((S)-4-(benzylamino)-3,4-dione-1-((S)-2-oxopyrrolidin-3-yl)but-2-yl)amino)-1-oxo-3-phenylpropan-2-yl)-benzofuran-2-carboxamide (A54)

1H NMR (500 MHz, Chloroform) δ 7.51 (d, J=8.2 Hz, 2H), 7.41 (s, 1H), 7.30-7.12 (m, 12H), 6.67 (s, 1H), 5.69-5.61 (m, 3H), 5.09 (s, 1H), 4.88 (s, 1H), 4.41 (s, 1H), 4.33 (s, 1H), 3.45 (s, 1H), 3.35 (s, 1H), 3.26 (s, 1H), 3.16 (s, 1H), 3.07 (s, 1H), 2.19 (s, 1H), 2.09-2.05 (m, 2H), 1.92 (s, 1H).

Example 55 N—((S)-1-(((S)-4-(tert-butylamino)-3,4-dione-1-((S)-2-oxopyrrolidin-3-yl)but-2-yl)amino)-1-oxo-3-phenylpropan-2-yl)-benzofuran-2-carboxamide (A55)

1H NMR (500 MHz, Chloroform) δ 7.54 (s, 1H), 7.47 (d, J=17.7 Hz, 2H), 7.28-7.22 (m, 3H), 7.18 (dd, J=20.8, 5.2 Hz, 4H), 6.42 (s, 1H), 6.05 (s, 1H), 5.83 (s, 1H), 5.27 (s, 1H), 4.98 (s, 1H), 4.85 (s, 1H), 3.45 (s, 1H), 3.35 (s, 1H), 3.19 (s, 1H), 2.96 (s, 1H), 2.61 (s, 1H), 2.18 (s, 1H), 2.09-2.05 (m, 2H), 1.93 (s, 1H), 1.34-1.30 (m, 9H).

Example 56 N—((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-benzofuran-2-carboxamide (A56)

1H NMR (500 MHz, Chloroform) δ 8.77 (s, 2H), 8.67 (s, 2H), 7.56 (s, 1H), 7.50 (s, 3H), 7.41 (s, 2H), 7.28-7.19 (m, 6H), 7.16 (d, J=4.9 Hz, 4H), 7.13-7.04 (m, 4H), 6.04 (s, 2H), 5.93 (s, 2H), 5.05 (s, 2H), 4.66 (s, 2H), 3.70 (s, 2H), 3.45 (s, 2H), 3.35 (s, 1H), 3.25 (s, 2H), 3.05 (s, 2H), 2.88 (s, 2H), 2.19 (s, 2H), 2.09-2.05 (m, 4H), 1.97-1.91 (m, 5H), 1.68-1.64 (m, 3H), 1.64-1.43 (m, 13H).

Example 57 N—((S)-1-(((S)-4-(benzylamino)-3,4-dione-1-((S)-2-oxopiperidin-3-yl)but-2-yl)amino)-1-oxo-3-phenylpropan-2-yl)-benzofuran-2-carboxamide (A57)

1H NMR (500 MHz, Chloroform) δ 7.48 (s, 1H), 7.29 (d, J=38.0 Hz, 2H), 7.25 (s, 1H), 7.27-7.19 (m, 3H), 7.19-7.05 (m, 10H), 6.97 (s, 1H), 6.43 (s, 1H), 6.07 (s, 1H), 5.18 (d, J=3.4 Hz, 2H), 4.73 (s, 1H), 4.63 (s, 1H), 4.36 (s, 1H), 4.29 (s, 1H), 3.24 (d, J=16.8 Hz, 2H), 3.10 (s, 1H), 2.86 (d, J=21.8 Hz, 2H), 2.43 (s, 1H), 2.08-2.04 (m, 2H), 1.85 (s, 1H), 1.79 (s, 1H), 1.64 (s, 1H).

Example 58 N—((S)-14 (S)-4-(tert-butylamino)-3,4-dione-14 (S)-2-oxopiperidin-3-yl)but-2-yl)amino)-1-oxo-3-phenylpropan-2-yl)-benzofuran-2-carboxamide (A58)

1H NMR (500 MHz, Chloroform) δ 9.35 (s, 5H), 7.60 (s, 5H), 7.48 (d, J=29.1 Hz, 10H), 7.28-7.18 (m, 27H), 7.16 (d, J=17.5 Hz, 8H), 5.86 (s, 5H), 5.55 (s, 5H), 4.94 (s, 5H), 4.69 (s, 5H), 3.24 (t, J=10.0 Hz, 14H), 2.90 (s, 5H), 2.66 (s, 5H), 2.09-2.02 (m, 10H), 1.92 (s, 4H), 1.84-1.80 (m, 8H), 1.76 (s, 4H), 1.30-1.26 (m, 44H).

Example 59 N—((S)-1-(((S)-4-(tert-butylamino)-3,4-dione-1-((S)-2-oxopiperidin-3-yl)but-2-yl)amino)-1-oxo-3-phenylpropan-2-yl)-benzofuran-2-carboxamide (A59)

1H NMR (500 MHz, Chloroform) δ 9.35 (s, 5H), 7.60 (s, 5H), 7.48 (d, J=29.1 Hz, 10H), 7.28-7.18 (m, 27H), 7.16 (d, J=17.5 Hz, 8H), 5.86 (s, 5H), 5.55 (s, 5H), 4.94 (s, 5H), 4.69 (s, 5H), 3.24 (t, J=10.0 Hz, 14H), 2.90 (s, 5H), 2.66 (s, 5H), 2.09-2.02 (m, 10H), 1.92 (s, 4H), 1.84-1.80 (m, 8H), 1.76 (s, 4H), 1.30-1.26 (m, 44H).

Example 60 N—((S)-1-(((S)-4-(benzylamino)-3,4-dione-1-((S)-2-oxopyrrolidin-3-yl)but-2-yl)amino)-1-oxo-3-phenylpropan-2-yl)-benzothiophene-2-carboxamide (A60)

1H NMR (500 MHz, Chloroform) δ 8.40 (s, 1H), 7.91 (s, 1H), 7.76 (s, 1H), 7.33 (d, J=3.7 Hz, 2H), 7.32-7.16 (m, 10H), 7.13 (d, J=16.7 Hz, 2H), 6.27 (s, 1H), 5.97 (s, 1H), 5.64 (s, 1H), 5.03 (s, 1H), 4.89 (s, 1H), 4.34 (d, J=4.2 Hz, 2H), 3.45 (s, 1H), 3.35 (s, 1H), 3.15-3.11 (m, 2H), 2.94 (s, 1H), 2.19 (s, 1H), 2.09-2.05 (m, 2H), 1.92 (s, 1H).

Example 61 N—((S)-1-(((S)-4-(tert-butylamino)-3,4-dione-1-((S)-2-oxopyrrolidin-3-yl)but-2-yl)amino)-1-oxo-3-phenylpropan-2-yl)-benzothiophene-2-carboxamide (A61)

1H NMR (500 MHz, Chloroform) δ 8.93 (s, 1H), 7.82 (d, J=4.4 Hz, 2H), 7.28 (dd, J=20.7, 7.2 Hz, 4H), 7.22-7.11 (m, 3H), 6.05 (s, 1H), 4.70 (s, 1H), 4.64 (s, 1H), 4.59 (s, 1H), 4.39 (s, 1H), 3.99 (s, 1H), 3.55 (s, 1H), 3.45 (s, 1H), 3.35 (s, 1H), 3.15 (s, 1H), 2.95 (s, 1H), 2.17 (s, 1H), 2.13-2.02 (m, 2H), 1.89 (s, 1H), 1.21-1.17 (m, 9H).

Example 62 N—((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-benzothiophene-2-carboxamide (A62)

1H NMR (500 MHz, Chloroform) δ 8.73 (s, 1H), 8.54 (s, 1H), 8.35 (s, 1H), 7.91 (s, 1H), 7.74 (s, 1H), 7.32 (d, J=1.5 Hz, 2H), 7.28-7.23 (m, 2H), 7.15 (s, 1H), 7.12-7.05 (m, 2H), 6.14 (s, 1H), 5.94 (s, 1H), 5.04 (s, 1H), 4.66 (s, 1H), 3.45 (d, J=3.2 Hz, 2H), 3.35 (s, 1H), 3.26 (s, 1H), 3.05 (s, 1H), 2.89 (s, 1H), 2.19 (s, 1H), 2.09-2.05 (m, 2H), 1.95-1.91 (m, 3H), 1.73-1.64 (m, 3H), 1.56-1.52 (m, 2H), 1.50 (s, 1H), 1.46-1.40 (m, 2H).

Example 63 N—((S)-1-(((S)-4-(benzylamino)-3,4-dione-1-((S)-2-oxopiperidin-3-yl)but-2-yl)amino)-1-oxo-3-phenylpropan-2-yl)-benzothiophene-2-carboxamide (A63)

1H NMR (500 MHz, Chloroform) δ 8.49 (s, 1H), 8.30 (s, 1H), 8.00 (s, 1H), 7.63 (s, 1H), 7.29 (dd, J=19.0, 2.9 Hz, 4H), 7.18-7.07 (m, 5H), 7.07-6.97 (m, 3H), 6.33 (s, 1H), 6.11 (s, 1H), 4.93-4.89 (m, 2H), 4.36 (d, J=9.1 Hz, 2H), 4.29 (s, 1H), 3.28-3.20 (m, 3H), 2.92 (s, 1H), 2.58 (s, 1H), 2.16 (s, 1H), 2.08-2.04 (m, 2H), 1.83 (s, 1H), 1.77 (s, 1H), 1.73 (s, 1H).

Example 64 N—((S)-1-(((S)-4-(tert-butylamino)-3,4-dione-1-((S)-2-oxopiperidin-3-yl)but-2-yl)amino)-1-oxo-3-phenylpropan-2-yl)-benzothiophene-2-carboxamide (A64)

1H NMR (500 MHz, Chloroform) δ 8.38 (s, 1H), 7.90 (s, 1H), 7.75 (s, 1H), 7.30 (dd, J=17.5, 1.0 Hz, 4H), 7.26-7.19 (m, 2H), 7.17 (s, 1H), 7.02 (s, 1H), 6.45 (s, 1H), 6.10 (s, 1H), 5.93 (s, 1H), 4.93 (s, 1H), 4.86 (s, 1H), 3.27-3.11 (m, 3H), 2.95 (s, 1H), 2.83 (s, 1H), 2.11-2.01 (m, 2H), 1.95 (s, 1H), 1.83 (s, 1H), 1.76 (s, 1H), 1.56 (s, 1H), 1.35-1.31 (m, 9H).

Example 65 N—((S)-3-cyclohexyl-1-(((S)-4-(cyclohexylamino)-3,4-dione-1-((S)-2-oxopiperidin-3-yl)but-2-yl)amino)-1-oxo-3-phenylpropan-2-yl)-benzothiophene-2-carboxamide (A65)

1H NMR (500 MHz, Chloroform) δ 8.28 (s, 6H), 7.86 (s, 6H), 7.60 (s, 6H), 7.27 (dd, J=17.2, 1.6 Hz, 20H), 7.24-7.12 (m, 22H), 5.78 (s, 6H), 5.41 (s, 6H), 5.09 (s, 6H), 4.97 (s, 6H), 4.85 (s, 6H), 3.31-3.10 (m, 30H), 2.97 (s, 6H), 2.60 (s, 4H), 2.51 (s, 5H), 2.12-2.00 (m, 12H), 1.97-1.86 (m, 12H), 1.71 (t, J=16.5 Hz, 17H), 1.58-1.45 (m, 30H), 1.45-1.36 (m, 12H), 1.12 (s, 4H).

Example 66 N—((S)-1-(((S)-4-(benzylamino)-3,4-dione-1-((S)-2-oxopyrrolidin-3-yl)but-2-yl)amino)-1-oxo-3-phenylpropan-2-yl)-1-methyl-1H-indole-2-carboxamide (A66)

1H NMR (500 MHz, Chloroform) δ 8.78 (s, 1H), 7.69 (s, 1H), 7.49 (s, 1H), 7.34-7.13 (m, 12H), 7.13-7.05 (m, 2H), 6.10 (s, 1H), 5.99 (s, 1H), 5.07 (s, 1H), 4.69 (s, 1H), 4.36 (d, J=3.5 Hz, 2H), 3.78-3.74 (m, 3H), 3.45 (s, 1H), 3.35 (s, 1H), 3.24 (s, 1H), 3.06 (s, 1H), 2.88 (s, 1H), 2.19 (s, 1H), 2.09-2.05 (m, 2H), 1.93 (s, 1H).

Example 67 N—((S)-1-(((S)-4-(tert-butylamino)-3,4-dione-1-((S)-2-oxopyrrolidin-3-yl)but-2-yl)amino)-1-oxo-3-phenylpropan-2-yl)-1-methyl-1H-indole-2-carboxamide (A67)

1H NMR (500 MHz, Chloroform) δ 7.38 (s, 1H), 7.29-7.13 (m, 9H), 6.07 (s, 1H), 5.82 (d, J=4.8 Hz, 2H), 5.28 (s, 1H), 4.94 (s, 1H), 4.87 (s, 1H), 3.67-3.63 (m, 3H), 3.45 (s, 1H), 3.35 (s, 1H), 3.19 (s, 1H), 2.93 (s, 1H), 2.68 (s, 1H), 2.18 (s, 1H), 2.09-2.05 (m, 2H), 1.94 (s, 1H), 1.34-1.30 (m, 9H).

Example 68 N—((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-1-methyl-1H-indole-2-carboxamide (A68)

1H NMR (500 MHz, Chloroform) δ 7.49 (s, 3H), 7.34-7.20 (m, 23H), 7.20 (s, 3H), 7.15 (s, 2H), 6.73 (s, 3H), 6.27 (s, 3H), 5.73 (s, 3H), 5.11 (s, 3H), 4.83 (s, 3H), 3.98 (s, 2H), 3.76 (s, 3H), 3.58-3.54 (m, 9H), 3.35 (s, 2H), 3.22 (s, 3H), 2.88 (s, 3H), 2.63 (s, 3H), 2.19 (s, 2H), 2.09-2.05 (m, 6H), 1.95-1.91 (m, 7H), 1.76-1.66 (m, 7H), 1.66-1.55 (m, 20H).

Example 69 N—((S)-1-(((S)-4-(benzylamino)-3,4-dione-1-((S)-2-oxopiperidin-3-yl)but-2-yl)amino)-1-oxo-3-phenylpropan-2-yl)-1-methyl-1H-indole-2-carboxamide (A69)

1H NMR (500 MHz, Chloroform) δ 7.35-7.29 (m, 2H), 7.29-7.26 (m, 1H), 7.26-7.06 (m, 11H), 6.67 (s, 1H), 6.05 (d, J=11.7 Hz, 2H), 5.74 (s, 1H), 4.95 (s, 1H), 4.77 (s, 1H), 4.39 (s, 1H), 4.34 (s, 1H), 3.86-3.82 (m, 3H), 3.29-3.17 (m, 3H), 2.95 (s, 1H), 2.56 (s, 1H), 2.44 (s, 1H), 2.12-2.00 (m, 2H), 1.85 (s, 1H), 1.78 (s, 1H), 1.41 (s, 1H), 1.15 (s, 1H).

Example 70 N—((S)-1-(((S)-4-(tert-butylamino)-3,4-dione-1-((S)-2-oxopiperidin-3-yl)but-2-yl)amino)-1-oxo-3-phenylpropan-2-yl)-1-methyl-1H-indole-2-carboxamide (A70)

1H NMR (500 MHz, Chloroform) δ 7.51 (s, 1H), 7.31 (s, 1H), 7.22 (ddd, J=42.8, 13.4, 8.7 Hz, 8H), 6.91 (s, 1H), 6.06 (s, 1H), 5.93 (s, 1H), 5.54 (s, 1H), 4.80 (s, 1H), 4.71 (s, 1H), 3.73-3.69 (m, 3H), 3.26 (t, J=14.0 Hz, 3H), 2.82 (d, J=27.3 Hz, 2H), 2.11-2.01 (m, 2H), 1.92 (s, 1H), 1.82 (s, 1H), 1.75 (s, 1H), 1.54 (s, 1H), 1.32-1.28 (m, 9H).

Example 71 N—((S)-3-cyclohexyl-1-(((S)-4-(cyclohexylamino)-3,4-dione-1-((S)-2-oxopiperidin-3-yl)but-2-yl)amino)-1-oxo-3-phenylpropan-2-yl)-1-methyl-1H-indole-2-carboxamide (A71)

1H NMR (500 MHz, Chloroform) δ 8.25 (s, 1H), 7.38 (s, 1H), 7.28 (dd, J=15.9, 3.4 Hz, 4H), 7.24-7.12 (m, 5H), 5.93 (s, 1H), 5.32 (s, 1H), 5.07 (s, 1H), 4.75 (s, 1H), 4.41 (s, 1H), 3.85-3.77 (m, 4H), 3.27-3.20 (m, 3H), 3.04 (s, 1H), 2.84 (s, 1H), 2.49 (s, 1H), 2.17-2.10 (m, 2H), 2.10-2.02 (m, 2H), 1.86-1.75 (m, 6H), 1.65 (s, 1H), 1.58-1.52 (m, 4H).

Example 72 N—((S)-1-(((S)-4-(benzylamino)-3,4-dione-1-((S)-2-oxopyrrolidin-3-yl)but-2-yl)amino)-1-oxo-3-phenylpropan-2-yl)-4,6-dichloro-1H-indole-2-carboxamide (A72)

1H NMR (500 MHz, Chloroform) δ 8.55 (s, 1H), 7.52 (s, 1H), 7.44 (s, 1H), 7.38 (s, 1H), 7.32-7.27 (m, 4H), 7.27-7.12 (m, 8H), 7.10 (s, 1H), 6.00 (s, 1H), 5.04 (s, 1H), 4.92 (s, 1H), 4.77 (s, 1H), 4.38 (s, 1H), 4.30 (s, 1H), 3.45 (s, 1H), 3.35 (s, 1H), 3.27 (s, 1H), 3.12 (s, 1H), 2.87 (s, 1H), 2.19 (s, 1H), 2.09-2.05 (m, 2H), 1.92 (s, 1H).

Example 73 N—((S)-1-(((S)-4-(tert-butylamino)-3,4-dione-1-((S)-2-oxopyrrolidin-3-yl)but-2-yl)amino)-1-oxo-3-phenylpropan-2-yl)-4,6-dichloro-1H-indole-2-carboxamide (A73)

1H NMR (500 MHz, Chloroform) δ 8.55 (s, 1H), 8.14 (s, 1H), 7.52 (s, 1H), 7.44 (s, 1H), 7.28-7.22 (m, 2H), 7.22-7.11 (m, 3H), 7.09 (s, 1H), 6.01 (s, 1H), 5.55 (s, 1H), 5.12 (s, 1H), 4.74 (s, 1H), 4.31 (s, 1H), 3.45 (s, 1H), 3.35 (s, 1H), 3.30 (s, 1H), 3.08 (s, 1H), 2.92 (s, 1H), 2.18 (s, 1H), 2.09-2.05 (m, 2H), 1.92 (s, 1H), 1.39-1.35 (m, 9H).

Example 74 N—((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-4,6-dichloro-1H-indole-2-carboxamide (A74)

1H NMR (500 MHz, Chloroform) δ 8.85 (s, 1H), 8.44 (s, 1H), 8.39 (s, 1H), 7.58 (s, 1H), 7.42 (s, 1H), 7.28-7.23 (m, 2H), 7.15 (s, 1H), 7.12-7.06 (m, 3H), 6.10 (s, 1H), 5.94 (s, 1H), 5.03 (s, 1H), 4.66 (s, 1H), 3.45 (d, J=5.0 Hz, 2H), 3.35 (s, 1H), 3.27 (s, 1H), 3.06 (s, 1H), 2.90 (s, 1H), 2.19 (s, 1H), 2.09-2.05 (m, 2H), 1.95-1.91 (m, 3H), 1.72-1.68 (m, 3H), 1.56-1.52 (m, 2H), 1.50 (s, 1H), 1.46-1.41 (m, 2H).

Example 75 N—((S)-1-(((S)-4-(benzylamino)-3,4-dione-1-((S)-2-oxopiperidin-3-yl)but-2-yl)amino)-1-oxo-3-phenylpropan-2-yl)-4,6-dichloro-1H-indole-2-carboxamide (A75)

1H NMR (500 MHz, Chloroform) δ 8.67 (s, 13H), 7.46 (s, 13H), 7.30-7.24 (m, 28H), 7.24-7.14 (m, 80H), 7.12-7.00 (m, 30H), 7.00 (s, 11H), 6.93 (d, J=12.0 Hz, 26H), 6.07 (s, 13H), 4.91 (s, 13H), 4.80 (s, 13H), 4.36 (s, 13H), 4.31 (s, 13H), 4.27 (s, 13H), 4.04 (s, 13H), 3.31 (d, J=52.2 Hz, 35H), 3.22 (s, 5H), 3.01 (s, 14H), 2.86 (s, 11H), 2.31 (s, 9H), 2.08-2.04 (m, 25H), 1.83 (s, 12H), 1.77 (s, 10H), 1.54 (s, 9H).

Example 76 N—((S)-1-(((S)-4-(tert-butylamino)-3,4-dione-1-((S)-2-oxopiperidin-3-yl)but-2-yl)amino)-1-oxo-3-phenylpropan-2-yl)-4,6-dichloro-1H-indole-2-carboxamide (A76)

1H NMR (500 MHz, Chloroform) δ 8.53 (s, 8H), 7.62 (s, 8H), 7.43 (s, 8H), 7.38 (s, 8H), 7.26-7.21 (m, 16H), 7.21-7.14 (m, 21H), 7.14-7.11 (m, 4H), 7.09 (s, 8H), 5.81 (s, 8H), 5.66 (s, 8H), 5.34 (s, 8H), 4.92 (s, 8H), 4.75 (s, 8H), 3.33-3.20 (m, 24H), 2.87 (s, 7H), 2.59 (s, 7H), 2.08-2.04 (m, 16H), 1.86 (s, 6H), 1.80 (s, 7H), 1.73 (s, 6H), 1.48 (s, 6H), 1.34-1.30 (m, 72H).

Example 77 N—((S)-3-cyclohexyl-1-(((S)-4-(cyclohexylamino)-3,4-dione-1-((S)-2-oxopiperidin-3-yl)but-2-yl)amino)-1-oxo-3-phenylpropan-2-yl)-4,6-dichloro-1H-indole-2-carboxamide (A77)

1H NMR (500 MHz, Chloroform) δ 9.14 (s, 1H), 9.09 (s, 1H), 7.58 (s, 1H), 7.47 (s, 1H), 7.33-7.27 (m, 2H), 7.27-7.14 (m, 3H), 7.10 (s, 1H), 6.82 (s, 1H), 5.96 (s, 1H), 5.80 (s, 1H), 4.98 (s, 1H), 4.82 (s, 1H), 3.35 (s, 1H), 3.24 (d, J=14.7 Hz, 2H), 3.16 (s, 1H), 2.96 (s, 1H), 2.83 (s, 1H), 2.16-2.04 (m, 5H), 1.82 (s, 1H), 1.75 (dd, J=19.9, 8.6 Hz, 4H), 1.59-1.49 (m, 4H), 1.44-1.40 (m, 2H).

Example 78 N—((S)-1-(((S)-4-(benzylamino)-3,4-dione-1-((S)-2-oxopyrrolidin-3-yl)but-2-yl)amino)-1-oxo-3-phenylpropan-2-yl)-quinoxaline-2-carboxamide (A78)

1H NMR (500 MHz, Chloroform) δ 9.21 (s, 1H), 8.80 (s, 1H), 8.10 (d, J=21.9 Hz, 2H), 7.71 (s, 1H), 7.63 (d, J=6.0 Hz, 2H), 7.30-7.11 (m, 10H), 6.38 (s, 1H), 5.97 (s, 1H), 4.90 (s, 1H), 4.69 (s, 1H), 4.36 (d, J=4.9 Hz, 2H), 3.45 (s, 1H), 3.35 (s, 1H), 3.16 (s, 1H), 2.95 (s, 1H), 2.86 (s, 1H), 2.19 (s, 1H), 2.09-2.05 (m, 2H), 1.93 (s, 1H).

Example 79 N—((S)-1-(((S)-4-(tert-butylamino)-3,4-dione-1-((S)-2-oxopyrrolidin-3-yl)but-2-yl)amino)-1-oxo-3-phenylpropan-2-yl)-quinoxaline-2-carb oxamide (A79)

1H NMR (500 MHz, Chloroform) δ 9.43 (s, 1H), 9.01 (s, 1H), 8.10 (d, J=11.8 Hz, 2H), 7.68-7.64 (m, 2H), 7.25-7.19 (m, 1H), 7.19-7.09 (m, 4H), 6.12 (s, 1H), 6.04 (s, 1H), 5.51 (s, 1H), 5.09 (s, 1H), 4.74 (s, 1H), 3.45 (s, 1H), 3.35 (d, J=2.3 Hz, 2H), 3.11 (s, 1H), 2.89 (s, 1H), 2.19 (s, 1H), 2.09-2.05 (m, 2H), 1.92 (s, 1H), 1.39-1.35 (m, 9H).

Example 80 N—((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-quinoxaline-2-carboxamide (A80)

1H NMR (500 MHz, Chloroform) δ 9.46 (s, 1H), 8.10 (d, J=1.3 Hz, 2H), 7.64 (d, J=1.4 Hz, 2H), 7.29-7.21 (m, 4H), 7.15 (s, 1H), 6.17 (s, 1H), 5.60 (s, 1H), 5.41 (s, 1H), 5.16 (s, 1H), 4.42 (s, 1H), 3.77 (s, 1H), 3.45 (s, 1H), 3.35 (d, J=2.0 Hz, 2H), 2.94 (s, 1H), 2.49 (s, 1H), 2.19 (s, 1H), 2.09-2.05 (m, 2H), 1.93 (s, 1H), 1.81-1.74 (m, 6H), 1.74-1.70 (m, 2H), 1.57-1.51 (m, 2H).

Example 81 N—((S)-1-(((S)-4-(benzylamino)-3,4-dione-1-((S)-2-oxopiperidin-3-yl)but-2-yl)amino)-1-oxo-3-phenylpropan-2-yl)-quinoxaline-2-carboxamide (A81)

1H NMR (500 MHz, Chloroform) δ 9.04 (s, 1H), 8.07 (d, J=5.3 Hz, 2H), 7.62 (d, J=0.9 Hz, 2H), 7.30-7.20 (m, 5H), 7.20-7.12 (m, 5H), 7.10 (s, 1H), 6.69 (s, 1H), 5.68 (d, J=19.5 Hz, 2H), 5.14 (s, 1H), 5.08 (s, 1H), 4.42 (s, 1H), 4.34 (s, 1H), 3.37 (s, 1H), 3.24 (d, J=17.2 Hz, 2H), 2.95 (s, 1H), 2.15 (s, 1H), 2.09-2.03 (m, 2H), 1.76 (s, 1H), 1.70 (s, 1H), 1.63 (s, 1H), 1.43 (s, 1H).

Example 82 N—((S)-1-(((S)-4-(tert-butylamino)-3,4-dione-1-((S)-2-oxopiperidin-3-yl)but-2-yl)amino)-1-oxo-3-phenylpropan-2-yl)-quinoxaline-2-carboxamide (A82)

1H NMR (500 MHz, Chloroform) δ 9.37 (s, 1H), 8.11 (d, J=1.9 Hz, 2H), 7.64 (d, J=1.0 Hz, 2H), 7.32-7.26 (m, 2H), 7.26-7.13 (m, 3H), 6.08 (s, 1H), 5.93 (d, J=13.8 Hz, 2H), 5.60 (s, 1H), 4.97 (s, 1H), 4.83 (s, 1H), 3.24 (d, J=16.7 Hz, 2H), 3.18 (s, 1H), 2.93 (s, 1H), 2.70 (s, 1H), 2.11-2.01 (m, 2H), 1.98 (s, 1H), 1.78 (s, 1H), 1.71 (s, 1H), 1.42 (s, 1H), 1.35-1.31 (m, 9H).

Example 83 N—((S)-3-cyclohexyl-1-(((S)-4-(cyclohexylamino)-3,4-dione-1-((S)-2-oxopiperidin-3-yl)but-2-yl)amino)-1-oxo-3-phenylpropan-2-yl)-quinoxaline-2-carboxamide (A83)

1H NMR (500 MHz, Chloroform) δ 9.67 (s, 6H), 8.12 (d, J=8.3 Hz, 12H), 7.66 (d, J=1.4 Hz, 12H), 7.26-7.16 (m, 25H), 7.14 (s, 6H), 6.12 (s, 6H), 5.79 (s, 6H), 5.56 (s, 6H), 5.33 (s, 6H), 5.10 (s, 6H), 4.95 (s, 6H), 3.84 (s, 6H), 3.27 (t, J=34.6 Hz, 16H), 3.21 (d, J=6.1 Hz, 2H), 3.02 (s, 6H), 2.83 (s, 6H), 2.11-2.01 (m, 13H), 2.01-1.94 (m, 18H), 1.75 (s, 4H), 1.71-1.55 (m, 59H).

Example 84 N—((S)-1-(((S)-4-(benzylamino)-3,4-dione-1-((S)-2-oxopyrrolidin-3-yl)but-2-yl)amino)-1-oxo-3-phenylpropan-2-yl)-quinoline-2-carboxamide (A84)

1H NMR (500 MHz, Chloroform) δ 8.46 (s, 1H), 8.12 (s, 1H), 7.78 (s, 1H), 7.65 (s, 1H), 7.54 (s, 1H), 7.44 (s, 1H), 7.31-7.24 (m, 4H), 7.24-7.14 (m, 4H), 7.12 (s, 2H), 5.72 (s, 1H), 5.54 (s, 1H), 5.14 (s, 1H), 4.70 (s, 1H), 4.59 (s, 1H), 4.29 (d, J=9.5 Hz, 2H), 3.74 (s, 1H), 3.35 (s, 1H), 3.31 (s, 1H), 3.08 (s, 1H), 2.72 (s, 1H), 2.17 (s, 1H), 2.10-2.05 (m, 2H), 1.89 (s, 1H).

Example 85 N—((S)-1-(((S)-4-(tert-butylamino)-3,4-dione-1-((S)-2-oxopyrrolidin-3-yl)but-2-yl)amino)-1-oxo-3-phenylpropan-2-yl)-quinoline-2-carboxamide (A85)

1H NMR (500 MHz, Chloroform) δ 8.40 (d, J=39.3 Hz, 11H), 8.36-8.34 (m, 1H), 8.19 (s, 6H), 7.80 (s, 6H), 7.71 (s, 6H), 7.49 (d, J=5.7 Hz, 12H), 7.30-7.25 (m, 12H), 7.25-7.15 (m, 14H), 7.14 (s, 4H), 6.20 (s, 6H), 5.92 (s, 6H), 5.07 (s, 6H), 4.75 (s, 6H), 3.45 (s, 6H), 3.38 (d, J=25.1 Hz, 12H), 3.32 (s, 1H), 3.02 (s, 6H), 2.35 (s, 5H), 2.19 (s, 4H), 2.09-2.05 (m, 12H), 1.92 (s, 5H), 1.36-1.32 (m, 53H).

Example 86 N—((S)-3-cyclohexyl-1-(((S)-4-(cyclohexylamino)-3,4-dione-1-((S)-2-oxopyrrolidin-3-yl)but-2-yl)amino)-1-oxo-3-phenylpropan-2-yl)-quinoline-2-carboxamide (A86)

1H NMR (500 MHz, Chloroform) δ 8.46 (s, 1H), 8.12 (s, 1H), 7.81 (s, 1H), 7.69 (s, 1H), 7.49 (d, J=7.1 Hz, 2H), 7.26-7.20 (m, 2H), 7.20-7.09 (m, 3H), 5.94 (d, J=1.5 Hz, 2H), 5.63 (s, 1H), 5.44 (s, 1H), 4.91 (s, 1H), 4.76 (s, 1H), 3.89 (s, 1H), 3.45 (s, 1H), 3.34 (d, J=11.1 Hz, 2H), 3.01 (s, 1H), 2.19 (d, J=10.9 Hz, 2H), 2.14-2.04 (m, 4H), 1.92 (s, 1H), 1.65-1.49 (m, 8H).

Example 87 N—((S)-14 (S)-4-(benzylamino)-3,4-dione-1-((S)-2-oxopiperidin-3-yl)but-2-yl)amino)-1-oxo-3-phenylpropan-2-yl)-quinoline-2-carboxamide (A87)

1H NMR (500 MHz, Chloroform) δ 8.46 (s, 1H), 8.10 (s, 1H), 7.78 (s, 1H), 7.66 (s, 1H), 7.55 (s, 1H), 7.45 (s, 1H), 7.26-7.11 (m, 10H), 6.86 (s, 1H), 5.98 (s, 1H), 5.89 (s, 1H), 5.56 (d, J=16.8 Hz, 2H), 4.75 (s, 1H), 4.44 (s, 1H), 4.32 (s, 1H), 3.44 (s, 1H), 3.23 (d, J=18.1 Hz, 2H), 2.84 (s, 1H), 2.72 (s, 1H), 2.11-2.01 (m, 2H), 1.98 (s, 1H), 1.63 (s, 1H), 1.56 (s, 1H), 1.25 (s, 1H).

Example 88 N—((S)-1-(((S)-4-(tert-butylamino)-3,4-dione-1-((S)-2-oxopiperidin-3-yl)but-2-yl)amino)-1-oxo-3-phenylpropan-2-yl)-quinoline-2-carboxamide (A88)

1H NMR (500 MHz, Chloroform) δ 8.50 (d, J=13.8 Hz, 2H), 8.17 (s, 1H), 7.81 (s, 1H), 7.69 (s, 1H), 7.65 (s, 1H), 7.48 (s, 1H), 7.28-7.24 (m, 1H), 7.24-7.11 (m, 4H), 6.95 (s, 1H), 6.17 (s, 1H), 5.50 (s, 1H), 5.00 (s, 1H), 4.79 (s, 1H), 3.24 (d, J=15.4 Hz, 2H), 3.08 (s, 1H), 2.90 (s, 1H), 2.69 (s, 1H), 2.11-2.01 (m, 2H), 1.90 (s, 1H), 1.84 (d, J=3.8 Hz, 2H), 1.78 (s, 1H), 1.29-1.25 (m, 9H).

Example 89 N—((S)-3-cyclohexyl-1-(((S)-4-(cyclohexylamino)-3,4-dione-1-((S)-2-oxopiperidin-3-yl)but-2-yl)amino)-1-oxo-3-phenylpropan-2-yl)-quinoline-2-carboxamide (A89)

1H NMR (500 MHz, Chloroform) δ 9.70 (s, 4H), 8.44 (s, 4H), 8.18 (s, 4H), 7.80 (s, 4H), 7.69 (d, J=18.4 Hz, 8H), 7.48 (d, J=4.0 Hz, 8H), 7.32-7.26 (m, 8H), 7.23-7.13 (m, 12H), 6.67 (s, 4H), 5.84 (s, 4H), 4.95 (s, 4H), 4.88 (s, 4H), 3.90 (s, 4H), 3.31 (d, J=56.1 Hz, 10H), 3.22 (s, 2H), 2.99 (s, 4H), 2.86 (s, 4H), 2.11-2.04 (m, 8H), 2.01 (t, J=7.0 Hz, 12H), 1.81 (s, 3H), 1.74 (s, 3H), 1.67-1.60 (m, 35H), 1.45 (s, 3H).

Example 90 N—((S)-1-(((S)-4-(benzylamino)-3,4-dione-1-((S)-2-oxopyrrolidin-3-yl)but-2-yl)amino)-4-methyl-1-oxopentan-2-yl)-1H-indole-2-carboxamide (A90)

1H NMR (500 MHz, Chloroform) δ 8.36 (s, 1H), 7.52 (d, J=19.2 Hz, 2H), 7.39 (s, 1H), 7.26-7.19 (m, 4H), 7.18 (s, 1H), 7.13 (s, 1H), 7.07 (s, 1H), 6.32 (s, 1H), 6.24 (s, 1H), 6.05 (s, 1H), 5.47 (s, 1H), 5.27 (s, 1H), 4.61 (s, 1H), 4.41 (s, 1H), 4.32 (s, 1H), 3.59 (s, 1H), 3.45 (s, 1H), 2.17 (s, 1H), 2.09-2.05 (m, 2H), 1.92 (s, 1H), 1.73 (d, J=11.4 Hz, 2H), 1.63 (s, 1H), 1.55 (s, 1H), 1.12-0.99 (m, 6H).

Example 91 N—((S)-1-(((S)-4-(tert-butylamino)-3,4-dione-1-((S)-2-oxopyrrolidin-3-yl)but-2-yl)amino)-3-cyclohexyl-1-oxopentan-2-yl)-1H-indole-2-carboxamide (A91)

1H NMR (500 MHz, Chloroform) δ 9.33 (s, 1H), 8.28 (s, 1H), 7.46 (d, J=15.1 Hz, 2H), 7.35 (s, 1H), 7.10 (s, 1H), 7.03 (s, 1H), 6.79 (s, 1H), 6.12 (s, 1H), 5.28 (s, 1H), 4.95 (s, 1H), 4.31 (s, 1H), 3.45 (s, 1H), 3.35 (s, 1H), 2.75 (s, 1H), 2.19 (s, 1H), 2.09-2.05 (m, 2H), 1.92 (s, 1H), 1.70 (d, J=19.2 Hz, 2H), 1.44 (s, 1H), 1.36-1.32 (m, 9H), 0.99-0.85 (m, 6H).

Example 92 N—((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-1H-indole-2-carboxamide (A92)

1H NMR (500 MHz, Chloroform) δ 8.38 (s, 1H), 7.51 (d, J=17.6 Hz, 2H), 7.37 (s, 1H), 7.12 (s, 1H), 7.06 (s, 1H), 6.50 (s, 1H), 6.00 (s, 1H), 5.60 (s, 1H), 5.50 (s, 1H), 5.00 (s, 1H), 4.68 (s, 1H), 3.45 (s, 1H), 3.35 (s, 1H), 3.29 (s, 1H), 2.71 (s, 1H), 2.19 (s, 1H), 2.09-2.05 (m, 2H), 1.97-1.91 (m, 3H), 1.70 (t, J=9.1 Hz, 3H), 1.59-1.55 (m, 2H), 1.50 (dd, J=10.4, 1.1 Hz, 4H), 1.43-1.38 (m, 2H), 1.13-1.00 (m, 6H).

Example 93 N—((S)-1-(((S)-4-(benzylamino)-3,4-dione-1-((S)-2-oxopiperidin-3-yl)but-2-yl)amino)-4-methyl-1-oxopentan-2-yl)-1H-indole-2-carboxamide (A93)

1H NMR (500 MHz, Chloroform) δ 8.63 (s, 1H), 7.56 (s, 1H), 7.46 (d, J=25.5 Hz, 2H), 7.29-7.24 (m, 2H), 7.24-7.17 (m, 3H), 7.17-7.06 (m, 3H), 6.14 (s, 1H), 5.63 (s, 1H), 5.02 (d, J=15.0 Hz, 2H), 4.43 (s, 1H), 4.37 (s, 1H), 4.30 (s, 1H), 3.24 (d, J=17.4 Hz, 2H), 2.81 (s, 1H), 2.21 (s, 1H), 2.08-2.04 (m, 2H), 1.85 (s, 1H), 1.77 (t, J=13.2 Hz, 3H), 1.51 (s, 1H), 1.41 (s, 1H), 1.04-0.90 (m, 6H).

Example 94 N—((S)-1-(((S)-4-(tert-butylamino)-3,4-dione-1-((S)-2-oxopiperidin-3-yl)but-2-yl)amino)-3-cyclohexyl-1-oxopentan-2-yl)-1H-indole-2-carboxamide (A94)

1H NMR (500 MHz, Chloroform) δ 8.38 (s, 1H), 8.13 (s, 1H), 7.49 (s, 1H), 7.41 (s, 1H), 7.37 (s, 1H), 7.12 (s, 1H), 7.04 (s, 1H), 5.95 (s, 1H), 5.30 (d, J=18.0 Hz, 2H), 4.86 (s, 1H), 4.51 (s, 1H), 3.23 (d, J=15.7 Hz, 2H), 2.45 (s, 1H), 2.19 (s, 1H), 2.08-2.04 (m, 2H), 1.96 (s, 1H), 1.75 (s, 1H), 1.69 (d, J=8.0 Hz, 2H), 1.51 (s, 1H), 1.36-1.27 (m, 10H), 1.12-0.99 (m, 6H).

Example 95 N—((S)-3-cyclohexyl-1-(((S)-4-(cyclohexylamino)-3,4-dione-1-((S)-2-oxopiperidin-3-yl)but-2-yl)amino)-3-cyclohexyl-1-oxopentan-2-yl)-1H-indole-2-carboxamide (A95)

1H NMR (500 MHz, Chloroform) δ 9.04 (s, 1H), 8.28 (s, 1H), 7.50 (d, J=31.2 Hz, 2H), 7.38 (s, 1H), 7.13 (s, 1H), 7.06 (s, 1H), 6.19 (s, 1H), 5.81 (s, 1H), 5.63 (s, 1H), 4.78 (s, 1H), 4.59 (s, 1H), 3.94 (s, 1H), 3.24 (d, J=18.2 Hz, 2H), 2.35 (s, 1H), 2.13-2.04 (m, 4H), 2.00 (s, 1H), 1.83-1.60 (m, 8H), 1.57 (s, 1H), 1.52-1.46 (m, 2H), 1.45-1.41 (m, 2H), 1.33 (s, 1H), 1.13-1.01 (m, 6H).

Example 96 N—((S)-1-(((S)-4-(benzylamino)-3,4-dione-1-((S)-2-oxopyrrolidin-3-yl)but-2-yl)amino)-4-methyl-1-oxopentan-2-yl)-benzofuran-2-carboxamide (A96)

1H NMR (500 MHz, Chloroform) δ 7.74 (s, 1H), 7.42 (s, 1H), 7.36-7.26 (m, 4H), 7.23 (s, 1H), 7.17 (s, 1H), 7.07 (s, 1H), 6.96 (s, 1H), 6.46 (s, 1H), 6.22 (s, 1H), 5.75 (s, 1H), 5.06 (s, 1H), 4.63 (s, 1H), 4.46 (d, J=17.5 Hz, 2H), 4.34 (s, 1H), 3.45 (s, 1H), 3.35 (s, 1H), 3.28 (s, 1H), 2.19 (s, 1H), 2.09-2.05 (m, 2H), 1.93 (s, 1H), 1.67 (s, 1H), 1.55 (s, 1H), 1.19 (s, 1H), 1.07-0.94 (m, 6H).

Example 97 N—((S)-1-(((S)-4-(tert-butylamino)-3,4-dione-1-((S)-2-oxopyrrolidin-3-yl)but-2-yl)amino)-3-cyclohexyl-1-oxopentan-2-yl)-benzofuran-2-carboxamide (A97)

1H NMR (500 MHz, Chloroform) δ 8.17 (s, 1H), 7.45 (d, J=28.3 Hz, 2H), 7.22 (s, 1H), 7.15 (s, 1H), 6.41 (s, 1H), 6.00 (s, 1H), 5.96 (s, 1H), 4.94 (s, 1H), 4.55 (s, 1H), 3.45 (s, 1H), 3.35 (s, 1H), 2.53 (s, 1H), 2.18 (s, 1H), 2.13-2.02 (m, 2H), 1.93 (s, 1H), 1.76 (s, 1H), 1.65 (s, 1H), 1.35-1.31 (m, 9H), 1.25 (s, 1H), 1.07-0.94 (m, 6H).

Example 98 N—((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-benzofuran-2-carboxamide (A98)

1H NMR (500 MHz, Chloroform) δ 7.59 (s, 4H), 7.55-7.39 (m, 12H), 7.22 (s, 4H), 7.15 (s, 4H), 6.04 (s, 4H), 5.94 (s, 4H), 5.89 (s, 4H), 4.87 (s, 4H), 4.48 (s, 4H), 3.80 (s, 4H), 3.45 (s, 4H), 3.35 (s, 3H), 2.58 (s, 4H), 2.18 (s, 4H), 2.11-2.04 (m, 8H), 1.95-1.88 (m, 19H), 1.87 (t, J=3.1 Hz, 4H), 1.75 (d, J=29.9 Hz, 6H), 1.71 (d, J=3.3 Hz, 2H), 1.69-1.64 (m, 8H), 1.62 (s, 3H), 1.59-1.51 (m, 8H), 1.06-0.93 (m, 24H).

Example 99 N—((S)-14 (S)-4-(benzylamino)-3,4-dione-1-((S)-2-oxopiperidin-3-yl)but-2-yl)amino)-4-methyl-1-oxopentan-2-yl)-benzofuran-2-carboxamide (A99)

1H NMR (500 MHz, Chloroform) δ 7.58 (s, 1H), 7.52 (d, J=13.8 Hz, 2H), 7.38-7.32 (m, 2H), 7.30 (s, 1H), 7.26 (s, 1H), 7.23-7.16 (m, 3H), 6.21 (s, 1H), 5.77 (s, 1H), 5.68 (s, 1H), 4.86 (s, 1H), 4.82 (s, 1H), 4.56 (s, 1H), 4.37 (s, 1H), 4.33 (s, 1H), 3.24 (d, J=17.0 Hz, 2H), 2.63 (s, 1H), 2.05 (t, J=5.4 Hz, 3H), 1.82 (s, 1H), 1.75 (s, 1H), 1.60 (d, J=3.4 Hz, 2H), 1.48 (s, 1H), 1.39 (s, 1H), 1.09-1.00 (m, 6H).

Example 100 N—((S)-1-(((S)-4-(benzylamino)-3,4-dione-1-((S)-2-oxopiperidin-3-yl)but-2-yl)amino)-4-methyl-1-oxopentan-2-yl)-benzofuran-2-carboxamide (A100)

1H NMR (500 MHz, Chloroform) δ 7.58 (s, 1H), 7.52 (d, J=13.8 Hz, 2H), 7.38-7.32 (m, 2H), 7.30 (s, 1H), 7.26 (s, 1H), 7.23-7.16 (m, 3H), 6.21 (s, 1H), 5.77 (s, 1H), 5.68 (s, 1H), 4.86 (s, 1H), 4.82 (s, 1H), 4.56 (s, 1H), 4.37 (s, 1H), 4.33 (s, 1H), 3.24 (d, J=17.0 Hz, 2H), 2.63 (s, 1H), 2.05 (t, J=5.4 Hz, 3H), 1.82 (s, 1H), 1.75 (s, 1H), 1.60 (d, J=3.4 Hz, 2H), 1.48 (s, 1H), 1.39 (s, 1H), 1.09-1.00 (m, 6H).

Example 101 N—((S)-3-cyclohexyl-1-(((S)-4-(cyclohexylamino)-3,4-dione-1-((S)-2-oxopiperidin-3-yl)but-2-yl)amino)-3-cyclohexyl-1-oxopentan-2-yl)-benzofuran-2-carboxamide (A101)

1H NMR (500 MHz, Chloroform) δ 7.59 (s, 1H), 7.48 (d, J=9.6 Hz, 2H), 7.20 (s, 1H), 7.14 (s, 1H), 5.80 (s, 1H), 5.26 (s, 1H), 5.11 (d, J=5.2 Hz, 2H), 4.91 (s, 1H), 3.81 (s, 1H), 3.24 (d, J=17.3 Hz, 2H), 2.61 (s, 1H), 2.09-2.02 (m, 4H), 1.95-1.87 (m, 2H), 1.84 (s, 1H), 1.77 (s, 1H), 1.69 (s, 1H), 1.58 (d, J=5.5 Hz, 2H), 1.51-1.44 (m, 4H), 1.26-1.22 (m, 4H), 1.08-0.95 (m, 6H).

Example 102 N—((S)-1-(((S)-4-(benzylamino)-3,4-dione-1-((S)-2-oxopyrrolidin-3-yl)but-2-yl)amino)-4-methyl-1-oxopentan-2-yl)-benzothiophene-2-carboxamide (A102)

1H NMR (500 MHz, Chloroform) δ 8.47 (s, 1H), 7.91 (s, 1H), 7.78 (s, 1H), 7.33 (d, J=6.1 Hz, 2H), 7.28-7.17 (m, 5H), 6.42 (s, 1H), 6.05 (s, 1H), 5.73 (s, 1H), 5.38 (s, 1H), 5.27 (s, 1H), 4.46 (s, 1H), 4.36 (d, J=16.9 Hz, 2H), 3.45 (s, 1H), 3.35 (s, 1H), 2.67 (s, 1H), 2.18 (s, 1H), 2.09-2.05 (m, 2H), 1.92 (s, 1H), 1.82 (s, 1H), 1.70 (s, 1H), 1.52 (s, 1H), 1.10-0.96 (m, 6H).

Example 103 N—((S)-1-(((S)-4-(tert-butylamino)-3,4-dione-1-((S)-2-oxopyrrolidin-3-yl)but-2-yl)amino)-3-cyclohexyl-1-oxopentan-2-yl)-benzothiophene-2-carboxamide (A103)

1H NMR (500 MHz, Chloroform) δ 8.37 (s, 1H), 7.89 (s, 1H), 7.73 (s, 1H), 7.30 (d, J=2.2 Hz, 2H), 6.58 (s, 1H), 6.03 (s, 1H), 5.61 (s, 1H), 5.53 (s, 1H), 5.02 (s, 1H), 4.70 (s, 1H), 3.45 (s, 1H), 3.35 (s, 1H), 2.69 (s, 1H), 2.19 (s, 1H), 2.09-2.05 (m, 2H), 1.93 (s, 1H), 1.69 (d, J=8.4 Hz, 2H), 1.49 (s, 1H), 1.32-1.28 (m, 9H), 1.10-1.02 (m, 6H).

Example 104 N—((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-benzothiophene-2-carboxamide (A104)

1H NMR (500 MHz, Chloroform) δ 8.63 (s, 1H), 7.91 (s, 1H), 7.74 (s, 1H), 7.34-7.30 (m, 2H), 6.18 (d, J=11.5 Hz, 2H), 6.02 (s, 1H), 4.62 (s, 1H), 4.48 (s, 1H), 3.45 (s, 1H), 3.35 (s, 1H), 3.27 (s, 1H), 2.56 (s, 1H), 2.19 (s, 1H), 2.11-2.05 (m, 3H), 1.92 (s, 1H), 1.83-1.70 (m, 3H), 1.69 (s, 1H), 1.59-1.54 (m, 3H), 1.50 (t, J=6.7 Hz, 3H), 1.42-1.37 (m, 2H), 1.12-0.98 (m, 6H).

Example 105 N—((S)-1-(((S)-4-(benzylamino)-3,4-dione-1-((S)-2-oxopiperidine-3-yl)but-2-yl)amino)-4-methyl-1-oxopentan-2-yl)-benzothiophene-2-carboxamide (A105)

1H NMR (500 MHz, Chloroform) δ 8.43 (s, 1H), 7.93 (d, J=0.7 Hz, 2H), 7.74 (s, 1H), 7.33 (d, J=2.2 Hz, 2H), 7.30-7.25 (m, 4H), 7.20 (s, 1H), 6.65 (s, 1H), 6.05 (s, 1H), 5.58 (s, 1H), 4.71 (s, 1H), 4.52 (s, 1H), 4.40 (s, 1H), 4.30 (s, 1H), 3.23 (d, J=15.8 Hz, 2H), 2.73 (s, 1H), 2.16 (s, 1H), 2.08-2.04 (m, 2H), 1.80 (s, 1H), 1.69 (d, J=6.6 Hz, 2H), 1.63 (s, 1H), 1.44 (s, 1H), 1.35 (s, 1H), 1.12-0.99 (m, 6H).

Example 106 N—((S)-1-(((S)-4-(tert-butylamino)-3,4-dione-1-((S)-2-oxopiperidin-3-yl)but-2-yl)amino)-3-cyclohexyl-1-oxopentan-2-yl)-benzothiophene-2-carboxamide (A106)

1H NMR (500 MHz, Chloroform) δ 8.39 (s, 1H), 7.91 (s, 1H), 7.71 (s, 1H), 7.31 (d, J=2.6 Hz, 2H), 6.50 (s, 1H), 5.87 (s, 1H), 5.71 (s, 1H), 5.57 (s, 1H), 4.80 (s, 1H), 4.75 (s, 1H), 3.23 (d, J=15.7 Hz, 2H), 2.64 (s, 1H), 2.08-2.04 (m, 2H), 1.87 (d, J=17.5 Hz, 2H), 1.68 (d, J=6.0 Hz, 2H), 1.61 (d, J=2.0 Hz, 2H), 1.37 (s, 1H), 1.32-1.28 (m, 9H), 1.10-0.97 (m, 6H).

Example 107 N—((S)-3-cyclohexyl-1-(((S)-4-(cyclohexylamino)-3,4-dione-1-((S)-2-oxopiperidin-3-yl)but-2-yl)amino)-3-cyclohexyl-1-oxopentan-2-yl)-benzothiophene-2-carboxamide (A107)

1H NMR (500 MHz, Chloroform) δ 8.30 (s, 15H), 8.25 (s, 15H), 7.87 (s, 15H), 7.71 (s, 15H), 7.30 (d, J=1.3 Hz, 30H), 6.03 (s, 15H), 5.58 (s, 15H), 5.39 (s, 15H), 5.03 (s, 15H), 4.37 (s, 15H), 3.85 (s, 15H), 3.24 (d, J=16.7 Hz, 29H), 2.67 (s, 11H), 2.57 (s, 13H), 2.08-2.04 (m, 30H), 1.96-1.90 (m, 46H), 1.86 (s, 15H), 1.79 (s, 12H), 1.76-1.53 (m, 169H), 1.58 (d, J=5.6 Hz, 3H), 1.05-0.92 (m, 93H).

Example 108 N—((S)-1-(((S)-4-(benzylamino)-3,4-dione-1-((S)-2-oxopyrrolidin-3-yl)but-2-yl)amino)-4-methyl-1-oxopentan-2-yl)-1-methyl-1H-indole-2-carboxamide (A108)

1H NMR (500 MHz, Chloroform) δ 7.39 (d, J=5.1 Hz, 10H), 7.31-7.22 (m, 12H), 7.22-7.06 (m, 35H), 5.99 (s, 5H), 5.29 (s, 5H), 4.40 (d, J=4.6 Hz, 10H), 4.30 (d, J=5.3 Hz, 1H), 4.24 (d, J=52.5 Hz, 9H), 3.68-3.64 (m, 15H), 3.58 (s, 5H), 3.45 (s, 5H), 2.78 (s, 5H), 2.17 (s, 3H), 2.15-1.95 (m, 17H), 1.89 (s, 4H), 1.81 (s, 5H), 1.62 (s, 5H), 1.48 (s, 4H), 1.07-0.94 (m, 31H).

Example 109 N—((S)-1-(((S)-4-(tert-butylamino)-3,4-dione-1-((S)-2-oxopyrrolidin-3-yl)but-2-yl) amino)-3-cyclohexyl-1-oxopentan-2-yl)-1-methyl-1H-indole-2-carboxamide (A109)

1H NMR (500 MHz, Chloroform) δ 8.20 (s, 1H), 7.48 (s, 1H), 7.27 (d, J=17.1 Hz, 2H), 7.18 (d, J=7.0 Hz, 2H), 6.13 (s, 1H), 5.90 (s, 1H), 5.38 (s, 1H), 5.08 (s, 1H), 4.65 (s, 1H), 3.79-3.75 (m, 3H), 3.45 (s, 1H), 3.35 (s, 1H), 2.81 (s, 1H), 2.17 (s, 1H), 2.13-2.02 (m, 2H), 1.93 (s, 1H), 1.67 (s, 1H), 1.60 (s, 1H), 1.55 (s, 1H), 1.34-1.30 (m, 9H), 1.13-1.00 (m, 6H).

Example 110 N—((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-1-methyl-1H-indole-2-carboxamide (A110)

1H NMR (500 MHz, Chloroform) δ 7.37 (s, 3H), 7.28 (d, J=4.7 Hz, 6H), 7.19 (d, J=11.4 Hz, 6H), 6.24 (s, 3H), 5.90 (s, 3H), 5.81 (s, 3H), 5.30 (s, 3H), 4.90 (s, 3H), 4.68 (s, 3H), 3.90-3.86 (m, 9H), 3.45 (s, 3H), 3.37-3.33 (m, 5H), 2.70 (s, 3H), 2.19 (s, 3H), 2.12-2.04 (m, 6H), 1.93 (s, 3H), 1.86-1.76 (m, 9H), 1.71-1.60 (m, 11H), 1.60-1.54 (m, 1H), 1.51 (dd, J=18.4, 1.5 Hz, 11H), 1.44-1.38 (m, 6H), 1.08-0.95 (m, 18H).

Example 111 N—((S)-14 (S)-4-(benzylamino)-3,4-dione-1-((S)-2-oxopiperidin-3-yl)but-2-yl)amino)-4-methyl-1-oxopentan-2-yl)-1-methyl-1H-indole-2-carboxamide (A111)

1H NMR (500 MHz, Chloroform) δ 7.62 (s, 1H), 7.34 (s, 1H), 7.30-7.17 (m, 8H), 6.58 (s, 1H), 6.10 (s, 1H), 5.61 (s, 1H), 5.41 (s, 1H), 4.83 (s, 1H), 4.48 (s, 1H), 4.37 (s, 1H), 4.32 (s, 1H), 3.76-3.72 (m, 3H), 3.24 (d, J=17.6 Hz, 2H), 2.57 (s, 1H), 2.08-2.04 (m, 2H), 1.80 (s, 1H), 1.76 (s, 1H), 1.71-1.65 (m, 2H), 1.56 (d, J=15.2 Hz, 2H), 1.21 (s, 1H), 1.10-0.97 (m, 6H).

Example 112 N—((S)-1-(((S)-4-(tert-butylamino)-3,4-dione-1-((S)-2-oxopiperidin-3-yl)but-2-yl)amino)-3-cyclohexyl-1-oxopentan-2-yl)-1-methyl-1H-indole-2-carboxamide (A112)

1H NMR (500 MHz, Chloroform) δ 7.57 (s, 1H), 7.51 (s, 1H), 7.31 (s, 1H), 7.25 (s, 1H), 7.18 (d, J=5.1 Hz, 2H), 5.92 (s, 1H), 5.59 (s, 1H), 5.43 (s, 1H), 4.99 (s, 1H), 4.47 (s, 1H), 3.74-3.70 (m, 3H), 3.24 (d, J=16.8 Hz, 2H), 2.71 (s, 1H), 2.41 (s, 1H), 2.08-2.04 (m, 2H), 1.76 (dd, J=34.2, 16.8 Hz, 4H), 1.55 (s, 1H), 1.45 (s, 1H), 1.30-1.26 (m, 9H), 1.09-0.96 (m, 6H).

Example 113 N—((S)-1-(((S)-4-(tert-butylamino)-3,4-dione-1-((S)-2-oxopiperidin-3-yl)but-2-yl)amino)-3-cyclohexyl-1-oxopentan-2-yl)-1-methyl-1H-indole-2-carboxamide (A113)

1H NMR (500 MHz, Chloroform) δ 7.57 (s, 1H), 7.51 (s, 1H), 7.31 (s, 1H), 7.25 (s, 1H), 7.18 (d, J=5.1 Hz, 2H), 5.92 (s, 1H), 5.59 (s, 1H), 5.43 (s, 1H), 4.99 (s, 1H), 4.47 (s, 1H), 3.74-3.70 (m, 3H), 3.24 (d, J=16.8 Hz, 2H), 2.71 (s, 1H), 2.41 (s, 1H), 2.08-2.04 (m, 2H), 1.76 (dd, J=34.2, 16.8 Hz, 4H), 1.55 (s, 1H), 1.45 (s, 1H), 1.30-1.26 (m, 9H), 1.09-0.96 (m, 6H).

Example 114 N—((S)-1-(((S)-4-(benzylamino)-3,4-dione-1-((S)-2-oxopyrrolidin-3-yl)but-2-yl)amino)-4-methyl-1-oxopentan-2-yl)-4,6-dichloro-1H-indole-2-carboxamide (A114)

1H NMR (500 MHz, Chloroform) δ 9.48 (s, 5H), 7.69 (s, 5H), 7.37 (s, 5H), 7.29 (d, J=6.5 Hz, 3H), 7.28-7.15 (m, 23H), 7.06 (s, 5H), 6.19 (s, 5H), 5.64 (s, 5H), 5.49 (s, 5H), 5.18 (s, 5H), 4.42 (s, 5H), 4.35 (d, J=14.2 Hz, 10H), 3.45 (s, 5H), 3.35 (d, J=1.5 Hz, 9H), 3.05 (s, 5H), 2.19 (s, 4H), 2.09-2.05 (m, 10H), 1.92 (s, 4H), 1.68 (s, 5H), 1.58 (s, 5H), 1.52 (s, 5H), 1.02-0.89 (m, 31H).

Example 115 N—((S)-14 (S)-4-(tert-butylamino)-3,4-dione-14 (S)-2-oxopyrrolidin-3-yl)but-2-yl) amino)-3-cyclohexyl-1-oxopentan-2-yl)-4,6-dichloro-1H-indole-2-carboxamide (A115)

1H NMR (500 MHz, Chloroform) δ 8.36 (s, 1H), 7.60 (s, 1H), 7.40 (s, 1H), 7.06 (s, 1H), 6.45 (s, 1H), 6.04 (s, 1H), 5.52 (d, J=2.2 Hz, 2H), 4.99 (s, 1H), 4.68 (s, 1H), 3.45 (s, 1H), 3.35 (s, 1H), 2.72 (s, 1H), 2.19 (s, 1H), 2.09-2.05 (m, 2H), 1.93 (s, 1H), 1.70 (d, J=9.3 Hz, 2H), 1.49 (s, 1H), 1.32-1.28 (m, 9H), 1.11-1.02 (m, 6H).

Example 116 N—((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-4,6-dichloro-1H-indole-2-carboxamide (A116)

1H NMR (500 MHz, Chloroform) δ 9.33 (s, 1H), 8.27 (s, 1H), 7.54 (s, 1H), 7.37 (s, 1H), 7.03 (s, 1H), 6.84 (s, 1H), 6.14 (s, 1H), 5.29 (s, 1H), 4.95 (s, 1H), 4.31 (s, 1H), 3.83 (s, 1H), 3.45 (s, 1H), 3.35 (s, 1H), 2.73 (s, 1H), 2.19 (s, 1H), 2.09-2.05 (m, 2H), 2.05-1.90 (m, 3H), 1.72 (s, 1H), 1.70-1.44 (m, 9H), 1.44 (d, J=5.3 Hz, 1H), 0.98-0.85 (m, 6H).

Example 117 N—((S)-1-(((S)-4-(benzylamino)-3,4-dione-1-((S)-2-oxopiperidin-3-yl)but-2-yl)amino)-4-methyl-1-oxopentan-2-yl)-4,6-dichloro-1H-indole-2-carboxamide (A117)

1H NMR (500 MHz, Chloroform) δ 8.38 (s, 1H), 7.67 (s, 1H), 7.42 (s, 1H), 7.29-7.22 (m, 4H), 7.19 (s, 1H), 7.10 (d, J=11.4 Hz, 2H), 6.65 (s, 1H), 5.62 (s, 1H), 5.55 (s, 1H), 4.99 (s, 1H), 4.48 (s, 1H), 4.37 (s, 1H), 4.33 (s, 1H), 3.24 (d, J=16.8 Hz, 2H), 2.56 (s, 1H), 2.45 (s, 1H), 2.08-2.04 (m, 2H), 1.80 (d, J=3.6 Hz, 2H), 1.72 (d, J=14.6 Hz, 2H), 1.55 (s, 1H), 1.46 (s, 1H), 1.10-0.97 (m, 6H).

Example 118 N—((S)-1-(((S)-4-(tert-butylamino)-3,4-dione-1-((S)-2-oxopiperidin-3-yl)but-2-yl)amino)-3-cyclohexyl-1-oxopentan-2-yl)-4,6-dichloro-1H-indole-2-carboxamide (A118)

1H NMR (500 MHz, Chloroform) δ 8.59 (s, 1H), 7.55 (s, 1H), 7.41 (s, 1H), 7.05 (s, 1H), 6.20 (s, 1H), 5.74 (s, 1H), 5.41 (s, 1H), 4.71 (s, 1H), 4.48 (s, 1H), 3.24 (d, J=17.3 Hz, 2H), 2.48 (s, 1H), 2.06 (t, J=2.1 Hz, 3H), 1.86-1.74 (m, 3H), 1.68 (s, 1H), 1.58 (s, 1H), 1.53 (s, 1H), 1.32-1.28 (m, 9H), 1.15-1.01 (m, 6H).

Example 119 N—((S)-3-cyclohexyl-1-(((S)-4-(cyclohexylamino)-3,4-dione-1-((S)-2-oxopiperidin-3-yl)but-2-yl)amino)-3-cyclohexyl-1-oxopentan-2-yl)-4,6-dichloro-1H-indole-2-carboxamide (A119)

1H NMR (500 MHz, Chloroform) δ 8.63 (s, 1H), 8.33 (s, 1H), 7.58 (s, 1H), 7.40 (s, 1H), 7.07 (s, 1H), 6.32 (s, 1H), 5.80 (s, 1H), 5.52 (s, 1H), 4.79 (s, 1H), 4.59 (s, 1H), 3.96 (s, 1H), 3.24 (d, J=17.9 Hz, 2H), 2.36 (s, 1H), 2.15-2.08 (m, 2H), 2.08-2.04 (m, 2H), 2.00 (s, 1H), 1.74-1.68 (m, 5H), 1.68-1.60 (m, 3H), 1.60-1.50 (m, 5H), 1.33 (s, 1H), 1.13-1.01 (m, 6H).

Example 120 N—((S)-1-(((S)-4-(benzylamino)-3,4-dione-1-((S)-2-oxopyrrolidin-3-yl)but-2-yl)amino)-4-methyl-1-oxopentan-2-yl)-quinoxaline-2-carboxamide (A120)

1H NMR (500 MHz, Chloroform) δ 8.79 (s, 1H), 8.05 (s, 1H), 8.01 (s, 1H), 7.64 (d, J=1.5 Hz, 2H), 7.36-7.25 (m, 4H), 7.20 (s, 1H), 5.82 (s, 1H), 5.78 (s, 1H), 5.24 (s, 1H), 4.97 (s, 1H), 4.68 (s, 1H), 4.36 (s, 1H), 4.23 (s, 1H), 3.68 (s, 1H), 3.45 (s, 1H), 3.35 (s, 1H), 2.21 (s, 1H), 2.09-2.05 (m, 2H), 1.90 (d, J=15.7 Hz, 2H), 1.76 (s, 1H), 1.65 (s, 1H), 1.45 (s, 1H), 1.10-0.97 (m, 6H).

Example 121 N—((S)-1-(((S)-4-(tert-butylamino)-3,4-dione-1-((S)-2-oxopyrrolidin-3-yl)but-2-yl)amino)-3-cyclohexyl-1-oxopentan-2-yl)-quinoxaline-2-carboxamide (A121)

1H NMR (500 MHz, Chloroform) δ 9.24 (s, 1H), 8.11 (d, J=7.7 Hz, 2H), 7.85 (s, 1H), 7.65 (d, J=1.9 Hz, 2H), 6.22 (s, 1H), 6.11 (s, 1H), 5.66 (s, 1H), 4.77 (s, 1H), 4.62 (s, 1H), 3.45 (s, 1H), 3.35 (s, 1H), 2.79 (s, 1H), 2.17 (s, 1H), 2.13-2.02 (m, 2H), 1.92 (s, 1H), 1.67 (d, J=2.5 Hz, 2H), 1.51 (s, 1H), 1.34-1.30 (m, 9H), 1.11-1.02 (m, 6H).

Example 122 N—((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-quinoxaline-2-carboxamide (A122)

1H NMR (500 MHz, Chloroform) δ 9.29 (s, 1H), 8.09 (d, J=18.4 Hz, 2H), 7.60 (d, J=2.0 Hz, 2H), 6.27 (s, 1H), 6.23 (s, 1H), 5.90 (s, 1H), 5.24 (s, 1H), 4.80 (s, 1H), 4.70 (s, 1H), 3.45 (s, 1H), 3.35 (d, J=1.2 Hz, 2H), 2.58 (s, 1H), 2.18 (s, 1H), 2.11-2.03 (m, 2H), 1.93 (s, 1H), 1.86-1.71 (m, 3H), 1.71-1.60 (m, 4H), 1.55-1.46 (m, 4H), 1.44-1.39 (m, 2H), 1.09-0.96 (m, 6H).

Example 123 N—((S)-1-(((S)-4-(benzylamino)-3,4-dione-1-((S)-2-oxopiperidin-3-yl)but-2-yl)amino)-4-methyl-1-oxopentan-2-yl)-quinoxaline-2-carboxamide (A123)

1H NMR (500 MHz, Chloroform) δ 9.35 (s, 1H), 8.12 (s, 1H), 7.95 (s, 1H), 7.64 (d, J=15.8 Hz, 2H), 7.33-7.26 (m, 3H), 7.26-7.21 (m, 2H), 6.55 (s, 1H), 6.29 (s, 1H), 5.62 (d, J=10.0 Hz, 2H), 4.84 (s, 1H), 4.54 (s, 1H), 4.16 (d, J=16.2 Hz, 2H), 3.24 (d, J=17.4 Hz, 2H), 2.98 (s, 1H), 2.32 (s, 1H), 2.10-2.04 (m, 3H), 1.85 (s, 1H), 1.78 (s, 1H), 1.71 (s, 1H), 1.59 (s, 1H), 1.45 (s, 1H), 1.13-1.00 (m, 6H).

Example 124 N—((S)-1-(((S)-4-(tert-butylamino)-3,4-dione-1-((S)-2-oxopiperidin-3-yl)but-2-yl)amino)-3-cyclohexyl-1-oxopentan-2-yl)-quinoxaline-2-carboxamide (A124)

1H NMR (500 MHz, Chloroform) δ 9.23 (s, 1H), 8.12 (d, J=11.8 Hz, 2H), 7.65 (d, J=2.9 Hz, 2H), 6.31 (s, 1H), 6.08 (s, 1H), 5.70 (s, 1H), 5.63 (s, 1H), 4.89 (s, 1H), 4.62 (s, 1H), 3.24 (d, J=17.3 Hz, 2H), 2.62 (s, 1H), 2.04 (t, J=12.6 Hz, 3H), 1.80 (s, 1H), 1.76-1.69 (m, 3H), 1.51 (s, 1H), 1.40 (s, 1H), 1.33-1.29 (m, 9H), 1.12-0.99 (m, 6H).

Example 125 N—((S)-3-cyclohexyl-1-(((S)-4-(cyclohexylamino)-3,4-dione-1-((S)-2-oxopiperidin-3-yl)but-2-yl)amino)-3-cyclohexyl-1-oxopentan-2-yl)-quinoxaline-2-carboxamide (A125)

1H NMR (500 MHz, Chloroform) δ 9.32 (s, 1H), 8.97 (s, 1H), 8.11 (d, J=3.7 Hz, 2H), 7.65 (d, J=2.2 Hz, 2H), 5.73 (s, 1H), 5.60 (s, 1H), 5.56 (s, 1H), 4.72 (s, 1H), 4.51 (s, 1H), 3.31-3.20 (m, 3H), 2.59 (s, 1H), 2.08-2.00 (m, 5H), 1.81 (s, 1H), 1.69 (d, J=9.0 Hz, 2H), 1.62 (s, 1H), 1.60-1.54 (m, 3H), 1.53-1.42 (m, 3H), 1.39 (dd, J=11.3, 3.2 Hz, 4H), 1.09-0.96 (m, 6H).

Example 126 N—((S)-1-(((S)-4-(benzylamino)-3,4-dione-1-((S)-2-oxopyrrolidin-3-yl)but-2-yl)amino)-4-methyl-1-oxopentan-2-yl)-quinoline-2-carboxamide (A126)

1H NMR (500 MHz, Chloroform) δ 8.47 (s, 1H), 8.14 (s, 1H), 7.80 (s, 1H), 7.68 (s, 1H), 7.52 (s, 1H), 7.47 (s, 1H), 7.30-7.26 (m, 1H), 7.26-7.17 (m, 5H), 6.50 (s, 1H), 6.42 (s, 1H), 6.10 (s, 1H), 5.27 (s, 1H), 4.65 (d, J=5.3 Hz, 2H), 4.40 (s, 1H), 4.32 (s, 1H), 3.45 (s, 1H), 3.35 (s, 1H), 2.65 (s, 1H), 2.19 (s, 1H), 2.09-2.05 (m, 2H), 1.93 (s, 1H), 1.69 (s, 1H), 1.59 (d, J=10.7 Hz, 2H), 1.13-1.00 (m, 7H).

Example 127 N—((S)-1-(((S)-4-(tert-butylamino)-3,4-dione-1-((S)-2-oxopyrrolidin-3-yl)but-2-yl)amino)-3-cyclohexyl-1-oxopentan-2-yl)-quinoline-2-carboxamide (A127)

1H NMR (500 MHz, Chloroform) δ 8.36 (s, 1H), 8.14 (s, 1H), 7.77 (s, 1H), 7.69 (s, 1H), 7.46 (s, 1H), 7.40 (s, 1H), 6.36 (s, 1H), 6.13 (s, 1H), 6.02 (s, 1H), 5.67 (s, 1H), 4.93 (s, 1H), 4.61 (s, 1H), 3.45 (s, 1H), 3.35 (s, 1H), 2.63 (s, 1H), 2.18 (s, 1H), 2.09-2.05 (m, 2H), 1.92 (s, 1H), 1.73 (d, J=1.3 Hz, 2H), 1.52 (s, 1H), 1.33-1.29 (m, 9H), 1.09-1.03 (m, 6H).

Example 128 N—((S)-3-cyclohexyl-1-(((S)-4-(cyclohexylamino)-3,4-dione-1-((S)-2-oxopyrrolidin-3-yl)but-2-yl)amino)-3-cyclohexyl-1-oxopentan-2-yl)-quinoline-2-carboxamide (A128)

1H NMR (500 MHz, Chloroform) δ 9.46 (s, 1H), 8.44 (s, 1H), 8.17 (s, 1H), 7.80 (s, 1H), 7.71 (s, 1H), 7.47 (d, J=10.8 Hz, 2H), 5.88 (s, 1H), 5.82 (s, 1H), 5.18 (s, 1H), 4.96 (s, 1H), 4.52 (s, 1H), 3.74 (s, 1H), 3.45 (s, 1H), 3.35 (s, 1H), 2.64 (s, 1H), 2.19 (s, 1H), 2.09-2.05 (m, 2H), 1.95 (t, J=7.9 Hz, 3H), 1.71 (s, 1H), 1.57 (tt, J=16.6, 2.2 Hz, 9H), 1.44 (s, 1H), 1.11-0.98 (m, 6H).

Example 129 N—((S)-1-(((S)-4-(benzylamino)-3,4-dione-1-((S)-2-oxopiperidin-3-yl)but-2-yl)amino)-4-methyl-1-oxopentan-2-yl)-quinoline-2-carboxamide (A129)

1H NMR (500 MHz, Chloroform) δ 8.45 (s, 1H), 8.18 (s, 1H), 7.81 (s, 1H), 7.72 (s, 1H), 7.47 (d, J=14.9 Hz, 2H), 7.29-7.21 (m, 4H), 7.19 (s, 1H), 6.66 (s, 1H), 6.36 (s, 1H), 5.90 (s, 1H), 5.60 (s, 1H), 5.00 (s, 1H), 4.50 (s, 1H), 4.34 (d, J=14.6 Hz, 2H), 3.24 (d, J=16.9 Hz, 2H), 2.47 (d, J=1.9 Hz, 2H), 2.08-2.04 (m, 2H), 1.80 (s, 1H), 1.77-1.69 (m, 3H), 1.55 (s, 1H), 1.46 (s, 1H), 1.09-0.96 (m, 6H).

Example 130 N—((S)-1-(((S)-4-(tert-butylamino)-3,4-dione-1-((S)-2-oxopiperidin-3-yl)but-2-yl)amino)-3-cyclohexyl-1-oxopentan-2-yl)-quinoline-2-carboxamide (A130)

1H NMR (500 MHz, Chloroform) δ 8.45 (s, 1H), 8.17 (s, 1H), 7.81 (s, 1H), 7.71 (s, 1H), 7.48 (d, J=2.3 Hz, 2H), 5.90 (s, 1H), 5.74 (s, 1H), 5.54 (s, 1H), 5.27 (s, 1H), 5.13 (s, 1H), 4.51 (s, 1H), 3.24 (d, J=17.6 Hz, 2H), 2.61 (s, 1H), 2.08-2.04 (m, 2H), 1.89-1.64 (m, 5H), 1.48 (d, J=18.1 Hz, 2H), 1.33-1.29 (m, 9H), 1.09-0.96 (m, 6H).

Example 131 N—((S)-3-cyclohexyl-1-(((S)-4-(cyclohexylamino)-3,4-dione-1-((S)-2-oxopiperidin-3-yl)but-2-yl)amino)-3-cyclohexyl-1-oxopentan-2-yl)-quinoline-2-carboxamide (A131)

1H NMR (500 MHz, Chloroform) δ 8.45 (s, 1H), 8.17 (s, 1H), 7.81 (s, 1H), 7.71 (s, 1H), 7.49 (d, J=4.2 Hz, 2H), 6.05 (s, 1H), 5.83 (s, 1H), 5.54 (s, 1H), 5.39 (s, 1H), 5.11 (s, 1H), 4.52 (s, 1H), 3.30-3.20 (m, 3H), 2.61 (s, 1H), 2.08-2.04 (m, 2H), 2.02-1.90 (m, 2H), 1.87-1.77 (m, 3H), 1.75-1.68 (m, 5H), 1.55-1.44 (m, 5H), 1.44-1.39 (m, 2H), 1.09-0.96 (m, 6H).

Example 132 N—((S)-1-(((S)-4-(benzylamino)-3,4-dione-1-((S)-2-oxopyrrolidin-3-yl)but-2-yl)amino)-1-oxo-3-phenylpropan-2-yl)-6-chloro-3,8a-dihydro-2H-benzopyran-3-carboxamide (A132)

1H NMR (500 MHz, Chloroform) δ 7.39-7.29 (m, 2H), 7.29-7.20 (m, 7H), 7.18 (s, 1H), 6.65 (s, 1H), 6.45 (d, J=4.2 Hz, 2H), 6.24 (s, 1H), 6.13 (d, J=3.8 Hz, 2H), 6.03 (s, 1H), 5.47 (s, 1H), 4.93 (d, J=16.9 Hz, 2H), 4.66 (s, 1H), 4.42 (s, 1H), 4.33 (s, 1H), 3.66 (s, 1H), 3.45 (s, 1H), 3.40-3.30 (m, 3H), 3.18 (s, 1H), 2.96 (d, J=11.1 Hz, 2H), 2.18 (s, 1H), 2.12-2.02 (m, 2H), 1.93 (s, 1H).

Example 133 N—((S)-14 (S)-4-(tert-butylamino)-3,4-dione-14 (S)-2-oxopyrrolidin-3-yl)but-2-yl)amino)-1-oxo-3-phenylpropan-2-yl)-6-chloro-3,8a-dihydro-2H-benzopyran-3-carboxamide (A133)

1H NMR (500 MHz, Chloroform) δ 7.27-7.21 (m, 2H), 7.21-7.11 (m, 3H), 7.10 (s, 1H), 6.49 (s, 1H), 6.31 (s, 1H), 6.20 (s, 1H), 6.13 (s, 1H), 5.96 (d, J=15.6 Hz, 2H), 5.67 (s, 1H), 4.90 (s, 1H), 4.85 (s, 1H), 4.66 (s, 1H), 4.14 (s, 1H), 3.69 (s, 1H), 3.42 (d, J=26.2 Hz, 2H), 3.33 (d, J=15.0 Hz, 2H), 3.23 (s, 1H), 2.83 (s, 1H), 2.68 (s, 1H), 2.17 (s, 1H), 2.09-2.05 (m, 2H), 1.91 (s, 1H), 1.36-1.32 (m, 10H).

Example 134 N—((S)-1-(((S)-4-(cyclohexylamino)-3,4-dione-1-((S)-2-oxopyrrolidin-3-yl)but-2-yl)amino)-1-oxo-3-phenylpropan-2-yl)-6-chloro-3,8a-dihydro-2H-benzopyran-3-carboxamide (A134)

1H NMR (500 MHz, Chloroform) δ 8.76 (s, 5H), 8.45 (s, 5H), 7.29-7.23 (m, 10H), 7.16 (s, 5H), 7.14-7.05 (m, 10H), 6.44 (s, 5H), 6.29 (s, 5H), 6.03 (s, 5H), 5.93 (d, J=10.5 Hz, 10H), 5.21 (s, 5H), 5.05 (s, 5H), 4.64 (d, J=18.2 Hz, 10H), 3.67 (s, 4H), 3.48-3.46 (m, 2H), 3.43 (t, J=11.4 Hz, 14H), 3.37 (dt, J=43.5, 18.6 Hz, 29H), 3.05 (s, 5H), 2.86 (s, 5H), 2.19 (s, 5H), 2.09-2.05 (m, 10H), 1.95-1.86 (m, 15H), 1.72-1.64 (m, 15H), 1.56-1.52 (m, 9H), 1.50 (s, 6H), 1.45-1.40 (m, 10H).

Example 135 N—((S)-1-(((S)-4-(benzylamino)-3,4-dione-1-((S)-2-oxopiperidin-3-yl)but-2-yl)amino)-1-oxo-3-phenylpropan-2-yl)-6-chloro-3,8a-dihydro-2H-benzopyran-3-carboxamide (A135)

1H NMR (500 MHz, Chloroform) δ 7.82 (s, 1H), 7.30-7.22 (m, 4H), 7.21-7.07 (m, 6H), 6.48 (s, 1H), 6.29 (s, 1H), 6.16 (s, 1H), 6.09 (s, 1H), 5.96 (d, J=19.6 Hz, 2H), 5.31 (s, 1H), 4.94 (s, 1H), 4.66 (s, 1H), 4.61 (s, 1H), 4.41 (s, 1H), 4.33 (s, 1H), 3.72 (s, 1H), 3.51-3.12 (m, 5H), 3.24 (d, J=16.9 Hz, 2H), 3.24 (d, J=16.9 Hz, 2H), 2.96 (s, 1H), 2.43 (s, 1H), 2.19 (s, 1H), 2.08-2.03 (m, 2H), 1.80 (s, 1H), 1.73 (s, 1H), 1.55 (s, 1H).

Example 136 N—((S)-14 (S)-4-(tert-butylamino)-3,4-dione-14 (S)-2-oxopiperidin-3-yl)but-2-yl)amino)-1-oxo-3-phenylpropan-2-yl)-6-chloro-3,8a-dihydro-2H-benzopyran-3-carboxamide (A136)

1H NMR (500 MHz, Chloroform) δ 7.32-7.26 (m, 2H), 7.18 (s, 1H), 7.15-7.08 (m, 2H), 6.45 (s, 1H), 6.28 (s, 1H), 6.02 (s, 1H), 5.94 (d, J=3.0 Hz, 2H), 5.80 (s, 1H), 5.63 (s, 1H), 5.14 (s, 1H), 4.66 (s, 1H), 4.55 (s, 1H), 3.91 (s, 1H), 3.65 (s, 1H), 3.49-3.10 (m, 5H), 3.25 (t, J=14.8 Hz, 3H), 3.25 (t, J=14.8 Hz, 3H), 3.01 (s, 1H), 2.53 (s, 1H), 2.08-2.04 (m, 2H), 1.94 (s, 1H), 1.80 (d, J=1.0 Hz, 2H), 1.73 (s, 1H), 1.34-1.30 (m, 9H).

Example 137 N—((S)-1-(((S)-4-(cyclohexylamino)-3,4-dione-1-((S)-2-oxopiperidin-3-yl)but-2-yl) amino)-1-oxo-3-phenylpropan-2-yl)-6-chloro-3,8a-dihydro-2H-benzopyran-3-carboxamide (A137)

1H NMR (500 MHz, Chloroform) δ 7.30-7.26 (m, 1H), 7.26-7.14 (m, 4H), 6.52 (s, 1H), 6.47 (s, 1H), 6.14 (s, 1H), 6.04 (s, 1H), 5.96 (s, 1H), 5.87 (d, J=16.5 Hz, 2H), 5.02 (d, J=1.5 Hz, 2H), 4.66 (s, 1H), 4.48 (s, 1H), 3.68 (s, 1H), 3.51 (s, 1H), 3.40 (s, 1H), 3.31 (d, J=10.7 Hz, 2H), 3.24 (d, J=17.3 Hz, 2H), 3.01 (d, J=17.6 Hz, 2H), 2.12-2.04 (m, 5H), 1.96 (s, 1H), 1.82 (s, 1H), 1.75 (s, 1H), 1.71-1.64 (m, 3H), 1.56-1.52 (m, 2H), 1.48 (s, 1H), 1.45-1.40 (m, 2H).

Example 138 N—((S)-14 (S)-4-(benzylamino)-3,4-dione-1-((S)-2-oxopyrrolidin-3-yl)but-2-yl)amino)-1-oxo-3-phenylpropan-2-yl)benzene [d][1,3] dioxol-5-carboxamide (A138)

1H NMR (500 MHz, Chloroform) δ 7.52 (s, 1H), 7.43-7.23 (m, 8H), 7.23-7.19 (m, 3H), 7.16 (s, 1H), 6.92 (s, 1H), 6.04 (s, 1H), 5.92-5.88 (m, 2H), 5.21 (s, 1H), 4.83 (s, 1H), 4.75 (s, 1H), 4.44 (s, 1H), 4.38 (s, 1H), 3.45 (s, 1H), 3.36 (d, J=13.2 Hz, 2H), 2.95 (s, 1H), 2.80 (s, 1H), 2.18 (s, 1H), 2.09-2.05 (m, 2H), 1.92 (s, 1H).

Example 139 N—((S)-14 (S)-4-(tert-butylamino)-3,4-dione-14 (S)-2-oxopyrrolidin-3-yl)but-2-yl) amino)-1-oxo-3-phenylpropan-2-yl)benzene[d][1,3] dioxol-5-carboxamide (A139)

1H NMR (500 MHz, Chloroform) δ 7.48 (s, 1H), 7.32 (s, 1H), 7.29-7.23 (m, 2H), 7.23-7.14 (m, 3H), 6.91 (s, 1H), 5.95 (s, 1H), 5.92-5.88 (m, 2H), 4.76 (d, J=1.1 Hz, 2H), 4.71 (s, 1H), 3.46 (d, J=12.3 Hz, 2H), 3.35 (s, 1H), 3.08 (s, 1H), 2.99 (s, 1H), 2.19 (s, 1H), 2.09-2.05 (m, 2H), 1.93 (s, 1H), 1.40-1.36 (m, 9H).

Example 140 N—((S)-14(S)-4-(cyclohexylamino)-3,4-dione-14(S)-2-oxopyrrolidin-3-yl)but-2-yl) amino)-1-oxo-3-phenylpropan-2-yl) benzo[d][1,3] dioxol-5-carboxamide (A140)

1H NMR (500 MHz, Chloroform) δ 7.30 (dd, J=21.6, 15.7 Hz, 4H), 7.28-7.23 (m, 1H), 7.28-7.14 (m, 4H), 6.89 (s, 1H), 6.05 (s, 1H), 5.92-5.88 (m, 2H), 5.08 (s, 1H), 4.75 (d, J=16.1 Hz, 2H), 3.59 (s, 1H), 3.45 (d, J=2.5 Hz, 2H), 3.35 (s, 1H), 3.12 (s, 1H), 2.99 (s, 1H), 2.19 (s, 1H), 2.10-2.04 (m, 4H), 1.93 (s, 1H), 1.81-1.70 (m, 3H), 1.58-1.54 (m, 2H), 1.51 (s, 1H), 1.47-1.42 (m, 2H).

Example 141 N—((S)-1-(((S)-4-(benzylamino)-3,4-dione-1-((S)-2-oxopiperidin-3-yl)but-2-yl) amino)-1-oxo-3-phenylpropan-2-yl) benzo[d][1,3] dioxol-5-carboxamide (A141)

1H NMR (500 MHz, Chloroform) δ 7.41 (s, 1H), 7.36 (s, 1H), 10.00-7.08 (m, 14H), 6.54 (s, 1H), 6.07 (s, 1H), 5.92-5.88 (m, 2H), 5.10 (s, 1H), 4.42 (s, 1H), 4.37 (d, J=6.5 Hz, 2H), 4.30 (s, 1H), 3.60 (s, 1H), 3.25 (t, J=13.9 Hz, 3H), 3.03 (s, 1H), 2.73 (s, 1H), 2.09-2.03 (m, 2H), 1.79 (d, J=5.2 Hz, 2H), 1.73 (s, 1H), 1.57 (s, 1H).

Example 142 N—((S)-1-(((S)-4-(tert-butylamino)-3,4-dione-14(S)-2-oxopiperidin-3-yl)but-2-yl) amino)-1-oxo-3-phenylpropan-2-yl) benzo[d][1,3] dioxol-5-carboxamide (A142)

1H NMR (500 MHz, Chloroform) δ 8.38 (s, 28H), 7.44 (s, 29H), 7.30-7.23 (m, 86H), 7.23-7.15 (m, 82H), 7.15 (d, J=1.8 Hz, 4H), 6.98 (s, 29H), 5.92-5.85 (m, 85H), 5.21 (s, 28H), 5.00 (s, 27H), 4.81 (s, 28H), 4.66 (s, 28H), 3.26 (t, J=21.5 Hz, 87H), 2.91 (s, 30H), 2.78 (s, 26H), 2.21 (s, 20H), 2.11-2.02 (m, 61H), 2.00 (s, 21H), 1.83 (s, 25H), 1.77 (s, 21H), 1.32-1.28 (m, 251H).

Example 143 N—((S)-1-(((S)-4-(cyclohexylamino)-3, 4-dione-14(S)-2-oxopiperidin-3-yl)but-2-yl) amino)-1-oxo-3-phenylpropan-2-yl) benzo[d][1,3] dioxol-5-carboxamide (A143)

1H NMR (500 MHz, Chloroform) δ 8.29 (s, 1H), 7.48 (s, 1H), 7.38 (s, 1H), 7.28-7.23 (m, 2H), 7.23-7.11 (m, 3H), 6.94 (s, 1H), 6.09 (s, 1H), 5.92-5.88 (m, 2H), 5.06 (s, 1H), 4.91 (s, 1H), 4.73 (s, 1H), 4.38 (s, 1H), 3.36 (s, 1H), 3.31-3.20 (m, 3H), 3.07 (s, 1H), 2.85 (s, 1H), 2.08-2.03 (m, 4H), 1.88 (s, 1H), 1.81 (s, 1H), 1.78-1.69 (m, 3H), 1.67 (s, 1H), 1.58 (s, 1H), 1.51 (t, J=7.6 Hz, 3H), 1.43-1.39 (m, 2H).

Example 144 N—((S)-1-(((S)-4-(cyclohexylamino)-3, 4-dione-14(S)-2-oxopiperidin-3-yl)but-2-yl) amino)-1-oxo-3-phenylpropan-2-yl) benzo[d][1,3] dioxol-5-carboxamide (A144)

1H NMR (500 MHz, Chloroform) δ 8.29 (s, 1H), 7.48 (s, 1H), 7.38 (s, 1H), 7.28-7.23 (m, 2H), 7.23-7.11 (m, 3H), 6.94 (s, 1H), 6.09 (s, 1H), 5.92-5.88 (m, 2H), 5.06 (s, 1H), 4.91 (s, 1H), 4.73 (s, 1H), 4.38 (s, 1H), 3.36 (s, 1H), 3.31-3.20 (m, 3H), 3.07 (s, 1H), 2.85 (s, 1H), 2.08-2.03 (m, 4H), 1.88 (s, 1H), 1.81 (s, 1H), 1.78-1.69 (m, 3H), 1.67 (s, 1H), 1.58 (s, 1H), 1.51 (t, J=7.6 Hz, 3H), 1.43-1.39 (m, 2H).

Example 145 N—((S)-1-(((S)-4-(tert-butylamino)-3,4-dione-1-((S)-2-oxopyrrolidin-3-yl)but-2-yl) amino)-1-oxo-3-phenylpropan-2-yl)-5-fluoro nicotinamide (A145)

1H NMR (500 MHz, Chloroform) δ 8.60 (d, J=2.3 Hz, 2H), 7.83 (s, 1H), 7.23 (d, J=6.4 Hz, 1H), 7.22-7.08 (m, 5H), 5.97 (s, 1H), 5.48 (s, 1H), 4.88 (s, 1H), 4.38 (s, 1H), 4.01 (s, 1H), 3.45 (s, 1H), 3.35 (s, 1H), 3.26 (s, 1H), 2.96 (s, 1H), 2.69 (s, 1H), 2.40 (s, 1H), 2.16 (s, 1H), 2.09-2.05 (m, 2H), 1.92 (s, 1H), 1.32-1.28 (m, 10H).

Example 146 N—((S)-1-(((S)-4-(cyclohexylamino)-3,4-dione-1-((S)-2-oxopyrrolidin-3-yl)but-2-yl) amino)-1-oxo-3-phenylpropan-2-yl)-5-fluoro nicotinamide (A146)

1H NMR (500 MHz, Chloroform) δ 8.82 (s, 1H), 8.50 (s, 1H), 7.89 (s, 1H), 7.31-7.24 (m, 4H), 7.17 (s, 1H), 6.22 (s, 1H), 5.95 (s, 1H), 5.47 (s, 1H), 5.14 (s, 1H), 4.38 (s, 1H), 3.45 (s, 1H), 3.37 (d, J=16.6 Hz, 2H), 3.29 (s, 1H), 2.86 (s, 1H), 2.47 (s, 1H), 2.19 (s, 1H), 2.09-2.05 (m, 2H), 1.93 (s, 1H), 1.91-1.79 (m, 2H), 1.70 (s, 1H), 1.58-1.51 (m, 4H), 1.50 (s, 1H), 1.45-1.40 (m, 2H).

Example 147 N—((S)-1-(((S)-4-(benzylamino)-3,4-dione-1-((S)-2-oxopiperidin-3-yl)but-2-yl)amino)-1-oxo-3-phenylpropan-2-yl)-5-fluoro nicotinamide (A147)

1H NMR (500 MHz, Chloroform) δ 8.80 (s, 1H), 8.58 (s, 1H), 7.99 (s, 1H), 7.41-7.32 (m, 2H), 7.32-7.18 (m, 6H), 7.16 (s, 1H), 7.09 (s, 1H), 6.51 (s, 1H), 6.23 (s, 1H), 5.85 (s, 1H), 4.87 (s, 1H), 4.36 (s, 1H), 4.30 (d, J=5.9 Hz, 2H), 3.24 (d, J=15.2 Hz, 2H), 3.09 (s, 1H), 2.82 (s, 1H), 2.57 (s, 1H), 2.08-2.04 (m, 2H), 1.98 (s, 1H), 1.82 (s, 1H), 1.76 (s, 1H), 1.65 (s, 1H).

Example 148 N—((S)-1-(((S)-4-(tert-butylamino)-3,4-dione-1-((S)-2-oxopiperidin-3-yl)but-2-yl)amino)-1-oxo-3-phenylpropan-2-yl)-5-fluoro nicotinamide (A148)

1H NMR (500 MHz, Chloroform) δ 8.82 (s, 1H), 8.52 (s, 1H), 8.05 (s, 1H), 7.30-7.22 (m, 4H), 7.15 (s, 1H), 6.03 (s, 1H), 5.79 (s, 1H), 5.01 (s, 1H), 4.84 (s, 1H), 4.27 (s, 1H), 3.36 (s, 1H), 3.24 (d, J=14.9 Hz, 2H), 2.95 (s, 1H), 2.72 (s, 1H), 2.07 (t, J=5.5 Hz, 3H), 1.85 (s, 1H), 1.78 (s, 1H), 1.70 (s, 1H), 1.32-1.28 (m, 9H).

Example 149 N—((S)-1-(((S)-4-(cyclohexylamino)-3,4-dione-1-((S)-2-oxopiperidin-3-yl)but-2-yl)amino)-1-oxo-3-phenylpropan-2-yl)-5-fluoronicotinamide (A149)

1H NMR (500 MHz, Chloroform) δ 8.86 (s, 7H), 8.52 (s, 7H), 7.93 (s, 7H), 7.42 (s, 7H), 7.24-7.19 (m, 14H), 7.14 (s, 7H), 7.12-7.04 (m, 14H), 6.15 (d, J=16.5 Hz, 14H), 5.79 (s, 7H), 4.89 (s, 7H), 4.62 (s, 7H), 3.87 (s, 7H), 3.27 (t, J=22.0 Hz, 22H), 3.17 (t, J=12.5 Hz, 1H), 3.11 (d, J=17.0 Hz, 14H), 2.12 (s, 5H), 2.10-2.01 (m, 16H), 2.01-1.94 (m, 14H), 1.87 (s, 5H), 1.80 (s, 5H), 1.67-1.58 (m, 67H).

Example 150 N—((S)-1-(((S)-4-(benzylamino)-3,4-dione-1-((S)-2-oxopyrrolidin-3-yl)but-2-yl)amino)-1-oxo-3-phenylpropan-2-yl)-1-methyl-1H-pyrazole-4-carboxamide (A150)

1H NMR (500 MHz, Chloroform) δ 7.52 (s, 5H), 7.32-7.14 (m, 55H), 7.13 (t, J=1.5 Hz, 1H), 7.07 (s, 5H), 6.09 (s, 5H), 6.01 (s, 5H), 5.64 (s, 5H), 5.02 (s, 5H), 4.84 (s, 5H), 4.36 (s, 5H), 4.29 (s, 5H), 3.89-3.85 (m, 15H), 3.45 (s, 5H), 3.35 (s, 4H), 3.17 (s, 4H), 3.11 (s, 5H), 2.93 (s, 5H), 2.19 (s, 4H), 2.10-2.04 (m, 10H), 1.92 (s, 4H).

Example 151 N—((S)-1-(((S)-4-(tert-butylamino)-3,4-dione-1-((S)-2-oxopyrrolidin-3-yl)but-2-yl)amino)-1-oxo-3-phenylpropan-2-yl)-1-methyl-1H-pyrazole-4-carboxamide (A151)

1H NMR (500 MHz, Chloroform) δ 7.86 (s, 1H), 7.42 (s, 1H), 10.00-7.19 (m, 6H), 7.17 (s, 1H), 7.05 (s, 1H), 5.92 (d, J=15.2 Hz, 2H), 5.77 (s, 1H), 5.06 (s, 1H), 4.87 (s, 1H), 3.89-3.85 (m, 3H), 3.45 (s, 1H), 3.35 (s, 1H), 3.18 (s, 1H), 2.88 (d, J=18.2 Hz, 2H), 2.17 (s, 1H), 2.13-2.02 (m, 2H), 1.92 (s, 1H), 1.34-1.30 (m, 9H).

Example 152 N—((S)-1-(((S)-4-(cyclohexylamino)-3,4-dione-1-((S)-2-oxopyrrolidin-3-yl)but-2-yl)amino)-1-oxo-3-phenylpropan-2-yl)-1-methyl-1H-pyrazole-4-carboxamide (A152)

1H NMR (500 MHz, Chloroform) δ 7.28-7.17 (m, 5H), 7.15 (s, 1H), 7.08 (s, 1H), 6.04 (s, 1H), 5.89 (s, 1H), 4.77 (s, 1H), 4.30 (s, 1H), 4.02-3.98 (m, 3H), 3.83 (s, 1H), 3.71 (s, 1H), 3.45 (s, 1H), 3.35 (s, 1H), 3.30 (s, 1H), 3.05 (s, 1H), 2.97 (s, 1H), 2.65 (s, 1H), 2.20 (s, 1H), 2.09-2.05 (m, 2H), 2.04-2.00 (m, 1H), 1.91 (s, 1H), 1.67-1.55 (m, 7H).

Example 153 N—((S)-14(S)-4-(benzylamino)-3,4-dione-1-((S)-2-oxopiperidine-3-yl)but-2-yl)amino)-1-oxo-3-phenylpropan-2-yl)-1-methyl-1H-pyrazole-4-carboxamide (A153)

1H NMR (500 MHz, Chloroform) δ 8.58 (s, 7H), 8.29 (s, 7H), 7.42 (s, 7H), 7.32-7.24 (m, 28H), 7.18 (dt, J=57.0, 25.2 Hz, 40H), 7.08-7.07 (m, 2H), 6.51 (s, 7H), 6.01 (s, 7H), 5.10 (s, 7H), 4.81 (s, 7H), 4.38 (s, 7H), 4.32 (s, 7H), 3.93-3.89 (m, 21H), 3.30 (d, J=53.3 Hz, 17H), 3.21 (s, 3H), 3.21 (s, 6H), 2.99 (s, 7H), 2.17 (s, 6H), 2.11-2.01 (m, 14H), 1.76 (d, J=12.9 Hz, 12H), 1.68 (s, 5H), 1.42 (s, 6H).

Example 154 N—((S)-14(S)-4-(tert-butylamino)-3,4-dione-14(S)-2-oxopiperidin-3-yl)but-2-yl)amino)-1-oxo-3-phenylpropan-2-yl)-1-methyl-1H-pyrazole-4-carboxamide (A154)

1H NMR (500 MHz, Chloroform) δ 9.02 (s, 1H), 7.53 (s, 1H), 7.31-7.25 (m, 2H), 7.17 (dd, J=16.8, 9.4 Hz, 4H), 6.20 (s, 1H), 6.11 (s, 1H), 5.60 (s, 1H), 5.16 (s, 1H), 4.76 (s, 1H), 3.90-3.86 (m, 3H), 3.24 (d, J=15.4 Hz, 2H), 3.12 (s, 1H), 2.92 (d, J=17.7 Hz, 2H), 2.05 (t, J=4.4 Hz, 3H), 1.82 (s, 1H), 1.76 (s, 1H), 1.56 (s, 1H), 1.31-1.27 (m, 9H).

Example 155 N—((S)-1-(((S)-4-(cyclohexylamino)-3,4-dione-1-((S)-2-oxopiperidin-3-yl)but-2-yl)amino)-1-oxo-3-phenylpropan-2-yl)-1-methyl-1H-pyrazole-4-carboxamide (A155)

1H NMR (500 MHz, Chloroform) δ 8.38 (s, 1H), 7.28-7.22 (m, 2H), 7.22-7.11 (m, 3H), 7.04 (s, 1H), 6.62 (s, 1H), 5.99 (s, 1H), 4.76 (s, 1H), 4.62 (s, 1H), 4.30 (s, 1H), 3.83-3.79 (m, 3H), 3.26 (dd, J=17.5, 12.1 Hz, 4H), 3.05 (s, 1H), 3.01 (s, 1H), 2.72 (s, 1H), 2.20-2.13 (m, 3H), 2.09-2.03 (m, 2H), 1.86 (s, 1H), 1.80 (s, 1H), 1.72-1.66 (m, 3H), 1.56 (t, J=5.2 Hz, 3H), 1.49 (s, 1H), 1.46-1.41 (m, 2H).

Example 156 N—((S)-14(S)-4-(benzylamino)-3,4-dione-1-((S)-2-oxopyrrolidin-3-yl)but-2-yl)amino)-1-oxo-3-phenylpropan-2-yl)-6-bromo imidazo[1,2-a]pyridine-2-carboxamide (A156)

1H NMR (500 MHz, Chloroform) δ 8.45 (s, 1H), 7.77 (s, 1H), 7.68 (s, 1H), 7.58 (s, 1H), 7.40 (s, 1H), 7.32-7.26 (m, 4H), 7.26-7.11 (m, 7H), 6.00 (s, 1H), 5.04 (s, 1H), 4.92 (s, 1H), 4.77 (s, 1H), 4.38 (s, 1H), 4.30 (s, 1H), 3.45 (s, 1H), 3.35 (s, 1H), 3.27 (s, 1H), 3.11 (s, 1H), 2.85 (s, 1H), 2.19 (s, 1H), 2.09-2.05 (m, 2H), 1.92 (s, 1H).

Example 157 N—((S)-1-(((S)-4-(tert-butylamino)-3,4-dione-1-((S)-2-oxopyrrolidin-3-yl)but-2-yl)amino)-1-oxo-3-phenylpropan-2-yl)-6-bromo imidazo[1,2-a]pyridine-2-carboxamide (A157)

1H NMR (500 MHz, Chloroform) δ 8.80 (s, 1H), 8.37 (s, 1H), 7.69 (d, J=2.2 Hz, 2H), 7.59 (s, 1H), 7.28-7.21 (m, 2H), 7.21-7.11 (m, 3H), 6.78 (s, 1H), 5.98 (s, 1H), 5.45 (s, 1H), 4.93 (s, 1H), 4.66 (s, 1H), 3.45 (s, 1H), 3.35 (s, 1H), 3.22 (s, 1H), 2.96 (d, J=29.5 Hz, 2H), 2.19 (s, 1H), 2.09-2.05 (m, 2H), 1.92 (s, 1H), 1.34-1.30 (m, 9H).

Example 158 N—((S)-1-(((S)-4-(benzylamino)-3,4-dione-1-((S)-2-oxopiperidin-3-yl)but-2-yl)amino)-1-oxo-3-phenylpropan-2-yl)-6-bromo imidazo[1,2-a]pyridine-2-carboxamide (A158)

1H NMR (500 MHz, Chloroform) δ 8.39 (s, 1H), 7.69 (d, J=16.1 Hz, 2H), 7.60 (s, 1H), 7.36-7.20 (m, 9H), 7.19 (d, J=13.6 Hz, 2H), 6.50 (s, 1H), 6.28 (s, 1H), 6.16 (s, 1H), 6.10 (s, 1H), 4.75 (d, J=4.7 Hz, 2H), 4.39 (s, 1H), 4.30 (s, 1H), 3.24 (t, J=8.9 Hz, 3H), 3.01 (s, 1H), 2.72 (s, 1H), 2.11-2.01 (m, 2H), 1.84 (s, 1H), 1.80 (s, 1H), 1.73 (s, 1H), 1.36 (s, 1H).

Example 159 N—((S)-1-(((S)-4-(tert-butylamino)-3,4-dione-1-((S)-2-oxopiperidin-3-yl)but-2-yl)amino)-1-oxo-3-phenylpropan-2-yl)-6-bromo imidazo[1,2-a]pyridine-2-carboxamide (A159)

1H NMR (500 MHz, Chloroform) δ 8.41 (s, 1H), 8.18 (s, 1H), 7.79-7.57 (m, 3H), 7.27-7.21 (m, 2H), 7.21-7.10 (m, 3H), 6.09 (s, 1H), 5.52 (s, 1H), 5.08 (s, 1H), 4.74 (s, 1H), 4.45 (s, 1H), 3.25 (t, J=9.9 Hz, 3H), 3.01 (s, 1H), 2.85 (s, 1H), 2.10-2.02 (m, 2H), 1.88 (s, 1H), 1.81 (s, 1H), 1.68 (s, 1H), 1.60 (s, 1H), 1.35-1.31 (m, 9H).

Example 160 N—((S)-14(S)-4-(cyclohexylamino)-3,4-dione-14(S)-2-oxopiperidin-3-yl)but-2-yl)amino)-1-oxo-3-phenylpropan-2-yl)-6-bromo imidazo[1,2-a]pyridine-2-carboxamide (A160)

1H NMR (500 MHz, Chloroform) δ 9.87 (s, 1H), 8.26 (s, 1H), 7.68 (s, 1H), 7.57 (d, J=11.2 Hz, 2H), 7.27-7.21 (m, 2H), 7.21-7.10 (m, 3H), 6.07 (s, 1H), 4.94 (s, 1H), 4.78 (s, 1H), 4.51 (s, 1H), 3.54 (s, 1H), 3.45 (s, 1H), 3.24 (d, J=16.2 Hz, 2H), 3.17 (s, 1H), 2.97 (s, 1H), 2.92 (s, 1H), 2.28 (s, 1H), 2.09-2.04 (m, 4H), 1.81 (s, 1H), 1.74 (s, 1H), 1.70 (s, 1H), 1.59-1.52 (m, 4H), 1.49 (d, J=1.6 Hz, 2H), 1.47-1.41 (m, 2H).

Example 161 N—((S)-1-(((S)-4-(phenylamino)-3,4-dione-1-((S)-2-oxopyrrolidin-3-yl)but-2-yl)amino)-1-oxo-3-phenylpropan-2-yl)-1H-benzo[d]imidazole-2-carboxamide (A161)

1H NMR (500 MHz, Chloroform) δ 7.62 (d, J=18.9 Hz, 2H), 7.34-7.23 (m, 9H), 7.23-7.12 (m, 3H), 6.92 (s, 1H), 6.17 (s, 1H), 5.35 (s, 1H), 5.03 (s, 1H), 4.70 (d, J=4.7 Hz, 2H), 4.38 (s, 1H), 4.33 (s, 1H), 4.03 (s, 1H), 3.35 (s, 1H), 3.27 (s, 1H), 3.04 (s, 1H), 2.82 (s, 1H), 2.17 (s, 1H), 2.12-2.03 (m, 2H), 1.93 (s, 1H).

Example 162 N—((S)-1-(((S)-4-(tert-butylamino)-3,4-dione-1-((S)-2-oxopyrrolidin-3-yl)but-2-yl)amino)-1-oxo-3-phenylpropan-2-yl)-1H-benzo[d]imidazole-2-carboxamide (A162)

1H NMR (500 MHz, Chloroform) δ 7.68 (s, 1H), 7.59 (s, 1H), 7.30-7.25 (m, 2H), 7.22-7.16 (m, 2H), 7.16-7.06 (m, 3H), 6.17 (s, 1H), 5.89 (s, 1H), 5.84 (s, 1H), 5.11 (s, 1H), 4.98 (s, 1H), 3.45 (s, 1H), 3.35 (s, 1H), 3.25 (s, 1H), 3.04 (s, 1H), 2.28 (s, 1H), 2.19 (s, 1H), 2.11-2.03 (m, 2H), 1.92 (s, 1H), 1.35-1.31 (m, 9H).

Example 163 N—((S)-1-(((S)-4-(cyclohexylamino)-3,4-dione-1-((S)-2-oxopyrrolidin-3-yl)but-2-yl)amino)-1-oxo-3-phenylpropan-2-yl)-1H-benzo[d]imidazole-2-carboxamide (A163)

1H NMR (500 MHz, Chloroform) δ 7.70 (s, 1H), 7.57 (d, J=4.5 Hz, 2H), 7.22 (dd, J=17.6, 7.1 Hz, 4H), 7.18-7.07 (m, 3H), 5.97 (s, 1H), 5.74 (s, 1H), 5.03 (s, 1H), 4.50 (d, J=11.0 Hz, 2H), 4.41 (s, 1H), 3.61 (s, 1H), 3.45 (s, 1H), 3.35 (s, 1H), 3.21 (s, 1H), 3.03 (s, 1H), 2.80 (s, 1H), 2.17 (s, 1H), 2.09-2.05 (m, 2H), 1.93-1.78 (m, 3H), 1.71 (s, 1H), 1.64-1.60 (m, 2H), 1.58-1.54 (m, 2H), 1.50 (s, 1H), 1.48-1.42 (m, 2H).

Example 164 N—((S)-14(S)-4-(phenylamino)-3,4-dione-1-((S)-2-oxopiperidin-3-yl)but-2-yl)amino)-1-oxo-3-phenylpropan-2-yl)-1H-benzo[d]imidazole-2-carboxamide (A164)

1H NMR (500 MHz, Chloroform) δ 7.73 (s, 1H), 7.67 (s, 1H), 7.38 (t, J=17.9 Hz, 3H), 7.27-7.13 (m, 9H), 7.11 (s, 1H), 6.99 (s, 1H), 6.45 (s, 1H), 5.48 (s, 1H), 4.94 (d, J=7.2 Hz, 2H), 4.89 (s, 1H), 4.32 (s, 1H), 4.26 (s, 1H), 3.42 (s, 1H), 3.24 (d, J=18.2 Hz, 2H), 3.06 (s, 1H), 2.92 (s, 1H), 2.13 (s, 1H), 2.11-2.00 (m, 2H), 1.92 (s, 1H), 1.86 (s, 1H), 1.79 (s, 1H).

Example 165 N—((S)-1-(((S)-4-(tert-butylamino)-3,4-dione-1-((S)-2-oxopiperidin-3-yl)but-2-yl)amino)-1-oxo-3-phenylpropan-2-yl)-1H-benzo[d]imidazole-2-carboxamide (A165)

1H NMR (500 MHz, Chloroform) δ 9.34 (s, 4H), 7.98 (s, 4H), 7.79 (s, 4H), 7.62 (s, 4H), 7.54 (s, 4H), 7.42-7.28 (m, 23H), 7.28-7.26 (m, 2H), 7.16 (s, 4H), 5.87 (s, 4H), 5.43 (s, 4H), 5.16 (s, 4H), 4.27 (s, 4H), 3.33-3.20 (m, 12H), 2.94 (s, 4H), 2.82 (s, 4H), 2.08-2.04 (m, 8H), 1.96 (s, 3H), 1.82 (s, 3H), 1.76 (s, 3H), 1.63 (s, 3H), 1.33-1.29 (m, 36H).

Example 166 N—((S)-1-(((S)-4-(cyclohexylamino)-3,4-dione-1-((S)-2-oxopiperidin-3-yl)but-2-yl)amino)-1-oxo-3-phenylpropan-2-yl)-1H-benzo[d]imidazole-2-carboxamide (A166)

1H NMR (500 MHz, Chloroform) δ 8.45 (s, 1H), 8.24 (s, 1H), 7.65 (s, 1H), 7.60 (s, 1H), 7.53 (s, 1H), 7.24 (dd, J=20.9, 2.1 Hz, 4H), 7.16-7.04 (m, 3H), 5.61 (s, 1H), 5.36 (s, 1H), 5.09 (s, 1H), 4.63 (s, 1H), 3.50 (s, 1H), 3.41 (s, 1H), 3.24 (d, J=15.7 Hz, 2H), 2.98 (s, 1H), 2.66 (s, 1H), 2.57 (s, 1H), 2.27-2.16 (m, 2H), 2.08-2.04 (m, 2H), 1.98 (s, 1H), 1.85 (s, 1H), 1.78 (s, 1H), 1.72 (s, 1H), 1.63-1.55 (m, 4H), 1.55-1.44 (m, 3H).

Example 167 N—((S)-1-(((S)-4-(benzylamino)-3,4-dione-1-((S)-2-oxopyrrolidin-3-yl)but-2-yl)amino)-1-oxo-3-phenylpropan-2-yl)-1H-indole-5-carboxamide (A167)

1H NMR (500 MHz, Chloroform) δ 9.78 (s, 1H), 8.99 (s, 1H), 8.23 (s, 1H), 7.81 (s, 1H), 7.49 (d, J=90.0 Hz, 2H), 7.40-7.38 (m, 4H), 7.30 (d, J=15.0 Hz, 5H), 7.19 (s, 34H), 7.14 (s, 4H), 7.07 (s, 1H), 6.56 (s, 1H), 6.10 (s, 1H), 5.29 (s, 1H), 5.09 (s, 1H), 4.85 (s, 1H), 4.34 (s, 2H), 3.63 (s, 21H), 3.51 (s, 1H), 3.33 (s, 1H), 3.08 (s, 1H), 2.65 (s, 1H), 2.20 (s, 1H), 2.02 (s, 1H), 1.90 (s, 1H).

Example 168 N—((S)-1-(((S)-4-(tert-butylamino)-3,4-dione-1-((S)-2-oxopyrrolidin-3-yl)but-2-yl)amino)-1-oxo-3-phenylpropan-2-yl)-1H-indole-5-carboxamide (A168)

1H NMR (500 MHz, Chloroform) δ 8.95 (s, 1H), 8.26 (d, J=60.3 Hz, 2H), 7.78 (s, 1H), 7.55 (s, 1H), 7.31-7.18 (m, 4H), 7.16 (s, 1H), 7.31-6.84 (m, 7H), 6.55 (d, J=16.4 Hz, 2H), 5.97 (s, 1H), 5.15 (s, 1H), 4.79 (s, 1H), 3.63 (s, 1H), 3.51 (s, 1H), 3.32 (s, 1H), 3.07 (s, 1H), 2.54 (s, 1H), 2.21 (s, 1H), 2.02 (s, 1H), 1.91 (s, 1H), 1.26 (s, 9H).

Example 169 N—((S)-1-(((S)-4-(cyclohexylamino)-3,4-dione-1-((S)-2-oxopyrrolidin-3-yl)but-2-yl)amino)-1-oxo-3-phenylpropan-2-yl)-1H-indole-5-carboxamide (A169)

1H NMR (500 MHz, Chloroform) δ 8.98 (s, 13H), 8.34 (s, 13H), 8.22 (s, 14H), 7.80 (s, 13H), 7.57 (s, 14H), 7.37-7.20 (m, 2H), 7.18 (s, 14H), 7.37-6.87 (m, 82H), 6.56 (s, 13H), 6.49 (s, 13H), 5.99 (s, 13H), 5.17 (s, 7H), 4.95 (s, 5H), 4.79 (s, 7H), 3.64 (s, 6H), 3.52 (s, 6H), 3.33 (s, 15H), 3.08 (s, 14H), 2.55 (s, 5H), 2.20 (d, J=14.4 Hz, 31H), 2.02 (s, 14H), 1.88 (d, J=38.0 Hz, 37H), 1.80 (s, 5H), 1.62 (s, 9H), 1.37 (s, 27H), 1.31 (s, 11H), 1.20 (s, 23H).

Example 170 N—((S)-1-(((S)-4-(benzylamino)-3,4-dione-1-((S)-2-oxopiperidin-3-yl)but-2-yl)amino)-1-oxo-3-phenylpropan-2-yl)-1H-indole-5-carboxamide (A170)

$^1$H NMR (500 MHz, Chloroform) δ 8.99 (s, 2H), 8.23 (s, 2H), 8.06 (s, 2H), 7.81 (s, 2H), 7.58 (s, 2H), 7.29 (d, J=15.0 Hz, 9H), 7.19 (s, 1H), 7.14 (s, 9H), 7.05 (d, J=24.0 Hz, 3H), 6.56 (s, 2H), 6.06 (s, 2H), 5.05 (s, 2H), 4.76 (s, 1H), 4.34 (s, 4H), 3.55-2.80 (m, 10H), 3.48-2.77 (m, 10H), 3.28-2.80 (m, 8H), 2.87-2.77 (m, 1H), 2.70 (s, 1H), 2.34 (s, 1H), 2.01 (s, 1H), 1.91 (d, J=2.6 Hz, 2H), 1.60 (s, 1H).

Example 171 N—((S)-1-(((S)-4-(tert-butylamino)-3,4-dione-1-((S)-2-oxopiperidin-3-yl)but-2-yl)amino)-1-oxo-3-phenylpropan-2-yl)-1H-indole-5-carboxamide (A171)

1H NMR (500 MHz, Chloroform) δ 8.99 (s, 1H), 8.23 (s, 1H), 7.91 (s, 1H), 7.81 (s, 1H), 7.58 (s, 1H), 7.26-7.21 (m, 4H), 7.19 (s, 1H), 7.26-6.88 (m, 6H), 6.57 (d, J=15.1 Hz, 2H), 6.06 (s, 1H), 5.06 (s, 1H), 4.71 (s, 1H), 3.33 (s, 1H), 3.21 (d, J=15.0 Hz, 2H), 3.08 (s, 1H), 2.93 (s, 1H), 2.43 (s, 1H), 2.39 (s, 1H), 2.01 (s, 1H), 1.91 (d, J=1.1 Hz, 1H), 1.58 (s, 13H), 1.27 (s, 9H).

Example 172 N—((S)-1-(((S)-4-(cyclohexylamino)-3,4-dione-1-((S)-2-oxopiperidin-3-yl)but-2-yl)amino)-1-oxo-3-phenylpropan-2-yl)-1H-indole-5-carboxamide (A172)

$^1$H NMR (500 MHz, Chloroform) δ 8.99 (s, 1H), 8.23 (s, 1H), 7.81 (s, 1H), 7.68 (s, 1H), 7.58 (s, 1H), 7.26-7.21 (m, 7H), 7.19 (s, 1H), 7.26-6.88 (m, 6H), 6.53 (d, J=28.7 Hz, 2H), 6.50-6.48 (m, 5H), 6.08 (s, 1H), 5.06 (s, 1H), 4.95 (s, 1H), 4.70 (s, 1H), 3.33 (s, 1H), 3.21 (d, J=15.0 Hz, 2H), 3.08 (s, 1H), 2.94 (s, 1H), 2.44 (d, J=13.0 Hz, 2H), 2.19 (s, 2H), 2.03-1.73 (m, 5H), 1.84 (s, 3H), 1.84 (s, 2H), 1.60 (d, J=15.4 Hz, 2H), 1.37 (s, 2H), 1.31 (s, 1H), 1.20 (s, 2H).

Example 173 N—((S)-1-(((S)-4-(benzylamino)-3,4-dione-1-((S)-2-oxopyrrolidin-3-yl)but-2-yl)amino)-1-oxo-3-phenylpropan-2-yl)-5-fluoro-1H-indole-2-carboxamide (A173)

$^1$H NMR (500 MHz, Chloroform) δ 8.75 (s, 2H), 8.14 (s, 2H), 7.54 (d, J=24.9 Hz, 4H), 7.37-7.24 (m, 13H), 7.17 (s, 1H), 7.11 (d, J=10.0 Hz, 11H), 6.85 (s, 2H), 6.14 (s, 2H), 5.18 (s, 2H), 4.86 (s, 1H), 4.33 (s, 4H), 3.65 (s, 1H), 3.53 (s, 1H), 3.28 (s, 4H), 3.03 (s, 1H), 2.54 (s, 2H), 2.22 (s, 2H), 2.02 (s, 2H), 1.93 (s, 1H).

Example 174 N—((S)-14(S)-4-(tert-butylamino)-3,4-dione-14(S)-2-oxopyrrolidin-3-yl)but-2-yl)amino)-1-oxo-3-phenylpropan-2-yl)-5-fluoro-1H-indole-2-carboxamide (A174)

$^1$H NMR (500 MHz, Chloroform) δ 8.73 (s, 1H), 8.12 (s, 1H), 7.55 (d, J=25.0 Hz, 2H), 7.51 (s, 3H), 7.16 (dd, J=31.6, 6.6 Hz, 7H), 6.56 (s, 1H), 6.10 (s, 1H), 5.19 (s, 1H), 4.83 (s, 1H), 3.65 (s, 1H), 3.54 (s, 1H)), 3.29 (s, 1H), 3.04 (s, 1H), 2.58 (s, 1H), 2.22 (s, 1H), 2.02 (s, 1H), 1.92 (s, 5H), 1.27 (s, 9H).

Example 175 N—((S)-1-(((S)-4-(cyclohexylamino)-3,4-dione-1-((S)-2-oxopyrrolidin-3-yl)but-2-yl)amino)-1-oxo-3-phenylpropan-2-yl)-5-fluoro-1H-indole-2-carboxamide (A175)

1H NMR (500 MHz, Chloroform) δ 8.74 (s, 1H), 8.08 (s, 1H), 7.55 (d, J=25.0 Hz, 2H), 7.51 (s, 3H), 7.19 (d, J=2.2 Hz, 2H), 7.13 (d, J=10.0 Hz, 5H), 6.44 (s, 1H), 6.11 (s, 1H), 5.19 (s, 1H), 4.83 (s, 1H), 3.67 (d, J=15.7 Hz, 1H), 3.54 (s, 1H), 3.29 (s, 1H), 3.04 (s, 1H), 2.58 (s, 1H), 2.22 (s, 1H), 2.02 (s, 1H), 1.92 (s, 1H), 1.74 (s, 1H), 1.46 (t, J=12.5 Hz, 3H), 1.21 (s, 1H), 1.11 (s, 1H).

Example 176 N—((S)-1-(((S)-4-(benzylamino)-3,4-dione-1-((S)-2-oxopiperidin-3-yl)but-2-yl)amino)-1-oxo-3-phenylpropan-2-yl)-5-fluoro-1H-indole-2-carboxamide (A176)

$^1$H NMR (500 MHz, Chloroform) δ 8.71 (s, 2H), 8.61 (s, 2H), 7.69 (s, 2H), 7.58 (s, 2H), 7.53 (s, 1H), 7.33-7.20 (m, 12H), 7.19 (s, 1H), 7.13 (d, J=10.0 Hz, 10H), 5.84 (s, 2H), 5.09 (s, 1H), 4.57 (s, 1H), 4.34 (s, 4H), 3.29 (s, 1H), 3.21 (d, J=15.0 Hz, 4H), 3.04 (s, 2H), 2.73 (s, 1H), 2.41 (s, 1H), 2.28 (s, 1H), 2.01 (s, 1H), 1.91 (d, J=4.5 Hz, 2H), 1.53 (s, 1H).

Example 177 N—((S)-1-(((S)-4-(tert-butylamino)-3,4-dione-1-((S)-2-oxopiperidin-3-yl)but-2-yl)amino)-1-oxo-3-phenylpropan-2-yl)-5-fluoro-1H-indole-2-carboxamide (A177)

$^1$H NMR (500 MHz, Chloroform) δ 8.68 (s, 1H), 8.29 (s, 1H), 7.54 (d, J=25.0 Hz, 2H), 7.49 (s, 3H), 7.24 (s, 1H), 7.17 (s, 1H), 7.11 (d, J=10.0 Hz, 5H), 6.61 (s, 1H), 5.90 (s, 1H), 5.05 (s, 1H), 4.68 (s, 1H), 3.28 (s, 1H), 3.22 (s, 1H), 3.11 (d, J=77.9 Hz, 2H), 2.85 (s, 1H), 2.33 (s, 1H), 2.13 (s, 1H), 2.01 (s, 1H), 1.89 (d, J=13.2 Hz, 11H), 1.53 (s, 5H), 1.27 (s, 9H).

Example 178 N—((S)-1-(((S)-4-(cyclohexylamino)-3,4-dione-1-((S)-2-oxopiperidin-3-yl)but-2-yl)amino)-1-oxo-3-phenylpropan-2-yl)-5-fluoro-1H-indole-2-carboxamide (A178)

$^1$H NMR (500 MHz, Chloroform) δ 8.69 (s, 1H), 8.21 (s, 1H), 7.58 (s, 1H), 7.53 (s, 1H), 7.23 (s, 1H), 7.19 (s, 1H), 7.13 (d, J=10.0 Hz, 5H), 6.53 (s, 1H), 5.93 (s, 1H), 5.07 (s, 1H), 4.95 (s, 1H), 4.67 (s, 1H), 3.29 (s, 1H), 3.25-2.88 (m, 3H), 2.85 (s, 1H), 2.36 (s, 1H), 2.17 (d, J=18.2 Hz, 3H), 2.01 (s, 1H), 1.90 (d, J=11.3 Hz, 1H), 1.84 (s, 2H), 1.62 (s, 1H), 1.53 (s, 1H), 1.37 (s, 2H), 1.31 (s, 1H), 1.20 (s, 2H).

Example 179 N—((S)-14(S)-4-(benzylamino)-3,4-dione-1-((S)-2-oxopyrrolidin-3-yl)but-2-yl)amino)-1-oxo-3-phenylpropan-2-yl)-6-fluoro-1H-indole-2-carboxamide (A179)

$^1$H NMR (500 MHz, Chloroform) δ 8.73 (s, 1H), 8.13 (s, 1H), 7.95 (s, 1H), 7.32-7.18 (m, 7H), 7.08 (d, J=49.9 Hz, 6H), 7.03 (s, 1H), 7.03 (s, 1H), 6.74 (s, 1H), 6.16 (s, 1H), 5.20 (s, 1H), 4.86 (s, 1H), 4.33 (s, 2H), 3.66 (s, 1H), 3.54 (s, 1H), 3.16 (d, J=124.8 Hz, 2H), 3.01 (d, J=6.4 Hz, 1H), 2.57 (s, 1H), 2.22 (s, 1H), 2.02 (s, 1H), 1.93 (s, 1H).

Example 180 N—((S)-1-(((S)-4-(tert-butylamino)-3,4-dione-1-((S)-2-oxopyrrolidin-3-yl)but-2-yl)amino)-1-oxo-3-phenylpropan-2-yl)-6-fluoro-1H-indole-2-carboxamide (A180)

$^1$H NMR (500 MHz, Chloroform) δ 8.71 (s, 1H), 8.11 (s, 1H), 7.96 (s, 1H), 7.46-6.88 (m, 8H), 7.04 (s, 1H), 7.04 (s, 1H), 6.57 (s, 1H), 6.10 (s, 1H), 5.19 (s, 1H), 4.83 (s, 1H), 3.65 (s, 1H), 3.54 (s, 1H), 3.29 (s, 1H), 3.04 (s, 1H), 2.58 (s, 1H), 2.22 (s, 1H), 2.02 (s, 1H), 1.92 (s, 1H), 1.27 (s, 9H).

Example 181 N—((S)-1-(((S)-4-(cyclohexylamino)-3,4-dione-1-((S)-2-oxopyrrolidin-3-yl)but-2-yl)amino)-1-oxo-3-phenylpropan-2-yl)-6-fluoro-1H-indole-2-carboxamide (A181)

$^1$H NMR (500 MHz, Chloroform) δ 8.71 (s, 2H), 8.04 (s, 2H), 7.96 (s, 2H), 7.46-6.88 (m, 16H), 7.04 (s, 2H), 7.04 (s, 2H), 6.46 (s, 2H), 6.12 (s, 2H), 5.20 (s, 2H), 4.83 (s, 1H), 3.67 (d, J=17.5 Hz, 3H), 3.54 (s, 1H), 3.29 (s, 3H), 3.04 (s, 1H), 2.58 (s, 1H), 2.22 (s, 1H), 2.02 (s, 2H), 1.93 (s, 1H), 1.74 (s, 2H), 1.46 (t, J=12.5 Hz, 6H), 1.21 (s, 3H), 1.11 (s, 2H).

Example 182 N—((S)-1-(((S)-4-(cyclohexylamino)-3,4-dione-1-((S)-2-oxopyrrolidin-3-yl)but-2-yl)amino)-1-oxo-3-phenylpropan-2-yl)-6-fluoro-1H-indole-2-carboxamide (A182)

$^1$H NMR (500 MHz, Chloroform) δ 8.68 (s, 2H), 8.30 (s, 2H), 7.96 (s, 2H), 7.40 (s, 2H), 7.28 (t, J=11.5 Hz, 12H), 7.15 (dd, J=57.0, 32.0 Hz, 15H), 7.04 (s, 2H), 7.04 (s, 2H), 5.92 (s, 2H), 5.05 (s, 1H), 4.71 (s, 1H)), 4.34 (s, 4H), 3.29 (s, 1H), 3.21 (d, J=15.0 Hz, 4H), 3.04 (s, 2H), 2.86 (s, 1H), 2.39 (s, 1H), 2.18 (s, 1H), 2.01 (s, 1H), 1.90 (d, J=6.3 Hz, 4H), 1.54 (s, 1H).

Example 183 N—((S)-14(S)-4-(tert-butylamino)-3,4-dione-14(S)-2-oxopiperidin-3-yl)but-2-yl)amino)-1-oxo-3-phenylpropan-2-yl)-6-fluoro-1H-indole-2-carboxamide (A183)

$^1$H NMR (500 MHz, Chloroform) δ 8.68 (s, 1H), 8.30 (s, 11H), 7.96 (s, 1H), 7.45-6.97 (m, 8H), 7.04 (s, 1H), 7.04 (s, 1H), 6.62 (s, 1H), 5.92 (s, 1H), 5.06 (s, 1H), 4.69 (s, 1H), 3.29 (s, 1H), 3.21 (d, J=15.0 Hz, 2H), 3.04 (s, 1H), 2.85 (s, 1H), 2.33 (s, 1H), 2.13 (s, 1H), 2.01 (s, 1H), 1.90 (d, J=13.5 Hz, 1H), 1.53 (s, 1H), 1.27 (s, 9H).

Example 184 N—((S)-1-(((S)-4-(cyclohexylamino)-3,4-dione-1-((S)-2-oxopiperidin-3-yl)but-2-yl)amino)-1-oxo-3-phenylpropan-2-yl)-6-fluoro-1H-indole-2-carboxamide (A184)

$^1$H NMR (500 MHz, Chloroform) δ 8.67 (s, 1H), 8.20 (s, 1H), 7.96 (s, 1H), 7.45-6.89 (m, 8H), 7.14 (s, 4H), 7.09 (d, J=50.0 Hz, 5H), 7.04 (s, 1H), 6.53 (s, 1H), 5.93 (s, 1H), 5.07 (s, 1H), 4.95 (s, 1H), 4.67 (s, 1H), 3.29 (s, 1H), 3.25-2.88 (m, 3H), 2.85 (s, 1H), 2.35 (s, 1H), 2.17 (d, J=17.6 Hz, 3H), 2.01 (s, 1H), 1.90 (d, J=11.7 Hz, 1H), 1.84 (s, 1H), 1.62 (s, 1H), 1.53 (s, 1H), 1.37 (s, 2H), 1.31 (s, 1H), 1.20 (s, 2H).

Example 185 N—((S)-14(S)-4-(benzylamino)-3,4-dione-1-((S)-2-oxopyrrolidin-3-yl)but-2-yl)amino)-3-(3-fluorophenyl)-1-oxopropan-2-yl)-4,6-dichloro-1H-indole-2-carboxamide (A185)

$^1$H NMR (500 MHz, Chloroform) δ 8.92 (s, 2H), 8.83 (s, 2H), 7.84 (s, 2H), 7.49 (s, 2H), 7.33-7.26 (m, 11H), 7.22 (s, 2H), 7.02 (d, J=21.6 Hz, 6H), 6.97 (dd, J=5.6, 2.6 Hz, 1H), 6.77 (s, 2H), 6.28 (s, 2H), 5.16 (s, 2H), 4.91 (s, 1H), 4.34 (s, 4H), 3.67 (s, 1H), 3.55 (s, 1H), 3.29 (s, 3H), 3.04 (s, 1H), 2.61 (s, 1H), 2.23 (s, 2H), 2.02 (s, 2H), 1.93 (s, 1H). Example 186 N—((S)-1-(((S)-4-(tert-butylamino)-3,4-dione-1-((S)-2-oxopyrrolidin-3-yl)but-2-yl)amino)-3-(3-fluorophenyl)-1-oxopropan-2-yl)-4,6-dichloro-1H-indole-2-carboxamide (A186)

$^1$H NMR (500 MHz, Chloroform) δ 8.75 (s, 1H), 7.97 (s, 1H), 7.45 (s, 1H), 7.31-7.15 (m, 3H), 6.97 (d, J=7.1 Hz, 5H), 6.50 (s, 1H), 6.15 (s, 1H), 5.18 (s, 1H), 4.82 (s, 1H), 3.65 (s, 1H), 3.53 (s, 1H), 3.27 (s, 1H), 3.03 (s, 3H), 2.60 (s, 1H), 2.22 (s, 1H), 2.01 (s, 1H), 1.92 (s, 1H), 1.26 (s, 9H).

Example 187 N—((S)-1-(((S)-4-(cyclohexylamino)-3,4-dione-1-((S)-2-oxopyrrolidin-3-yl)but-2-yl)amino)-3-(3-fluorophenyl)-1-oxopropan-2-yl)-4,6-dichloro-1H-indole-2-carboxamide (A187)

$^1$H NMR (500 MHz, Chloroform) δ 8.79 (s, 2H), 8.00 (s, 2H), 7.48 (s, 2H), 7.31 (d, J=14.5 Hz, 4H), 7.19 (s, 2H), 7.01 (d, J=5.2 Hz, 5H), 6.40 (s, 2H), 6.18 (s, 2H), 5.20 (s, 2H), 4.85 (s, 1H), 3.68 (d, J=15.6 Hz, 3H), 3.55 (s, 1H), 3.29 (s, 1H), 3.04 (s, 3H), 2.61 (s, 2H), 2.23 (s, 1H), 2.02 (s, 2H), 1.93 (s, 1H), 1.74 (s, 2H), 1.46 (t, J=12.5 Hz, 6H), 1.21 (s, 3H), 1.11 (s, 2H).

Example 188 N—((S)-1-(((S)-4-(cyclohexylamino)-3,4-dione-1-((S)-2-oxopyrrolidin-3-yl)but-2-yl)amino)-3-(3-fluorophenyl)-1-oxopropan-2-yl)-4,6-dichloro-1H-indole-2-carboxamide (A188)

$^1$H NMR (500 MHz, Chloroform) δ 9.00 (s, 4H), 8.91 (s, 4H), 7.70 (s, 4H), 7.49 (d, J=3.7 Hz, 8H), 7.29 (dd, J=9.6, 5.4 Hz, 26H), 7.21 (s, 5H), 7.00 (d, J=5.1 Hz, 11H), 6.69 (s, 4H), 4.96 (d, J=17.8 Hz, 6H), 4.33 (s, 8H), 3.29 (s, 3H), 3.21 (d, J=15.0 Hz, 8H), 2.96 (d, J=80.6 Hz, 8H), 2.85-2.81 (m, 1H), 2.48 (s, 4H), 2.27 (s, 4H), 2.00 (d, J=2.8 Hz, 4H), 1.91 (s, 6H), 1.53 (s, 2H).

Example 189 N—((S)-14(S)-4-(tert-butylamino)-3,4-dione-14(S)-2-oxopiperidin-3-yl)but-2-yl)amino)-3-(3-fluorophenyl)-1-oxopropan-2-yl)-4,6-dichloro-1H-indole-2-carboxamide (A189)

$^1$H NMR (500 MHz, Chloroform) δ 8.57 (s, 1H), 7.45 (s, 1H), 7.32 (d, J=18.3 Hz, 2H), 7.20 (d, J=6.7 Hz, 2H), 7.04 (s, 1H), 7.00 (s, 1H), 6.57 (s, 1H), 5.75 (s, 1H), 5.11 (s, 1H), 4.79 (s, 1H), 3.29 (s, 1H), 3.21 (d, J=15.0 Hz, 2H), 3.04 (s, 1H), 2.75 (s, 1H), 2.47 (s, 1H), 2.36 (s, 1H), 2.01 (s, 1H), 1.95 (s, 1H), 1.91 (s, 1H), 1.51 (s, 1H), 1.27 (s, 9H).

Example 190 N—((S)-14(S)-4-(cyclohexylamino)-3,4-dione-14(S)-2-oxopiperidin-3-yl)but-2-yl) amino)-3-(3-fluorophenyl)-1-oxopropan-2-yl)-4,6-dichloro-1H-indole-2-carboxamide (A190)

$^{1}$H NMR (500 MHz, Chloroform) δ 8.77 (s, 1H), 7.93 (s, 1H), 7.48 (s, 41H), 7.34-7.15 (m, 3H), 7.00 (s, 1H), 6.83 (s, 2H), 6.56 (s, 1H), 6.15 (s, 1H), 5.71 (s, 1H), 5.05 (s, 2H), 4.95 (s, 2H), 4.90 (s, 1H), 3.36-3.12 (m, 4H), 3.20 (s, 1H), 3.12 (d, J=78.0 Hz, 2H), 2.32 (s, 2H), 2.31-2.17 (m, 3H), 2.03-1.86 (m, 3H), 1.84 (s, 2H), 1.62 (s, 1H), 1.49 (s, 2H), 1.37 (s, 2H), 1.31 (s, 1H), 1.20 (s, 2H).

Example 191 N—((S)-1-(((S)-4-(benzylamino)-3,4-dione-1-((S)-2-oxopyrrolidin-3-yl)but-2-yl)amino)-1-oxo-3-phenylpropan-2-yl)-5-methoxy-1H-indole-2-carboxamide (A191)

$^{1}$H NMR (500 MHz, Chloroform) δ 8.78 (s, 1H), 8.27 (s, 1H), 7.75-7.37 (m, 3H), 7.38 (s, 1H), 7.38 (s, 1H), 7.28 (d, J=15.0 Hz, 5H), 7.20-6.87 (m, 6H), 6.90 (s, 1H), 6.90 (s, 1H), 6.78 (s, 1H), 5.71 (s, 1H), 5.15 (s, 1H), 5.06 (s, 1H), 4.33 (s, 2H), 3.80 (s, 3H), 3.63 (s, 1H), 3.50 (s, 1H), 3.29 (s, 2H), 3.04 (s, 1H), 2.54 (s, 1H), 2.22 (s, 1H), 2.02 (s, 2H), 1.91 (s, 1H).

Example 192 N—((S)-1-(((S)-4-(tert-butylamino)-3,4-dione-1-((S)-2-oxopyrrolidin-3-yl)but-2-yl) amino)-1-oxo-3-phenylpropan-2-yl)-5-methoxy-1H-indole-2-carboxamide (A192)

$^{1}$H NMR (500 MHz, Chloroform) δ 8.78 (s, 1H), 8.27 (s, 1H), 7.75-7.37 (m, 3H), 7.38 (s, 1H), 7.38 (s, 1H), 7.28 (d, J=15.0 Hz, 5H), 7.20-6.87 (m, 6H), 6.90 (s, 1H), 6.90 (s, 1H), 6.78 (s, 1H), 5.71 (s, 1H), 5.15 (s, 1H), 5.06 (s, 1H), 4.33 (s, 2H), 3.80 (s, 3H), 3.63 (s, 1H), 3.50 (s, 1H), 3.29 (s, 2H), 3.04 (s, 1H), 2.54 (s, 1H), 2.22 (s, 1H), 2.02 (s, 2H), 1.91 (s, 1H), 1.27 (s, 9H).

Example 193 N—((S)-1-(((S)-4-(cyclohexylamino)-3,4-dione-1-((S)-2-oxopyrrolidin-3-yl)but-2-yl) amino)-1-oxo-3-phenylpropan-2-yl)-5-methoxy-1H-indole-2-carboxamide (A193)

$^{1}$H NMR (500 MHz, Chloroform) δ 8.68 (s, 1H), 8.12 (s, 1H), 7.59 (s, 1H), 7.45 (s, 1H), 7.16 (t, J=12.5 Hz, 6H), 6.79 (s, 1H), 6.44 (s, 1H), 6.10 (s, 1H), 5.19 (s, 1H), 4.95 (s, 1H), 4.82 (s, 2H), 3.81 (s, 3H), 3.65 (s, 1H), 3.54 (s, 1H), 3.29 (s, 1H), 3.04 (s, 1H), 2.58 (s, 2H), 2.21 (d, J=16.4 Hz, 2H), 2.02 (s, 1H), 1.88 (d, J=41.9 Hz, 3H), 1.80 (s, 1H), 1.62 (s, 2H), 1.37 (s, 2H), 1.31 (s, 1H), 1.20 (s, 2H).

Example 194 N—((S)-1-(((S)-4-(benzylamino)-3,4-dione-1-((S)-2-oxopiperidin-3-yl)but-2-yl)amino)-1-oxo-3-phenylpropan-2-yl)-5-methoxy-1H-indole-2-carboxamide (A194)

$^{1}$H NMR (500 MHz, Chloroform) δ 8.66 (s, 1H), 8.34 (s, 1H), 7.59 (s, 1H), 7.45 (s, 1H), 7.29 (d, J=15.0 Hz, 5H), 7.24-6.99 (m, 7H), 6.79 (s, 1H), 5.90 (s, 1H), 5.04 (s, 1H), 4.72 (s, 1H), 4.34 (s, 2H), 3.81 (s, 3H), 3.29 (s, 1H), 3.21 (d, J=15.0 Hz, 2H), 3.04 (s, 1H), 2.86 (s, 1H), 2.29 (s, 1H), 2.11 (s, 1H), 2.01 (s, 21H), 1.90 (d, J=11.7 Hz, 1H), 1.52 (s, 1H).

Example 195 N—((S)-1-(((S)-4-(tert-butylamino)-3,4-dione-1-((S)-2-oxopiperidin-3-yl)but-2-yl)amino)-1-oxo-3-phenylpropan-2-yl)-5-methoxy-1H-indole-2-carboxamide (A195)

$^{1}$H NMR (500 MHz, Chloroform) δ 8.46 (s, 1H), 7.57 (s, 1H), 7.43 (s, 1H), 7.17 (s, 1H), 7.12 (s, 4H), 7.00 (s, 1H), 6.92 (s, 1H), 6.77 (s, 1H), 6.49 (s, 1H), 5.75 (s, 1H), 5.20 (s, 1H), 4.67 (s, 1H), 3.80 (s, 3H), 3.28 (s, 1H), 3.20 (d, J=15.0 Hz, 2H), 3.03 (s, 1H), 2.77 (s, 1H), 2.40 (s, 1H), 2.30 (s, 1H), 2.00 (s, 1H), 1.94 (s, 41H), 1.90 (s, 1H), 1.51 (s, 1H), 1.27 (s, 9H).

Example 196 N—((S)-1-(((S)-4-(cyclohexylamino)-3,4-dione-1-((S)-2-oxopiperidin-3-yl)but-2-yl) amino)-1-oxo-3-phenylpropan-2-yl)-5-methoxy-1H-indole-2-carboxamide (A196)

$^{1}$H NMR (500 MHz, Chloroform) δ 8.61 (s, 1H), 8.10 (s, 1H), 7.59 (s, 1H), 7.45 (s, 1H), 7.19 (d, J=2.6 Hz, 2H), 7.14 (s, 4H), 6.72 (d, J=66.4 Hz, 2H), 5.95 (s, 1H), 5.05 (s, 1H), 4.95 (s, 1H), 4.71 (s, 1H), 3.81 (s, 3H), 3.29 (s, 1H), 3.21 (d, J=15.0 Hz, 2H), 3.04 (s, 1H), 2.86 (s, 1H), 2.37 (s, 61H), 2.21-2.17 (m, 2H), 2.01 (s, 1H), 1.90 (d, J=11.5 Hz, 1H), 1.84 (s, 2H), 1.62 (s, 1H), 1.54 (s, 1H), 1.37 (s, 2H), 1.31 (s, 1H), 1.20 (s, 2H).

Example 197 N—((S)-1-(((S)-4-(benzylamino)-3,4-dione-1-((S)-2-oxopyrrolidin-3-yl)but-2-yl)amino)-3-cyclopropyl-1-oxopropan-2-yl)-1H-indole-2-carboxamide (A197)

$^{1}$H NMR (500 MHz, Chloroform) δ 8.60 (s, 1H), 7.97 (s, 1H), 7.59 (s, 1H), 7.38 (s, 1H), 7.29 (d, J=15.0 Hz, 5H), 7.16 (s, 1H), 7.10 (d, J=9.2 Hz, 2H), 6.97 (s, 1H), 6.16 (s, 1H), 4.87 (s, 1H), 4.67 (s, 1H), 4.34 (s, 2H), 3.65 (s, 1H), 3.54 (s, 1H), 2.61 (s, 1H), 2.22 (s, 1H), 2.02 (s, 1H), 1.92 (s, 1H), 1.76 (s, 1H), 1.11 (s, 1H), 0.60 (s, 1H), 0.35 (s, 1H).

Example 198 N—((S)-1-(((S)-4-(tert-butylamino)-3,4-dione-1-((S)-2-oxopyrrolidin-3-yl)but-2-yl) amino)-3-cyclopropyl-1-oxopropan-2-yl)-1H-indole-2-carboxamide (A198)

$^{1}$H NMR (500 MHz, Chloroform) δ 8.59 (s, 1H), 7.98 (s, 1H), 7.61 (d, J=10.9 Hz, 2H), 7.12 (d, J=16.2 Hz, 2H), 6.98 (s, 1H), 6.56 (s, 1H), 6.12 (s, 1H), 4.81 (s, 1H), 4.67 (s, 1H), 3.65 (s, 1H), 3.54 (s, 1H), 2.59 (s, 1H), 2.22 (s, 1H), 2.02 (s, 1H), 1.92 (s, 1H), 1.76 (s, 1H), 1.27 (s, 9H), 1.11 (s, 1H), 0.58 (s, 1H), 0.33 (s, 1H).

Example 199 N—((S)-1-(((S)-4-(cyclohexylamino)-3,4-dione-1-((S)-2-oxopyrrolidin-3-yl)but-2-yl) amino)-3-cyclopropyl-1-oxopropan-2-yl)-1H-indole-2-carboxamide (A199)

$^{1}$H NMR (500 MHz, Chloroform) δ 8.65 (s, 1H), 8.25 (s, 1H), 7.98 (s, 1H), 7.60 (s, 1H), 7.12 (d, J=24.7 Hz, 2H), 7.10-7.07 (m, 1H), 6.98 (s, 1H), 6.41 (s, 1H), 6.15 (s, 1H), 4.82 (s, 1H), 4.58 (s, 1H), 3.66 (d, J=5.6 Hz, 2H), 3.54 (s, 1H), 2.59 (s, 1H), 2.23 (s, 1H), 2.02 (s, 1H), 1.93 (s, 1H), 1.75 (d, J=10.0 Hz, 3H), 1.46 (t, J=12.5 Hz, 3H), 1.21 (s, 2H), 1.11 (d, J=0.5 Hz, 2H), 0.57 (s, 21H), 0.28 (s, 1H).

Example 200 N—((S)-1-(((S)-4-(benzylamino)-3,4-dione-1-((S)-2-oxopiperidin-3-yl)but-2-yl)amino)-3-cyclopropan-1-oxopropan-2-yl)-1H-indole-2-carboxamide (A200)

$^1$H NMR (500 MHz, Chloroform) δ 8.62 (s, 1H), 8.00 (d, J=20.6 Hz, 2H), 7.60 (s, 1H), 7.30 (d, J=15.0 Hz, 5H), 7.18 (d, J=6.9 Hz, 2H), 7.10 (s, 1H), 6.98 (s, 1H), 6.09 (s, 1H), 4.85 (s, 1H), 4.33 (d, J=13.7 Hz, 3H), 3.21 (d, J=15.0 Hz, 2H), 2.91 (s, 1H), 2.62 (s, 1H), 2.54 (s, 1H), 2.01 (s, 1H), 1.92 (d, J=12.0 Hz, 1H), 1.76 (s, 2H), 1.59 (s, 1H), 1.11 (s, 1H), 0.45 (s, 1H), 0.13 (s, 1H).

Example 201 N—((S)-1-(((S)-4-(benzylamino)-3,4-dione-1-((S)-2-oxopyrrolidin-3-yl)but-2-yl)amino)-3-cyclobutyl-1-oxopropan-2-yl)-1H-indole-2-carboxamide (A201)

$^1$H NMR (500 MHz, Chloroform) δ 7.98 (s, 1H), 7.60 (s, 1H), 7.29 (d, J=15.0 Hz, 5H), 7.10 (s, 1H), 6.98 (s, 1H), 4.34 (s, 2H), 2.75 (s, 1H), 2.67 (s, 1H), 2.09 (s, 1H), 2.03 (d, J=6.8 Hz, 4H), 1.94 (s, 1H), 1.92-1.82 (m, 3H), 1.76 (s, 1H), 1.66 (d, J=10.0 Hz, 2H), 1.61 (s, 1H), 0.45 (s, 1H), Example 202 N—((S)-1-(((S)-4-(tert-butylamino)-3,4-dione-1-((S)-2-oxopyrrolidin-3-yl)but-2-yl)amino)-3-cyclobutyl-1-oxopropan-2-yl)-1H-indole-2-carboxamide (A202)

$^1$H NMR (500 MHz, Chloroform) δ 7.98 (s, 1H), 7.60 (s, 1H), 7.29 (m, 3H), 7.10 (s, 1H), 6.98 (s, 1H), 6.29 (m, 3H), 2.75 (s, 1H), 2.67 (s, 1H), 2.09 (s, 2H), 2.03 (d, J=6.8 Hz, 3H), 1.94 (s, 1H), 1.92-1.82 (m, 3H), 1.76 (s, 1H), 1.66 (d, J=10.0 Hz, 2H), 1.61 (s, 1H), 1.27 (s, 9H), 0.45 (s, 1H)

Example 203 N—((S)-1-(((S)-4-(cyclohexylamino)-3,4-dione-1-((S)-2-oxopyrrolidin-3-yl)but-2-yl)amino)-3-cyclobutyl-1-oxopropan-2-yl)-1H-indole-2-carboxamide (A203)

1H NMR (500 MHz, Chloroform) δ 7.98 (s, 1H), 7.60 (s, 1H), 7.10 (s, 1H), 6.98 (s, 1H), 4.95 (s, 1H), 2.74 (s, 1H), 2.66 (s, 1H), 2.19 (s, 2H), 2.09 (s, 1H), 2.03 (d, J=6.9 Hz, 2H), 1.94 (s, 1H), 1.86 (dd, J=18.2, 10.2 Hz, 5H), 1.76 (s, 2H), 1.64 (dd, J=22.9, 7.1 Hz, 3H), 1.37 (s, 1H), 1.31 (s, 2H), 1.20 (s, 2H), 0.45 (s, 1H)

Example 204 N—((S)-1-(((S)-4-(benzylamino)-3,4-dione-1-((S)-2-oxopiperidin-3-yl)but-2-yl)amino)-3-cyclobutyl-1-oxopropan-2-yl)-1H-indole-2-carboxamide (A204)

$^1$H NMR (500 MHz, Chloroform) δ 7.98 (s, 1H), 7.60 (s, 1H), 7.29 (d, J=15.0 Hz, 4H), 7.10 (s, 1H), 6.98 (s, 1H), 6.05 (m, 2H), 4.34 (s, 2H), 3.21 (d, J=15.0 Hz, 2H), 2.09 (s, 1H), 2.06-1.69 (m, 9H), 1.76 (s, 2H), 1.76 (s, 2H), 1.65 (s, 1H), 1.61 (s, 1H), 0.53 (s, 1H), 0.39 (s, 1H).

Example 205 N—((S)-1-(((S)-4-(tert-butylamino)-3,4-dione-1-((S)-2-oxopiperidin-3-yl)but-2-yl)amino)-3-cyclobutyl-1-oxopropan-2-yl)-1H-indole-2-carboxamide (A205)

$^1$H NMR (500 MHz, Chloroform) δ 8.62 (s, 1H), 8.00 (d, J=20.6 Hz, 2H), 7.60 (s, 1H), 7.30 (d, J=15.0 Hz, 5H), 7.18 (d, J=6.9 Hz, 2H), 7.10 (s, 1H), 6.98 (s, 1H), 6.09 (s, 1H), 4.85 (s, 1H), 4.33 (d, J=13.7 Hz, 3H), 3.21 (d, J=15.0 Hz, 2H), 2.91 (s, 1H), 2.62 (s, 1H), 2.54 (s, 1H), 2.01 (s, 1H), 1.92 (d, J=12.0 Hz, 1H), 1.76 (s, 2H), 1.59 (s, 1H), 1.27 (s, 9H), 1.11 (s, 3H), 0.45 (s, 1H), 0.13 (s, 1H).

Example 206 N—((S)-1-(((S)-4-(cyclohexylamino)-3,4-dione-1-((S)-2-oxopiperidin-3-yl)but-2-yl)amino)-3-cyclobutyl-1-oxopropan-2-yl)-1H-indole-2-carboxamide (A206)

$^1$H NMR (500 MHz, Chloroform) δ 8.62 (s, 1H), 8.00 (d, J=20.6 Hz, 2H), 7.60 (s, 1H), 7.30 (d, J=15.0 Hz, 5H), 7.18 (d, J=6.9 Hz, 2H), 7.10 (s, 1H), 6.98 (s, 1H), 6.09 (s, 1H), 4.85 (s, 1H), 4.33 (d, J=13.7 Hz, 3H), 3.21 (d, J=15.0 Hz, 2H), 2.91 (s, 1H), 2.62 (s, 1H), 2.54 (s, 1H), 2.01 (s, 1H), 1.92 (d, J=12.0 Hz, 1H), 1.76 (s, 2H), 1.59 (s, 1H), 1.11 (s, 1H), 0.45 (s, 21H), 0.13 (s, 1H).

Example 207 N—((S)-1-(((S)-4-(benzylamino)-3,4-dione-1-((S)-2-oxopyrrolidin-3-yl)but-2-yl)amino)-3-cyclopentyl-1-oxopropan-2-yl)-1H-indole-2-carboxamide (A207)

$^1$H NMR (500 MHz, Chloroform) δ 8.57 (s, 1H), 7.98 (s, 1H), 7.60 (s, 1H), 7.38 (s, 1H), 7.30 (d, J=15.0 Hz, 5H), 7.13-7.07 (m, 2H), 6.98 (d, J=4.1 Hz, 2H), 6.13 (s, 1H), 4.81 (d, J=3.3 Hz, 1H), 4.34 (s, 2H), 3.65 (s, 1H), 3.55 (s, 1H), 2.60 (s, 1H), 2.22 (s, 1H), 2.02 (s, 1H), 1.92 (s, 3H), 1.76 (s, 3H), 1.66 (d, J=4.7 Hz, 3H), 1.36 (s, 1H), 1.23 (s, 1H).

Example 208 N—((S)-1-(((S)-4-(tert-butylamino)-3,4-dione-1-((S)-2-oxopyrrolidine-3-yl)but-2-yl)amino)-3-cyclopentyl-1-oxopropan-2-yl)-1H-indole-2-carboxamide (A208)

$^1$H NMR (500 MHz, Chloroform) δ 8.60 (s, 1H), 7.98 (s, 1H), 7.77 (s, 1H), 7.60 (s, 1H), 7.11 (d, J=5.1 Hz, 82H), 6.98 (s, 1H), 6.57 (s, 1H), 6.14 (s, 1H), 4.83 (s, 1H), 4.61 (s, 1H), 3.66 (s, 1H), 3.54 (s, 1H), 2.59 (s, 1H), 2.22 (s, 1H), 2.02 (s, 1H), 1.93 (s, 1H), 1.76 (s, 3H), 1.65 (d, J=11.9 Hz, 5H), 1.34 (s, 4H), 1.26 (d, J=8.6 Hz, 9H).

Example 209 N—((S)-1-(((S)-4-(cyclohexylamino)-3,4-dione-1-((S)-2-oxopyrrolidin-3-yl)but-2-yl)amino)-3-cyclopentyl-1-oxopropan-2-yl)-1H-indole-2-carboxamide (A209)

$^1$H NMR (500 MHz, Chloroform) δ 8.54 (s, 1H), 7.98 (s, 1H), 7.60 (s, 1H), 7.28 (s, 1H), 7.08 (d, J=16.5 Hz, 2H), 6.98 (s, 1H), 6.46 (s, 1H), 6.14 (s, 1H), 4.80 (s, 1H), 4.75 (s, 1H), 3.64 (d, J=19.8 Hz, 2H), 3.54 (s, 1H), 2.59 (s, 1H), 2.22 (s, 1H), 2.02 (s, 1H), 1.93 (s, 1H), 1.75 (d, J=10.0 Hz, 6H), 1.65 (d, J=6.5 Hz, 63H), 1.46 (t, J=12.5 Hz, 4H), 1.35 (s, 3H), 1.27 (s, 1H), 1.21 (s, 2H), 1.11 (s, 1H).

Example 210 N—((S)-1-(((S)-4-(benzylamino)-3,4-dione-1-((S)-2-oxopiperidin-3-yl)but-2-yl)amino)-3-cyclopentyl-1-oxopropan-2-yl)-1H-indole-2-carboxamide (A210)

$^1$H NMR (500 MHz, Chloroform) δ 8.51 (s, 1H), 7.98 (s, 1H), 7.60 (s, 1H), 7.30 (d, J=15.0 Hz, 5H), 7.24 (s, 1H), 7.09 (d, J=13.7 Hz, 2H), 6.98 (s, 1H), 6.89 (s, 1H), 6.11 (s, 1H), 4.79 (s, 1H), 4.65 (s, 11H), 4.34 (s, 2H), 3.21 (d, J=15.0 Hz, 2H), 2.91 (s, 1H), 2.50 (d, J=13.8 Hz, 2H), 2.01 (s, 1H), 1.92 (d, J=5.3 Hz, 1H), 1.76 (s, 3H), 1.65 (d, J=5.8 Hz, 3H), 1.58 (s, 1H), 1.36 (s, 1H), 1.23 (s, 1H).

Example 211 N—((S)-1-(((S)-4-(tert-butylamino)-3,4-dione-1-((S)-2-oxopiperidin-3-yl)but-2-yl)amino)-3-cyclopentyl-1-oxopropan-2-yl)-1H-indole-2-carboxamide (A211)

$^1$H NMR (500 MHz, Chloroform) δ 8.45 (s, 1H), 7.98 (s, 1H), 7.60 (s, 1H), 7.10 (s, 1H), 7.00 (d, J=18.5 Hz, 2H), 6.89 (s, 1H), 6.53 (s, 1H), 6.10 (s, 1H), 4.78 (s, 1H), 4.65 (s, 1H), 3.21 (d, J=15.0 Hz, 2H), 2.90 (s, 1H), 2.49 (d, J=13.5 Hz, 2H), 2.01 (s, 1H), 1.91 (d, J=1.6 Hz, 1H), 1.76 (s, 3H), 1.63 (t, J=21.9 Hz, 4H), 1.55-1.52 (m, 1H), 1.37 (s, 1H), 1.27 (s, 9H), 1.22 (s, 1H).

Example 212 N—((S)-1-(((S)-4-(cyclohexylamino)-3,4-dione-1-((S)-2-oxopiperidin-3-yl)but-2-yl)amino)-3-cyclopentyl-1-oxopropan-2-yl)-1H-indole-2-carboxamide (A212)

$^1$H NMR (500 MHz, Chloroform) δ 8.45 (s, 1H), 7.98 (s, 1H), 7.60 (s, 1H), 7.10 (s, 1H), 7.00 (d, J=19.1 Hz, 42H), 6.88 (s, 1H), 6.44 (s, 1H), 6.10 (s, 1H), 4.95 (s, 1H), 4.77 (s, 1H), 4.64 (s, 1H), 3.21 (d, J=15.0 Hz, 2H), 2.90 (s, 1H), 2.49 (d, J=19.3 Hz, 2H), 2.19 (s, 2H), 2.01 (s, 1H), 1.93-1.89 (m, 1H), 1.84 (s, 2H), 1.76 (s, 3H), 1.73-1.60 (m, 6H), 1.57 (s, 1H), 1.37 (d, J=2.4 Hz, 3H), 1.31 (s, 1H), 1.21 (d, J=13.0 Hz, 2H).

Example 213 N—((S)-1-(((S)-4-(benzylamino)-3,4-dione-1-((S)-2-oxopyrrolidin-3-yl)but-2-yl)amino)-3-cyclohexyl-1-oxopropan-2-yl)-2,2-difluorobenzo[d][1,3]dioxol-5-carboxamide (A213)

$^1$H NMR (500 MHz, Chloroform) δ 7.97 (s, 1H), 7.61 (s, 1H), 7.49 (s, 1H), 7.55-7.23 (m, 6H), 7.55-6.98 (m, 8H), 6.13 (s, 1H), 4.86 (s, 1H), 4.49 (s, 1H), 4.34 (s, 2H), 3.66 (s, 1H), 3.54 (s, 1H), 2.59 (s, 1H), 2.23 (s, 1H), 2.02 (s, 1H), 1.93 (s, 1H), 1.80 (s, 3H), 1.69 (d, J=10.0 Hz, 3H), 1.31 (s, 1H), 1.26 (s, 1H), 1.11 (s, 1H), 1.03 (s, 1H).

Example 214 N—((S)-1-(((S)-4-(tert-butylamino)-3,4-dione-1-((S)-2-oxopyrrolidin-3-yl)but-2-yl)amino)-3-cyclohexyl-1-oxopropan-2-yl)-2,2-difluorobenzo[d][1,3]dioxol-5-carboxamide (A214)

$^1$H NMR (500 MHz, Chloroform) δ 7.73 (s, 1H), 7.61 (s, 1H), 7.49 (s, 1H), 7.16 (s, 1H), 6.52 (s, 1H), 6.13 (s, 1H), 4.83 (s, 1H), 4.55 (s, 1H), 3.66 (s, 1H), 3.54 (s, 1H), 2.58 (s, 1H), 2.22 (s, 1H), 2.02 (s, 1H), 1.93 (s, 1H), 1.80 (s, 2H), 1.58 (s, 1H), 1.51 (d, J=15.0 Hz, 3H), 1.48-1.41 (m, 4H), 1.28 (d, J=5.4 Hz, 9H).

Example 215 N—((S)-1-(((S)-4-(cyclohexylamino)-3,4-dione-1-((S)-2-oxopyrrolidin-3-yl)but-2-yl)amino)-3-cyclohexyl-1-oxopropan-2-yl)-2,2-difluorobenzo[d][1,3]dioxol-5-carboxamide (A215)

$^1$H NMR (500 MHz, Chloroform) δ 7.55 (d, J=60.0 Hz, 2H), 7.16 (d, J=2.8 Hz, 2H), 6.45 (s, 1H), 6.14 (s, 1H), 4.95 (s, 1H), 4.77 (s, 1H), 4.66 (s, 1H), 3.66 (s, 1H), 3.54 (s, 1H), 2.58 (s, 1H), 2.21 (d, J=17.0 Hz, 2H), 2.02 (s, 1H), 1.92 (s, 1H), 1.84 (s, 2H), 1.80 (s, 1H), 1.64 (d, J=16.1 Hz, 3H), 1.51 (d, J=15.0 Hz, 2H), 1.44 (dd, J=12.8, 7.8 Hz, 6H), 1.37 (s, 3H), 1.31 (s, 1H), 1.20 (s, 2H).

Example 216 N—((S)-1-(((S)-4-(benzylamino)-3,4-dione-1-((S)-2-oxopiperidin-3-yl)but-2-yl)amino)-3-cyclohexyl-1-oxopropan-2-yl)-2,2-difluorobenzo[d][1,3]dioxol-5-carboxamide (A216)

$^1$H NMR (500 MHz, Chloroform) δ 7.55 (d, J=60.0 Hz, 2H), 7.46-7.26 (m, 6H), 7.16 (s, 1H), 7.09 (s, 1H), 6.08 (s, 1H), 4.79 (s, 1H), 4.41 (s, 1H), 4.34 (s, 2H), 3.21 (d, J=15.0 Hz, 2H), 2.85 (s, 1H), 2.53 (d, J=12.1 Hz, 2H), 2.01 (s, 1H), 1.91 (d, J=3.6 Hz, 1H), 1.80 (s, 1H), 1.72 (s, 1H), 1.58 (s, 1H), 1.52 (d, J=15.0 Hz, 2H), 1.48-1.41 (m, 4H), 1.34 (s, 1H).

Example 217 N—((S)-1-(((S)-4-(tert-butylamino)-3,4-dione-1-((S)-2-oxopiperidin-3-yl)but-2-yl)amino)-3-cyclohexyl-1-oxopropan-2-yl)-2,2-difluorobenzo[d][1,3]dioxol-5-carboxamide (A217)

$^1$H NMR (500 MHz, Chloroform) δ 7.61 (s, 2H), 7.49 (s, 2H), 7.16 (s, 2H), 6.89 (s, 2H), 6.53 (s, 2H), 6.09 (s, 2H), 4.76 (s, 1H), 4.44 (s, 1H), 3.21 (d, J=15.0 Hz, 4H), 2.88 (s, 2H), 2.49 (d, J=3.0 Hz, 4H), 2.01 (s, 1H), 1.93-1.89 (m, 2H), 1.80 (s, 3H), 1.69 (d, J=10.0 Hz, 2H), 1.57 (s, 1H), 1.31 (d, J=4.8 Hz, 2H), 1.27 (s, 9H), 1.11 (s, 1H), 1.03 (s, 3H).

Example 218 N—((S)-1-(((S)-4-(cyclohexylamino)-3,4-dione-1-((S)-2-oxopiperidin-3-yl)but-2-yl)amino)-3-cyclohexyl-1-oxopropan-2-yl)-2,2-difluorobenzo[d][1,3]dioxol-5-carboxamide (A218)

$^1$H NMR (500 MHz, Chloroform) δ 7.58 (s, 1H), 7.46 (s, 1H), 7.13 (s, 1H), 6.47 (d, J=5.5 Hz, 2H), 5.81 (s, 1H), 4.93 (d, J=6.0 Hz, 2H), 4.37 (s, 1H), 3.34 (s, 1H), 3.20 (d, J=15.0 Hz, 2H), 2.37 (d, J=18.2 Hz, 2H), 2.18 (s, 2H), 2.00 (s, 1H), 1.90 (d, J=0.5 Hz, 1H), 1.81 (d, J=19.9 Hz, 6H), 1.69 (s, 2H), 1.64 (d, J=29.9 Hz, 3H), 1.51 (s, 1H), 1.37 (s, 3H), 1.31 (s, 2H), 1.18 (d, J=16.6 Hz, 3H), 1.11 (s, 1H), 1.03 (s, 2H).

Example 219 N—((S)-1-(((S)-4-(cyclohexylamino)-3,4-dione-1-((S)-2-oxopiperidin-3-yl)but-2-yl)amino)-3-cyclohexyl-1-oxopropan-2-yl)-2,2-difluorobenzo[d][1,3]dioxol-5-carboxamide (A219)

1H NMR (500 MHz, Chloroform) δ 7.58 (s, 1H), 7.46 (s, 1H), 7.13 (s, 1H), 6.47 (d, J=5.5 Hz, 2H), 5.81 (s, 1H), 4.93 (d, J=6.0 Hz, 2H), 4.37 (s, 1H), 3.34 (s, 1H), 3.20 (d, J=15.0 Hz, 2H), 2.37 (d, J=18.2 Hz, 2H), 2.18 (s, 2H), 2.00 (s, 1H), 1.90 (d, J=0.5 Hz, 1H), 1.81 (d, J=19.9 Hz, 6H), 1.69 (s, 2H), 1.64 (d, J=29.9 Hz, 3H), 1.51 (s, 1H), 1.37 (s, 3H), 1.31 (s, 2H), 1.18 (d, J=16.6 Hz, 3H), 1.11 (s, 1H), 1.03 (s, 2H).

Example 220 N—((S)-1-(((S)-4-(benzylamino)-3,4-dione-1-((S)-2-oxopyrrolidin-3-yl)but-2-yl)amino)-1-oxo-3-phenylpropan-2-yl)-4,6-dimethoxy-1H-indole-2-carboxamide (A220)

1H NMR (500 MHz, Chloroform) δ 9.90 (s, 1H), 8.66 (s, 1H), 8.26 (s, 1H), 7.77 (s, 1H), 7.30 (d, J=15.0 Hz, 5H), 7.23-7.03 (m, 6H), 6.71 (s, 1H), 6.26 (s, 1H), 5.98 (s, 1H), 5.15 (s, 1H), 4.87 (s, 1H), 4.34 (s, 2H), 3.79 (s, 6H), 3.64 (s, 1H), 3.52 (s, 1H), 3.29 (s, 1H), 3.04 (s, 1H), 2.52 (s, 1H), 2.22 (s, 1H), 2.02 (s, 1H), 1.92 (s, 2H).

Example 221 N—((S)-1-(((S)-4-(tert-butylamino)-3,4-dione-1-((S)-2-oxopyrrolidin-3-yl)but-2-yl)amino)-1-oxo-3-phenylpropan-2-yl)-4,6-dimethoxy-1H-indole-2-carboxamide (A221)

1H NMR (500 MHz, Chloroform) δ 8.60 (s, 1H), 8.35 (s, 1H), 7.76 (s, 1H), 7.17 (d, J=25.0 Hz, 5H), 6.69 (s, 1H), 6.58 (s, 1H), 6.23 (s, 1H), 6.00 (s, 1H), 5.18 (s, 1H), 4.81 (s, 1H), 3.79 (s, 6H), 3.64 (s, 1H), 3.53 (s, 1H), 3.29 (s, 1H), 3.04 (s, 1H), 2.55 (s, 1H), 2.22 (s, 1H), 2.02 (s, 1H), 1.92 (s, 1H), 1.27 (s, 9H).

Example 222 N—((S)-1-(((S)-4-(cyclohexylamino)-3,4-dione-1-((S)-2-oxopyrrolidin-3-yl)but-2-yl)amino)-1-oxo-3-phenylpropan-2-yl)-4,6-dimethoxy-1H-indole-2-carboxamide (A222)

1H NMR (500 MHz, Chloroform) δ 8.59 (s, 1H), 8.10 (s, 1H), 7.68 (s, 1H), 7.15 (d, J=25.0 Hz, 5H), 6.67 (s, 1H), 6.45 (s, 1H), 6.21 (s, 1H), 6.07 (s, 1H), 5.18 (s, 1H), 4.94 (s, 1H), 4.80 (s, 1H), 3.78 (s, 6H), 3.64 (s, 1H), 3.53 (s, 1H), 3.28 (s, 1H), 3.03 (s, 1H), 2.56 (s, 1H), 2.20 (d, J=16.3 Hz, 3H), 2.02 (s, 1H)), 1.88 (d, J=41.4 Hz, 3H), 1.80 (s, 1H), 1.62 (s, 1H), 1.37 (s, 2H), 1.31 (s, 1H), 1.20 (s, 2H).

Example 223 N—((S)-1-(((S)-4-(benzylamino)-3,4-dione-1-((S)-2-oxopiperidin-3-yl)but-2-yl)amino)-1-oxo-3-phenylpropan-2-yl)-4,6-dimethoxy-1H-indole-2-carboxamide (A223)

1H NMR (500 MHz, Chloroform) δ 8.65 (s, 1H), 8.29 (s, 1H), 8.02 (s, 1H), 7.27 (d, J=15.0 Hz, 5H), 7.14 (d, J=24.9 Hz, 5H), 6.92 (s, 1H), 6.59 (s, 1H), 6.20 (s, 1H), 6.08 (s, 1H), 5.01 (s, 1H), 4.76 (s, 1H), 4.33 (s, 2H), 3.78 (s, 6H), 3.28 (s, 1H), 3.20 (d, J=15.0 Hz, 2H), 3.03 (s, 1H), 2.85 (d, J=1.0 Hz, 2H), 2.32 (s, 1H), 2.00 (s, 1H), 1.90 (d, J=1.3 Hz, 1H), 1.61 (s, 1H).

Example 224 N—((S)-1-(((S)-4-(tert-butylamino)-3,4-dione-1-((S)-2-oxopiperidin-3-yl)but-2-yl)amino)-1-oxo-3-phenylpropan-2-yl)-4,6-dimethoxy-1H-indole-2-carboxamide (A224)

1H NMR (500 MHz, Chloroform) δ 8.80 (d, J=11.2 Hz, 2H), 7.09 (t, J=61.7 Hz, 6H), 6.94 (s, 1H), 6.94 (s, 1H), 6.77 (s, 1H), 6.63 (s, 1H), 6.56 (s, 1H), 5.04 (d, J=1.0 Hz, 2H), 4.99 (s, 1H), 3.79 (s, 6H), 3.29 (s, 1H), 3.21 (d, J=15.0 Hz, 3H), 2.93 (d, J=106.3 Hz, 2H), 2.79-2.70 (m, 1H), 2.40 (s, 1H), 2.27 (s, 1H), 2.01 (s, 1H), 1.92 (d, J=8.4 Hz, 1H), 1.46 (s, 1H), 1.27 (s, 9H).

Example 225 N—((S)-1-(((S)-4-(cyclohexylamino)-3,4-dione-1-((S)-2-oxopiperidin-3-yl)but-2-yl)amino)-1-oxo-3-phenylpropan-2-yl)-4,6-dimethoxy-1H-indole-2-carboxamide (A225)

1H NMR (500 MHz, Chloroform) δ 8.67 (s, 1H), 7.80 (s, 1H), 7.65 (s, 1H), 7.08 (t, J=67.3 Hz, 6H), 6.91 (s, 1H), 6.91 (s, 1H), 6.55 (s, 1H), 6.49 (s, 1H), 6.07 (s, 1H), 5.09 (s, 1H), 4.95 (s, 1H), 4.69 (s, 1H), 3.79 (s, 6H), 3.29 (s, 1H), 3.21 (d, J=15.0 Hz, 2H), 3.04 (s, 1H), 2.93 (s, 1H), 2.42 (d, J=15.8 Hz, 2H), 2.19 (s, 2H), 2.03-1.73 (m, 5H), 1.84 (s, 3H), 1.84 (s, 2H), 1.60 (d, J=16.9 Hz, 2H), 1.37 (s, 2H), 1.31 (s, 1H), 1.20 (s, 2H).

Example 226 N—((S)-1-(((S)-4-(benzylamino)-3,4-dione-1-((S)-2-oxopyrrolidin-3-yl)but-2-yl)amino)-3-(3,4-difluorophenyl)-1-oxopropan-2-yl)-1H-indole-2-carboxamide (A226)

$^1$H NMR (500 MHz, Chloroform) δ 8.76 (s, 1H), 8.12 (s, 1H), 7.98 (s, 1H), 7.89 (s, 1H), 7.60 (s, 1H), 7.29 (d, J=15.0 Hz, 5H), 7.19 (d, J=17.1 Hz, 2H), 7.10 (d, J=2.2 Hz, 2H), 6.99 (d, J=15.0 Hz, 2H), 6.31 (s, 1H), 5.05 (s, 1H), 4.91 (s, 1H), 4.34 (s, 2H), 3.67 (s, 1H), 3.56 (s, 1H), 3.29 (s, 1H), 3.04 (s, 1H), 2.70 (s, 1H), 2.23 (s, 1H), 2.02 (s, 2H), 1.93 (s, 1H).

Example 227 N—((S)-1-(((S)-4-(tert-butylamino)-3,4-dione-1-((S)-2-oxopyrrolidin-3-yl)but-2-yl)amino)-3-(3,4-difluorophenyl)-1-oxopropan-2-yl)-1H-indole-2-carboxamide (A227)

$^1$H NMR (500 MHz, Chloroform) δ 8.72 (s, 1H), 8.44 (s, 1H), 7.96 (s, 1H), 7.59 (s, 1H), 7.25 (s, 1H), 7.16 (s, 1H), 7.09 (d, J=2.1 Hz, 2H), 6.98 (d, J=15.0 Hz, 2H), 6.60 (s, 1H), 5.97 (s, 1H), 5.12 (s, 1H), 4.82 (s, 1H), 3.64 (s, 1H), 3.52 (s, 1H), 3.28 (s, 1H), 3.03 (s, 1H), 2.54 (s, 1H), 2.22 (s, 1H), 2.02 (s, 1H), 1.92 (s, 1H), 1.27 (s, 9H).

Example 228 N—((S)-1-(((S)-4-(cyclohexylamino)-3,4-dione-1-((S)-2-oxopyrrolidin-3-yl)but-2-yl)amino)-3-(3,4-difluorophenyl)-1-oxopropan-2-yl)-1H-indole-2-carboxamide (A228)

$^1$H NMR (500 MHz, Chloroform) δ 8.69 (s, 1H), 8.41 (s, 1H), 7.94 (s, 1H), 7.56 (s, 1H), 7.23 (s, 1H), 7.13 (s, 1H), 7.06 (d, J=0.9 Hz, 2H), 6.96 (d, J=14.9 Hz, 2H), 6.65 (s, 1H), 5.95 (s, 1H), 5.11 (s, 1H), 4.92 (s, 1H), 4.81 (s, 1H), 3.63 (s, 1H), 3.51 (s, 1H), 3.27 (s, 1H), 3.02 (s, 1H), 2.53 (s, 1H), 2.19 (d, J=14.6 Hz, 2H), 2.01 (s, 1H), 1.87 (d, J=40.1 Hz, 3H), 1.79 (s, 1H), 1.61 (s, 1H), 1.36 (s, 2H), 1.30 (s, 1H), 1.19 (s, 2H).

Example 229 N—((S)-1-(((S)-4-(benzylamino)-3,4-dione-1-((S)-2-oxopiperidin-3-yl)but-2-yl)amino)-3-(3,4-difluorophenyl)-1-oxopropan-2-yl)-1H-indole-2-carboxamide (A229)

$^1$H NMR (500 MHz, Chloroform) δ 8.69 (s, 1H), 8.11 (s, 1H), 7.95 (s, 1H), 7.57 (s, 1H), 7.43 (s, 1H), 7.27 (d, J=15.0 Hz, 5H), 7.14 (s, 1H), 7.07 (s, 1H), 6.97 (d, J=15.0 Hz, 2H), 6.82 (s, 1H), 6.58 (s, 1H), 6.04 (s, 1H), 5.01 (s, 21H), 4.83 (s, 1H), 4.32 (s, 2H), 3.28 (s, 1H), 3.20 (d, J=15.0 Hz, 2H), 3.03 (s, 1H), 2.89 (s, 1H), 2.70 (s, 1H), 2.25 (s, 1H), 2.00 (s, 1H), 1.90 (d, J=2.9 Hz, 1H), 1.60 (s, 1H).

Example 230 N—((S)-14(S)-4-(tert-butylamino)-3,4-dione-14(S)-2-oxopiperidin-3-yl)but-2-yl)amino)-3-(3,4-difluorophenyl)-1-oxopropan-2-yl)-1H-indole-2-carboxamide (A230)

$^1$H NMR (500 MHz, Chloroform) δ 8.74 (s, 1H), 8.06 (s, 1H), 7.98 (s, 1H), 7.60 (s, 1H), 7.17 (s, 1H), 7.11 (d, J=8.4 Hz, 2H), 7.03-6.90 (m, 3H), 6.53 (s, 1H), 5.75 (s, 1H), 5.12 (s, 1H), 4.72 (s, 1H), 3.29 (s, 1H), 3.21 (d, J=15.0 Hz, 2H), 3.04 (s, 1H), 2.75 (s, 1H), 2.43 (s, 1H), 2.33 (s, 1H), 2.01 (s, 1H), 1.96 (s, 1H), 1.91 (s, 1H), 1.52 (s, 1H), 1.27 (s, 9H).

Example 231 N—((S)-1-(((S)-4-(cyclohexylamino)-3,4-dione-1-((S)-2-oxopiperidin-3-yl)but-2-yl)amino)-3-(3,4-difluorophenyl)-1-oxopropan-2-yl)-1H-indole-2-carboxamide (A231)

$^1$H NMR (500 MHz, Chloroform) δ 8.72 (s, 1H), 7.99 (d, J=25.5 Hz, 2H), 7.59 (s, 1H), 7.16 (s, 1H), 7.09 (d, J=4.0 Hz, 2H), 6.97 (t, J=11.7 Hz, 3H), 6.45 (s, 1H), 6.07 (s, 1H), 5.09 (s, 1H), 4.94 (s, 1H), 4.68 (s, 1H), 3.28 (s, 1H), 3.21 (d, J=15.0 Hz, 2H), 3.03 (s, 1H), 2.95 (s, 1H), 2.44 (d, J=17.0 Hz, 2H), 2.19 (s, 2H), 2.03-1.73 (m, 5H), 1.84 (s, 2H), 1.84 (s, 2H), 1.60 (d, J=13.6 Hz, 2H), 1.37 (s, 2H), 1.31 (s, 1H), 1.20 (s, 2H).

Example 232 N—((S)-1-(((S)-4-(benzyl)-3,4-dione-1-(isopropylamino)-2-yl)amino)-3-(cyclohexyl)-1-oxopropan-2-yl)-1H-indole-2-carboxamide (A232)

$^1$H NMR (500 MHz, Chloroform) δ 8.57 (s, 1H), 7.94 (s, 1H), 7.57 (s, 1H), 7.40 (s, 1H), 7.26 (d, J=14.9 Hz, 4H), 7.16-7.03 (m, 3H), 6.95 (s, 1H), 6.45 (s, 1H), 5.67 (s, 1H), 4.95 (s, 1H), 4.48 (s, 1H), 4.32 (s, 2H), 3.79 (s, 1H), 2.20 (s, 1H), 2.15 (s, 1H), 2.04 (s, 2H), 1.77 (d, J=19.9 Hz, 3H), 1.68 (d, J=10.0 Hz, 4H), 1.37 (s, 1H), 1.30 (s, 1H), 1.11 (s, 1H), 1.01 (d, J=14.9 Hz, 6H).

Example 233 N—((S)-14(S)-4-(benzyl)-3,4-dione-1-(isopropylamino)-2-yl)amino)-3-(phenyl)-1-oxopropan-2-yl)-1H-indole-2-carboxamide (A233)

1H NMR (500 MHz, Chloroform) δ 8.85 (s, 1H), 8.41 (s, 1H), 7.98 (s, 1H), 7.60 (s, 1H), 7.29 (d, J=15.0 Hz, 5H), 7.20 (d, J=16.0 Hz, 2H), 7.12 (d, J=20.0 Hz, 5H), 6.98 (s, 1H), 6.69 (s, 1H), 5.05 (s, 1H), 5.01 (s, 1H), 4.74 (s, 1H), 4.34 (s, 2H), 3.81 (s, 1H), 3.29 (s, 2H), 3.04 (s, 1H), 2.21 (d, J=5.4 Hz, 2H), 2.05 (s, 2H), 1.00 (s, 6H).

Example 234 N—((S)-14(S)-4-(cyclohexyl)-3,4-dione-1-(isopropylamino)-2-yl)amino)-3-(phenyl)-1-oxopropan-2-yl)-1H-indole-2-carboxamide (A234)

1H NMR (500 MHz, Chloroform) δ 8.73 (s, 1H), 8.16 (s, 1H), 7.98 (s, 1H), 7.60 (s, 1H), 7.27 (s, 1H), 7.19 (s, 1H), 7.12 (d, J=20.0 Hz, 5H), 7.07 (s, 1H), 6.98 (s, 1H), 6.53 (s, 1H), 5.87 (s, 1H), 5.64 (s, 1H), 4.92 (s, 1H), 4.86 (s, 1H), 3.81 (s, 1H), 3.29 (s, 3H), 3.02 (d, J=18.8 Hz, 3H), 2.19 (d, J=11.4 Hz, 2H), 2.05 (s, 2H), 1.80 (s, 1H), 1.69 (d, J=10.0 Hz, 3H), 1.58 (s, 1H), 1.31 (s, 1H), 1.11 (s, 1H), 1.01 (d, J=15.0 Hz, 8H).

Example 235 N—((S)-14(S)-4-(cyclohexyl)-3,4-dione-1-(cyclohexylamino)-2-yl)amino)-3-(phenyl)-1-oxopropan-2-yl)-1H-indole-2-carboxamide (A235)

1H NMR (500 MHz, Chloroform) δ 8.73 (s, 1H), 8.14 (s, 1H), 7.98 (s, 1H), 7.60 (s, 1H), 7.26 (s, 1H), 7.19 (s, 1H), 7.12 (d, J=20.0 Hz, 5H), 6.98 (s, 1H), 6.56 (s, 1H), 5.90 (s, 1H), 5.63 (s, 1H), 4.93 (d, J=16.9 Hz, 2H), 4.86 (s, 1H), 3.29 (s, 1H), 3.02 (d, J=18.8 Hz, 3H), 2.23-2.14 (m, 4H), 2.05 (s, 2H), 1.82 (d, J=20.0 Hz, 4H), 1.69 (d, J=10.0 Hz, 3H), 1.62 (s, 1H), 1.37 (d, J=0.9 Hz, 3H), 1.31 (s, 3H), 1.20 (s, 2H), 1.11 (s, 1H), 1.03 (s, 2H).

Example 236 N—((S)-1-(((S)-4-(benzyl)-3,4-dione-1-(isopropylamino)-2-yl)amino)-3-(cyclohexyl)-1-oxopropan-2-yl)-quinoxaline-2-carboxamide (A236)

$^1$H NMR (500 MHz, Chloroform) δ 9.45 (s, 1H), 7.80 (s, 2H), 7.67 (s, 2H), 7.35-7.26 (m, 6H), 7.11 (s, 1H), 6.67 (s, 1H), 5.75 (s, 1H), 5.11 (s, 1H), 4.33 (d, J=6.4 Hz, 3H), 3.81 (s, 1H), 2.16 (d, J=10.5 Hz, 2H), 2.05 (s, 1H), 1.76 (s, 1H), 1.60 (s, 1H), 1.51 (d, J=15.0 Hz, 2H), 1.48-1.41 (m, 4H), 1.32 (s, 1H), 1.00 (s, 6H).

Example 237 N—((S)-1-(((S)-4-(cyclohexyl)-3,4-dione-1-(isopropylamino)2-yl)amino)-3-(cyclohexyl)-1-oxopropan-2-yl)-quinoxaline-2-carboxamide (A237)

$^1$H NMR (500 MHz, Chloroform) δ 9.32 (s, 1H), 8.17 (s, 1H), 8.12 (s, 1H), 7.76 (s, 1H), 7.66 (d, J=4.6 Hz, 2H), 7.33-7.27 (m, 4H), 7.19 (s, 1H), 5.70 (s, 1H), 4.93 (s, 1H), 4.80 (s, 1H), 4.75 (s, 1H), 4.03 (s, 1H), 3.98 (s, 1H), 3.24 (s, 1H), 3.02-2.98 (m, 3H), 2.30-2.26 (m, 2H), 2.18 (s, 1H), 2.10 (s, 1H), 1.82-1.75 (m, 2H), 1.75-1.71 (m, 2H), 1.67 (s, 1H), 1.45-1.41 (m, 2H), 1.33 (s, 1H), 1.30-1.20 (m, 6H), 1.14-1.07 (m, 3H).

Example 238 N—((S)-14(S)-4-(benzyl)-3,4-dione-1-(isopropylamino)-2-yl)amino)-3-(phenyl)-1-oxopropan-2-yl)-quinoxaline-2-carboxamide (A238)

$^1$H NMR (500 MHz, Chloroform) δ 9.34 (s, 1H), 8.08 (d, J=10.7 Hz, 2H), 7.62 (d, J=0.9 Hz, 2H), 7.30-7.21 (m, 8H), 7.19 (s, 1H), 7.14 (s, 1H), 6.23 (s, 1H), 6.03 (s, 1H), 5.22 (s, 1H), 5.08 (s, 1H), 4.95 (s, 1H), 4.88 (s, 1H), 4.33 (s, 1H), 4.28 (s, 1H), 3.96 (s, 1H), 3.22 (s, 1H), 2.99 (s, 1H), 2.38-2.34 (m, 2H), 2.21 (s, 1H), 2.16 (s, 1H), 1.33-1.20 (m, 6H).

Example 239 N—((S)-1-(((S)-4-(benzyl)-3,4-dione-1-(cyclohexylamino)-2-yl)amino)-3-(phenyl)-1-oxopropan-2-yl)-quinoxaline-2-carboxamide (A239)

1H NMR (500 MHz, Chloroform) δ 9.31 (s, 1H), 8.12 (d, J=31.2 Hz, 2H), 7.73 (s, 1H), 7.63 (d, J=6.0 Hz, 2H), 7.36-7.24 (m, 8H), 7.17 (d, J=11.8 Hz, 2H), 6.32 (s, 1H), 5.10 (s, 1H), 4.76 (s, 1H), 4.67 (s, 1H), 4.36 (s, 1H), 4.30 (d, J=18.6 Hz, 2H), 4.12 (s, 1H), 3.24 (s, 1H), 2.97 (s, 1H), 2.31-2.27 (m, 2H), 2.12 (d, J=3.2 Hz, 2H), 1.94-1.87 (m, 2H), 1.73-1.63 (m, 4H), 1.61-1.55 (m, 4H).

Example 240 N—((S)-1-(((S)-4-(benzylamino)-3,4-dione-1-((S)-2-oxopiperidin-3-yl)but-2-yl)amino)-3-cyclohexyl-1-oxopropan-2-yl)-1H-indole-6-fluoro-2-carboxamide (A240)

$^1$H NMR (500 MHz, Chloroform) δ 8.12 (s, 1H), 7.57 (s, 1H), 7.52 (s, 1H), 7.36-7.25 (m, 4H), 7.20 (d, J=7.7 Hz, 2H), 6.84 (s, 1H), 6.18 (s, 1H), 5.49 (d, J=11.0 Hz, 2H), 4.70 (s, 1H), 4.39 (d, J=17.7 Hz, 2H), 4.08 (s, 1H), 3.24 (d, J=17.5 Hz, 2H), 2.54 (s, 1H), 2.08-2.04 (m, 2H), 1.82 (s, 1H), 1.78-1.67 (m, 6H), 1.66-1.62 (m, 2H), 1.58 (dd, J=9.5, 3.3 Hz, 5H), 1.44 (s, 1H), 1.37-1.27 (m, 3H).

Example 241 N—((S)-1-(((S)-4-(benzylamino)-3,4-dione-1-((S)-2-oxopiperidin-3-yl)but-2-yl)amino)-3-cyclohexyl-1-oxopropan-2-yl)-5-methyloxazole-2-carboxamide (A241)

$^1$H NMR (500 MHz, Chloroform) δ 7.33-7.27 (m, 4H), 7.23 (s, 1H), 6.79 (d, J=13.7 Hz, 2H), 6.29 (s, 1H), 6.09 (s, 1H), 5.05 (s, 1H), 4.99 (d, J=9.8 Hz, 2H), 4.41 (s, 1H), 4.34 (s, 1H), 3.24 (d, J=14.9 Hz, 2H), 2.92 (s, 1H), 2.36-2.32 (m, 3H), 2.08-2.04 (m, 2H), 1.85 (s, 1H), 1.79 (s, 1H), 1.74-1.55 (m, 11H), 1.48 (s, 1H), 1.46-1.23 (m, 3H).

Example 242 N—((S)-1-(((S)-4-(benzylamino)-3,4-dione-1-((S)-2-oxopyrrolidin-3-yl)but-2-yl)amino)-3-cyclohexyl-1-oxopropan-2-yl)-5-methyloxazole-2-carboxamide (A242)

$^1$H NMR (500 MHz, Chloroform) δ 7.33-7.30 (m, 22H), 7.28 (t, J=15.0 Hz, 33H), 6.83 (s, 9H), 6.14 (s, 9H), 6.09 (s, 9H), 5.94 (s, 9H), 5.19 (s, 9H), 5.01 (s, 9H), 4.36 (d, J=0.5 Hz, 18H), 3.45 (s, 9H), 3.35 (s, 7H), 2.59 (s, 9H), 2.38-2.34 (m, 27H), 2.18 (s, 8H), 2.09-2.05 (m, 18H), 1.96-1.88 (m, 24H), 1.88 (s, 3H), 1.73-1.60 (m, 46H), 1.40-1.36 (m, 16H), 1.32 (s, 9H), 1.15 (s, 7H), 1.12-1.08 (m, 17H).

Example 243 N—((S)-1-(((S)-4-(benzylamino)-3,4-dione-1-((S)-2-oxopiperidin-3-yl)but-2-yl)amino)-3-cyclohexyl-1-oxopropan-2-yl)-benzo[d]1,3-dioxole-5-carboxamide (A243)

$^1$H NMR (500 MHz, Chloroform) δ 7.54 (s, 6H), 7.45 (s, 6H), 7.29-7.18 (m, 30H), 6.96 (s, 6H), 6.49 (s, 6H), 6.01 (s, 6H), 5.92-5.88 (m, 12H), 5.58 (s, 6H), 5.11 (s, 6H), 4.93 (s, 6H), 4.63 (s, 6H), 4.29 (s, 6H), 4.24 (s, 6H), 3.24 (d, J=17.5 Hz, 11H), 2.86 (s, 6H), 2.05 (t, J=4.2 Hz, 18H), 1.95-1.87 (m, 12H), 1.84 (s, 6H), 1.76 (t, J=4.8 Hz, 17H), 1.63 (dd, J=40.8, 34.9 Hz, 22H), 1.51 (dd, J=4.6, 1.3 Hz, 1H), 1.40-1.36 (m, 10H), 1.32 (s, 6H), 1.17-1.09 (m, 17H).

Example 244 N—((S)-1-(((S)-4-(benzylamino)-3,4-dione-1-((S)-2-oxopiperidin-3-yl)but-2-yl)amino)-3-cyclohexyl-1-oxopropan-2-yl)-1H-benzo[d]imidazole-2-carboxamide (A244)

$^1$H NMR (500 MHz, Chloroform) δ 7.84 (s, 1H), 7.73 (s, 1H), 7.62 (s, 1H), 7.38 (s, 1H), 7.31-7.23 (m, 6H), 7.16 (s, 1H), 6.17 (s, 1H), 5.59 (s, 1H), 5.10 (s, 1H), 4.75 (s, 1H), 4.53 (s, 1H), 4.36 (d, J=17.3 Hz, 2H), 3.24 (d, J=17.5 Hz, 2H), 2.88 (s, 1H), 2.06 (t, J=2.7 Hz, 3H), 1.96-1.81 (m, 3H), 1.77 (s, 1H), 1.73-1.60 (m, 5H), 1.53 (s, 1H), 1.40-1.36 (m, 2H), 1.32 (s, 1H), 1.22-1.15 (m, 3H).

Example 245 N—((S)-1-(((S)-4-(benzylamino)-3,4-dione-1-((S)-2-oxopyrrolidinpiperidin-3-yl)but-2-yl)amino)-3-cyclohexyl-1-oxopropan-2-yl)-7-methoxybenzofuran-2-carboxamide (A245)

$^1$H NMR (500 MHz, Chloroform) δ 7.60 (s, 8H), 7.34-7.22 (m, 33H), 7.15 (d, J=10.0 Hz, 16H), 7.06 (s, 8H), 6.81 (s, 8H), 6.54 (s, 8H), 6.22 (s, 8H), 5.59 (s, 8H), 5.08 (s, 8H), 4.92 (s, 8H), 4.63 (s, 8H), 4.32 (d, J=1.1 Hz, 16H), 3.89-3.85 (m, 24H), 3.24 (d, J=17.4 Hz, 15H), 2.94 (s, 8H), 2.07 (t, J=5.1 Hz, 23H), 1.93-1.85 (m, 18H), 1.84 (s, 6H), 1.78 (s, 6H), 1.73-1.51 (m, 49H), 1.51 (d, J=5.5 Hz, 1H), 1.40-1.36 (m, 14H), 1.32 (s, 8H), 1.16-1.07 (m, 23H).

Example 246 N—((S)-1-(((S)-4-(benzylamino)-3,4-dione-1-((S)-2-oxopiperidin-3-yl)but-2-yl)amino)-3-cyclohexyl-1-oxopropan-2-yl)-3-methyl-benzofuran-2-carboxamide (A246)

$^1$H NMR (500 MHz, Chloroform) δ 7.60-7.40 (m, 3H), 7.32-7.18 (m, 7H), 6.67 (s, 1H), 5.57 (s, 1H), 5.15 (s, 1H), 4.67 (s, 1H), 4.55 (s, 1H), 4.30 (d, J=14.7 Hz, 2H), 3.24 (d, J=17.3 Hz, 2H), 2.73 (s, 1H), 2.15-2.10 (m, 4H), 2.08-2.04 (m, 2H), 1.88-1.81 (m, 3H), 1.77 (s, 1H), 1.73-1.59 (m, 5H), 1.55 (s, 1H), 1.40-1.36 (m, 2H), 1.32 (s, 1H), 1.14-1.05 (m, 3H).

Example 247 N—((S)-1-(((S)-4-(benzylamino)-3,4-dione-1-((S)-2-oxopiperidin-3-yl)but-2-yl)amino)-3-cyclohexyl-1-oxopropan-2-yl)-3,5-dimethyl-benzofuran-2-carboxamide (A247)

$^1$H NMR (500 MHz, Chloroform) δ 7.50-7.34 (m, 3H), 7.32-7.26 (m, 4H), 7.23 (s, 1H), 7.11 (s, 1H), 6.68 (s, 1H), 5.57 (s, 1H), 5.15 (s, 1H), 4.69 (s, 1H), 4.55 (s, 1H), 4.30 (d, J=14.8 Hz, 2H), 3.24 (d, J=17.3 Hz, 2H), 2.73 (s, 1H), 2.45-2.41 (m, 3H), 2.15-2.10 (m, 4H), 2.08-2.04 (m, 2H), 1.88-1.81 (m, 3H), 1.77 (s, 1H), 1.73-1.59 (m, 5H), 1.55 (s, 1H), 1.40-1.36 (m, 2H), 1.32 (s, 1H), 1.14-1.05 (m, 3H).

Example 248 N—((S)-1-(((S)-4-(benzylamino)-3,4-dione-1-((S)-2-oxopiperidin-3-yl)but-2-yl)amino)-3-cyclohexyl-1-oxopropan-2-yl)-4,7-dimethoxy-benzofuran-2-carboxamide (A248)

$^1$H NMR (500 MHz, Chloroform) δ 7.59 (s, 1H), 7.34-7.27 (m, 2H), 7.27-7.22 (m, 2H), 7.10 (s, 1H), 6.86 (s, 1H), 6.82 (s, 1H), 6.38 (s, 1H), 6.32 (s, 1H), 5.56 (s, 1H), 5.35 (s, 1H), 4.66 (d, J=18.6 Hz, 2H), 4.28 (s, 1H), 4.17 (s, 1H), 3.91-3.87 (m, 3H), 3.85-3.81 (m, 3H), 3.24 (d, J=17.8 Hz, 2H), 3.06 (s, 1H), 2.05 (t, J=6.8 Hz, 3H), 1.96-1.88 (m, 2H), 1.84 (s, 1H), 1.77 (s, 1H), 1.73-1.54 (m, 5H), 1.52 (s, 1H), 1.40-1.36 (m, 2H), 1.32 (s, 1H), 1.17-1.08 (m, 3H).

Example 249 N—((S)-1-(((S)-4-(benzylamino)-3,4-dione-1-((S)-2-oxopiperidin-3-yl)but-2-yl)amino)-3-cyclohexyl-1-oxopropan-2-yl)-benzofuran-3-carboxamide (A249)

$^1$H NMR (500 MHz, Chloroform) δ 8.07 (s, 91H), 7.62 (s, 92H), 7.58 (s, 94H), 7.47 (s, 94H), 7.27 (dd, J=9.9, 8.1 Hz, 379H), 7.20 (t, J=5.8 Hz, 274H), 6.24 (s, 91H), 5.61 (s, 91H), 5.16 (s, 90H), 4.93 (s, 91H), 4.52 (s, 89H), 4.32 (d, J=0.6 Hz, 182H), 3.24 (d, J=17.5 Hz, 174H), 2.89 (s, 93H), 2.06 (t, J=2.7 Hz, 257H), 1.92-1.80 (m, 277H), 1.81 (s, 7H), 1.77 (s, 70H), 1.73-1.51 (m, 541H), 1.51 (d, J=1.8 Hz, 6H), 1.40-1.36 (m, 160H), 1.32 (s, 86H), 1.22-1.16 (m, 264H).

Example 250 N—((S)-1-(((S)-4-(benzylamino)-3,4-dione-1-((S)-2-oxopiperidin-3-yl)but-2-yl)amino)-3-cyclohexyl-1-oxopropan-2-yl)-6-chloro-2H-chromene-3-carboxamide (A250)

$^1$H NMR (500 MHz, Chloroform) δ 8.16 (s, 1H), 7.32 (s, 1H), 7.32-7.24 (m, 4H), 7.23-7.09 (m, 3H), 6.84 (s, 1H), 6.05 (s, 1H), 5.64 (s, 1H), 5.33 (s, 1H), 5.06-5.02 (m, 2H), 4.50 (d, J=9.3 Hz, 2H), 4.39 (s, 1H), 4.32 (s, 1H), 3.24 (d, J=17.4 Hz, 2H), 2.99 (s, 1H), 2.15 (s, 1H), 2.08-2.04 (m, 2H), 1.85 (s, 1H), 1.79 (s, 1H), 1.73-1.69 (m, 2H), 1.69-1.62 (m, 5H), 1.55 (s, 1H), 1.39-1.35 (m, 2H), 1.31 (s, 1H), 1.23-1.19 (m, 2H), 1.17 (s, 1H).

Example 251 N—((S)-1-(((S)-4-(cyclohexylamino)-3,4-dione-1-((S)-2-oxopyrrolidin-3-yl)but-2-yl)amino)-3-cyclohexyl-1-oxopropan-2-yl)-6-chloro-2,3-dihydrobenzo[b]1,4-dioxin-6-carboxamide (A251)

$^1$H NMR (500 MHz, Chloroform) δ 8.51 (s, 1H), 7.66 (s, 1H), 7.55 (s, 1H), 7.11 (s, 1H), 5.40 (s, 1H), 5.16 (s, 1H), 4.65 (s, 1H), 4.52 (s, 1H), 4.38-4.34 (m, 4H), 3.45 (s, 1H), 3.36 (d, J=13.4 Hz, 2H), 2.68 (s, 1H), 2.18 (s, 1H), 2.11-2.02 (m, 2H), 1.99-1.84 (m, 3H), 1.78-1.72 (m, 2H), 1.71-1.62 (m, 5H), 1.58 (dd, J=9.0, 3.3 Hz, 5H), 1.55-1.50 (m, 2H), 1.48 (s, 1H), 1.43-1.39 (m, 4H), 1.37-1.29 (m, 3H).

Example 252 N—((S)-1-(((S)-4-(cyclohexylamino)-3,4-dione-1-((S)-2-oxopyrrolidin-3-yl)but-2-yl)amino)-3-phenyl-1-oxopropan-2-yl)-6-chloro-2,3-dihydrobenzo[b]1,4-dioxin-6-carboxamide (A252)

$^1$H NMR (500 MHz, Chloroform) δ 9.01 (s, 1H), 7.52 (s, 1H), 7.29-7.23 (m, 2H), 7.23-7.17 (m, 2H), 7.15 (s, 1H), 7.04 (s, 1H), 6.92 (s, 1H), 6.21 (s, 1H), 5.12 (s, 1H), 5.05 (s, 1H), 4.87 (s, 1H), 4.52 (s, 1H), 4.38-4.34 (m, 4H), 3.44 (d, J=12.5 Hz, 2H), 3.37-3.20 (m, 3H), 2.98 (s, 1H), 2.19 (s, 1H), 2.12-2.04 (m, 2H), 1.92 (s, 1H), 1.85-1.78 (m, 2H), 1.66 (s, 1H), 1.56-1.52 (m, 2H), 1.48-1.39 (m, 3H), 1.23-1.11 (m, 2H).

Example 253 N—((S)-1-(((S)-4-(cyclohexylamino)-3,4-dione-1-((S)-2-oxopyrrolidin-3-yl)but-2-yl)amino)-3-cyclohexyl-1-oxopropan-2-yl)-5-methoxy-indole-6-carboxamide (A253)

$^1$H NMR (500 MHz, Chloroform) δ 8.73 (s, 5H), 8.50 (s, 5H), 7.45 (s, 5H), 7.37 (s, 5H), 7.18 (s, 5H), 6.75 (s, 5H), 6.03 (s, 5H), 5.67 (s, 5H), 5.61 (s, 5H), 4.89 (s, 5H), 4.57 (s, 5H), 3.84-3.80 (m, 15H), 3.43 (d, J=16.9 Hz, 10H), 3.35 (s, 4H), 2.70 (s, 5H), 2.19 (s, 5H), 2.09-2.06 (m, 9H), 2.06-2.04 (m, 1H), 2.06-1.91 (m, 16H), 1.73-1.61 (m, 35H), 1.60-1.46 (m, 47H), 1.46-1.39 (m, 11H), 1.35-1.26 (m, 9H), 1.22 (s, 4H). Example 254 N—((S)-1-(((S)-4-(benzylamino)-3,4-dione-1-((S)-2-oxopiperidin-3-yl)but-2-yl)amino)-3-4-fluorophenyl-1-oxopropan-2-yl)-5-methyl-benzofuran-2-carboxamide (A254)

$^1$H NMR (500 MHz, Chloroform-d) δ 8.35 (d, J=9.7 Hz, 1H), 8.11 (t, J=5.8 Hz, 1H), 7.83 (d, J=9.3 Hz, 1H), 7.68 (d, J=2.1 Hz, 1H), 7.60 (dd, J=2.7, 1.8 Hz, 1H), 7.41 (d, J=8.2 Hz, 1H), 7.35-7.22 (m, 7H), 7.22-7.17 (m, 1H), 7.07-7.00 (m, 2H), 6.26 (t, J=4.0 Hz, 1H), 4.75 (dt, J=9.7, 6.2 Hz, 1H), 4.54-4.46 (m, 1H), 4.50-4.45 (m, 1H), 4.47 (t, J=0.9 Hz, 1H), 3.27-3.14 (m, 2H), 3.08 (ddt, J=6.2, 2.9, 1.1 Hz, 2H), 2.61 (tdd, J=8.9, 6.9, 4.3 Hz, 1H), 2.13 (ddd, J=15.0, 8.8, 7.3 Hz, 1H), 1.99 (ddd, J=15.2, 8.8, 7.3 Hz, 1H), 1.81-1.61 (m, 4H).

Example 255 N—((S)-1-(((S)-4-(benzylamino)-3,4-dione-1-((S)-2-oxopiperidin-3-yl)but-2-yl)amino)-3-cyclohexyl-1-oxopropan-2-yl)-3-chloro-benzofuran-2-carboxamide (A255)

1H NMR (500 MHz, Chloroform) δ 7.75 (s, 1H), 7.58 (s, 1H), 7.49 (s, 1H), 7.29 (d, J=15.0 Hz, 6H), 7.21 (s, 1H), 6.10 (s, 1H), 4.78 (s, 1H), 4.52 (s, 1H), 4.34 (s, 2H), 3.21 (d, J=15.0 Hz, 2H), 2.91 (s, 1H), 2.53 (d, J=13.0 Hz, 2H), 2.01 (s, 1H), 1.91 (d, J=6.4 Hz, 1H), 1.76 (s, 1H), 1.64 (s, 1H), 1.58 (s, 1H), 1.55-1.37 (m, 9H).

Example 256 N—((S)-1-(((S)-4-(cyclohexylamino)-3, 4-dione-1-((S)-2-oxopiperidin-3-yl)but-2-yl)amino)-3-cyclohexyl-1-oxopropan-2-yl)-5-chloro-benzofuran-2-carboxamide (A256)

1H NMR (500 MHz, Chloroform) δ 7.66 (s, 1H), 7.44 (s, 1H), 7.23 (s, 1H), 7.15 (s, 1H), 6.88 (s, 1H), 6.44 (s, 1H), 6.11 (s, 1H), 4.95 (s, 1H), 4.76 (s, 1H), 4.54 (s, 1H), 3.21 (d, J=15.0 Hz, 2H), 2.88 (s, 1H), 2.50 (d, J=13.5 Hz, 2H), 2.19 (s, 2H), 2.01 (s, 1H), 1.91 (d, J=0.5 Hz, 1H), 1.84 (s, 2H), 1.76 (s, 1H), 1.59 (dd, J=42.7, 19.7 Hz, 5H), 1.53 (s, 1H), 1.51 (d, J=15.0 Hz, 3H), 1.44 (dd, J=9.2, 5.8 Hz, 5H), 1.37 (s, 3H), 1.31 (s, 1H), 1.20 (s, 2H).

Example 257 N—((S)-1-(((S)-4-(cyclohexylamino)-3,4-dione-1-((S)-2-oxopiperidin-3-yl)but-2-yl)amino)-3-cyclohexyl-1-oxopropan-2-yl)-6-bromo-benzofuran-2-carboxamide (A257)

1H NMR (500 MHz, Chloroform) δ 7.54 (t, J=2.6 Hz, 1H), 7.46 (d, J=71.6 Hz, 5H), 7.18 (s, 3H), 7.11 (d, J=2.3 Hz, 4H), 6.42 (s, 3H), 5.73 (s, 3H), 5.65 (s, 3H), 5.03 (s, 2H), 4.95 (s, 1H), 4.47 (s, 1H), 3.21 (d, J=15.0 Hz, 6H), 2.99 (s, 2H), 2.72 (s, 3H), 2.34 (s, 2H), 2.19 (s, 5H), 2.01 (s, 1H), 1.93 (d, J=16.1 Hz, 5H), 1.89-1.74 (m, 10H), 1.69 (d, J=10.0 Hz, 8H), 1.62 (s, 2H), 1.51 (s, 1H), 1.39 (d, J=6.9 Hz, 1H), 1.38-1.28 (m, 4H), 1.20 (s, 3H), 1.11 (s, 2H), 1.03 (s, 3H).

Example 258 N—((S)-1-(((S)-4-(benzylamino)-3,4-dione-1-((S)-2-oxopiperidin-3-yl)but-2-yl)amino)-1-oxo-3-cyclohexylpropan-2-yl)-5-fluoronicotinamide (A258)

1H NMR (500 MHz, Chloroform) δ 8.58 (s, 1H), 8.40 (s, 1H), 7.77 (s, 1H), 7.29 (d, J=15.0 Hz, 4H), 7.22 (s, 1H), 7.05 (s, 1H), 6.30 (s, 1H), 5.77 (s, 1H), 4.90 (s, 1H), 4.45 (s, 1H), 4.34 (s, 2H), 3.21 (d, J=15.0 Hz, 2H), 2.97 (s, 1H), 2.67 (s, 1H), 2.13 (s, 1H), 2.01 (s, 1H), 1.93 (d, J=16.5 Hz, 2H), 1.78 (m, 2H), 1.75 (d, J=7.8 Hz, 1H), 1.57 (s, 1H), 1.46 (m, 9H).

Example 259 N—((S)-1-(((S)-4-(benzylamino)-3,4-dione-1-((S)-2-oxopiperidin-3-yl)but-2-yl)amino)-3-cyclohexyl-1-oxopropan-2-yl)-5-ethoxyl-benzofuran-2-carboxamide (A259)

1H NMR (500 MHz, Chloroform) δ 7.78-7.52 (m, 1H), 7.29 (d, J=15.0 Hz, 1H), 7.23 (d, J=10.0 Hz, 1H), 7.11 (s, 1H), 6.36 (s, 1H), 5.85 (s, 1H), 4.82 (s, 1H), 4.45 (s, 1H), 4.34 (s, 1H), 4.06 (s, 1H), 3.21 (d, J=15.0 Hz, 1H), 2.82 (s, 2H), 2.45 (d, J=1.0 Hz, 1H), 2.01 (s, 1H), 1.91 (s, 2H), 1.79-1.57 (m, 2H), 1.62-1.57 (m, 2H), 1.55-1.41 (m, 2H), 1.33 (d, J=7.5 Hz, 1H).

Example 260 N—((S)-1-(((S)-4-(3-methylbenzyl amino)-3,4-dione-1-((S)-2-oxopiperidin-3-yl)but-2-yl)amino)-3-cyclohexyl-1-oxopropan-2-yl)-benzofuran-2-carboxamide (A260)

1H NMR (500 MHz, Chloroform) δ 7.59 (s, 1H), 7.50 (d, J=5.0 Hz, 2H), 7.28 (s, 1H), 7.21 (d, J=5.0 Hz, 1H), 7.11 (d, J=1.5 Hz, 2H), 7.03 (s, 1H), 6.94 (s, 1H), 6.88 (s, 1H), 5.72 (s, 1H), 4.68 (s, 1H), 4.63 (s, 1H), 4.34 (s, 2H), 3.21 (d, J=15.0 Hz, 2H), 2.78 (s, 1H), 2.38-2.29 (m, 5H), 2.08-2.03 (m, 1H), 2.08-1.89 (m, 2H), 1.76 (s, 1H), 1.67 (s, 1H), 1.55-1.41 (m, 8H).

Example 261 N—((S)-14(S)-4-(4 fluorobenzylamino)-3,4-dione-1-((S)-2-oxopiperidin-3-yl)but-2-yl)amino)-3-cyclohexyl-1-oxopropan-2-yl)-benzofuran-2-carboxamide (A261)

1H NMR (500 MHz, Chloroform) δ 7.59 (s, 1H), 7.50 (s, 1H), 7.38 (d, J=2.0 Hz, 2H), 7.28 (s, 1H), 7.22 (s, 1H), 7.16 (s, 1H), 7.07 (s, 1H), 6.86 (s, 1H), 6.12 (s, 1H), 4.80 (s, 1H), 4.53 (s, 1H), 4.34 (s, 1H), 3.21 (d, J=15.0 Hz, 2H), 2.91 (s, 1H), 2.51 (d, J=9.5 Hz, 2H), 2.01 (s, 1H), 1.91 (d, J=4.1 Hz, 1H), 1.76 (s, 1H), 1.65 (s, 1H), 1.58 (s, 1H), 1.51 (d, J=15.0 Hz, 2H), 1.44 (dd, J=8.0, 7.0 Hz, 6H).

Example 262 N—((S)-1-(((S)-4-(benzylamino)-3,4-dione-1-((S)-2-oxopiperidin-3-yl)but-2-yl)amino)-3-cyclohexyl-1-oxopropan-2-yl)-5-chloro-7-azaindole-2-carboxamide (A262)

1H NMR (500 MHz, Chloroform) δ 8.71 (s, 1H), 8.52 (s, 1H), 8.09 (s, 1H), 7.29 (d, J=15.0 Hz, 5H), 7.19 (s, 1H), 7.14 (s, 1H), 6.93 (s, 1H), 6.09 (s, 1H), 4.80 (s, 1H), 4.45 (s, 1H), 4.34 (s, 2H), 3.21 (d, J=15.0 Hz, 2H), 2.90 (s, 1H), 2.44 (d, J=5.0 Hz, 2H), 2.01 (s, 1H), 1.91 (d, J=1.4 Hz, 1H), 1.76 (s, 1H), 1.72 (s, 1H), 1.59-1.48 (m, 3H), 1.48-1.41 (m, 4H), 1.36 (s, 1H).

Example 263 N—((S)-1-(((S)-4-(4-chlorobenzylamino)-3,4-dione-1-((S)-2-oxopiperidin-3-yl)but-2-yl)amino)-3-cyclohexyl-1-oxopropan-2-yl)-benzofuran-2-carboxamide (A263)

1H NMR (500 MHz, Chloroform) δ 7.59 (s, 1H), 7.50 (s, 1H), 7.38 (d, J=9.2 Hz, 5H), 7.28 (s, 1H), 7.22 (s, 1H), 7.16 (s, 1H), 6.86 (s, 1H), 6.12 (s, 1H), 4.80 (s, 1H), 4.53 (s, 1H), 4.34 (s, 2H), 3.21 (d, J=15.0 Hz, 2H), 2.92 (s, 1H), 2.51 (d, J=13.5 Hz, 2H), 2.01 (s, 1H), 1.91 (d, J=3.7 Hz, 1H), 1.76 (s, 1H), 1.65 (s, 1H), 1.58 (s, 1H), 1.51 (d, J=15.0 Hz, 2H), 1.44 (dd, J=8.3, 6.7 Hz, 6H).

Example 264 N—((S)-1-(((S)-4-(benzylamino)-3,4-dione-1-((S)-2-oxopiperidin-3-yl)but-2-yl)amino)-3-cyclohexyl-1-oxopropan-2-yl)-6-bromo-benzofuran-2-carboxamide (A264)

1H NMR (500 MHz, Chloroform) δ 7.50 (d, J=32.8 Hz, 1H), 7.34-7.26 (m, 3H), 7.18 (s, 1H), 7.11 (s, 1H), 6.87 (s, 1H), 6.12 (s, 1H), 4.78 (s, 1H), 4.54 (s, 1H), 4.34 (s, 1H), 3.21 (d, J=15.0 Hz, 1H), 2.90 (s, 2H), 2.54 (d, J=18.2 Hz, 1H), 2.01 (s, 1H), 1.92 (d, J=6.0 Hz, 1H), 1.76 (s, 2H), 1.65 (s, 2H), 1.58 (s, 2H), 1.51 (d, J=15.0 Hz, 1H), 1.44 (dd, J=8.2, 6.8 Hz, 3H).

Example 265 N—((S)-1-(((S)-4-(3, 4-difluorobenzylamino)-3,4-dione-1-(2-oxopiperidin-3-yl)but-2-yl)amino)-3-cyclohexyl-1-oxopropan-2-yl)-benzofuran-2-carboxamide (A265)

1H NMR (500 MHz, Chloroform) δ 7.53 (d, J=44.9 Hz, 1H), 7.34 (s, 1H), 7.28-7.12 (m, 2H), 7.05 (s, 1H), 6.84 (s, 1H), 6.11 (s, 1H), 4.79 (s, 1H), 4.53 (s, 1H), 4.33 (s, 1H), 3.21 (d, J=15.0 Hz, 1H), 2.92 (s, 1H), 2.50 (d, J=17.5 Hz, 1H), 2.01 (s, 1H), 1.91 (d, J=3.9 Hz, 2H), 1.76 (s, 1H), 1.65 (s, 1H), 1.58 (s, 1H), 1.55-1.41 (m, 4H).

Example 266 N—((S)-1-(((S)-4-(2-chlorobenzylamino)-3,4-dione-1-(2-oxopiperidin-3-yl)but-2-yl)amino)-3-cyclohexyl-1-oxopropan-2-yl)-benzofuran-2-carboxamide (A266)

1H NMR (500 MHz, Chloroform) δ 7.66 (s, 1H), 7.44 (s, 1H), 7.23 (s, 1H), 7.15 (s, 1H), 6.88 (s, 1H), 6.44 (s, 1H), 6.11 (s, 1H), 4.95 (s, 1H), 4.76 (s, 1H), 4.54 (s, 1H), 3.21 (d, J=15.0 Hz, 2H), 2.88 (s, 1H), 2.50 (d, J=13.5 Hz, 1H), 2.19 (s, 2H), 2.01 (s, 1H), 1.91 (d, J=0.5 Hz, 1H), 1.84 (s, 1H), 1.76 (s, 1H), 1.59 (dd, J=42.7, 19.7 Hz, 5H), 1.53 (s, 1H), 1.51 (d, J=15.0 Hz, 3H), 1.44 (dd, J=9.2, 5.8 Hz, 5H), 1.37 (s, 3H), 1.31 (s, 1H), 1.20 (s, 2H).

Example 267 N—((S)-1-(((S)-4-(2-methoxybenzylamino)-3, 4-dione-1-((S)-2-oxopiperidin-3-yl)but-2-yl)amino)-3-cyclohexyl-1-oxopropan-2-yl)-benzofuran-2-carboxamide (A267)

1H NMR (500 MHz, Chloroform) δ 7.54 (s, 1H), 7.30-7.20 (m, 2H), 7.15 (s, 1H), 6.95-6.82 (m, 2H), 6.11 (s, 1H), 4.78 (s, 1H), 4.53 (s, 1H), 4.23 (s, 1H), 3.72 (s, 1H), 3.21 (d, J=15.0 Hz, 1H), 2.89 (s, 1H), 2.55 (d, J=18.5 Hz, 1H), 2.01 (s, 1H), 1.91 (d, J=5.9 Hz, 1H), 1.76 (s, 1H), 1.65 (s, 1H), 1.58 (s, 1H), 1.55-1.35 (m, 4H).

Example 268 N—((S)-1-(((S)-4-(benzylamino)-3, 4-dione-1-((S)-2-oxopiperidin-3-yl)but-2-yl) amino)-3-cyclohexyl-1-oxopropan-2-yl)-pyridazine-2-carboxamide (A268)

1H NMR (500 MHz, Chloroform) δ 9.81 (s, 1H), 8.52 (s, 1H), 7.99 (s, 1H), 7.33-7.26 (m, 6H), 6.71 (s, 1H), 6.06 (s, 1H), 4.75 (s, 1H), 4.45 (s, 1H), 4.34 (s, 2H), 3.21 (d, J=15.0 Hz, 2H), 2.83 (s, 1H), 2.65 (s, 1H), 2.52 (s, 1H), 2.01 (s, 1H), 1.90 (d, J=8.1 Hz, 1H), 1.76 (s, 1H), 1.65-1.28 (m, 9H), 1.39-1.28 (m, 1H).

Example 269 N—((S)-1-(((S)-4-(benzylamino)-3, 4-dione-1-((S)-2-oxopiperidin-3-yl)but-2-yl) amino)-3-cyclohexyl-1-oxopropan-2-yl)-4, 5-indole-2-carboxamide (A269)

1H NMR (500 MHz, Chloroform) δ 8.49 (s, 1H), 7.33-7.26 (m, 7H), 7.20 (s, 2H), 7.10 (s, 1H), 6.87 (s, 1H), 6.11 (s, 1H), 4.78 (s, 1H), 4.52 (s, 1H), 4.34 (s, 2H), 3.21 (d, J=15.0 Hz, 2H), 2.92 (s, 1H), 2.54 (d, J=17.0 Hz, 3H), 2.01 (s, 1H), 1.92 (d, J=8.4 Hz, 2H), 1.76 (s, 1H), 1.64 (s, 1H), 1.58 (s, 1H), 1.51 (d, J=15.0 Hz, 4H), 1.44 (dd, J=9.9, 5.2 Hz, 6H).

Example 270 N—((S)-1-(((S)-4-(3,5-difluorobenzylamino)-3,4-dione-1-((S)-2-oxopiperidin-3-yl)but-2-yl)amino)-3-cyclohexyl-1-oxopropan-2-yl)-benzofuran-2-carboxamide (A270)

1H NMR (500 MHz, Chloroform) δ 7.54 (d, J=45.0 Hz, 1H), 7.35 (s, 1H), 7.27 (s, 1H), 7.21 (s, 1H), 7.15 (s, 2H), 6.85 (d, J=1.8 Hz, 5H), 6.79 (s, 1H), 6.11 (s, 2H), 4.79 (s, 1H), 4.53 (s, 1H), 4.33 (s, 3H), 3.21 (d, J=15.0 Hz, 4H), 2.91 (s, 1H), 2.52 (s, 2H), 2.48 (s, 2H), 2.01 (s, 1H), 1.91 (d, J=3.5 Hz, 2H), 1.76 (s, 2H), 1.65 (s, 2H), 1.58 (s, 2H), 1.55-1.41 (m, 7H).

Example 271 N—((S)-1-((S)-4-(4 methoxybenzylamino)-3, 4-dione-1-((S)-2-oxopiperidin-3-yl)butyl-2-yl)amino)-3-cyclohexyl-1-oxopropan-2-yl)-benzofuran-2-carboxamide (A271)

$^1$H NMR (500 MHz, Chloroform-d) δ 8.19 (d, J=9.9 Hz, 1H), 8.13 (t, J=5.7 Hz, 1H), 7.89 (d, J=9.3 Hz, 1H), 7.76 (d, J=2.0 Hz, 1H), 7.75-7.68 (m, 1H), 7.60-7.52 (m, 1H), 7.43-7.34 (m, 2H), 7.19 (dt, J=8.4, 1.0 Hz, 2H), 6.87-6.82 (m, 2H), 6.26 (t, J=4.0 Hz, 1H), 4.50 (ddt, J=5.8, 3.7, 1.1 Hz, 2H), 4.44 (dt, J=9.2, 7.4 Hz, 1H), 4.26 (dt, J=9.9, 6.7 Hz, 1H), 3.78 (s, 2H), 3.27-3.14 (m, 2H), 2.61 (tdd, J=8.9, 6.9, 4.2 Hz, 1H), 2.13 (ddd, J=15.0, 8.8, 7.3 Hz, 1H), 1.99 (ddd, J=15.2, 8.8, 7.3 Hz, 1H), 1.86-1.59 (m, 7H), 1.57-1.34 (m, 8H), 1.31-1.20 (m, 2H). ESI-MS m/z 631.31 $[M+H]^+$.

Example 272 N—((S)-1-(((S)-4-(4-methylbenzylmethylamino)-3,4-dione-1-((S)-2-oxopiperidin-3-yl) but-2-yl)amino)-3-cyclohexyl-1-oxopropan-2-yl)-benzofuran-2-carboxamide (A272)

$^1$H NMR (500 MHz, Chloroform-d) δ 8.19 (d, J=9.9 Hz, 1H), 7.85 (d, J=9.7 Hz, 1H), 7.76 (d, J=1.9 Hz, 1H), 7.75-7.68 (m, 1H), 7.60-7.52 (m, 1H), 7.43-7.34 (m, 2H), 7.14 (dt, J=8.0, 1.1 Hz, 2H), 7.10 (dq, J=7.3, 0.7 Hz, 2H), 6.26 (t, J=4.0 Hz, 1H), 4.55-4.48 (m, 2H), 4.50-4.43 (m, 1H), 4.26 (dt, J=9.9, 6.7 Hz, 1H), 3.27-3.14 (m, 2H), 2.99 (s, 2H), 2.61 (tdd, J=8.7, 6.8, 4.1 Hz, 1H), 2.16 (ddd, J=15.0, 8.8, 7.6 Hz, 1H), 1.94 (ddd, J=15.0, 8.8, 7.6 Hz, 1H), 1.86-1.59 (m, 7H), 1.57-1.34 (m, 8H), 1.31-1.20 (m, 2H). ESI-MS m/z 629.33 $[M+H]^+$.

Example 273 N—((S)-1-(((S)-4-(4-nitrobenzylamino)-3, 4-dione-1-((S)-2-oxopiperidin-3-yl)but-2-yl)amino)-3-cyclohexyl-1-oxopropan-2-yl)-benzofuran-2-carboxamide (A273)

$^1$H NMR (500 MHz, Chloroform-d) δ 8.21-8.13 (m, 3H), 8.10 (t, J=5.8 Hz, 1H), 7.89 (d, J=9.3 Hz, 1H), 7.76 (d, J=1.9 Hz, 1H), 7.75-7.68 (m, 1H), 7.60 (q, J=1.1 Hz, 1H), 7.60-7.52 (m, 2H), 7.43-7.34 (m, 2H), 6.26 (t, J=4.0 Hz, 1H), 4.50 (ddt, J=5.6, 4.6, 0.9 Hz, 2H), 4.44 (dt, J=9.2, 7.4 Hz, 1H), 4.26 (dt, J=9.9, 6.7 Hz, 1H), 3.27-3.14 (m, 2H), 2.61 (tdd, J=8.9, 6.9, 4.2 Hz, 1H), 2.13 (ddd, J=15.0, 8.8, 7.3 Hz, 1H), 1.99 (ddd, J=15.2, 8.8, 7.3 Hz, 1H), 1.86-1.71 (m, 4H), 1.74-1.59 (m, 3H), 1.57-1.34 (m, 8H), 1.31-1.20 (m, 2H). ESI-MS m/z 646.28 $[M+H]^+$.

Example 274 N—((S)-1-(((S)-4-(2,4,6-trimethylbenzylamino)-3,4-dione-1-((S)-2-oxopiperidin-3-yl)but-2-yl)amino)-3-cyclohexyl-1-oxopropan-2-yl)-benzofuran-2-carboxamide (A274)

$^1$H NMR (500 MHz, Chloroform-d) δ 8.19 (d, J=9.9 Hz, 1H), 7.89 (d, J=9.3 Hz, 1H), 7.80-7.75 (m, 2H), 7.75-7.68 (m, 1H), 7.60-7.52 (m, 1H), 7.43-7.34 (m, 2H), 6.78 (s, 2H), 6.26 (t, J=4.0 Hz, 1H), 4.50 (dd, J=6.0, 2.9 Hz, 2H), 4.44 (dt, J=9.2, 7.4 Hz, 1H), 4.26 (dt, J=9.9, 6.7 Hz, 1H), 3.27-3.14 (m, 2H), 2.61 (tdd, J=8.9, 6.9, 4.2 Hz, 1H), 2.23 (s, 2H), 2.13 (ddd, J=15.0, 8.8, 7.3 Hz, 1H), 1.99 (ddd, J=15.2, 8.8, 7.3 Hz, 1H), 1.86-1.59 (m, 7H), 1.57-1.34 (m, 8H), 1.31-1.20 (m, 2H). ESI-MS m/z 643.34 $[M+H]^+$.

Example 275 N—((S)-1-((S)-4-(4-phenylbenzylamino)-3, 4-dione-1-((S)-2-oxopiperidin-3-yl)but-2-yl)amino)-3-cyclohexyl-1-oxopropan-2-yl)-benzofuran-2-carboxamide (A275)

$^1$H NMR (500 MHz, Chloroform-d) δ 8.19 (d, J=9.9 Hz, 1H), 8.13 (t, J=5.7 Hz, 1H), 7.89 (d, J=9.3 Hz, 1H), 7.76 (d, J=1.9 Hz, 1H), 7.75-7.68 (m, 1H), 7.62-7.49 (m, 5H), 7.48-7.41 (m, 2H), 7.43-7.34 (m, 3H), 7.30 (dt, J=8.4, 1.0 Hz, 2H), 6.26 (t, J=4.0 Hz, 1H), 4.49 (ddt, J=5.7, 2.1, 1.0 Hz, 2H), 4.44 (dt, J=9.2, 7.4 Hz, 1H), 4.26 (dt, J=9.9, 6.7 Hz, 1H), 3.27-3.14 (m, 2H), 2.61 (tdd, J=8.9, 6.9, 4.2 Hz, 1H), 2.13 (ddd, J=15.0, 8.8, 7.3 Hz, 1H), 1.99 (ddd, J=15.2, 8.8, 7.3 Hz, 1H), 1.86-1.59 (m, 7H), 1.57-1.34 (m, 8H), 1.31-1.20 (m, 2H). ESI-MS m/z 677.33 $[M+H]^+$.

Example 276 N—((S)-14(S)-4-(2,4,6-trimethylbenzylamino)-3,4-dione-1-((S)-2-oxopiperidin-3-yl)but-2-yl)amino)-3-cyclohexyl-1-oxopropan-2-yl)-benzofuran-2-carboxamide (A276)

$^1$H NMR (500 MHz, Chloroform-d) δ 8.19 (d, J=9.9 Hz, 1H), 7.89 (d, J=9.3 Hz, 1H), 7.79-7.72 (m, 2H), 7.75-7.68 (m, 1H), 7.60-7.52 (m, 1H), 7.43-7.34 (m, 2H), 7.08 (dd, J=8.1, 7.1 Hz, 1H), 7.00-6.95 (m, 2H), 6.26 (t, J=4.0 Hz, 1H), 4.53-4.44 (m, 2H), 4.46-4.39 (m, 1H), 4.26 (dt, J=9.9, 6.7 Hz, 1H), 3.27-3.14 (m, 2H), 2.61 (tdd, J=8.9, 6.9, 4.2 Hz, 1H), 2.13 (ddd, J=15.0, 8.8, 7.3 Hz, 1H), 1.99 (ddd, J=15.2, 8.8, 7.3 Hz, 1H), 1.86-1.59 (m, 7H), 1.57-1.34 (m, 8H), 1.31-1.20 (m, 2H). ESI-MS m/z 629.33 $[M+H]^+$.

Example 277 N—((S)-1-(((S)-4-(4-cyanobenzylamino)-3,4-dione-1-((S)-2-oxopiperidin-3-yl)but-2-yl)amino)-3-cyclohexyl-1-oxopropan-2-yl)-benzofuran-2-carboxamide (A277)

$^1$H NMR (500 MHz, Chloroform-d) δ 8.19 (d, J=9.9 Hz, 1H), 8.13 (t, J=5.7 Hz, 1H), 7.89 (d, J=9.3 Hz, 1H), 7.76 (d, J=1.9 Hz, 1H), 7.75-7.68 (m, 1H), 7.62-7.56 (m, 2H), 7.59-7.52 (m, 1H), 7.44-7.34 (m, 4H), 6.26 (t, J=4.0 Hz, 1H), 4.49 (ddt, J=5.7, 2.1, 0.9 Hz, 2H), 4.44 (dt, J=9.2, 7.4 Hz, 1H), 4.26 (dt, J=9.9, 6.7 Hz, 1H), 3.27-3.14 (m, 2H), 2.61 (tdd, J=8.9, 6.9, 4.2 Hz, 1H), 2.13 (ddd, J=15.0, 8.8, 7.3 Hz, 1H), 1.99 (ddd, J=15.2, 8.8, 7.3 Hz, 1H), 1.86-1.59 (m, 7H), 1.57-1.34 (m, 8H), 1.31-1.20 (m, 2H). ESI-MS m/z 626.29 $[M+H]^+$.

Example 278 N—((S)-1-(((S)-4-(4-trifluoromethoxybenzylamino)-3, 4-dione-1-((S)-2-oxopiperidin-3-yl)but-2-yl) amino)-3-cyclohexyl-1-oxopropan-2-yl)-benzofuran-2-carboxamide (A278)

$^1$H NMR (500 MHz, Chloroform-d) δ 8.19 (d, J=9.9 Hz, 1H), 8.13 (t, J=5.7 Hz, 1H), 7.89 (d, J=9.3 Hz, 1H), 7.76 (d, J=1.9 Hz, 1H), 7.75-7.68 (m, 1H), 7.60-7.52 (m, 1H), 7.43-7.34 (m, 2H), 7.23 (dt, J=8.3, 1.1 Hz, 2H), 7.17-7.11 (m, 2H), 6.26 (t, J=4.0 Hz, 1H), 4.50 (ddt, J=5.8, 3.6, 1.0 Hz, 2H), 4.44 (dt, J=9.2, 7.4 Hz, 1H), 4.26 (dt, J=9.9, 6.7 Hz, 1H), 3.27-3.14 (m, 2H), 2.61 (tdd, J=8.9, 6.9, 4.2 Hz, 1H), 2.13 (ddd, J=15.0, 8.8, 7.3 Hz, 1H), 1.99 (ddd, J=15.2, 8.8, 7.3 Hz, 1H), 1.86-1.59 (m, 7H), 1.57-1.34 (m, 8H), 1.31-1.20 (m, 2H). ESI-MS m/z 685.27 $[M+H]^+$.

Example 279 N—((S)-1-(((S)-4-(2-cyanobenzylamino)-3, 4-dione-1-((S)-2-oxopiperidin-3-yl)but-2-yl) amino)-3-cyclohexyl-1-oxopropan-2-yl)-benzofuran-2-carboxamide (A279)

$^1$H NMR (500 MHz, Chloroform-d) δ 8.23-8.16 (m, 2H), 7.89 (d, J=9.3 Hz, 1H), 7.76 (d, J=1.9 Hz, 1H), 7.75-7.68 (m, 1H), 7.64-7.58 (m, 1H), 7.61-7.52 (m, 1H), 7.43-7.32 (m, 5H), 6.26 (t, J=4.0 Hz, 1H), 4.56 (dd, J=5.7, 1.0 Hz, 2H), 4.44 (dt, J=9.2, 7.4 Hz, 1H), 4.26 (dt, J=9.9, 6.7 Hz, 1H), 3.27-3.14 (m, 2H), 2.61 (tdd, J=8.9, 6.9, 4.2 Hz, 1H), 2.13 (ddd, J=15.0, 8.8, 7.3 Hz, 1H), 1.99 (ddd, J=15.2, 8.8, 7.3 Hz, 1H), 1.86-1.59 (m, 7H), 1.57-1.34 (m, 8H), 1.31-1.20 (m, 2H). ESI-MS m/z 626.30 $[M+H]^+$.

Example 280 N—((S)-1-(((S)-4-(benzylamino)-3,4-dione-1-((S)-2-oxopiperidin-3-yl)but-2-yl)amino)-3-cyclohexyl-1-oxopropan-2-yl)-7-azaindole-2-carboxamide (A280)

$^1$H NMR (500 MHz, Chloroform-d) δ 8.69 (dd, J=3.8, 1.8 Hz, 1H), 8.48 (d, J=8.2 Hz, 1H), 8.28 (dt, J=7.3, 1.9 Hz, 1H), 8.11 (t, J=5.8 Hz, 1H), 7.89 (d, J=9.3 Hz, 1H), 7.54 (d, J=2.2 Hz, 1H), 7.40-7.32 (m, 1H), 7.34-7.30 (m, 1H), 7.32-7.27 (m, 2H), 7.30-7.22 (m, 2H), 6.26 (t, J=4.0 Hz, 1H), 4.48 (t, J=1.0 Hz, 1H), 4.49-4.39 (m, 3H), 3.27-3.14 (m, 2H), 2.61 (tdd, J=8.9, 6.9, 4.2 Hz, 1H), 2.13 (ddd, J=15.0, 8.8, 7.3 Hz, 1H), 1.99 (ddd, J=15.2, 8.8, 7.3 Hz, 1H), 1.86-1.59 (m, 7H), 1.57-1.34 (m, 8H), 1.31-1.20 (m, 2H). ESI-MS m/z 601.31 $[M+H]^+$.

Example 281 N—((S)-1-(((S)-4-(benzylamino)-3,4-dione-1-((S)-2-oxopiperidin-3-yl)but-2-yl)amino)-3-cyclohexyl-1-oxopropan-2-yl)-5-chloro-benzofuran-2-carboxamide (A281)

$^1$H NMR (500 MHz, Chloroform-d) δ 8.19-8.08 (m, 2H), 7.89 (d, J=9.3 Hz, 1H), 7.83 (t, J=2.1 Hz, 1H), 7.75 (d, J=2.1 Hz, 1H), 7.69 (d, J=8.4 Hz, 1H), 7.48 (dd, J=8.4, 2.0 Hz, 1H), 7.35-7.22 (m, 5H), 6.26 (t, J=4.0 Hz, 1H), 4.50-4.39 (m, 3H), 4.26 (dt, J=9.9, 6.7 Hz, 1H), 3.27-3.14 (m, 2H), 2.61 (tdd, J=8.9, 6.9, 4.2 Hz, 1H), 2.13 (ddd, J=15.0, 8.8, 7.3 Hz, 1H), 1.99 (ddd, J=15.2, 8.8, 7.3 Hz, 1H), 1.86-1.74 (m, 3H), 1.77-1.59 (m, 4H), 1.57-1.34 (m, 8H), 1.31-1.20 (m, 2H). ESI-MS m/z 635.26 $[M+H]^+$.

Example 282 N—((S)-1-(((S)-4-(benzylamino)-3,4-dione-1-((S)-2-oxopiperidin-3-yl)but-2-yl)amino)-3-cyclohexyl-1-oxopropan-2-yl)-5-methoxy-benzofuran-2-carboxamide (A282)

$^1$H NMR (500 MHz, Chloroform-d) δ 8.16 (d, J=9.9 Hz, 1H), 8.11 (t, J=5.8 Hz, 1H), 7.89 (d, J=9.3 Hz, 1H), 7.67 (d, J=2.1 Hz, 1H), 7.51 (d, J=8.4 Hz, 1H), 7.35-7.22 (m, 5H), 7.16 (t, J=2.0 Hz, 1H), 7.08 (dd, J=8.4, 1.8 Hz, 1H), 6.26 (t, J=4.0 Hz, 1H), 4.47 (dt, J=5.7, 1.0 Hz, 2H), 4.44 (dt, J=9.2, 7.4 Hz, 1H), 4.26 (dt, J=9.9, 6.7 Hz, 1H), 3.82 (s, 2H), 3.27-3.14 (m, 2H), 2.61 (tdd, J=8.9, 6.9, 4.2 Hz, 1H), 2.13 (ddd, J=15.0, 8.8, 7.3 Hz, 1H), 1.99 (ddd, J=15.2, 8.8, 7.3 Hz, 1H), 1.86-1.71 (m, 4H), 1.75-1.59 (m, 3H), 1.57-1.34 (m, 8H), 1.31-1.20 (m, 2H). ESI-MS m/z 631.31 $[M+H]^+$.

Example 283 N—((R)-1-(((S)-4-(benzylamino)-3,4-dione-1-((S)-2-oxopiperidin-3-yl)but-2-yl)amino)-3-cyclohexyl-1-oxopropan-2-yl)-benzofuran-2-carboxamide (A283)

$^1$H NMR (500 MHz, Chloroform-d) δ 8.19 (d, J=9.9 Hz, 1H), 8.11 (t, J=5.8 Hz, 1H), 7.89 (d, J=9.3 Hz, 1H), 7.76 (d, J=1.9 Hz, 1H), 7.75-7.68 (m, 1H), 7.60-7.52 (m, 1H), 7.43-7.35 (m, 2H), 7.35-7.22 (m, 5H), 6.26 (t, J=4.0 Hz, 1H), 4.50-4.39 (m, 3H), 4.26 (dt, J=9.9, 6.7 Hz, 1H), 3.27-3.14 (m, 2H), 2.61 (tdd, J=8.9, 6.9, 4.2 Hz, 1H), 2.13 (ddd, J=15.0, 8.8, 7.3 Hz, 1H), 1.99 (ddd, J=15.2, 8.8, 7.3 Hz, 1H), 1.86-1.59 (m, 7H), 1.57-1.34 (m, 8H), 1.32-1.20 (m, 2H). ESI-MS m/z 601.29 $[M+H]^+$.

Example 284 N—((S)-1-(((S)-4-(benzylamino)-3,4-dione-14(S)-2-oxopiperidin-3-yl)but-2-yl)amino)-3-(3-fluorophenyl)-1-oxopropan-2-yl)-benzofuran-2-carboxamide (A284)

$^1$H NMR (500 MHz, Chloroform-d) δ 8.37 (d, J=9.7 Hz, 1H), 8.11 (t, J=5.8 Hz, 1H), 7.83 (d, J=9.3 Hz, 1H), 7.76 (d, J=1.9 Hz, 1H), 7.75-7.68 (m, 1H), 7.60-7.52 (m, 1H), 7.43-7.35 (m, 2H), 7.35-7.22 (m, 6H), 7.01 (td, J=7.8, 1.9 Hz, 2H), 6.96 (dtt, J=7.9, 1.9, 1.0 Hz, 1H), 6.26 (t, J=4.0 Hz, 1H), 4.78 (dt, J=9.7, 6.2 Hz, 1H), 4.54-4.46 (m, 1H), 4.48 (s, 1H), 4.47 (t, J=0.9 Hz, 1H), 3.27-3.14 (m, 2H), 3.05-2.93 (m, 2H), 2.61 (tdd, J=8.9, 6.9, 4.3 Hz, 1H), 2.13 (ddd, J=15.0, 8.8, 7.3 Hz, 1H), 1.99 (ddd, J=15.2, 8.8, 7.3 Hz, 1H), 1.81-1.61 (m, 4H). ESI-MS m/z 613.24 $[M+H]^+$.

Example 285 N—((S)-1-(((S)-4-(tert-butylamino)-3,4-dione-1-((S)-2-oxopyrrolidin-3-yl)but-2-yl)amino)-3-phenyl-1-oxopropan-2-yl)-5-fluoro-indole-2-carboxamide (A285)

$^1$H NMR (500 MHz, Chloroform-d) δ 9.91 (s, 1H), 8.35 (d, J=8.1 Hz, 1H), 7.83 (d, J=9.3 Hz, 1H), 7.63 (dt, J=8.0, 2.5 Hz, 1H), 7.50 (dd, J=7.2, 5.0 Hz, 1H), 7.30-7.14 (m, 7H), 7.08 (ddd, J=8.1, 7.1, 2.7 Hz, 1H), 6.13 (t, J=3.1 Hz, 1H), 4.78 (dt, J=8.1, 6.2 Hz, 1H), 4.44 (dt, J=9.3, 7.3 Hz, 1H), 3.33-3.26 (m, 1H), 3.29-3.22 (m, 1H), 3.08-3.01 (m, 1H), 3.04-2.97 (m, 1H), 2.68 (tdd, J=7.7, 5.7, 3.9 Hz, 1H), 2.17-2.08 (m, 1H), 2.02 (dt, J=15.0, 7.5 Hz, 1H), 1.94-1.86 (m, 1H), 1.82 (dtd, J=12.2, 3.7, 2.3 Hz, 1H). ESI-MS m/z 564.25 $[M+H]^+$.

Example 286 N—((S)-1-(((S)-4-(cyclohexylamino)-3,4-dione-1-((S)-2-oxopyrrolidin-3-yl)but-2-yl)amino)-3-cyclohexyl-1-oxopropan-2-yl)-5-methoxy-indole-2-carboxamide (A286)

$^1$H NMR (500 MHz, Chloroform-d) δ 9.91 (s, 1H), 8.32 (d, J=8.2 Hz, 1H), 7.89 (d, J=9.3 Hz, 1H), 7.48 (d, J=8.2 Hz, 1H), 7.37-7.31 (m, 2H), 6.82 (dd, J=7.3, 2.4 Hz, 1H), 6.13 (t, J=3.1 Hz, 1H), 4.49-4.36 (m, 2H), 3.83 (s, 2H), 3.67 (dp, J=8.2, 4.9 Hz, 1H), 3.33-3.22 (m, 2H), 2.68 (tdd, J=7.7, 5.7, 3.9 Hz, 1H), 2.13 (dt, J=15.2, 7.5 Hz, 1H), 2.02 (dt, J=15.0, 7.5 Hz, 1H), 1.94-1.33 (m, 21H), 1.31-1.20 (m, 2H). ESI-MS m/z 608.34 $[M+H]^+$.

Example 287 N—((S)-1-(((S)-4-(cyclohexylamino)-3,4-dione-1-((S)-2-oxopyrrolidin-3-yl)but-2-yl)amino)-3-phenyl-1-oxopropan-2-yl)-1-methyl-indole-2-carboxamide (A287)

$^1$H NMR (500 MHz, Chloroform-d) δ 8.18 (d, J=7.7 Hz, 1H), 7.85-7.75 (m, 2H), 7.48 (d, J=8.2 Hz, 1H), 7.43 (dd, J=8.3, 1.2 Hz, 1H), 7.31-7.15 (m, 8H), 6.13 (t, J=3.1 Hz, 1H), 4.75 (dt, J=7.5, 6.2 Hz, 1H), 4.41 (dt, J=9.2, 7.4 Hz, 1H), 3.93 (s, 2H), 3.67 (dp, J=8.2, 4.9 Hz, 1H), 3.33-3.26 (m, 1H), 3.29-3.22 (m, 1H), 3.02 (ddt, J=6.2, 3.2, 1.0 Hz, 2H), 2.67 (tdd, J=7.8, 5.7, 3.9 Hz, 1H), 2.13 (dt, J=15.3, 7.5 Hz, 1H), 2.02 (dt, J=15.0, 7.5 Hz, 1H), 1.94-1.86 (m, 1H), 1.82 (dtd, J=12.2, 3.7, 2.3 Hz, 1H), 1.75-1.40 (m, 8H), 1.43-1.36 (m, 2H), 1.40-1.33 (m, 1H). ESI-MS m/z 586.29 $[M+H]^+$.

Example 288 N—((S)-1-(((S)-4-(cyclohexylamino)-3,4-dione-1-((S)-2-oxopyrrolidin-3-yl)but-2-yl)amino)-3-phenyl-1-oxopropan-2-yl)-5-fluoro-indole-2-carboxamide (A288)

$^1$H NMR (500 MHz, Chloroform-d) δ 9.91 (s, 1H), 8.35 (d, J=8.0 Hz, 1H), 7.83 (d, J=9.3 Hz, 1H), 7.63 (dt, J=7.9, 2.5 Hz, 1H), 7.53-7.46 (m, 2H), 7.30-7.14 (m, 5H), 7.08 (ddd, J=8.1, 7.1, 2.7 Hz, 1H), 6.13 (t, J=3.1 Hz, 1H), 4.78 (dt, J=8.1, 6.2 Hz, 1H), 4.41 (dt, J=9.2, 7.4 Hz, 1H), 3.67 (dp, J=8.2, 4.9 Hz, 1H), 3.33-3.26 (m, 1H), 3.29-3.22 (m, 1H), 3.02 (ddt, J=6.2, 3.2, 1.0 Hz, 2H), 2.68 (tdd, J=7.7, 5.7, 3.9 Hz, 1H), 2.13 (dt, J=15.2, 7.5 Hz, 1H), 2.02 (dt, J=15.0, 7.5 Hz, 1H), 1.94-1.86 (m, 1H), 1.82 (dtd, J=12.2, 3.7, 2.3 Hz, 1H), 1.75-1.33 (m, 11H). ESI-MS m/z 590.27 $[M+H]^+$.

Example 289 N—((S)-1-(((S)-4-(benzylamino)-3,4-dione-14(S)-2-oxopiperidin-3-yl)but-2-yl)amino)-3-(4-fluorophenyl)-1-oxopropan-2-yl)-benzofuran-2-carboxamide (A289)

$^1$H NMR (500 MHz, Chloroform-d) δ 8.37 (d, J=9.7 Hz, 1H), 8.11 (t, J=5.8 Hz, 1H), 7.83 (d, J=9.3 Hz, 1H), 7.76 (d, J=1.9 Hz, 1H), 7.75-7.68 (m, 1H), 7.60-7.52 (m, 1H), 7.43-7.35 (m, 2H), 7.38-7.22 (m, 8H), 7.07-7.00 (m, 2H), 6.26 (t, J=4.0 Hz, 1H), 4.75 (dt, J=9.7, 6.2 Hz, 1H), 4.54-4.46 (m, 1H), 4.50-4.45 (m, 1H), 4.47 (t, J=0.9 Hz, 1H), 3.27-3.14 (m, 2H), 3.08 (ddt, J=6.2, 2.9, 1.1 Hz, 2H), 2.61 (tdd, J=8.9, 6.9, 4.3 Hz, 1H), 2.13 (ddd, J=15.0, 8.8, 7.3 Hz, 1H), 1.99 (ddd, J=15.2, 8.8, 7.3 Hz, 1H), 1.81-1.61 (m, 4H). ESI-MS m/z 613.24 [M+H]$^+$.

Example 290 N—((R)-1-(((S)-4-(benzylamino)-3,4-dione-14(S)-2-oxopiperidin-3-yl)but-2-yl) amino)-3-(3,4-difluorophenyl)-1-oxopropan-2-yl)-benzofuran-2-carboxamide (A290)

$^1$H NMR (500 MHz, Chloroform-d) δ 8.37 (d, J=9.7 Hz, 1H), 8.11 (t, J=5.8 Hz, 1H), 7.83 (d, J=9.3 Hz, 1H), 7.76 (d, J=1.9 Hz, 1H), 7.75-7.68 (m, 1H), 7.60-7.52 (m, 1H), 7.43-7.35 (m, 2H), 7.35-7.22 (m, 5H), 7.10-7.03 (m, 1H), 7.03-6.96 (m, 2H), 6.26 (t, J=4.0 Hz, 1H), 4.78 (dt, J=9.7, 6.2 Hz, 1H), 4.54-4.46 (m, 1H), 4.50-4.45 (m, 1H), 4.47 (t, J=0.9 Hz, 1H), 3.27-3.14 (m, 2H), 3.07-2.95 (m, 2H), 2.61 (tdd, J=8.9, 6.9, 4.3 Hz, 1H), 2.13 (ddd, J=15.0, 8.8, 7.3 Hz, 1H), 1.99 (ddd, J=15.2, 8.8, 7.3 Hz, 1H), 1.81-1.61 (m, 4H). ESI-MS m/z 631.23 [M+H]$^+$.

Example 291 N—((S)-1-(((S)-4-(tert-butylamino)-3,4-dione-1-((S)-2-oxopyrrolidin-3-yl)but-2-yl) amino)-3-phenyl-1-oxopropan-2-yl)-benzofuran-2-carboxamide (A291)

$^1$H NMR (500 MHz, Chloroform-d) δ 8.37 (d, J=9.7 Hz, 1H), 7.83 (d, J=9.2 Hz, 1H), 7.76 (d, J=2.2 Hz, 1H), 7.75-7.68 (m, 1H), 7.60-7.52 (m, 1H), 7.43-7.34 (m, 2H), 7.30-7.16 (m, 6H), 6.13 (t, J=3.1 Hz, 1H), 4.70 (dt, J=9.7, 6.2 Hz, 1H), 4.44 (dt, J=9.3, 7.3 Hz, 1H), 3.33-3.26 (m, 1H), 3.29-3.22 (m, 1H), 3.08-2.97 (m, 2H), 2.68 (tdd, J=7.7, 5.7, 3.9 Hz, 1H), 2.17-2.08 (m, 1H), 2.02 (dt, J=15.0, 7.5 Hz, 1H), 1.94-1.86 (m, 1H), 1.82 (dtd, J=12.2, 3.7, 2.3 Hz, 1H). ESI-MS m/z 547.25 [M+H]$^+$.

Example 292 N—((S)-1-(((S)-4-(cyclohexylamino)-3,4-dione-1-((S)-2-oxopyrrolidin-3-yl)but-2-yl) amino)-3-cyclohexyl-1-oxopropan-2-yl)-2,3-dihydrobenzo[b]1, 4-dioxin-6-carboxamide (A292)

$^1$H NMR (500 MHz, Chloroform-d) δ 7.95-7.87 (m, 2H), 7.54-7.46 (m, 2H), 7.40 (d, J=2.1 Hz, 1H), 6.89 (d, J=8.5 Hz, 1H), 6.13 (t, J=3.1 Hz, 1H), 4.40 (dt, J=9.3, 7.3 Hz, 1H), 4.36-4.29 (m, 1H), 4.29 (dd, J=4.8, 2.4 Hz, 2H), 4.27 (ddd, J=4.7, 3.0, 2.2 Hz, 2H), 3.67 (dp, J=8.2, 4.9 Hz, 1H), 3.33-3.26 (m, 1H), 3.29-3.22 (m, 1H), 2.67 (tdd, J=7.8, 5.7, 3.9 Hz, 1H), 2.13 (dt, J=15.2, 7.5 Hz, 1H), 2.02 (dt, J=15.0, 7.5 Hz, 1H), 1.94-1.86 (m, 1H), 1.86-1.77 (m, 2H), 1.80-1.66 (m, 4H), 1.68-1.61 (m, 1H), 1.64-1.58 (m, 1H), 1.61-1.49 (m, 2H), 1.53-1.38 (m, 10H), 1.41-1.33 (m, 2H), 1.31-1.20 (m, 2H). ESI-MS m/z 597.33 [M+H]$^+$.

Example 293 N—((S)-1-(((S)-4-((R)-1-phenyl-ethyl)-amino)-3,4-dione-1-((S)-2-oxopyrrolidin-3-yl) but-2-yl)amino)-3-cyclohexyl-1-oxopropan-2-yl)-quinoline-2-carboxamide (A293)

$^1$H NMR (500 MHz, Chloroform-d) δ 8.39-8.32 (m, 2H), 8.20 (d, J=8.3 Hz, 1H), 8.07-8.01 (m, 1H), 7.97-7.91 (m, 1H), 7.89 (d, J=9.3 Hz, 1H), 7.73 (td, J=7.9, 1.1 Hz, 1H), 7.53 (td, J=7.8, 1.2 Hz, 1H), 7.36-7.29 (m, 2H), 7.32-7.22 (m, 4H), 6.13 (t, J=3.1 Hz, 1H), 5.01 (dtdd, J=8.4, 6.1, 5.1, 1.1 Hz, 1H), 4.48-4.37 (m, 2H), 3.33-3.26 (m, 1H), 3.29-3.22 (m, 1H), 2.68 (tdd, J=7.7, 5.7, 3.9 Hz, 1H), 2.17-2.08 (m, 1H), 2.02 (dt, J=15.0, 7.5 Hz, 1H), 1.94-1.86 (m, 1H), 1.86-1.68 (m, 4H), 1.57-1.34 (m, 12H), 1.31-1.20 (m, 2H). ESI-MS m/z 612.31 [M+H]$^+$.

Example 294 N—((S)-1-(((S)-4-morpholinyl-3,4-dione-1-((S)-2-oxopyrrolidin-3-yl)but-2-yl)amino)-3-cyclohexyl-1-oxopropan-2-yl)-quinoline-2-carboxamide (A294)

$^1$H NMR (500 MHz, Chloroform-d) δ 8.39-8.32 (m, 2H), 8.20 (d, J=8.3 Hz, 1H), 8.07-8.01 (m, 1H), 7.94 (dt, J=8.0, 0.8 Hz, 1H), 7.84 (d, J=9.7 Hz, 1H), 7.73 (td, J=7.9, 1.1 Hz, 1H), 7.53 (td, J=7.9, 1.2 Hz, 1H), 6.13 (t, J=3.1 Hz, 1H), 4.52 (dt, J=9.7, 7.7 Hz, 1H), 4.41 (dt, J=9.3, 6.6 Hz, 1H), 3.71 (ddd, J=9.7, 6.3, 3.6 Hz, 4H), 3.63 (dd, J=6.4, 3.6 Hz, 2H), 3.55 (dd, J=6.4, 3.6 Hz, 2H), 3.33-3.26 (m, 1H), 3.29-3.22 (m, 1H), 2.64 (tdd, J=7.8, 5.7, 3.9 Hz, 1H), 2.16 (dt, J=15.3, 7.6 Hz, 1H), 2.01 (dt, J=15.1, 7.7 Hz, 1H), 1.94-1.86 (m, 1H), 1.86-1.80 (m, 1H), 1.82-1.77 (m, 1H), 1.80-1.75 (m, 1H), 1.77-1.68 (m, 1H), 1.57-1.34 (m, 8H), 1.31-1.20 (m, 2H). ESI-MS m/z 578.29 [M+H]$^+$.

Example 295 N—((S)-14(S)-4-((S)-1-phenyl-ethyl)-amino)-3,4-dione-1-((S)-2-oxopyrrolidin-3-yl)but-2-yl)amino)-3-cyclohexyl-1-oxopropan-2-yl)-quinoline-2-carboxamide (A295)

$^1$H NMR (500 MHz, Chloroform-d) δ 8.39-8.32 (m, 2H), 8.20 (d, J=8.3 Hz, 1H), 8.07-8.01 (m, 1H), 7.97-7.91 (m, 1H), 7.89 (d, J=9.3 Hz, 1H), 7.73 (td, J=7.9, 1.1 Hz, 1H), 7.53 (td, J=7.8, 1.2 Hz, 1H), 7.36-7.29 (m, 2H), 7.32-7.22 (m, 4H), 6.13 (t, J=3.1 Hz, 1H), 5.03 (dqt, J=8.1, 6.1, 1.1 Hz, 1H), 4.48-4.37 (m, 2H), 3.33-3.26 (m, 1H), 3.29-3.22 (m, 1H), 2.68 (tdd, J=7.7, 5.7, 3.9 Hz, 1H), 2.17-2.08 (m, 1H), 2.02 (dt, J=15.0, 7.5 Hz, 1H), 1.94-1.86 (m, 1H), 1.86-1.68 (m, 4H), 1.57-1.34 (m, 12H), 1.31-1.20 (m, 2H). ESI-MS m/z 612.31 [M+H]$^+$.

Example 296 N—((S)-14(S)-4-diethylamino)-3,4-dione-1-((S)-2-oxopyrrolidin-3-yl)but-2-yl)amino)-3-cyclohexyl-1-oxopropan-2-yl)-quinoline-2-carboxamide (A296)

$^1$H NMR (500 MHz, Chloroform-d) δ 8.39-8.32 (m, 2H), 8.20 (d, J=8.3 Hz, 1H), 8.07-8.01 (m, 1H), 7.97-7.91 (m, 1H), 7.85 (d, J=9.7 Hz, 1H), 7.73 (td, J=7.9, 1.1 Hz, 1H), 7.53 (td, J=7.8, 1.2 Hz, 1H), 6.13 (t, J=3.1 Hz, 1H), 4.52 (dt, J=9.7, 7.7 Hz, 1H), 4.41 (dt, J=9.3, 6.6 Hz, 1H), 3.45 (q, J=7.3 Hz, 4H), 3.33-3.26 (m, 1H), 3.29-3.22 (m, 1H), 2.67 (tdd, J=7.9, 5.7, 3.9 Hz, 1H), 2.17 (dt, J=15.3, 7.7 Hz, 1H), 2.01 (dt, J=15.1, 7.6 Hz, 1H), 1.94-1.86 (m, 1H), 1.86-1.70 (m, 4H), 1.57-1.34 (m, 8H), 1.31-1.20 (m, 2H), 1.20 (t, J=7.3 Hz, 6H). ESI-MS m/z 564.31 [M+H]$^+$.

Example 297 N—((S)-14(S)-4-(4-fluorobenzylamino)-3,4-dione-1-((S)-2-oxopyrrolidin-3-yl)but-2-yl)amino)-3-cyclohexyl-1-oxopropan-2-yl)-quinoline-2-carboxamide (A297)

$^1$H NMR (500 MHz, Chloroform-d) δ 8.39-8.32 (m, 2H), 8.20 (d, J=8.2 Hz, 1H), 8.13 (t, J=5.7 Hz, 1H), 8.07-8.01 (m, 1H), 7.97-7.91 (m, 1H), 7.89 (d, J=9.3 Hz, 1H), 7.73 (td, J=7.9, 1.1 Hz, 1H), 7.53 (td, J=7.7, 1.1 Hz, 1H), 7.32 (ddt, J=7.5, 5.0, 1.0 Hz, 2H), 7.11-7.03 (m, 2H), 6.13 (t, J=3.1 Hz, 1H), 4.55-4.45 (m, 3H), 4.41 (dt, J=9.3, 6.6 Hz, 1H), 3.33-3.26 (m, 1H), 3.29-3.22 (m, 1H), 2.67 (tdd, J=7.8, 5.7, 3.9 Hz, 1H), 2.13 (dt, J=15.2, 7.5 Hz, 1H), 2.02 (dt, J=15.0, 7.5 Hz, 1H), 1.94-1.86 (m, 1H), 1.86-1.77 (m, 2H), 1.80-1.75 (m, 1H), 1.77-1.68 (m, 1H), 1.57-1.34 (m, 8H), 1.31-1.20 (m, 2H). ESI-MS m/z 616.28 [M+H]$^+$.

Example 298 N—((S)-14(S)-4-(benzylamino)-3,4-dione-1-((S)-2-oxopyrrolidin-3-yl)but-2-yl)amino)-3-cyclohexyl-1-oxopropan-2-yl)-5-bromoimidazolo [1,2-a]pyridine-2-carboxamide (A298)

$^1$H NMR (500 MHz, Chloroform-d) δ 8.39-8.32 (m, 2H), 8.20 (d, J=8.2 Hz, 1H), 8.13 (t, J=5.7 Hz, 1H), 8.07-8.01 (m, 1H), 7.94 (dt, J=8.0, 0.8 Hz, 1H), 7.89 (d, J=9.3 Hz, 1H), 7.73 (td, J=7.9, 1.1 Hz, 1H), 7.53 (td, J=7.9, 1.2 Hz, 1H), 7.19 (dt, J=8.4, 1.0 Hz, 2H), 6.87-6.82 (m, 2H), 6.13 (t, J=3.1 Hz, 1H), 4.55-4.49 (m, 1H), 4.52-4.44 (m, 2H), 4.41 (dt, J=9.3, 6.6 Hz, 1H), 3.78 (s, 2H), 3.33-3.26 (m, 1H), 3.29-3.22 (m, 1H), 2.67 (tdd, J=7.8, 5.7, 3.9 Hz, 1H), 2.13 (dt, J=15.2, 7.5 Hz, 1H), 2.07-1.99 (m, 1H), 1.94-1.86 (m, 1H), 1.86-1.68 (m, 4H), 1.57-1.34 (m, 8H), 1.31-1.20 (m, 2H). ESI-MS m/z 628.31 [M+H]$^+$.

Example 299 N—((S)-14(S)-4-(benzylamino)-3,4-dione-1-((S)-2-oxopyrrolidin-3-yl)but-2-yl)amino)-3-cyclohexyl-1-oxopropan-2-yl)-5-bromoimidazolo [1,2-a]pyridine-2-carboxamide (A299)

$^1$H NMR (500 MHz, Chloroform-d) δ 9.03 (d, J=6.6 Hz, 1H), 8.11 (t, J=5.8 Hz, 1H), 8.01 (t, J=1.6 Hz, 1H), 7.92 (dd, J=23.3, 8.9 Hz, 2H), 7.79 (dd, J=7.4, 1.6 Hz, 1H), 7.44 (s, OH), 7.35-7.17 (m, 6H), 6.69 (dd, J=3.3, 2.0 Hz, 1H), 6.13 (t, J=3.1 Hz, 1H), 4.54-4.46 (m, 1H), 4.47 (dd, J=5.8, 0.9 Hz, 2H), 4.33 (dt, J=8.4, 6.7 Hz, 1H), 3.33-3.26 (m, 1H), 3.29-3.22 (m, 1H), 2.68 (tdd, J=7.7, 5.7, 3.9 Hz, 1H), 2.17-2.08 (m, 1H), 2.02 (dt, J=15.0, 7.5 Hz, 1H), 1.94-1.86 (m, 1H), 1.86-1.69 (m, 4H), 1.57-1.34 (m, 9H), 1.31-1.20 (m, 2H). ESI-MS m/z 586.30 [M+H]$^+$.

Example 300 N—((S)-14(S)-4-(benzylamino)-3,4-dione-1-((S)-2-oxopyrrolidin-3-yl)but-2-yl) amino)-3-cyclohexyl-1-oxopropan-2-yl)-5-bromo-imidazolo[1,2-a]pyridine-2-carboxamide (A300)

$^1$H NMR (500 MHz, Chloroform-d) δ 8.74-8.70 (m, 1H), 8.58 (d, J=9.3 Hz, 1H), 8.47 (s, 1H), 8.11 (t, J=5.8 Hz, 1H), 7.89 (d, J=9.3 Hz, 1H), 7.52 (dd, J=8.8, 1.3 Hz, 1H), 7.42 (d, J=8.8 Hz, 1H), 7.35-7.22 (m, 5H), 6.13 (t, J=3.1 Hz, 1H), 4.54-4.46 (m, 1H), 4.48 (d, J=0.9 Hz, 1H), 4.47 (t, J=0.9 Hz, 1H), 4.41 (dt, J=9.3, 6.6 Hz, 1H), 3.33-3.26 (m, 1H), 3.29-3.22 (m, 1H), 2.68 (tdd, J=7.7, 5.7, 3.9 Hz, 1H), 2.17-2.08 (m, 1H), 2.02 (dt, J=15.0, 7.5 Hz, 1H), 1.94-1.86 (m, 1H), 1.86-1.68 (m, 4H), 1.57-1.34 (m, 8H), 1.31-1.20 (m, 2H). ESI-MS m/z 665.20 [M+H]$^+$.

Example 301 N—((S)-1-(((S)-4-(benzylamino)-3,4-dione-1-((S)-2-oxopyrrolidin-3-yl)but-2-yl)amino)-3-cyclohexyl-1-oxopropan-2-yl)-7-bromo-quinoline-2-carboxamide (A301)

$^1$H NMR (500 MHz, Chloroform-d) δ 8.36-8.30 (m, 2H), 8.19 (d, J=2.1 Hz, 1H), 8.15 (d, J=8.2 Hz, 1H), 8.11 (t, J=5.8 Hz, 1H), 7.94-7.86 (m, 2H), 7.62 (dd, J=8.5, 2.3 Hz, 1H), 7.35-7.22 (m, 5H), 6.13 (t, J=3.1 Hz, 1H), 4.54-4.45 (m, 3H), 4.41 (dt, J=9.3, 6.6 Hz, 1H), 3.33-3.26 (m, 1H), 3.29-3.22 (m, 1H), 2.68 (tdd, J=7.7, 5.7, 3.9 Hz, 1H), 2.17-2.08 (m, 1H), 2.02 (dt, J=15.0, 7.5 Hz, 1H), 1.94-1.86 (m, 1H), 1.86-1.80 (m, 1H), 1.82-1.77 (m, 1H), 1.80-1.75 (m, 1H), 1.77-1.68 (m, 1H), 1.57-1.34 (m, 8H), 1.31-1.20 (m, 2H). ESI-MS m/z 676.20 [M+H]$^+$.

Example 302 N—((S)-1-(((S)-4-(benzylamino)-3,4-dione-1-((S)-2-oxopyrrolidin-3-yl)but-2-yl) amino)-3-cyclohexyl-1-oxopropan-2-yl)-2,3-dihydrobenzo [b]1, 4-dioxin-6-carboxamide (A302)

$^1$H NMR (500 MHz, Chloroform-d) δ 8.11 (t, J=5.8 Hz, 1H), 7.95-7.87 (m, 2H), 7.52 (dd, J=8.4, 2.2 Hz, 1H), 7.40 (d, J=2.1 Hz, 1H), 7.35-7.22 (m, 5H), 6.89 (d, J=8.5 Hz, 1H), 6.13 (t, J=3.1 Hz, 1H), 4.54-4.46 (m, 1H), 4.48 (d, J=0.9 Hz, 1H), 4.47 (t, J=0.9 Hz, 1H), 4.36-4.29 (m, 1H), 4.29 (dd, J=4.8, 2.4 Hz, 2H), 4.27 (ddd, J=4.7, 3.0, 2.2 Hz, 2H), 3.33-3.26 (m, 1H), 3.29-3.22 (m, 1H), 2.68 (tdd, J=7.7, 5.7, 3.9 Hz, 1H), 2.17-2.08 (m, 1H), 2.02 (dt, J=15.0, 7.5 Hz, 1H), 1.94-1.86 (m, 1H), 1.86-1.69 (m, 4H), 1.57-1.34 (m, 9H), 1.31-1.20 (m, 2H). ESI-MS m/z 605.29 [M+H]$^+$.

Example 303 N—((S)-1-(((S)-4-(benzylamino)-3,4-dione-1-((S)-2-oxopyrrolidin-3-yl)but-2-yl)amino)-3-cyclohexyl-1-oxopropan-2-yl)-5-methyl-isoxazole-2-carboxamide (A303)

$^1$H NMR (500 MHz, Chloroform-d) δ 8.36 (d, J=9.3 Hz, 1H), 8.11 (t, J=5.8 Hz, 1H), 7.89 (d, J=9.3 Hz, 1H), 7.35-7.22 (m, 5H), 6.50 (s, 1H), 6.13 (t, J=3.1 Hz, 1H), 4.47 (dt, J=5.4, 0.9 Hz, 2H), 4.48-4.37 (m, 2H), 3.33-3.26 (m, 1H), 3.29-3.22 (m, 1H), 2.67 (tdd, J=7.8, 5.7, 3.9 Hz, 1H), 2.52 (s, 2H), 2.13 (dt, J=15.2, 7.5 Hz, 1H), 2.02 (dt, J=15.0, 7.5 Hz, 1H), 1.94-1.86 (m, 1H), 1.86-1.80 (m, 1H), 1.82-1.77 (m, 1H), 1.80-1.75 (m, 1H), 1.77-1.68 (m, 1H), 1.57-1.34 (m, 8H), 1.31-1.20 (m, 2H). ESI-MS m/z 552.27 [M+H]$^+$.

Example 304 N—((S)-1-(((S)-4-(benzylamino)-3,4-dione-1-((S)-2-oxopyrrolidin-3-yl)but-2-yl)amino)-3-(2-fluorophenyl)-1-oxopropan-2-yl)-quinoline-2-carboxamide (A304)

$^1$H NMR (500 MHz, Chloroform-d) δ 8.43-8.32 (m, 2H), 8.20 (d, J=8.2 Hz, 1H), 8.11 (t, J=5.8 Hz, 1H), 8.04 (dd, J=8.1, 1.2 Hz, 1H), 7.97-7.91 (m, 1H), 7.83 (d, J=9.1 Hz, 1H), 7.73 (td, J=7.9, 1.1 Hz, 1H), 7.53 (td, J=7.7, 1.2 Hz, 1H), 7.36-7.15 (m, 7H), 7.10 (td, J=7.9, 1.2 Hz, 1H), 6.13 (t, J=3.1 Hz, 1H), 4.80 (dt, J=9.2, 7.3 Hz, 1H), 4.54-4.46 (m, 1H), 4.47 (dd, J=5.8, 0.9 Hz, 2H), 3.33-3.22 (m, 2H), 3.21 (ddd, J=15.8, 7.4, 0.9 Hz, 1H), 3.09 (ddd, J=15.9, 7.3, 0.7 Hz, 1H), 2.68 (tdd, J=7.7, 5.7, 3.9 Hz, 1H), 2.13 (dt, J=15.2, 7.5 Hz, 1H), 2.07-1.99 (m, 1H), 1.90 (dddd, J=12.1, 6.1, 3.8, 2.5 Hz, 1H), 1.82 (dtd, J=12.2, 3.7, 2.3 Hz, 1H). ESI-MS m/z 610.24 [M+H]$^+$.

Example 305 N—((S)-1-(((S)-4-(benzylamino)-3,4-dione-1-((S)-2-oxopyrrolidin-3-yl)but-2-yl) amino)-3-(3-fluorophenyl)-1-oxopropan-2-yl)-quinoline-2-carboxamide (A305)

$^1$H NMR (500 MHz, Chloroform-d) δ 8.43 (d, J=9.1 Hz, 1H), 8.35 (d, J=8.3 Hz, 1H), 8.20 (d, J=8.2 Hz, 1H), 8.11 (t, J=5.8 Hz, 1H), 8.04 (dd, J=8.1, 1.2 Hz, 1H), 7.97-7.91 (m, 1H), 7.83 (d, J=9.3 Hz, 1H), 7.73 (td, J=7.9, 1.1 Hz, 1H), 7.53 (td, J=7.7, 1.2 Hz, 1H), 7.35-7.22 (m, 6H), 7.01 (td, J=7.8, 1.9 Hz, 2H), 6.96 (dtt, J=7.9, 1.9, 1.0 Hz, 1H), 6.13 (t, J=3.1 Hz, 1H), 4.80 (dt, J=9.3, 6.3 Hz, 1H), 4.54-4.46 (m, 1H), 4.47 (dd, J=5.8, 0.9 Hz, 2H), 3.33-3.22 (m, 2H), 3.05-2.93 (m, 2H), 2.68 (tdd, J=7.7, 5.7, 3.9 Hz, 1H), 2.13 (dt, J=15.2, 7.5 Hz, 1H), 2.07-1.99 (m, 1H), 1.90 (dddd, J=12.1, 6.1, 3.8, 2.4 Hz, 1H), 1.82 (dtd, J=12.3, 3.7, 2.3 Hz, 1H). ESI-MS m/z 610.23 $[M+H]^+$.

Example 306 N—((S)-1-(((S)-4-(benzylamino)-3,4-dione-1-((S)-2-oxopyrrolidin-3-yl)but-2-yl)amino)-3-(4-fluorophenyl)-1-oxopropan-2-yl)-quinoline-2-carboxamide (A306)

$^1$H NMR (500 MHz, Chloroform-d) δ 8.43 (d, J=9.1 Hz, 1H), 8.35 (d, J=8.2 Hz, 1H), 8.20 (d, J=8.3 Hz, 1H), 8.11 (t, J=5.8 Hz, 1H), 8.07-8.01 (m, 1H), 7.97-7.91 (m, 1H), 7.83 (d, J=9.3 Hz, 1H), 7.73 (td, J=7.9, 1.1 Hz, 1H), 7.53 (td, J=7.8, 1.2 Hz, 1H), 7.35-7.22 (m, 7H), 7.07-7.00 (m, 2H), 6.13 (t, J=3.1 Hz, 1H), 4.77 (dt, J=9.2, 6.2 Hz, 1H), 4.54-4.46 (m, 1H), 4.48 (d, J=0.9 Hz, 1H), 4.47 (t, J=0.9 Hz, 1H), 3.33-3.26 (m, 1H), 3.29-3.22 (m, 1H), 3.13-3.01 (m, 2H), 2.67 (tdd, J=7.8, 5.7, 3.9 Hz, 1H), 2.13 (dt, J=15.2, 7.5 Hz, 1H), 2.07-1.99 (m, 1H), 1.94-1.86 (m, 1H), 1.82 (dtd, J=12.2, 3.7, 2.2 Hz, 1H). ESI-MS m/z 610.24 $[M+H]^+$.

Example 307 N—((S)-1-(((S)-4-(benzylamino)-3,4-dione-1-((S)-2-oxopyrrolidin-3-yl)but-2-yl)amino)-3-(3,4-difluorophenyl)-1-oxopropan-2-yl)-quinoline-2-carboxamide (A307)

$^1$H NMR (500 MHz, Chloroform-d) δ 8.43 (d, J=9.1 Hz, 1H), 8.35 (d, J=8.2 Hz, 1H), 8.20 (d, J=8.3 Hz, 1H), 8.11 (t, J=5.8 Hz, 1H), 8.07-8.01 (m, 1H), 7.97-7.91 (m, 1H), 7.83 (d, J=9.3 Hz, 1H), 7.73 (td, J=7.9, 1.1 Hz, 1H), 7.53 (td, J=7.8, 1.2 Hz, 1H), 7.35-7.22 (m, 5H), 7.10-7.03 (m, 1H), 7.03-6.96 (m, 2H), 6.13 (t, J=3.1 Hz, 1H), 4.80 (dt, J=9.3, 6.3 Hz, 1H), 4.54-4.46 (m, 1H), 4.47 (dd, J=5.7, 0.9 Hz, 2H), 3.33-3.26 (m, 1H), 3.29-3.22 (m, 1H), 3.00 (ddt, J=6.2, 2.8, 1.0 Hz, 2H), 2.68 (tdd, J=7.7, 5.7, 3.9 Hz, 1H), 2.17-2.08 (m, 1H), 2.07-1.99 (m, 1H), 1.94-1.86 (m, 1H), 1.82 (dtd, J=12.2, 3.7, 2.2 Hz, 1H). ESI-MS m/z 628.23 $[M+H]^+$.

Example 308 N—((S)-1-(((S)-4-(benzylamino)-3,4-dione-14(S)-2-oxopiperidin-3-yl)but-2-yl)amino)-3-(2-fluorophenyl)-1-oxopropan-2-yl)-benzofuran-2-carboxamide (A308)

$^1$H NMR (500 MHz, Chloroform-d) δ 8.33 (d, J=9.7 Hz, 1H), 8.11 (t, J=5.8 Hz, 1H), 7.83 (d, J=9.1 Hz, 1H), 7.76 (d, J=1.9 Hz, 1H), 7.75-7.68 (m, 1H), 7.60-7.52 (m, 1H), 7.43-7.34 (m, 2H), 7.37-7.26 (m, 5H), 7.29-7.23 (m, 1H), 7.26-7.18 (m, 1H), 7.21-7.17 (m, 1H), 7.10 (td, J=7.9, 1.2 Hz, 1H), 6.26 (t, J=4.0 Hz, 1H), 4.77 (dt, J=9.7, 7.3 Hz, 1H), 4.54-4.46 (m, 1H), 4.48 (s, 1H), 4.47 (t, J=0.9 Hz, 1H), 3.27-3.14 (m, 3H), 3.09 (ddd, J=15.9, 7.3, 0.8 Hz, 1H), 2.61 (tdd, J=8.9, 6.9, 4.3 Hz, 1H), 2.13 (ddd, J=15.0, 8.8, 7.3 Hz, 1H), 1.99 (ddd, J=15.2, 8.8, 7.3 Hz, 1H), 1.81-1.61 (m, 4H). ESI-MS m/z 613.23 $[M+H]^+$.

Example 309 N—((S)-1-(((S)-4-(cyclopropylamino)-3,4-dione-1-((S)-2-oxopiperidin-3-yl)but-2-yl)amino)-3-cyclohexyl-1-oxopropan-2-yl)-benzofuran-2-carboxamide (A309)

1H NMR (500 MHz, DMSO-d6) δ 8.71 (d, J=5.1 Hz, 1H), 8.57 (t, J=8.4 Hz, 2H), 7.81-7.75 (m, 1H), 7.68 (dd, J=8.4, 1.0 Hz, 1H), 7.63 (d, J=1.0 Hz, 1H), 7.47 (m, 2H), 7.37-7.30 (m, 1H), 5.08 (m, 1H), 4.59 (m, 1H), 3.10 (m, 2H), 2.72 (m, 1H), 2.28 (m, 1H), 2.11 (m, 1H), 1.90 (m, 1H), 1.77-1.49 (m, 6H), 1.45-1.34 (m, 2H), 1.29-1.06 (m, 3H), 0.97-0.87 (m, 2H), 0.74-0.59 (m, 2H), 0.59-0.26 (m, 2H). ESI-MS m/z 551.27 $[M+H]^+$.

Example 310 N—((S)-1-(((S)-4-(cyclopropylamino)-3,4-dione-1-((S)-2-oxopiperidin-3-yl)but-2-yl)amino)-3-(4-fluorophenyl)-1-oxopropan-2-yl)-benzofuran-2-carboxamide (A310)

1H NMR (500 MHz, DMSO-d6) δ 8.78-8.63 (m, 3H), 7.76 (d, J=7.8 Hz, 1H), 7.65 (d, J=8.4 Hz, 1H), 7.55 (s, 1H), 7.49-7.43 (m, 2H), 7.41-7.35 (m, 2H), 7.32 (t, J=7.8 Hz, 1H), 7.07 (t, J=8.4 Hz, 2H), 5.13 (m, 1H), 4.78 (m, 1H), 3.16-3.06 (m, 3H), 3.06-2.97 (m, 1H), 2.73 (m, 1H), 2.27 (m, 1H), 2.14 (m, 1H), 2.08-1.89 (m, 1H), 1.73 (m, 2H), 1.56 (m, 1H), 1.42 (m, 1H), 0.71-0.60 (m, 2H), 0.60-0.42 (m, 2H). ESI-MS m/z 563.22 $[M+H]^+$.

Activity Test Example 1

Evaluation of Inhibitory Activity Against 3CL Protease of 2019 Novel Coronavirus To determine the inhibitory activity of the compound against 3CL protease of 2019 novel coronavirus (2019-nCoV $3CL^{pro}$): the enzyme level inhibitory activity of inhibitors against 3CL protease was determined by fluorescence resonance energy transfer (FRET) technology. In a 96-well plate, 27.5 μL of buffer (20 mM Tris, 100 mM NaCl, 1 mM EDTA, pH 7.4) was added to each well, 2.5 μL compounds (final concentrations were 2 μM, 4 μM, 6 μM, 8 μM, 10 μM, 12 μM, 14 μM, 16 μM, 18 μM, 20 μM, respectively) and 5 μL EV713Cpro (final concentration was 3 μM) were added at the same time. Incubated at 37° C. for 15 min. Then 15 μL fluorescent substrate diluted with buffer (final concentration was 20 μM) was added. The fluorescence parameters were determined by Ge n5 fluorescence spectrophotometer. The excitation wavelength and emission wavelength were 340 nm and 490 nm respectively, kept at 37° C., and the data were read after 10 min. A negative control was used, in which no compound was added to the control, and the rest was the same. The obtained data was processed by software GraphPad Prism 5, and the experimental results are shown in Table 1.

TABLE 1

Inhibitory Activity against 3CL Protease of 2019 Novel Coronavirus

| Compound number | $IC_{50}$ (μM) |
|---|---|
| A6 | 25.3 |
| A13(DC403113) | 2.4 |
| A17 | 12.5 |
| A28 | 15.2 |
| A29 | 9.8 |
| A42(DC404001) | 3.0 |
| A56 | 24.1 |
| A59 | 23.5 |
| A90 | 25.2 |
| A115 | 6.5 |
| A156 | 4.7 |
| A167 | 5.6 |
| A189 | 6.8 |
| A190 | 5.9 |
| A200 | 4.9 |
| A221 | 5.8 |

TABLE 1-continued

| Inhibitory Activity against 3CL Protease of 2019 Novel Coronavirus | |
|---|---|
| Compound number | $IC_{50}$ (μM) |
| A234 | 10.3 |
| A236 | 4.5 |
| A238 | 4.8 |
| A239 | 3.8 |
| A257 | 5.2 |
| A259 | 9.5 |
| A268 | 5.6 |
| A269 | 8.8 |
| A270 | 7.6 |
| A272 | 4.8 |
| A275 | 5.8 |
| A289(DC406009) | 10 uM inhibition rate = 40.8<br>1 uM inhibition rate = 13.5 |
| A291 | 15.2 |
| A293 | 26.4 |
| A305 | 8.5 |
| A306 | 6.7 |

Note:
Compound A42, or DC404001, or 4001(omitting "DC40" in "DC40XXXX") refers to the same compound; other compounds follow in this order.

The experimental results show that most compounds have good inhibitory activity on 2019-nCoV 3CL protease, and the inhibitory activity $IC_{50}$ of compounds A13 (DC403113) and A42 (DC404001) against 2019-nCoV 3CL protease reach 2.4 μM and 3.0 μM.

Activity Test Example 2

Evaluation of Inhibitory Activity Against Human Cathepsin L

To determine the inhibitory activity of the compound against human cathepsin L (CatL): the enzyme level inhibitory activity against cathepsin L was determined by fluorescence resonance energy transfer (FRET) technique. In a 96-well plate, 10 μL buffer (50 mM $CH_3COONa$, pH 5.5, 1 mM DTT, 2 mM EDTA) was added to each well, while 0.2 μL of compound (final concentrations were 100 nM, 10 nM, 1 nM, 0.1 nM and 0.01 nM, respectively) and 10 μL cathepsin L were added, and incubated at 25° C. for 15 min. Then 10 μL fluorescent substrate (Z-Phe-Arg-AMC, final concentration was 20 μM) diluted with buffer was added. The fluorescence parameters were determined by Tecan Infinite 200pro fluorescence spectrophotometer. The excitation wavelength and emission wavelength were 360 nm and 465 nm respectively, kept at 25° C., and the data were read after 30 min. A negative control was used, in which no compound was added to the control, and the rest was the same. The obtained data was processed by software GraphPad Prism 8.0, and the experimental results are shown in Table 2.

TABLE 2

| Inhibitory activity against human cathepsin L | | | |
|---|---|---|---|
| Compound number | $IC_{50}$ (nM) | Compound number | $IC_{50}$ (nM) |
| A5(DC406104) | 0.45 ± 0.02 | A13(DC403113) | 1.36 ± 0.04 |
| A284(DC406016) | 0.45 ± 0.01 | A289(DC406009) | 0.66 ± 0.008 |
| A290(DC406020) | 0.47 ± 0.06 | A309(DC406068) | 0.63 ± 0.08 |
| A310(DC406067) | 0.57 ± 0.01 | | |

The experimental results show that the test compounds have excellent inhibitory activity against human cathepsin L, and the $IC_{50}$ is in nanomolar level, even less than 1 nM (such as compounds A5, A284, A289, A290, A309, and A310).

Activity Test Example 3

Evaluation of Inhibitory Activity of Compounds on Replication of 2019 Novel Coronavirus To determine the inhibitory activity of the compound on replication of each 2019 novel coronavirus (2019-nCov): in a 96 well plate, 100 μL/well gradient compound was added, then 50 μL/well virus buffer was added, then well-cultured RD cells (rhabdomyosarcoma cells) were immediately added at 50 μL/well. The mixture was incubated at 37° C. for 3-4 days, until the maximum cytopathic effect was observed. The medium was aspirated, 75 μl of 5% MTS phenol red medium was added, and the wells were incubated at 37° C. with 5% $CO_2$ for 1.5 h. The fluorescence values of each well were measured at 498 nM, and a graph of compound concentration versus cell response was drawn. The $EC_{50}$ of compound inhibiting virus was calculated by using the software customized by Accelrys company.

Figure 2:
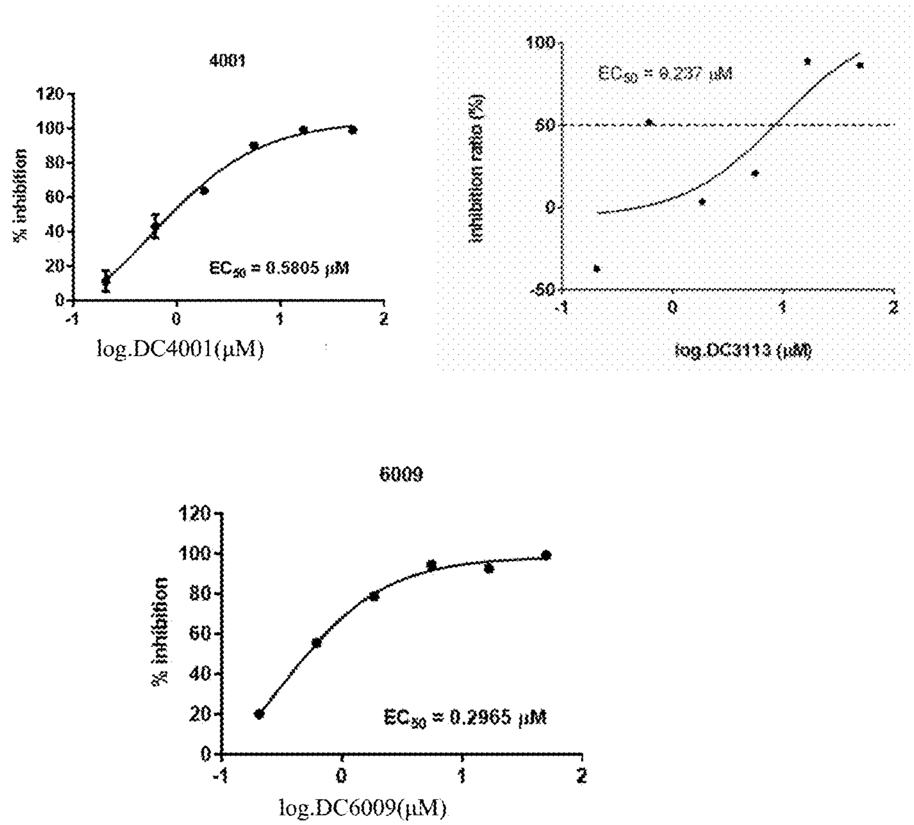
FIG. 2 shows the inhibition curve and EC50 value of some compounds of the present invention that inhibit the 2019 novel coronavirus (2019-nCov).

The test results are shown in FIGS. 1 and 2.

The results show that the ketoamide compound of the present invention can effectively inhibit the replication of the 2019 novel coronavirus (FIG. 1), and has certain inhibition on different isolated virus strains.

At present, the positive compound against 2019-nCoV is CQ, and its inhibition rate of 2019-nCoV virus replication $EC_{50}$=1.13 μM. The results showed that CQ was used as positive control to test the patented compounds under different concentration gradients. Compounds A13 (3113, DC403113), A42 (4001, DC404001), A289 (6009, DC406009) all have excellent virus inhibitory activity. Among them, the $EC_{50}$ for 3113 is 9237 nM, and the $EC_{50}$ for 6009 and 4001 are 296.5 nM and 580.5 nM respectively. The inhibition rate of 6009 and 4001 against 2019-nCoV at virus level is better than that of positive control CQ, showing excellent anti-2019-nCoV potential (FIG. 2).

Activity Test Example 4

DC406009: Toxicity Test in SD Rats With Repeated Intravenous Infusion for 14-Day The purpose of this experiment is to observe the potential toxicity of SD rats after intravenous DC406009 for 7 consecutive days and to determine the possible toxic target organs. To provide non-toxic dose and/or toxic dose for the subsequent toxicity test design and clinical trial protocol design. To assess the level of drug exposure in vivo, a toxicokinetic evaluation is accompanied.

36 SD rats were divided into 8 groups (3 in toxicity test group/gender/group, a total of 5 groups; 1 in toxic satellite group/gender/group, 3 groups), intravenous injection of solvent (5% DMSO/5% EtOH/40% PEG300/50% NaCl), 0.9% sodium chloride injection and DC406009 (5, 15, 30 mg/kg/day), once a day for 7 consecutive days, all animals were euthanized on Day 8. During the test, the following indicators were evaluated: toxicology (only samples were collected), clinical observation, body weight, food consumption, clinical pathology (hematology, hemagglutination, plasma biochemistry) and anatomical macroscopic morphological observation.

The results showed that under the experimental conditions, SD rats were given DC406009 (5, 15, 30 mg/kg/day) intravenously once a day for 7 consecutive days, animals can tolerate, and the maximum tolerated dose (MTD) was greater than 30 mg/kg/day, indicating that the compound DC406009 has good safety.

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A method for treating related diseases caused by 2019 novel coronavirus (2019-nCov) infection comprising administering to a subject in need thereof a therapeutically effective amount of a ketoamide compound represented by formula (A), or a pharmaceutically acceptable salt, enantiomer, diastereomer or racemate thereof:

(A)

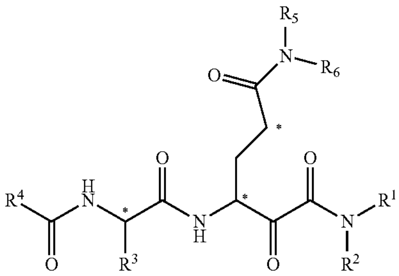

wherein,

* indicates that the stereochemical isomerism of carbon atoms is independently R and/or S respectively;

$R^1$ is selected from the group consisting of substituted or unsubstituted C1-C10 alkyl, substituted or unsubstituted C3-C8 cycloalkyl, substituted or unsubstituted C3-C8 cycloalkyl C1-C10 alkylene, and substituted or unsubstituted C6-C10 aryl C1-C10 alkylene;

$R^2$ is selected from the group consisting of hydrogen, deuterium, and C1-C6 alkyl;

$R^3$ is selected from the group consisting of substituted or unsubstituted C1-C6 alkyl, substituted or unsubstituted C3-C8 cycloalkyl, substituted or unsubstituted C3-C8 cycloalkyl C1-C5 alkylene, substituted or unsubstituted C6-C10 aryl, and substituted or unsubstituted C6-C10 aryl C1-C5 alkylene;

$R^4$ is selected from the group consisting of substituted or unsubstituted quinoxalinyl, substituted or unsubstituted quinazolinyl, substituted or unsubstituted cinnolinyl, substituted or unsubstituted indolyl, substituted or unsubstituted isoindolyl, substituted or unsubstituted benzimidazolyl, substituted or unsubstituted indazolyl, substituted or unsubstituted imidazole [1,2-A] pyridyl, substituted or unsubstituted imidazole [1,5-A] pyridyl, substituted or unsubstituted quinolinyl, substituted or unsubstituted isoquinolinyl, substituted or unsubstituted benzothienyl, and substituted or unsubstituted benzofuranyl; wherein the substituted means that the hydrogen atom on the group is substituted by 1, 2 or 3 substituents selected from the group consisting of F, Cl, Br, I, hydroxyl, C1-C6 alkyl, halogenated C1-C6 alkyl, C1-C6 alkoxy, halogenated C1-C6 alkoxy, and C1-C6 alkylthio;

$R^6$ is hydrogen or C1-C6 alkyl;

when $—NR^5$ and its adjacent $—(C{=}O)—CH_2—$ form a ring, $R^5$ is $—(CH_2)_n—$, n is 2 or 3;

when $—NR^5$ does not form a ring with its adjacent $—(C{=}O)—CH_2—$, $R^5$ is selected from the group consisting of hydrogen C1-C6 alkyl, and C3-C8 cycloalkyl;

wherein, in $R^1$, and $R^3$, each of the term "substituted" independently refers to being substituted by 1, 2, 3 or 4 substituents selected from the group consisting of halogen, hydroxyl, mercapto, nitro, cyano, amino, imino, tertiary amino, azido, C1-C8 alkyl, halogenated C1-C8 alkyl, C1-C8 alkoxy, halogenated C1-C8 alkoxy, C1-C6 alkylcarbonyl, C1-C6 alkylthio, C1-C8 alkoxycarbonyl, and trifluoromethyl;

wherein the related diseases caused by 2019 novel coronavirus (2019-nCov) infection is selected from the group consisting of pneumonia, respiratory infections, and a combination thereof.

2. The method of claim 1, wherein the related disease caused by 2019 novel coronavirus infection is pneumonia.

3. The method of claim 1, wherein $R^1$ is selected from the group consisting of C1-C6 alkyl, C3-C8 cycloalkyl, C3-C8 cycloalkyl C1-C5 alkylene, and substituted or unsubstituted C6 aryl C1-C5 alkylene;

$R^2$ is selected from the group consisting of hydrogen and C1 alkyl;

$R^3$ is selected from the group consisting of C1-C6 alkyl, C3-C8 cycloalkyl, C3-C8 cycloalkyl C1-C5 alkylene, and C6 aryl C1-C5 alkylene;

wherein, in $R^1$ and $R^3$, the substituted each independently refer to being substituted by 1, 2, or 3 substituents selected from the group consisting of halogen, hydroxy, C1-C6 alkyl, halogenated C1-C6 alkyl, C1-C6 alkoxy, and halogenated C1-C6 alkoxy.

4. The method of claim 1, wherein the compound is a compound represented by formula AA, formula AA

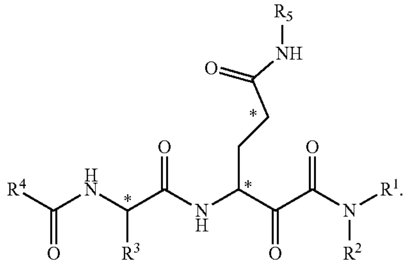

5. The method of claim 1, wherein $R^4$ is selected from the group consisting of substituted or unsubstituted quinoxalinyl,
substituted or unsubstituted indolyl,
substituted or unsubstituted benzimidazolyl,
substituted or unsubstituted imidazole [1,2-A] pyridyl,
substituted or unsubstituted quinolinyl,
substituted or unsubstituted benzothienyl, and
substituted or unsubstituted benzofuranyl;

wherein, the substituted means that the hydrogen atom on the group is substituted by 1, 2 or 3 substituents selected from the group consisting of F, Cl, Br, I, hydroxyl, C1-C6 alkyl, halogenated C1-C6 alkyl, C1-C6 alkoxy, halogenated C1-C6 alkoxy, and C1-C6 alkylthio.

6. The method of claim 1, wherein the compound is selected from the group consisting of:
| number | structure |
| --- | --- |
| A1 | 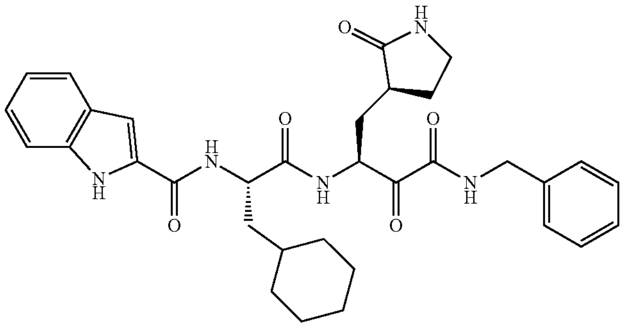 [SMILES: O=C(NCc1ccccc1)C(=O)[C@H](C[C@@H]1CCNC1=O)NC(=O)[C@H](CC1CCCCC1)NC(=O)c1cc2ccccc2[nH]1] |
| A2 | 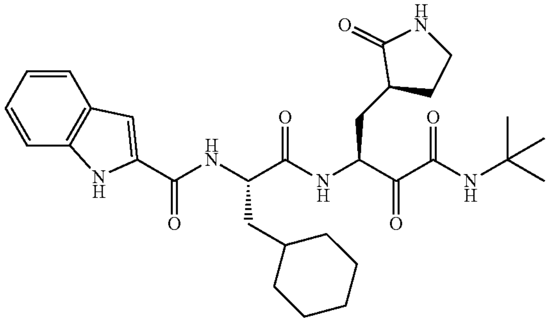 [SMILES: CC(C)(C)NC(=O)C(=O)[C@H](C[C@@H]1CCNC1=O)NC(=O)[C@H](CC1CCCCC1)NC(=O)c1cc2ccccc2[nH]1] |
| A3 | 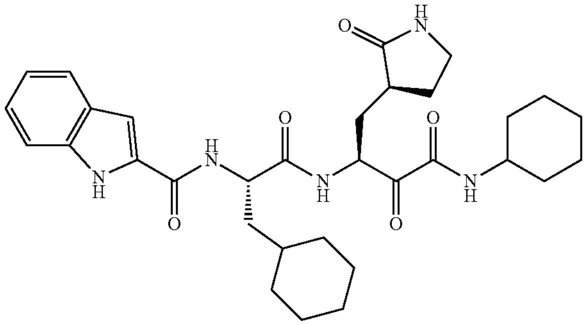 [SMILES: O=C(NC1CCCCC1)C(=O)[C@H](C[C@@H]1CCNC1=O)NC(=O)[C@H](CC1CCCCC1)NC(=O)c1cc2ccccc2[nH]1] |
| A4 | 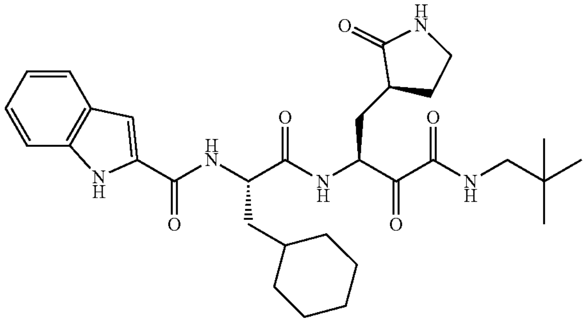 [SMILES: CC(C)(C)CNC(=O)C(=O)[C@H](C[C@@H]1CCNC1=O)NC(=O)[C@H](CC1CCCCC1)NC(=O)c1cc2ccccc2[nH]1] |

-continued
| number | structure |
|---|---|
| A5 | 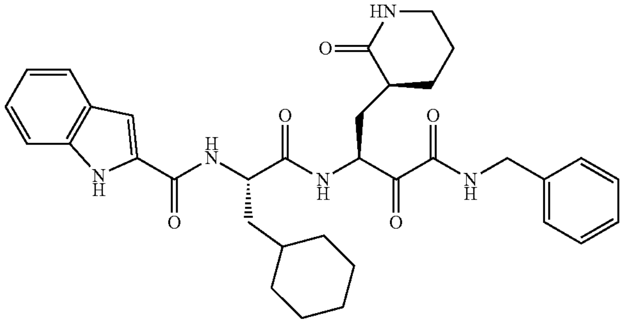 [SMILES: O=C(NCc1ccccc1)C(=O)[C@H](C[C@@H]1CCCNC1=O)NC(=O)[C@H](CC1CCCCC1)NC(=O)c1cc2ccccc2[nH]1] |
| A6 | 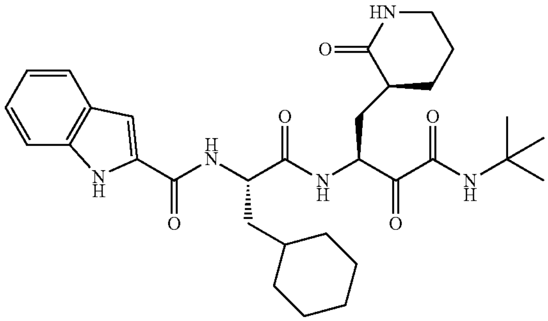 [SMILES: CC(C)(C)NC(=O)C(=O)[C@H](C[C@@H]1CCCNC1=O)NC(=O)[C@H](CC1CCCCC1)NC(=O)c1cc2ccccc2[nH]1] |
| A7 | 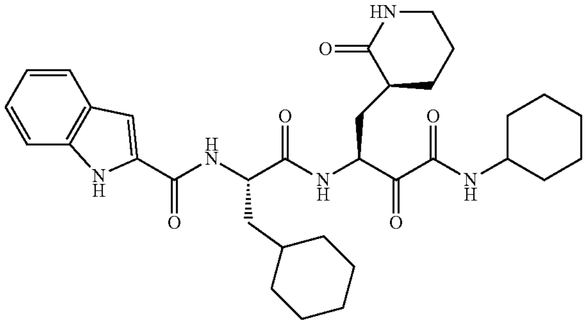 [SMILES: O=C(NC1CCCCC1)C(=O)[C@H](C[C@@H]1CCCNC1=O)NC(=O)[C@H](CC1CCCCC1)NC(=O)c1cc2ccccc2[nH]1] |
| A8 | 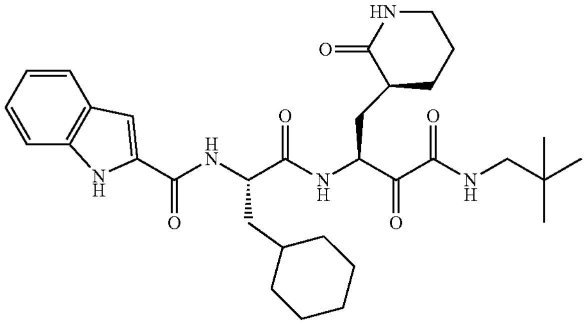 [SMILES: CC(C)(C)CNC(=O)C(=O)[C@H](C[C@@H]1CCCNC1=O)NC(=O)[C@H](CC1CCCCC1)NC(=O)c1cc2ccccc2[nH]1] |

-continued
| number | structure |
|---|---|
| A9 | 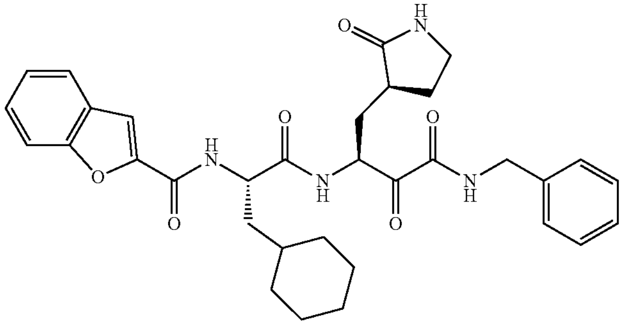 [SMILES: O=C(NCc1ccccc1)C(=O)[C@H](C[C@@H]1CCNC1=O)NC(=O)[C@H](CC1CCCCC1)NC(=O)c1cc2ccccc2o1] |
| A10 | 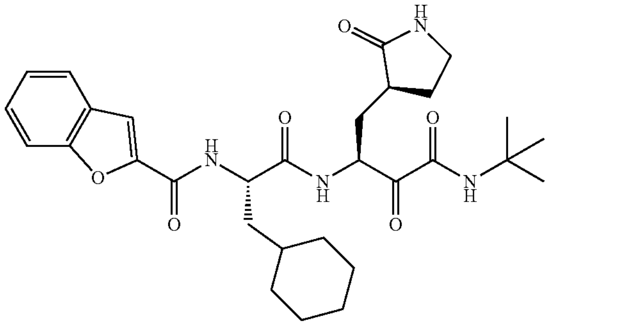 |
| A11 | 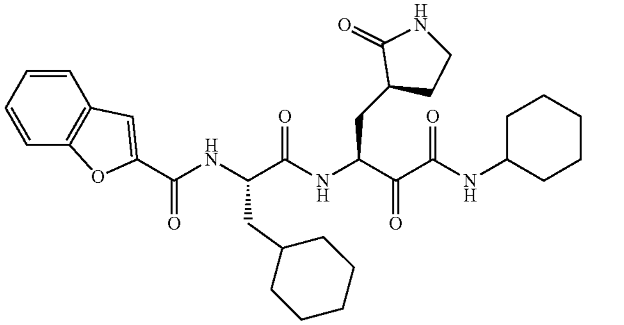 [SMILES: O=C(NC1CCCCC1)C(=O)[C@H](C[C@@H]1CCNC1=O)NC(=O)[C@H](CC1CCCCC1)NC(=O)c1cc2ccccc2o1] |
| A12 | 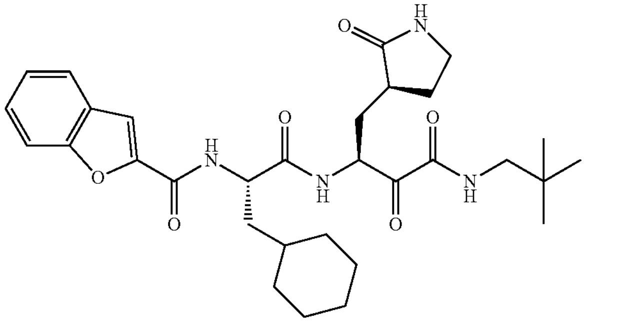 [SMILES: CC(C)(C)CNC(=O)C(=O)[C@H](C[C@@H]1CCNC1=O)NC(=O)[C@H](CC1CCCCC1)NC(=O)c1cc2ccccc2o1] |

-continued
| number | structure |
|---|---|
| A13 | 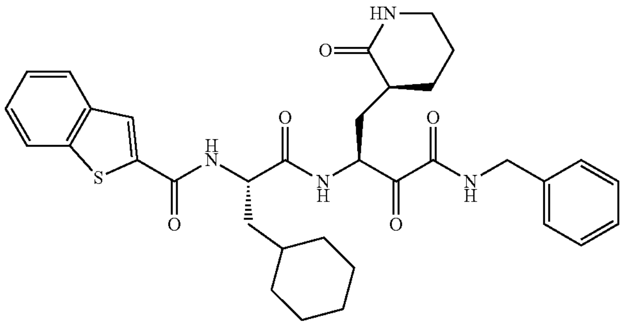 [SMILES: O=C(NCc1ccccc1)C(=O)[C@H](C[C@@H]1CCCNC1=O)NC(=O)[C@H](CC1CCCCC1)NC(=O)c1cc2ccccc2s1] |
| A14 | 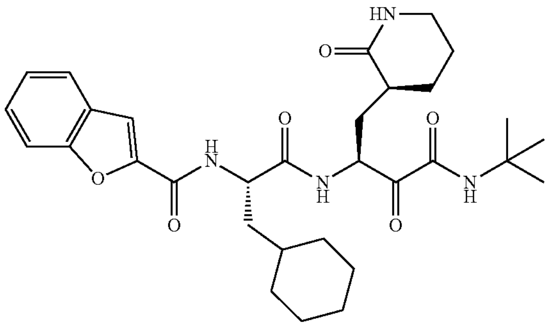 [SMILES: CC(C)(C)NC(=O)C(=O)[C@H](C[C@@H]1CCCNC1=O)NC(=O)[C@H](CC1CCCCC1)NC(=O)c1cc2ccccc2o1] |
| A15 | 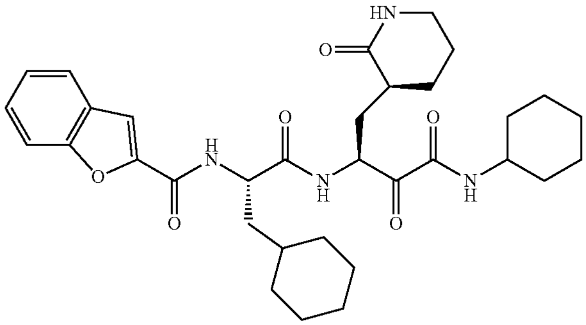 [SMILES: O=C(NC1CCCCC1)C(=O)[C@H](C[C@@H]1CCCNC1=O)NC(=O)[C@H](CC1CCCCC1)NC(=O)c1cc2ccccc2o1] |
| A16 | 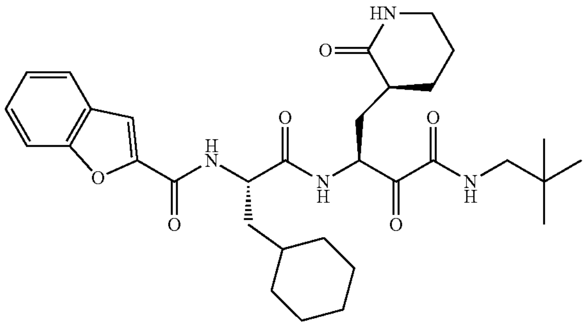 [SMILES: CC(C)(C)CNC(=O)C(=O)[C@H](C[C@@H]1CCCNC1=O)NC(=O)[C@H](CC1CCCCC1)NC(=O)c1cc2ccccc2o1] |

-continued
| number | structure |
|---|---|
| A17 | 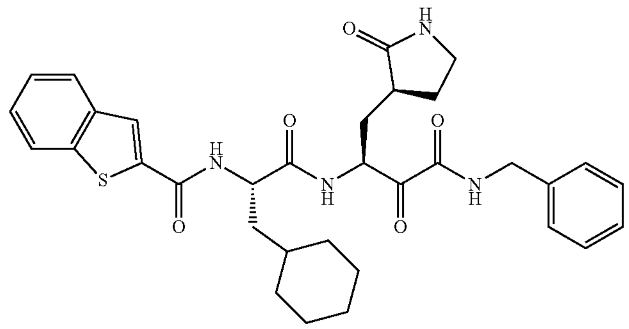 [SMILES: O=C(NCc1ccccc1)C(=O)[C@H](C[C@@H]1CCNC1=O)NC(=O)[C@H](CC1CCCCC1)NC(=O)c1cc2ccccc2s1] |
| A18 | 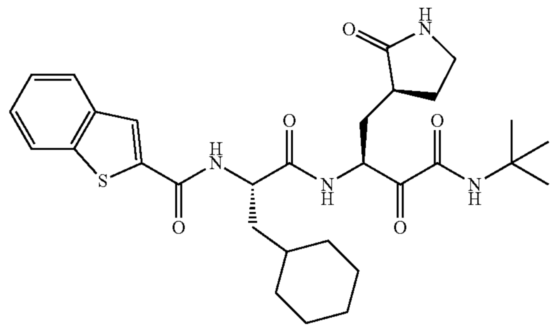 |
| A19 | 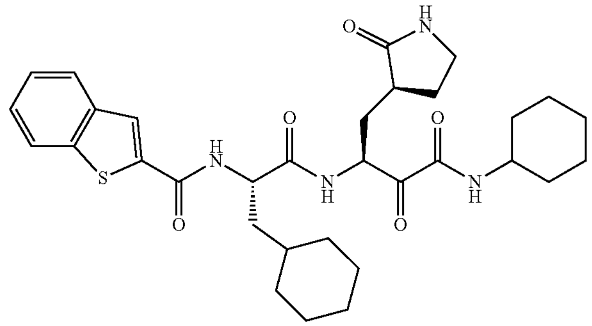 [SMILES: O=C(NC1CCCCC1)C(=O)[C@H](C[C@@H]1CCNC1=O)NC(=O)[C@H](CC1CCCCC1)NC(=O)c1cc2ccccc2s1] |
| A20 | 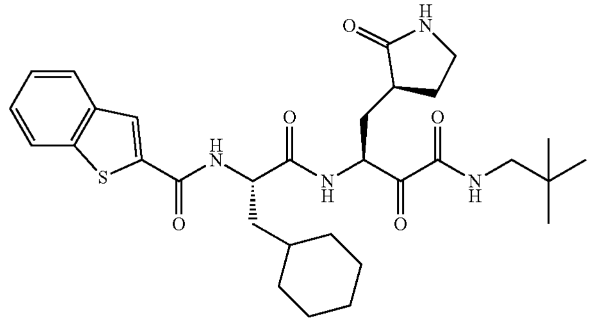 [SMILES: CC(C)(C)CNC(=O)C(=O)[C@H](C[C@@H]1CCNC1=O)NC(=O)[C@H](CC1CCCCC1)NC(=O)c1cc2ccccc2s1] |

-continued
| number | structure |
| --- | --- |
| A21 | 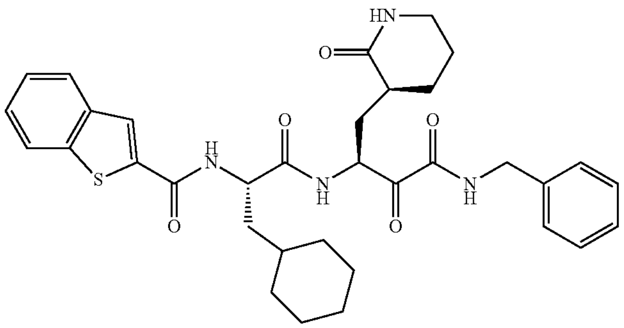 [SMILES: O=C(NCc1ccccc1)C(=O)[C@H](C[C@@H]1CCCNC1=O)NC(=O)[C@H](CC1CCCCC1)NC(=O)c1cc2ccccc2s1] |
| A22 | 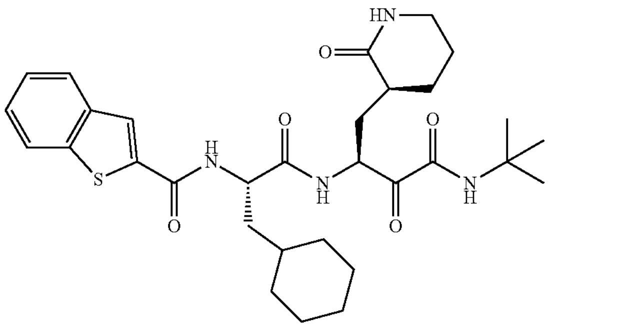 [SMILES: CC(C)(C)NC(=O)C(=O)[C@H](C[C@@H]1CCCNC1=O)NC(=O)[C@H](CC1CCCCC1)NC(=O)c1cc2ccccc2s1] |
| A23 | 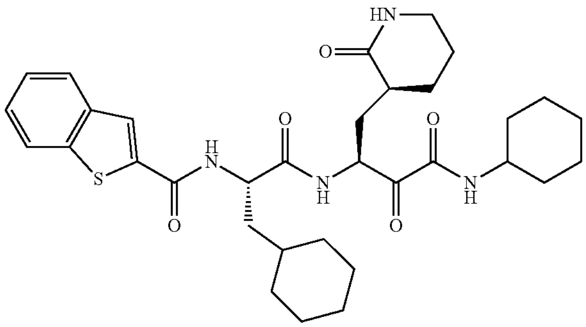 [SMILES: O=C(NC1CCCCC1)C(=O)[C@H](C[C@@H]1CCCNC1=O)NC(=O)[C@H](CC1CCCCC1)NC(=O)c1cc2ccccc2s1] |
| A24 | 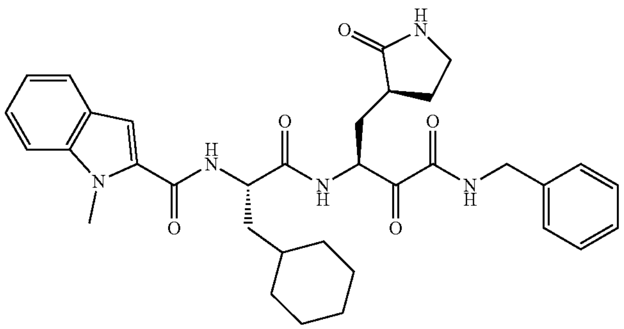 [SMILES: Cn1c(C(=O)N[C@@H](CC2CCCCC2)C(=O)N[C@@H](C[C@@H]2CCNC2=O)C(=O)C(=O)NCc2ccccc2)cc2ccccc21] |

-continued
| number | structure |
|---|---|
| A25 | 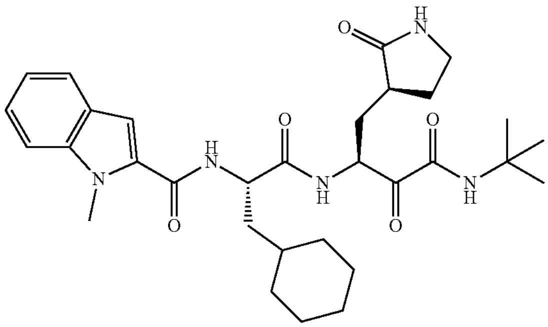 [SMILES: Cn1c(C(=O)N[C@@H](CC2CCCCC2)C(=O)N[C@@H](C[C@@H]2CCNC2=O)C(=O)C(=O)NC(C)(C)C)cc2ccccc21] |
| A26 | 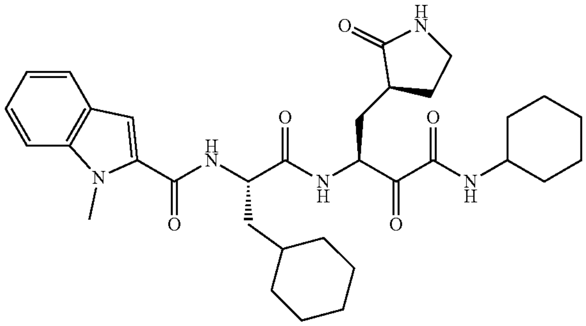 [SMILES: Cn1c(C(=O)N[C@@H](CC2CCCCC2)C(=O)N[C@@H](C[C@@H]2CCNC2=O)C(=O)C(=O)NC2CCCCC2)cc2ccccc21] |
| A27 | 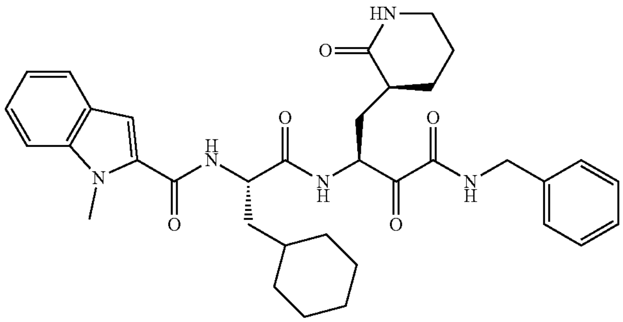 [SMILES: Cn1c(C(=O)N[C@@H](CC2CCCCC2)C(=O)N[C@@H](C[C@@H]2CCCNC2=O)C(=O)C(=O)NCc2ccccc2)cc2ccccc21] |
| A28 | 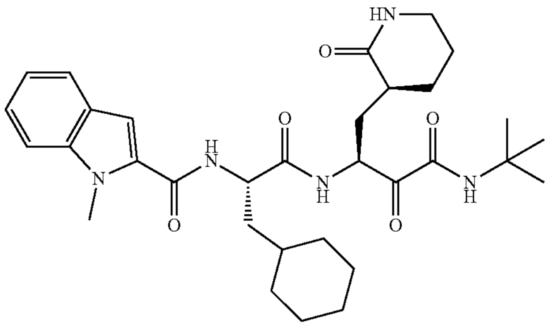 [SMILES: Cn1c(C(=O)N[C@@H](CC2CCCCC2)C(=O)N[C@@H](C[C@@H]2CCCNC2=O)C(=O)C(=O)NC(C)(C)C)cc2ccccc21] |

-continued
| number | structure |
| --- | --- |
| A29 | 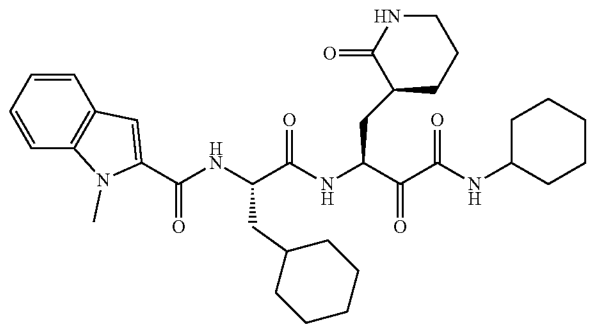 [SMILES: Cn1c(C(=O)N[C@@H](CC2CCCCC2)C(=O)N[C@@H](C[C@@H]2CCCNC2=O)C(=O)C(=O)NC2CCCCC2)cc2ccccc21] |
| A30 | 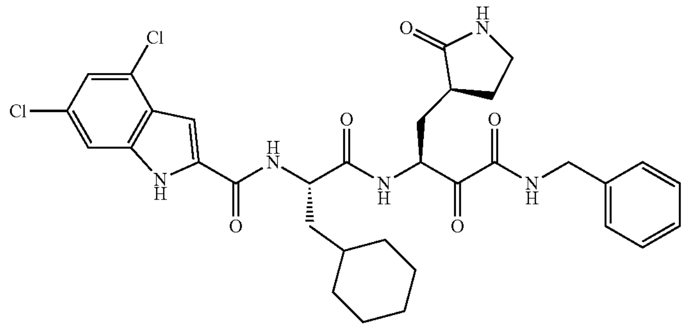 [SMILES: O=C(NCc1ccccc1)C(=O)[C@H](C[C@@H]1CCNC1=O)NC(=O)[C@H](CC1CCCCC1)NC(=O)c1cc2c(Cl)cc(Cl)cc2[nH]1] |
| A31 | 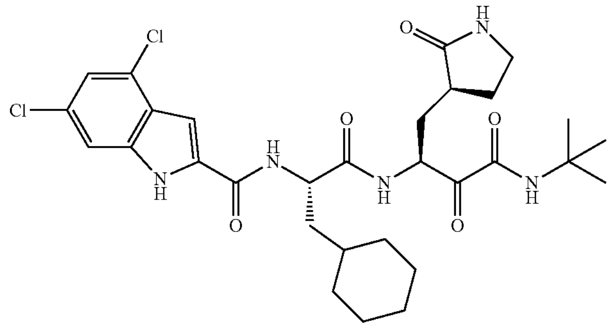 [SMILES: CC(C)(C)NC(=O)C(=O)[C@H](C[C@@H]1CCNC1=O)NC(=O)[C@H](CC1CCCCC1)NC(=O)c1cc2c(Cl)cc(Cl)cc2[nH]1] |
| A32 | 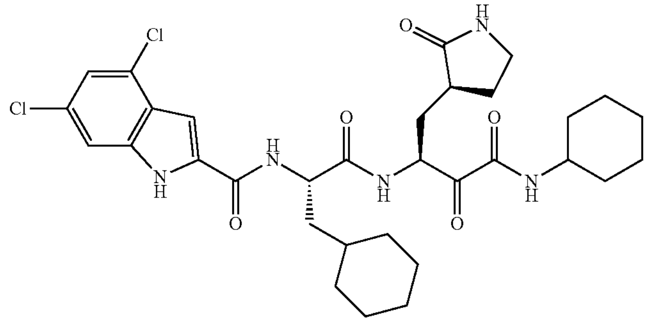 [SMILES: O=C(NC1CCCCC1)C(=O)[C@H](C[C@@H]1CCNC1=O)NC(=O)[C@H](CC1CCCCC1)NC(=O)c1cc2c(Cl)cc(Cl)cc2[nH]1] |

-continued
| number | structure |
|---|---|
| A33 | 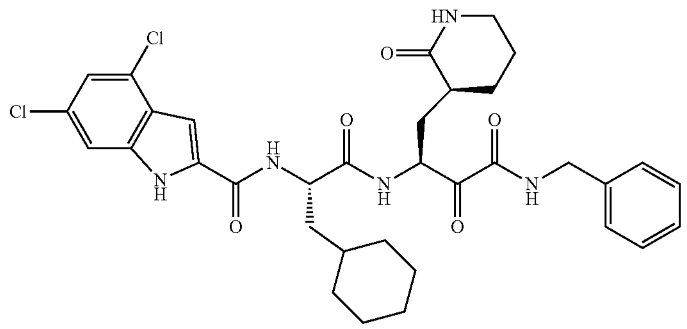 [SMILES: O=C(NCc1ccccc1)C(=O)[C@H](C[C@@H]1CCCNC1=O)NC(=O)[C@H](CC1CCCCC1)NC(=O)c1cc2c(Cl)cc(Cl)cc2[nH]1] |
| A34 | 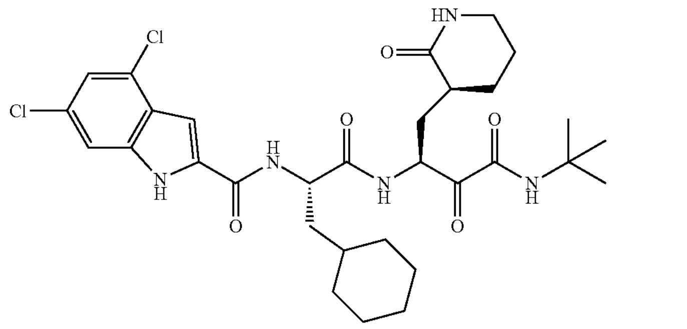 [SMILES: CC(C)(C)NC(=O)C(=O)[C@H](C[C@@H]1CCCNC1=O)NC(=O)[C@H](CC1CCCCC1)NC(=O)c1cc2c(Cl)cc(Cl)cc2[nH]1] |
| A35 | 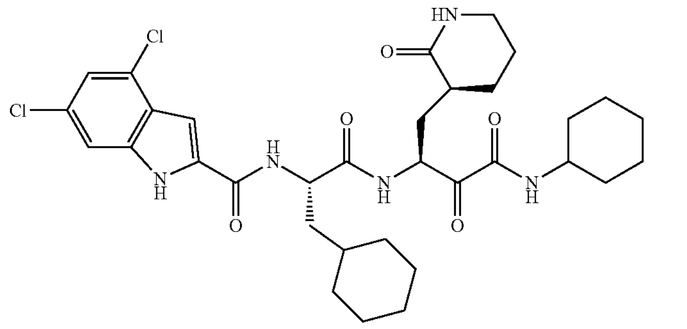 [SMILES: O=C(NC1CCCCC1)C(=O)[C@H](C[C@@H]1CCCNC1=O)NC(=O)[C@H](CC1CCCCC1)NC(=O)c1cc2c(Cl)cc(Cl)cc2[nH]1] |
| A36 | 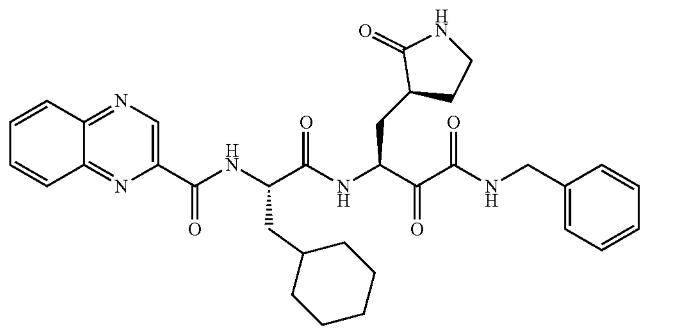 [SMILES: O=C(NCc1ccccc1)C(=O)[C@H](C[C@@H]1CCNC1=O)NC(=O)[C@H](CC1CCCCC1)NC(=O)c1cnc2ccccc2n1] |

-continued
| number | structure |
|---|---|
| A37 | 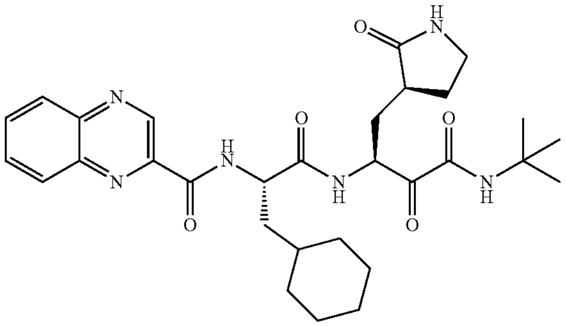 [SMILES: CC(C)(C)NC(=O)C(=O)[C@H](C[C@@H]1CCNC1=O)NC(=O)[C@H](CC1CCCCC1)NC(=O)c1cnc2ccccc2n1] |
| A38 | 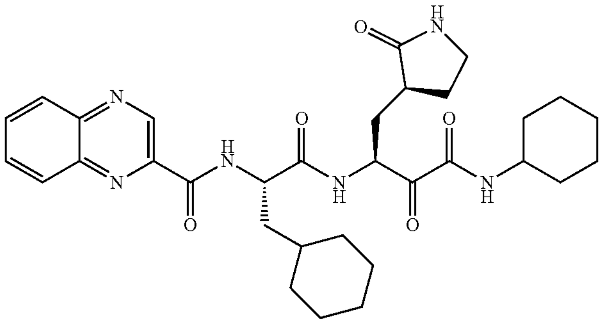 [SMILES: O=C(NC1CCCCC1)C(=O)[C@H](C[C@@H]1CCNC1=O)NC(=O)[C@H](CC1CCCCC1)NC(=O)c1cnc2ccccc2n1] |
| A39 | 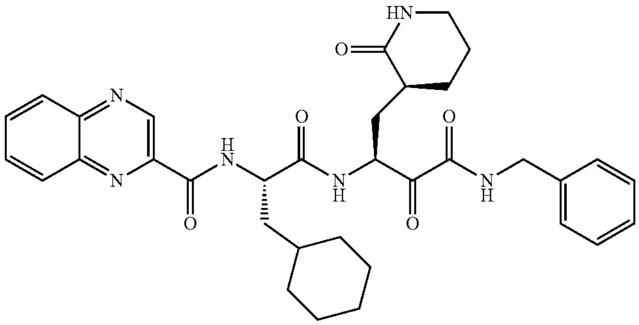 |
| A40 | 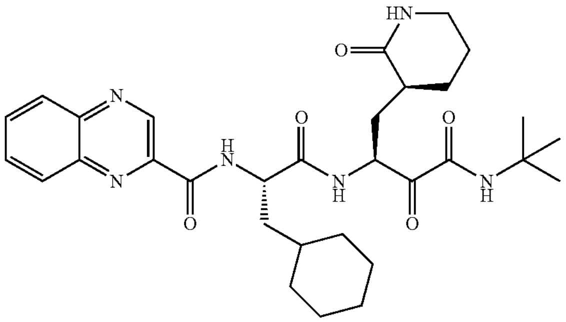 [SMILES: CC(C)(C)NC(=O)C(=O)[C@H](C[C@@H]1CCCNC1=O)NC(=O)[C@H](CC1CCCCC1)NC(=O)c1cnc2ccccc2n1] |

-continued
| number | structure |
|---|---|
| A41 | 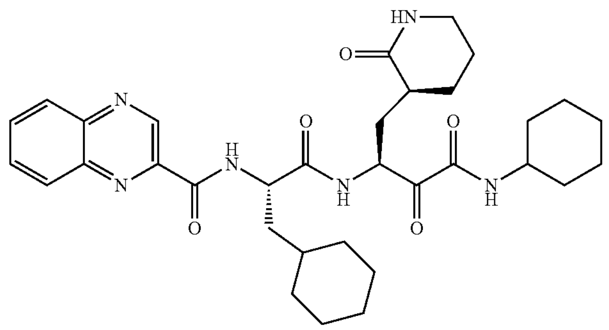 [SMILES: O=C(NC1CCCCC1)C(=O)[C@H](C[C@@H]1CCCNC1=O)NC(=O)[C@H](CC1CCCCC1)NC(=O)c1cnc2ccccc2n1] |
| A42 | 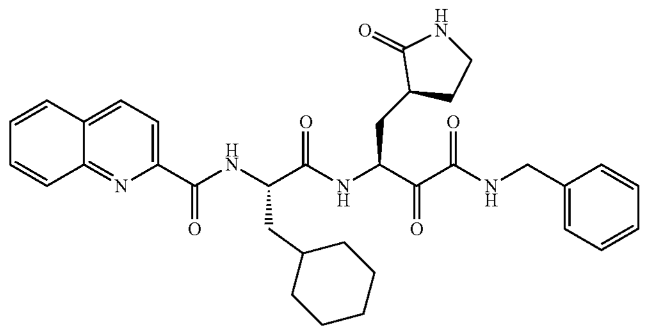 [SMILES: O=C(NCc1ccccc1)C(=O)[C@H](C[C@@H]1CCNC1=O)NC(=O)[C@H](CC1CCCCC1)NC(=O)c1ccc2ccccc2n1] |
| A43 | 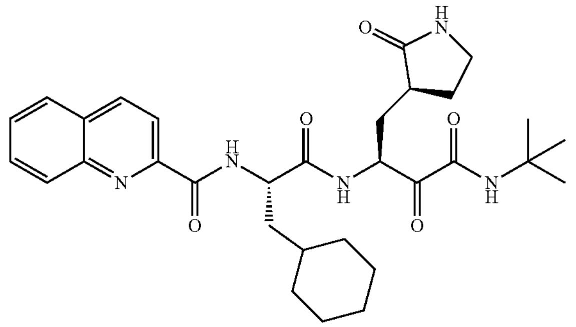 [SMILES: CC(C)(C)NC(=O)C(=O)[C@H](C[C@@H]1CCNC1=O)NC(=O)[C@H](CC1CCCCC1)NC(=O)c1ccc2ccccc2n1] |
| A44 | 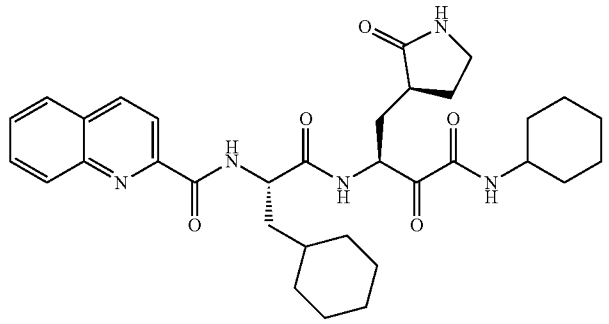 [SMILES: O=C(NC1CCCCC1)C(=O)[C@H](C[C@@H]1CCNC1=O)NC(=O)[C@H](CC1CCCCC1)NC(=O)c1ccc2ccccc2n1] |

-continued
| number | structure |
|---|---|
| A45 | 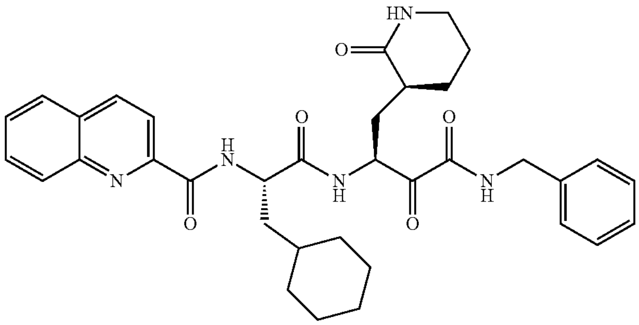 [SMILES: O=C(NCc1ccccc1)C(=O)[C@H](C[C@@H]1CCCNC1=O)NC(=O)[C@H](CC1CCCCC1)NC(=O)c1ccc2ccccc2n1] |
| A46 | 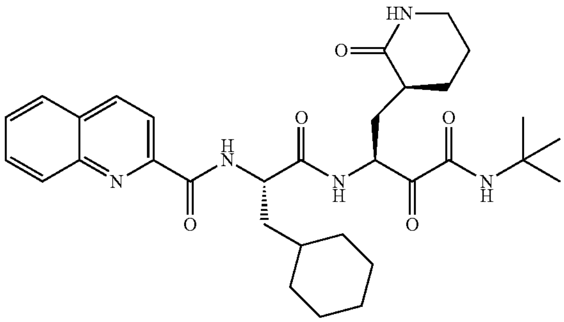 |
| A47 | 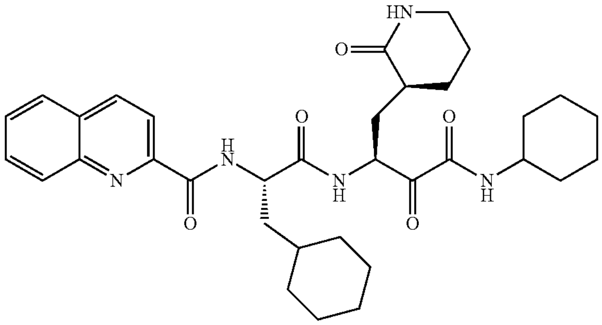 [SMILES: O=C(NC1CCCCC1)C(=O)[C@H](C[C@@H]1CCCNC1=O)NC(=O)[C@H](CC1CCCCC1)NC(=O)c1ccc2ccccc2n1] |
| A48 | 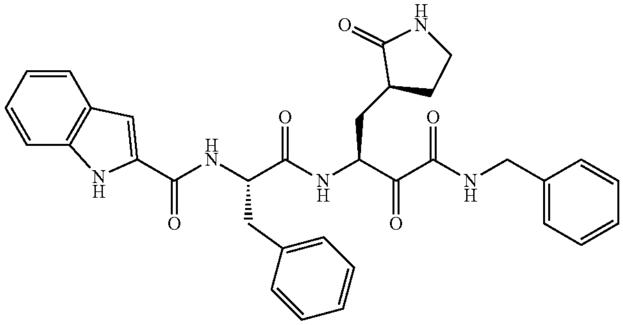 [SMILES: O=C(NCc1ccccc1)C(=O)[C@H](C[C@@H]1CCNC1=O)NC(=O)[C@H](Cc1ccccc1)NC(=O)c1cc2ccccc2[nH]1] |

-continued
| number | structure |
|---|---|
| A49 | 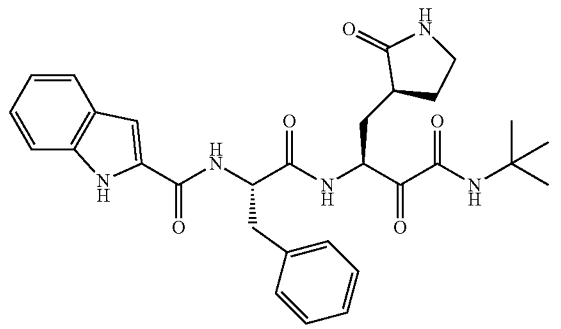 |
| A50 | 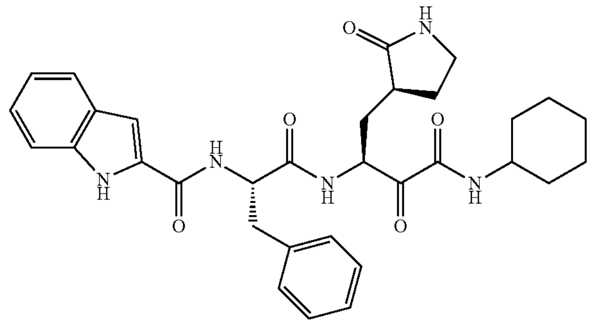 [SMILES: O=C(NC1CCCCC1)C(=O)[C@H](C[C@@H]1CCNC1=O)NC(=O)[C@H](Cc1ccccc1)NC(=O)c1cc2ccccc2[nH]1] |
| A51 | 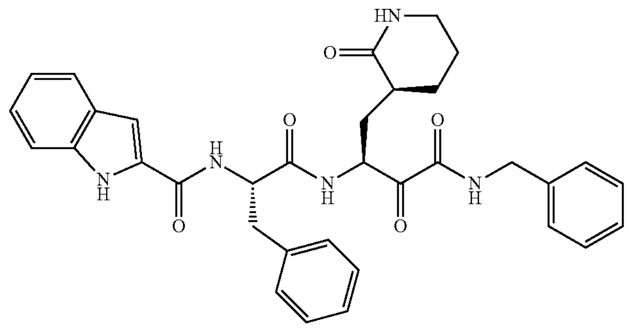 [SMILES: O=C(NCc1ccccc1)C(=O)[C@H](C[C@@H]1CCCNC1=O)NC(=O)[C@H](Cc1ccccc1)NC(=O)c1cc2ccccc2[nH]1] |
| A52 | 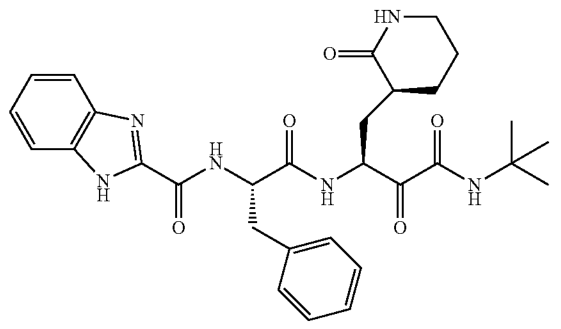 [SMILES: CC(C)(C)NC(=O)C(=O)[C@H](C[C@@H]1CCCNC1=O)NC(=O)[C@H](Cc1ccccc1)NC(=O)c1nc2ccccc2[nH]1] |

-continued
| number | structure |
|---|---|
| A53 | 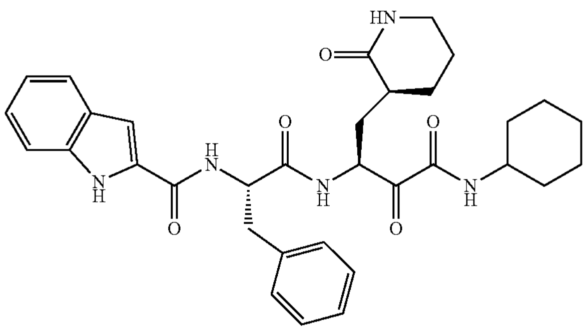 |
| A54 | 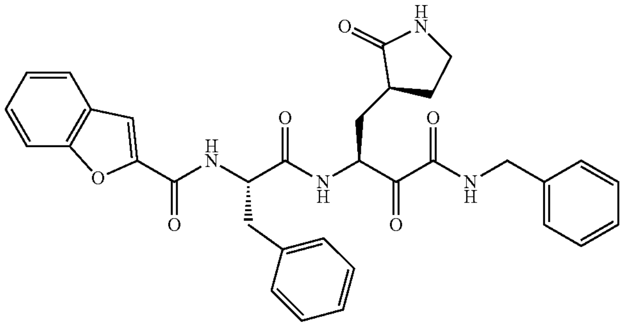 [SMILES: O=C(NCc1ccccc1)C(=O)[C@H](C[C@@H]1CCNC1=O)NC(=O)[C@H](Cc1ccccc1)NC(=O)c1cc2ccccc2o1] |
| A55 | 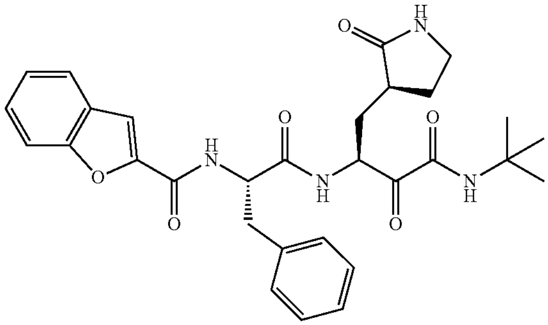 |
| A56 | 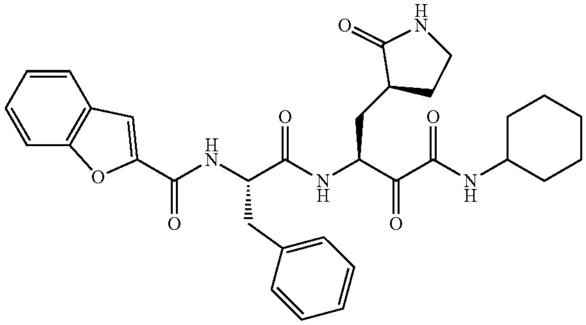 [SMILES: O=C(NC1CCCCC1)C(=O)[C@H](C[C@@H]1CCNC1=O)NC(=O)[C@H](Cc1ccccc1)NC(=O)c1cc2ccccc2o1] |

-continued
| number | structure |
|---|---|
| A57 | 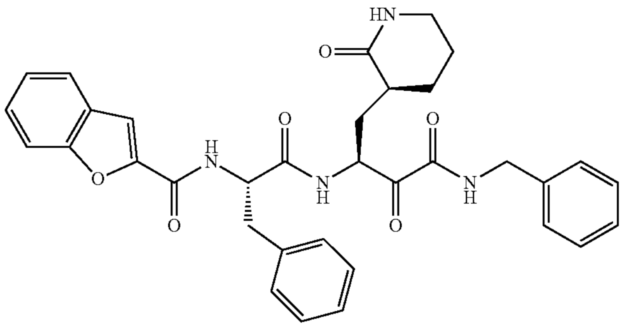 [SMILES: O=C(NCc1ccccc1)C(=O)[C@H](C[C@@H]1CCCNC1=O)NC(=O)[C@H](Cc1ccccc1)NC(=O)c1cc2ccccc2o1] |
| A58 | 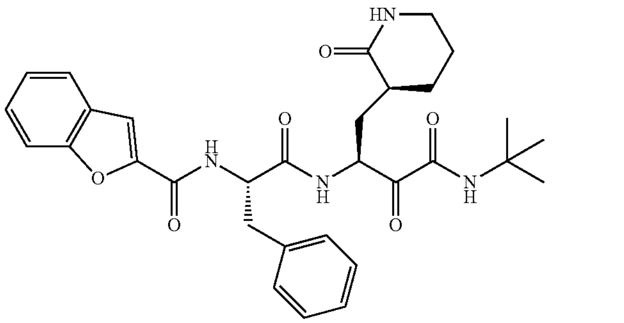 |
| A59 | 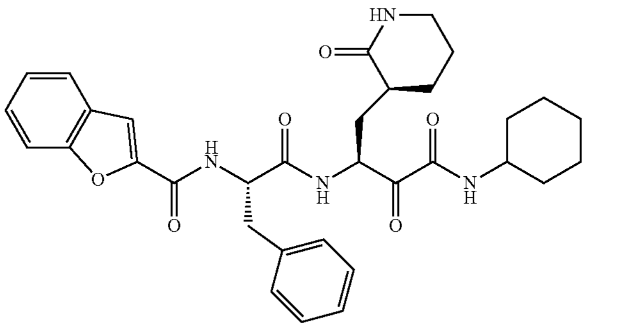 [SMILES: O=C(NC1CCCCC1)C(=O)[C@H](C[C@@H]1CCCNC1=O)NC(=O)[C@H](Cc1ccccc1)NC(=O)c1cc2ccccc2o1] |
| A60 | 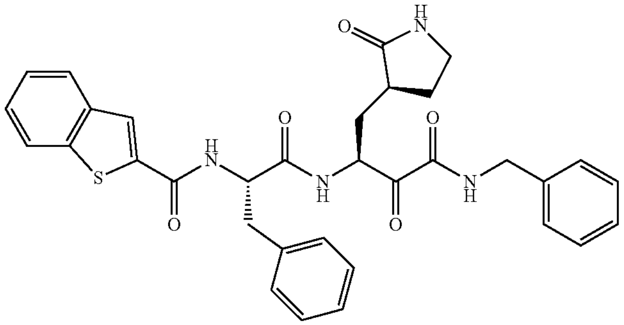 [SMILES: O=C(NCc1ccccc1)C(=O)[C@H](C[C@@H]1CCNC1=O)NC(=O)[C@H](Cc1ccccc1)NC(=O)c1cc2ccccc2s1] |

-continued
| number | structure |
|---|---|
| A61 | 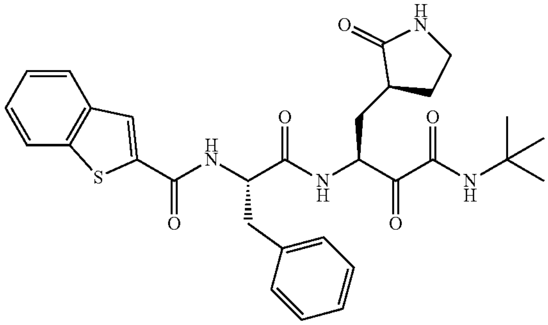 [SMILES: CC(C)(C)NC(=O)C(=O)[C@H](C[C@@H]1CCNC1=O)NC(=O)[C@H](Cc1ccccc1)NC(=O)c1cc2ccccc2s1] |
| A62 | 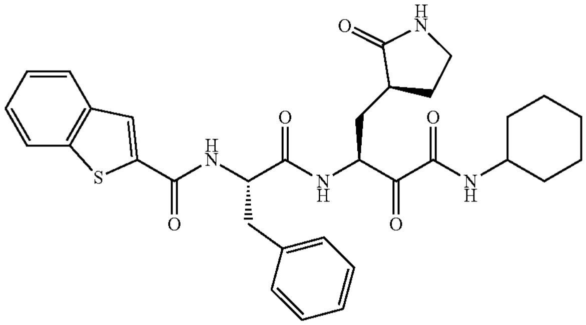 |
| A63 | 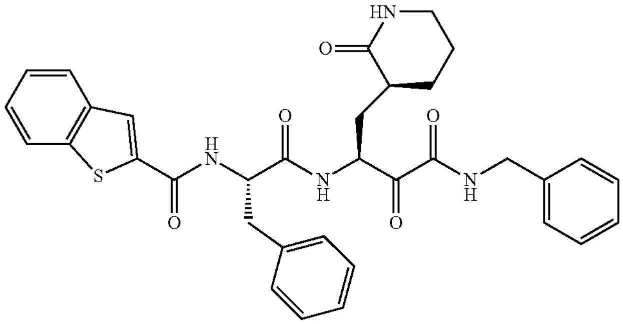 |
| A64 | 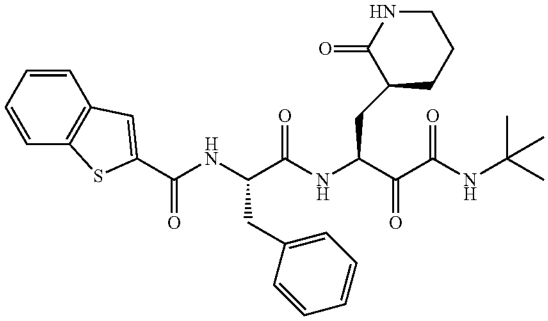 [SMILES: CC(C)(C)NC(=O)C(=O)[C@H](C[C@@H]1CCCNC1=O)NC(=O)[C@H](Cc1ccccc1)NC(=O)c1cc2ccccc2s1] |

-continued
| number | structure |
|---|---|
| A65 | 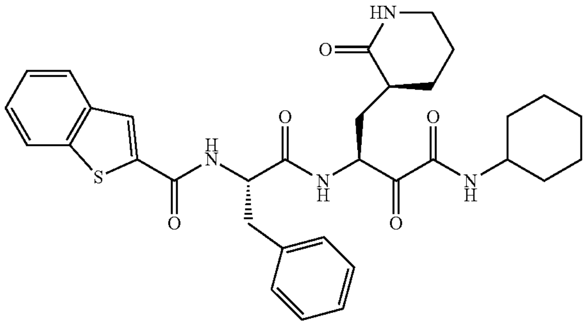 [SMILES: O=C(NC1CCCCC1)C(=O)[C@H](C[C@@H]1CCCNC1=O)NC(=O)[C@H](Cc1ccccc1)NC(=O)c1cc2ccccc2s1] |
| A66 | 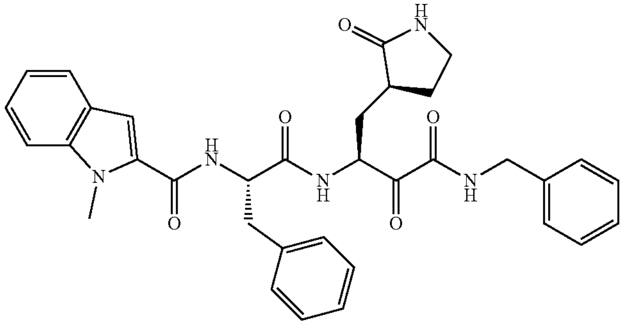 [SMILES: Cn1c(C(=O)N[C@@H](Cc2ccccc2)C(=O)N[C@@H](C[C@@H]2CCNC2=O)C(=O)C(=O)NCc2ccccc2)cc2ccccc21] |
| A67 | 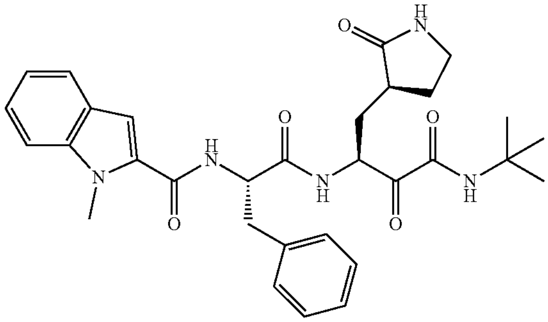 [SMILES: Cn1c(C(=O)N[C@@H](Cc2ccccc2)C(=O)N[C@@H](C[C@@H]2CCNC2=O)C(=O)C(=O)NC(C)(C)C)cc2ccccc21] |
| A68 | 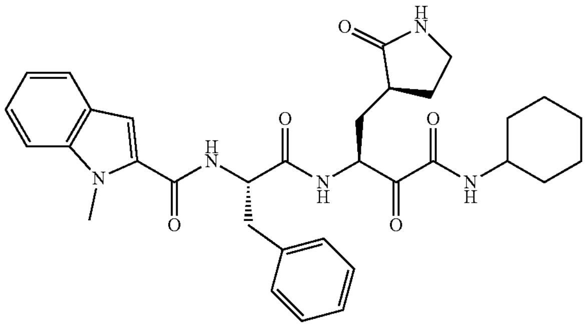 |

-continued
| number | structure |
|---|---|
| A69 | 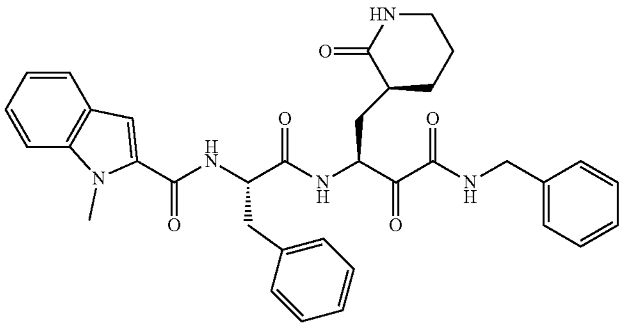 [SMILES: Cn1c(C(=O)N[C@@H](Cc2ccccc2)C(=O)N[C@@H](C[C@@H]2CCCNC2=O)C(=O)C(=O)NCc2ccccc2)cc2ccccc21] |
| A70 | 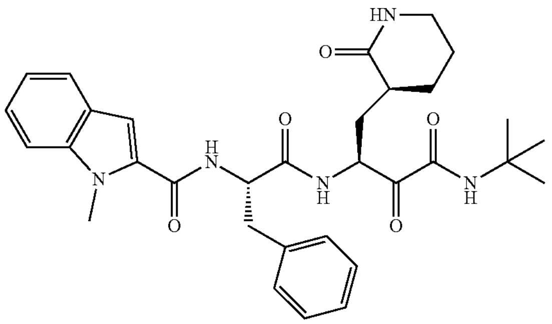 [SMILES: Cn1c(C(=O)N[C@@H](Cc2ccccc2)C(=O)N[C@@H](C[C@@H]2CCCNC2=O)C(=O)C(=O)NC(C)(C)C)cc2ccccc21] |
| A71 | 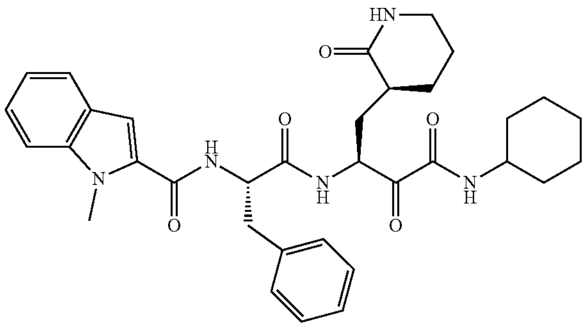 |
| A72 | 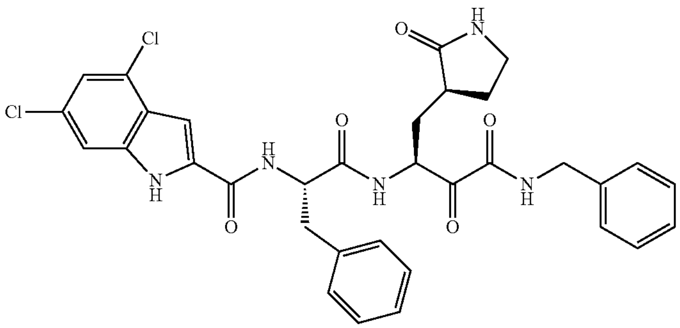 [SMILES: O=C(NCc1ccccc1)C(=O)[C@H](C[C@@H]1CCNC1=O)NC(=O)[C@H](Cc1ccccc1)NC(=O)c1cc2c(Cl)cc(Cl)cc2[nH]1] |

-continued
| number | structure |
| --- | --- |
| A73 | 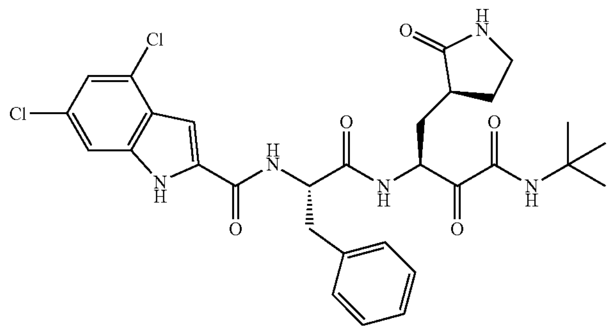 [SMILES: CC(C)(C)NC(=O)C(=O)[C@H](C[C@@H]1CCNC1=O)NC(=O)[C@H](Cc1ccccc1)NC(=O)c1cc2c(Cl)cc(Cl)cc2[nH]1] |
| A74 | 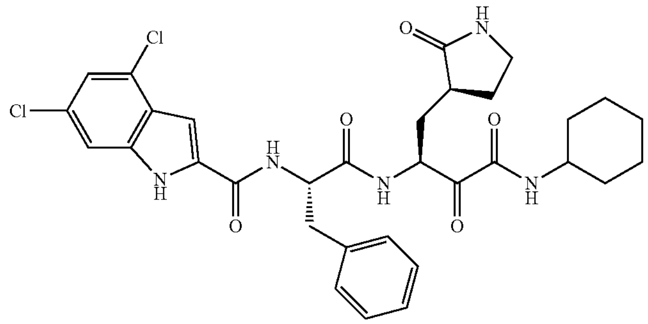 [SMILES: O=C(NC1CCCCC1)C(=O)[C@H](C[C@@H]1CCNC1=O)NC(=O)[C@H](Cc1ccccc1)NC(=O)c1cc2c(Cl)cc(Cl)cc2[nH]1] |
| A75 | 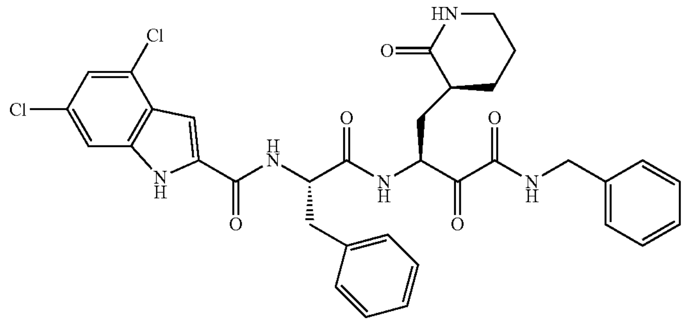 [SMILES: O=C(NCc1ccccc1)C(=O)[C@H](C[C@@H]1CCCNC1=O)NC(=O)[C@H](Cc1ccccc1)NC(=O)c1cc2c(Cl)cc(Cl)cc2[nH]1] |
| A76 | 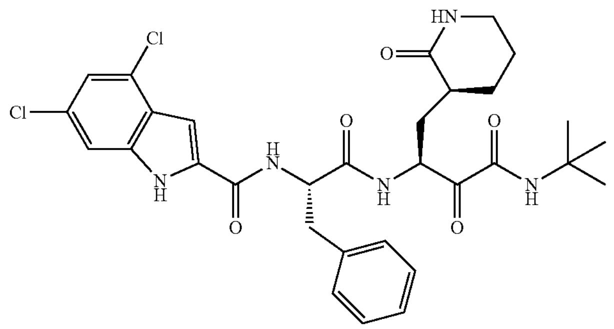 [SMILES: CC(C)(C)NC(=O)C(=O)[C@H](C[C@@H]1CCCNC1=O)NC(=O)[C@H](Cc1ccccc1)NC(=O)c1cc2c(Cl)cc(Cl)cc2[nH]1] |

-continued
| number | structure |
| --- | --- |
| A77 | 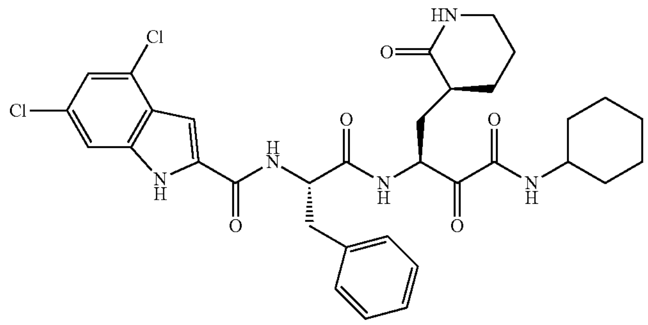 [SMILES: O=C(NC1CCCCC1)C(=O)[C@H](C[C@@H]1CCCNC1=O)NC(=O)[C@H](Cc1ccccc1)NC(=O)c1cc2c(Cl)cc(Cl)cc2[nH]1] |
| A78 | 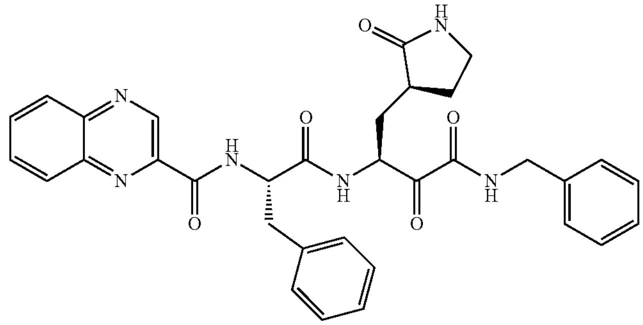 [SMILES: O=C(NCc1ccccc1)C(=O)[C@H](C[C@@H]1CCNC1=O)NC(=O)[C@H](Cc1ccccc1)NC(=O)c1cnc2ccccc2n1] |
| A79 | 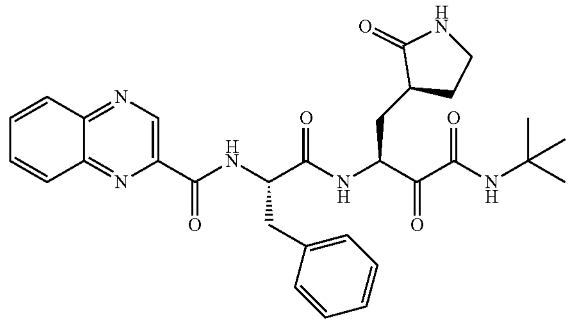 [SMILES: CC(C)(C)NC(=O)C(=O)[C@H](C[C@@H]1CCNC1=O)NC(=O)[C@H](Cc1ccccc1)NC(=O)c1cnc2ccccc2n1] |
| A80 | 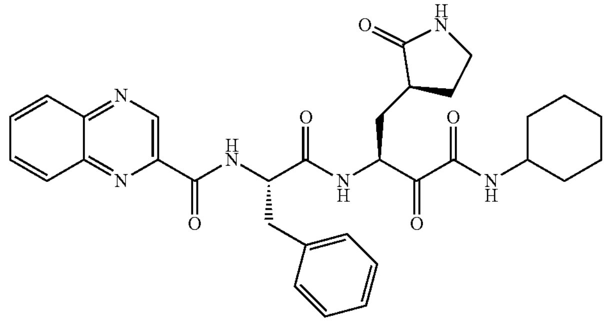 [SMILES: O=C(NC1CCCCC1)C(=O)[C@H](C[C@@H]1CCNC1=O)NC(=O)[C@H](Cc1ccccc1)NC(=O)c1cnc2ccccc2n1] |

-continued
| number | structure |
|---|---|
| A81 | 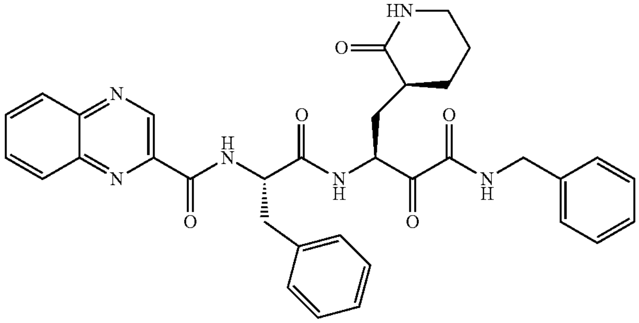 [SMILES: O=C(NCc1ccccc1)C(=O)[C@H](C[C@@H]1CCCNC1=O)NC(=O)[C@H](Cc1ccccc1)NC(=O)c1cnc2ccccc2n1] |
| A82 | 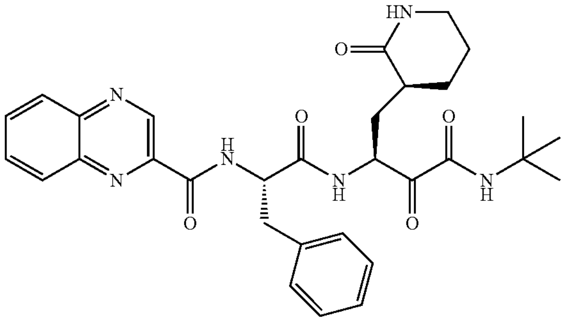 [SMILES: CC(C)(C)NC(=O)C(=O)[C@H](C[C@@H]1CCCNC1=O)NC(=O)[C@H](Cc1ccccc1)NC(=O)c1cnc2ccccc2n1] |
| A83 | 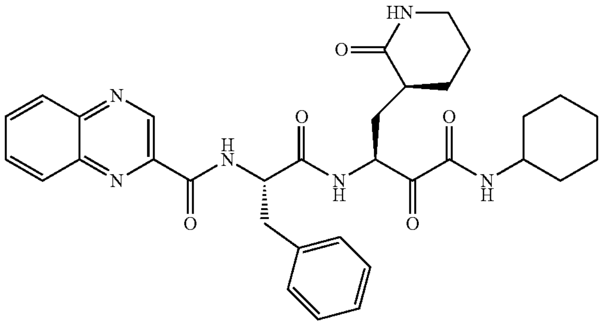 [SMILES: O=C(NC1CCCCC1)C(=O)[C@H](C[C@@H]1CCCNC1=O)NC(=O)[C@H](Cc1ccccc1)NC(=O)c1cnc2ccccc2n1] |
| A84 | 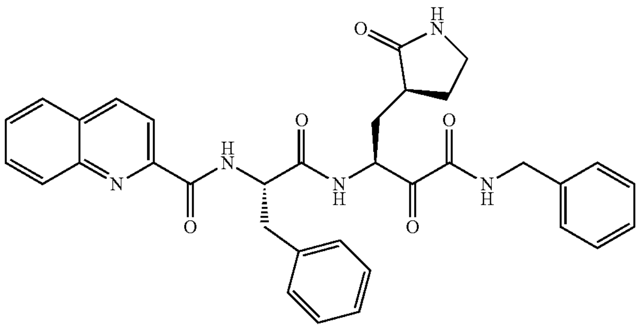 [SMILES: O=C(NCc1ccccc1)C(=O)[C@H](C[C@@H]1CCNC1=O)NC(=O)[C@H](Cc1ccccc1)NC(=O)c1ccc2ccccc2n1] |

-continued
| number | structure |
|---|---|
| A85 | 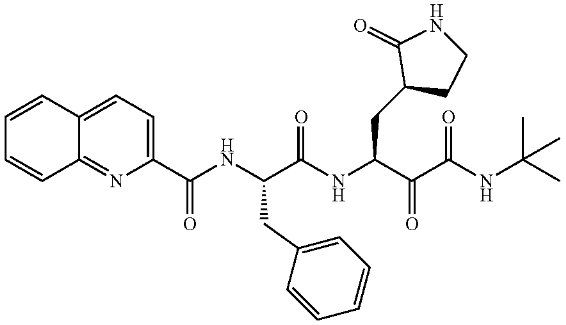 [SMILES: CC(C)(C)NC(=O)C(=O)[C@H](C[C@@H]1CCNC1=O)NC(=O)[C@H](Cc1ccccc1)NC(=O)c1ccc2ccccc2n1] |
| A86 | 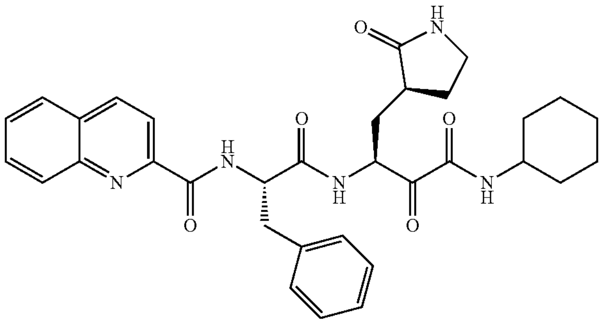 [SMILES: O=C(NC1CCCCC1)C(=O)[C@H](C[C@@H]1CCNC1=O)NC(=O)[C@H](Cc1ccccc1)NC(=O)c1ccc2ccccc2n1] |
| A87 | 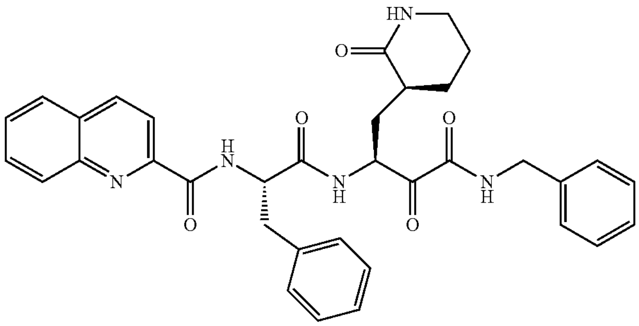 [SMILES: O=C(NCc1ccccc1)C(=O)[C@H](C[C@@H]1CCCNC1=O)NC(=O)[C@H](Cc1ccccc1)NC(=O)c1ccc2ccccc2n1] |
| A88 | 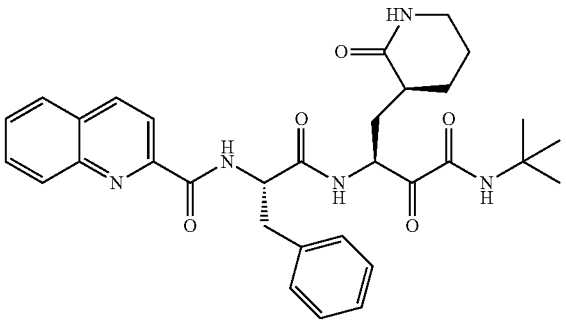 |

-continued
| number | structure |
|---|---|
| A89 | 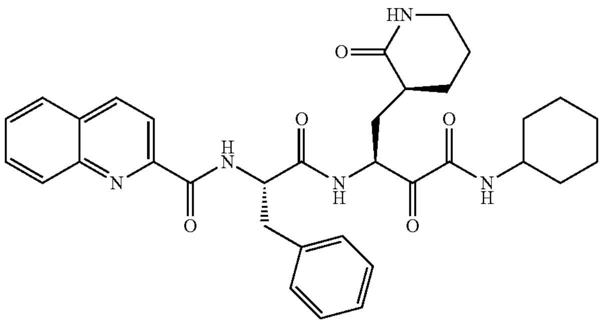 [SMILES: O=C(NC1CCCCC1)C(=O)[C@H](C[C@@H]1CCCNC1=O)NC(=O)[C@H](Cc1ccccc1)NC(=O)c1ccc2ccccc2n1] |
| A90 | 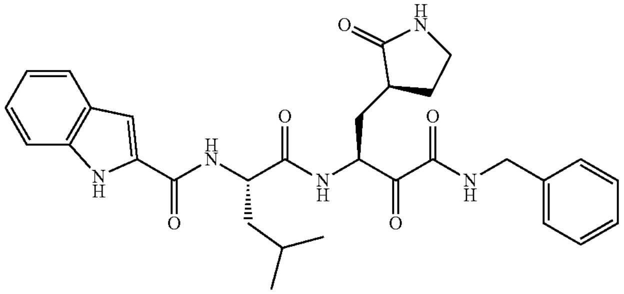 [SMILES: CC(C)C[C@H](NC(=O)c1cc2ccccc2[nH]1)C(=O)N[C@@H](C[C@@H]1CCNC1=O)C(=O)C(=O)NCc1ccccc1] |
| A91 | 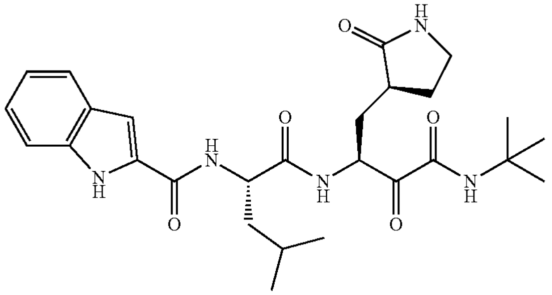 [SMILES: CC(C)C[C@H](NC(=O)c1cc2ccccc2[nH]1)C(=O)N[C@@H](C[C@@H]1CCNC1=O)C(=O)C(=O)NC(C)(C)C] |
| A92 | 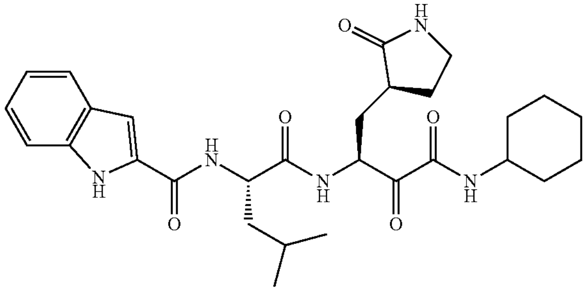 [SMILES: CC(C)C[C@H](NC(=O)c1cc2ccccc2[nH]1)C(=O)N[C@@H](C[C@@H]1CCNC1=O)C(=O)C(=O)NC1CCCCC1] |
| A93 | 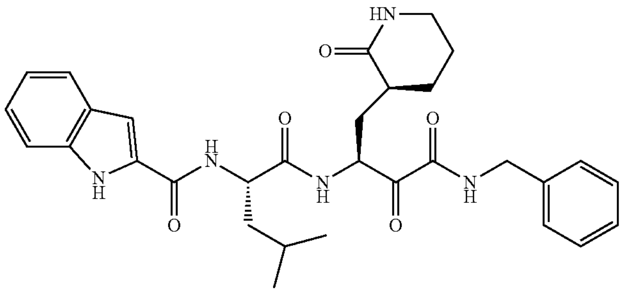 [SMILES: CC(C)C[C@H](NC(=O)c1cc2ccccc2[nH]1)C(=O)N[C@@H](C[C@@H]1CCCNC1=O)C(=O)C(=O)NCc1ccccc1] |

-continued
| number | structure |
|---|---|
| A94 | 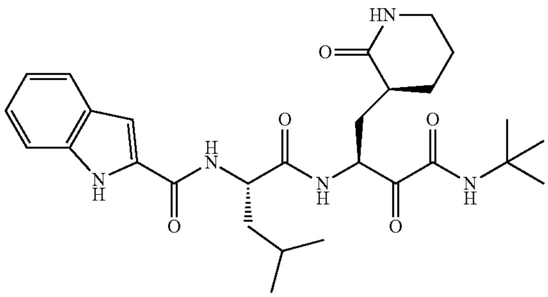 [SMILES: CC(C)C[C@H](NC(=O)c1cc2ccccc2[nH]1)C(=O)N[C@@H](C[C@@H]1CCCNC1=O)C(=O)C(=O)NC(C)(C)C] |
| A95 | 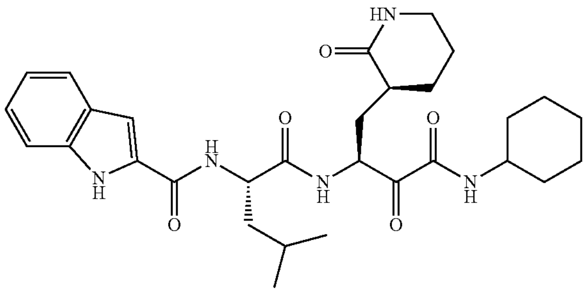 [SMILES: CC(C)C[C@H](NC(=O)c1cc2ccccc2[nH]1)C(=O)N[C@@H](C[C@@H]1CCCNC1=O)C(=O)C(=O)NC1CCCCC1] |
| A96 | 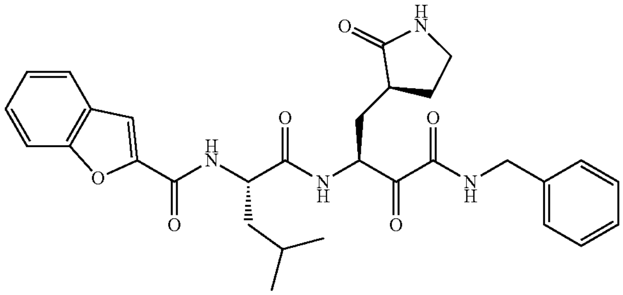 |
| A97 | 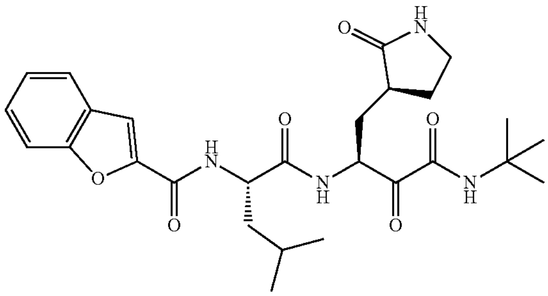 |
| A98 | 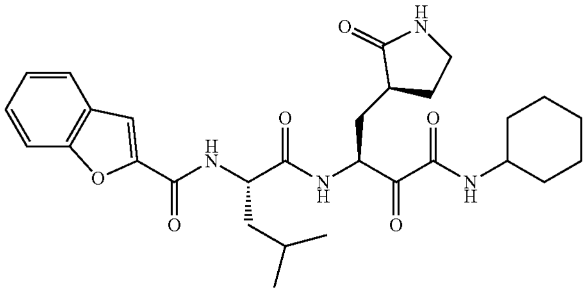 [SMILES: CC(C)C[C@H](NC(=O)c1cc2ccccc2o1)C(=O)N[C@@H](C[C@@H]1CCNC1=O)C(=O)C(=O)NC1CCCCC1] |

-continued
| number | structure |
|---|---|
| A99 | 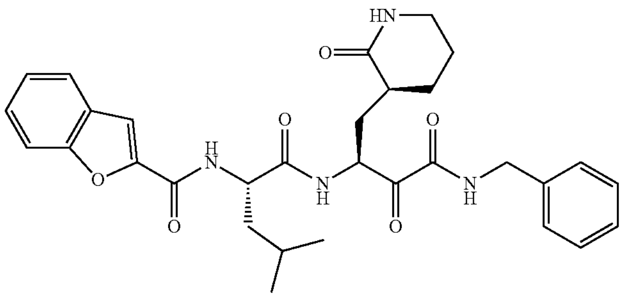 [SMILES: CC(C)C[C@H](NC(=O)c1cc2ccccc2o1)C(=O)N[C@@H](C[C@@H]1CCCNC1=O)C(=O)C(=O)NCc1ccccc1] |
| A100 | 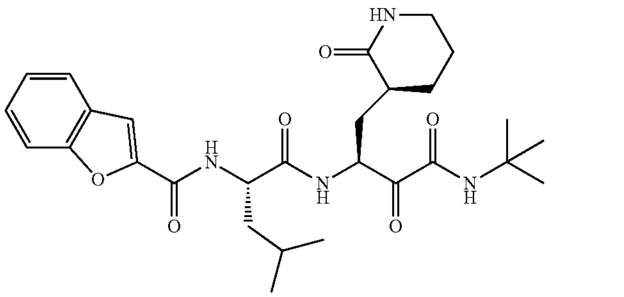 [SMILES: CC(C)C[C@H](NC(=O)c1cc2ccccc2o1)C(=O)N[C@@H](C[C@@H]1CCCNC1=O)C(=O)C(=O)NC(C)(C)C] |
| A101 | 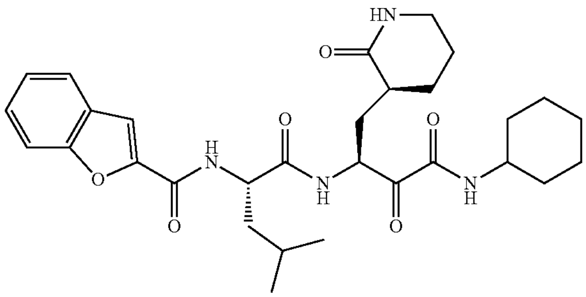 [SMILES: CC(C)C[C@H](NC(=O)c1cc2ccccc2o1)C(=O)N[C@@H](C[C@@H]1CCCNC1=O)C(=O)C(=O)NC1CCCCC1] |
| A102 | 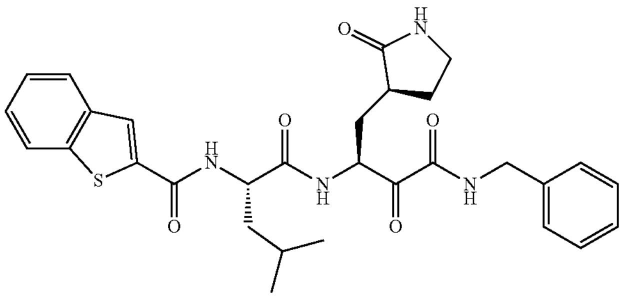 [SMILES: CC(C)C[C@H](NC(=O)c1cc2ccccc2s1)C(=O)N[C@@H](C[C@@H]1CCNC1=O)C(=O)C(=O)NCc1ccccc1] |
| A103 | 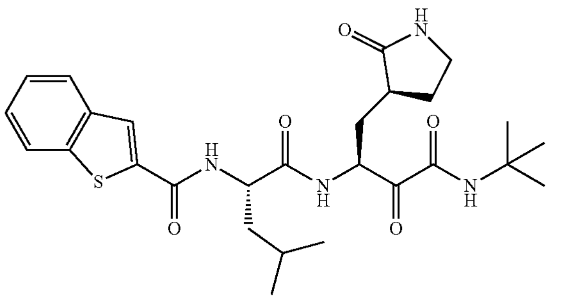 |

-continued
| number | structure |
| --- | --- |
| A104 | 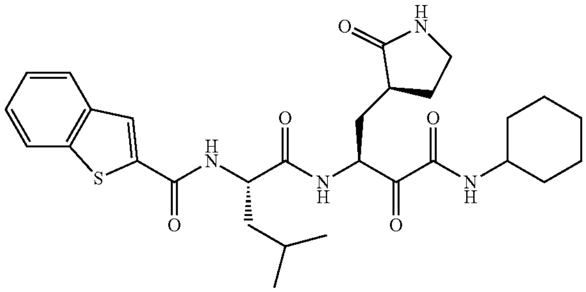 [SMILES: CC(C)C[C@H](NC(=O)c1cc2ccccc2s1)C(=O)N[C@@H](C[C@@H]1CCNC1=O)C(=O)C(=O)NC1CCCCC1] |
| A105 | 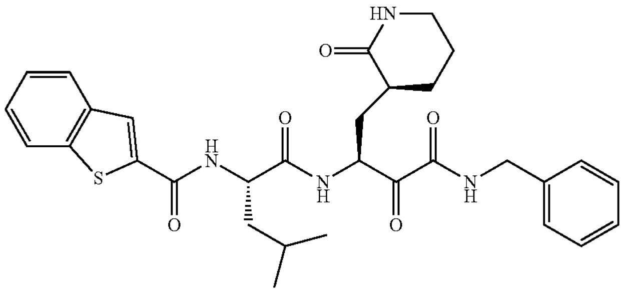 [SMILES: CC(C)C[C@H](NC(=O)c1cc2ccccc2s1)C(=O)N[C@@H](C[C@@H]1CCCNC1=O)C(=O)C(=O)NCc1ccccc1] |
| A106 | 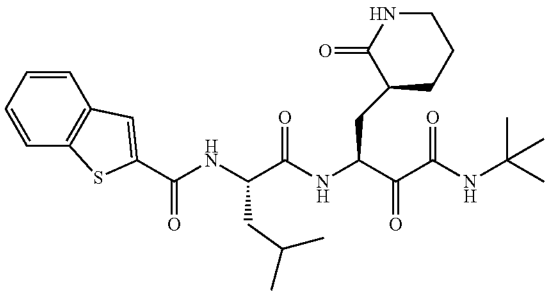 [SMILES: CC(C)C[C@H](NC(=O)c1cc2ccccc2s1)C(=O)N[C@@H](C[C@@H]1CCCNC1=O)C(=O)C(=O)NC(C)(C)C] |
| A107 | 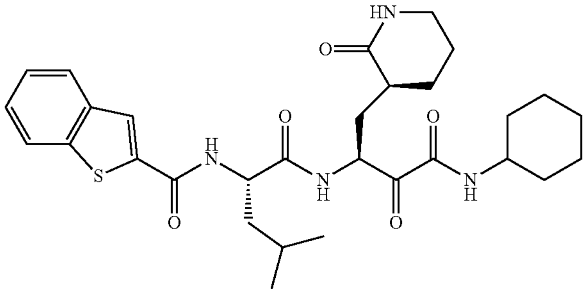 [SMILES: CC(C)C[C@H](NC(=O)c1cc2ccccc2s1)C(=O)N[C@@H](C[C@@H]1CCCNC1=O)C(=O)C(=O)NC1CCCCC1] |
| A108 | 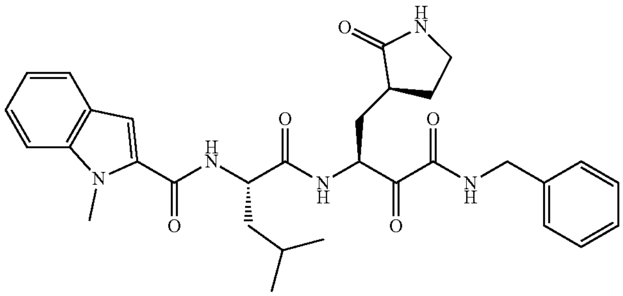 [SMILES: CC(C)C[C@H](NC(=O)c1cc2ccccc2n1C)C(=O)N[C@@H](C[C@@H]1CCNC1=O)C(=O)C(=O)NCc1ccccc1] |

-continued
| number | structure |
|---|---|
| A109 | 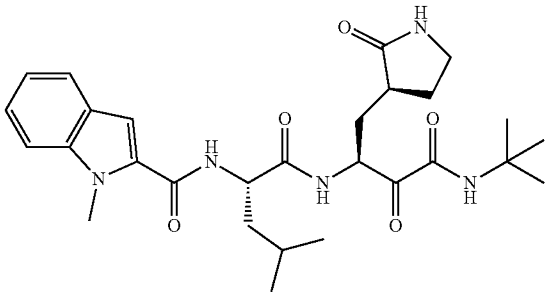 [SMILES: CC(C)C[C@H](NC(=O)c1cc2ccccc2n1C)C(=O)N[C@@H](C[C@@H]1CCNC1=O)C(=O)C(=O)NC(C)(C)C] |
| A110 | 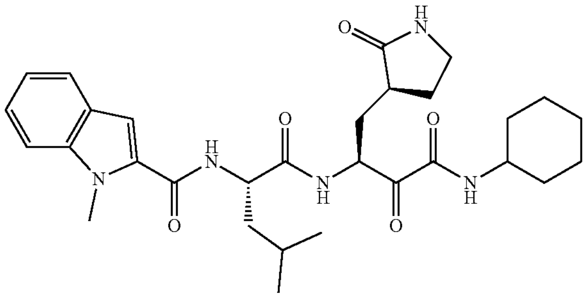 [SMILES: CC(C)C[C@H](NC(=O)c1cc2ccccc2n1C)C(=O)N[C@@H](C[C@@H]1CCNC1=O)C(=O)C(=O)NC1CCCCC1] |
| A111 | 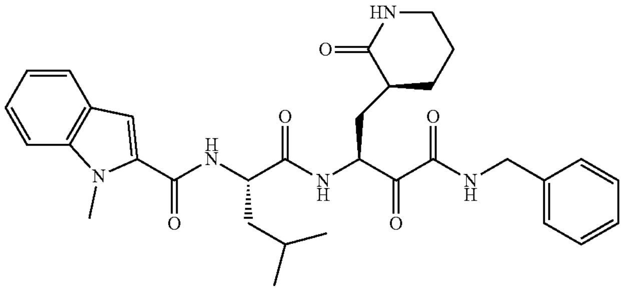 [SMILES: CC(C)C[C@H](NC(=O)c1cc2ccccc2n1C)C(=O)N[C@@H](C[C@@H]1CCCNC1=O)C(=O)C(=O)NCc1ccccc1] |
| A112 | 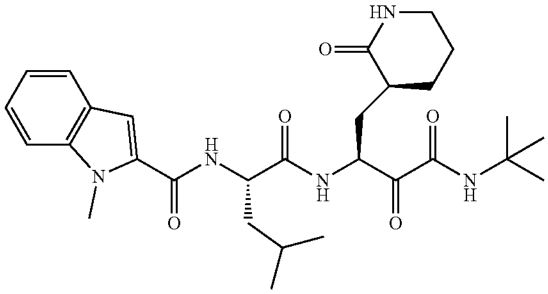 [SMILES: CC(C)C[C@H](NC(=O)c1cc2ccccc2n1C)C(=O)N[C@@H](C[C@@H]1CCCNC1=O)C(=O)C(=O)NC(C)(C)C] |
| A113 | 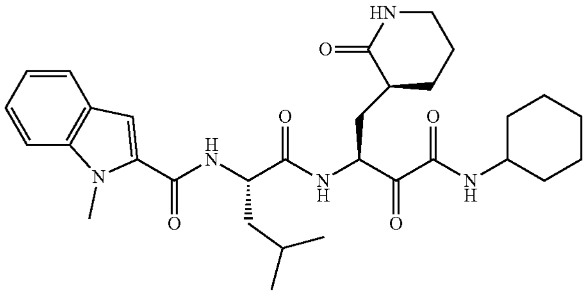 [SMILES: CC(C)C[C@H](NC(=O)c1cc2ccccc2n1C)C(=O)N[C@@H](C[C@@H]1CCCNC1=O)C(=O)C(=O)NC1CCCCC1] |

-continued
| number | structure |
| --- | --- |
| A114 | 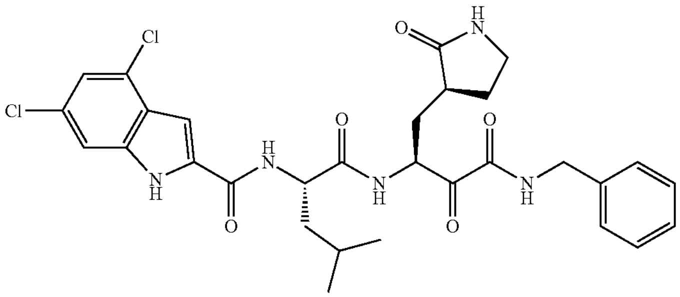 [SMILES: CC(C)C[C@H](NC(=O)c1cc2c(Cl)cc(Cl)cc2[nH]1)C(=O)N[C@@H](C[C@@H]1CCNC1=O)C(=O)C(=O)NCc1ccccc1] |
| A115 | 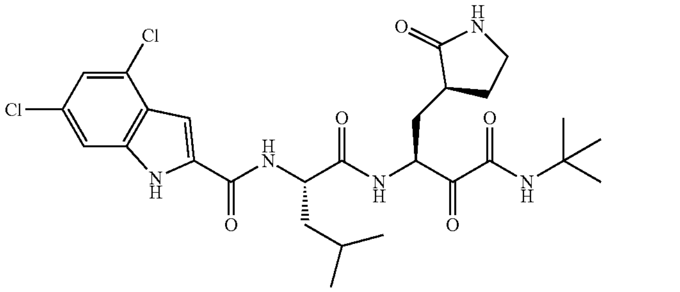 [SMILES: CC(C)C[C@H](NC(=O)c1cc2c(Cl)cc(Cl)cc2[nH]1)C(=O)N[C@@H](C[C@@H]1CCNC1=O)C(=O)C(=O)NC(C)(C)C] |
| A116 | 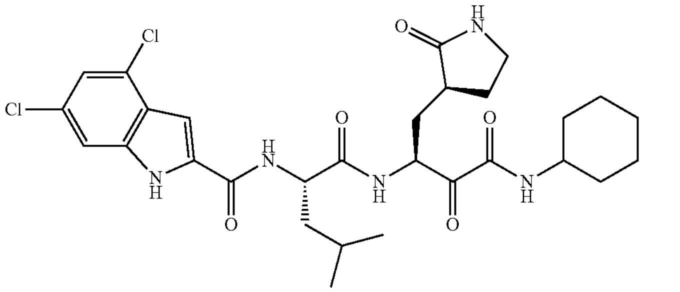 [SMILES: CC(C)C[C@H](NC(=O)c1cc2c(Cl)cc(Cl)cc2[nH]1)C(=O)N[C@@H](C[C@@H]1CCNC1=O)C(=O)C(=O)NC1CCCCC1] |
| A117 | 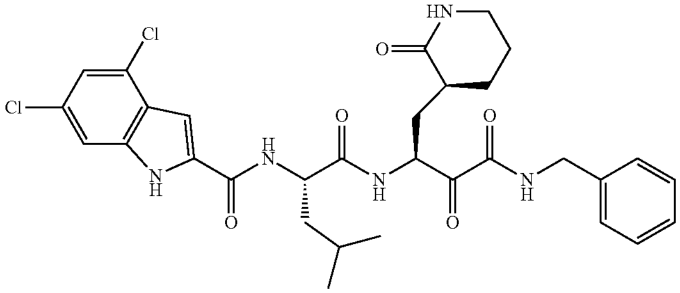 [SMILES: CC(C)C[C@H](NC(=O)c1cc2c(Cl)cc(Cl)cc2[nH]1)C(=O)N[C@@H](C[C@@H]1CCCNC1=O)C(=O)C(=O)NCc1ccccc1] |
| A118 | 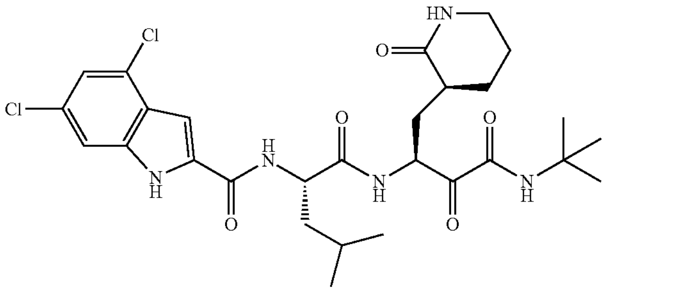 [SMILES: CC(C)C[C@H](NC(=O)c1cc2c(Cl)cc(Cl)cc2[nH]1)C(=O)N[C@@H](C[C@@H]1CCCNC1=O)C(=O)C(=O)NC(C)(C)C] |

-continued
| number | structure |
|---|---|
| A119 | 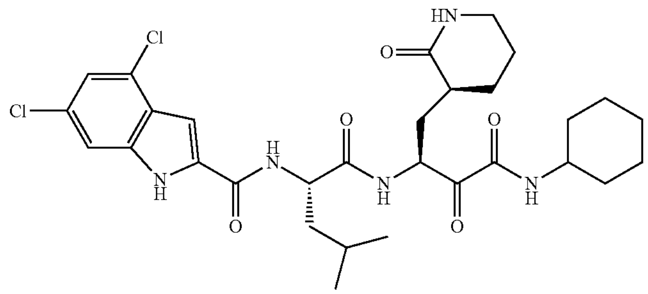 [SMILES: CC(C)C[C@H](NC(=O)c1cc2c(Cl)cc(Cl)cc2[nH]1)C(=O)N[C@@H](C[C@@H]1CCCNC1=O)C(=O)C(=O)NC1CCCCC1] |
| A120 | 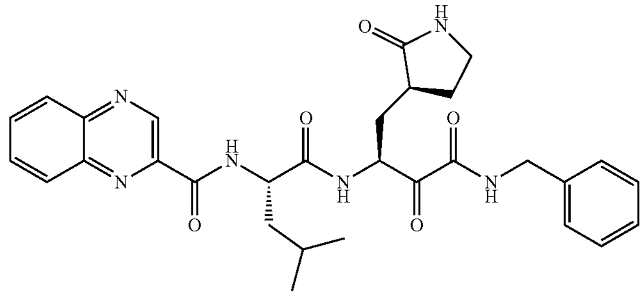 [SMILES: CC(C)C[C@H](NC(=O)c1cnc2ccccc2n1)C(=O)N[C@@H](C[C@@H]1CCNC1=O)C(=O)C(=O)NCc1ccccc1] |
| A121 | 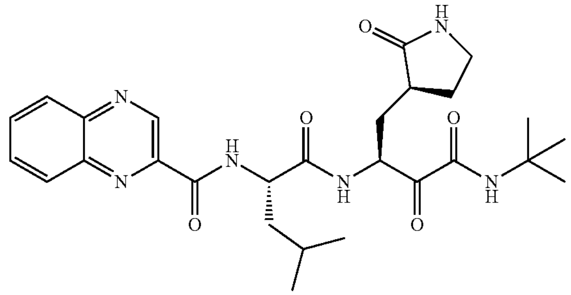 [SMILES: CC(C)C[C@H](NC(=O)c1cnc2ccccc2n1)C(=O)N[C@@H](C[C@@H]1CCNC1=O)C(=O)C(=O)NC(C)(C)C] |
| A122 | 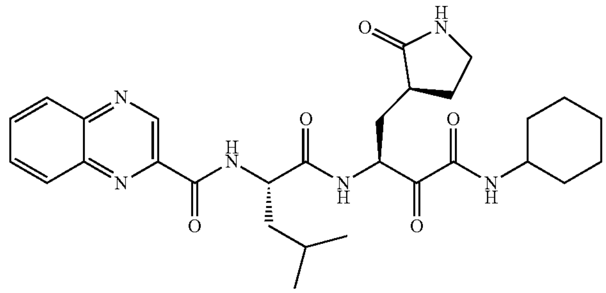 [SMILES: CC(C)C[C@H](NC(=O)c1cnc2ccccc2n1)C(=O)N[C@@H](C[C@@H]1CCNC1=O)C(=O)C(=O)NC1CCCCC1] |
| A123 | 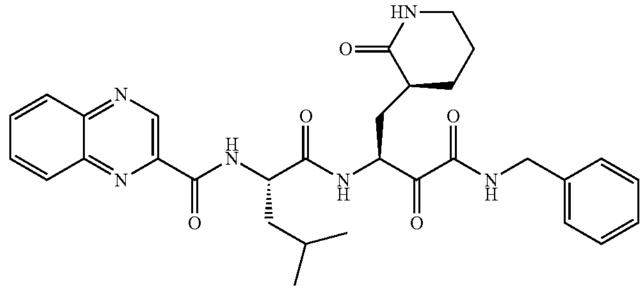 [SMILES: CC(C)C[C@H](NC(=O)c1cnc2ccccc2n1)C(=O)N[C@@H](C[C@@H]1CCCNC1=O)C(=O)C(=O)NCc1ccccc1] |

-continued
| number | structure |
|---|---|
| A124 | 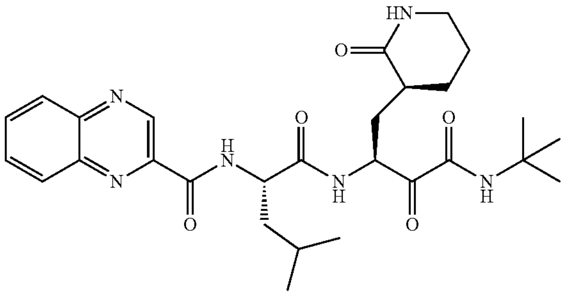 [SMILES: CC(C)C[C@H](NC(=O)c1cnc2ccccc2n1)C(=O)N[C@@H](C[C@@H]1CCCNC1=O)C(=O)C(=O)NC(C)(C)C] |
| A125 | 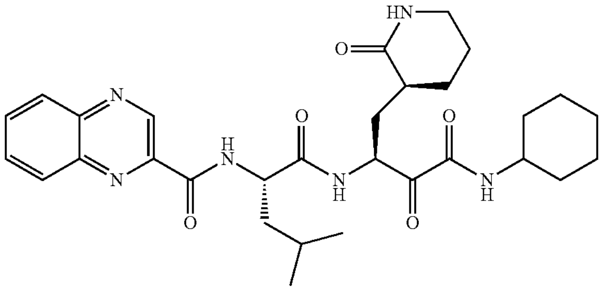 [SMILES: CC(C)C[C@H](NC(=O)c1cnc2ccccc2n1)C(=O)N[C@@H](C[C@@H]1CCCNC1=O)C(=O)C(=O)NC1CCCCC1] |
| A126 | 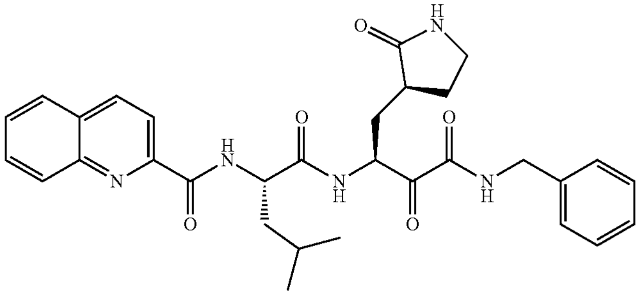 [SMILES: CC(C)C[C@H](NC(=O)c1ccc2ccccc2n1)C(=O)N[C@@H](C[C@@H]1CCNC1=O)C(=O)C(=O)NCc1ccccc1] |
| A127 | 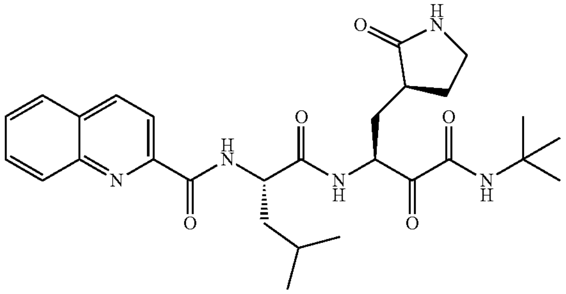 [SMILES: CC(C)C[C@H](NC(=O)c1ccc2ccccc2n1)C(=O)N[C@@H](C[C@@H]1CCNC1=O)C(=O)C(=O)NC(C)(C)C] |
| A128 | 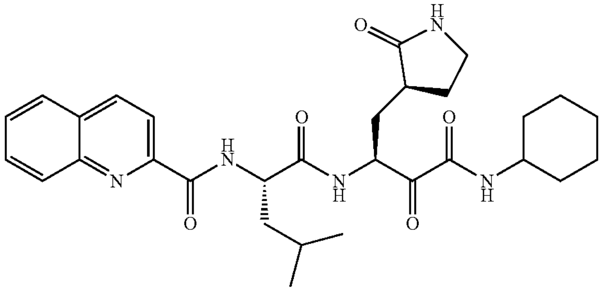 [SMILES: CC(C)C[C@H](NC(=O)c1ccc2ccccc2n1)C(=O)N[C@@H](C[C@@H]1CCNC1=O)C(=O)C(=O)NC1CCCCC1] |

-continued
| number | structure |
| --- | --- |
| A129 | 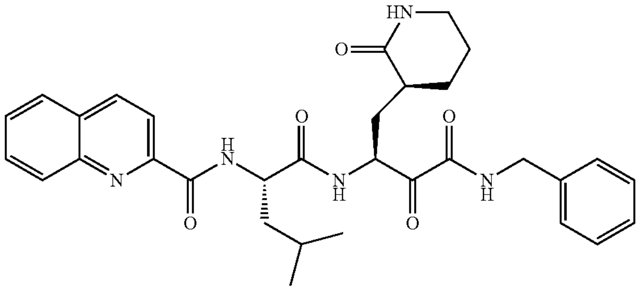 [SMILES: CC(C)C[C@H](NC(=O)c1ccc2ccccc2n1)C(=O)N[C@@H](C[C@@H]1CCCNC1=O)C(=O)C(=O)NCc1ccccc1] |
| A130 | 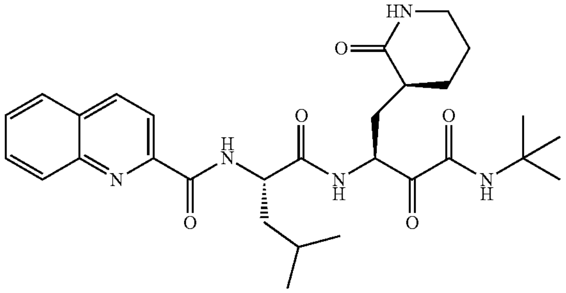 [SMILES: CC(C)C[C@H](NC(=O)c1ccc2ccccc2n1)C(=O)N[C@@H](C[C@@H]1CCCNC1=O)C(=O)C(=O)NC(C)(C)C] |
| A131 | 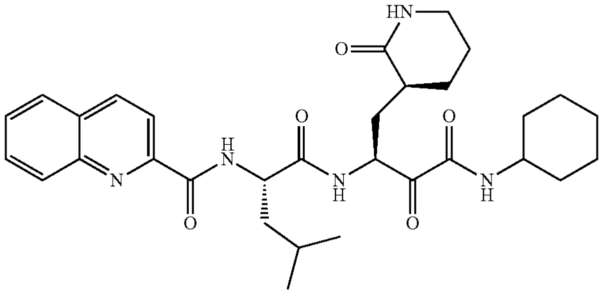 [SMILES: CC(C)C[C@H](NC(=O)c1ccc2ccccc2n1)C(=O)N[C@@H](C[C@@H]1CCCNC1=O)C(=O)C(=O)NC1CCCCC1] |
| A156 | 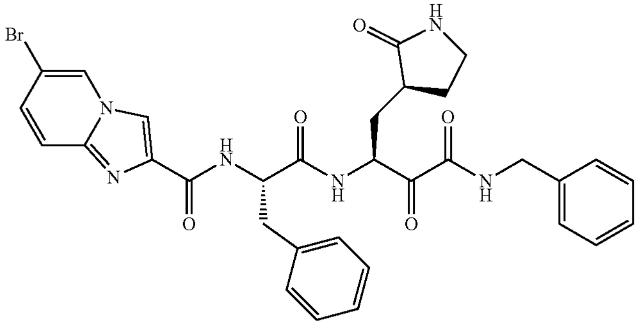 [SMILES: O=C(NCc1ccccc1)C(=O)[C@H](C[C@@H]1CCNC1=O)NC(=O)[C@H](Cc1ccccc1)NC(=O)c1cn2cc(Br)ccc2n1] |
| A157 | 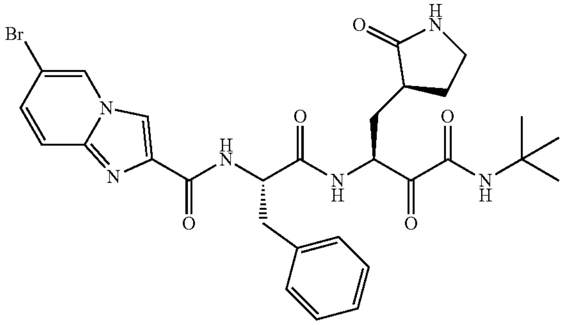 [SMILES: CC(C)(C)NC(=O)C(=O)[C@H](C[C@@H]1CCNC1=O)NC(=O)[C@H](Cc1ccccc1)NC(=O)c1cn2cc(Br)ccc2n1] |

-continued
| number | structure |
|---|---|
| A158 | 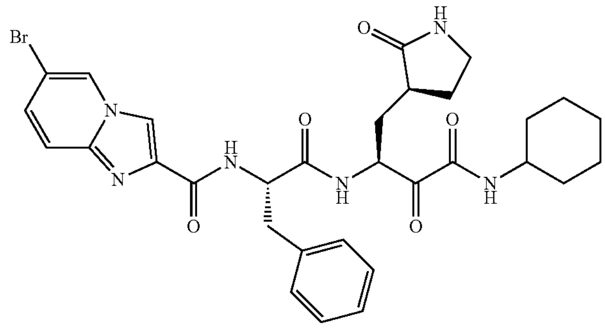 [SMILES: O=C(NC1CCCCC1)C(=O)[C@H](C[C@@H]1CCNC1=O)NC(=O)[C@H](Cc1ccccc1)NC(=O)c1cn2cc(Br)ccc2n1] |
| A159 | 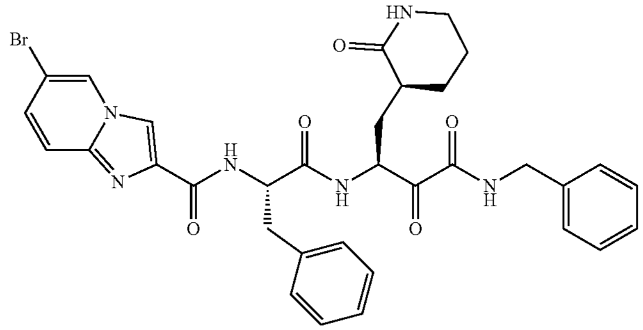 [SMILES: O=C(NCc1ccccc1)C(=O)[C@H](C[C@@H]1CCCNC1=O)NC(=O)[C@H](Cc1ccccc1)NC(=O)c1cn2cc(Br)ccc2n1] |
| A160 | 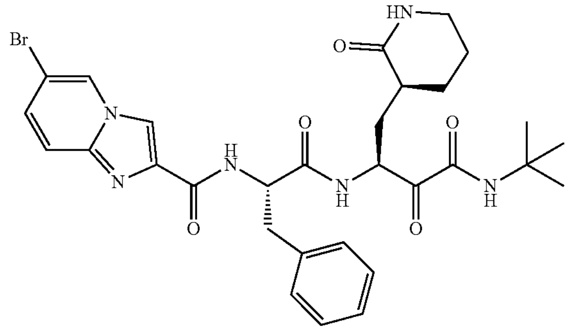 [SMILES: CC(C)(C)NC(=O)C(=O)[C@H](C[C@@H]1CCCNC1=O)NC(=O)[C@H](Cc1ccccc1)NC(=O)c1cn2cc(Br)ccc2n1] |
| A161 | 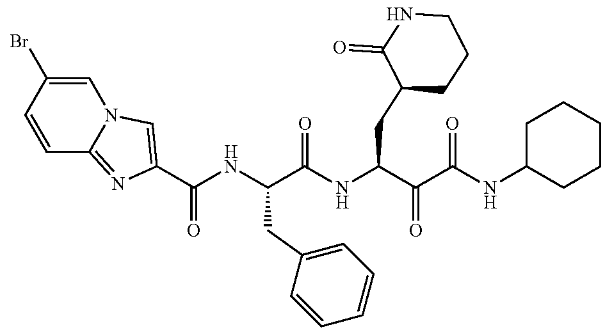 [SMILES: O=C(NC1CCCCC1)C(=O)[C@H](C[C@@H]1CCCNC1=O)NC(=O)[C@H](Cc1ccccc1)NC(=O)c1cn2cc(Br)ccc2n1] |

-continued
| number | structure |
|---|---|
| A162 | 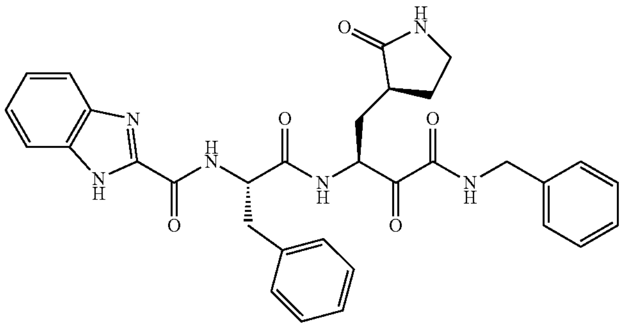 [SMILES: O=C(NCc1ccccc1)C(=O)[C@H](C[C@@H]1CCNC1=O)NC(=O)[C@H](Cc1ccccc1)NC(=O)c1nc2ccccc2[nH]1] |
| A163 | 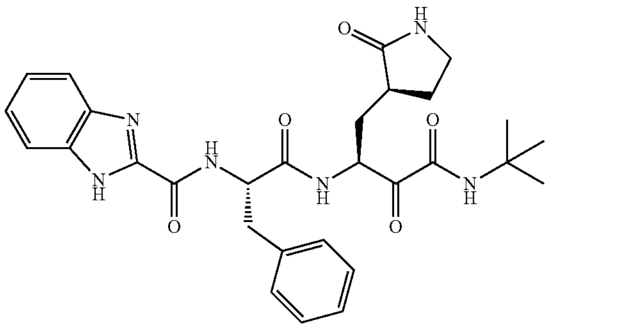 [SMILES: CC(C)(C)NC(=O)C(=O)[C@H](C[C@@H]1CCNC1=O)NC(=O)[C@H](Cc1ccccc1)NC(=O)c1nc2ccccc2[nH]1] |
| A164 | 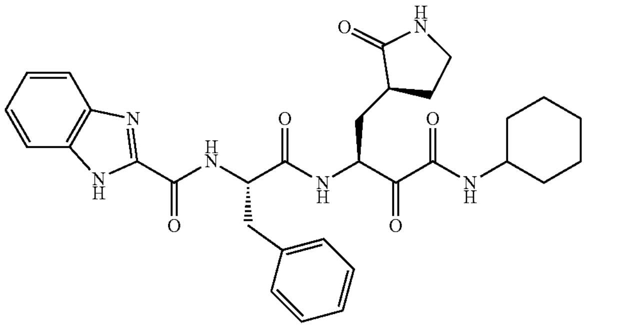 [SMILES: O=C(NC1CCCCC1)C(=O)[C@H](C[C@@H]1CCNC1=O)NC(=O)[C@H](Cc1ccccc1)NC(=O)c1nc2ccccc2[nH]1] |
| A165 | 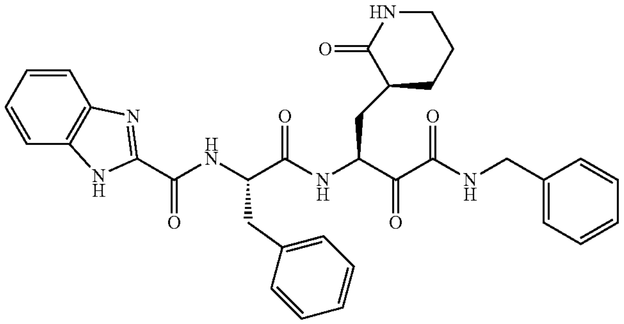 |

-continued
| number | structure |
|---|---|
| A166 | 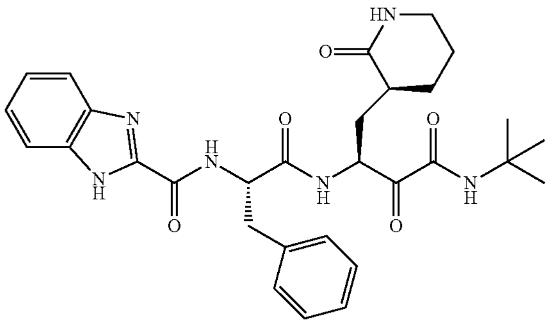 [SMILES: CC(C)(C)NC(=O)C(=O)[C@H](C[C@@H]1CCCNC1=O)NC(=O)[C@H](Cc1ccccc1)NC(=O)c1nc2ccccc2[nH]1] |
| A167 | 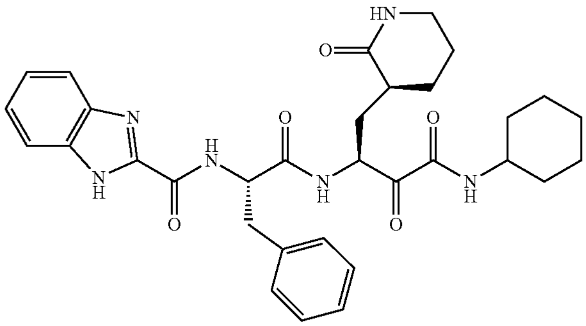 |
| A174 | 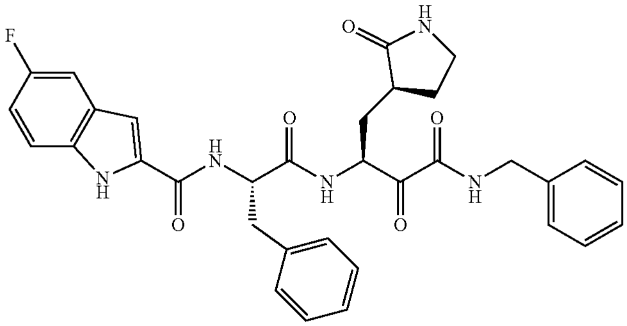 [SMILES: O=C(NCc1ccccc1)C(=O)[C@H](C[C@@H]1CCNC1=O)NC(=O)[C@H](Cc1ccccc1)NC(=O)c1cc2cc(F)ccc2[nH]1] |
| A175 | 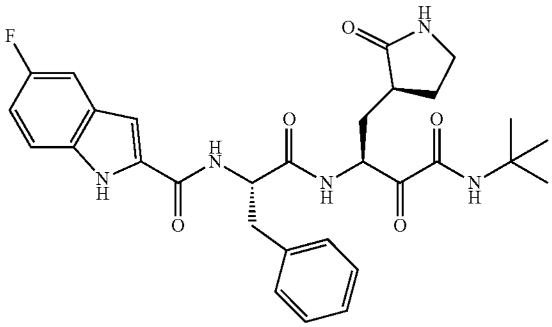 [SMILES: CC(C)(C)NC(=O)C(=O)[C@H](C[C@@H]1CCNC1=O)NC(=O)[C@H](Cc1ccccc1)NC(=O)c1cc2cc(F)ccc2[nH]1] |

-continued
| number | structure |
|---|---|
| A176 | 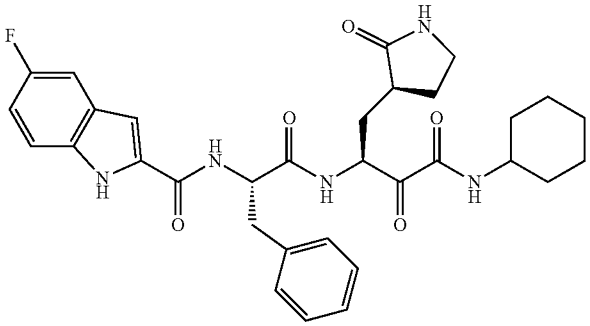 [SMILES: O=C(NC1CCCCC1)C(=O)[C@H](C[C@@H]1CCNC1=O)NC(=O)[C@H](Cc1ccccc1)NC(=O)c1cc2cc(F)ccc2[nH]1] |
| A177 | 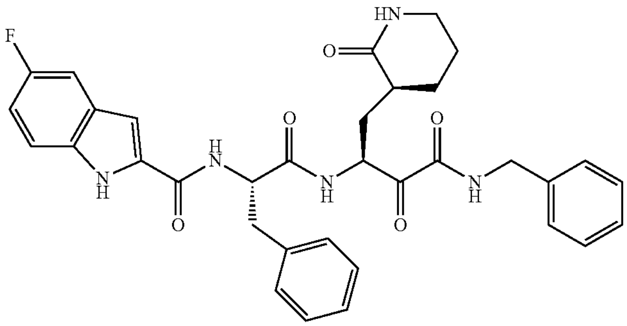 [SMILES: O=C(NCc1ccccc1)C(=O)[C@H](C[C@@H]1CCCNC1=O)NC(=O)[C@H](Cc1ccccc1)NC(=O)c1cc2cc(F)ccc2[nH]1] |
| A178 | 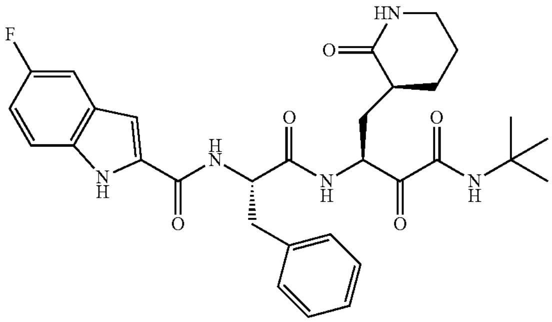 [SMILES: CC(C)(C)NC(=O)C(=O)[C@H](C[C@@H]1CCCNC1=O)NC(=O)[C@H](Cc1ccccc1)NC(=O)c1cc2cc(F)ccc2[nH]1] |
| A179 | 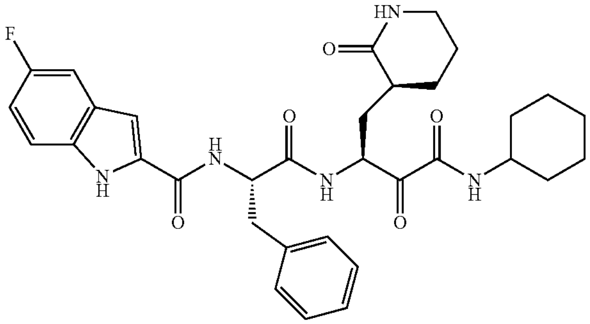 [SMILES: O=C(NC1CCCCC1)C(=O)[C@H](C[C@@H]1CCCNC1=O)NC(=O)[C@H](Cc1ccccc1)NC(=O)c1cc2cc(F)ccc2[nH]1] |

-continued
| number | structure |
|---|---|
| A180 | 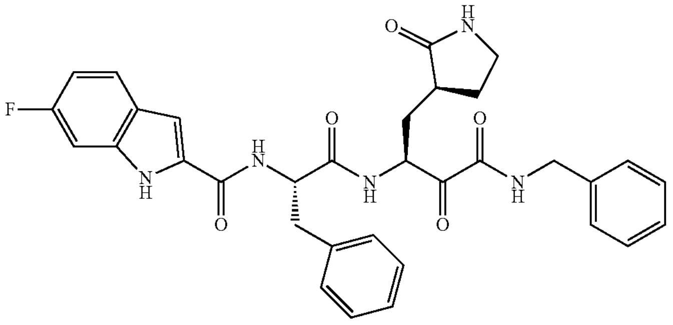 [SMILES: O=C(NCc1ccccc1)C(=O)[C@H](C[C@@H]1CCNC1=O)NC(=O)[C@H](Cc1ccccc1)NC(=O)c1cc2ccc(F)cc2[nH]1] |
| A181 | 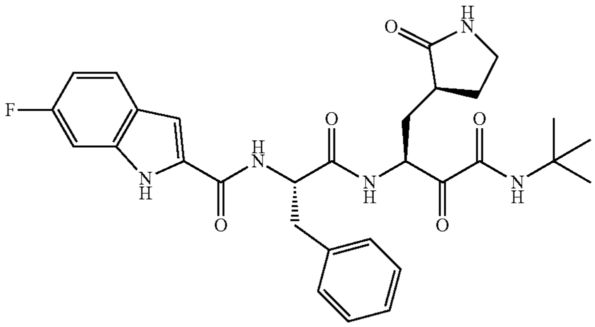 [SMILES: CC(C)(C)NC(=O)C(=O)[C@H](C[C@@H]1CCNC1=O)NC(=O)[C@H](Cc1ccccc1)NC(=O)c1cc2ccc(F)cc2[nH]1] |
| A182 | 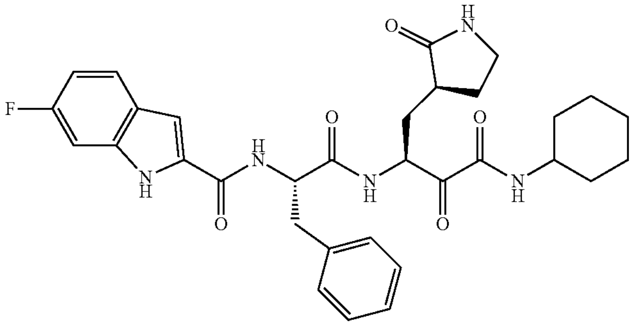 [SMILES: O=C(NC1CCCCC1)C(=O)[C@H](C[C@@H]1CCNC1=O)NC(=O)[C@H](Cc1ccccc1)NC(=O)c1cc2ccc(F)cc2[nH]1] |
| A183 | 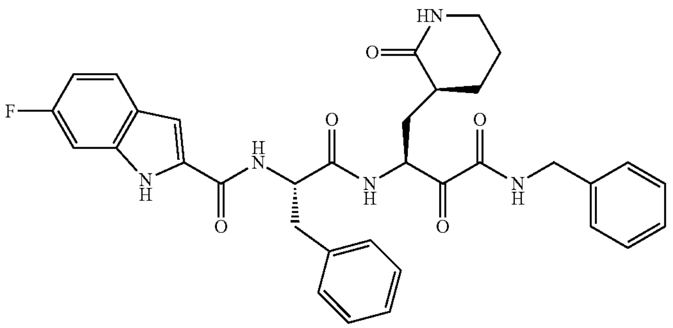 [SMILES: O=C(NCc1ccccc1)C(=O)[C@H](C[C@@H]1CCCNC1=O)NC(=O)[C@H](Cc1ccccc1)NC(=O)c1cc2ccc(F)cc2[nH]1] |

-continued
| number | structure |
|---|---|
| A184 | 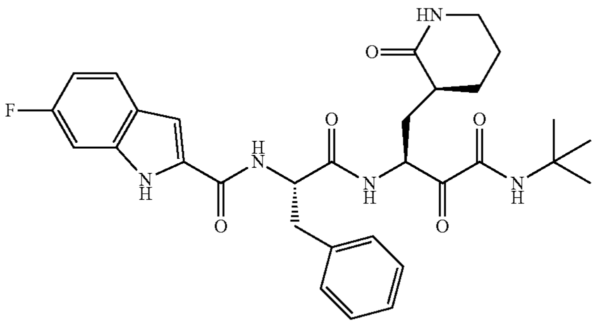 [SMILES: CC(C)(C)NC(=O)C(=O)[C@H](C[C@@H]1CCCNC1=O)NC(=O)[C@H](Cc1ccccc1)NC(=O)c1cc2ccc(F)cc2[nH]1] |
| A185 | 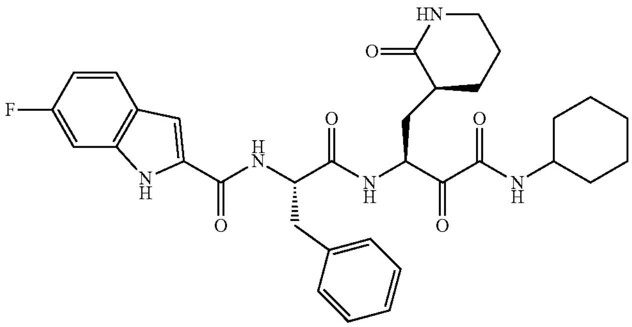 [SMILES: O=C(NC1CCCCC1)C(=O)[C@H](C[C@@H]1CCCNC1=O)NC(=O)[C@H](Cc1ccccc1)NC(=O)c1cc2ccc(F)cc2[nH]1] |
| A186 | 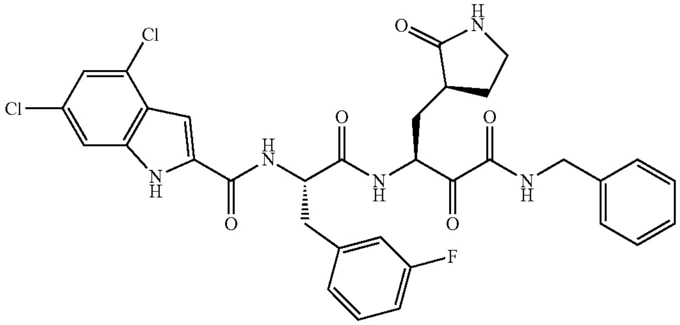 [SMILES: O=C(NCc1ccccc1)C(=O)[C@H](C[C@@H]1CCNC1=O)NC(=O)[C@H](Cc1cccc(F)c1)NC(=O)c1cc2c(Cl)cc(Cl)cc2[nH]1] |
| A187 | 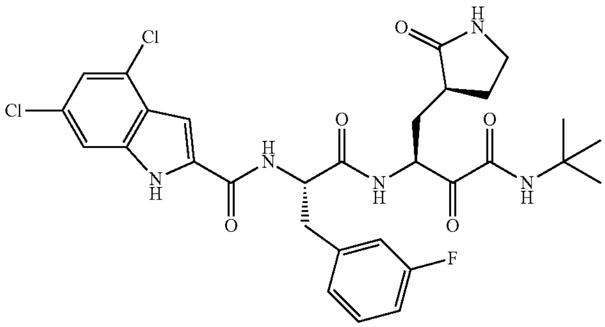 [SMILES: CC(C)(C)NC(=O)C(=O)[C@H](C[C@@H]1CCNC1=O)NC(=O)[C@H](Cc1cccc(F)c1)NC(=O)c1cc2c(Cl)cc(Cl)cc2[nH]1] |

-continued
| number | structure |
| --- | --- |
| A188 | 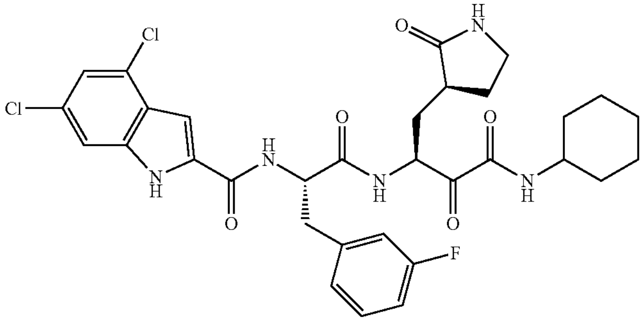 [SMILES: O=C(NC1CCCCC1)C(=O)[C@H](C[C@@H]1CCNC1=O)NC(=O)[C@H](Cc1cccc(F)c1)NC(=O)c1cc2c(Cl)cc(Cl)cc2[nH]1] |
| A189 | 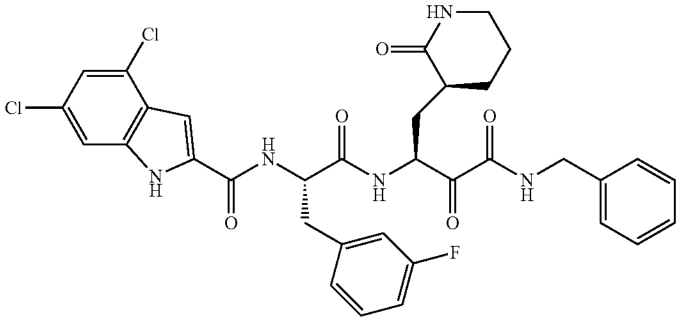 [SMILES: O=C(NCc1ccccc1)C(=O)[C@H](C[C@@H]1CCCNC1=O)NC(=O)[C@H](Cc1cccc(F)c1)NC(=O)c1cc2c(Cl)cc(Cl)cc2[nH]1] |
| A190 | 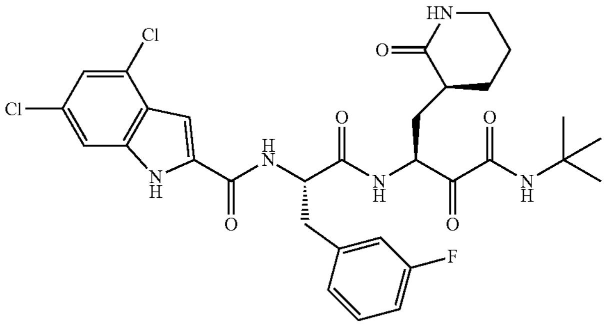 [SMILES: CC(C)(C)NC(=O)C(=O)[C@H](C[C@@H]1CCCNC1=O)NC(=O)[C@H](Cc1cccc(F)c1)NC(=O)c1cc2c(Cl)cc(Cl)cc2[nH]1] |
| A191 | 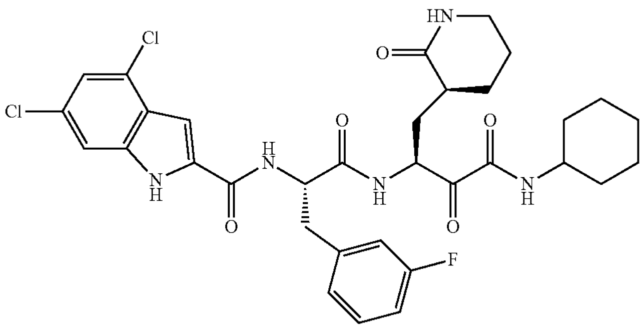 [SMILES: O=C(NC1CCCCC1)C(=O)[C@H](C[C@@H]1CCCNC1=O)NC(=O)[C@H](Cc1cccc(F)c1)NC(=O)c1cc2c(Cl)cc(Cl)cc2[nH]1] |

-continued
| number | structure |
|---|---|
| A192 | 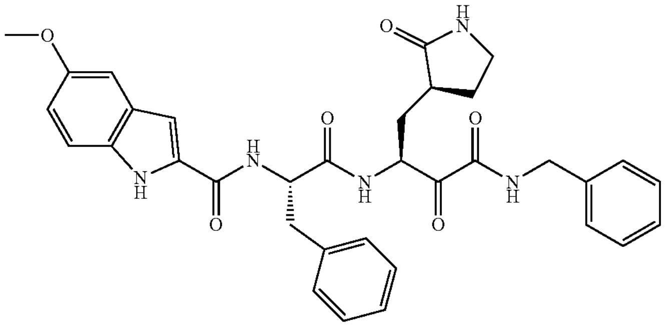 [SMILES: COc1ccc2[nH]c(C(=O)N[C@@H](Cc3ccccc3)C(=O)N[C@@H](C[C@@H]3CCNC3=O)C(=O)C(=O)NCc3ccccc3)cc2c1] |
| A193 | 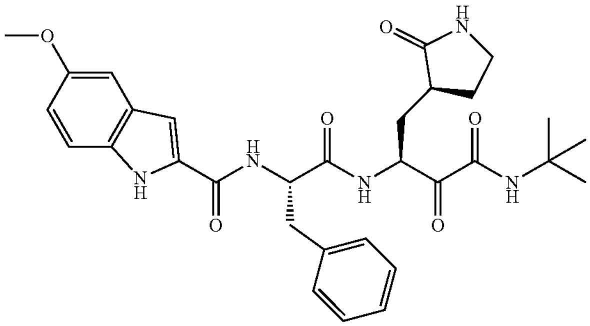 [SMILES: COc1ccc2[nH]c(C(=O)N[C@@H](Cc3ccccc3)C(=O)N[C@@H](C[C@@H]3CCNC3=O)C(=O)C(=O)NC(C)(C)C)cc2c1] |
| A194 | 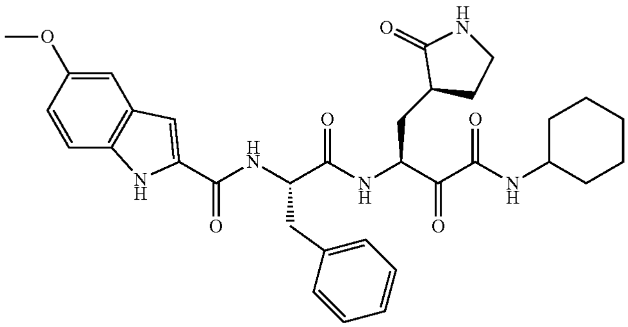 [SMILES: COc1ccc2[nH]c(C(=O)N[C@@H](Cc3ccccc3)C(=O)N[C@@H](C[C@@H]3CCNC3=O)C(=O)C(=O)NC3CCCCC3)cc2c1] |
| A195 | 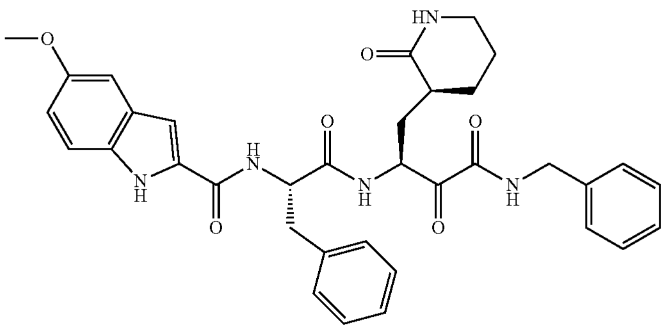 [SMILES: COc1ccc2[nH]c(C(=O)N[C@@H](Cc3ccccc3)C(=O)N[C@@H](C[C@@H]3CCCNC3=O)C(=O)C(=O)NCc3ccccc3)cc2c1] |

-continued
| number | structure |
| --- | --- |
| A196 | 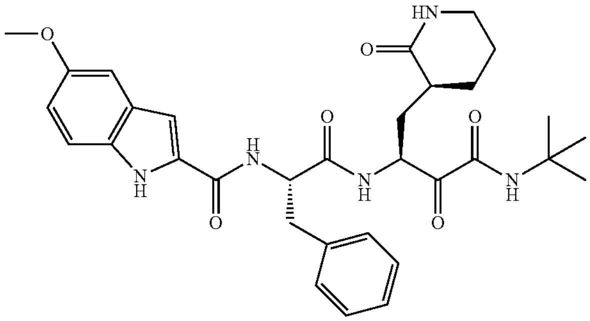 [SMILES: COc1ccc2[nH]c(C(=O)N[C@@H](Cc3ccccc3)C(=O)N[C@@H](C[C@@H]3CCCNC3=O)C(=O)C(=O)NC(C)(C)C)cc2c1] |
| A197 | 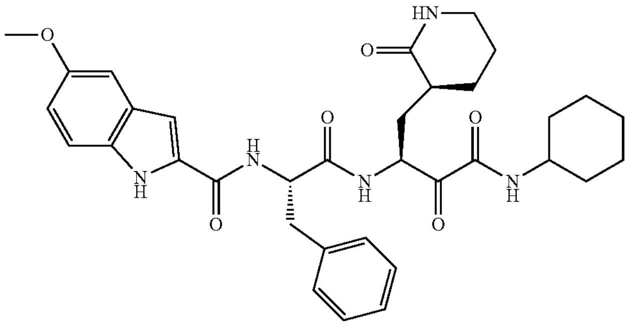 [SMILES: COc1ccc2[nH]c(C(=O)N[C@@H](Cc3ccccc3)C(=O)N[C@@H](C[C@@H]3CCCNC3=O)C(=O)C(=O)NC3CCCCC3)cc2c1] |
| A198 | 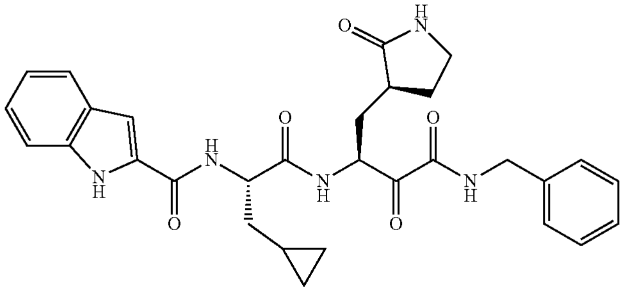 [SMILES: O=C(NCc1ccccc1)C(=O)[C@H](C[C@@H]1CCNC1=O)NC(=O)[C@H](CC1CC1)NC(=O)c1cc2ccccc2[nH]1] |
| A199 | 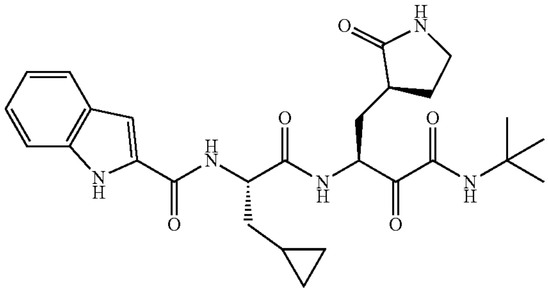 [SMILES: CC(C)(C)NC(=O)C(=O)[C@H](C[C@@H]1CCNC1=O)NC(=O)[C@H](CC1CC1)NC(=O)c1cc2ccccc2[nH]1] |
| A200 | 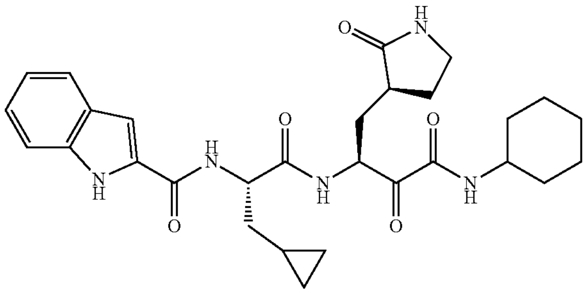 [SMILES: O=C(NC1CCCCC1)C(=O)[C@H](C[C@@H]1CCNC1=O)NC(=O)[C@H](CC1CC1)NC(=O)c1cc2ccccc2[nH]1] |

-continued
| number | structure |
| --- | --- |
| A201 | 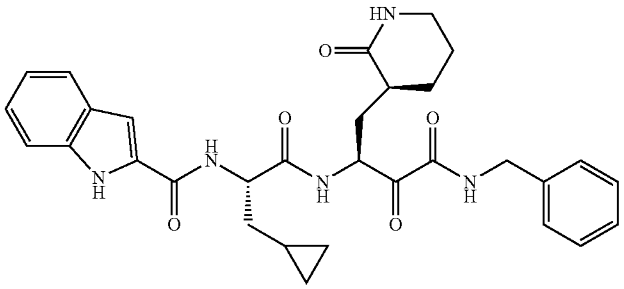 [SMILES: O=C(NCc1ccccc1)C(=O)[C@H](C[C@@H]1CCCNC1=O)NC(=O)[C@H](CC1CC1)NC(=O)c1cc2ccccc2[nH]1] |
| A202 | 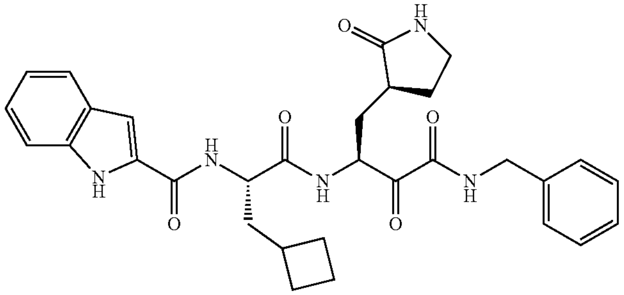 [SMILES: O=C(NCc1ccccc1)C(=O)[C@H](C[C@@H]1CCNC1=O)NC(=O)[C@H](CC1CCC1)NC(=O)c1cc2ccccc2[nH]1] |
| A203 | 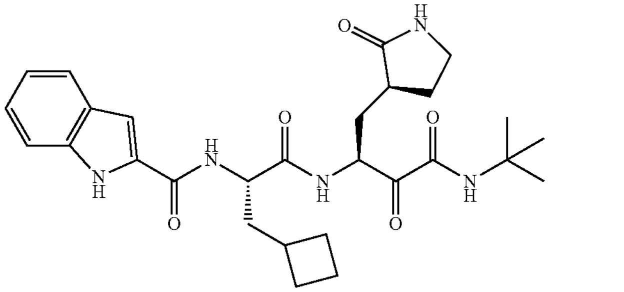 [SMILES: CC(C)(C)NC(=O)C(=O)[C@H](C[C@@H]1CCNC1=O)NC(=O)[C@H](CC1CCC1)NC(=O)c1cc2ccccc2[nH]1] |
| A204 | 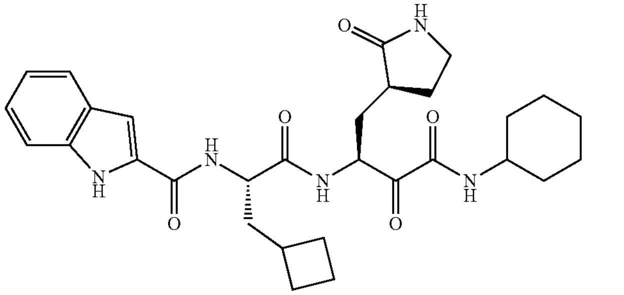 [SMILES: O=C(NC1CCCCC1)C(=O)[C@H](C[C@@H]1CCNC1=O)NC(=O)[C@H](CC1CCC1)NC(=O)c1cc2ccccc2[nH]1] |
| A205 | 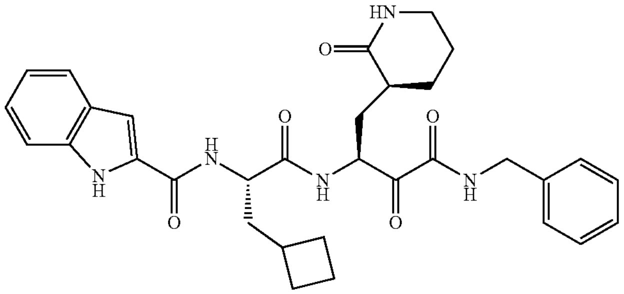 [SMILES: O=C(NCc1ccccc1)C(=O)[C@H](C[C@@H]1CCCNC1=O)NC(=O)[C@H](CC1CCC1)NC(=O)c1cc2ccccc2[nH]1] |

-continued
| number | structure |
|---|---|
| A206 | 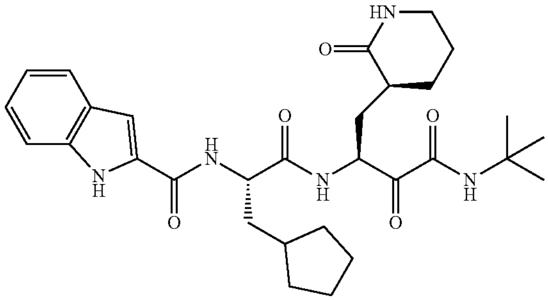 [SMILES: CC(C)(C)NC(=O)C(=O)[C@H](C[C@@H]1CCCNC1=O)NC(=O)[C@H](CC1CCCC1)NC(=O)c1cc2ccccc2[nH]1] |
| A207 | 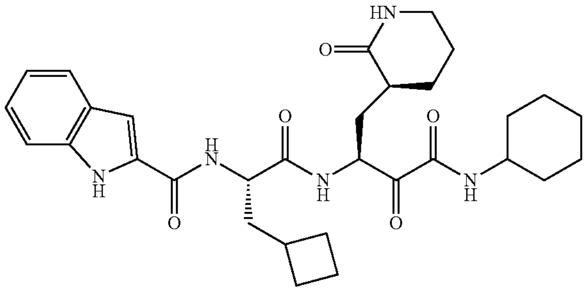 [SMILES: O=C(NC1CCCCC1)C(=O)[C@H](C[C@@H]1CCCNC1=O)NC(=O)[C@H](CC1CCC1)NC(=O)c1cc2ccccc2[nH]1] |
| A208 | 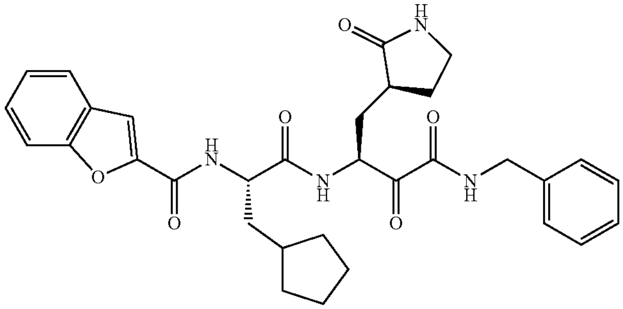 [SMILES: O=C(NCc1ccccc1)C(=O)[C@H](C[C@@H]1CCNC1=O)NC(=O)[C@H](CC1CCCC1)NC(=O)c1cc2ccccc2o1] |
| A209 | 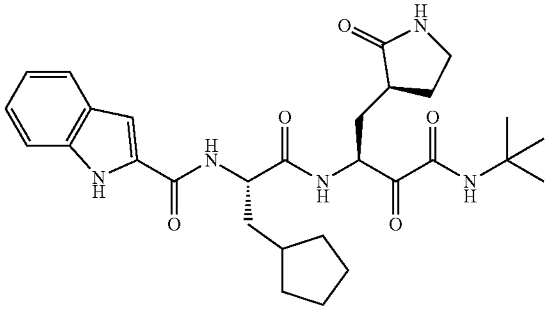 [SMILES: CC(C)(C)NC(=O)C(=O)[C@H](C[C@@H]1CCNC1=O)NC(=O)[C@H](CC1CCCC1)NC(=O)c1cc2ccccc2[nH]1] |
| A210 | 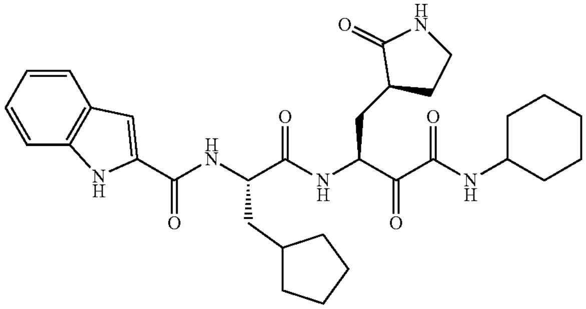 [SMILES: O=C(NC1CCCCC1)C(=O)[C@H](C[C@@H]1CCNC1=O)NC(=O)[C@H](CC1CCCC1)NC(=O)c1cc2ccccc2[nH]1] |

-continued
| number | structure |
|---|---|
| A211 | 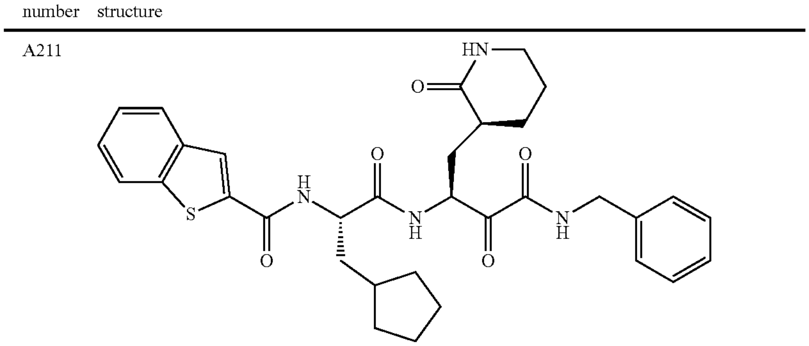 |
| A212 | 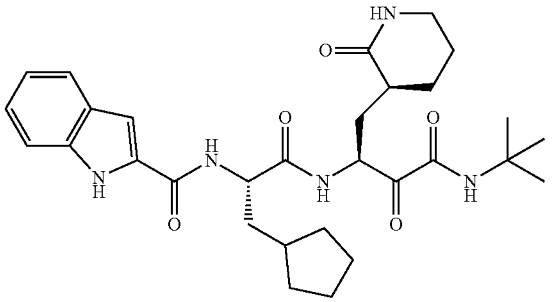 [SMILES: CC(C)(C)NC(=O)C(=O)[C@H](C[C@@H]1CCCNC1=O)NC(=O)[C@H](CC1CCCC1)NC(=O)c1cc2ccccc2[nH]1] |
| A213 | 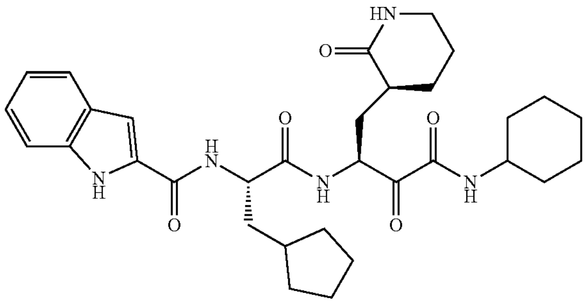 [SMILES: O=C(NC1CCCCC1)C(=O)[C@H](C[C@@H]1CCCNC1=O)NC(=O)[C@H](CC1CCCC1)NC(=O)c1cc2ccccc2[nH]1] |
| A220 | 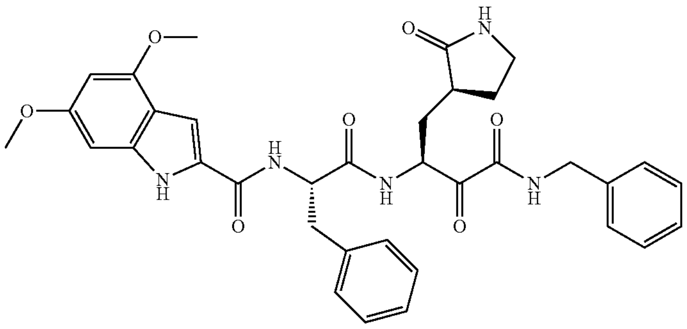 [SMILES: COc1cc(OC)c2cc(C(=O)N[C@@H](Cc3ccccc3)C(=O)N[C@@H](C[C@@H]3CCNC3=O)C(=O)C(=O)NCc3ccccc3)[nH]c2c1] |
| A221 | 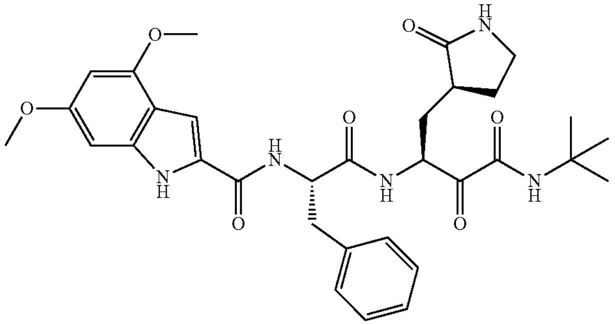 [SMILES: COc1cc(OC)c2cc(C(=O)N[C@@H](Cc3ccccc3)C(=O)N[C@@H](C[C@@H]3CCNC3=O)C(=O)C(=O)NC(C)(C)C)[nH]c2c1] |

-continued
| number | structure |
|---|---|
| A222 | 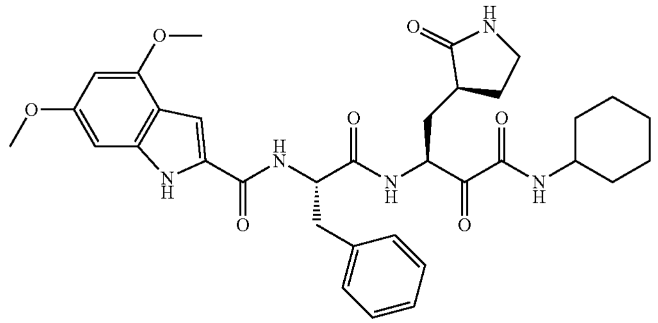 [SMILES: COc1cc(OC)c2cc(C(=O)N[C@@H](Cc3ccccc3)C(=O)N[C@@H](C[C@@H]3CCNC3=O)C(=O)C(=O)NC3CCCCC3)[nH]c2c1] |
| A223 | 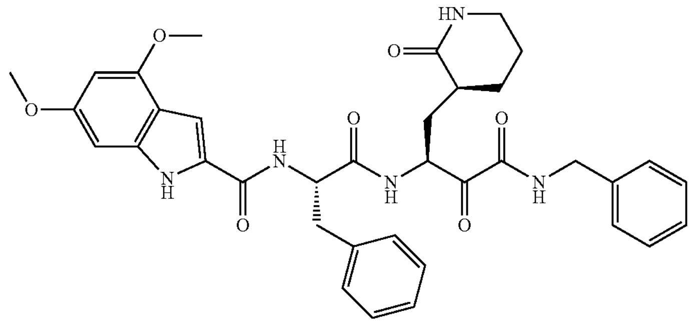 [SMILES: COc1cc(OC)c2cc(C(=O)N[C@@H](Cc3ccccc3)C(=O)N[C@@H](C[C@@H]3CCCNC3=O)C(=O)C(=O)NCc3ccccc3)[nH]c2c1] |
| A224 | 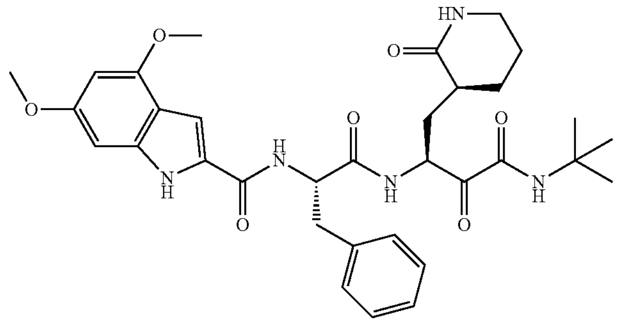 [SMILES: COc1cc(OC)c2cc(C(=O)N[C@@H](Cc3ccccc3)C(=O)N[C@@H](C[C@@H]3CCCNC3=O)C(=O)C(=O)NC(C)(C)C)[nH]c2c1] |
| A225 | 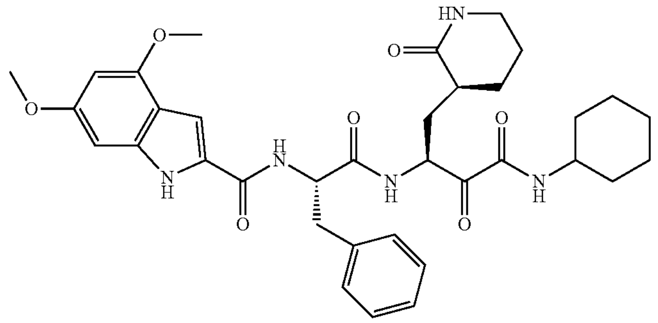 [SMILES: COc1cc(OC)c2cc(C(=O)N[C@@H](Cc3ccccc3)C(=O)N[C@@H](C[C@@H]3CCCNC3=O)C(=O)C(=O)NC3CCCCC3)[nH]c2c1] |

-continued
| number | structure |
|---|---|
| A226 | 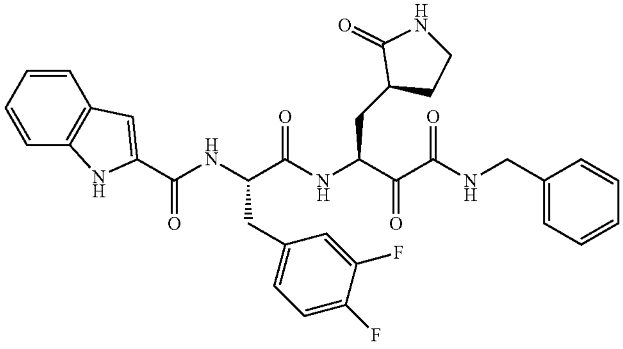 [SMILES: O=C(NCc1ccccc1)C(=O)[C@H](C[C@@H]1CCNC1=O)NC(=O)[C@H](Cc1ccc(F)c(F)c1)NC(=O)c1cc2ccccc2[nH]1] |
| A227 | 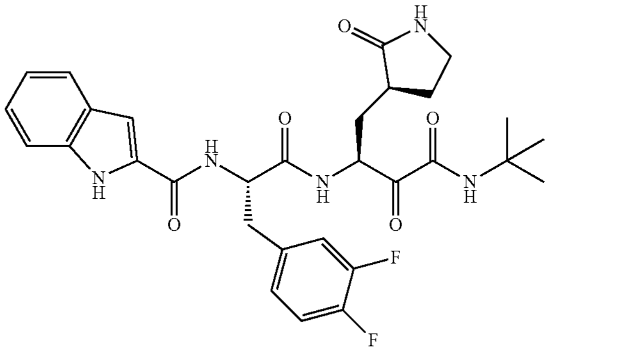 [SMILES: CC(C)(C)NC(=O)C(=O)[C@H](C[C@@H]1CCNC1=O)NC(=O)[C@H](Cc1ccc(F)c(F)c1)NC(=O)c1cc2ccccc2[nH]1] |
| A228 | 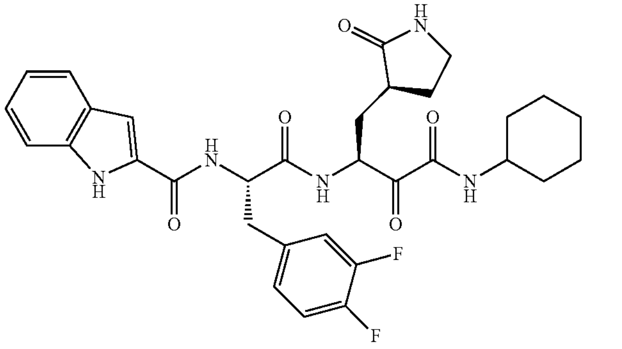 [SMILES: O=C(NC1CCCCC1)C(=O)[C@H](C[C@@H]1CCNC1=O)NC(=O)[C@H](Cc1ccc(F)c(F)c1)NC(=O)c1cc2ccccc2[nH]1] |
| A229 | 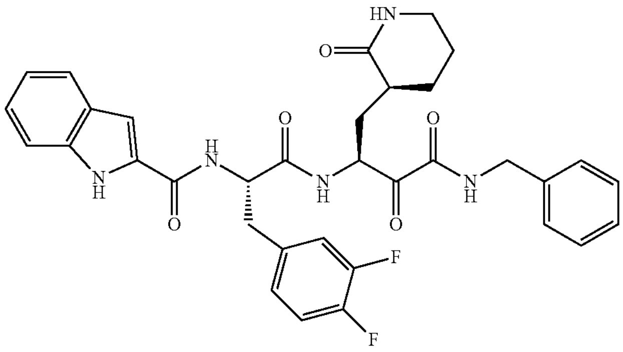 [SMILES: O=C(NCc1ccccc1)C(=O)[C@H](C[C@@H]1CCCNC1=O)NC(=O)[C@H](Cc1ccc(F)c(F)c1)NC(=O)c1cc2ccccc2[nH]1] |

-continued
| number | structure |
|---|---|
| A230 | 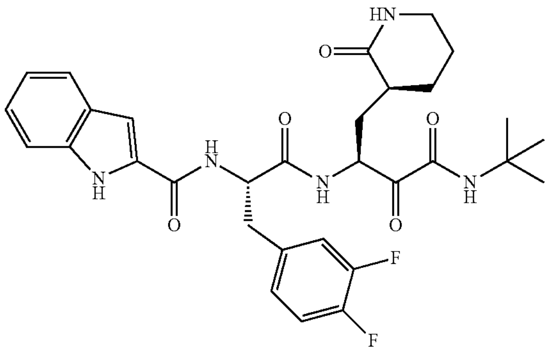 [SMILES: CC(C)(C)NC(=O)C(=O)[C@H](C[C@@H]1CCCNC1=O)NC(=O)[C@H](Cc1ccc(F)c(F)c1)NC(=O)c1cc2ccccc2[nH]1] |
| A231 | 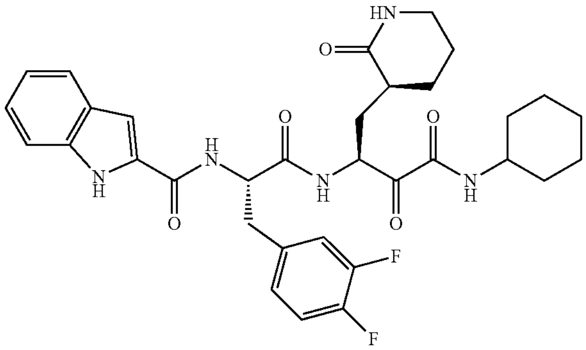 [SMILES: O=C(NC1CCCCC1)C(=O)[C@H](C[C@@H]1CCCNC1=O)NC(=O)[C@H](Cc1ccc(F)c(F)c1)NC(=O)c1cc2ccccc2[nH]1] |
| A232 | 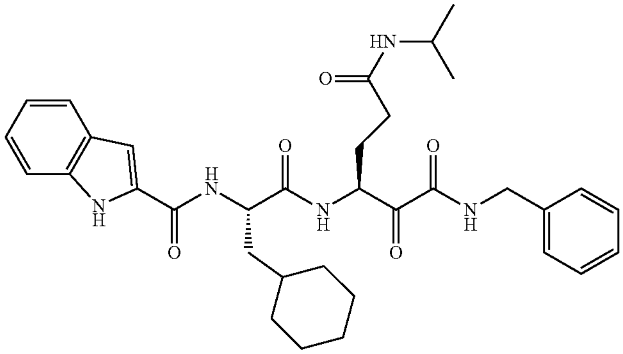 [SMILES: CC(C)NC(=O)CC[C@H](NC(=O)[C@H](CC1CCCCC1)NC(=O)c1cc2ccccc2[nH]1)C(=O)C(=O)NCc1ccccc1] |
| A233 | 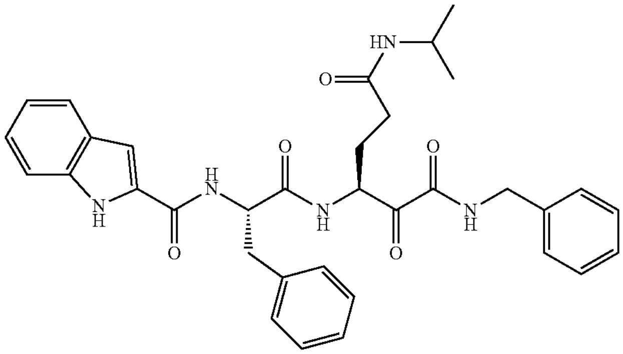 [SMILES: CC(C)NC(=O)CC[C@H](NC(=O)[C@H](Cc1ccccc1)NC(=O)c1cc2ccccc2[nH]1)C(=O)C(=O)NCc1ccccc1] |

-continued
| number | structure |
| --- | --- |
| A234 | 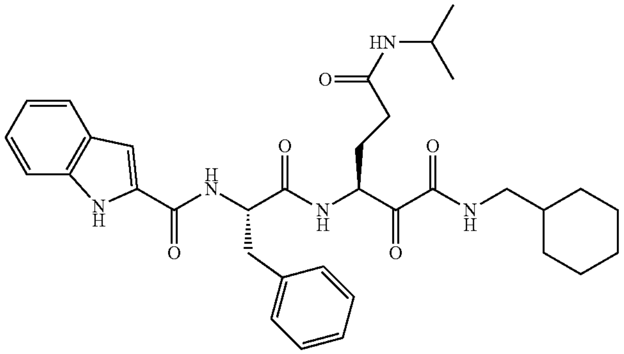 [SMILES: CC(C)NC(=O)CC[C@H](NC(=O)[C@H](Cc1ccccc1)NC(=O)c1cc2ccccc2[nH]1)C(=O)C(=O)NCC1CCCCC1] |
| A235 | 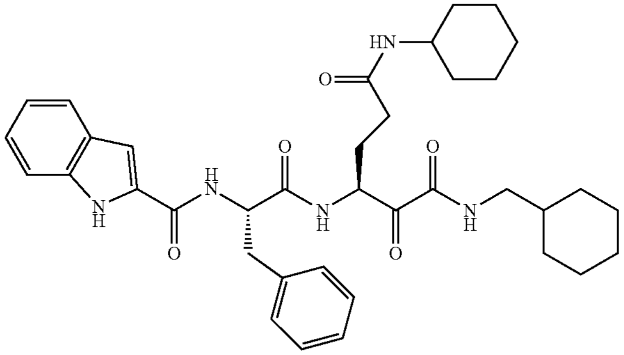 [SMILES: O=C(CC[C@H](NC(=O)[C@H](Cc1ccccc1)NC(=O)c1cc2ccccc2[nH]1)C(=O)C(=O)NCC1CCCCC1)NC1CCCCC1] |
| A236 | 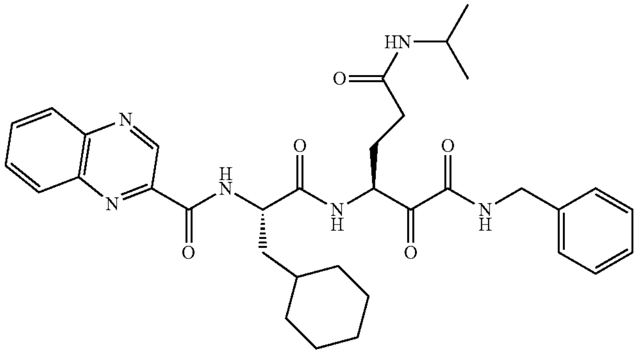 [SMILES: CC(C)NC(=O)CC[C@H](NC(=O)[C@H](CC1CCCCC1)NC(=O)c1cnc2ccccc2n1)C(=O)C(=O)NCc1ccccc1] |
| A237 | 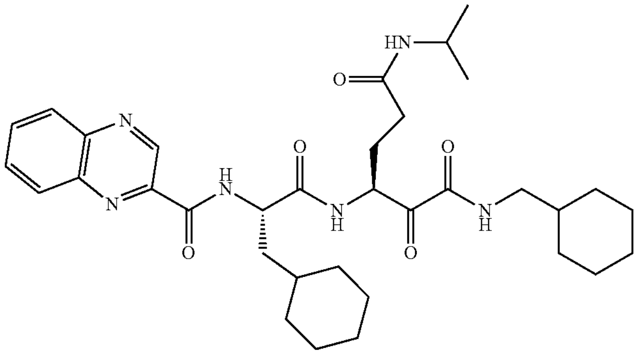 [SMILES: CC(C)NC(=O)CC[C@H](NC(=O)[C@H](CC1CCCCC1)NC(=O)c1cnc2ccccc2n1)C(=O)C(=O)NCC1CCCCC1] |

-continued
| number | structure |
|---|---|
| A238 | 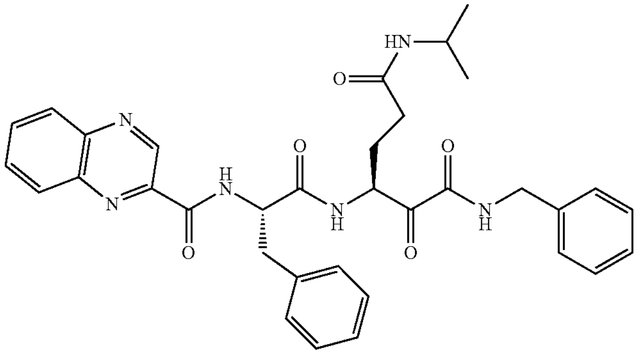 [SMILES: CC(C)NC(=O)CC[C@H](NC(=O)[C@H](Cc1ccccc1)NC(=O)c1cnc2ccccc2n1)C(=O)C(=O)NCc1ccccc1] |
| A239 | 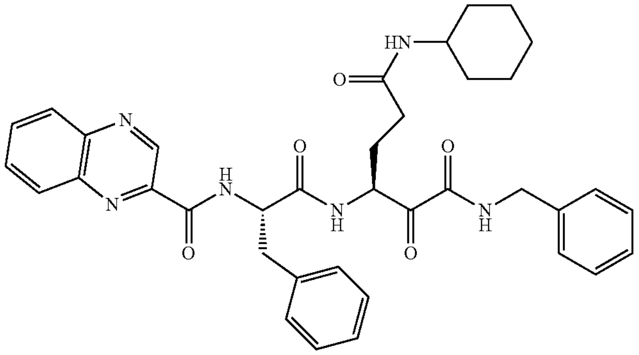 [SMILES: O=C(CC[C@H](NC(=O)[C@H](Cc1ccccc1)NC(=O)c1cnc2ccccc2n1)C(=O)C(=O)NCc1ccccc1)NC1CCCCC1] |
| A240 | 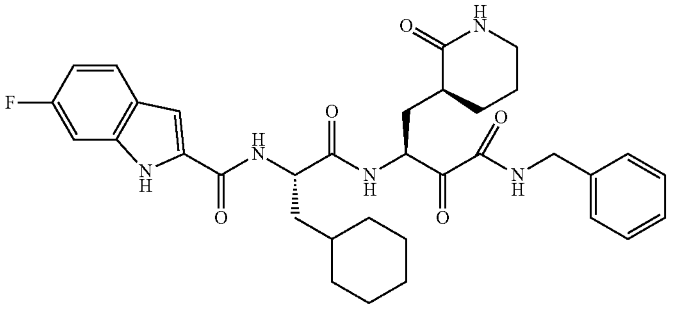 [SMILES: O=C(NCc1ccccc1)C(=O)[C@H](C[C@@H]1CCCNC1=O)NC(=O)[C@H](CC1CCCCC1)NC(=O)c1cc2ccc(F)cc2[nH]1] |
| A241 | 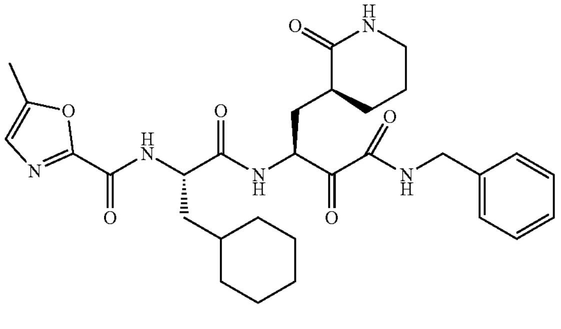 [SMILES: Cc1cnc(C(=O)N[C@@H](CC2CCCCC2)C(=O)N[C@@H](C[C@@H]2CCCNC2=O)C(=O)C(=O)NCc2ccccc2)o1] |

-continued
| number | structure |
|---|---|
| A242 | 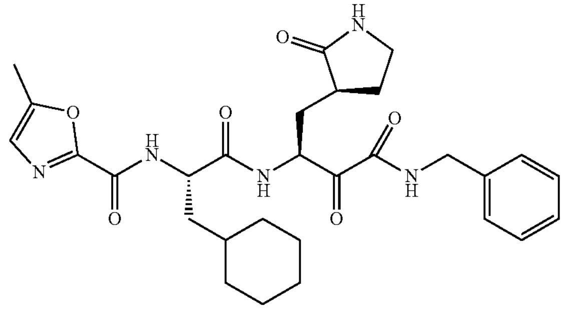 [SMILES: Cc1cnc(C(=O)N[C@@H](CC2CCCCC2)C(=O)N[C@@H](C[C@@H]2CCNC2=O)C(=O)C(=O)NCc2ccccc2)o1] |
| A244 | 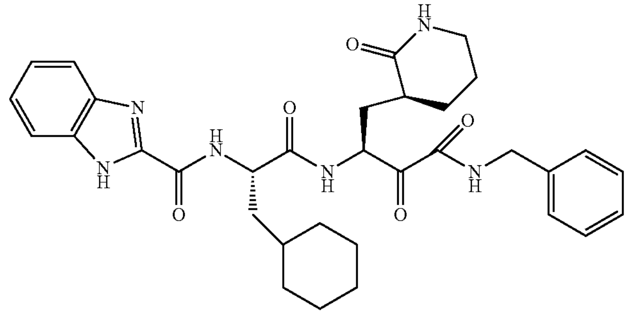 [SMILES: O=C(NCc1ccccc1)C(=O)[C@H](C[C@@H]1CCCNC1=O)NC(=O)[C@H](CC1CCCCC1)NC(=O)c1nc2ccccc2[nH]1] |
| A245 | 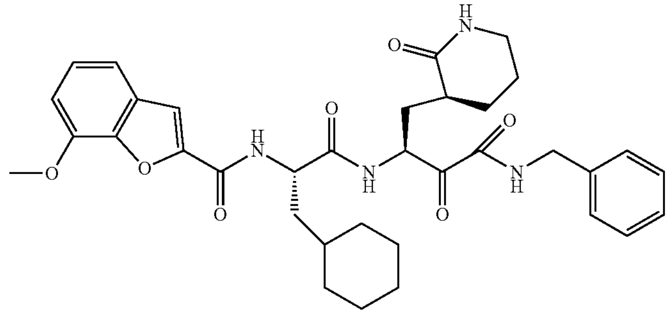 [SMILES: COc1cccc2cc(C(=O)N[C@@H](CC3CCCCC3)C(=O)N[C@@H](C[C@@H]3CCCNC3=O)C(=O)C(=O)NCc3ccccc3)oc12] |
| A246 | 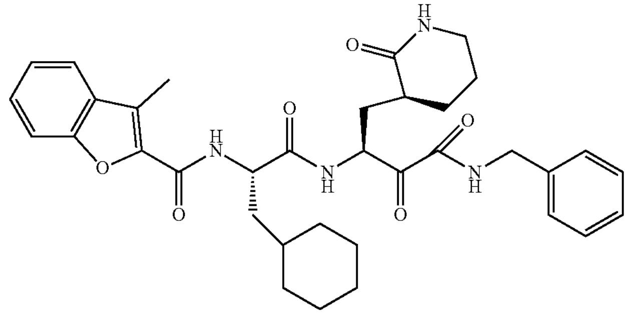 [SMILES: Cc1c(C(=O)N[C@@H](CC2CCCCC2)C(=O)N[C@@H](C[C@@H]2CCCNC2=O)C(=O)C(=O)NCc2ccccc2)oc2ccccc12] |
| A247 | 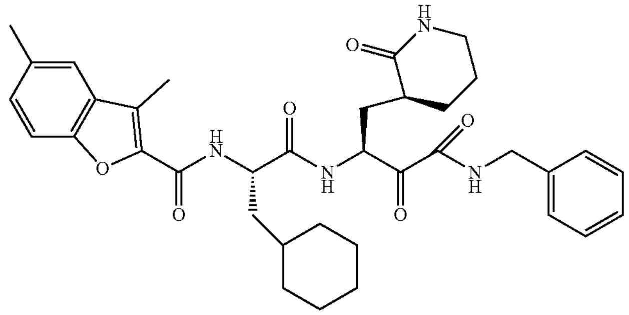 [SMILES: Cc1ccc2oc(C(=O)N[C@@H](CC3CCCCC3)C(=O)N[C@@H](C[C@@H]3CCCNC3=O)C(=O)C(=O)NCc3ccccc3)c(C)c2c1] |

-continued
| number | structure |
|---|---|
| A248 | 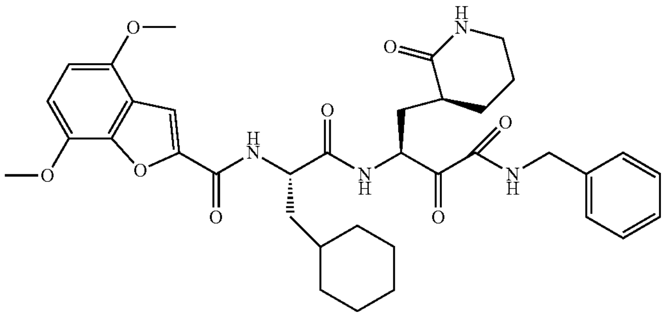 [SMILES: COc1ccc(OC)c2oc(C(=O)N[C@@H](CC3CCCCC3)C(=O)N[C@@H](C[C@@H]3CCCNC3=O)C(=O)C(=O)NCc3ccccc3)cc12] |
| A249 | 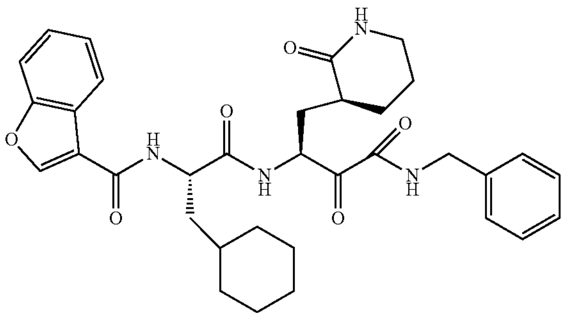 [SMILES: O=C(NCc1ccccc1)C(=O)[C@H](C[C@@H]1CCCNC1=O)NC(=O)[C@H](CC1CCCCC1)NC(=O)c1coc2ccccc12] |
| A253 | 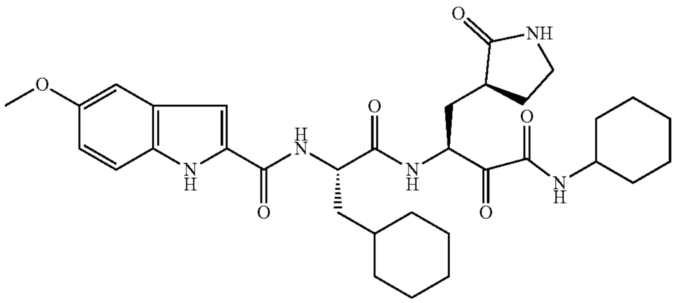 [SMILES: COc1ccc2[nH]c(C(=O)N[C@@H](CC3CCCCC3)C(=O)N[C@@H](C[C@@H]3CCNC3=O)C(=O)C(=O)NC3CCCCC3)cc2c1] |
| A254 | 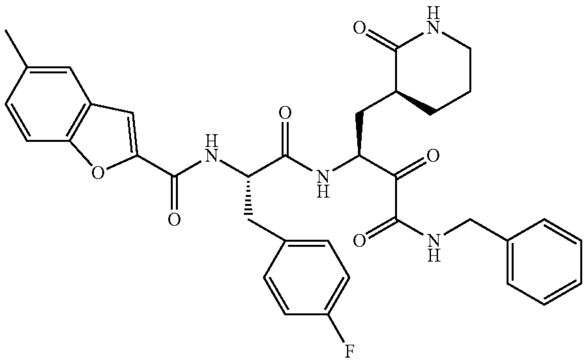 [SMILES: Cc1ccc2oc(C(=O)N[C@@H](Cc3ccc(F)cc3)C(=O)N[C@@H](C[C@@H]3CCCNC3=O)C(=O)C(=O)NCc3ccccc3)cc2c1] |

-continued
| number | structure |
| --- | --- |
| A255 | 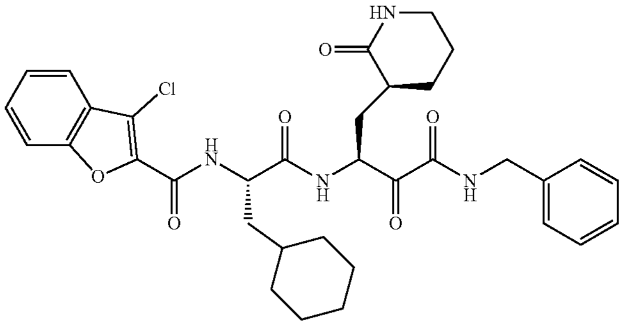 [SMILES: O=C(NCc1ccccc1)C(=O)[C@H](C[C@@H]1CCCNC1=O)NC(=O)[C@H](CC1CCCCC1)NC(=O)c1oc2ccccc2c1Cl] |
| A256 | 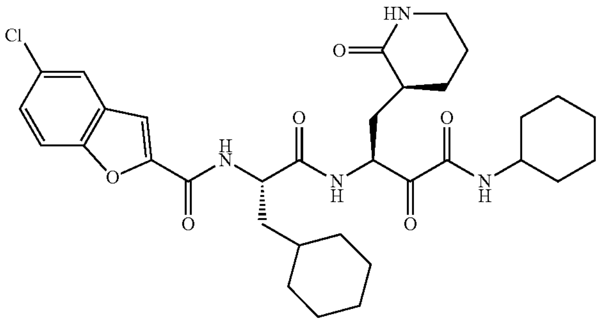 [SMILES: O=C(NC1CCCCC1)C(=O)[C@H](C[C@@H]1CCCNC1=O)NC(=O)[C@H](CC1CCCCC1)NC(=O)c1cc2cc(Cl)ccc2o1] |
| A257 | 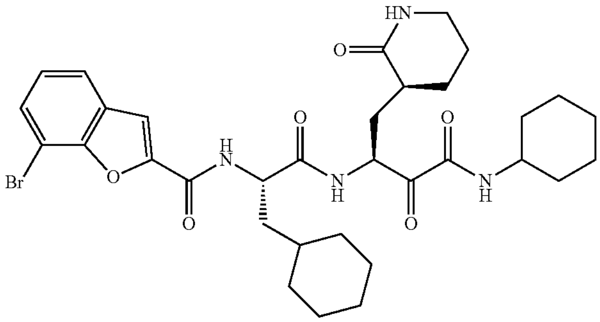 [SMILES: O=C(NC1CCCCC1)C(=O)[C@H](C[C@@H]1CCCNC1=O)NC(=O)[C@H](CC1CCCCC1)NC(=O)c1cc2cccc(Br)c2o1] |
| A259 | 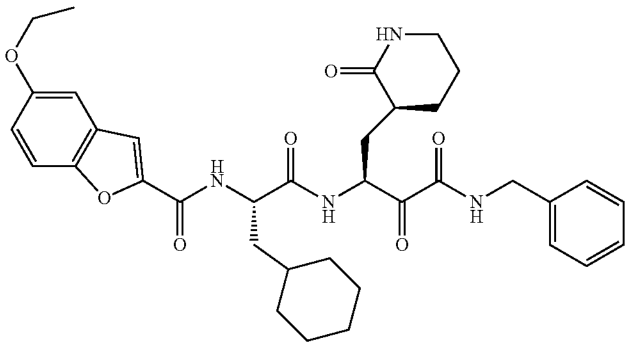 [SMILES: CCOc1ccc2oc(C(=O)N[C@@H](CC3CCCCC3)C(=O)N[C@@H](C[C@@H]3CCCNC3=O)C(=O)C(=O)NCc3ccccc3)cc2c1] |

-continued
| number | structure |
|---|---|
| A260 | 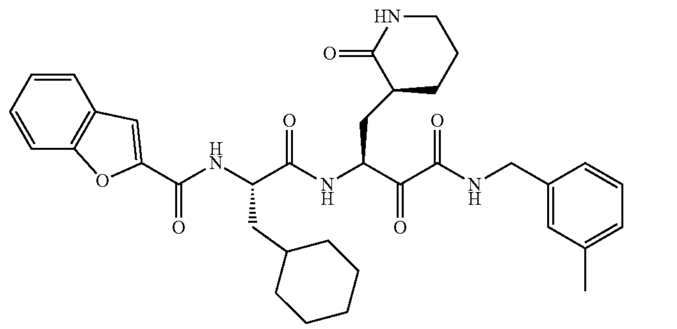 [SMILES: Cc1cccc(CNC(=O)C(=O)[C@H](C[C@@H]2CCCNC2=O)NC(=O)[C@H](CC2CCCCC2)NC(=O)c2cc3ccccc3o2)c1] |
| A261 | 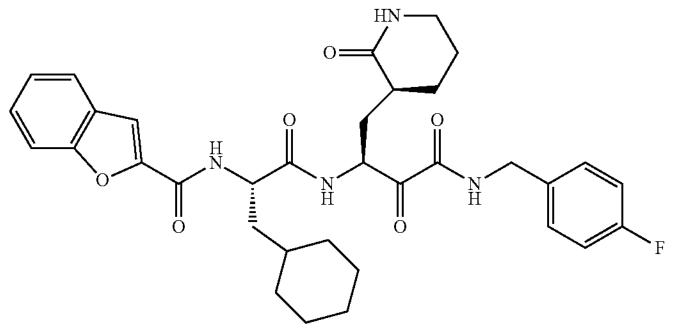 [SMILES: O=C(NCc1ccc(F)cc1)C(=O)[C@H](C[C@@H]1CCCNC1=O)NC(=O)[C@H](CC1CCCCC1)NC(=O)c1cc2ccccc2o1] |
| A263 | 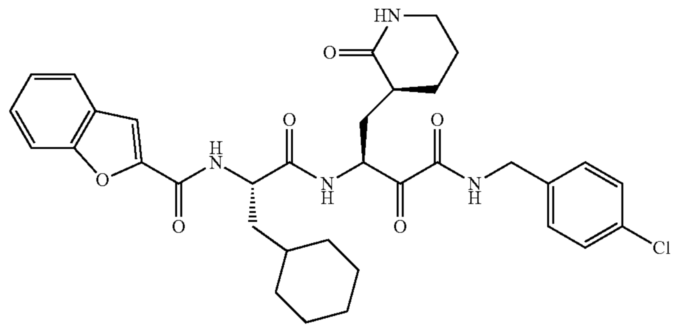 [SMILES: O=C(NCc1ccc(Cl)cc1)C(=O)[C@H](C[C@@H]1CCCNC1=O)NC(=O)[C@H](CC1CCCCC1)NC(=O)c1cc2ccccc2o1] |
| A264 | 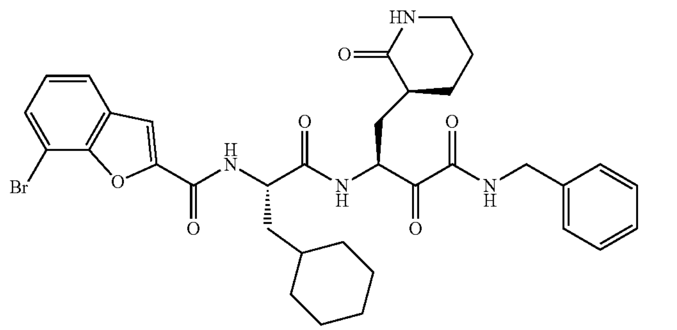 [SMILES: O=C(NCc1ccccc1)C(=O)[C@H](C[C@@H]1CCCNC1=O)NC(=O)[C@H](CC1CCCCC1)NC(=O)c1cc2cccc(Br)c2o1] |

-continued
| number | structure |
|---|---|
| A265 | 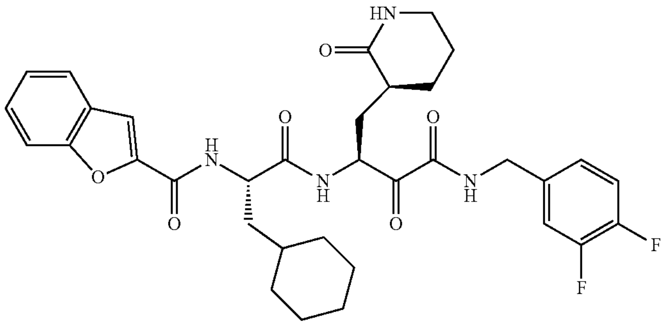 |
| A266 | 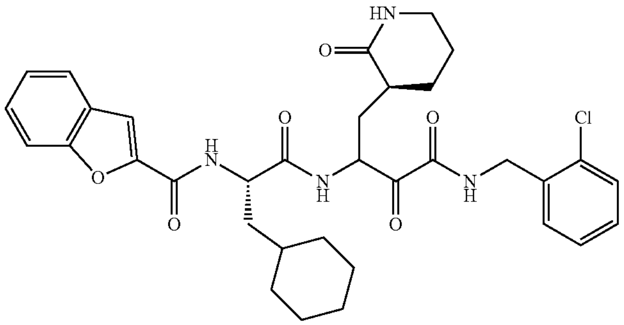 [SMILES: O=C(NCc1ccccc1Cl)C(=O)C(C[C@@H]1CCCNC1=O)NC(=O)[C@H](CC1CCCCC1)NC(=O)c1cc2ccccc2o1] |
| A267 | 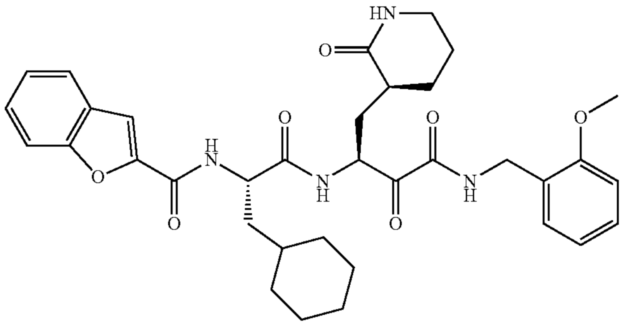 [SMILES: COc1ccccc1CNC(=O)C(=O)[C@H](C[C@@H]1CCCNC1=O)NC(=O)[C@H](CC1CCCCC1)NC(=O)c1cc2ccccc2o1] |
| A269 | 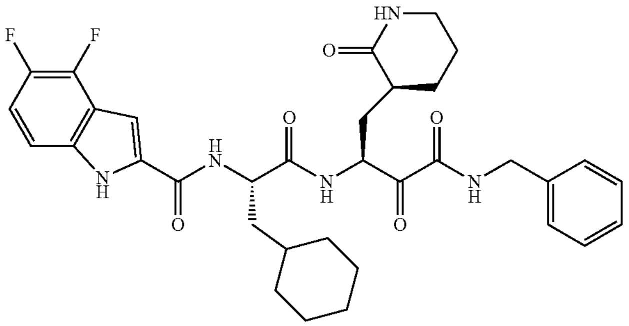 [SMILES: O=C(NCc1ccccc1)C(=O)[C@H](C[C@@H]1CCCNC1=O)NC(=O)[C@H](CC1CCCCC1)NC(=O)c1cc2c(F)c(F)ccc2[nH]1] |

-continued
| number | structure |
|---|---|
| A270 | 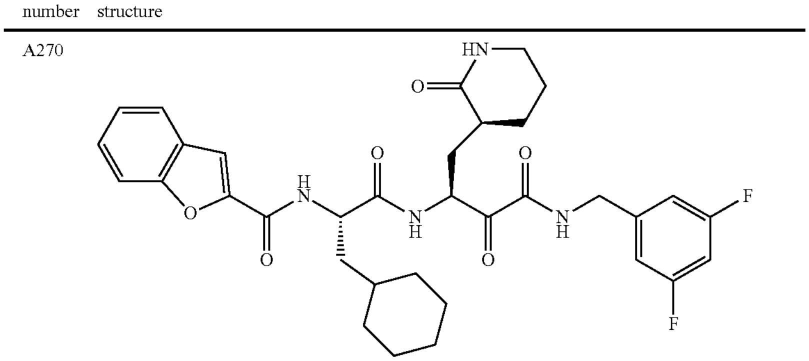 |
| A271 | 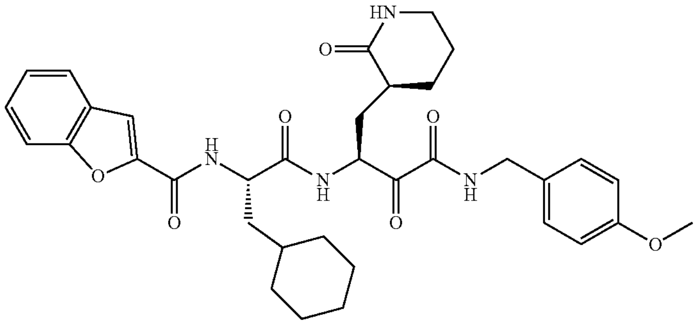 [SMILES: COc1ccc(CNC(=O)C(=O)[C@H](C[C@@H]2CCCNC2=O)NC(=O)[C@H](CC2CCCCC2)NC(=O)c2cc3ccccc3o2)cc1] |
| A272 | 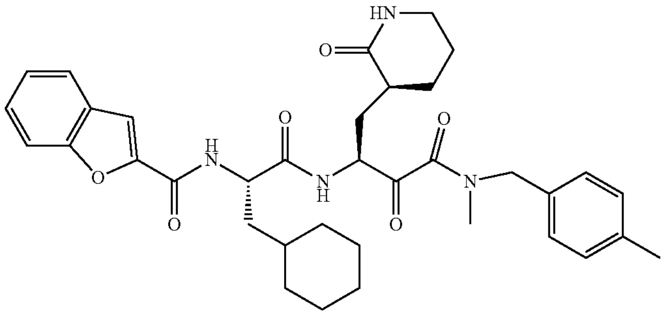 [SMILES: Cc1ccc(CN(C)C(=O)C(=O)[C@H](C[C@@H]2CCCNC2=O)NC(=O)[C@H](CC2CCCCC2)NC(=O)c2cc3ccccc3o2)cc1] |
| A274 | 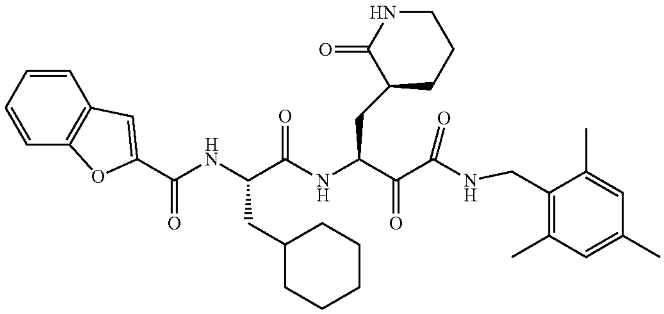 [SMILES: Cc1cc(C)c(CNC(=O)C(=O)[C@H](C[C@@H]2CCCNC2=O)NC(=O)[C@H](CC2CCCCC2)NC(=O)c2cc3ccccc3o2)c(C)c1] |
| A276 | 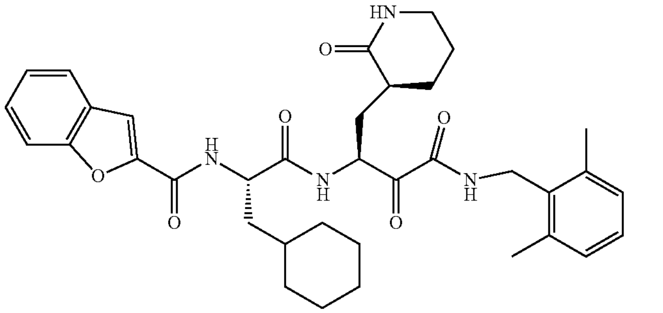 [SMILES: Cc1cccc(C)c1CNC(=O)C(=O)[C@H](C[C@@H]1CCCNC1=O)NC(=O)[C@H](CC1CCCCC1)NC(=O)c1cc2ccccc2o1] |

-continued
| number | structure |
|---|---|
| A277 | 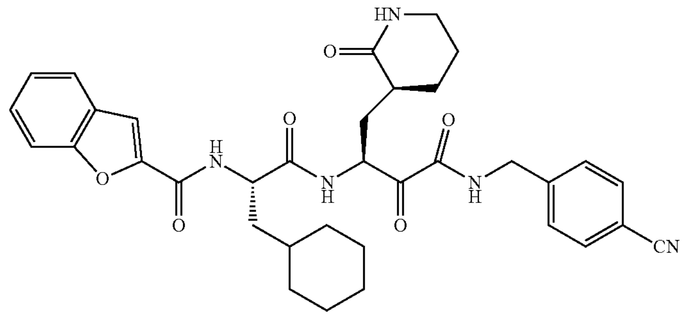 [SMILES: N#Cc1ccc(CNC(=O)C(=O)[C@H](C[C@@H]2CCCNC2=O)NC(=O)[C@H](CC2CCCCC2)NC(=O)c2cc3ccccc3o2)cc1] |
| A278 | 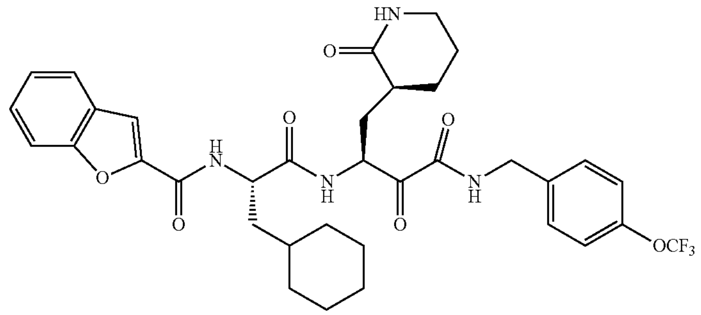 [SMILES: O=C(NCc1ccc(OC(F)(F)F)cc1)C(=O)[C@H](C[C@@H]1CCCNC1=O)NC(=O)[C@H](CC1CCCCC1)NC(=O)c1cc2ccccc2o1] |
| A279 | 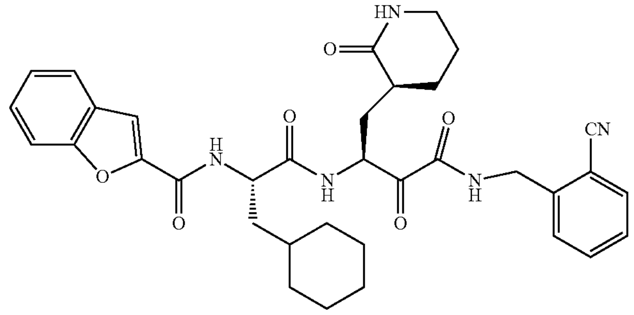 [SMILES: N#Cc1ccccc1CNC(=O)C(=O)[C@H](C[C@@H]1CCCNC1=O)NC(=O)[C@H](CC1CCCCC1)NC(=O)c1cc2ccccc2o1] |
| A281 | 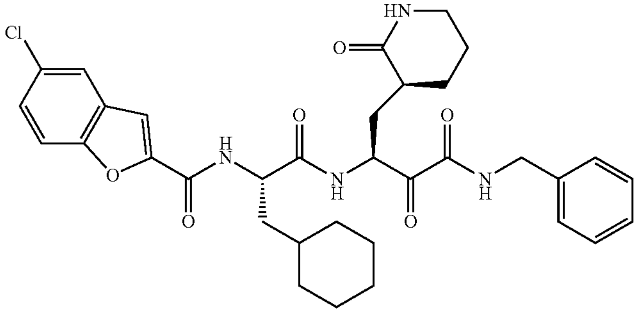 [SMILES: O=C(NCc1ccccc1)C(=O)[C@H](C[C@@H]1CCCNC1=O)NC(=O)[C@H](CC1CCCCC1)NC(=O)c1cc2cc(Cl)ccc2o1] |

-continued
| number | structure |
|---|---|
| A282 | 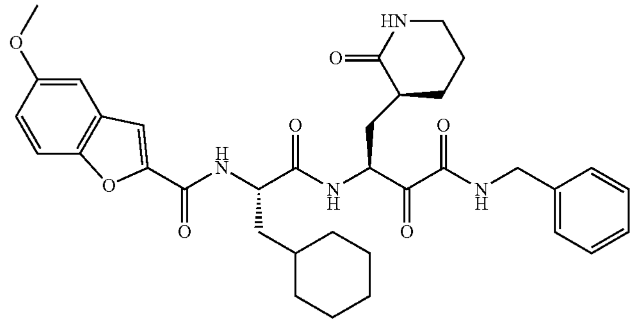 [SMILES: COc1ccc2oc(C(=O)N[C@@H](CC3CCCCC3)C(=O)N[C@@H](C[C@@H]3CCCNC3=O)C(=O)C(=O)NCc3ccccc3)cc2c1] |
| A283 | 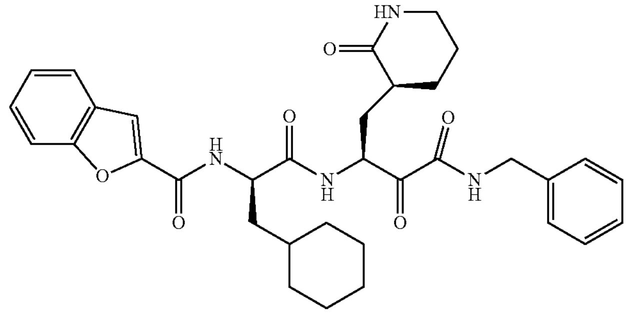 [SMILES: O=C(NCc1ccccc1)C(=O)[C@H](C[C@@H]1CCCNC1=O)NC(=O)[C@@H](CC1CCCCC1)NC(=O)c1cc2ccccc2o1] |
| A284 | 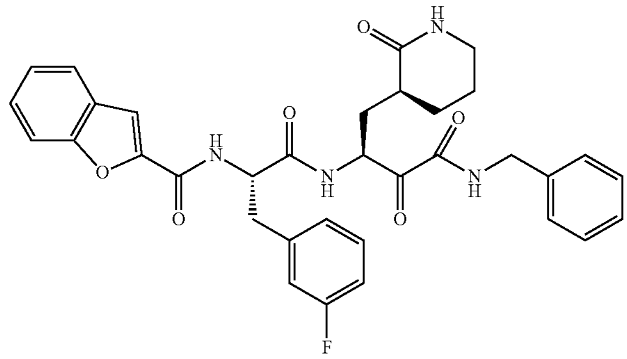 [SMILES: O=C(NCc1ccccc1)C(=O)[C@H](C[C@@H]1CCCNC1=O)NC(=O)[C@H](Cc1cccc(F)c1)NC(=O)c1cc2ccccc2o1] |
| A285 | 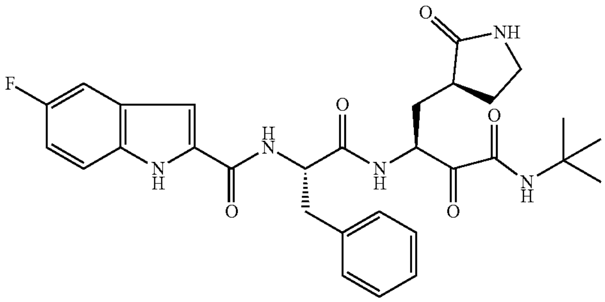 [SMILES: CC(C)(C)NC(=O)C(=O)[C@H](C[C@@H]1CCNC1=O)NC(=O)[C@H](Cc1ccccc1)NC(=O)c1cc2cc(F)ccc2[nH]1] |

-continued
| number | structure |
|---|---|
| A286 | 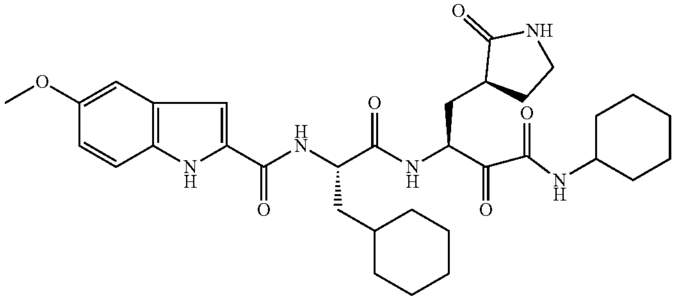 [SMILES: COc1ccc2[nH]c(C(=O)N[C@@H](CC3CCCCC3)C(=O)N[C@@H](C[C@@H]3CCNC3=O)C(=O)C(=O)NC3CCCCC3)cc2c1] |
| A287 | 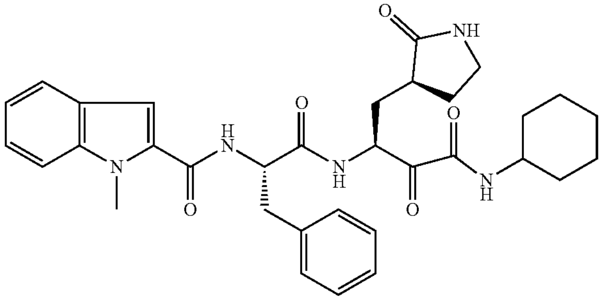 [SMILES: Cn1c(C(=O)N[C@@H](Cc2ccccc2)C(=O)N[C@@H](C[C@@H]2CCNC2=O)C(=O)C(=O)NC2CCCCC2)cc2ccccc21] |
| A288 | 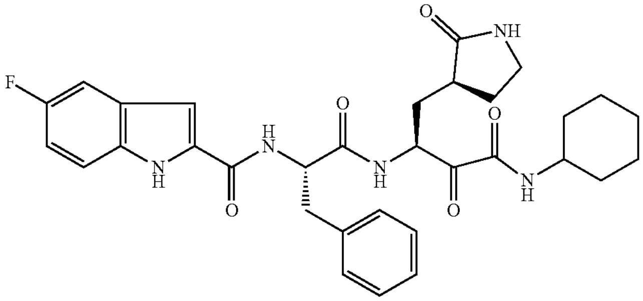 [SMILES: O=C(NC1CCCCC1)C(=O)[C@H](C[C@@H]1CCNC1=O)NC(=O)[C@H](Cc1ccccc1)NC(=O)c1cc2cc(F)ccc2[nH]1] |
| A289 | 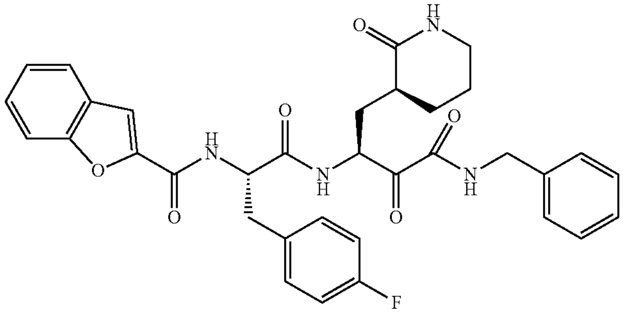 [SMILES: O=C(NCc1ccccc1)C(=O)[C@H](C[C@@H]1CCCNC1=O)NC(=O)[C@H](Cc1ccc(F)cc1)NC(=O)c1cc2ccccc2o1] |
| A290 | 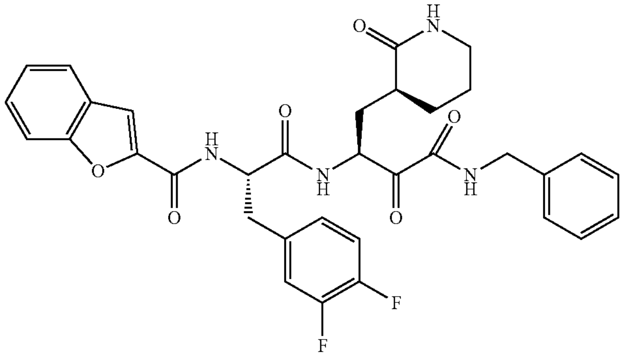 [SMILES: O=C(NCc1ccccc1)C(=O)[C@H](C[C@@H]1CCCNC1=O)NC(=O)[C@H](Cc1ccc(F)c(F)c1)NC(=O)c1cc2ccccc2o1] |

-continued
| number | structure |
| --- | --- |
| A291 | 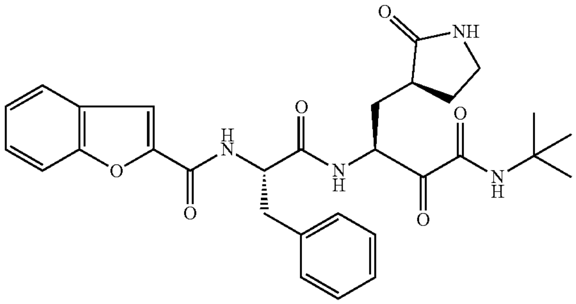 [SMILES: CC(C)(C)NC(=O)C(=O)[C@H](C[C@@H]1CCNC1=O)NC(=O)[C@H](Cc1ccccc1)NC(=O)c1cc2ccccc2o1] |
| A293 | 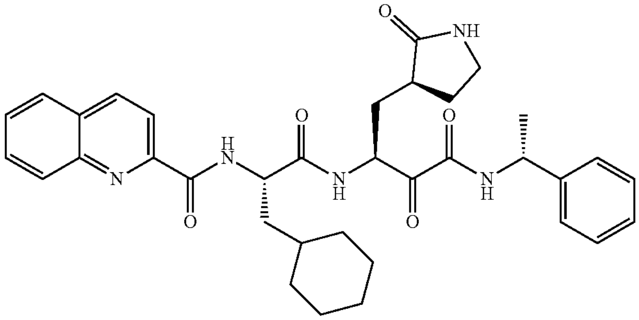 [SMILES: C[C@@H](NC(=O)C(=O)[C@H](C[C@@H]1CCNC1=O)NC(=O)[C@H](CC1CCCCC1)NC(=O)c1ccc2ccccc2n1)c1ccccc1] |
| A295 | 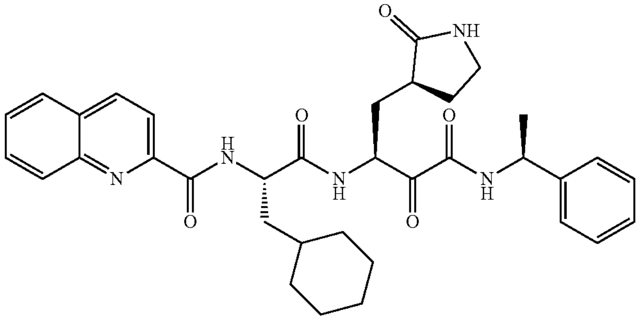 [SMILES: C[C@H](NC(=O)C(=O)[C@H](C[C@@H]1CCNC1=O)NC(=O)[C@H](CC1CCCCC1)NC(=O)c1ccc2ccccc2n1)c1ccccc1] |
| A296 | 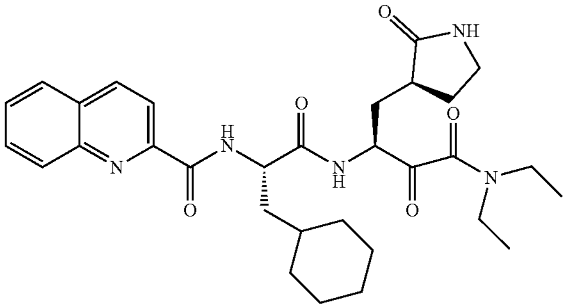 [SMILES: CCN(CC)C(=O)C(=O)[C@H](C[C@@H]1CCNC1=O)NC(=O)[C@H](CC1CCCCC1)NC(=O)c1ccc2ccccc2n1] |
| A297 | 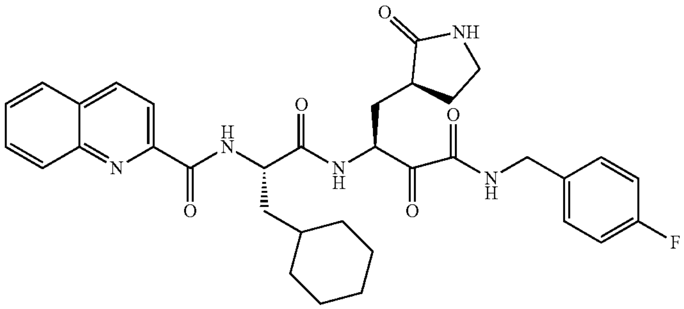 [SMILES: O=C(NCc1ccc(F)cc1)C(=O)[C@H](C[C@@H]1CCNC1=O)NC(=O)[C@H](CC1CCCCC1)NC(=O)c1ccc2ccccc2n1] |

-continued
| number | structure |
|---|---|
| A298 | 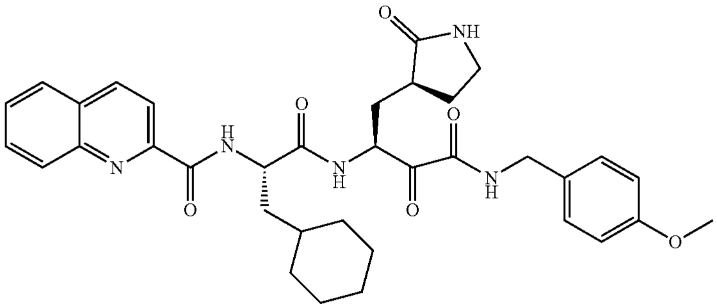 [SMILES: COc1ccc(CNC(=O)C(=O)[C@H](C[C@@H]2CCNC2=O)NC(=O)[C@H](CC2CCCCC2)NC(=O)c2ccc3ccccc3n2)cc1] |
| A300 | 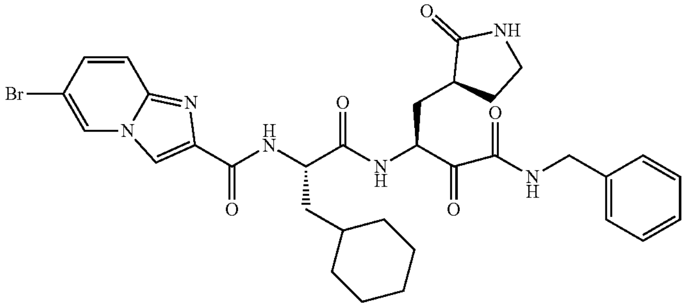 [SMILES: O=C(NCc1ccccc1)C(=O)[C@H](C[C@@H]1CCNC1=O)NC(=O)[C@H](CC1CCCCC1)NC(=O)c1cn2cc(Br)ccc2n1] |
| A301 | 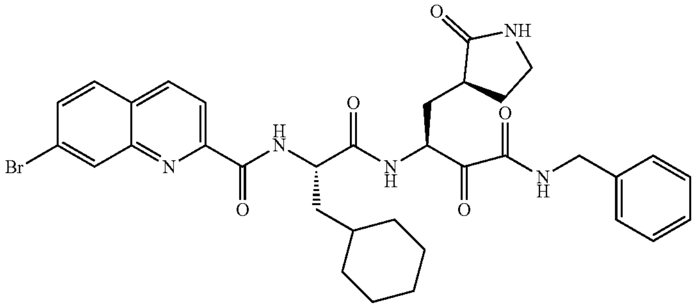 [SMILES: O=C(NCc1ccccc1)C(=O)[C@H](C[C@@H]1CCNC1=O)NC(=O)[C@H](CC1CCCCC1)NC(=O)c1ccc2ccc(Br)cc2n1] |
| A303 | 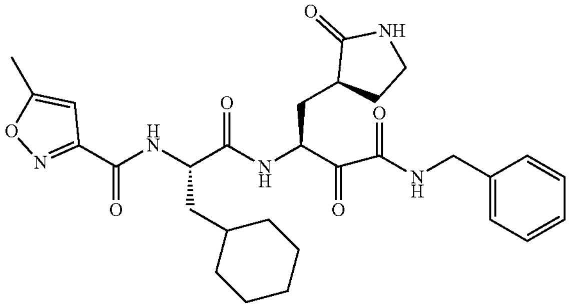 [SMILES: Cc1cc(C(=O)N[C@@H](CC2CCCCC2)C(=O)N[C@@H](C[C@@H]2CCNC2=O)C(=O)C(=O)NCc2ccccc2)no1] |
| A304 | 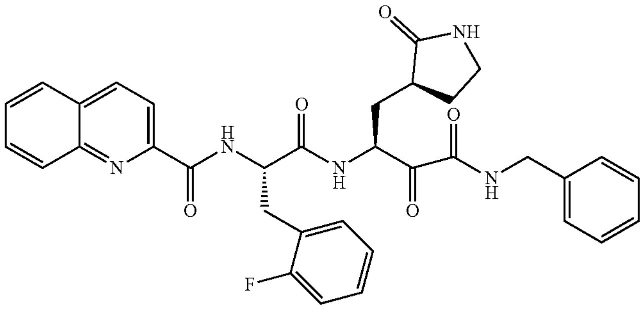 [SMILES: O=C(NCc1ccccc1)C(=O)[C@H](C[C@@H]1CCNC1=O)NC(=O)[C@H](Cc1ccccc1F)NC(=O)c1ccc2ccccc2n1] |

-continued
| number | structure |
|---|---|
| A305 | 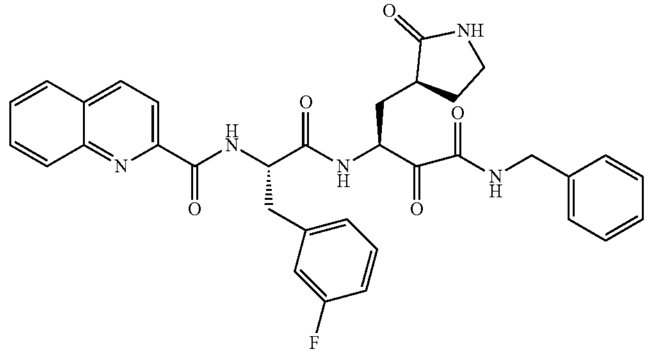 [SMILES: O=C(NCc1ccccc1)C(=O)[C@H](C[C@@H]1CCNC1=O)NC(=O)[C@H](Cc1cccc(F)c1)NC(=O)c1ccc2ccccc2n1] |
| A306 | 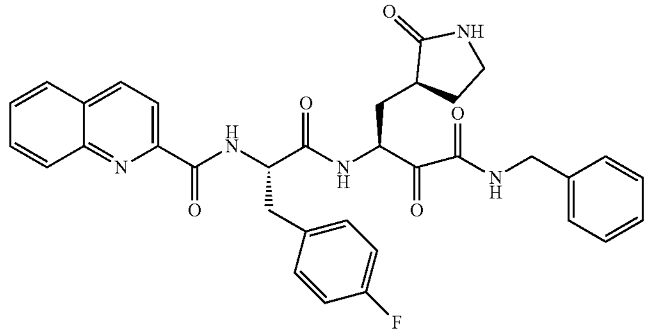 [SMILES: O=C(NCc1ccccc1)C(=O)[C@H](C[C@@H]1CCNC1=O)NC(=O)[C@H](Cc1ccc(F)cc1)NC(=O)c1ccc2ccccc2n1] |
| A307 | 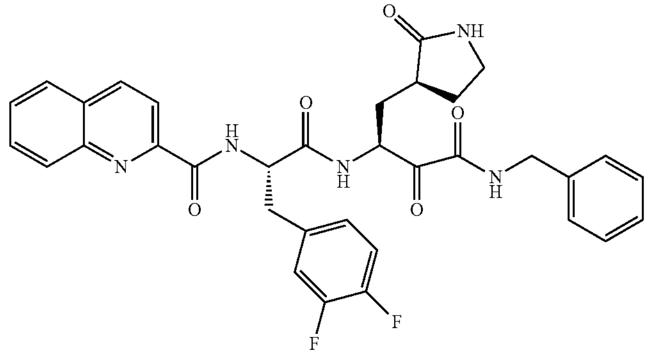 [SMILES: O=C(NCc1ccccc1)C(=O)[C@H](C[C@@H]1CCNC1=O)NC(=O)[C@H](Cc1ccc(F)c(F)c1)NC(=O)c1ccc2ccccc2n1] |
| A308 | 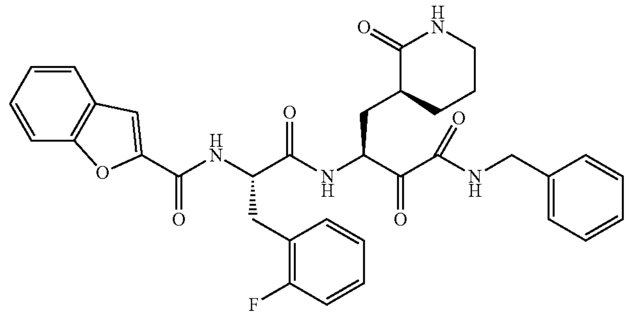 [SMILES: O=C(NCc1ccccc1)C(=O)[C@H](C[C@@H]1CCCNC1=O)NC(=O)[C@H](Cc1ccccc1F)NC(=O)c1cc2ccccc2o1] |

-continued

| number | structure |
|---|---|
| A309 | 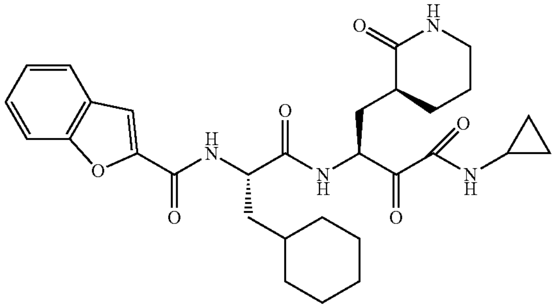 [SMILES: O=C(NC1CC1)C(=O)[C@H](C[C@@H]1CCCNC1=O)NC(=O)[C@H](CC1CCCCC1)NC(=O)c1cc2ccccc2o1] |
| A310 | 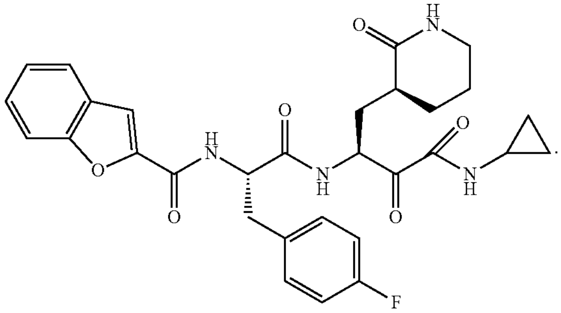 [SMILES: O=C(NC1CC1)C(=O)[C@H](C[C@@H]1CCCNC1=O)NC(=O)[C@H](Cc1ccc(F)cc1)NC(=O)c1cc2ccccc2o1] |

7. A pharmaceutical composition comprising (a) the keto-amide compound represented by formula (A), or the pharmaceutically acceptable salt, enantiomer, diastereomer or racemate thereof; and (b) a pharmaceutically acceptable carrier,

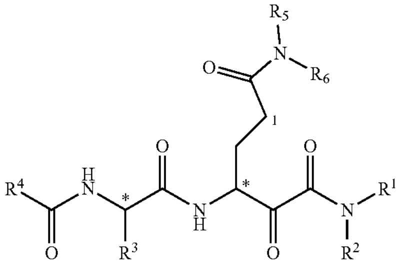

(A)

wherein,

* indicates that the stereochemical isomerism of carbon atoms is independently R and/or S respectively;

$R^1$ and $R^2$ are each independently selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 cycloalkyl C1-C10 alkylene, substituted or unsubstituted C3-C10 heterocycloalkyl, substituted or unsubstituted C3-C10 heterocycloalkyl C1-C10 alkylene, substituted or unsubstituted C6-C20 aryl, substituted or unsubstituted C3-C20 heteroaryl, substituted or unsubstituted C6-C20 aryl C1-C10 alkylene, substituted or unsubstituted C3-C20 heteroaryl C1-C10 alkylene, substituted or unsubstituted C6-C20 aryl C2-C10 alkenylene, substituted or unsubstituted C3-C20 heteroaryl C2-C10 alkenylene, acyl, and sulfonyl;

$R^3$ is selected from the group consisting of substituted or unsubstituted C1-C10 alkyl, substituted or unsubstituted C2-C10 alkenyl, substituted or unsubstituted C2-C10 alkynyl, substituted or unsubstituted C3-C8 cycloalkyl, substituted or unsubstituted C3-C8 cycloalkyl C1-C10 alkylene, substituted or unsubstituted C3-C8 heterocycloalkyl, substituted or unsubstituted C3-C8 heterocycloalkyl C1-C10 alkylene, substituted or unsubstituted C6-C20 aryl, substituted or unsubstituted C3-C20 heteroaryl, substituted or unsubstituted C6-C20 aryl C1-C10 alkylene, substituted or unsubstituted C3-C20 heteroaryl C1-C10 alkylene, substituted or unsubstituted C6-C20 aryl C2-C6 alkenylene, substituted or unsubstituted C3-C20 heteroaryl C2-C6 alkenylene, substituted or unsubstituted C6-C20 aryl C2-C6 alkynylene, and substituted or unsubstituted C3-C20 heteroaryl C2-C6 alkynylene;

$R^4$ is selected from the group consisting of substituted or unsubstituted C1-C10 alkyl, substituted or unsubstituted C2-C10 alkenyl, substituted or unsubstituted C2-C10 alkynyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C6-C20 aryl C2-C6 alkynylene, substituted or unsubstituted C3-C20 heteroaryl C1-C9 alkylene, substituted or unsubstituted C3-C20 heteroaryl C2-C9 alkenylene, and substituted or unsubstituted C3-C20 heteroaryl C2-C9 alkynylene;

$R^6$ is selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C3-C20 heteroaryl C1-C9 alkylene, substituted or unsubstituted C3-C20 heteroaryl C2-C9 alkenylene, acyl and sulfonyl;

when $—NR^5$ and its adjacent $—(C{=}O)—CH_2—$ form a ring, $R^5$ is $—(CH_2)_n—$, n is 2 or 3;

when $—NR^5$ does not form a ring with its adjacent $—(C{=}O)—CH_2—$, $R^5$ is selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C3-C20 heteroaryl C1-C9 alkylene, substituted or unsubstituted C3-C20 heteroaryl C2-C9 alkenylene, acyl and sulfonyl;

wherein, in $R^1$, $R^2$, $R^3$, $R^4$, $R^5$ and $R^6$, the "substituted" each independently refers to being substituted by 1, 2, 3 or 4 substituents selected from the group consisting of halogen, hydroxyl, mercapto, nitro, cyano, amino, imino, tertiary amino, azido, C1-C8 alkyl, halogenated C1-C8 alkyl, C1-C8 alkoxy, halogenated C1-C8 alkoxy, C1-C6 alkylcarbonyl, C1-C6 alkylthio, C1-C8 alkoxycarbonyl, and trifluoromethyl; the heterocycloalkyl and the heteroaryl each independently contain 1, 2, 3 or 4 heteroatoms selected from N, O, and S.

8. The pharmaceutical composition of claim 7, wherein the pharmaceutical composition is used in the manufacture of a medicament for treating and/or preventing and alleviating related diseases caused by 2019 novel coronavirus (2019-nCov) infection.

9. The pharmaceutical composition of claim 8, wherein the related diseases caused by 2019 novel coronavirus infection is selected from the group consisting of respiratory infections, pneumonia and complications thereof, and a combination thereof.

10. A method for inhibiting the activity of the 3CL protease of the 2019 novel coronavirus (2019-nCov), comprising the step of contacting a ketoamide compound represented by formula (A), or its pharmaceutically acceptable salt, enantiomer, diastereomer or racemate with the 3CL protease of 2019-nCov, thereby inhibiting the activity of the 3CL protease of 2019-nCov:

(A)

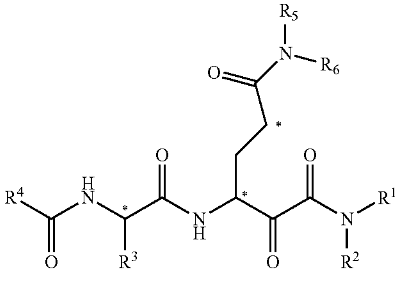

wherein,

* indicates that the stereochemical isomerism of carbon atoms is independently R and/or S respectively;

$R^1$ is selected from the group consisting of substituted or unsubstituted C1-C10 alkyl, substituted or unsubstituted C3-C8 cycloalkyl, substituted or unsubstituted C3-C8 cycloalkyl C1-C10 alkylene, and substituted or unsubstituted C6-C10 aryl C1-C10 alkylene;

$R^2$ is selected from the group consisting of hydrogen, deuterium, and C1-C6 alkyl;

$R^3$ is selected from the group consisting of substituted or unsubstituted C1-C6 alkyl, substituted or unsubstituted C3-C8 cycloalkyl, substituted or unsubstituted C3-C8 cycloalkyl C1-C5 alkylene, substituted or unsubstituted C6-C10 aryl, and substituted or unsubstituted C6-C10 aryl C1-C5 alkylene;

$R^4$ is selected from the group consisting of substituted or unsubstituted quinoxalinyl, substituted or unsubstituted quinazolinyl, substituted or unsubstituted cinnolinyl, substituted or unsubstituted indolyl, substituted or unsubstituted isoindolyl, substituted or unsubstituted benzimidazolyl, substituted or unsubstituted indazolyl, substituted or unsubstituted imidazole [1,2-A] pyridyl, substituted or unsubstituted imidazole [1,5-A] pyridyl, substituted or unsubstituted quinolinyl, substituted or unsubstituted isoquinolinyl, substituted or unsubstituted benzothienyl, and substituted or unsubstituted benzofuranyl; wherein the substituted means that the hydrogen atom on the group is substituted by 1, 2 or 3 substituents selected from the group consisting of F, Cl, Br, I, hydroxyl, C1-C6 alkyl, halogenated C1-C6 alkyl, C1-C6 alkoxy, halogenated C1-C6 alkoxy, and C1-C6 alkylthio;

$R^6$ is hydrogen or C1-C6 alkyl;

when $—NR^5$ and its adjacent $—(C{=}O)—CH_2—$ form a ring, $R^5$ is $—(CH_2)_n—$, n is 2 or 3;

when $—NR^5$ does not form a ring with its adjacent $—(C{=}O)—CH_2—$, $R^5$ is selected from the group consisting of hydrogen, deuterium, tritium, amino, hydroxyl, substituted or unsubstituted C1-C6 alkyl, and C3-C8 cycloalkyl;

wherein, in $R^1$ and $R^3$, each of the term "substituted" independently refers to being substituted by 1, 2, 3 or 4 substituents selected from the group consisting of halogen, hydroxyl, mercapto, nitro, cyano, amino, imino, tertiary amino, azido, C1-C8 alkyl, halogenated C1-C8 alkyl, C1-C8 alkoxy, halogenated C1-C8 alkoxy, C1-C6 alkylcarbonyl, C1-C6 alkylthio, C1-C8 alkoxycarbonyl, and trifluoromethyl.

11. A method for inhibiting the activity of human cathepsin L, comprising the step of contacting a ketoamide compound represented by formula (A), or the pharmaceutically acceptable salt, enantiomer, diastereomer or racemate thereof with human cathepsin L, thereby inhibiting the activity of human cathepsin L:

(A)

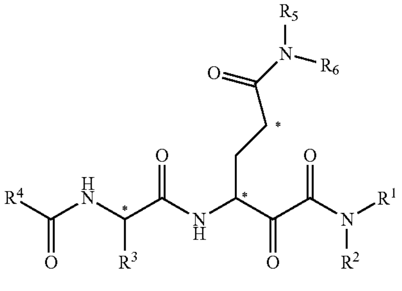

wherein,

* indicates that the stereochemical isomerism of carbon atoms is independently R and/or S respectively;

$R^1$ is selected from the group consisting of substituted or unsubstituted C1-C10 alkyl, substituted or unsubstituted C3-C8 cycloalkyl, substituted or unsubstituted C3-C8 cycloalkyl C1-C10 alkylene, and substituted or unsubstituted C6-C10 aryl C1-C10 alkylene, $R^2$ is selected from the group consisting of hydrogen, deuterium, and C1-C6 alkyl;

$R^3$ is selected from the group consisting of substituted or unsubstituted C1-C6 alkyl, substituted or unsubstituted C3-C8 cycloalkyl, substituted or unsubstituted C3-C8 cycloalkyl C1-C5 alkylene, substituted or unsubstituted C6-C10 aryl, and substituted or unsubstituted C3-C20 heteroaryl, substituted or unsubstituted C6-C10 aryl C1-C5 alkylene;

$R^4$ is selected from the group consisting of substituted or unsubstituted quinoxalinyl, substituted or unsubstituted quinazolinyl, substituted or unsubstituted cinnolinyl, substituted or unsubstituted indolyl, substituted or unsubstituted isoindolyl, substituted or unsubstituted benzimidazolyl, substituted or unsubstituted indazolyl, substituted or unsubstituted imidazole [1,2-A] pyridyl, substituted or unsubstituted imidazole [1,5-A] pyridyl, substituted or unsubstituted quinolinyl, substituted or unsubstituted isoquinolinyl, substituted or unsubstituted benzothienyl, and substituted or unsubstituted benzofuranyl; wherein the substituted means that the hydrogen atom on the group is substituted by 1, 2 or 3 substituents selected from the group consisting of F, Cl, Br, I, hydroxyl, C1-C6 alkyl, halogenated C1-C6 alkyl, C1-C6 alkoxy, halogenated C1-C6 alkoxy, and C1-C6 alkylthio;

$R^6$ is hydrogen or C1-C6 alkyl;

when $-NR^5$ and its adjacent $-(C{=}O)-CH_2-$ form a ring, $R^5$ is $-(CH_2)_n-$, n is 2 or 3;

when $-NR^5$ does not form a ring with its adjacent $-(C{=}O)-CH_2-$, $R^5$ is selected from the group consisting of hydrogen C1-C6 alkyl, and C3-C8 cycloalkyl;

wherein, in $R^1$ and $R^3$, each of the term "substituted" independently refers to being substituted by 1, 2, 3 or 4 substituents selected from the group consisting of halogen, hydroxyl, mercapto, nitro, cyano, amino, imino, tertiary amino, azido, C1-C8 alkyl, halogenated C1-C8 alkyl, C1-C8 alkoxy, halogenated C1-C8 alkoxy, C1-C6 alkylcarbonyl, C1-C6 alkylthio, C1-C8 alkoxycarbonyl, and trifluoromethyl.

12. A compound of formula (A), or a pharmaceutically acceptable salt, enantiomer, diastereomer or racemate thereof, (A)

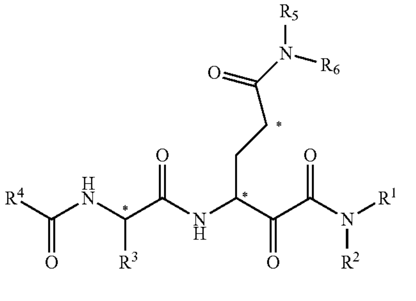

wherein,

* indicates that the stereochemical isomerism of carbon atoms is independently R and/or S respectively;

$R^1$ and $R^2$ are each independently selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 cycloalkyl C1-C10 alkylene, substituted or unsubstituted C3-C10 heterocycloalkyl, substituted or unsubstituted C3-C10 heterocycloalkyl C1-C10 alkylene, substituted or unsubstituted C6-C20 aryl, substituted or unsubstituted C3-C20 heteroaryl, substituted or unsubstituted C6-C20 aryl C1-C10 alkylene, substituted or unsubstituted C3-C20 heteroaryl C1-C10 alkylene, substituted or unsubstituted C6-C20 aryl C2-C10 alkenylene, substituted or unsubstituted C3-C20 heteroaryl C2-C10 alkenylene, acyl, and sulfonyl;

$R^3$ is selected from the group consisting of substituted or unsubstituted C1-C10 alkyl, substituted or unsubstituted C2-C10 alkenyl, substituted or unsubstituted C2-C10 alkynyl, substituted or unsubstituted C3-C8 cycloalkyl, substituted or unsubstituted C3-C8 cycloalkyl C1-C10 alkylene, substituted or unsubstituted C3-C8 heterocycloalkyl, substituted or unsubstituted C3-C8 heterocycloalkyl C1-C10 alkylene, substituted or unsubstituted C6-C20 aryl, substituted or unsubstituted C3-C20 heteroaryl, substituted or unsubstituted C6-C20 aryl C1-C10 alkylene, substituted or unsubstituted C3-C20 heteroaryl C1-C10 alkylene, substituted or unsubstituted C6-C20 aryl C2-C6 alkenylene, substituted or unsubstituted C3-C20 heteroaryl C2-C6 alkenylene, substituted or unsubstituted C6-C20 aryl C2-C6 alkynylene, and substituted or unsubstituted C3-C20 heteroaryl C2-C6 alkynylene;

$R^4$ is selected from the group consisting of substituted or unsubstituted C1-C10 alkyl, substituted or unsubstituted C2-C10 alkenyl, substituted or unsubstituted C2-C10 alkynyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C6-C20 aryl C2-C6 alkynylene, substituted or unsubstituted C3-C20 heteroaryl C1-C9 alkylene, substituted or unsubstituted C3-C20 heteroaryl C2-C9 alkenylene, and substituted or unsubstituted C3-C20 heteroaryl C2-C9 alkynylene;

$R^6$ is selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C3-C20 heteroaryl C1-C9 alkylene, substituted or unsubstituted C3-C20 heteroaryl C2-C9 alkenylene, acyl and sulfonyl;

when $-NR^5$ and its adjacent $-(C{=}O)-CH_2-$ form a ring, $R^5$ is $-(CH_2)_n-$, n is 2 or 3;

when $-NR^5$ does not form a ring with its adjacent $-(C{=}O)-CH_2-$, $R^5$ is selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C3-C20 heteroaryl C1-C9 alkylene, substituted or unsubstituted C3-C20 heteroaryl C2-C9 alkenylene, acyl and sulfonyl;

wherein, in $R^1$, $R^2$, $R^3$, $R^4$, $R^5$ and $R^6$, each of the "substituted" independently refers to being substituted by 1, 2, 3 or 4 substituents selected from the group consisting of halogen, hydroxyl, mercapto, nitro, cyano, amino, imino, tertiary amino, azido, C1-C8 alkyl, halogenated C1-C8 alkyl, C1-C8 alkoxy, halogenated C1-C8 alkoxy, C1-C6 alkylcarbonyl, C1-C6 alkylthio, C1-C8 alkoxycarbonyl, and trifluoromethyl; the heterocycloalkyl and the heteroaryl each independently comprise 1, 2, 3 or 4 heteroatoms selected from N, O, and S.

13. The compound, or the pharmaceutically acceptable salt, enantiomer, diastereomer or racemate thereof of claim 12, wherein the compound is selected from the group consisting of:

| number | structure |
|---|---|
| A254 | 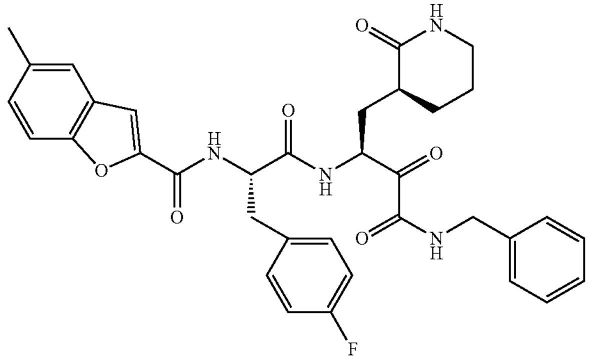 [SMILES: Cc1ccc2oc(C(=O)N[C@@H](Cc3ccc(F)cc3)C(=O)N[C@@H](C[C@@H]3CCCNC3=O)C(=O)C(=O)NCc3ccccc3)cc2c1] |
| A255 | 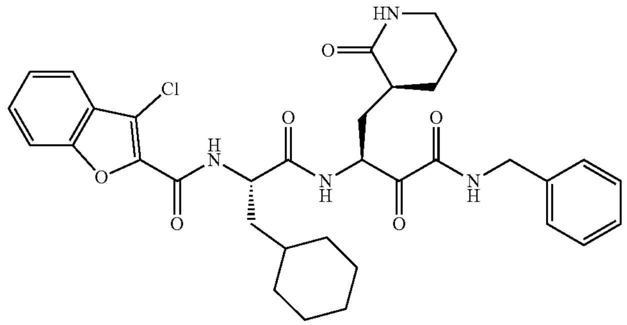 [SMILES: O=C(NCc1ccccc1)C(=O)[C@H](C[C@@H]1CCCNC1=O)NC(=O)[C@H](CC1CCCCC1)NC(=O)c1oc2ccccc2c1Cl] |
| A256 | 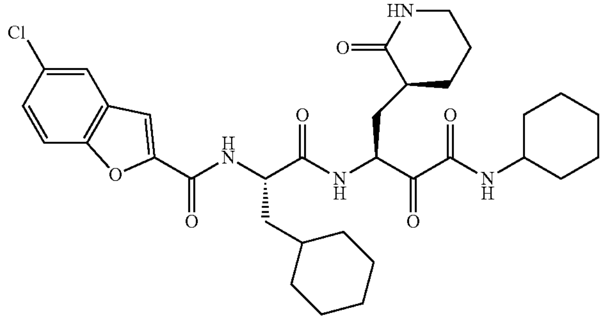 [SMILES: O=C(NC1CCCCC1)C(=O)[C@H](C[C@@H]1CCCNC1=O)NC(=O)[C@H](CC1CCCCC1)NC(=O)c1cc2cc(Cl)ccc2o1] |

-continued
| number | structure |
|---|---|
| A257 | 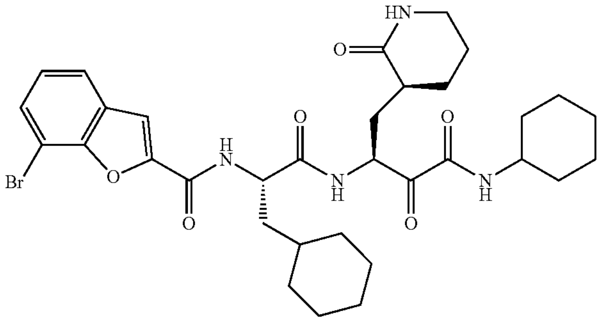 [SMILES: O=C(NC1CCCCC1)C(=O)[C@H](C[C@@H]1CCCNC1=O)NC(=O)[C@H](CC1CCCCC1)NC(=O)c1cc2cccc(Br)c2o1] |
| A258 | 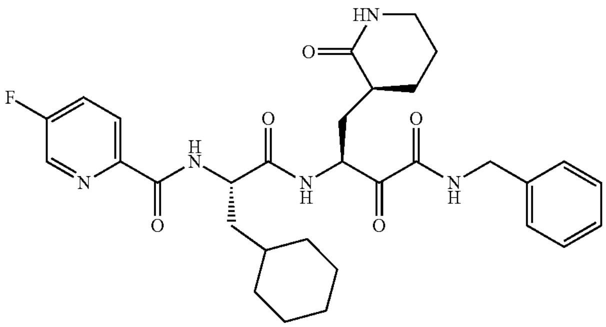 [SMILES: O=C(NCc1ccccc1)C(=O)[C@H](C[C@@H]1CCCNC1=O)NC(=O)[C@H](CC1CCCCC1)NC(=O)c1ccc(F)cn1] |
| A259 | 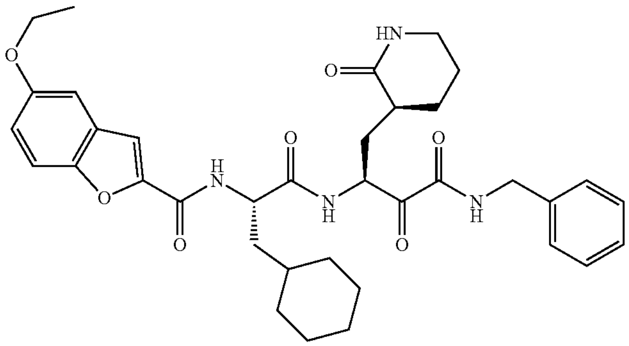 [SMILES: CCOc1ccc2oc(C(=O)N[C@@H](CC3CCCCC3)C(=O)N[C@@H](C[C@@H]3CCCNC3=O)C(=O)C(=O)NCc3ccccc3)cc2c1] |
| A260 | 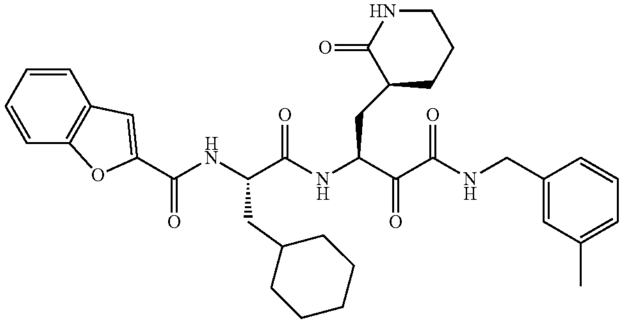 [SMILES: Cc1cccc(CNC(=O)C(=O)[C@H](C[C@@H]2CCCNC2=O)NC(=O)[C@H](CC2CCCCC2)NC(=O)c2cc3ccccc3o2)c1] |

-continued
| number | structure |
|---|---|
| A261 | 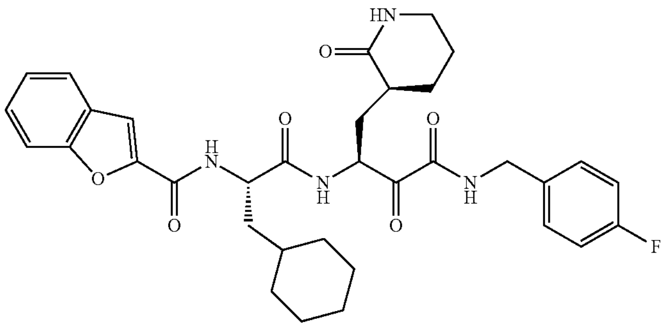 [SMILES: O=C(NCc1ccc(F)cc1)C(=O)[C@H](C[C@@H]1CCCNC1=O)NC(=O)[C@H](CC1CCCCC1)NC(=O)c1cc2ccccc2o1] |
| A262 | 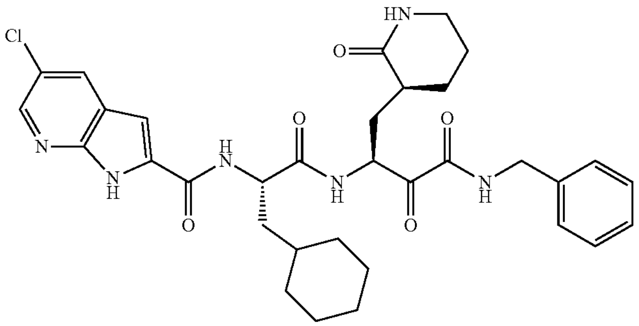 [SMILES: O=C(NCc1ccccc1)C(=O)[C@H](C[C@@H]1CCCNC1=O)NC(=O)[C@H](CC1CCCCC1)NC(=O)c1cc2cc(Cl)cnc2[nH]1] |
| A263 | 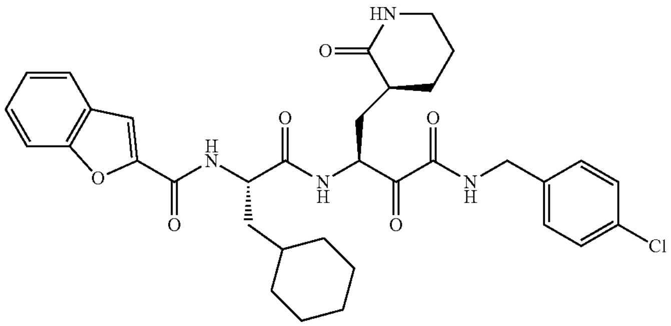 [SMILES: O=C(NCc1ccc(Cl)cc1)C(=O)[C@H](C[C@@H]1CCCNC1=O)NC(=O)[C@H](CC1CCCCC1)NC(=O)c1cc2ccccc2o1] |
| A264 | 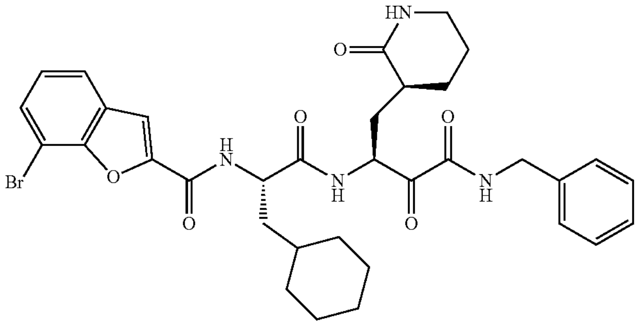 [SMILES: O=C(NCc1ccccc1)C(=O)[C@H](C[C@@H]1CCCNC1=O)NC(=O)[C@H](CC1CCCCC1)NC(=O)c1cc2cccc(Br)c2o1] |

-continued
| number | structure |
| --- | --- |
| A265 | 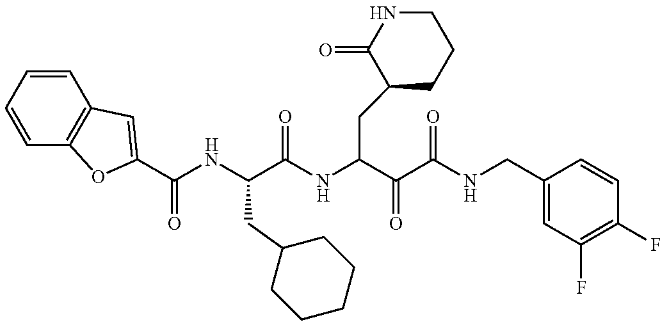 [SMILES: O=C(NCc1ccc(F)c(F)c1)C(=O)C(C[C@@H]1CCCNC1=O)NC(=O)[C@H](CC1CCCCC1)NC(=O)c1cc2ccccc2o1] |
| A266 | 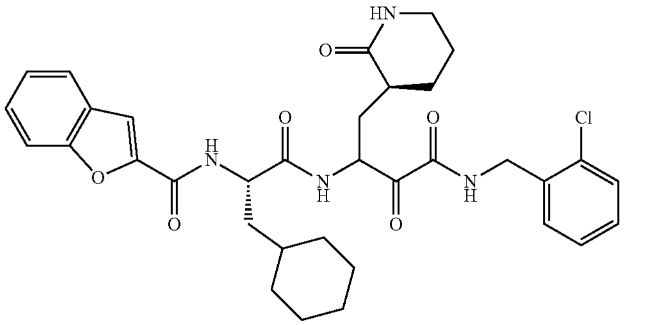 [SMILES: O=C(NCc1ccccc1Cl)C(=O)C(C[C@@H]1CCCNC1=O)NC(=O)[C@H](CC1CCCCC1)NC(=O)c1cc2ccccc2o1] |
| A267 | 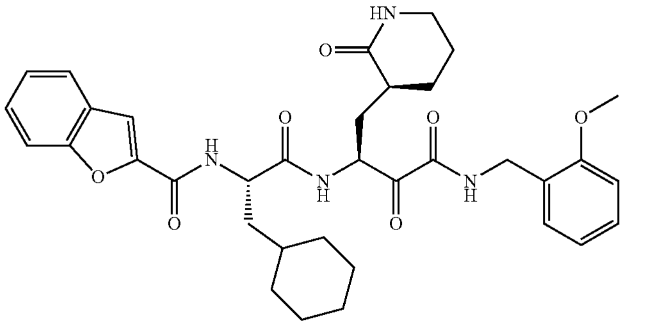 [SMILES: COc1ccccc1CNC(=O)C(=O)[C@H](C[C@@H]1CCCNC1=O)NC(=O)[C@H](CC1CCCCC1)NC(=O)c1cc2ccccc2o1] |
| A268 | 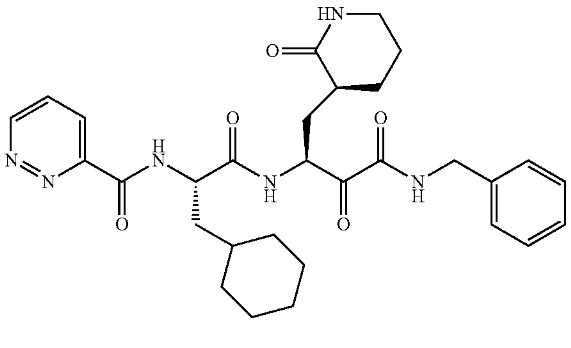 [SMILES: O=C(NCc1ccccc1)C(=O)[C@H](C[C@@H]1CCCNC1=O)NC(=O)[C@H](CC1CCCCC1)NC(=O)c1cccnn1] |

-continued
| number | structure |
|---|---|
| A269 | 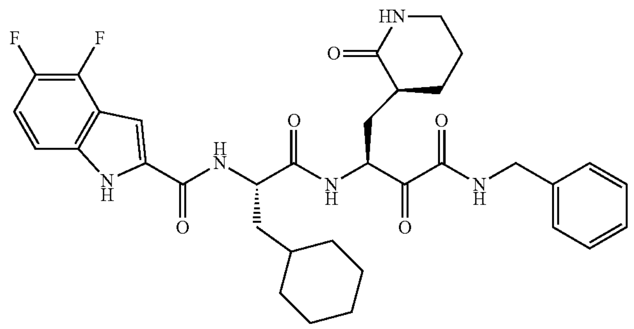 [SMILES: O=C(NCc1ccccc1)C(=O)[C@H](C[C@@H]1CCCNC1=O)NC(=O)[C@H](CC1CCCCC1)NC(=O)c1cc2c(F)c(F)ccc2[nH]1] |
| A270 | 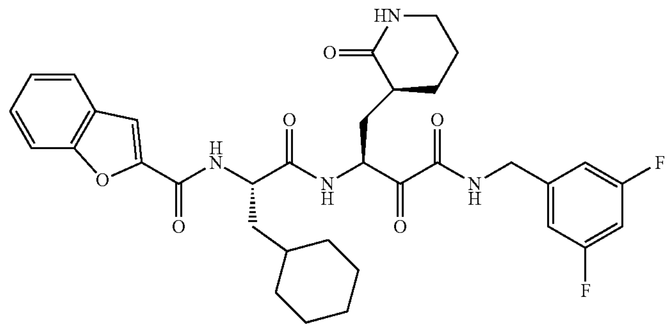 [SMILES: O=C(NCc1cc(F)cc(F)c1)C(=O)[C@H](C[C@@H]1CCCNC1=O)NC(=O)[C@H](CC1CCCCC1)NC(=O)c1cc2ccccc2o1] |
| A271 | 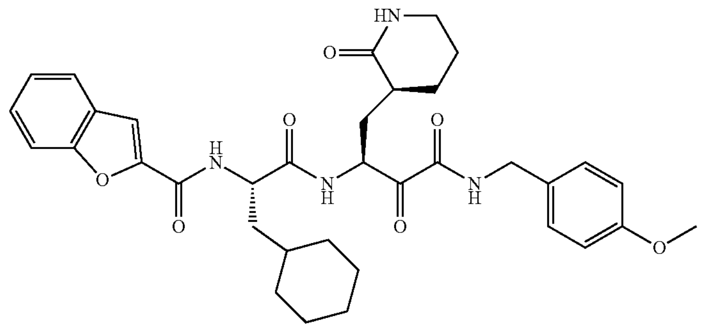 [SMILES: COc1ccc(CNC(=O)C(=O)[C@H](C[C@@H]2CCCNC2=O)NC(=O)[C@H](CC2CCCCC2)NC(=O)c2cc3ccccc3o2)cc1] |
| A272 | 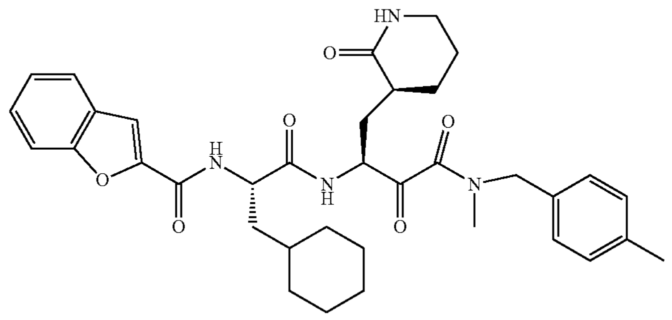 [SMILES: Cc1ccc(CN(C)C(=O)C(=O)[C@H](C[C@@H]2CCCNC2=O)NC(=O)[C@H](CC2CCCCC2)NC(=O)c2cc3ccccc3o2)cc1] |

-continued
| number | structure |
|---|---|
| A273 | 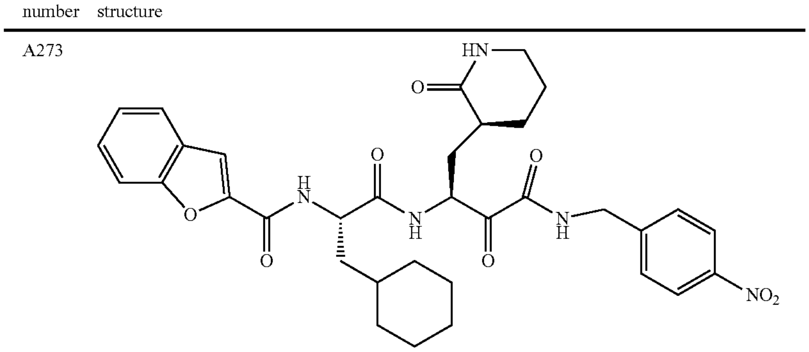 |
| A274 | 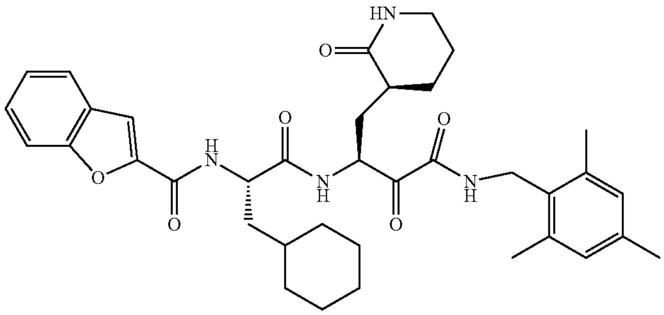 [SMILES: Cc1cc(C)c(CNC(=O)C(=O)[C@H](C[C@@H]2CCCNC2=O)NC(=O)[C@H](CC2CCCCC2)NC(=O)c2cc3ccccc3o2)c(C)c1] |
| A275 | 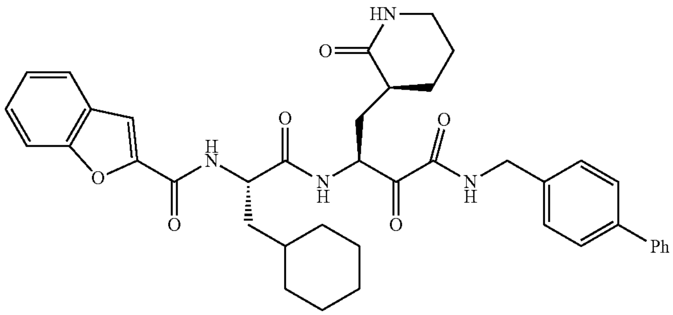 [SMILES: O=C(NCc1ccc(-c2ccccc2)cc1)C(=O)[C@H](C[C@@H]1CCCNC1=O)NC(=O)[C@H](CC1CCCCC1)NC(=O)c1cc2ccccc2o1] |
| A276 | 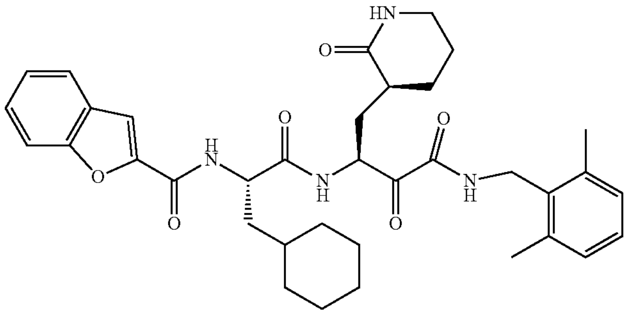 [SMILES: Cc1cccc(C)c1CNC(=O)C(=O)[C@H](C[C@@H]1CCCNC1=O)NC(=O)[C@H](CC1CCCCC1)NC(=O)c1cc2ccccc2o1] |
| A277 | 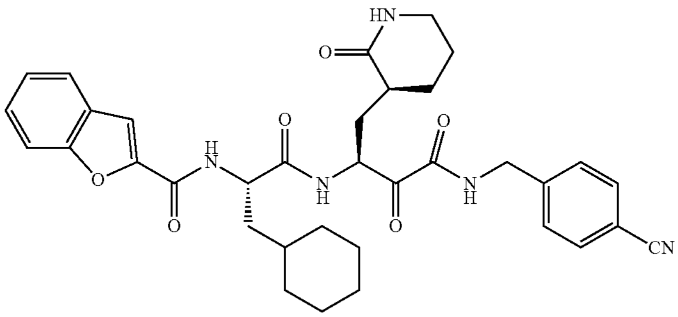 [SMILES: N#Cc1ccc(CNC(=O)C(=O)[C@H](C[C@@H]2CCCNC2=O)NC(=O)[C@H](CC2CCCCC2)NC(=O)c2cc3ccccc3o2)cc1] |

-continued
| number | structure |
| --- | --- |
| A278 | 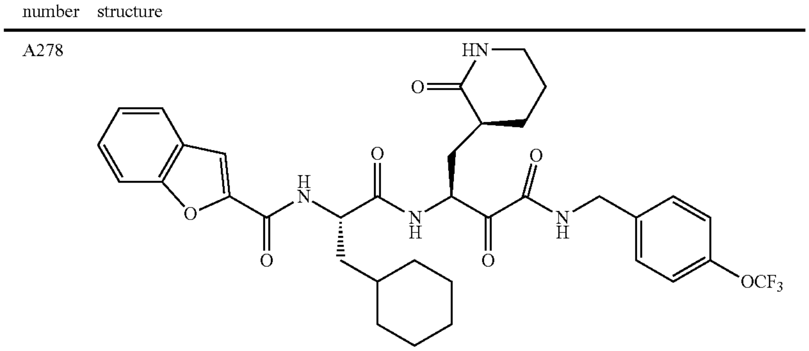 |
| A279 | 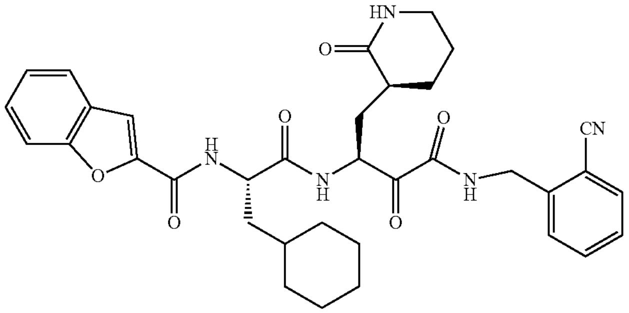 [SMILES: N#Cc1ccccc1CNC(=O)C(=O)[C@H](C[C@@H]1CCCNC1=O)NC(=O)[C@H](CC1CCCCC1)NC(=O)c1cc2ccccc2o1] |
| A280 | 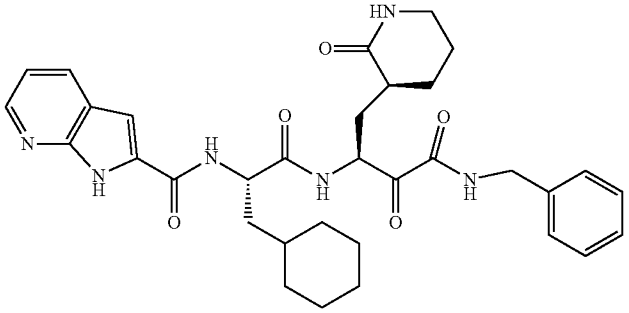 [SMILES: O=C(NCc1ccccc1)C(=O)[C@H](C[C@@H]1CCCNC1=O)NC(=O)[C@H](CC1CCCCC1)NC(=O)c1cc2cccnc2[nH]1] |
| A281 | 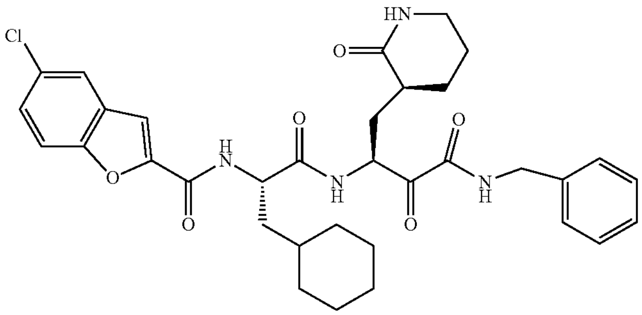 [SMILES: O=C(NCc1ccccc1)C(=O)[C@H](C[C@@H]1CCCNC1=O)NC(=O)[C@H](CC1CCCCC1)NC(=O)c1cc2cc(Cl)ccc2o1] |
| A282 | 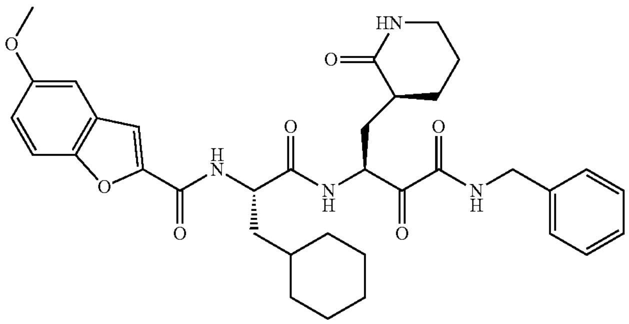 [SMILES: COc1ccc2oc(C(=O)N[C@@H](CC3CCCCC3)C(=O)N[C@@H](C[C@@H]3CCCNC3=O)C(=O)C(=O)NCc3ccccc3)cc2c1] |

-continued
| number | structure |
|---|---|
| A283 | 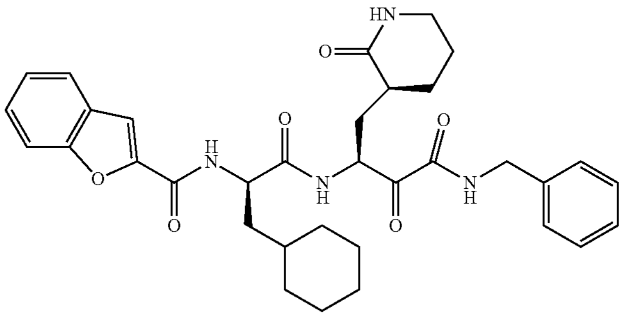 [SMILES: O=C(NCc1ccccc1)C(=O)[C@H](C[C@@H]1CCCNC1=O)NC(=O)[C@@H](CC1CCCCC1)NC(=O)c1cc2ccccc2o1] |
| A284 | 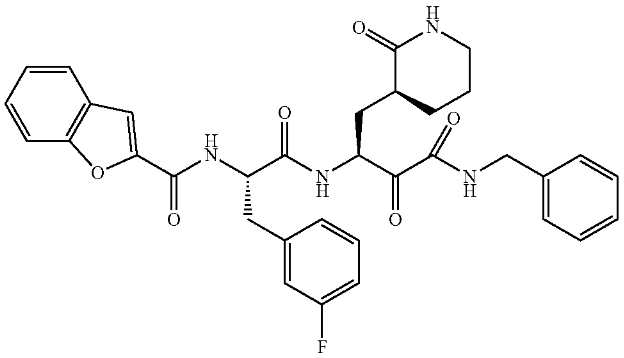 [SMILES: O=C(NCc1ccccc1)C(=O)[C@H](C[C@@H]1CCCNC1=O)NC(=O)[C@H](Cc1cccc(F)c1)NC(=O)c1cc2ccccc2o1] |
| A285 | 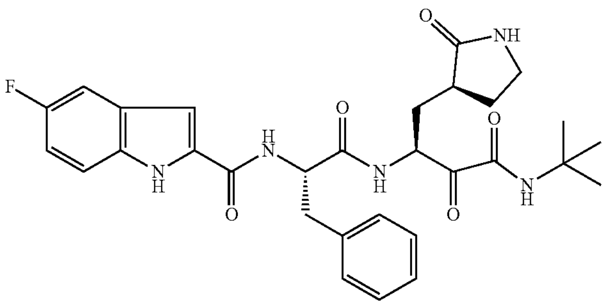 [SMILES: CC(C)(C)NC(=O)C(=O)[C@H](C[C@@H]1CCNC1=O)NC(=O)[C@H](Cc1ccccc1)NC(=O)c1cc2cc(F)ccc2[nH]1] |
| A286 | 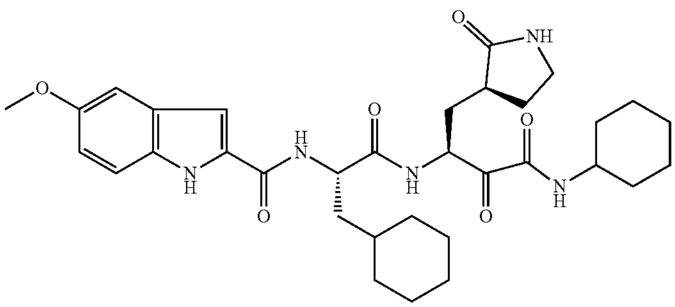 [SMILES: COc1ccc2[nH]c(C(=O)N[C@@H](CC3CCCCC3)C(=O)N[C@@H](C[C@@H]3CCNC3=O)C(=O)C(=O)NC3CCCCC3)cc2c1] |

-continued
| number | structure |
|---|---|
| A287 | 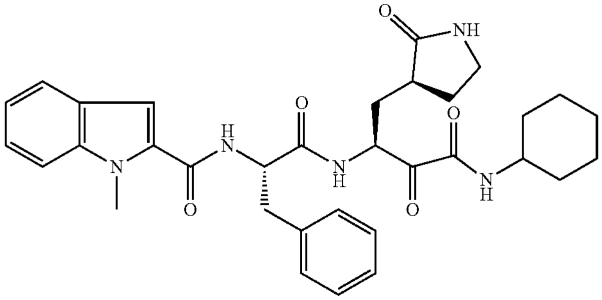 [SMILES: Cn1c(C(=O)N[C@@H](Cc2ccccc2)C(=O)N[C@@H](C[C@@H]2CCNC2=O)C(=O)C(=O)NC2CCCCC2)cc2ccccc21] |
| A288 | 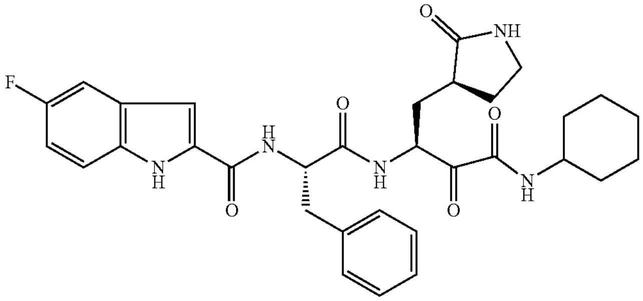 [SMILES: O=C(NC1CCCCC1)C(=O)[C@H](C[C@@H]1CCNC1=O)NC(=O)[C@H](Cc1ccccc1)NC(=O)c1cc2cc(F)ccc2[nH]1] |
| A289 | 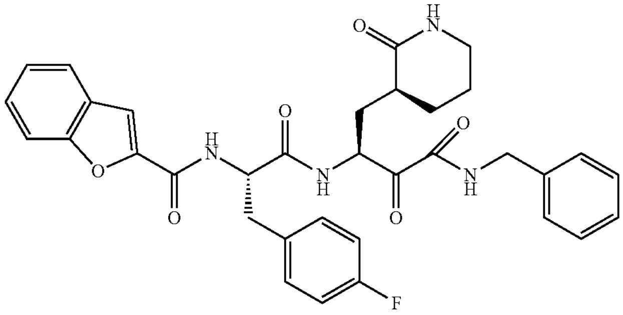 [SMILES: O=C(NCc1ccccc1)C(=O)[C@H](C[C@@H]1CCCNC1=O)NC(=O)[C@H](Cc1ccc(F)cc1)NC(=O)c1cc2ccccc2o1] |
| A290 | 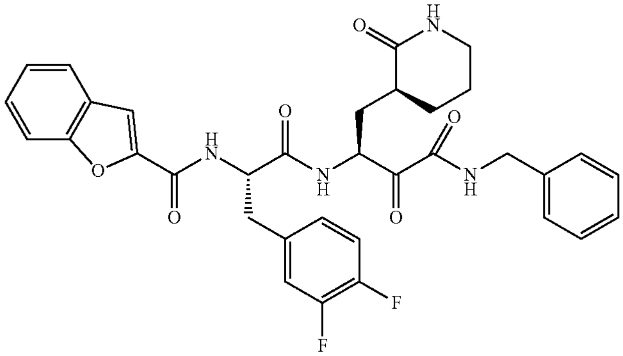 [SMILES: O=C(NCc1ccccc1)C(=O)[C@H](C[C@@H]1CCCNC1=O)NC(=O)[C@H](Cc1ccc(F)c(F)c1)NC(=O)c1cc2ccccc2o1] |
| A291 | 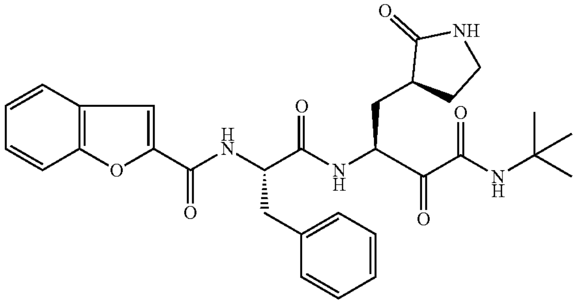 [SMILES: CC(C)(C)NC(=O)C(=O)[C@H](C[C@@H]1CCNC1=O)NC(=O)[C@H](Cc1ccccc1)NC(=O)c1cc2ccccc2o1] |

-continued
| number | structure |
| --- | --- |
| A292 | 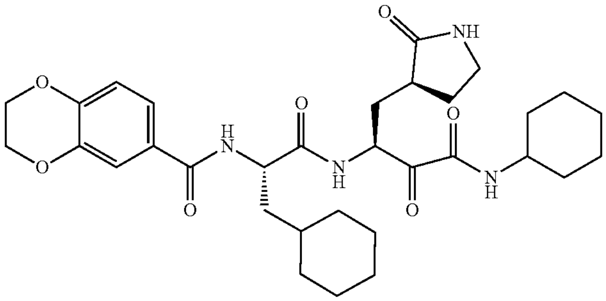 [SMILES: O=C(NC1CCCCC1)C(=O)[C@H](C[C@@H]1CCNC1=O)NC(=O)[C@H](CC1CCCCC1)NC(=O)c1ccc2c(c1)OCCO2] |
| A293 | 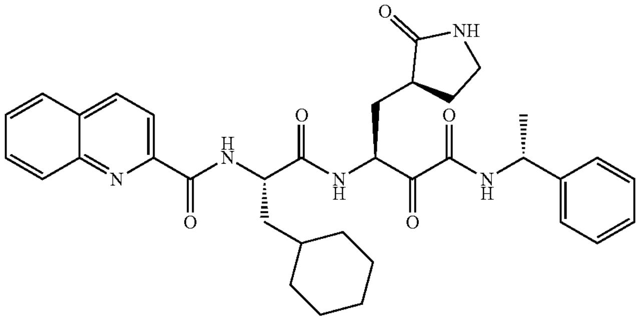 [SMILES: C[C@@H](NC(=O)C(=O)[C@H](C[C@@H]1CCNC1=O)NC(=O)[C@H](CC1CCCCC1)NC(=O)c1ccc2ccccc2n1)c1ccccc1] |
| A294 | 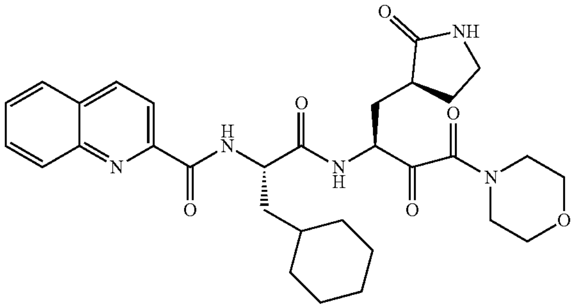 [SMILES: O=C(N[C@@H](CC1CCCCC1)C(=O)N[C@@H](C[C@@H]1CCNC1=O)C(=O)C(=O)N1CCOCC1)c1ccc2ccccc2n1] |
| A295 | 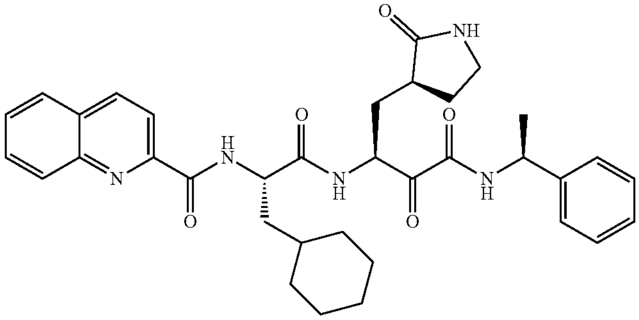 [SMILES: C[C@H](NC(=O)C(=O)[C@H](C[C@@H]1CCNC1=O)NC(=O)[C@H](CC1CCCCC1)NC(=O)c1ccc2ccccc2n1)c1ccccc1] |
| A296 | 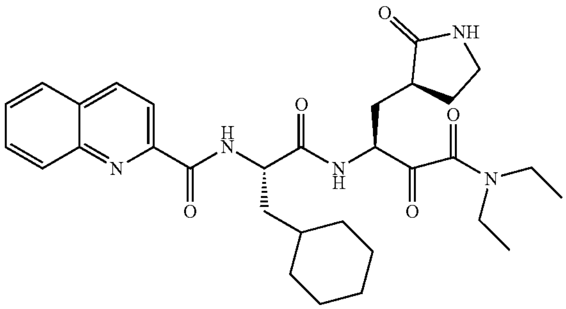 [SMILES: CCN(CC)C(=O)C(=O)[C@H](C[C@@H]1CCNC1=O)NC(=O)[C@H](CC1CCCCC1)NC(=O)c1ccc2ccccc2n1] |

-continued
| number | structure |
|---|---|
| A297 | 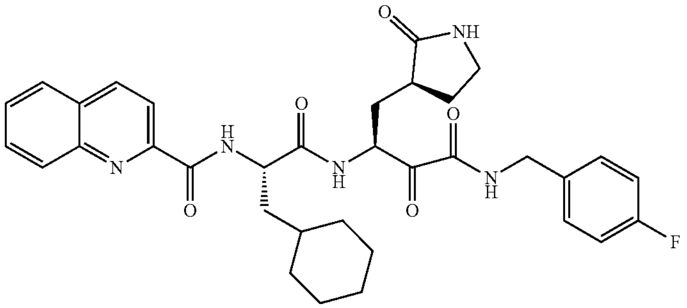 [SMILES: O=C(NCc1ccc(F)cc1)C(=O)[C@H](C[C@@H]1CCNC1=O)NC(=O)[C@H](CC1CCCCC1)NC(=O)c1ccc2ccccc2n1] |
| A298 | 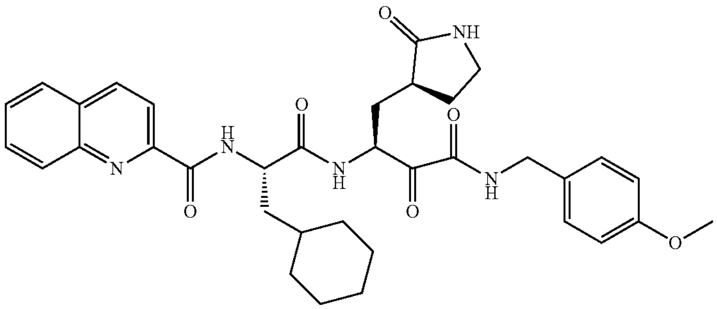 [SMILES: COc1ccc(CNC(=O)C(=O)[C@H](C[C@@H]2CCNC2=O)NC(=O)[C@H](CC2CCCCC2)NC(=O)c2ccc3ccccc3n2)cc1] |
| A299 | 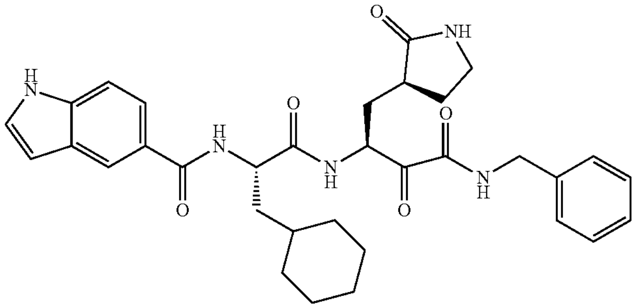 [SMILES: O=C(NCc1ccccc1)C(=O)[C@H](C[C@@H]1CCNC1=O)NC(=O)[C@H](CC1CCCCC1)NC(=O)c1ccc2[nH]ccc2c1] |
| A300 | 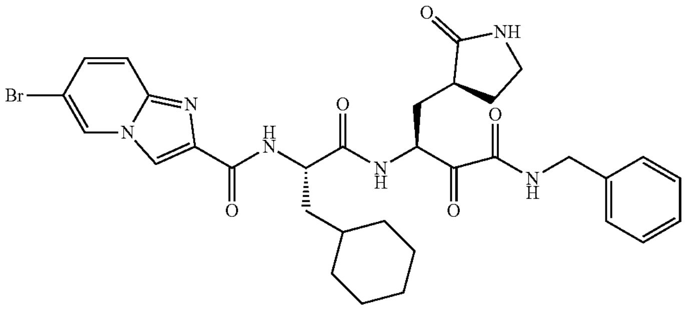 [SMILES: O=C(NCc1ccccc1)C(=O)[C@H](C[C@@H]1CCNC1=O)NC(=O)[C@H](CC1CCCCC1)NC(=O)c1cn2cc(Br)ccc2n1] |
| A301 | 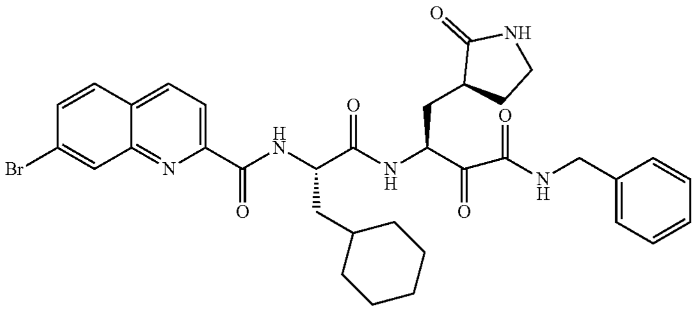 [SMILES: O=C(NCc1ccccc1)C(=O)[C@H](C[C@@H]1CCNC1=O)NC(=O)[C@H](CC1CCCCC1)NC(=O)c1ccc2ccc(Br)cc2n1] |

-continued
| number | structure |
| --- | --- |
| A302 | 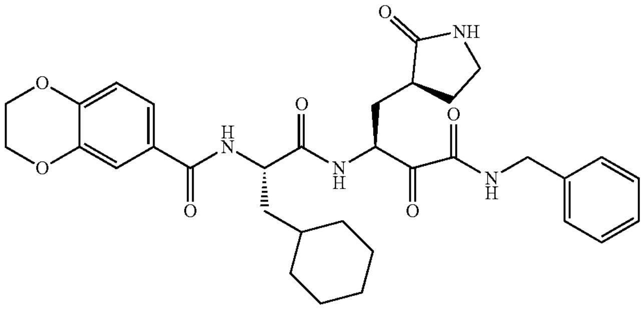 [SMILES: O=C(NCc1ccccc1)C(=O)[C@H](C[C@@H]1CCNC1=O)NC(=O)[C@H](CC1CCCCC1)NC(=O)c1ccc2c(c1)OCCO2] |
| A303 | 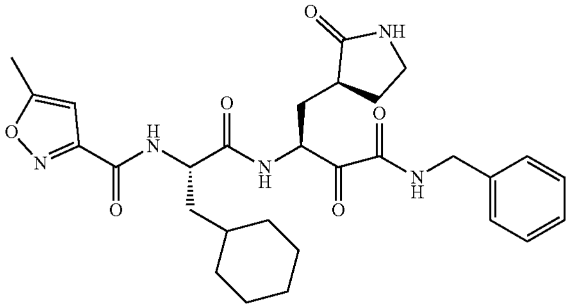 [SMILES: Cc1cc(C(=O)N[C@@H](CC2CCCCC2)C(=O)N[C@@H](C[C@@H]2CCNC2=O)C(=O)C(=O)NCc2ccccc2)no1] |
| A304 | 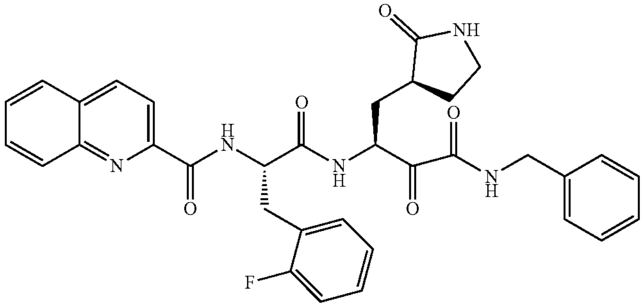 [SMILES: O=C(NCc1ccccc1)C(=O)[C@H](C[C@@H]1CCNC1=O)NC(=O)[C@H](Cc1ccccc1F)NC(=O)c1ccc2ccccc2n1] |
| A305 | 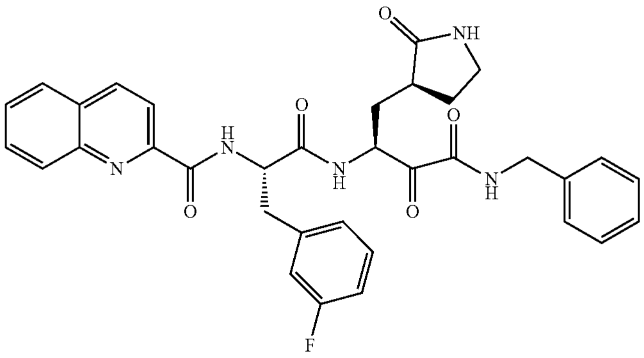 [SMILES: O=C(NCc1ccccc1)C(=O)[C@H](C[C@@H]1CCNC1=O)NC(=O)[C@H](Cc1cccc(F)c1)NC(=O)c1ccc2ccccc2n1] |

-continued
| number | structure |
| --- | --- |
| A306 | 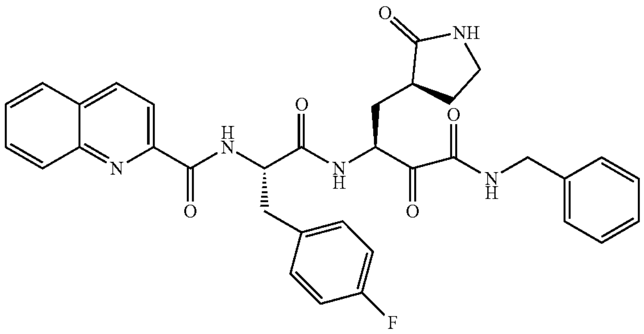 [SMILES: O=C(NCc1ccccc1)C(=O)[C@H](C[C@@H]1CCNC1=O)NC(=O)[C@H](Cc1ccc(F)cc1)NC(=O)c1ccc2ccccc2n1] |
| A307 | 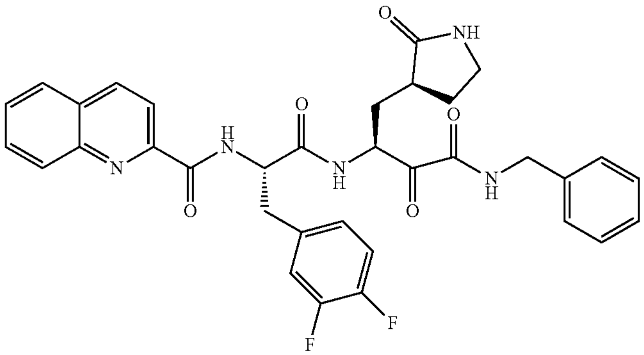 [SMILES: O=C(NCc1ccccc1)C(=O)[C@H](C[C@@H]1CCNC1=O)NC(=O)[C@H](Cc1ccc(F)c(F)c1)NC(=O)c1ccc2ccccc2n1] |
| A308 | 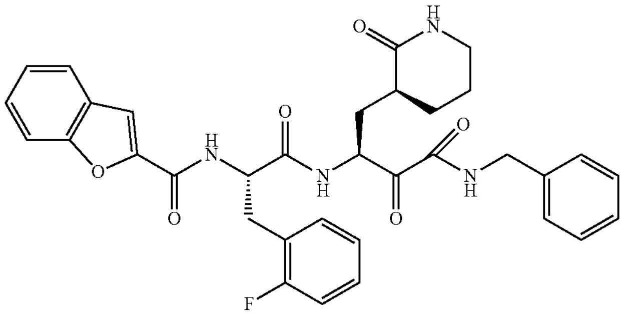 [SMILES: O=C(NCc1ccccc1)C(=O)[C@H](C[C@@H]1CCCNC1=O)NC(=O)[C@H](Cc1ccccc1F)NC(=O)c1cc2ccccc2o1] |
| A309 | 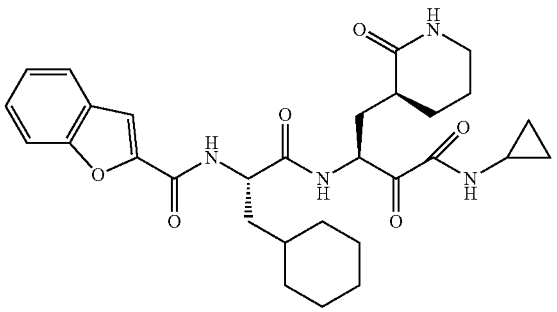 [SMILES: O=C(NC1CC1)C(=O)[C@H](C[C@@H]1CCCNC1=O)NC(=O)[C@H](CC1CCCCC1)NC(=O)c1cc2ccccc2o1] |

-continued
| number | structure |
|---|---|
| A310 | 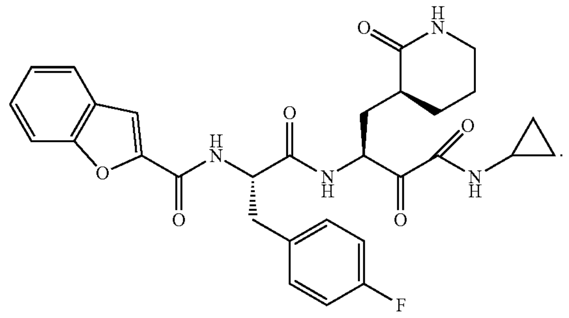 [SMILES: O=C(NC1CC1)C(=O)[C@H](C[C@@H]1CCCNC1=O)NC(=O)[C@H](Cc1ccc(F)cc1)NC(=O)c1cc2ccccc2o1] |
14. The method of claim 1, wherein $R^1$ is selected from the group consisting of C3-C6 cycloalkyl and C6 aryl C1 alkylene.
15. The method of claim 1, wherein the compound is selected from the group consisting of:
| | |
|---|---|
| A254 | 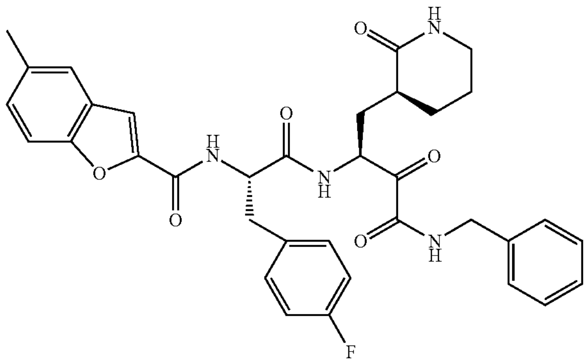 [SMILES: Cc1ccc2oc(C(=O)N[C@@H](Cc3ccc(F)cc3)C(=O)N[C@@H](C[C@@H]3CCCNC3=O)C(=O)C(=O)NCc3ccccc3)cc2c1] |
| A255 | 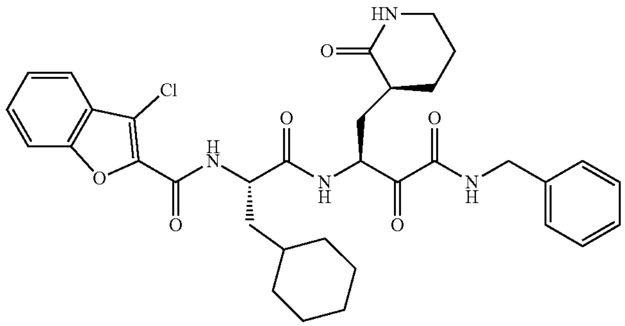 [SMILES: O=C(NCc1ccccc1)C(=O)[C@H](C[C@@H]1CCCNC1=O)NC(=O)[C@H](CC1CCCCC1)NC(=O)c1oc2ccccc2c1Cl] |
| A256 | 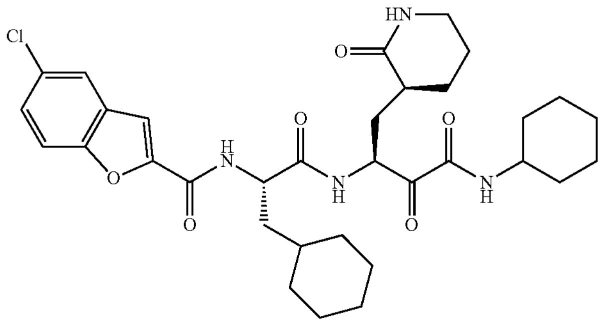 [SMILES: O=C(NC1CCCCC1)C(=O)[C@H](C[C@@H]1CCCNC1=O)NC(=O)[C@H](CC1CCCCC1)NC(=O)c1cc2cc(Cl)ccc2o1] |

-continued
A257
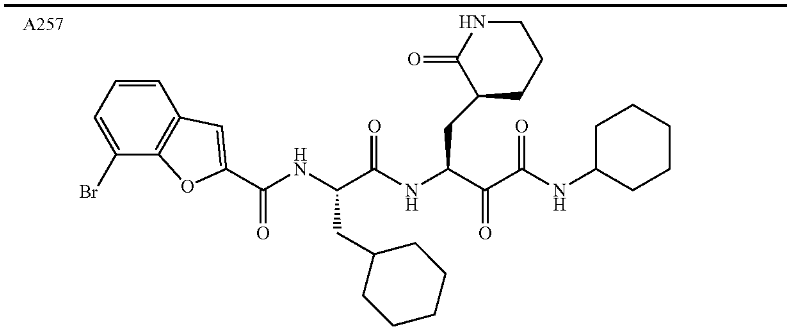
A259
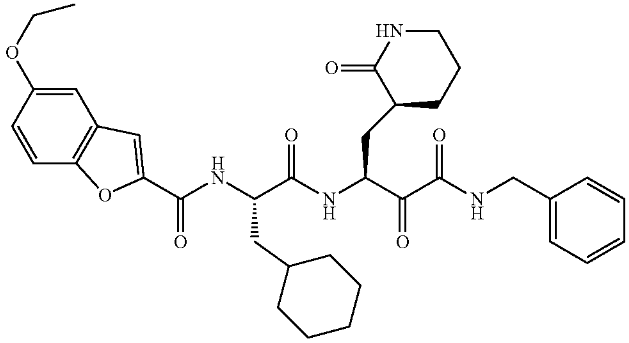 [SMILES: CCOc1ccc2oc(C(=O)N[C@@H](CC3CCCCC3)C(=O)N[C@@H](C[C@@H]3CCCNC3=O)C(=O)C(=O)NCc3ccccc3)cc2c1]
A260
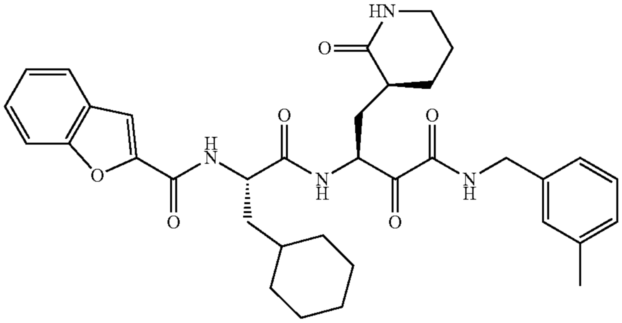 [SMILES: Cc1cccc(CNC(=O)C(=O)[C@H](C[C@@H]2CCCNC2=O)NC(=O)[C@H](CC2CCCCC2)NC(=O)c2cc3ccccc3o2)c1]
A261
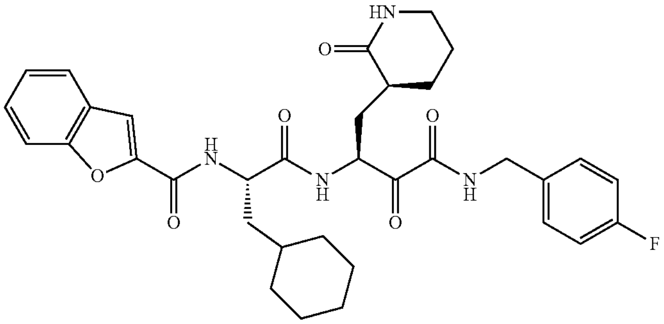 [SMILES: O=C(NCc1ccc(F)cc1)C(=O)[C@H](C[C@@H]1CCCNC1=O)NC(=O)[C@H](CC1CCCCC1)NC(=O)c1cc2ccccc2o1]
A263
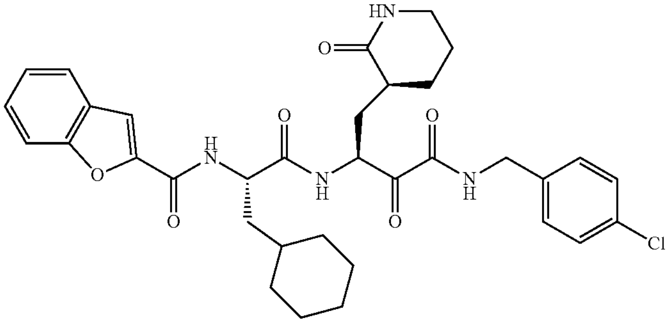 [SMILES: O=C(NCc1ccc(Cl)cc1)C(=O)[C@H](C[C@@H]1CCCNC1=O)NC(=O)[C@H](CC1CCCCC1)NC(=O)c1cc2ccccc2o1]

-continued
A264
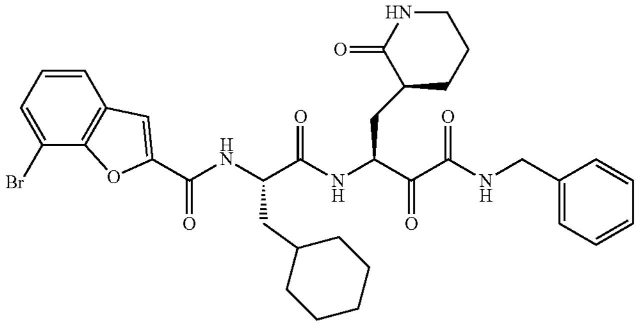 [SMILES: O=C(NCc1ccccc1)C(=O)[C@H](C[C@@H]1CCCNC1=O)NC(=O)[C@H](CC1CCCCC1)NC(=O)c1cc2cccc(Br)c2o1]
A265
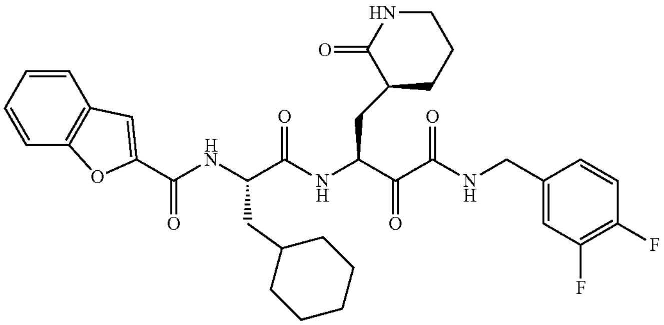 [SMILES: O=C(NCc1ccc(F)c(F)c1)C(=O)[C@H](C[C@@H]1CCCNC1=O)NC(=O)[C@H](CC1CCCCC1)NC(=O)c1cc2ccccc2o1]
A266
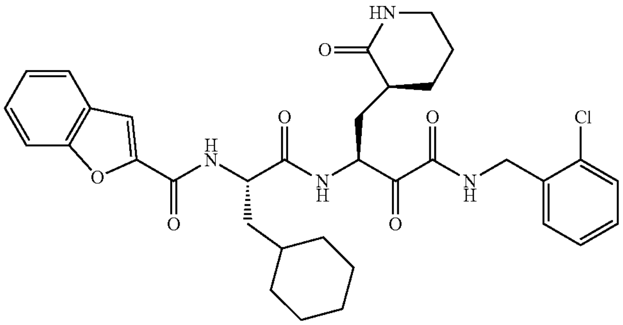 [SMILES: O=C(NCc1ccccc1Cl)C(=O)[C@H](C[C@@H]1CCCNC1=O)NC(=O)[C@H](CC1CCCCC1)NC(=O)c1cc2ccccc2o1]
A267
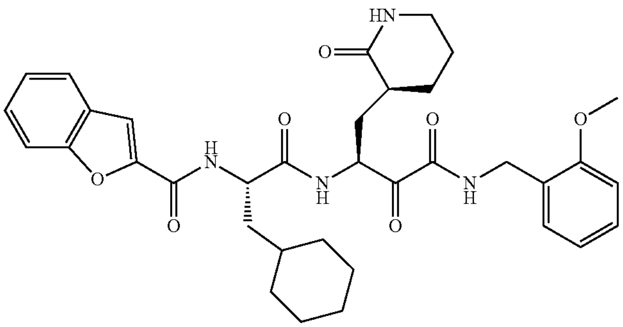 [SMILES: COc1ccccc1CNC(=O)C(=O)[C@H](C[C@@H]1CCCNC1=O)NC(=O)[C@H](CC1CCCCC1)NC(=O)c1cc2ccccc2o1]

-continued
A269
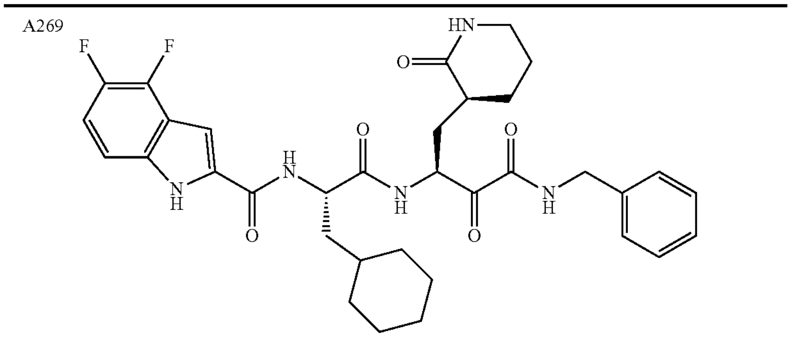
A270
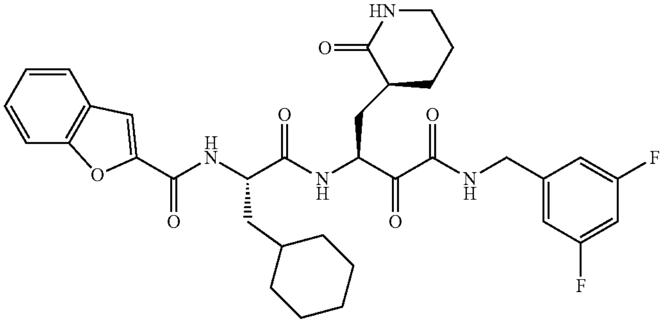 [SMILES: O=C(NCc1cc(F)cc(F)c1)C(=O)[C@H](C[C@@H]1CCCNC1=O)NC(=O)[C@H](CC1CCCCC1)NC(=O)c1cc2ccccc2o1]
A271
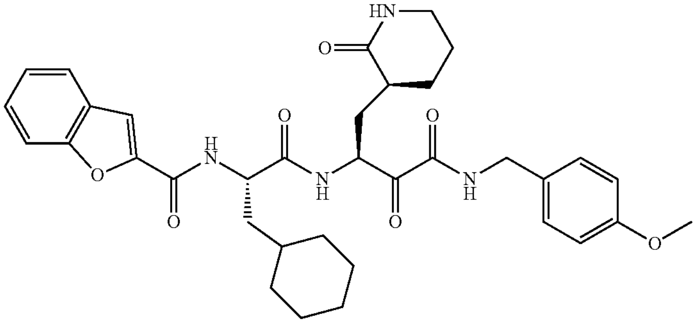 [SMILES: COc1ccc(CNC(=O)C(=O)[C@H](C[C@@H]2CCCNC2=O)NC(=O)[C@H](CC2CCCCC2)NC(=O)c2cc3ccccc3o2)cc1]
A272
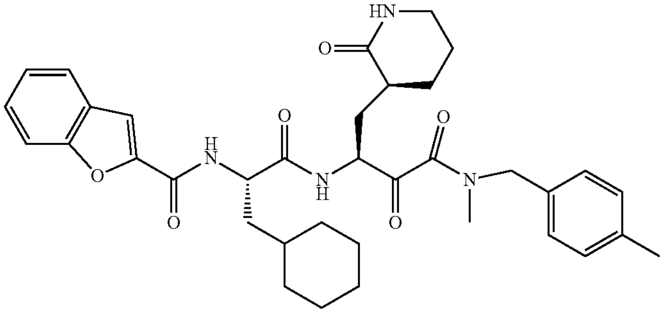 [SMILES: Cc1ccc(CN(C)C(=O)C(=O)[C@H](C[C@@H]2CCCNC2=O)NC(=O)[C@H](CC2CCCCC2)NC(=O)c2cc3ccccc3o2)cc1]
A274
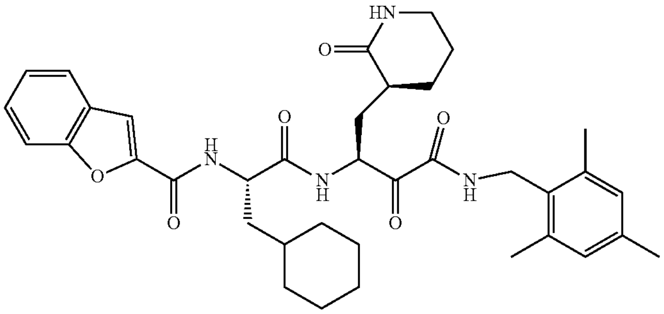 [SMILES: Cc1cc(C)c(CNC(=O)C(=O)[C@H](C[C@@H]2CCCNC2=O)NC(=O)[C@H](CC2CCCCC2)NC(=O)c2cc3ccccc3o2)c(C)c1]

-continued
A276
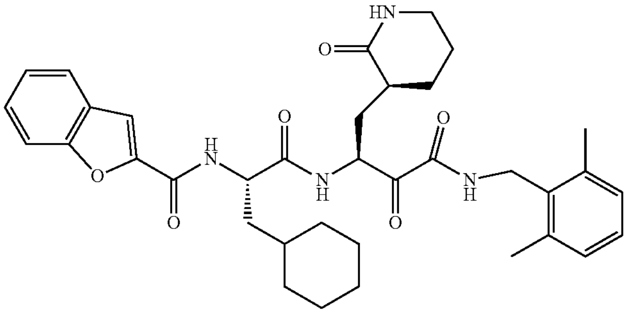 [SMILES: Cc1cccc(C)c1CNC(=O)C(=O)[C@H](C[C@@H]1CCCNC1=O)NC(=O)[C@H](CC1CCCCC1)NC(=O)c1cc2ccccc2o1]
A277
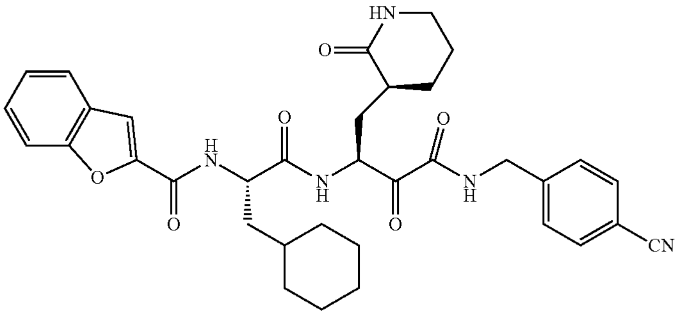 [SMILES: N#Cc1ccc(CNC(=O)C(=O)[C@H](C[C@@H]2CCCNC2=O)NC(=O)[C@H](CC2CCCCC2)NC(=O)c2cc3ccccc3o2)cc1]
A278
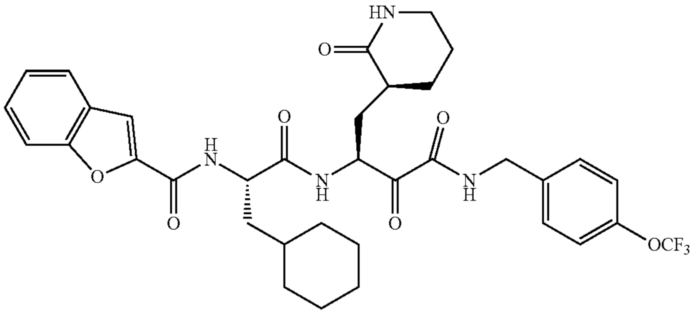 [SMILES: O=C(NCc1ccc(OC(F)(F)F)cc1)C(=O)[C@H](C[C@@H]1CCCNC1=O)NC(=O)[C@H](CC1CCCCC1)NC(=O)c1cc2ccccc2o1]
A279
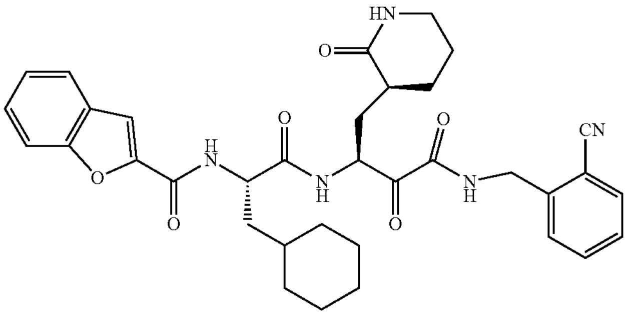 [SMILES: N#Cc1ccccc1CNC(=O)C(=O)[C@H](C[C@@H]1CCCNC1=O)NC(=O)[C@H](CC1CCCCC1)NC(=O)c1cc2ccccc2o1]
A281
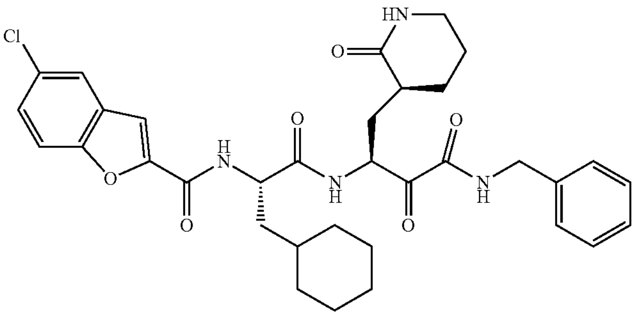 [SMILES: O=C(NCc1ccccc1)C(=O)[C@H](C[C@@H]1CCCNC1=O)NC(=O)[C@H](CC1CCCCC1)NC(=O)c1cc2cc(Cl)ccc2o1]

-continued
A282
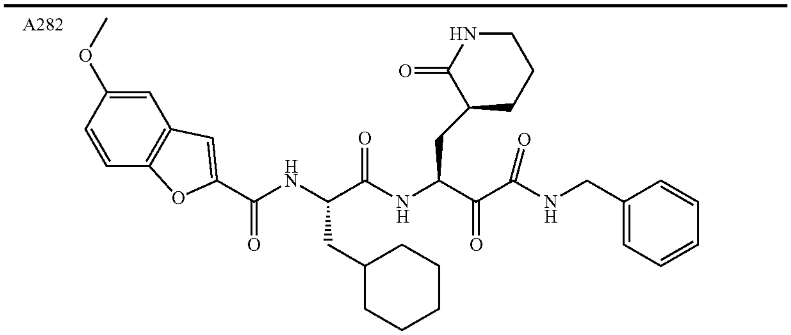
A283
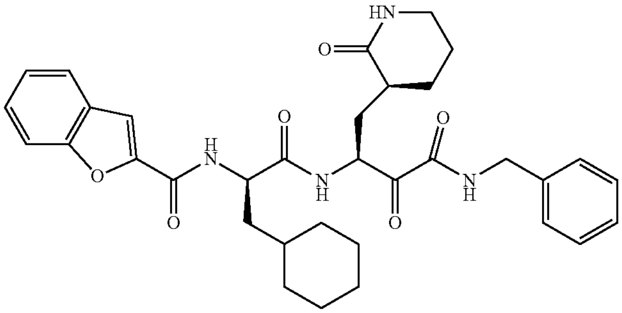 [SMILES: O=C(NCc1ccccc1)C(=O)[C@H](C[C@@H]1CCCNC1=O)NC(=O)[C@@H](CC1CCCCC1)NC(=O)c1cc2ccccc2o1]
A284
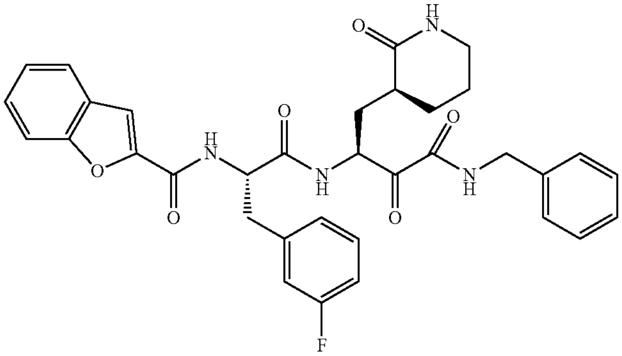 [SMILES: O=C(NCc1ccccc1)C(=O)[C@H](C[C@@H]1CCCNC1=O)NC(=O)[C@H](Cc1cccc(F)c1)NC(=O)c1cc2ccccc2o1]
A285
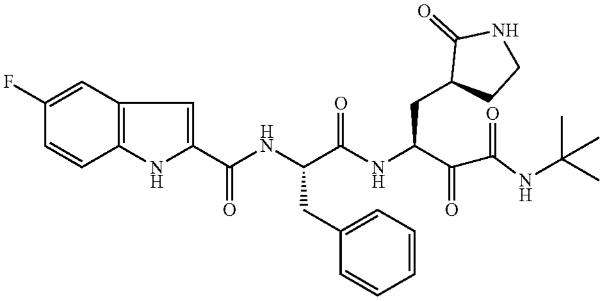 [SMILES: CC(C)(C)NC(=O)C(=O)[C@H](C[C@@H]1CCNC1=O)NC(=O)[C@H](Cc1ccccc1)NC(=O)c1cc2cc(F)ccc2[nH]1]
A286
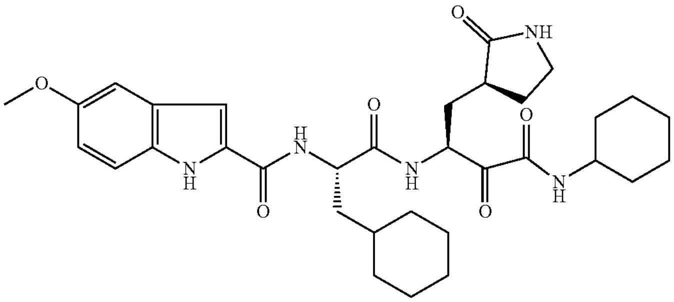 [SMILES: COc1ccc2[nH]c(C(=O)N[C@@H](CC3CCCCC3)C(=O)N[C@@H](C[C@@H]3CCNC3=O)C(=O)C(=O)NC3CCCCC3)cc2c1]

-continued
A287
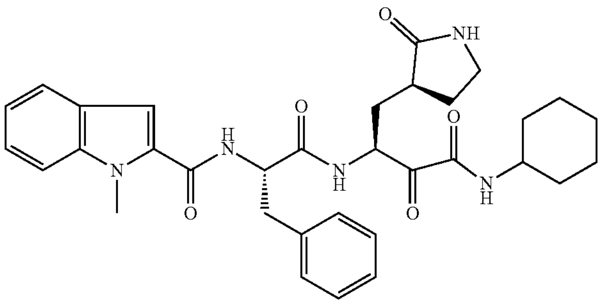 [SMILES: Cn1c(C(=O)N[C@@H](Cc2ccccc2)C(=O)N[C@@H](C[C@@H]2CCNC2=O)C(=O)C(=O)NC2CCCCC2)cc2ccccc21]
A288
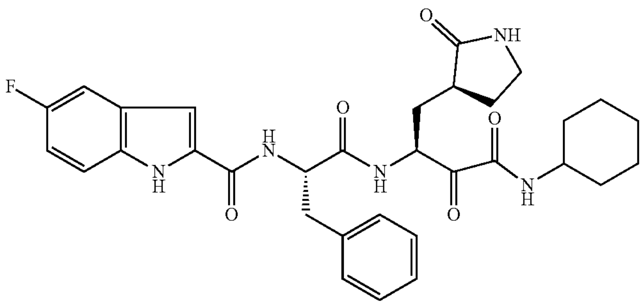 [SMILES: O=C(NC1CCCCC1)C(=O)[C@H](C[C@@H]1CCNC1=O)NC(=O)[C@H](Cc1ccccc1)NC(=O)c1cc2cc(F)ccc2[nH]1]
A289
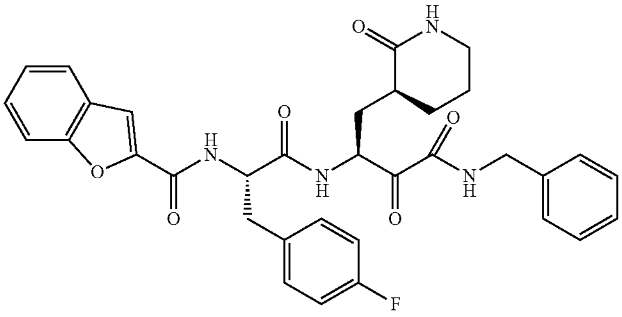 [SMILES: O=C(NCc1ccccc1)C(=O)[C@H](C[C@@H]1CCCNC1=O)NC(=O)[C@H](Cc1ccc(F)cc1)NC(=O)c1cc2ccccc2o1]
A290
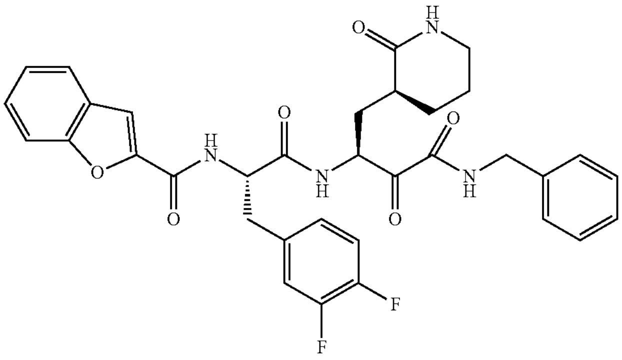 [SMILES: O=C(NCc1ccccc1)C(=O)[C@H](C[C@@H]1CCCNC1=O)NC(=O)[C@H](Cc1ccc(F)c(F)c1)NC(=O)c1cc2ccccc2o1]
A291
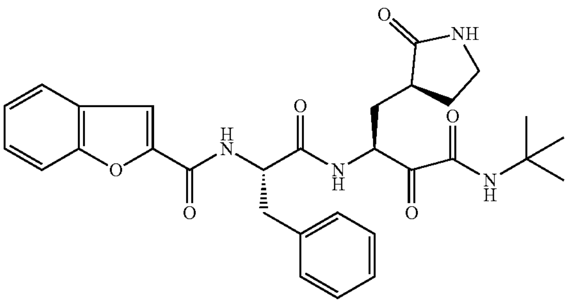 [SMILES: CC(C)(C)NC(=O)C(=O)[C@H](C[C@@H]1CCNC1=O)NC(=O)[C@H](Cc1ccccc1)NC(=O)c1cc2ccccc2o1]

-continued
A293
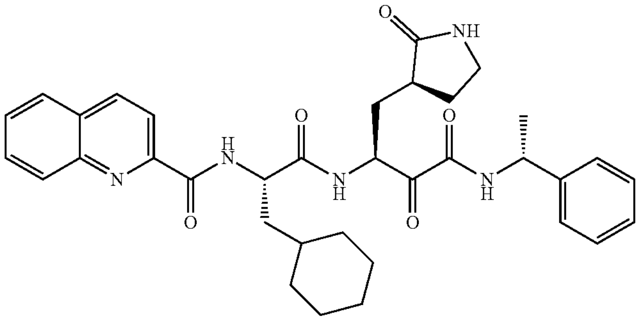 [SMILES: C[C@@H](NC(=O)C(=O)[C@H](C[C@@H]1CCNC1=O)NC(=O)[C@H](CC1CCCCC1)NC(=O)c1ccc2ccccc2n1)c1ccccc1]
A295
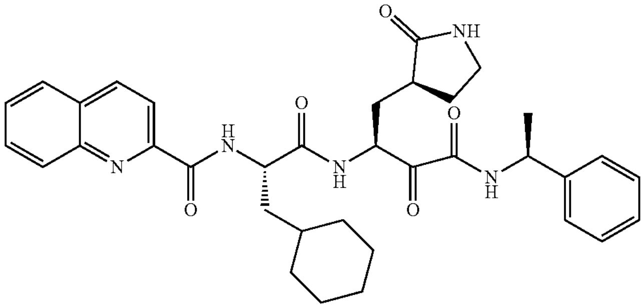 [SMILES: C[C@H](NC(=O)C(=O)[C@H](C[C@@H]1CCNC1=O)NC(=O)[C@H](CC1CCCCC1)NC(=O)c1ccc2ccccc2n1)c1ccccc1]
A296
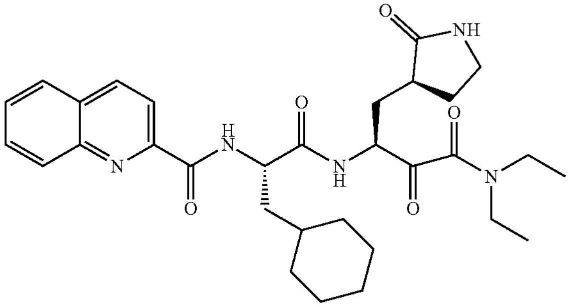 [SMILES: CCN(CC)C(=O)C(=O)[C@H](C[C@@H]1CCNC1=O)NC(=O)[C@H](CC1CCCCC1)NC(=O)c1ccc2ccccc2n1]
A297
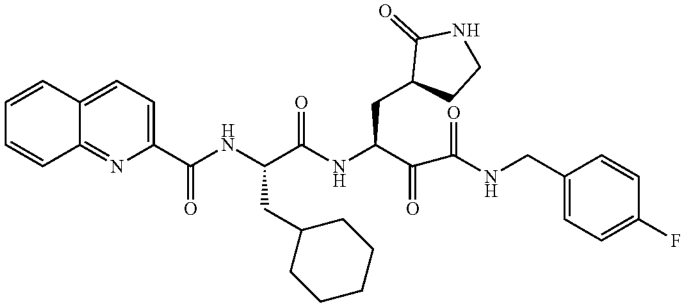 [SMILES: O=C(NCc1ccc(F)cc1)C(=O)[C@H](C[C@@H]1CCNC1=O)NC(=O)[C@H](CC1CCCCC1)NC(=O)c1ccc2ccccc2n1]
A298
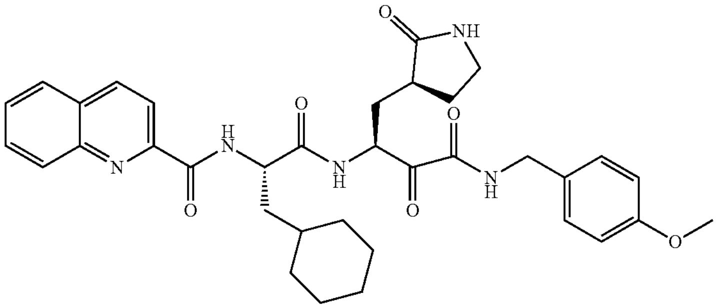 [SMILES: COc1ccc(CNC(=O)C(=O)[C@H](C[C@@H]2CCNC2=O)NC(=O)[C@H](CC2CCCCC2)NC(=O)c2ccc3ccccc3n2)cc1]

-continued
A300
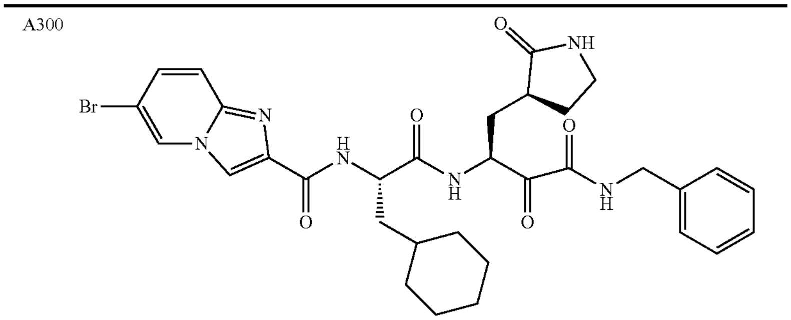
A301
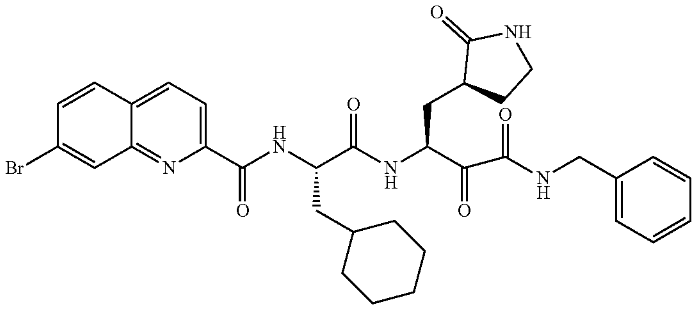 [SMILES: O=C(NCc1ccccc1)C(=O)[C@H](C[C@@H]1CCNC1=O)NC(=O)[C@H](CC1CCCCC1)NC(=O)c1ccc2ccc(Br)cc2n1]
A304
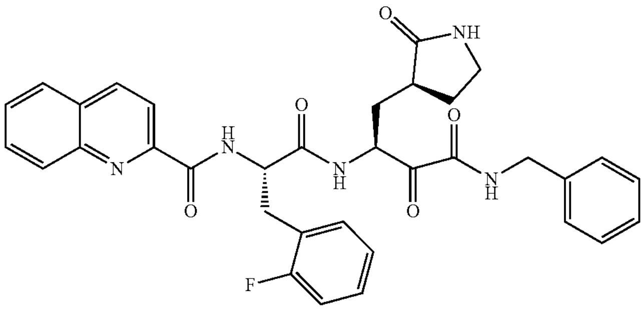 [SMILES: O=C(NCc1ccccc1)C(=O)[C@H](C[C@@H]1CCNC1=O)NC(=O)[C@H](Cc1ccccc1F)NC(=O)c1ccc2ccccc2n1]
A305
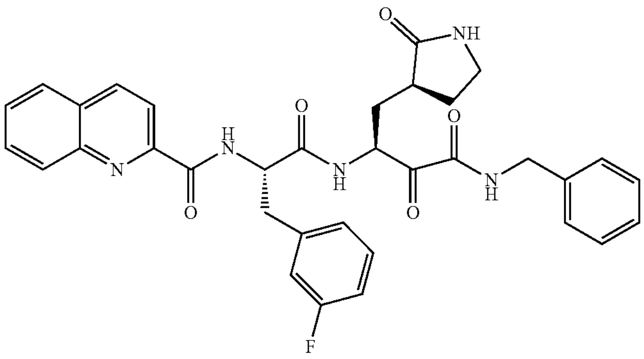 [SMILES: O=C(NCc1ccccc1)C(=O)[C@H](C[C@@H]1CCNC1=O)NC(=O)[C@H](Cc1cccc(F)c1)NC(=O)c1ccc2ccccc2n1]
A306
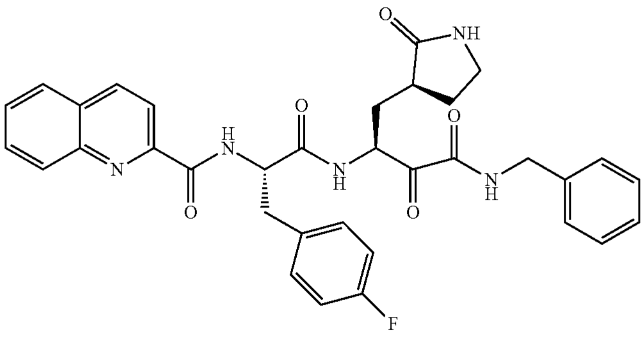 [SMILES: O=C(NCc1ccccc1)C(=O)[C@H](C[C@@H]1CCNC1=O)NC(=O)[C@H](Cc1ccc(F)cc1)NC(=O)c1ccc2ccccc2n1]

-continued
A307
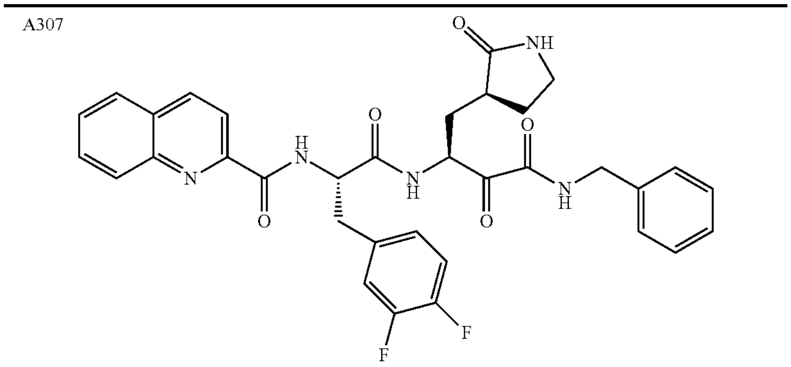
A308
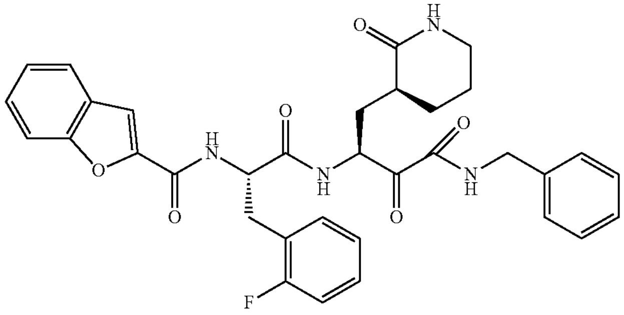 [SMILES: O=C(NCc1ccccc1)C(=O)[C@H](C[C@@H]1CCCNC1=O)NC(=O)[C@H](Cc1ccccc1F)NC(=O)c1cc2ccccc2o1]
A309
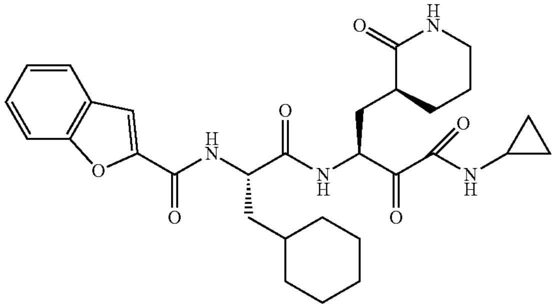 [SMILES: O=C(NC1CC1)C(=O)[C@H](C[C@@H]1CCCNC1=O)NC(=O)[C@H](CC1CCCCC1)NC(=O)c1cc2ccccc2o1]
A310
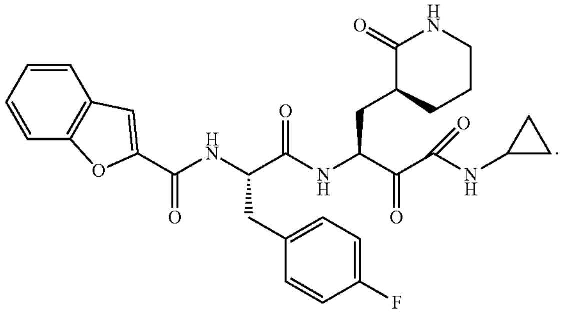 [SMILES: O=C(NC1CC1)C(=O)[C@H](C[C@@H]1CCCNC1=O)NC(=O)[C@H](Cc1ccc(F)cc1)NC(=O)c1cc2ccccc2o1]
* * * * *